US008883826B2

(12) United States Patent
Bessis et al.

(10) Patent No.: US 8,883,826 B2
(45) Date of Patent: Nov. 11, 2014

(54) ALKYNYL DERIVATIVES AS MODULATORS OF METABOTROPIC GLUTAMATE RECEPTORS

(75) Inventors: Anne-Sophie Bessis, Ferney-Voltaire (FR); Christelle Bolea, Carouge (CH); Beatrice Bonnet, Andilly (FR); Mark Epping-Jordan, Nyon (CH); Nicolas Poirier, Ville-la-Grand (FR); Sonia-Maria Poli, Onex-Ge (CH); Jean-Philippe Rocher, Vetraz-Monthoux (FR); Yves Thollon, Annemasse (FR)

(73) Assignee: Addex Pharma SA, Geneva (CH)

( * ) Notice: Subject to any disclaimer, the term of this patent is extended or adjusted under 35 U.S.C. 154(b) by 0 days.

(21) Appl. No.: 13/332,364

(22) Filed: Dec. 20, 2011

(65) Prior Publication Data

US 2012/0277237 A1 Nov. 1, 2012

Related U.S. Application Data

(63) Continuation of application No. 11/630,013, filed on Dec. 18, 2006, now Pat. No. 8,101,637, which is a continuation of application No. PCT/IB2005/002390, filed on Jun. 17, 2005.

(30) Foreign Application Priority Data

Jun. 17, 2004 (GB) .................................. 0413605.7

(51) Int. Cl.
| | |
|---|---|
| *A61K 31/4439* | (2006.01) |
| *A61K 31/4188* | (2006.01) |
| *A61K 31/427* | (2006.01) |
| *A61K 31/56* | (2006.01) |
| *C07D 233/56* | (2006.01) |
| *C07D 239/26* | (2006.01) |
| *C07D 413/06* | (2006.01) |
| *C07D 403/06* | (2006.01) |
| *C07D 213/56* | (2006.01) |
| *C07D 263/56* | (2006.01) |
| *C07D 215/06* | (2006.01) |
| *C07D 471/04* | (2006.01) |
| *C07D 401/06* | (2006.01) |
| *C07D 417/06* | (2006.01) |
| *C07D 277/22* | (2006.01) |

(52) U.S. Cl.
CPC ............ *C07D 471/04* (2013.01); *C07D 233/56* (2013.01); *C07D 239/26* (2013.01); *C07D 413/06* (2013.01); *C07D 403/06* (2013.01); *C07D 213/56* (2013.01); *C07D 263/56* (2013.01); *C07D 215/06* (2013.01); *C07D 401/06* (2013.01); *C07D 417/06* (2013.01); *C07D 277/22* (2013.01)
USPC ............ 514/338; 514/365; 514/393; 514/406

(58) Field of Classification Search
USPC .................. 514/338, 365, 393, 406
See application file for complete search history.

(56) References Cited

U.S. PATENT DOCUMENTS

| | | | |
|---|---|---|---|
| 6,166,060 | A | 12/2000 | Phillips et al. |
| 7,056,942 | B2 | 6/2006 | Hildesheim et al. |
| 7,205,411 | B2 | 4/2007 | Bolea et al. |
| 8,101,637 | B2 | 1/2012 | Bessis et al. |
| 2004/0209865 | A1 | 10/2004 | Stenkamp et al. |
| 2006/0030601 | A1 | 2/2006 | Bolea et al. |

FOREIGN PATENT DOCUMENTS

| | | |
|---|---|---|
| DE | 102 50 708 A1 | 5/1984 |
| GB | 2 124 227 A | 2/1984 |
| WO | 92/05159 | 4/1992 |
| WO | WO 92/07831 A1 | 5/1992 |
| WO | WO 99/02497 A2 | 1/1999 |
| WO | WO 01/16121 A1 | 3/2001 |
| WO | 01/94339 | 12/2001 |
| WO | WO 02/46166 A1 | 6/2002 |
| WO | WO 03/013247 A1 | 2/2003 |
| WO | WO 03/022846 A1 | 3/2003 |
| WO | WO 03/050087 A2 | 6/2003 |
| WO | WO 03/093236 A1 | 11/2003 |
| WO | WO 03/104206 A2 | 12/2003 |
| WO | WO 2004/038374 A2 | 5/2004 |
| WO | 2004/078729 | 9/2004 |
| WO | WO 2004/078728 | 9/2004 |
| WO | WO 2005/044265 A1 | 5/2005 |
| WO | WO 2005/044266 A1 | 5/2005 |
| WO | WO 2005/044267 A1 | 5/2005 |
| WO | 2005/097777 | 10/2005 |

OTHER PUBLICATIONS

Marin et al. "Glutamatergic fine tuning with ADX-10059: a novel therapeutic approach for migraine?" Expert Opinion on Investigational Drugs, 2010, vol. 19, pp. 555-561.*
Bermudo-Soriano et al. "New perspectives in glutamate and anxiety" Pharmacology, Biochemistry, and Behavior, 2012, vol. 100, pp. 752-774.*
Armengol et al., "Synthesis of thieno[2,3-b]quinoxalines and pyrrolo[1,2-a]-quinoxalines from 2-haloquinoxalines," J. Chem. Soc., Perkin Trans., 1 2001, pp. 978-984.
Camaioni et al., "New Substituted 9-Alkylpurines as Adenosine Receptor Ligands," Bioorg. Med. Chem., 1998, vol. 6, p. 523-533.

(Continued)

*Primary Examiner* — Joseph Kosack
(74) *Attorney, Agent, or Firm* — McDonnell Boehnen Hulbert & Berghoff LLP

(57) ABSTRACT

The present invention relates to novel compounds of formula I wherein W, n, X and W' are defined in the description; invention compounds are modulators of metabotropic glutamate receptors—subtype 5 ("mGluR5") which are useful for the treatment of central nervous system disorders as well as other disorders modulated by mGluR5 receptors.

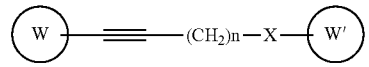

19 Claims, 4 Drawing Sheets

(56) References Cited

OTHER PUBLICATIONS

Draper et al., "Synthesis of Unsymmetrical 3,6-Disubstituted Pyridazines. A Palladium-Catalyzed Approach from 3-Iodopyridazines"; J. Org. Chem. 1995, 60, pp. 748-750.

Iso et al., "Synthesis and Structure—Activity Relationships of 3-[(2-Methyl-1,3-thiazol-4-yl)ethynyl]pyridine Analogues as Potent, Noncompetitive Metabotropic Glutamate Receptor Subtype 5 Antagonists; Search for Cocaine Medications"; J. Med. Chem. 2006, 49, pp. 1080-1100.

Langille et al., "Sonogashira Coupling of Functionalized Trifloyl Oxazoles and Thiazoles with Terminal Alkynes: Synthesis of Disubstituted Heterocycles"; Organic Letters 2002, 4(15), pp. 2485-2488.

Shiotani et al. "Furopyridines. XIII [1]. Reaction of 2-Methylfuro [2,3-b]-, [3,2-b], -(2,3-c] and -[3,2-c]pyridines with Lithium Diisoproplamide", J. Heterocyclic Chem. 1993, 30, pp. 1025-1033.

International Search Report in corresponding PCT Application No. PCT/IB2005/002390, mailed Aug. 10, 2006.

* cited by examiner

* p < 0.01

* p < 0.05

ALKYNYL DERIVATIVES AS MODULATORS OF METABOTROPIC GLUTAMATE RECEPTORS

CROSS-REFERENCE TO RELATED APPLICATIONS

This application is a continuation of U.S. patent application Ser. No. 11/630,013, filed Dec. 18, 2006, now U.S. Pat. No. 8,101,637 allowed, which is a continuation of PCT Patent Application No. PCT/IB2005/002390, filed Jun. 17, 2005, which claims priority to UK Patent Application No. GB 0413605.7, filed Jun. 17, 2004. The contents of each of the foregoing applications are incorporated herein by reference in their entirety.

SUMMARY OF THE INVENTION

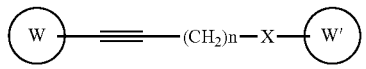

I

The present invention provides new compounds of formula I, wherein W, n, X and W' are defined as in formula I; invention compounds are modulators of metabotropic glutamate receptors—subtype 5 ("mGluR5") which are useful for the treatment of central nervous system disorders as well as other disorders modulated by mGluR5 receptors.

BACKGROUND OF THE INVENTION

Glutamate, the major amino-acid transmitter in the mammalian central nervous system (CNS), mediates excitatory synaptic neurotransmission through the activation of ionotropic glutamate receptors receptor-channels (iGluRs, namely NMDA, AMPA and kainate) and metabotropic glutamate receptors (mGluRs). iGluRs are responsible for fast excitatory transmission (Nakanishi S. et al., (1998) Brain Res. Rev., 26:230-235) while mGluRs have a more modulatory role that contributes to the fine-tuning of synaptic efficacy. Glutamate is associated with numerous physiological functions such as long-term potentiation (LTP), a process believed to underlie learning and memory but also cardiovascular regulation, sensory perception, and the development of synaptic plasticity. In addition, glutamate plays an important role in the pathophysiology of different neurological and psychiatric diseases, especially when an imbalance in glutamatergic neurotransmission occurs.

The mGluRs are seven-transmembrane G protein-coupled receptors. The eight members of the family are classified into three groups (Groups I, II & III) according to their sequence homology and pharmacological properties (Schoepp D. D. et al. (1999) Neuropharmacology, 38:1431-1476). Activation of mGluRs leads to a large variety of intracellular responses and activation of different transductional cascades. Among mGluR members, the mGluR5 subtype is of high interest for counterbalancing the deficit or excesses of neurotransmission in neuropsychiatric diseases. mGluR5 belongs to Group I and its activation initiates cellular responses through G-protein mediated mechanisms. mGluR5 is coupled to phospholipase C and stimulates phosphoinositide hydrolysis and intracellular calcium mobilization.

mGluR5 proteins have been demonstrated to be localized in post-synaptic elements adjacent to the post-synaptic density (Lujan R. et al. (1996) Eur. J. Neurosci. 8:1488-500; Lujan R. et al. (1997) J. Chem. Neuroanat., 13:219-41) and are also detected in the pre-synaptic elements (Romano C. et al. (1995) J. Comp. Neurol. 355:455-69). MGluR5 receptors can therefore modify the post-synaptic responses to neurotransmitter or regulate neurotransmitter release.

In the CNS, mGluR5 receptors are abundant mainly throughout cortex, hippocampus, caudate-putamen and nucleus accumbens. As these brain areas have been shown to be involved in emotion, motivational processes and in numerous aspects of cognitive function, mGluR5 modulators are predicted to be of therapeutic interest.

A variety of clinical indications have been suggested to be targets for the development of subtype selective mGluR modulators. These include epilepsy, neuropathic and inflammatory pain, numerous psychiatric disorders (e.g. anxiety and schizophrenia), movement disorders (e.g. Parkinson disease), neuroprotection (stroke and head injury), migraine and addiction/drug dependency (for reviews, see Brauner-Osborne H. et al. (2000) J. Med. Chem. 43:2609-45; Bordi F. and Ugolini A. (1999) Prog. Neurobiol. 59:55-79; Spooren W. et al. (2003) Behav. Pharmacol. 14:257-77).

mGluR5 receptor is considered as a potential drug target for the treatment of psychiatric and neurological disorders Anxiety Disorders, Attentional disorders, Eating Disorders, Mood Disorders, Psychotic Disorders, Cognitive Disorders, Personality Disorders and Substance of Abuse related disorders Other research supports a role of mGluR5 modulation in the treatment of Fragile X syndrome (Laura N. Antar et al. The Journal of Neuroscience, Mar. 17, 2004, 24-11, 2648-2655, Weiler I. J., Proc. Natl. Acad. Sci. USA, 1997, 94, 5395-5400), Obesity and Gastro-Esophageal Reflux Disease (Blackshaw L. A. et al., presentation at the conference Neurogastroentorology & Mortility, Madison, Wis., 14 Nov. 2001).

International Patent Publications WO03/104206, GB2124227, WO03/050087 and WO03/013247 describe 3-phenoxyprop-1-ynyl and 3-pyridinoxyprop-1-ynyl, having herbicidal properties. In U.S. Pat. No. 6,166,060, 4-(5-phenylpent-1-ynyl)-1H-imidazole is described as an $H_3$ histamine antagonist.

International patent publications WO99/02497, WO01/16121 and WO02/46166 describe heteroaryl ethynyl compounds and their use as metabotropic glutamate receptor antagonists. International patent publications WO2005/044265, WO2005/044266 and WO2005/044267 disclose a class of 3-(pyridin-2-yl)prop-2-ynyl derivatives as being useful in GERD indication.

Compounds of general formula I can show potent activity and selectivity on mGluR5 receptor. The compounds of the invention can demonstrate advantageous properties over compounds of the prior art. Improvements have been observed in one or more of the following characteristics of the compounds of the invention: the potency on the target, the selectivity for the target, the solubility, the bioavailability, the brain penetration, and the activity in behavioural models of psychiatric and neurological disorders.

The present invention relates to a method of treating or preventing a condition in a mammal, including a human, the treatment or prevention of which is affected or facilitated by the neuromodulatory effect of mGluR5 modulators.

FIGURES

DETAILED DESCRIPTION OF THE INVENTION

Figure 1:
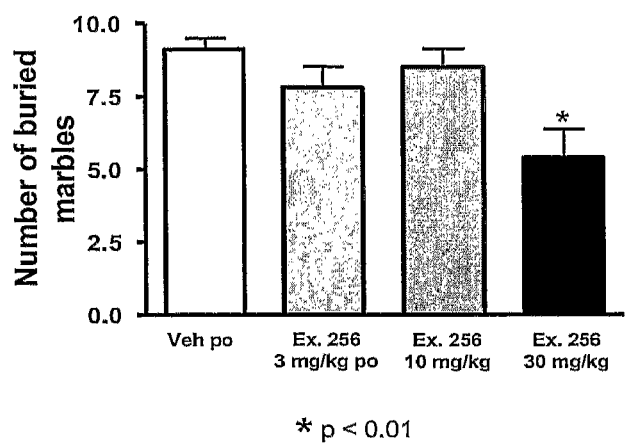
FIG. 1 shows that the representative Example 256 of the invention significantly attenuates marble burying in mice at doses of 30 mg/kg po.

According to the present invention, there are provided new compounds of the general formula I

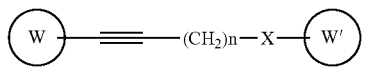

I

Or a pharmaceutically acceptable salt, hydrate or solvate of such compound

Wherein:

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

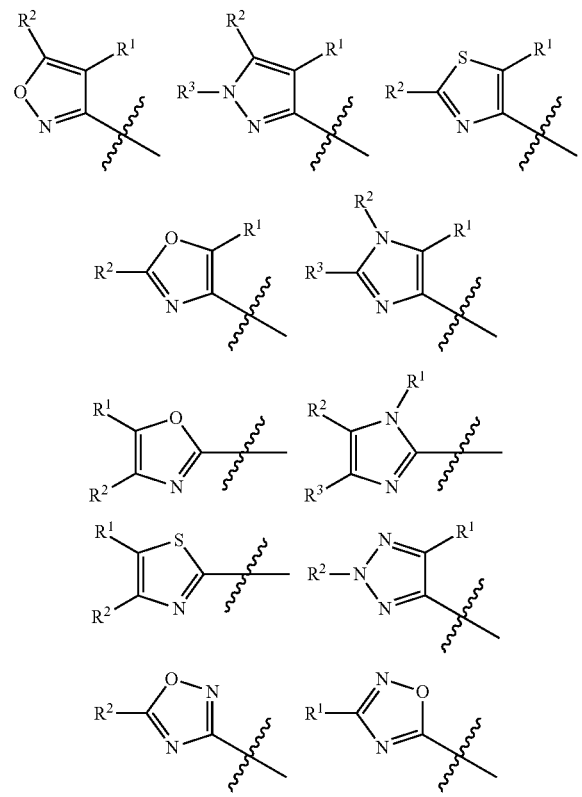

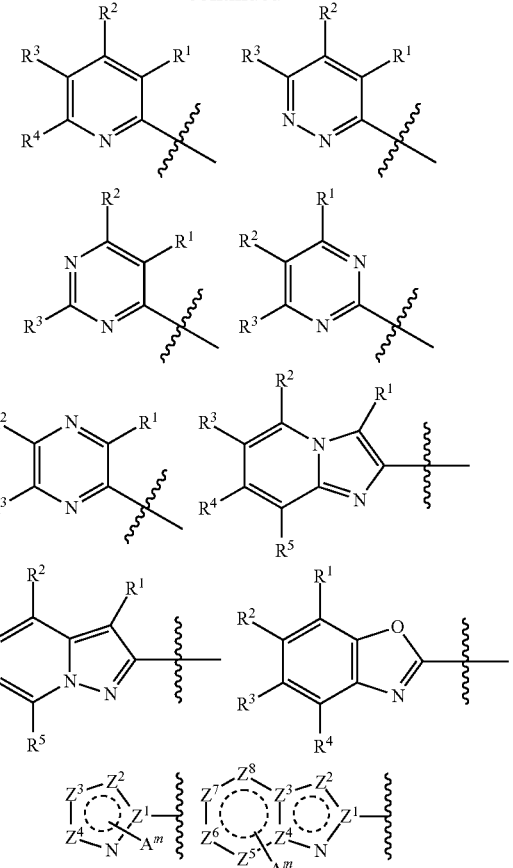

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6C$(=O)—$R^7$, O—$C_1$-$C_6$-alkyl-C(=O)—$NR^6R^7$, O—$C_2$-$C_6$-alkyl-$NR^6C$(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

n is an integer from 1 to 6;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^9$, $C_0$-$C_6$—NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR$^9$—C(=O)—O, $C_0$-$C_6$-alkyl-O—C(=O)—NR$^9$, $C_0$-$C_6$-alkyl-NR$^9$—C(=O)—NR$^{10}$, $C_0$-$C_6$-alkyl-NR$^9$—C(=NR$^{10}$)NR$^{11}$, $C_0$-$C_6$-alkyl-(C=NR$^9$)NR$^{10}$, $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-C(=NOR$^9$) or $C_0$-$C_6$-alkyl-O—N=CR$^9$ substituents;

$R^9$, $R^{10}$ and $R^{11}$ are each independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

W' denotes a 5- or 6-membered ring containing one or more atoms independently selected from C, N, O and S, which ring may optionally be fused with a 5- or 6-membered ring containing one or more atoms independently selected from C, N, O and S, provided that W' is a aryl, heteroaryl or heterocycle selected from the group of formula:

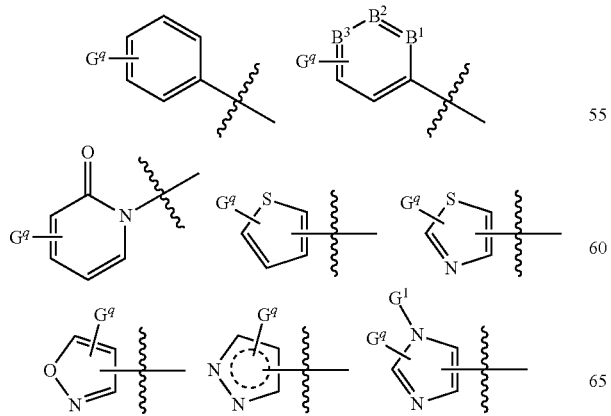

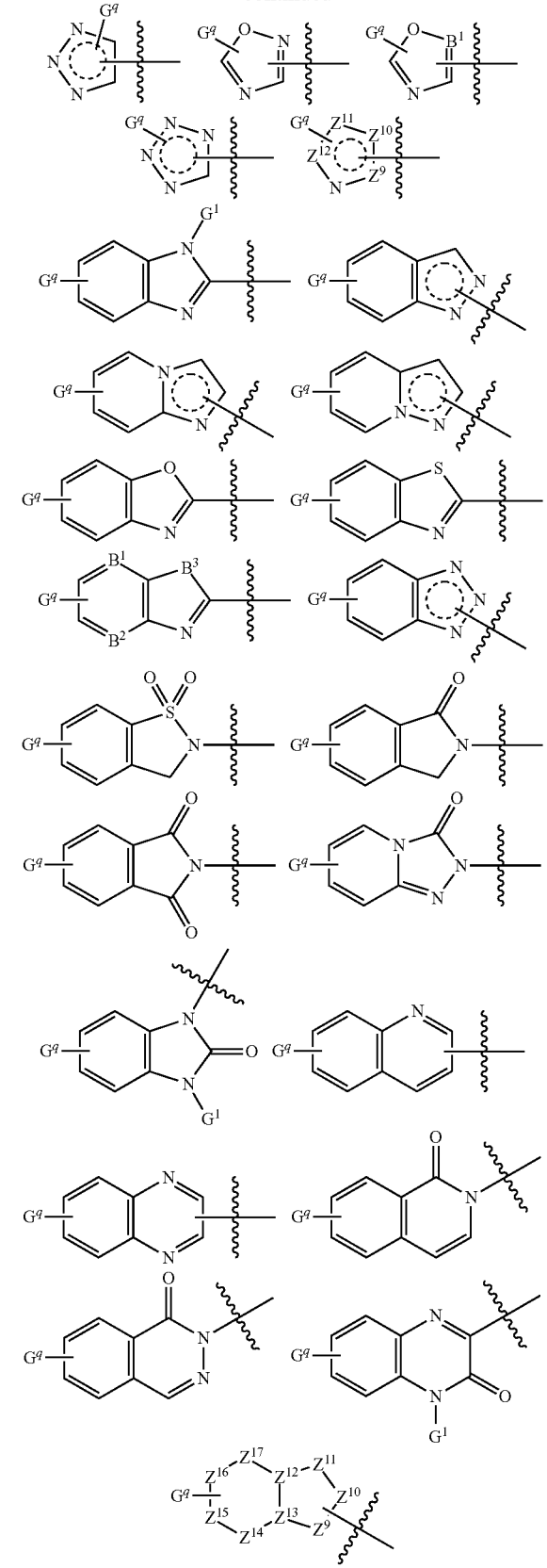

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{12}$, $C_3$-$C_6$-alkynyl-$OR^{12}$, $C_3$-$C_6$-alkenyl-$OR^{12}$, $C_0$-$C_6$-alkyl-S—$R^{12}$, O—$C_2$-$C_6$-alkyl-S—$R^{12}$, $C_0$-$C_6$-alkyl-S(=O)—$R^{12}$, O—$C_2$-$C_6$-alkyl-S(=O)—$R^{12}$, $C_0$-$C_6$-alkyl-S(=O)$_2$—$R^{12}$, O—$C_1$-$C_6$-alkyl-S(=O)$_2$—$R^{12}$, $C_0$-$C_6$-alkyl-$NR^{12}R^{13}$, O—$C_2$-$C_6$-alkyl-$NR^{12}R^{13}$, $C_0$-$C_6$-alkyl-S(=O)$_2NR^{12}R^{13}$, $C_0$-$C_6$-alkyl-$NR^{12}$—S(=O)$_2R^{13}$, O—$C_1$-$C_6$-alkyl-S(=O)$_2NR^{12}R^{13}$, O—$C_2$-$C_6$-alkyl-$NR^{12}$—S(=O)$_2R^{13}$, $C_0$-$C_6$-alkyl-C(=O)—$NR^{12}R^{13}$, $C_0$-$C_6$-alkyl-$NR^{12}$C(=O)—$R^{13}$, O—$C_1$-$C_6$-alkyl-C(=O)—$NR^{12}R^{13}$, O—$C_2$-$C_6$-alkyl-$NR^{12}$C(=O)—$R^{13}$, $C_0$-$C_6$-alkyl-OC(=O)—$R^{12}$, $C_0$-$C_6$-alkyl-C(=O)—$OR^{12}$, O—$C_2$-$C_6$-alkyl-OC(=O)—$R^{12}$, O—$C_1$-$C_6$-alkyl-C(=O)—$OR^{12}$, $C_0$-$C_6$-alkyl-C(=O)—$R^{12}$, O—$C_1$-$C_6$-alkyl-C(=O)—$R^{12}$, $C_0$-$C_6$-alkyl-$NR^{12}$—C(=O)—$OR^{13}$, $C_0$-$C_6$-alkyl-O—C(=O)—$NR^{12}R^{13}$ or $C_0$-$C_6$-alkyl-$NR^{12}$—C(=O)—$NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^9$, $Z^{10}$, $Z^{11}$, $Z^{12}$, $Z^{13}$, $Z^{14}$, $Z^{15}$, $Z^{16}$ and $Z^{17}$ are each independently selected from the group consisting of —C=, —C=C—, —C(=O)—, —C(=S)—, —C—, —O—, —N=, —N— or —S— which may further be substituted by 1 to 5$G^q$ groups;

$B^1$, $B^2$ and $B^3$ are each selected independently from C, C=C, C=N, S, O or N which may further be substituted by one $G^q$ group;

Any N may be an N-oxide;

provided that:

when X is independently selected from $NR^{15}$, O, S or an optionally substituted $C_1$-$C_6$-alkyl, n is 1, W is an optionally substituted 2-pyridinyl and $R^{15}$ is independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl or aryl, W' can not be an optionally substituted aryl;

when X is O, n is 1 and W' is an optionally substituted aryl or heteroaryl, W can not be an optionally substituted 3-pyridazinyl or 4-pyrimidinyl;

when X is $CH_2$, n is 1 and W' is aryl, W can not be 2-phenyloxazol-4-yl, 4-phenyloxazol-2-yl, 4-(3-(benzyloxy)propyl)-oxazol-2-yl, 4-phenylthiazol-2-yl, 4-methylthiazol-2-yl or benzo[d]oxazol-2-yl, benzo[d]thiazol-2-yl;

when X is O, n is 1 and W is an optionally substituted pyridinyl, W' can not be an optionally substituted 2-pyridinyl;

when X is $CH_2$, n is 2 and W' is aryl, W can not be 4-imidazolyl.

The present invention includes both possible stereoisomers and includes not only racemic compounds but the individual enantiomers as well.

DEFINITION OF TERMS

Listed below are definitions of various terms used in the specification and claims to describe the present invention.

For the avoidance of the doubt it is to be understood that in this specification "$C_1$-$C_6$" means a carbon group having 1, 2, 3, 4, 5 or 6 carbons atoms. "$C_0$-$C_6$" means a carbon group having 0, 1, 2, 3, 4, 5 or 6 carbon atoms.

In this specification "C" means a carbon atom.

In the case where a subscript is the integer 0 (zero) the group to which the subscript refers to indicates that the group is absent, i.e. there is a direct bond between the groups.

In this specification, unless stated otherwise, the term "bond" is a saturated bond.

In the above definition, the term "$C_1$-$C_6$-alkyl" includes both straight and branched chain alkyl groups and may be groups such as methyl, ethyl, n-propyl, i-propyl n-butyl, i-butyl, s-butyl, t-butyl, n-pentyl, i-pentyl, t-pentyl, neo-pentyl, n-hexyl, i-hexyl, t-hexyl or the like.

In this specification, unless stated otherwise, the term "alkenyl" includes both straight and branched chain alkenyl groups. The term "$C_2$-$C_6$-alkenyl" refers to an alkenyl group having 2 to 6 carbon atoms and one or two double bonds, and may be, but is not limited to vinyl, allyl, 1-propenyl, i-propenyl, 1-butenyl, i-butenyl, crotyl, pentenyl, i-pentenyl, hexenyl and the like.

In this specification, unless stated otherwise, the term "alkynyl" includes both straight and branched chain alkynyl groups. The term $C_2$-$C_6$-alkynyl having 2 to 6 carbon atoms and one or two triple bonds, and may be, but is not limited to ethynyl, propargyl, butynyl, ibutynyl, pentynyl, i-pentynyl, hexynyl and the like.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4,-tetrahydronaphthyl, indyl, indenyl and the like.

In this specification, unless stated otherwise, the term "halo" or "halogen" may be fluoro, chloro, bromo or iodo.

In this specification, unless stated otherwise, a 5- or 6-membered ring containing one or more atoms independently selected from C, N, O, or S, includes aromatic and heteroaromatic rings as well as carbocyclic and heterocyclic rings which may be saturated or unsaturated. Example of such rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, triazolyl, morpholinyl, piperazinyl, piperidinyl, piperidonyl, pyrazolinyl, pyrrolidinyl, pyrrolinyl, tetrahydropyranyl, thiomorpholinyl, phenyl, cyclohexyl, cyclohexenyl, cyclopentyl and the like.

In this specification, unless stated otherwise, the term "alkylaryl", "alkylheteroaryl" and "alkylcycloalkyl" refer to a substituent that is attached via the alkyl group to an aryl, heteroaryl and cycloalkyl group. The term "$C_1$-$C_6$-alkylaryl"

includes aryl-$C_1$-$C_6$-alkyl group such as benzyl group, 1-phenylethyl group, 2-phenylethyl group, 1-phenylpropyl group, 2-phenylpropyl group, 3-phenylpropyl group, 1-naphthylmethyl group, 2-naphthylmethyl group or the like. The term "$C_1$-$C_6$-alkylheteroaryl" includes heteroaryl-$C_1$-$C_3$-alkyl group, wherein examples of heteroaryl are the same as those illustrated in the above definition, such as 2-furylmethyl group, 3-furylmethyl group, 2-thienylmethyl group, 3-thienylmethyl group, 1-imidazolylmethyl group, 2-imidazolylmethyl group, 2-thiazolylmethyl group, 2-pyridylmethyl group, 3-pyridylmethyl group, 1-quinolylmethyl group or the like.

In this specification, unless stated otherwise, the term "alkylhalo" means an alkyl group as defined above, substituted with one or more halogen. The term "$C_1$-$C_6$-alkylhalo" may include, but not limited to fluoroethyl, difluoromethyl, trifluoromethyl, fluoroethyl, difluoroethyl, bromoethyl and the like. The term "O—$C_1$-$C_6$-alkylhalo" may include, but is not limited to fluoromethoxy, difluoromethoxy, trifluoromethoxy, fluoroethoxy and the like.

In the specification, unless stated otherwise, the term "heteroaryl" refers to an optionally substituted monocyclic or bicyclic unsaturated, aromatic ring system containing at least on heteroatom selected independently from O, N or S to form a ring such as furyl (furan ring), benzofuranyl (benzofuran), thienyl (thiophene), benzothiophenyl (benzothiophene), oxadiazolyl (oxadiazole ring), pyrrolyl (pyrrole ring), imidazolyl (imidazole ring), pyrazolyl (pyrazole ring), thiazolyl (thiazole ring), isothiazolyl (isothiazole ring), triazolyl (triazole ring), tetrazolyl (tetrazole ring), pyridil (pyridine ring), pyrazynyl (pyrazine ring), pyrimidinyl (pyrimidine ring), pyridazinyl (pyridazine ring), indolyl (indole ring), isoindolyl (isoindole ring), benzoimidazolyl (benzimidazole ring), purinyl group (purine ring), quinolyl (quinoline ring), phtalazinyl (phtalazine ring), naphtyridinyl (naphtyridine ring), quinoxalinyl (quinoxaline ring), cinnolyl (cinnoline ring), pteridinyl (pteridine ring), oxazolyl (oxazole ring), isoxazolyl (isoxazole ring), benzoxazolyl (benzoxazole ring), benzothiazolyl (benzothiaziole ring), furazanyl (furazan ring), benzotriazolyl (benzotriazol ring), imidazopyridinyl (imidazopyridine ring), pyrazolopyridinyl (pyrazolopyridine ring), and the like.

In this specification, unless stated otherwise, the term "heterocycle" refers to an optionally substituted, mono cyclic or bicyclic saturated, partially saturated or unsaturated ring system containing at least one heteroatom selected independently from N, O or S.

In this specification, unless stated otherwise, the term "cycloalkyl" refers to an optionally substituted carbocycles containing no heteroatoms, includes mono-, bi-, and tricyclic saturated carbocycles, as well as fused ring systems. Such fused ring systems can include on ring that is partially or fully unsaturated such as a benzene ring to form fused ring systems such as benzo fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl, 1,2,3,4-tetrahydronaphthalene and the like. The term "($C_3$-$C_7$)cycloalkyl" may be cyclopropyl, cyclobutyl, cyclopentyl, cyclohexyl, cycloheptyl and the like.

"Solvate" refers to a complex of variable stoichiometry formed by a solute (e.g. a compound of formula I) and a solvent. The solvent is a pharmaceutically acceptable solvent as water preferably; such solvent may not interfere with the biological activity of the solute.

In this specification, unless stated otherwise, the term "optionally substituted" refers to radicals further bearing one or more substituents which may be, but are not limited to, hydroxyl, alkoxy, mercapto, aryl, heterocycle, halogen, trifluoromethyl, pentafluoroethyl, cyano, cyanomethyl, nitro, amino, amido, amidine, carboxyl, carboxamide, carbamate, ester, sulfonyl, sulfonamide, and the like.

Preferred compounds of the present invention are compounds of formula II depicted below

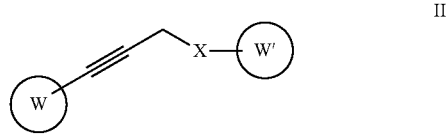

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from a group consisting of C, N, O and S; provided that W is a heteroaryl selected from the group of formula:

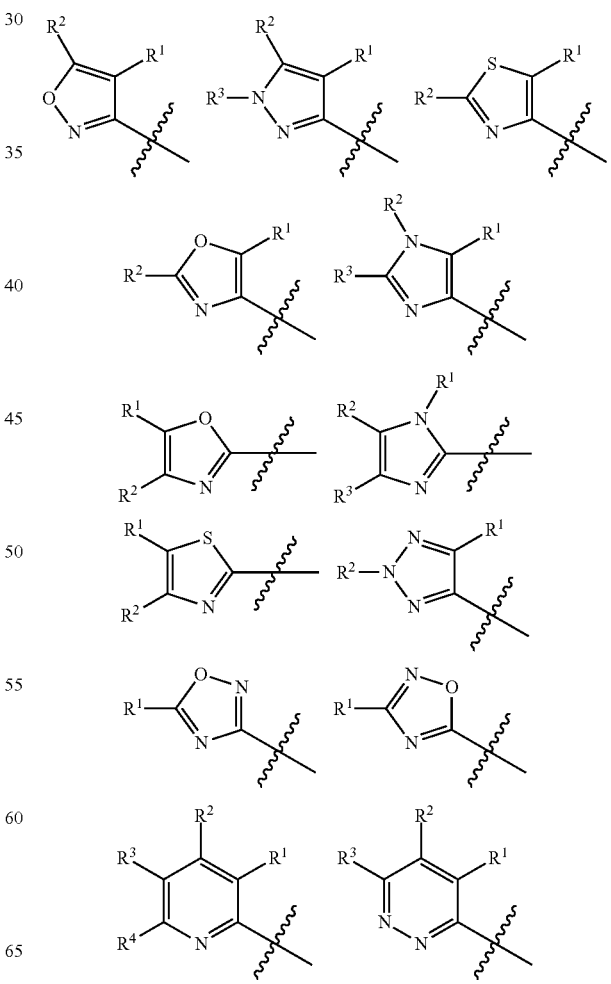

R¹, R², R³, R⁴, R⁵ and A^m are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR⁶, O—$C_3$-$C_7$-cycloalkyl, O—$C_1$-$C_6$-alkyl-heteroaryl, O—$C_1$-$C_6$-alkylaryl, $C_0$-$C_6$-alkyl-OR⁶, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR⁶, $C_3$-$C_6$-alkynyl-OR⁶, $C_3$-$C_6$-alkenyl-OR⁶, $C_0$-$C_6$-alkyl-S—R⁶, O—$C_2$-$C_6$-alkyl-S—R⁶, $C_0$-$C_6$-alkyl-S(=O)—R⁶, O—$C_2$-$C_6$-alkyl-S(=O)—R⁶, $C_0$-$C_6$-alkyl-S(=O)$_2$—R⁶, O—$C_1$-$C_6$-alkyl-S(=O)$_2$—R⁶, $C_0$-$C_6$-alkyl-NR⁶R⁷, O—$C_2$-$C_6$-alkyl-NR⁶R⁷, $C_0$-$C_6$-alkyl-S(=O)$_2$NR⁶R⁷, $C_0$-$C_6$-alkyl-NR⁶—S(=O)$_2$R⁷, O—$C_1$-$C_6$-alkyl-S(=O)$_2$NR⁶R⁷, O—$C_1$-$C_6$-alkyl-NR⁶—S(=O)$_2$R⁷, $C_0$-$C_6$-alkyl-C(=O)—NR⁶R⁷, $C_0$-$C_6$-alkyl-NR⁶C(=O)—R⁷, O—$C_1$-$C_6$-alkyl-C(=O)—NR⁶R⁷, O—$C_2$-$C_6$-alkyl-NR⁶C(=O)—R⁷, $C_0$-$C_6$-alkyl-OC(=O)—R⁶, $C_0$-$C_6$-alkyl-C(=O)—OR⁶, O—$C_2$-$C_6$-alkyl-OC(=O)—R⁶, O—$C_1$-$C_6$-alkyl-C(=O)—OR⁶, $C_0$-$C_6$-alkyl-C(=O)—R⁶, O—$C_1$-$C_6$-alkyl-C(=O)—R⁶, $C_0$-$C_6$-alkyl-NR⁶—C(=O)—OR⁷, $C_0$-$C_6$-alkyl-O—C(=O)—NR⁶R⁷ or $C_0$-$C_6$-alkyl-NR⁶—C(=O)—NR⁷R⁸ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

R⁶, R⁷ and R⁸ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Z¹, Z², Z³, Z⁴, Z⁵, Z⁶, Z⁷ and Z⁸ are each independently selected from the group consisting of —C=, —C=C—, —O—, —N=, —N— or —S— which may further be substituted by 1 to 5 A^m groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR⁹, $C_0$-$C_6$—NR⁹S(=O)$_2$, $C_0$-$C_6$-alkyl-S(=O)$_2$NR⁹, $C_0$-$C_6$-alkyl-C(=O)—NR⁹, $C_0$-$C_6$-alkyl-NR⁹C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR⁹—C(=O)—O, $C_0$-$C_6$-alkyl-O—C(=O)—NR⁹, $C_0$-$C_6$-alkyl-NR⁹—C(=O)—NR¹⁰, $C_0$-$C_6$-alkyl-NR⁹—C(=NR¹⁰)NR¹¹, $C_0$-$C_6$-alkyl-(C=NR⁹)NR¹⁰, $C_0$-$C_6$-alkyl-C(=O)—O—$C_0$-$C_6$-alkyl, $C_0$-$C_6$-alkyl-C(=O)—NR⁹—$C_0$-$C_6$-alkyl, $C_0$-$C_6$-alkyl-C(=NOR⁹) or $C_0$-$C_6$-alkyl-O—N=CR⁹ substituents;

R⁹, R¹⁰ and R¹¹ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

W' denotes a 5- or 6-membered ring containing one or more atoms independently selected from C, N, O and S, which ring may optionally be fused with a 5- or 6-membered ring containing one or more atoms independently selected from C, N, O and S, provided that W' is a aryl, heteroaryl or heterocycle selected from the group of formula:

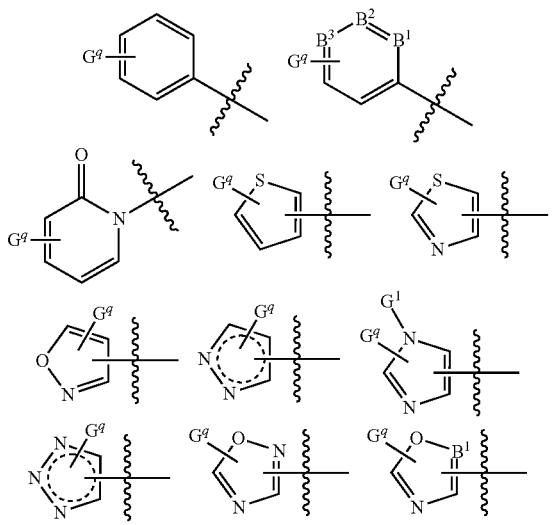

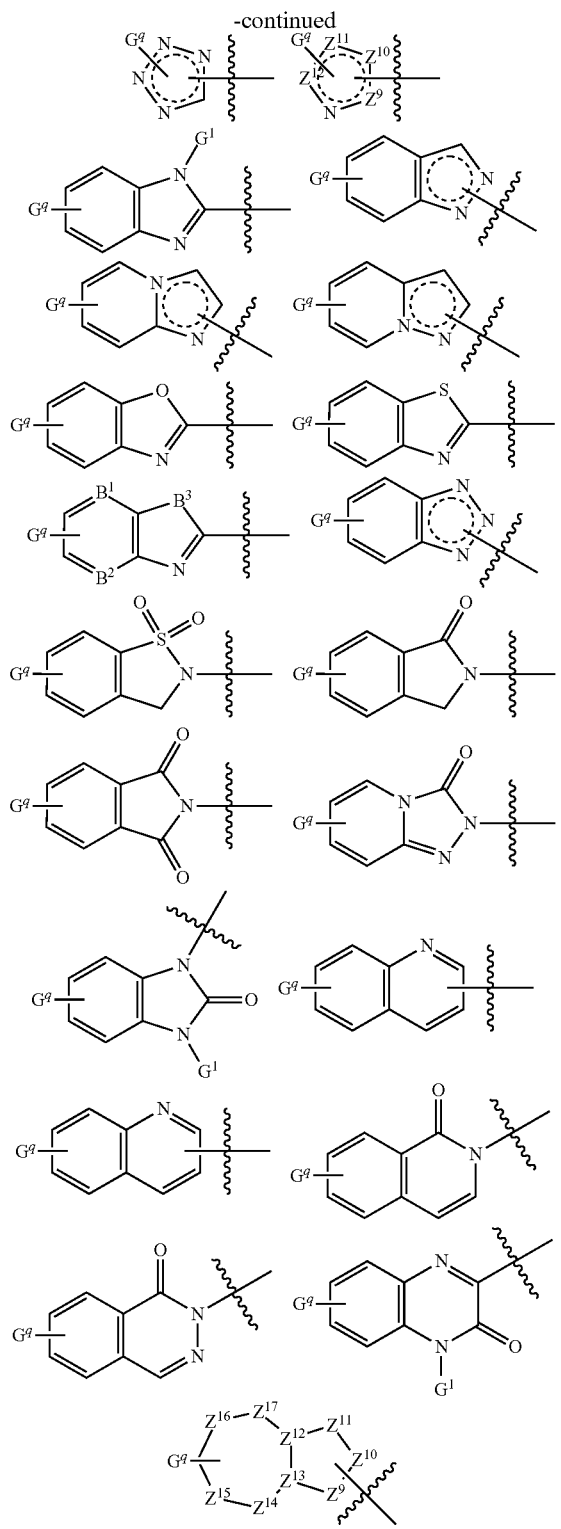

G$^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{12}$, $C_3$-$C_6$-alkenyl-OR$^{12}$, $C_3$-$C_6$-alkynyl-OR$^{12}$, $C_0$-$C_6$-alkyl-S—R$^{12}$, O—$C_2$-$C_6$-alkyl-S—R$^{12}$, $C_0$-$C_6$-alkyl-S(=O)—R$^{12}$, O—$C_2$-$C_6$-alkyl-S(=O)—R$^{12}$, $C_0$-$C_6$-alkyl-S(=O)$_2$—R$^{12}$, O—$C_1$-$C_6$-alkyl-S(=O)$_2$—R$^{12}$, $C_0$-$C_6$-alkyl-NR$^{12}$R$^{13}$, O—$C_2$-$C_6$-alkyl-NR$^{12}$R$^{13}$, $C_0$-$C_6$-alkyl-S(=O)$_2$NR$^{12}$R$^{13}$, $C_0$-$C_6$-alkyl-NR$^{12}$—S(=O)$_2$R$^{13}$, O—$C_1$-$C_6$-alkyl-S(=O)$_2$NR$^{12}$R$^{13}$, O—$C_2$-$C_6$-alkyl-NR$^{12}$—S(=O)$_2$R$^{13}$, $C_0$-$C_6$-alkyl-C(=O)—NR$^{12}$R$^{13}$, $C_0$-$C_6$-alkyl-NR$^{12}$C(=O)—R$^{13}$, O—$C_1$-$C_6$-alkyl-C(=O)—NR$^{12}$R$^{13}$, O—$C_2$-$C_6$-alkyl-NR$^{12}$C(=O)—R$^{13}$, $C_0$-$C_6$-alkyl-OC(=O)—R$^{12}$, $C_0$-$C_6$-alkyl-C(=O)—OR$^{12}$, O—$C_2$-$C_6$-alkyl-OC(=O)—R$^{12}$, O—$C_1$-$C_6$-alkyl-C(=O)—OR$^{12}$, $C_0$-$C_6$-alkyl-C(=O)—R$^{12}$, O—$C_1$-$C_6$-alkyl-C(=O)—R$^{12}$, $C_0$-$C_6$-alkyl-NR$^{12}$—C(=O)—OR$^{13}$, $C_0$-$C_6$-alkyl-O—C(=O)—NR$^{12}$R$^{13}$ or $C_0$-$C_6$-alkyl-NR$^{12}$—C(=O)—NR$^{13}$R$^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

R$^{12}$, R$^{13}$ and R$^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Z$^9$, Z$^{10}$, Z$^{11}$, Z$^{12}$, Z$^{13}$, Z$^{14}$, Z$^{15}$, Z$^{16}$ and Z$^{17}$ are each independently selected from the group consisting of —C=, —C=C—, —C(=O)—, —C(=S)—, —C—, —O—, —N=, —N— or —S— which may further be substituted by 1 to 5 G$^q$ groups;

B$^1$, B$^2$ and B$^3$ are each selected independently from the group consisting of C, C=C, C=N, S, O or N which may further be substituted by one G$^q$ group;

Any N may be an N-oxide;

provided that:

when X is independently selected from NR$^{15}$, O, S or an optionally substituted $C_1$-$C_6$-alkyl, W is an optionally substituted 2-pyridinyl and R$^{15}$ is independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl or aryl, W' can not be an optionally substituted aryl;

when X is O and W' is an optionally substituted aryl or heteroaryl, W can not be an optionally substituted 3-pyridazinyl or 4-pyrimidinyl;

when X is CH$_2$ and W' is aryl, W can not be 2-phenyloxazol-4-yl, 4-phenyloxazol-2-yl, 4-(3-(benzyloxy)propyl)-oxazol-2-yl, 4-phenylthiazol-2-yl, 4-methylthiazol-2-yl or benzo[d]oxazol-2-yl, benzo[d]thiazol-2-yl;

when X is O and W is an optionally substituted pyridinyl, W' can not be an optionally substituted 2-pyridinyl;

when X is CH$_2$CH$_2$ and W' is aryl, W can not be 4-imidazolyl.

The present invention includes both possible stereoisomers and includes not only racemic compounds but the individual enantiomers as well.

More preferred compounds of the present invention are compounds of formula II-A depicted below

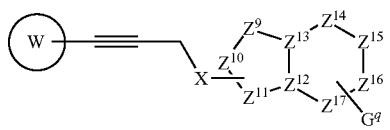

II-A

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

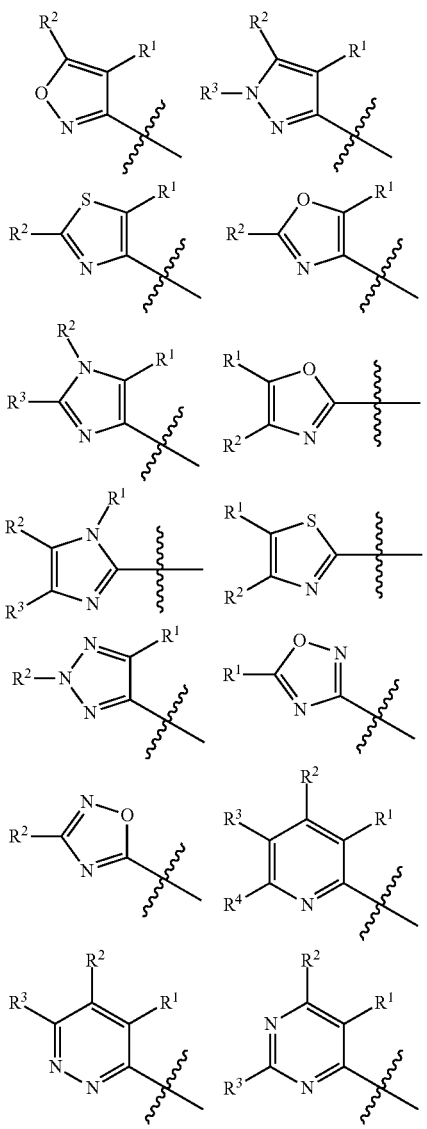

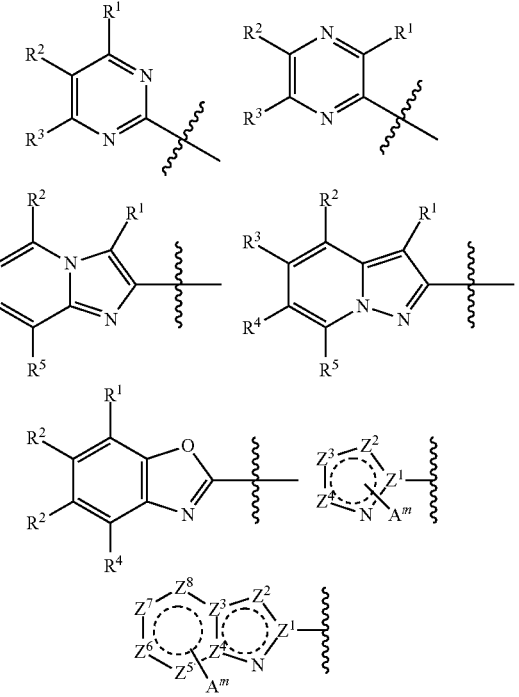

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^6$, $C_3$-$C_6$-alkynyl-OR$^6$, $C_3$-$C_6$-alkenyl-OR$^6$, $C_0$-$C_6$-alkyl-S—R$^6$, O—$C_2$-$C_6$-alkyl-S—R$^6$, $C_0$-$C_6$-alkyl-S(=O)—R$^6$, O—$C_2$-$C_6$-alkyl-S(=O)—R$^6$, $C_0$-$C_6$-alkyl-S(=O)$_2$—R$^6$, O—$C_1$-$C_6$-alkyl-S(=O)$_2$—R$^6$, $C_0$-$C_6$-alkyl-NR$^6$R$^7$, O—$C_2$-$C_6$-alkyl-NR$^6$R$^7$, $C_0$-$C_6$-alkyl-S(=O)$_2$NR$^6$R$^7$, $C_0$-$C_6$-alkyl-NR$^6$—S(=O)$_2$R$^7$, O—$C_1$-$C_6$-alkyl-S(=O)$_2$NR$^6$R$^7$, O—$C_1$-$C_6$-alkyl-NR$^6$—S(=O)$_2$R$^7$, $C_0$-$C_6$-alkyl-C(=O)—NR$^6$R$^7$, $C_0$-$C_6$-alkyl-NR$^6$C(=O)—R$^7$, O—$C_1$-$C_6$-alkyl-C(=O)—NR$^6$R$^7$, O—$C_2$-$C_6$-alkyl-NR$^6$C(=O)—R$^7$, $C_0$-$C_6$-alkyl-OC(=O)—R$^6$, $C_0$-$C_6$-alkyl-C(=O)—OR$^6$, O—$C_2$-$C_6$-alkyl-OC(=O)—R$^6$, O—$C_1$-$C_6$-alkyl-C(=O)—OR$^6$, $C_0$-$C_6$-alkyl-C(=O)—R$^6$, O—$C_1$-$C_6$-alkyl-C(=O)—R$^6$, $C_0$-$C_6$-alkyl-NR$^6$—C(=O)—OR$^7$, $C_0$-$C_6$-alkyl-O—C(=O)—NR$^6$R$^7$ or $C_0$-$C_6$-alkyl-NR$^6$—C(=O)—NR$^7$R$^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^9$, $C_0$-$C_6$—$NR^9$S(=O)$_2$, $C_0$-$C_6$-alkyl-S(=O)$_2NR^9$, $C_0$-$C_6$-alkyl-C(=O)—$NR^9$, $C_0$-$C_6$-alkyl-$NR^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^9$—C(=O)—O, $C_0$-$C_6$-alkyl-O—C(=O)—$NR^9$, $C_0$-$C_6$-alkyl-$NR^9$—C(=O)—$NR^{10}$, $C_0$-$C_6$-alkyl-$NR^9$—C(=$NR^{10}$)$NR^{11}$, $C_0$-$C_6$-alkyl-(C=$NR^9$)$NR^{10}$, $C_0$-$C_6$-alkyl-C(=O)—O—$C_0$-$C_6$-alkyl, $C_0$-$C_6$-alkyl-C(=O)—$NR^9$—$C_0$-$C_6$-alkyl, $C_0$-$C_6$-alkyl-C(=$NOR^9$) or $C_0$-$C_6$-alkyl-O—N=$CR^9$ substituents;

$R^9$, $R^{10}$ and $R^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$Z^9$, $Z^{10}$, $Z^{11}$, $Z^{12}$, $Z^{13}$, $Z^{14}$, $Z^{15}$, $Z^{16}$ and $Z^{17}$ are each independently selected from the group consisting of —C=, —C=C—, —C(=O)—, —C(=S)—, —C—, —O—, —N=, —N— or —S— which may further be substituted by 1 to 5 $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{12}$, $C_3$-$C_6$-alkynyl-$OR^{12}$, $C_3$-$C_6$-alkenyl-$OR^{12}$, $C_0$-$C_6$-alkyl-S—$R^{12}$, O—$C_2$-$C_6$-alkyl-S—$R^{12}$, $C_0$-$C_6$-alkyl-S(=O)—$R^{12}$, O—$C_2$-$C_6$-alkyl-S(=O)—$R^{12}$, $C_0$-$C_6$-alkyl-S(=O)$_2$—$R^{12}$, O—$C_1$-$C_6$-alkyl-S(=O)$_2$—$R^{12}$, $C_0$-$C_6$-alkyl-$NR^{12}R^{13}$, O—$C_2$-$C_6$-alkyl-$NR^{12}R^{13}$, $C_0$-$C_6$-alkyl-S(=O)$_2NR^{12}R^{13}$, $C_0$-$C_6$-alkyl-$NR^{12}$—S(=O)$_2R^{13}$, O—$C_1$-$C_6$-alkyl-S(=O)$_2NR^{12}R^{13}$, O—$C_2$-$C_6$-alkyl-$NR^{12}$—S(=O)$_2R^{13}$, $C_0$-$C_6$-alkyl-C(=O)—$NR^{12}R^{13}$, $C_0$-$C_6$-alkyl-$NR^{12}$C(=O)—$R^{13}$, O—$C_1$-$C_6$-alkyl-C(=O)—$NR^{12}R^{13}$, O—$C_2$-$C_6$-alkyl-$NR^{12}$C(=O)—$R^{13}$, $C_0$-$C_6$-alkyl-OC(=O)—$R^{12}$, $C_0$-$C_6$-alkyl-C(=O)—$OR^{12}$, O—$C_2$-$C_6$-alkyl-OC(=O)—$R^{12}$, O—$C_1$-$C_6$-alkyl-C(=O)—$OR^{12}$, $C_0$-$C_6$-alkyl-C(=O)—$R^{12}$, O—$C_1$-$C_6$-alkyl-C(=O)—$R^{12}$, $C_0$-$C_6$-alkyl-$NR^{12}$—C(=O)—$OR^{13}$, $C_0$-$C_6$-alkyl-O—C(=O)—$NR^{12}R^{13}$ or $C_0$-$C_6$-alkyl-$NR^{12}$—C(=O)—$NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In one aspect, the compounds of the present invention are represented by Formula II-A wherein the heterocyclic ring system is specified as in the formula II-A1 depicted below

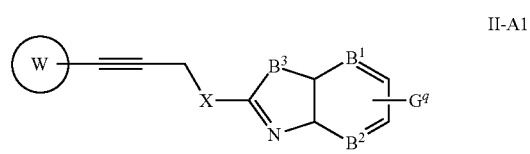

II-A1

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

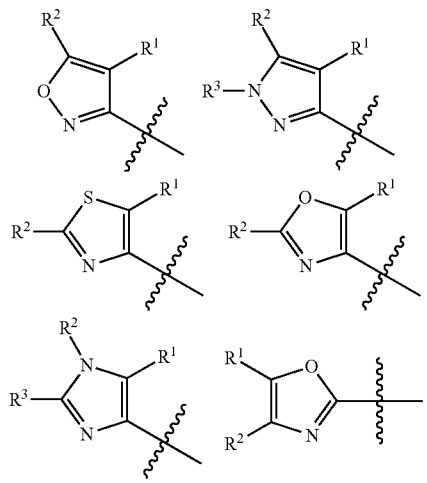

-continued

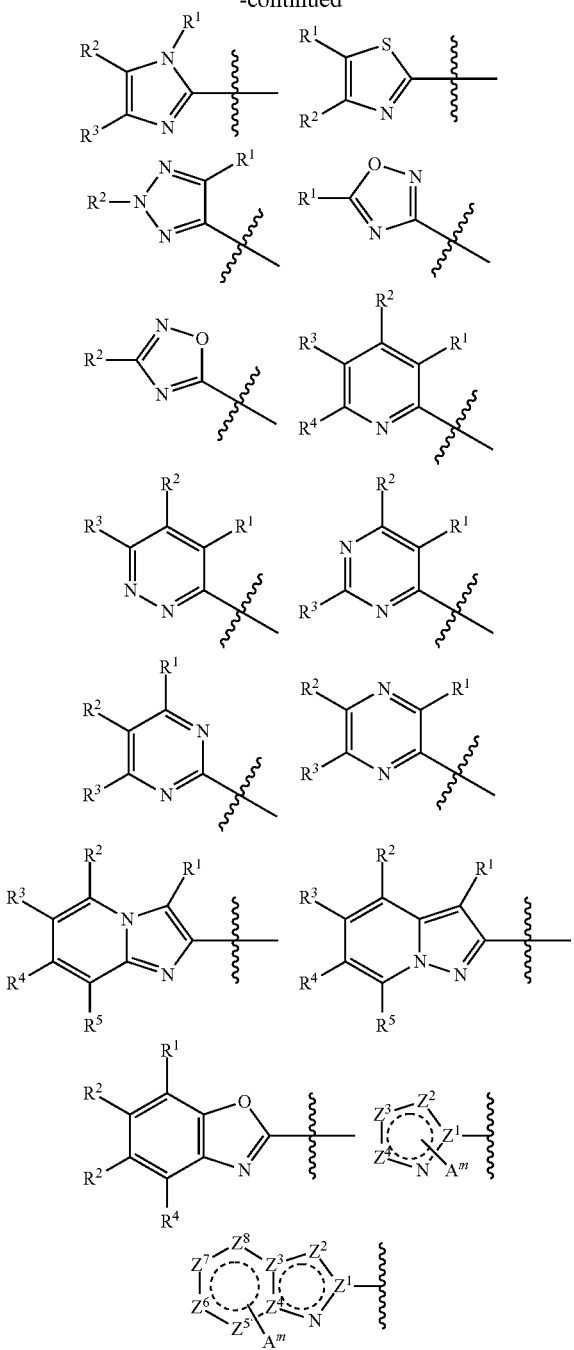

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6C$(=O)—$R^7$, O—$C_1$-$C_6$-alkyl-C(=O)—$NR^6R^7$, O—$C_2$-$C_6$-alkyl-$NR^6C$(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^9$, $C_0$-$C_6$—$NR^9S$(=O)$_2$, $C_0$-$C_6$-alkyl-S(=O)$_2NR^9$, $C_0$-$C_6$-alkyl-C(=O)—$NR^9$, $C_0$-$C_6$-alkyl-$NR^9C$(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^9$—C(=O)—O, $C_0$-$C_6$-alkyl-O—C(=O)—$NR^9$, $C_0$-$C_6$-alkyl-$NR^9$—C(=O)—$NR^{10}$, $C_0$-$C_6$-alkyl-$NR^9$—C(=$NR^{10}$)$NR^{11}$, $C_0$-$C_6$-alkyl-(C=$NR^9$)$NR^{10}$, $C_0$-$C_6$-alkyl-C(=O)—O—$C_0$-$C_6$-alkyl, $C_0$-$C_6$-alkyl-C(=O)—$NR^9$—$C_0$-$C_6$-alkyl, $C_0$-$C_6$-alkyl-C(=$NOR^9$) or $C_0$-$C_6$-alkyl-O—N=$CR^9$ substituents;

$R^9$, $R^{10}$ and $R^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$B^1$ and $B^2$ are each selected independently from N or C which may further be substituted by $G^q$ groups;

$B^3$ is selected independently from C, C=C, C=N, S, O or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—C$_3$-C$_6$-alkynyl, O—C$_3$-C$_6$-alkenyl, O—C$_2$-C$_6$-alkyl-OR$^{12}$, O—C$_3$-C$_7$-cycloalkyl, O—C$_1$-C$_6$-alkyl-heteroaryl, O—C$_1$-C$_6$-alkylaryl, C$_0$-C$_6$-alkyl-OR$^{12}$, C$_3$-C$_7$-cycloalkyl, C$_3$-C$_7$-cycloalkyl-C$_1$-C$_6$-alkyl, O—C$_3$-C$_7$-cycloalkyl-C$_1$-C$_6$-alkyl, O-heteroaryl, heteroaryl, C$_1$-C$_6$-alkyl-heteroaryl, aryl, O-aryl, C$_1$-C$_6$-alkylaryl, C$_1$-C$_6$-alkylhalo-OR$^{12}$, C$_3$-C$_6$-alkynyl-OR$^{12}$, C$_3$-C$_6$-alkenyl-OR$^{12}$, C$_0$-C$_6$-alkyl-S—R$^{12}$, O—C$_2$-C$_6$-alkyl-S—R$^{12}$, C$_0$-C$_6$-alkyl-S(=O)—R$^{12}$, O—C$_2$-C$_6$-alkyl-S(=O)—R$^{12}$, C$_0$-C$_6$-alkyl-S(=O)$_2$—R$^{12}$, O—C$_1$-C$_6$-alkyl-S(=O)$_2$—R$^{12}$, C$_0$-C$_6$-alkyl-NR$^{12}$R$^{13}$, O—C$_2$-C$_6$-alkyl-NR$^{12}$R$^{13}$, C$_0$-C$_6$-alkyl-S(=O)$_2$NR$^{12}$R$^{13}$, C$_0$-C$_6$-alkyl-NR$^{12}$—S(=O)$_2$R$^{13}$, O—C$_1$-C$_6$-alkyl-S(=O)$_2$NR$^{12}$R$^{13}$, O—C$_2$-C$_6$-alkyl-NR$^{12}$—S(=O)$_2$R$^{13}$, C$_0$-C$_6$-alkyl-C(=O)—NR$^{12}$R$^{13}$, C$_0$-C$_6$-alkyl-NR$^{12}$C(=O)—R$^{13}$, O—C$_1$-C$_6$-alkyl-C(=O)—NR$^{12}$R$^{13}$, O—C$_2$-C$_6$-alkyl-NR$^{12}$C(=O)—R$^{13}$, C$_0$-C$_6$-alkyl-OC(=O)—R$^{12}$, C$_0$-C$_6$-alkyl-C(=O)—OR$^{12}$, O—C$_2$-C$_6$—alkyl-OC(=O)—R$^{12}$, O—C$_1$-C$_6$-alkyl-C(=O)—OR$^{12}$, C$_0$-C$_6$-alkyl-C(=O)—R$^{12}$, O—C$_1$-C$_6$-alkyl-C(=O)—R$^{12}$, C$_0$-C$_6$-alkyl-NR$^{12}$—C(=O)—OR$^{13}$, C$_0$-C$_6$-alkyl-O—C(=O)—NR$^{12}$R$^{13}$ or C$_0$-C$_6$-alkyl-NR$^{12}$—C(=O)—NR$^{13}$R$^{14}$ substituents;

q is an integer from 1 to 5;

R$^{12}$, R$^{13}$ and R$^{14}$ are each independently selected from the group consisting of hydrogen, an optionally substituted C$_1$-C$_6$-alkyl, C$_1$-C$_6$-alkylhalo, C$_2$-C$_6$-alkynyl, C$_2$-C$_6$-alkenyl, C$_3$-C$_7$-cycloalkyl, C$_3$-C$_7$-cycloalkyl-C$_1$-C$_6$-alkyl, heteroaryl, C$_1$-C$_6$-alkyl-heteroaryl, aryl;

Any N may be an N-oxide;

The present invention includes both possible stereoisomers and includes not only racemic compounds but the individual enantiomers as well.

In a second aspect, the compounds of the present invention are represented by Formula II-A wherein the heterocyclic ring system is specified as in the formula II-A2 depicted below

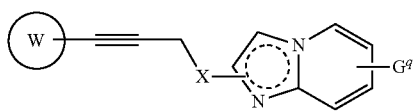

II-A2

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

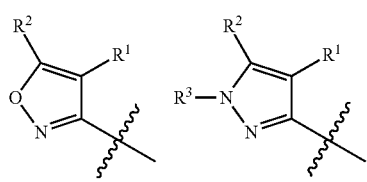

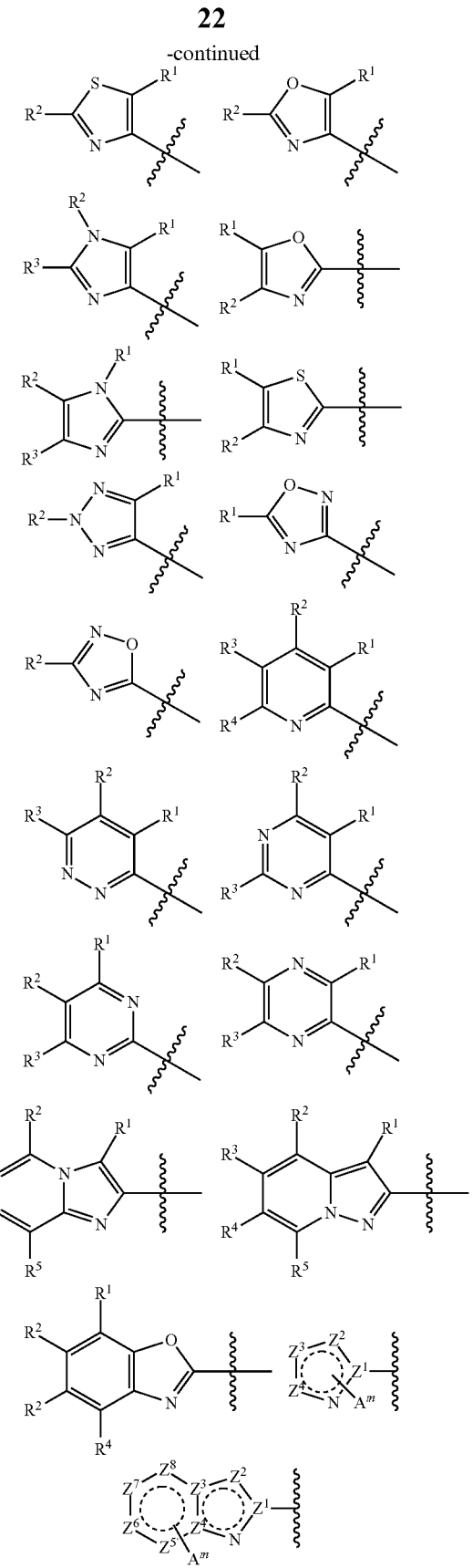

R$^1$, R$^2$, R$^3$, R$^4$, R$^5$ and A$^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^6$, $C_3$-$C_6$-alkynyl-OR$^6$, $C_3$-$C_6$-alkenyl-OR$^6$, $C_0$-$C_6$-alkyl-S—R$^6$, O—$C_2$-$C_6$-alkyl-S—R$^6$, $C_0$-$C_6$-alkyl-S(=O)—R$^6$, O—$C_2$-$C_6$-alkyl-S(=O)—R$^6$, $C_0$-$C_6$-alkyl-S(=O)$_2$—R$^6$, O—$C_1$-$C_6$-alkyl-S(=O)$_2$—R$^6$, $C_0$-$C_6$-alkyl-NR$^6$R$^7$, O—$C_2$-$C_6$-alkyl-NR$^6$R$^7$, $C_0$-$C_6$-alkyl-S(=O)$_2$NR$^6$R$^7$, $C_0$-$C_6$-alkyl-NR$^6$—S(=O)$_2$R$^7$, O—$C_1$-$C_6$-alkyl-S(=O)$_2$NR$^6$R$^7$, O—$C_1$-$C_6$-alkyl-NR$^6$—S(=O)$_2$R$^7$, $C_0$-$C_6$-alkyl-C(=O)—NR$^6$R$^7$, $C_0$-$C_6$-alkyl-NR$^6$C(=O)—R$^7$, O—$C_1$-$C_6$-alkyl-C(=O)—NR$^6$R$^7$, O—$C_2$-$C_6$-alkyl-NR$^6$C(=O)—R$^7$, $C_0$-$C_6$-alkyl-OC(=O)—R$^6$, $C_0$-$C_6$-alkyl-C(=O)—OR$^6$, O—$C_2$-$C_6$-alkyl-OC(=O)—R$^6$, O—$C_1$-$C_6$-alkyl-C(=O)—OR$^6$, $C_0$-$C_6$-alkyl-C(=O)—R$^6$, O—$C_1$-$C_6$-alkyl-C(=O)—R$^6$, $C_0$-$C_6$-alkyl-NR$^6$—C(=O)—OR$^7$, $C_0$-$C_6$-alkyl-O—C(=O)—NR$^6$R$^7$ or $C_0$-$C_6$-alkyl-NR$^6$—C(=O)—NR$^7$R$^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

R$^6$, R$^7$ and R$^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 A$^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^9$, $C_0$-$C_6$—NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR$^9$—C(=O)—O, $C_0$-$C_6$-alkyl-O—C(=O)—NR$^9$, $C_0$-$C_6$-alkyl-NR$^9$—C(=O)—NR$^{10}$, $C_0$-$C_6$-alkyl-NR$^9$—C(=NR$^{10}$)NR$^{11}$, $C_0$-$C_6$-alkyl-(C=NR$^9$)NR$^{10}$, $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-C(=NOR$^9$) or $C_0$-$C_6$-alkyl-O—N=CR$^9$ substituents;

R$^9$, R$^{10}$ and R$^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

G$^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{12}$, $C_3$-$C_6$-alkynyl-OR$^{12}$, $C_3$-$C_6$-alkenyl-OR$^{12}$, $C_0$-$C_6$-alkyl-S—R$^{12}$, O—$C_2$-$C_6$-alkyl-S—R$^{12}$, $C_0$-$C_6$-alkyl-S(=O)—R$^{12}$, O—$C_2$-$C_6$-alkyl-S(=O)—R$^{12}$, $C_0$-$C_6$-alkyl-S(=O)$_2$—R$^{12}$, O—$C_1$-$C_6$-alkyl-S(=O)$_2$—R$^{12}$, $C_0$-$C_6$-alkyl-NR$^{12}$R$^{13}$, O—$C_2$-$C_6$-alkyl-NR$^{12}$R$^{13}$, $C_0$-$C_6$-alkyl-S(=O)$_2$NR$^{12}$R$^{13}$, $C_0$-$C_6$-alkyl-NR$^{12}$—S(=O)$_2$R$^{13}$, O—$C_1$-$C_6$-alkyl-S(=O)$_2$NR$^{12}$R$^{13}$, O—$C_2$-$C_6$-alkyl-NR$^{12}$—S(=O)$_2$R$^{13}$, $C_0$-$C_6$-alkyl-C(=O)—NR$^{12}$R$^{13}$, $C_0$-$C_6$-alkyl-NR$^{12}$C(=O)—R$^{13}$, O—$C_1$-$C_6$-alkyl-C(=O)—NR$^{12}$R$^{13}$, O—$C_2$-$C_6$-alkyl-NR$^{12}$C(=O)—R$^{13}$, $C_0$-$C_6$-alkyl-OC(=O)—R$^{12}$, $C_0$-$C_6$-alkyl-C(=O)—OR$^{12}$, O—$C_2$-$C_6$-alkyl-OC(=O)—R$^{12}$, O—$C_1$-$C_6$-alkyl-C(=O)—OR$^{12}$, $C_0$-$C_6$-alkyl-C(=O)—R$^{12}$, O—$C_1$-$C_6$-alkyl-C(=O)—R$^{12}$, $C_0$-$C_6$-alkyl-NR$^{12}$—C(=O)—OR$^{13}$, $C_0$-$C_6$-alkyl-O—C(=O)—NR$^{12}$R$^{13}$ or $C_0$-$C_6$-alkyl-NR$^{12}$—C(=O)—NR$^{13}$R$^{14}$ substituents;

q is an integer from 1 to 5;

R$^{12}$, R$^{13}$ and R$^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a more preferred aspect of Formula II-A2, the compounds of the invention are represented by Formula II-A2-a

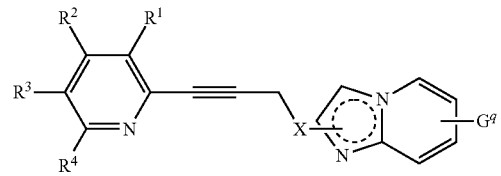

II-A2-a

Or a pharmaceutically acceptable salt, hydrate or solvate of such compound

Wherein

R$^1$, R$^2$, R$^3$ and R$^4$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^5$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^5$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^5$, $C_3$-$C_6$-alkynyl-$OR^5$, $C_3$-$C_6$-alkenyl-$OR^5$, $C_0$-$C_6$-alkyl-S—$R^5$, O—$C_2$-$C_6$-alkyl-S—$R^5$, $C_0$-$C_6$-alkyl-S(=O)—$R^5$, O—$C_2$-$C_6$-alkyl-S(=O)—$R^5$, $C_0$-$C_6$-alkyl-S(=O)$_2$—$R^5$, O—$C_1$-$C_6$-alkyl-S(=O)$_2$—$R^5$, $C_0$-$C_6$-alkyl-$NR^5R^6$, O—$C_2$-$C_6$-alkyl-$NR^5R^6$, $C_0$-$C_6$-alkyl-S(=O)$NR^5R^6$, $C_0$-$C_6$-alkyl-$NR^5$—S(=O)$_2R^6$, O—$C_1$-$C_6$-alkyl-S(=O)$_2NR^5R^6$, O—$C_2$-$C_6$-alkyl-$NR^5$—S(=O)$_2R^6$, $C_0$-$C_6$-alkyl-C(=O)—$NR^5R^6$, $C_0$-$C_6$-alkyl-$NR^5$C(=O)—$R^6$, O—$C_1$-$C_6$-alkyl-C(=O)—$NR^5R^6$, O—$C_2$-$C_6$-alkyl-$NR^5$C(=O)—$R^6$, $C_0$-$C_6$-alkyl-OC(=O)—$R^5$, $C_0$-$C_6$-alkyl-C(=O)—$OR^5$, O—$C_2$-$C_6$-alkyl-OC(=O)—$R^5$, O—$C_1$-$C_6$-alkyl-C(=O)—$OR^5$, $C_0$-$C_6$-alkyl-C(=O)—$R^5$, O—$C_1$-$C_6$-alkyl-C(=O)—$R^5$, $C_0$-$C_6$-alkyl-$NR^5$—C(=O)—$OR^6$, $C_0$-$C_6$-alkyl-O—C(=O)—$NR^5R^6$ or $C_0$-$C_6$-alkyl-$NR^5$—C(=O)—$NR^6R^7$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^5$, $R^6$ and $R^7$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_1$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^8$, $C_0$-$C_6$—$NR^8$S(=O)$_2$, $C_0$-$C_6$-alkyl-S(=O)$_2NR^8$, $C_0$-$C_6$-alkyl-C(=O)—$NR^8$, $C_0$-$C_6$-alkyl-$NR^8$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^8$—C(=O)—O, $C_0$-$C_6$-alkyl-O—C(=O)—$NR^8$, $C_0$-$C_6$-alkyl-$NR^8$—C(=O)—$NR^9$, $C_0$-$C_6$-alkyl-$NR^8$—C(=$NR^9$)$NR^{10}$, $C_0$-$C_6$-alkyl-(C=$NR^8$)$NR^9$, $C_0$-$C_6$-alkyl-C(=O)—O—$C_0$-$C_6$-alkyl, $C_0$-$C_6$-alkyl-C(=O)—$NR^8$—$C_0$-$C_6$-alkyl, $C_0$-$C_6$-alkyl-C(=$NOR^8$) or $C_0$-$C_6$-alkyl-O—N=$CR^8$ substituents;

$R^8$, $R^9$ and $R^{10}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{11}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{11}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{11}$, $C_3$-$C_6$-alkynyl-$OR^{11}$, $C_3$-$C_6$-alkenyl-$OR^{11}$, $C_0$-$C_6$-alkyl-S—$R^{11}$, O—$C_2$-$C_6$-alkyl-S—$R^{11}$, $C_0$-$C_6$-alkyl-S(=O)—$R^{11}$, O—$C_2$-$C_6$-alkyl-S(=O)—$R^{11}$, $C_0$-$C_6$-alkyl-S(=O)$_2$—$R^{11}$, O—$C_1$-$C_6$-alkyl-S(=O)$_2$—$R^{11}$, $C_0$-$C_6$-alkyl-$NR^{11}R^{12}$, O—$C_2$-$C_6$-alkyl-$NR^{11}R^{12}$, $C_0$-$C_6$-alkyl-S(=O)$_2NR^{11}R^{12}$, $C_0$-$C_6$-alkyl-$NR^{11}$—S(=O)$_2R^{12}$, O—$C_1$-$C_6$-alkyl-S(=O)$_2NR^{11}R^{12}$, O—$C_2$-$C_6$-alkyl-$NR^{11}$—S(=O)$_2R^{12}$, $C_0$-$C_6$-alkyl-C(=O)—$NR^{11}R^{12}$, $C_0$-$C_6$-alkyl-$NR^{11}$C(=O)—$R^{12}$, O—$C_1$-$C_6$-alkyl-C(=O)—$NR^{11}R^{12}$, O—$C_2$-$C_6$-alkyl-$NR^{11}$C(=O)—$R^{12}$, $C_0$-$C_6$-alkyl-OC(=O)—$R^{11}$, $C_0$-$C_6$-alkyl-C(=O)—$OR^{11}$, O—$C_2$-$C_6$-alkyl-OC(=O)—$R^{11}$, O—$C_1$-$C_6$-alkyl-C(=O)—$OR^{11}$, $C_0$-$C_6$-alkyl-C(=O)—$R^{11}$, O—$C_1$-$C_6$-alkyl-C(=O)—$R^{11}$, $C_0$-$C_6$-alkyl-$NR^{11}$—C(=O)—$OR^{12}$, $C_0$-$C_6$-alkyl-O—C(=O)—$NR^{11}R^{12}$ or $C_0$-$C_6$-alkyl-$NR^{11}$—C(=O)—$NR^{12}R^{13}$ substituents;

q is an integer from 1 to 5;

$R^{11}$, $R^{12}$ and $R^{13}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a more preferred aspect of Formula II-A2-a, the compounds of the invention are represented by Formula II-A2-a1

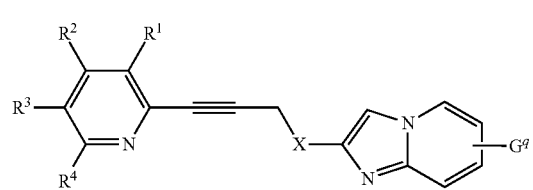

II-A2-a1

Or a pharmaceutically acceptable salt, hydrate or solvate of such compound

Wherein $R^1$, $R^2$, $R^3$ and $R^4$ are each independently selected from the group consisting of hydrogen, halogen, CN, OH, an optionally substituted $C_1$-$C_6$-alkyl, $C_1$-$C_6$-alkylhalo, $C_0$-$C_6$-alkyl-$NR^5R^6$, $C_0$-$C_6$-alkyl-S(=O)$_2NR^5R^6$, $C_0$-$C_6$-alkyl-$NR^5$—S(=O)$_2R^6$, $C_0$-$C_6$-alkyl-C(=O)—$NR^5R^6$, $C_0$-$C_6$-alkyl-$NR^5$C(=O)—$R^6$, $C_0$-$C_6$-alkyl-OC(=O)—$R^5$, $C_0$-$C_6$-alkyl-C(=O)—$OR^5$, $C_0$-$C_6$-alkyl-C(=O)—$R^5$ or $C_0$-$C_6$-alkyl-$NR^5$—C(=O)—$NR^6R^7$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^5$, $R^6$ and $R^7$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-hetero aryl, aryl;

X is selected from an optionally substituted $C_1$-$C_6$-alkyl, $C_1$-$C_6$-alkylhalo, O—$C_0$-$C_6$-alkyl, $C_0$-$C_6$-alkyl-O, S—$C_0$-$C_6$-alkyl, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^8$, $C_0$-$C_6$—NR$^8$S(=O)$_2$, $C_0$-$C_6$-alkyl-S(=O)$_2$NR$^8$, $C_0$-$C_6$-alkyl-C(=O)—NR$^8$, $C_0$-$C_6$-alkyl-NR$^8$C(=O), $C_0$-$C_6$-alkyl-C(=O)—O—$C_0$-$C_6$-alkyl, $C_0$-$C_6$-alkyl-C(=O)—NR$^8$—$C_0$-$C_6$-alkyl, $C_0$-$C_6$-alkyl-C(=O) or $C_0$-$C_6$-alkyl-NR$^8$—C(=O)—NR$^9$ substituents;

R$^8$ and R$^9$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

G$^q$ groups are each independently selected from the group consisting of hydrogen, halogen, CN, OH, nitro, an optionally substituted $C_1$-$C_6$-alkyl, $C_1$-$C_6$-alkylhalo, O—$C_1$-$C_6$-alkyl, O—$C_1$-$C_6$-alkylhalo, O—$C_2$-$C_6$-alkyl-OR$^{10}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{10}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{10}$, $C_0$-$C_6$-alkyl-S(=O)—R$^{10}$, O—$C_2$-$C_6$-alkyl-S(=O)—R$^{10}$, $C_0$-$C_6$-alkyl-S(=O)$_2$—R$^{10}$, O—$C_1$-$C_6$-alkyl-S(=O)$_2$—R$^{10}$, $C_0$-$C_6$-alkyl-NR$^{10}$R$^{11}$, O—$C_2$-$C_6$-alkyl-NR$^{10}$R$^{11}$, $C_0$-$C_6$-alkyl-S(=O)$_2$NR$^{10}$R$^{11}$, $C_0$-$C_6$-alkyl-NR$^{10}$—S(=O)$_2$R$^{11}$, O—$C_1$-$C_6$-alkyl-S(=O)$_2$NR$^{10}$R$^{11}$, O—$C_2$-$C_6$-alkyl-NR$^{10}$—S(=O)$_2$R$^{11}$, $C_0$-$C_6$-alkyl-C(=O)—NR$^{10}$R$^{11}$, $C_0$-$C_6$-alkyl-NR$^{10}$C(=O)—R$^{11}$, O—$C_1$-$C_6$-alkyl-C(=O)—NR$^{10}$R$^{11}$, O—$C_2$-$C_6$-alkyl-NR$^{10}$C(=O)—R$^{11}$, $C_0$-$C_6$-alkyl-C(=O)—R$^{10}$, O—$C_1$-$C_6$-alkyl-C(=O)—R$^{10}$ or $C_0$-$C_6$-alkyl-NR$^{10}$—C(=O)—NR$^{11}$R$^{12}$ substituents;

q is an integer from 1 to 5;

R$^{10}$, R$^{11}$ and R$^{12}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a more preferred aspect, the compounds of the present invention are represented by Formula II-A2-a1 wherein the linker is specified as in the formula II-A2-a2 depicted below II-A2-a2

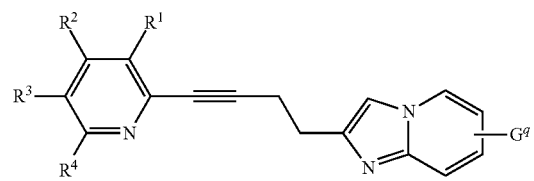

Or a pharmaceutically acceptable salt, hydrate or solvate of such compound

Wherein

R$^1$, R$^2$, R$^3$ and R$^4$ are each independently selected from the group consisting of hydrogen, halogen, an optionally substituted $C_1$-$C_6$-alkyl, $C_1$-$C_6$-alkylhalo or $C_0$-$C_6$-alkyl-NR$^5$R$^6$ substituents;

R$^5$ and R$^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

G$^q$ groups are each independently selected from the group consisting of hydrogen, halogen, CN, an optionally substituted $C_1$-$C_6$-alkyl, $C_1$-$C_6$-alkylhalo, O—$C_0$-$C_6$-alkyl, O—$C_0$-$C_6$-alkylaryl, heteroaryl or aryl;

q is an integer from 1 to 5;

Any N may be an N-oxide;

The present invention includes both possible stereoisomers and includes not only racemic compounds but the individual enantiomers as well.

In a third aspect, the compounds of the present invention are represented by Formula II-A wherein the heterocyclic ring system is specified as in the formula II-A3 depicted below

II-A3

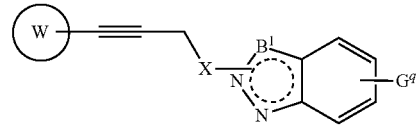

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

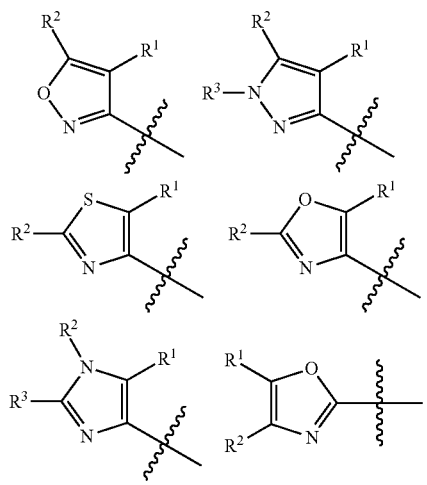

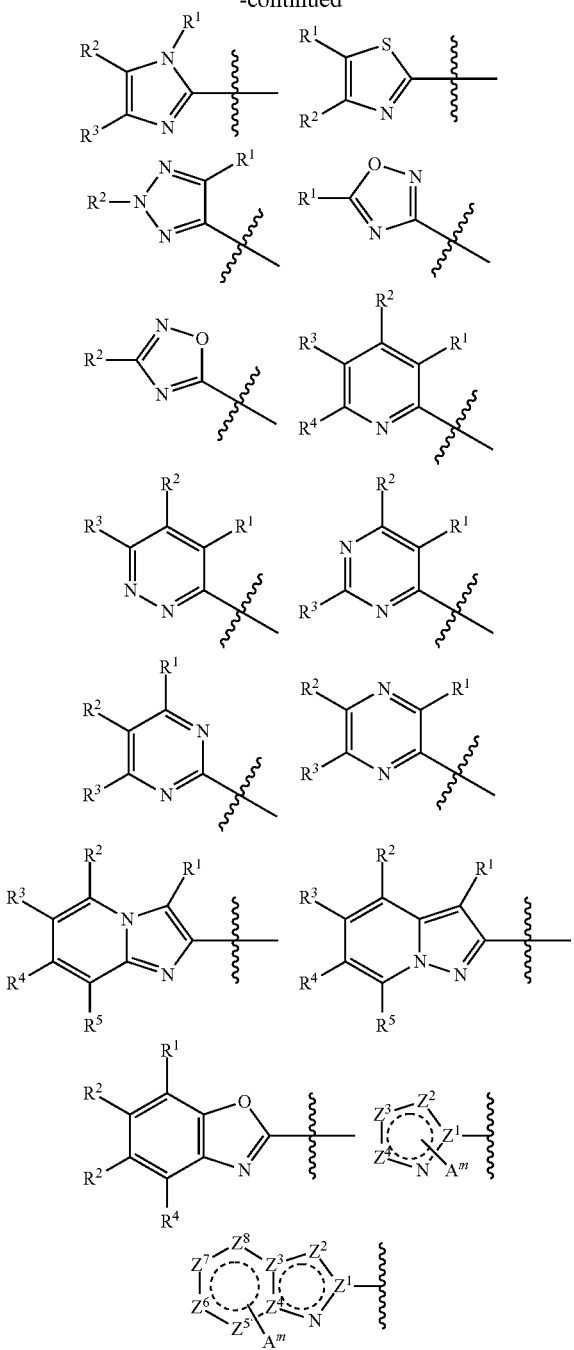

$R^1$, $R^2$, $R^3$, $R^4$, $R^5$ and $A^m$ are each independently selected the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^6$, $C_3$-$C_6$-alkynyl-OR$^6$, $C_3$-$C_6$-alkenyl-OR$^6$, $C_0$-$C_6$-alkyl-S—R$^6$, O—$C_2$-$C_6$-alkyl-S—R$^6$, $C_0$-$C_6$-alkyl-S(=O)—R$^6$, O—$C_2$-$C_6$-alkyl-S(=O)—R$^6$, $C_0$-$C_6$-alkyl-S(=O)$_2$—R$^6$, O—$C_1$-$C_6$-alkyl-S(=O)$_2$—R$^6$, $C_0$-$C_6$-alkyl-NR$^6$R$^7$, O—$C_2$-$C_6$-alkyl-NR$^6$R$^7$, $C_0$-$C_6$-alkyl-S(=O)$_2$NR$^6$R$^7$, $C_0$-$C_6$-alkyl-NR$^6$—S(=O)$_2$R$^7$, O—$C_1$-$C_6$-alkyl-S(=O)$_2$NR$^6$R$^7$, O—$C_1$-$C_6$-alkyl-NR$^6$—S(=O)$_2$R$^7$, $C_0$-$C_6$-alkyl-C(=O)—NR$^6$R$^7$, $C_0$-$C_6$-alkyl-NR$^6$C(=O)—R$^7$, O—$C_1$-$C_6$-alkyl-C(=O)—NR$^6$R$^7$, O—$C_2$-$C_6$-alkyl-NR$^6$C(=O)—R$^7$, $C_0$-$C_6$-alkyl-OC(=O)—R$^6$, $C_0$-$C_6$-alkyl-C(=O)—OR$^6$, O—$C_2$-$C_6$-alkyl-OC(=O)—R$^6$, O—$C_1$-$C_6$-alkyl-C(=O)—OR$^6$, $C_0$-$C_6$-alkyl-C(=O)—R$^6$, O—$C_1$-$C_6$-alkyl-C(=O)—R$^6$, $C_0$-$C_6$-alkyl-NR$^6$—C(=O)—OR$^7$, $C_0$-$C_6$-alkyl-O—C(=O)—NR$^6$R$^7$ or $C_0$-$C_6$-alkyl-NR$^6$—C(=O)—NR$^7$R$^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^9$, $C_0$-$C_6$—NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR$^9$—C(=O)—O, $C_0$-$C_6$-alkyl-O—C(=O)—NR$^9$, $C_0$-$C_6$-alkyl-NR$^9$—C(=O)—NR$^{10}$, $C_0$-$C_6$-alkyl-NR$^9$—C(=NR$^{10}$)NR$^{11}$, $C_0$-$C_6$-alkyl-(C=NR$^9$)NR$^{10}$, $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-C(=NOR$^9$) or $C_0$-$C_6$-alkyl-O—N=CR$^9$ substituents;

$R^9$, $R^{10}$ and $R^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$B^1$ represents independently C or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{12}$, O—$C_3$-$C_7$-cycloalkyl, O—$C_1$-$C_6$-alkylheteroaryl, O—$C_1$-$C_6$-alkylaryl, $C_0$-$C_6$-alkyl-$OR^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{12}$, $C_3$-$C_6$-alkynyl-$OR^{12}$, $C_3$-$C_6$-alkenyl-$OR^{12}$, $C_0$-$C_6$-alkyl-S—$R^{12}$, O—$C_2$-$C_6$-alkyl-S—$R^{12}$, $C_0$-$C_6$-alkyl-S(=O)—$R^{12}$, O—$C_2$-$C_6$-alkyl-S(=O)—$R^{12}$, $C_0$-$C_6$-alkyl-S(=O)$_2$—$R^{12}$, O—$C_1$-$C_6$-alkyl-S(=O)$_2$—$R^{12}$, $C_0$-$C_6$-alkyl-$NR^{12}R^{13}$, O—$C_2$-$C_6$-alkyl-$NR^{12}R^{13}$, $C_0$-$C_6$-alkyl-S(=O)$_2NR^{12}R^{13}$, $C_0$-$C_6$-alkyl-$NR^{12}$—S(=O)$_2R^{13}$, O—$C_1$-$C_6$-alkyl-S(=O)$_2NR^{12}R^{13}$, O—$C_2$-$C_6$-alkyl-$NR^{12}$—S(=O)$_2R^{13}$, $C_0$-$C_6$-alkyl-C(=O)—$NR^{12}R^{13}$, $C_0$-$C_6$-alkyl-$NR^{12}$C(=O)—$R^{13}$, O—$C_1$-$C_6$-alkyl-C(=O)—$NR^{12}R^{13}$, O—$C_2$-$C_6$-alkyl-$NR^{12}$C(=O)—$R^{13}$, $C_0$-$C_6$-alkyl-OC(=O)—$R^{12}$, $C_0$-$C_6$-alkyl-C(=O)—$OR^{12}$, O—$C_2$-$C_6$-alkyl-OC(=O)—$R^{12}$, O—$C_1$-$C_6$-alkyl-C(=O)—$OR^{12}$, $C_0$-$C_6$-alkyl-C(=O)—$R^{12}$, O—$C_1$-$C_6$-alkyl-C(=O)—$R^{12}$, $C_0$-$C_6$-alkyl-$NR^{12}$—C(=O)—$OR^{13}$, $C_0$-$C_6$-alkyl-O—C(=O)—$NR^{12}R^{13}$ or $C_0$-$C_6$-alkyl-$NR^{12}$—C(=O)—$NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a more preferred aspect of Formula II-A3, the compounds of the present invention are represented by Formula II-A3-a II-A3-a

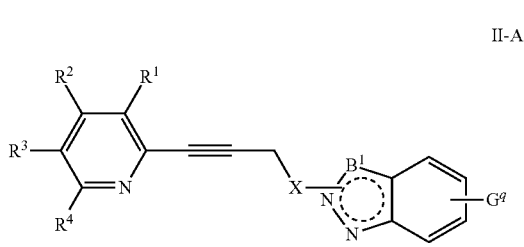

Or a pharmaceutically acceptable salt, hydrate or solvate of such compound

Wherein $R^1$, $R^2$, $R^3$ and $R^4$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^5$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^5$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^5$, $C_3$-$C_6$-alkynyl-$OR^5$, $C_3$-$C_6$-alkenyl-$OR^5$, $C_0$-$C_6$-alkyl-S—$R^5$, O—$C_2$-$C_6$-alkyl-S—$R^5$, $C_0$-$C_6$-alkyl-S(=O)—$R^5$, O—$C_2$-$C_6$-alkyl-S(=O)—$R^5$, $C_0$-$C_6$-alkyl-S(=O)$_2$—$R^5$, O—$C_1$-$C_6$-alkyl-S(=O)$_2$—$R^5$, $C_0$-$C_6$-alkyl-$NR^5R^6$, O—$C_2$-$C_6$-alkyl-$NR^5R^6$, $C_0$-$C_6$-alkyl-S(=O)$_2NR^5R^6$, $C_0$-$C_6$-alkyl-$NR^5$—S(=O)$_2R^6$, O—$C_1$-$C_6$-alkyl-S(=O)$_2NR^5R^6$, O—$C_2$-$C_6$-alkyl-$NR^5$—S(=O)$_2R^6$, $C_0$-$C_6$-alkyl-C(=O)—$NR^5R^6$, $C_0$-$C_6$-alkyl-$NR^5$C(=O)—$R^6$, O—$C_1$-$C_6$-alkyl-C(=O)—$NR^5R^6$, O—$C_2$-$C_6$-alkyl-$NR^5$C(=O)—$R^6$, $C_0$-$C_6$-alkyl-OC(=O)—$R^5$, $C_0$-$C_6$-alkyl-C(=O)—$OR^5$, O—$C_2$-$C_6$-alkyl-OC(=O)—$R^5$, O—$C_1$-$C_6$-alkyl-C(=O)—$OR^5$, $C_0$-$C_6$-alkyl-C(=O)—$R^5$, O—$C_1$-$C_6$-alkyl-C(=O)—$R^5$, $C_0$-$C_6$-alkyl-$NR^5$—C(=O)—$OR^6$, $C_0$-$C_6$-alkyl-O—C(=O)—$NR^5R^6$ or $C_0$-$C_6$-alkyl-$NR^5$—C(=O)—$NR^6R^7$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^5$, $R^6$ and $R^7$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^8$, $C_0$-$C_6$—$NR^8$S(=O)$_2$, $C_0$-$C_6$-alkyl-S(=O)$_2NR^8$, $C_0$-$C_6$-alkyl-C(=O)—$NR^8$, $C_0$-$C_6$-alkyl-$NR^8$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^8$—C(=O)—O, $C_0$-$C_6$-alkyl-O—C(=O)—$NR^8$, $C_0$-$C_6$-alkyl-$NR^8$—C(=O)—$NR^9$, $C_0$-$C_6$-alkyl-$NR^8$—C(=$NR^9$)$NR^{10}$, $C_0$-$C_6$-alkyl-(C=$NR^8$)$NR^9$, $C_0$-$C_6$-alkyl-C(=O)—O—$C_0$-$C_6$-alkyl, $C_0$-$C_6$-alkyl-C(=O)—$NR^8$—$C_0$-$C_6$-alkyl, $C_0$-$C_6$-alkyl-C(=$NOR^8$) or $C_0$-$C_6$-alkyl-O—N=$CR^8$ substituents;

$R^8$, $R^9$ and $R^{10}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$B^1$ represent independently C or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$- alkyl-OR$^{11}$, O—C$_3$-C$_7$-cycloalkyl, O—C$_1$-C$_6$-alkyl-heteroaryl, O—C$_1$-C$_6$-alkylaryl, C$_0$-C$_6$-alkyl-OR$^{11}$, C$_3$-C$_7$-cycloalkyl, C$_3$-C$_7$-cycloalkyl-C$_1$-C$_6$-alkyl, O—C$_3$-C$_7$-cycloalkyl-C$_1$-C$_6$-alkyl, O-heteroaryl, heteroaryl, C$_1$-C$_6$-alkyl-heteroaryl, aryl, O-aryl, C$_1$-C$_6$-alkylaryl, C$_1$-C$_6$-alkylhalo-OR$^{11}$, C$_3$-C$_6$-alkynyl-OR$^{11}$, C$_3$-C$_6$-alkenyl-OR$^{11}$, C$_0$-C$_6$-alkyl-S—R$^{11}$, O—C$_2$-C$_6$-alkyl-S—R$^{11}$, C$_0$-C$_6$-alkyl-S(=O)—R$^{11}$, O—C$_2$-C$_6$-alkyl-S(=O)—R$^{11}$, C$_0$-C$_6$-alkyl-S(=O)$_2$—R$^{11}$, O—C$_1$-C$_6$-alkyl-S(=O)$_2$—R$^{11}$, C$_0$-C$_6$-alkyl-NR$^{11}$R$^{12}$, O—C$_2$-C$_6$-alkyl-NR$^{11}$R$^{12}$, C$_0$-C$_6$-alkyl-S(=O)$_2$NR$^{11}$R$^{12}$, C$_0$-C$_6$-alkyl-NR$^{11}$—S(=O)$_2$R$^{12}$, O—C$_1$-C$_6$-alkyl-S(=O)$_2$NR$^{11}$R$^{12}$, O—C$_2$-C$_6$-alkyl-NR$^{11}$—S(=O)$_2$R$^{12}$, C$_0$-C$_6$-alkyl-C(=O)—NR$^{11}$R$^{12}$, C$_0$-C$_6$-alkyl-NR$^{11}$C(=O)—R$^{12}$, O—C$_1$-C$_6$-alkyl-C(=O)—NR$^{11}$R$^{12}$, O—C$_2$-C$_6$-alkyl-NR$^{11}$C(=O)—R$^{12}$, C$_0$-C$_6$-alkyl-OC(=O)—R$^{11}$, C$_0$-C$_6$-alkyl-C(=O)—OR$^{11}$, O—C$_2$-C$_6$-alkyl-OC(=O)—R$^{11}$, O—C$_1$-C$_6$-alkyl-C(=O)—OR$^{11}$, C$_0$-C$_6$-alkyl-C(=O)—R$^{11}$, O—C$_1$-C$_6$-alkyl-C(=O)—R$^{11}$, C$_0$-C$_6$-alkyl-NR$^{11}$—C(=O)—OR$^{12}$, C$_0$-C$_6$-alkyl-O—C(=O)—NR$^{11}$R$^{12}$ or C$_0$-C$_6$-alkyl-NR$^{11}$—C(=O)—NR$^{12}$R$^{13}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent halogen, CN, OH, nitro, an optionally substituted C$_1$-C$_6$-alkyl, C$_1$-C$_6$-alkylhalo, C$_2$-C$_6$-alkynyl, C$_2$-C$_6$-alkenyl, O—C$_1$-C$_6$-alkyl, O—C$_1$-C$_6$-alkylhalo, O—C$_3$-C$_6$-alkynyl, O—C$_3$-C$_6$-alkenyl, O—C$_3$-C$_7$-cycloalkyl, O—C$_1$-C$_6$-alkyl-hetero aryl, O—C$_1$-C$_6$-alkylaryl, C$_3$-C$_7$-cycloalkyl, C$_3$-C$_7$-cycloalkyl-C$_1$-C$_6$-alkyl, O—C$_3$-C$_7$-cycloalkyl-C$_1$-C$_6$-alkyl, O-heteroaryl, heteroaryl, C$_1$-C$_6$-alkyl-heteroaryl, aryl, O-aryl;

q is an integer from 1 to 5;

R$^{11}$, R$^{12}$ and R$^{13}$ are each independently selected from the group consisting of hydrogen, an optionally substituted C$_1$-C$_6$-alkyl, C$_1$-C$_6$-alkylhalo, C$_2$-C$_6$-alkynyl, C$_2$-C$_6$-alkenyl, C$_3$-C$_7$-cycloalkyl, C$_3$-C$_7$-cycloalkyl-C$_1$-C$_6$-alkyl, heteroaryl, C$_1$-C$_6$-alkyl-heteroaryl, aryl;

Any N may be an N-oxide;

The present invention includes both possible stereoisomers and includes not only racemic compounds but the individual enantiomers as well.

In a more preferred aspect of Formula II-A3-a, the compounds of the present invention are represented by Formula II-A3-a1 below

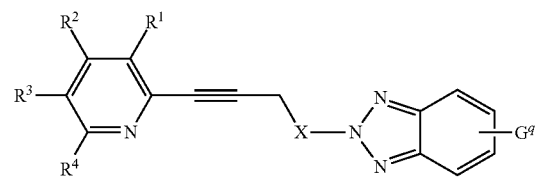

II-A3-a1

Or a pharmaceutically acceptable salt, hydrate or solvate of such compound

Wherein

R$^1$, R$^2$, R$^3$ and R$^4$ are each independently selected from the group consisting of hydrogen, halogen, an optionally substituted C$_1$-C$_6$-alkyl, C$_1$-C$_6$-alkylhalo, C$_0$-C$_6$-alkyl-OR$^5$, C$_0$-C$_6$-alkyl-NR$^5$R$^6$, C$_0$-C$_6$-alkyl-NR$^5$C(=O)—R$^6$ or C$_0$-C$_6$-alkyl-NR$^5$S(=O)$_2$—R$^6$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted C$_1$-C$_6$-alkyl, C$_1$-C$_6$-alkylhalo, C$_2$-C$_6$-alkynyl, C$_2$-C$_6$-alkenyl, O—C$_1$-C$_6$-alkyl, O—C$_1$-C$_6$-alkylhalo, O—C$_3$-C$_6$-alkynyl, O—C$_3$-C$_6$-alkenyl, O—C$_3$-C$_7$-cycloalkyl, O—C$_1$-C$_6$-alkyl-heteroaryl, O—C$_1$-C$_6$-alkylaryl, C$_1$-C$_6$-alkylaryl, C$_3$-C$_7$-cycloalkyl, C$_3$-C$_7$-cycloalkyl-C$_1$-C$_6$-alkyl, O—C$_3$-C$_7$-cycloalkyl-C$_1$-C$_6$-alkyl, O-heteroaryl, heteroaryl, C$_1$-C$_6$-alkyl-heteroaryl, aryl, O-aryl;

R$^5$ and R$^6$ are each independently selected from the group consisting of hydrogen, an optionally substituted C$_1$-C$_6$-alkyl, C$_1$-C$_6$-alkylhalo, C$_3$-C$_7$-cycloalkyl, C$_3$-C$_7$-cycloalkyl-C$_1$-C$_6$-alkyl, heteroaryl, C$_1$-C$_6$-alkyl-heteroaryl, aryl;

X is selected from an optionally substituted C$_1$-C$_6$-alkyl and C$_1$-C$_6$-alkylhalo;

G$^q$ groups are each independently selected from the group consisting of hydrogen, halogen, CN, OH, nitro, an optionally substituted C$_1$-C$_6$-alkyl, C$_1$-C$_6$-alkylhalo, O—C$_1$-C$_6$-alkyl, O—C$_1$-C$_6$-alkylhalo, O—C$_2$-C$_6$-alkyl-OR$^7$, O—C$_3$-C$_7$-cycloalkyl, O—C$_1$-C$_6$-alkyl-heteroaryl, O—C$_1$-C$_6$-alkylaryl, C$_0$-C$_6$-alkyl-OR$^7$, C$_3$-C$_7$-cycloalkyl, C$_3$-C$_7$-cycloalkyl-C$_1$-C$_6$-alkyl, O—C$_3$-C$_7$-cycloalkyl-C$_1$-C$_6$-alkyl, O-heteroaryl, heteroaryl, C$_1$-C$_6$-alkyl-heteroaryl, aryl, O-aryl, C$_1$-C$_6$-alkylaryl, C$_1$-C$_6$-alkylhalo-OR$^7$, C$_0$-C$_6$-alkyl-S(=O)—R$^7$, O—C$_2$-C$_6$-alkyl-S(=O)—R$^7$, C$_0$-C$_6$-alkyl-S(=O)$_2$—R$^7$, O—C$_1$-C$_6$-alkyl-S(=O)$_2$—R$^7$, C$_0$-C$_6$-alkyl-NR$^7$R$^8$, O—C$_2$-C$_6$-alkyl-NR$^7$R$^8$, C$_0$-C$_6$-alkyl-S(=O)$_2$NR$^7$R$^8$, C$_0$-C$_6$-alkyl-NR$^7$—S(=O)$_2$R$^8$, O—C$_1$-C$_6$-alkyl-S(=O)$_2$NR$^7$R$^8$, O—C$_2$-C$_6$-alkyl-NR$^7$—S(=O)$_2$R$^8$, C$_0$-C$_6$-alkyl-C(=O)—NR$^7$R$^8$, C$_0$-C$_6$-alkyl-NR$^7$C(=O)—R$^8$, O—C$_1$-C$_6$-alkyl-C(=O)—NR$^7$R$^8$, O—C$_2$-C$_6$-alkyl-NR$^7$C(=O)—R$^8$, C$_0$-C$_6$-alkyl-C(=O)—R$^7$, O—C$_1$-C$_6$-alkyl-C(=O)—R$^7$ or C$_0$-C$_6$-alkyl-NR$^7$—C(=O)—NR$^8$R$^9$ substituents;

q is an integer from 1 to 4;

R$^7$, R$^8$ and R$^9$ are each independently selected from the group consisting of hydrogen, an optionally substituted C$_1$-C$_6$-alkyl, C$_1$-C$_6$-alkylhalo, C$_2$-C$_6$-alkynyl, C$_2$-C$_6$-alkenyl, C$_3$-C$_7$-cycloalkyl, C$_3$-C$_7$-cycloalkyl-C$_1$-C$_6$-alkyl, heteroaryl, C$_1$-C$_6$-alkyl-heteroaryl, aryl;

Any N may be an N-oxide;

The present invention includes both possible stereoisomers and includes not only racemic compounds but the individual enantiomers as well.

In a second aspect, the compounds of the present invention are represented by Formula II-A3-a1 wherein the linker is specified as in the formula II-A3-a2 depicted below

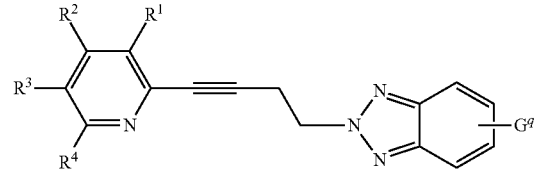

II-A3-a2

Or a pharmaceutically acceptable salt, hydrate or solvate of such compound

Wherein $R^1$, $R^2$, $R^3$ and $R^4$ are each independently selected from the group consisting of hydrogen, halogen, an optionally substituted $C_1$-$C_6$-alkyl, $C_1$-$C_6$-alkylhalo, $C_0$-$C_6$-alkyl-$OR^5$, $C_0$-$C_6$-alkyl-$NR^5R^6$, $C_0$-$C_6$-alkyl-$NR^5C(=O)$—$R^6$ or $C_0$-$C_6$-alkyl-$NR^5S(=O)_2$—$R^6$ substituents;

$R^5$ and $R^6$ are each independently selected from the group consisting of hydrogen, an optionally substituted $C_1$-$C_6$-alkyl, $C_1$-$C_6$-alkylhalo, $C_3$-$C_7$-cycloalkyl, heteroaryl, aryl;

$G^q$ groups are each independently selected from the group consisting of hydrogen, halogen, nitro, CN, an optionally substituted $C_1$-$C_6$-alkyl, $C_1$-$C_6$-alkylhalo, O—$C_0$-$C_6$-alkyl, O—$C_0$-$C_6$-alkylaryl, heteroaryl, aryl or $C_0$-$C_6$-alkyl-$NR^7R^8$ substituents;

q is an integer from 1 to 4;

$R^7$ and $R^8$ are each independently selected from the group consisting of hydrogen, an optionally substituted $C_1$-$C_6$-alkyl, $C_1$-$C_6$-alkylhalo, heteroaryl, aryl;

Any N may be an N-oxide;

The present invention includes both possible stereoisomers and includes not only racemic compounds but the individual enantiomers as well.

In a fourth aspect, the compounds of the present invention are represented by Formula II-A wherein the heterocyclic ring system is specified as in the formula II-A4 depicted below

II-A4

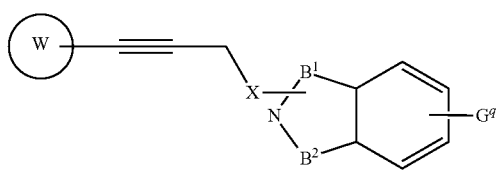

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

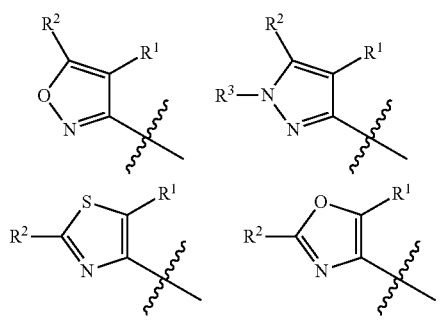

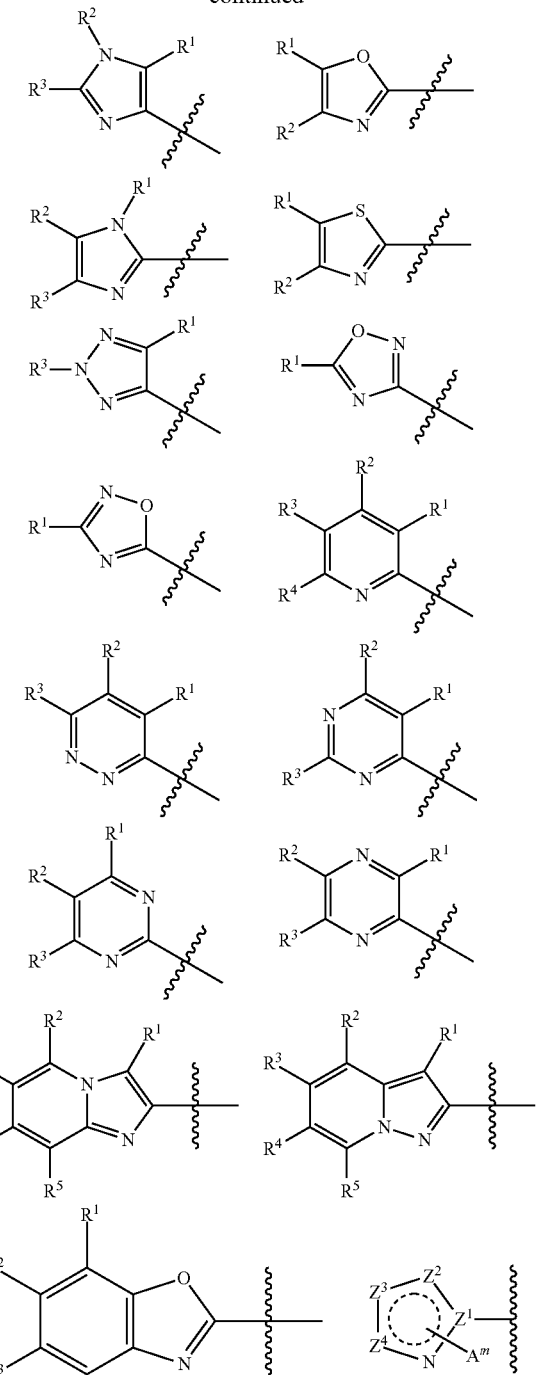

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-

$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6$C(=O)—$R^7$, O—$C_1$-$C_6$-alkyl-C(=O)—$NR^6R^7$, O—$C_2$-$C_6$-alkyl-$NR^6$C(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^9$, $C_0$-$C_6$—$NR^9S$(=O)$_2$, $C_0$-$C_6$-alkyl-S(=O)$_2NR^9$, $C_0$-$C_6$-alkyl-C(=O)—$NR^9$, $C_0$-$C_6$-alkyl-$NR^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^9$—C(=O)—O, $C_0$-$C_6$-alkyl-O—C(=O)—$NR^9$, $C_0$-$C_6$-alkyl-$NR^9$—C(=O)—$NR^{10}$, $C_0$-$C_6$-alkyl-$NR^9$—C(=$NR^{10}$)$NR^{11}$, $C_0$-$C_6$-alkyl-(C=$NR^9$)$NR^{10}$, $C_0$-$C_6$-alkyl-C(=O)—O—$C_0$-$C_6$-alkyl, $C_0$-$C_6$-alkyl-C(=O)—$NR^9$—$C_0$-$C_6$-alkyl, $C_0$-$C_6$-alkyl-C(=$NOR^9$) or $C_0$-$C_6$-alkyl-O—N=$CR^9$ substituents;

$R^9$, $R^{10}$ and $R^{11}$ are each independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$B^1$ and $B^2$ are each independently selected from —C=C—, —C(=O)—, —S(=O)$_2$—, —C=N— or —C-which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{12}$, $C_3$-$C_6$-alkynyl-$OR^{12}$, $C_3$-$C_6$-alkenyl-$OR^{12}$, $C_0$-$C_6$-alkyl-S—$R^{12}$, O—$C_2$-$C_6$-alkyl-S—$R^{12}$, $C_0$-$C_6$-alkyl-S(=O)—$R^{12}$, O—$C_2$-$C_6$-alkyl-S(=O)—$R^{12}$, $C_0$-$C_6$-alkyl-S(=O)$_2$—$R^{12}$, O—$C_1$-$C_6$-alkyl-S(=O)$_2$—$R^{12}$, $C_0$-$C_6$-alkyl-$NR^{12}R^{13}$, O—$C_2$-$C_6$-alkyl-$NR^{12}R^{13}$, $C_0$-$C_6$-alkyl-S(=O)$_2NR^{12}R^{13}$, $C_0$-$C_6$-alkyl-$NR^{12}$—S(=O)$_2R^{13}$, O—$C_1$-$C_6$-alkyl-S(=O)$_2NR^{12}R^{13}$, O—$C_2$-$C_6$-alkyl-$NR^{12}$—S(=O)$_2R^{13}$, $C_0$-$C_6$-alkyl-C(=O)—$NR^{12}R^{13}$, $C_0$-$C_6$-alkyl-$NR^{12}$C(=O)—$R^{13}$, O—$C_1$-$C_6$-alkyl-C(=O)—$NR^{12}R^{13}$, O—$C_2$-$C_6$-alkyl-$NR^{12}$C(=O)—$R^{13}$, $C_0$-$C_6$-alkyl-OC(=O)—$R^{12}$, $C_0$-$C_6$-alkyl-C(=O)—$OR^{12}$, O—$C_2$-$C_6$-alkyl-OC(=O)—$R^{12}$, O—$C_1$-$C_6$-alkyl-C(=O)—$OR^{12}$, $C_0$-$C_6$-alkyl-C(=O)—$R^{12}$, O—$C_1$-$C_6$-alkyl-C(=O)—$R^{12}$, $C_0$-$C_6$-alkyl-$NR^{12}$—C(=O)—$OR^{13}$, $C_0$-$C_6$-alkyl-O—C(=O)—$NR^{12}R^{13}$ or $C_0$-$C_6$-alkyl-$NR^{12}$—C(=O)—$NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

Particularly preferred compounds of the present invention are compounds of Formula II-B

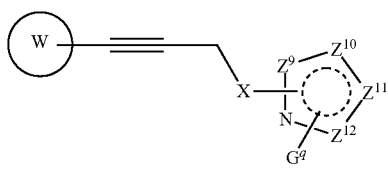

II-B

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

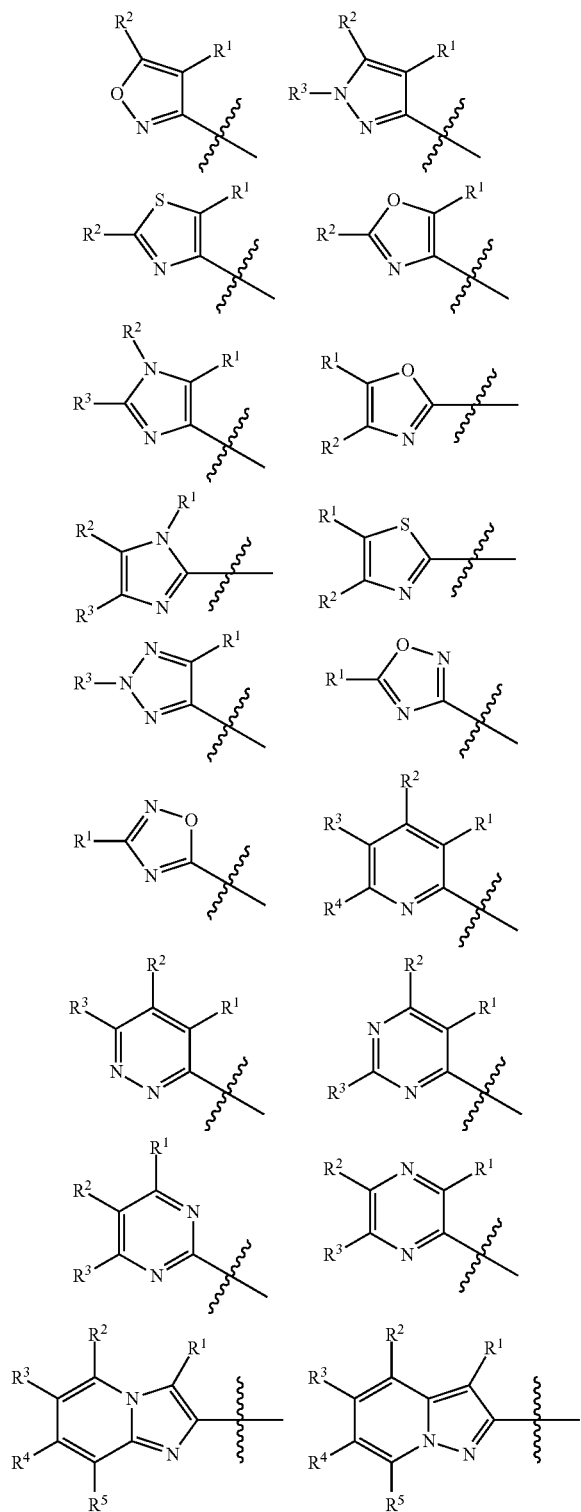

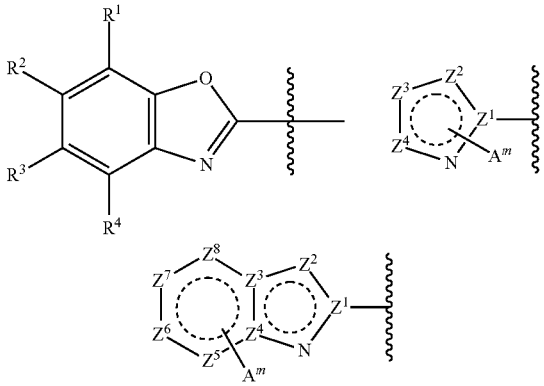

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6C$(=O)—$R^7$, O—$C_1$-$C_6$-alkyl-C(=O)—$NR^6R^7$, O—$C_2$-$C_6$-alkyl-$NR^6C$(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-$NR^9$, $C_0$-$C_6$—$NR^9S(=O)_2$, $C_0$-$C_6$-alkyl-S(=O)$_2NR^9$, $C_0$-$C_6$-alkyl-C(=O)—$NR^9$, $C_0$-$C_6$-alkyl-$NR^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-$NR^9$—C(=O)—O, $C_0$-$C_6$-alkyl-O—C(=O)—$NR^9$, $C_0$-$C_6$-alkyl-$NR^9$—C(=O)—$NR^{10}$, $C_0$-$C_6$-alkyl-$NR^9$—C(=$NR^{10}$)$NR^{11}$, $C_0$-$C_6$-alkyl-(C=$NR^9$)$NR^{10}$, $C_0$-$C_6$-alkyl-C(=O)—O—$C_0$-$C_6$-alkyl, $C_0$-$C_6$-alkyl-C(=O)—$NR^9$—$C_0$-$C_6$-alkyl, $C_0$-$C_6$-alkyl-C(=$NOR^9$) or $C_0$-$C_6$-alkyl-O—N=$CR^9$ substituents;

$R^9$, $R^{10}$ and $R^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$Z^9$, $Z^{10}$, $Z^{11}$ and $Z^{12}$ are each independently selected from the group consisting of —C=, —C=C—, —C—, —O—, =N—, —N— or —S— which may further be substituted by 1 to 4 $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{12}$, $C_3$-$C_6$-alkynyl-$OR^{12}$, $C_3$-$C_6$-alkenyl-$OR^{12}$, $C_0$-$C_6$-alkyl-S—$R^{12}$, O—$C_2$-$C_6$-alkyl-S—$R^{12}$, $C_0$-$C_6$-alkyl-S(=O)—$R^{12}$, O—$C_2$-$C_6$-alkyl-S(=O)—$R^{12}$, $C_0$-$C_6$-alkyl-S(=O)$_2$—$R^{12}$, O—$C_1$-$C_6$-alkyl-S(=O)$_2$—$R^{12}$, $C_0$-$C_6$-alkyl-$NR^{12}R^{13}$, O—$C_2$-$C_6$-alkyl-$NR^{12}R^{13}$, $C_0$-$C_6$-alkyl-S(=O)$_2NR^{12}R^{13}$, $C_0$-$C_6$-alkyl-$NR^{12}$—S(=O)$_2R^{13}$, O—$C_1$-$C_6$-alkyl-S(=O)$_2NR^{12}R^{13}$, O—$C_2$-$C_6$-alkyl-$NR^{12}$—S(=O)$_2R^{13}$, $C_0$-$C_6$-alkyl-C(=O)—$NR^{12}R^{13}$, $C_0$-$C_6$-alkyl-$NR^{12}C(=O)$—$R^{13}$, O—$C_1$-$C_6$-alkyl-C(=O)—$NR^{12}R^{13}$, O—$C_2$-$C_6$-alkyl-$NR^{12}C(=O)$—$R^{13}$, $C_0$-$C_6$-alkyl-OC(=O)—$R^{12}$, $C_0$-$C_6$-alkyl-C(=O)—$OR^{12}$, O—$C_2$-$C_6$-alkyl-OC(=O)—$R^{12}$, O—$C_1$-$C_6$-alkyl-C(=O)—$OR^{12}$, $C_0$-$C_6$-alkyl-C(=O)—$R^{12}$, O—$C_1$-$C_6$-alkyl-C(=O)—$R^{12}$, $C_0$-$C_6$-alkyl-$NR^{12}$—C(=O)—$OR^{13}$, $C_0$-$C_6$-alkyl-O—C(=O)—$NR^{12}R^{13}$ or $C_0$-$C_6$-alkyl-$NR^{12}$—C(=O)—$NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 4;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In one aspect, the compounds of the present invention are represented by Formula II-B wherein the heterocyclic ring system is specified as in the formula II-B1 depicted below

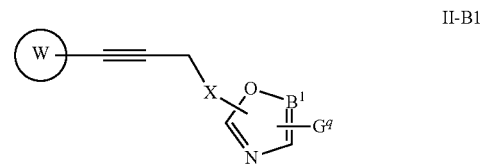

II-B1

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

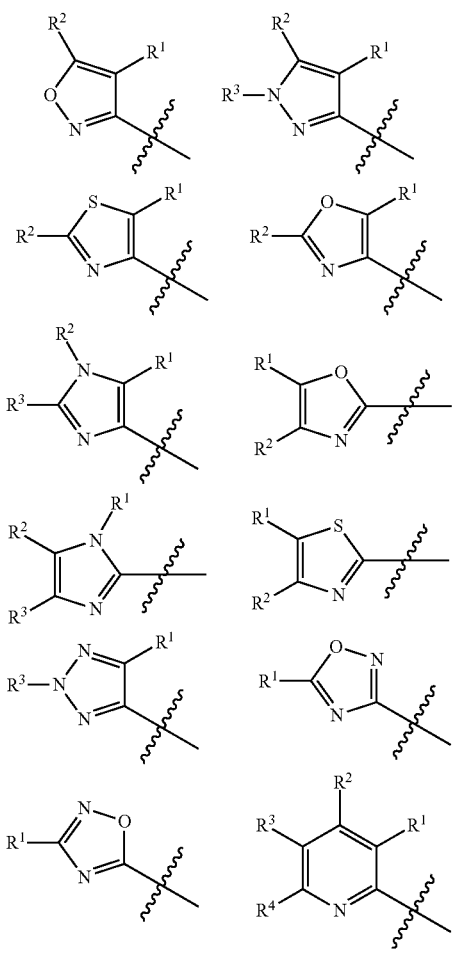

-continued

[Chemical structures shown: various substituted pyridazine, pyrimidine, pyrazine, imidazopyridine, pyrazolopyridine, benzoxazole, and generic heteroaryl ring systems with substituents $R^1$, $R^2$, $R^3$, $R^4$, $R^5$ and $Z^1$–$Z^8$, $A^m$, $B^1$]

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^6$, $C_3$-$C_6$-alkynyl-OR$^6$, $C_3$-$C_6$-alkenyl-OR$^6$, $C_0$-$C_6$-alkyl-S—R$^6$, O—$C_2$-$C_6$-alkyl-S—R$^6$, $C_0$-$C_6$-alkyl-S(=O)—R$^6$, O—$C_2$-$C_6$-alkyl-S(=O)—R$^6$, $C_0$-$C_6$-alkyl-S(=O)$_2$—R$^6$, O—$C_1$-$C_6$-alkyl-S(=O)$_2$—R$^6$, $C_0$-$C_6$-alkyl-NR$^6$R$^7$, O—$C_2$-$C_6$-alkyl-NR$^6$R$^7$, $C_0$-$C_6$-alkyl-S(=O)$_2$NR$^6$R$^7$, $C_0$-$C_6$-alkyl-NR$^6$—S(=O)$_2$R$^7$, O—$C_1$-$C_6$-alkyl-S(=O)$_2$NR$^6$R$^7$, O—$C_1$-$C_6$-alkyl-NR$^6$—S(=O)$_2$R$^7$, $C_0$-$C_6$-alkyl-C(=O)—NR$^6$R$^7$, $C_0$-$C_6$-alkyl-NR$^6$C(=O)—R$^7$, O—$C_1$-$C_6$-alkyl-C(=O)—NR$^6$R$^7$, O—$C_2$-$C_6$-alkyl-NR$^6$C(=O)—R$^7$, $C_0$-$C_6$-alkyl-OC(=O)—R$^6$, $C_0$-$C_6$-alkyl-C(=O)—OR$^6$, O—$C_2$-$C_6$-alkyl-OC(=O)—R$^6$, O—$C_1$-$C_6$-alkyl-C(=O)—OR$^6$, $C_0$-$C_6$-alkyl-C(=O)—R$^6$, O—$C_1$-$C_6$-alkyl-C(=O)—R$^6$, $C_0$-$C_6$-alkyl-NR$^6$—C(=O)—OR$^7$, $C_0$-$C_6$-alkyl-O—C(=O)—NR$^6$R$^7$ or $C_0$-$C_6$-alkyl-NR$^6$—C(=O)—NR$^7$R$^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^9$, $C_0$-$C_6$—NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR$^9$—C(=O)—O, $C_0$-$C_6$-alkyl-O—C(=O)—NR$^9$, $C_0$-$C_6$-alkyl-NR$^9$—C(=O)—NR$^{10}$, $C_0$-$C_6$-alkyl-NR$^9$—C(=NR$^{10}$)NR$^{11}$, $C_0$-$C_6$-alkyl-(C=NR$^9$)NR$^{10}$, $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-C(=NOR$^9$) or $C_0$-$C_6$-alkyl-O—N=CR$^9$ substituents;

$R^9$, $R^{10}$ and $R^{11}$ are each independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

$B^1$ represents independently C or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{12}$, $C_3$-$C_6$-alkynyl-OR$^{12}$, $C_3$-$C_6$-alkenyl-OR$^{12}$, $C_0$-$C_6$-alkyl-S—R$^{12}$, O—$C_2$-$C_6$-alkyl-S—R$^{12}$, $C_0$-$C_6$-alkyl-S(=O)—R$^{12}$, O—$C_2$-$C_6$-alkyl-S(=O)—R$^{12}$, $C_0$-$C_6$-alkyl-S(=O)$_2$—R$^{12}$, O—$C_1$-$C_6$-alkyl-S(=O)$_2$—R$^{12}$, $C_0$-$C_6$-alkyl-NR$^{12}$R$^{13}$, O—$C_2$-$C_6$-alkyl-NR$^{12}$R$^{13}$, $C_0$-$C_6$-alkyl-S(=O)$_2$NR$^{12}$R$^{13}$, $C_0$-$C_6$-alkyl-NR$^{12}$—S(=O)$_2$R$^{13}$, O—$C_1$-$C_6$-alkyl-S(=O)$_2$NR$^{12}$R$^{13}$, O—$C_2$-$C_6$-alkyl-NR$^{12}$—S(=O)$_2$R$^{13}$, $C_0$-$C_6$-alkyl-C(=O)—NR$^{12}$R$^{13}$, $C_0$-$C_6$-alkyl-NR$^{12}$C(=O)—R$^{13}$, O—$C_1$-$C_6$-alkyl-C(=O)—NR$^{12}$R$^{13}$, O—$C_2$-$C_6$-alkyl-NR$^{12}$C(=O)—R$^{13}$, $C_0$-$C_6$-alkyl-OC(=O)—R$^{12}$, $C_0$-$C_6$-alkyl-C(=O)—OR$^{12}$, O—$C_2$-$C_6$-alkyl-OC (=O)—R[12], O—C[1]-C[6]-alkyl-C(=O)—OR[12], C[0]-C[6]-alkyl-C(=O)—R[12], O—C[1]-C[6]-alkyl-C(=O)—R[12], C[0]-C[6]-alkyl-NR[12]—C(=O)—OR[13], C[0]-C[6]-alkyl-O—C(=O)—NR[12]R[13] or C[0]-C[6]-alkyl-NR[12]—C(=O)—NR[13]R[14] substituents;

wherein optionally two substituents are combined to the intervening atoms to form a bicyclic aryl, cycloalkyl, heterocycloalkyl or heteroaryl ring; wherein each ring is optionally further substituted with 1-5 independent halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 2;

$R^{12}$, $R^{13}$ and $R^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a second aspect, the compounds of the present invention are represented by Formula II-B wherein the heterocyclic ring system is specified as in the formula II-B2 depicted below

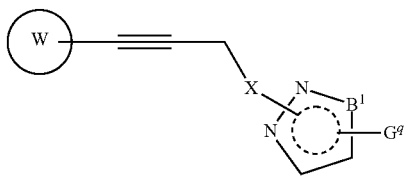

II-B2

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

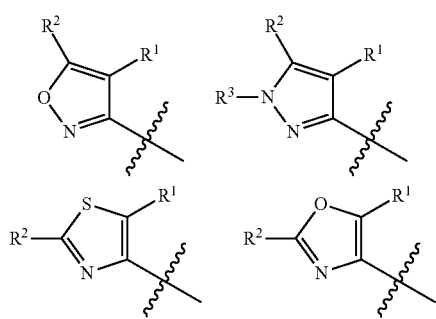

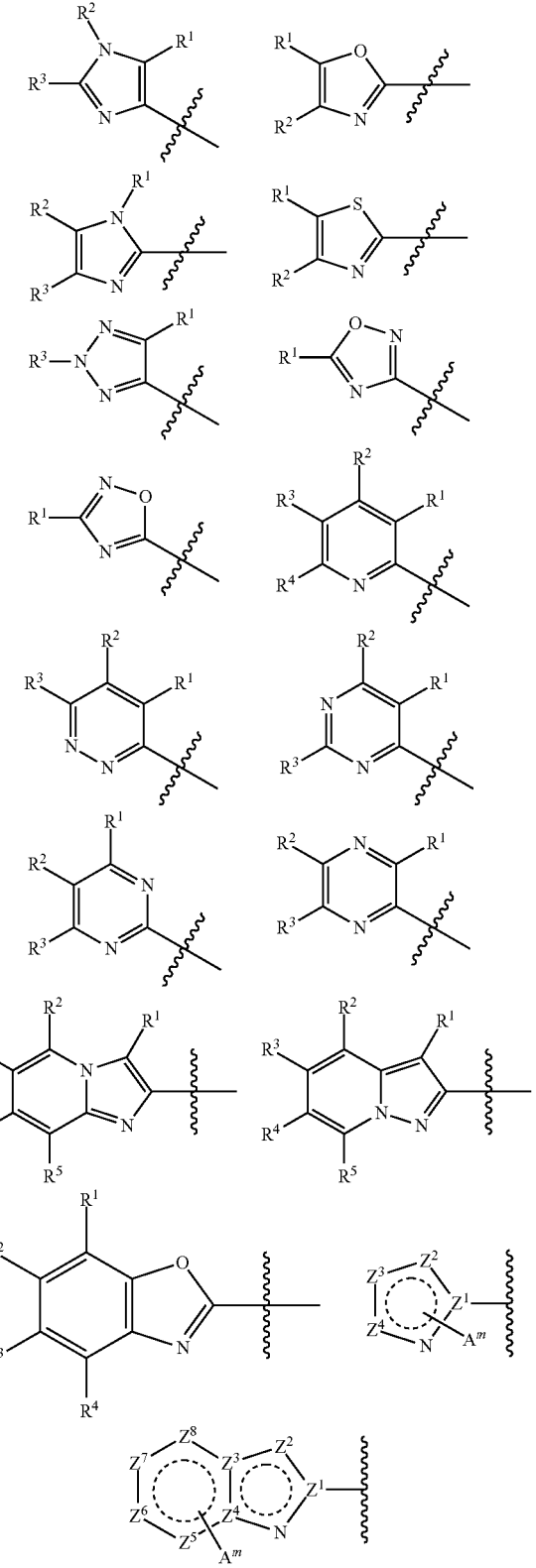

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-

$C_6$-alkenyl, $O-C_2-C_6$-alkyl-$OR^6$, $O-C_3-C_7$-cycloalkyl, $O-C_1-C_6$-alkyl-heteroaryl, $O-C_1-C_6$-alkylaryl, $C_0-C_6$-alkyl-$OR^6$, $C_3-C_7$-cycloalkyl, $C_3-C_7$-cycloalkyl-$C_1-C_6$-alkyl, $O-C_3-C_7$-cycloalkyl-$C_1-C_6$-alkyl, O-heteroaryl, heteroaryl, $C_1-C_6$-alkyl-heteroaryl, aryl, O-aryl, $C_1-C_6$-alkylaryl, $C_1-C_6$-alkylhalo-$OR^6$, $C_3-C_6$-alkynyl-$OR^6$, $C_3-C_6$-alkenyl-$OR^6$, $C_0-C_6$-alkyl-$S-R^6$, $O-C_2-C_6$-alkyl-$S-R^6$, $C_0-C_6$-alkyl-$S(=O)-R^6$, $O-C_2-C_6$-alkyl-$S(=O)-R^6$, $C_0-C_6$-alkyl-$S(=O)_2-R^6$, $O-C_1-C_6$-alkyl-$S(=O)_2-R^6$, $C_0-C_6$-alkyl-$NR^6R^7$, $O-C_2-C_6$-alkyl-$NR^6R^7$, $C_0-C_6$-alkyl-$S(=O)_2NR^6R^7$, $C_0-C_6$-alkyl-$NR^6-S(=O)_2R^7$, $O-C_1-C_6$-alkyl-$S(=O)_2NR^6R^7$, $O-C_1-C_6$-alkyl-$NR^6-S(=O)_2R^7$, $C_0-C_6$-alkyl-$C(=O)-NR^6R^7$, $C_0-C_6$-alkyl-$NR^6C(=O)-R^7$, $O-C_1-C_6$-alkyl-$C(=O)-NR^6R^7$, $O-C_2-C_6$-alkyl-$NR^6C(=O)-R^7$, $C_0-C_6$-alkyl-$OC(=O)-R^6$, $C_0-C_6$-alkyl-$C(=O)-OR^6$, $O-C_2-C_6$-alkyl-$OC(=O)-R^6$, $O-C_1-C_6$-alkyl-$C(=O)-OR^6$, $C_0-C_6$-alkyl-$C(=O)-R^6$, $O-C_1-C_6$-alkyl-$C(=O)-R^6$, $C_0-C_6$-alkyl-$NR^6-C(=O)-OR^7$, $C_0-C_6$-alkyl-$O-C(=O)-NR^6R^7$ or $C_0-C_6$-alkyl-$NR^6-C(=O)-NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1-C_6$-alkyl, $C_1-C_6$-alkylhalo, $C_2-C_6$-alkynyl, $C_2-C_6$-alkenyl, $O-C_1-C_6$-alkyl, $O-C_1-C_6$-alkylhalo, $O-C_3-C_6$-alkynyl, $O-C_3-C_6$-alkenyl, $O-C_3-C_7$-cycloalkyl, $O-C_1-C_6$-alkyl-heteroaryl, $O-C_1-C_6$-alkylaryl, $C_1-C_6$-alkylaryl, $C_3-C_7$-cycloalkyl, $C_3-C_7$-cycloalkyl-$C_1-C_6$-alkyl, $O-C_3-C_7$-cycloalkyl-$C_1-C_6$-alkyl, O-heteroaryl, heteroaryl, $C_1-C_6$-alkyl-heteroaryl, aryl, O-aryl;

$R^6$, $R^7$ and $R^8$ are each independently selected from the group consisting of hydrogen, an optionally substituted $C_1-C_6$-alkyl, $C_1-C_6$-alkylhalo, $C_2-C_6$-alkynyl, $C_2-C_6$-alkenyl, $C_3-C_7$-cycloalkyl, $C_3-C_7$-cycloalkyl-$C_1-C_6$-alkyl, heteroaryl, $C_1-C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of $-C=$, $-C=C-$, $-O-$, $-N=$, $-N-$ or $-S-$ which may further be substituted by 1 to 5 $A^m$ groups;

m is an integer from 1 to 5;

X is selected from an optionally substituted $C_1-C_6$-alkyl, $C_1-C_6$-alkylhalo, $C_2-C_6$-alkynyl, $C_2-C_6$-alkenyl, $O-C_0-C_6$-alkyl, $O-C_1-C_6$-alkylhalo, $O-C_3-C_6$-alkynyl, $O-C_3-C_6$-alkenyl, $O-C_3-C_7$-cycloalkyl, $C_0-C_6$-alkyl-O, $C_3-C_7$-cycloalkyl, $C_3-C_7$-cycloalkyl-$C_0-C_6$-alkyl, $S-C_0-C_6$-alkyl, $C_1-C_6$-alkylhalo-O, $C_3-C_6$-alkynyl-O, $C_3-C_6$-alkenyl-O, $C_0-C_6$-alkyl-S, $C_0-C_6$-alkyl-$S(=O)$, $C_0-C_6$-alkyl-$S(=O)_2$, $C_0-C_6$-alkyl-$NR^9$, $C_0-C_6-NR^9S(=O)_2$, $C_0-C_6$-alkyl-$S(=O)_2NR^9$, $C_0-C_6$-alkyl-$C(=O)-NR^9$, $C_0-C_6$-alkyl-$NR^9C(=O)$, $C_0-C_6$-alkyl-$OC(=O)$, $C_0-C_6$-alkyl-$C(=O)-O$, $C_0-C_6$-alkyl-$C(=O)$, $C_0-C_6$-alkyl-$NR^9-C(=O)-O$, $C_0-C_6$-alkyl-$O-C(=O)-NR^9$, $C_0-C_6$-alkyl-$NR^9-C(=O)-NR^{10}$, $C_0-C_6$-alkyl-$NR^9-C(=NR^{10})NR^{11}$, $C_0-C_6$-alkyl-$(C=NR^9)NR^{10}$, $C_0-C_6$-alkyl-$C(=O)-O-C_0-C_6$-alkyl, $C_0-C_6$-alkyl-$C(=O)-NR^9-C_0-C_6$-alkyl, $C_0-C_6$-alkyl-$C(=NOR^9)$ or $C_0-C_6$-alkyl-$O-N=CR^9$ substituents;

$R^9$, $R^{10}$ and $R^{11}$ are each independently selected from the group consisting of hydrogen, an optionally substituted $C_1-C_6$-alkyl, $C_1-C_6$-alkylhalo, $C_2-C_6$-alkynyl, $C_2-C_6$-alkenyl, $C_3-C_7$-cycloalkyl, $C_3-C_7$-cycloalkyl-$C_1-C_6$-alkyl, heteroaryl, $C_1-C_6$-alkyl-heteroaryl, aryl, heterocycle;

$B^1$ represents independently C or N which may further be substituted by one $G^q$ group;

$G^q$ groups are each independently selected from the group consisting of hydrogen, halogen, CN, OH, nitro, an optionally substituted $C_1-C_6$-alkyl, $C_1-C_6$-alkylhalo, $C_2-C_6$-alkynyl, $C_2-C_6$-alkenyl, $O-C_1-C_6$-alkyl, $O-C_1-C_6$-alkylhalo, $O-C_3-C_6$-alkynyl, $O-C_3-C_6$-alkenyl, $O-C_2-C_6$-alkyl-$OR^{12}$, $O-C_3-C_7$-cycloalkyl, $O-C_1-C_6$-alkyl-heteroaryl, $O-C_1-C_6$-alkylaryl, $C_0-C_6$-alkyl-$OR^{12}$, $C_3-C_7$-cycloalkyl, $C_3-C_7$-cycloalkyl-$C_1-C_6$-alkyl, $O-C_3-C_7$-cycloalkyl-$C_1-C_6$-alkyl, O-heteroaryl, heteroaryl, $C_1-C_6$-alkyl-heteroaryl, aryl, O-aryl, $C_1-C_6$-alkylaryl, $C_1-C_6$-alkylhalo-$OR^{12}$, $C_3-C_6$-alkynyl-$OR^{12}$, $C_3-C_6$-alkenyl-$OR^{12}$, $C_0-C_6$-alkyl-$S-R^{12}$, $O-C_2-C_6$-alkyl-$S-R^{12}$, $C_0-C_6$-alkyl-$S(=O)-R^{12}$, $O-C_2-C_6$-alkyl-$S(=O)-R^{12}$, $C_0-C_6$-alkyl-$S(=O)_2-R^{12}$, $O-C_1-C_6$-alkyl-$S(=O)_2-R^{12}$, $C_0-C_6$-alkyl-$NR^{12}R^{13}$, $O-C_2-C_6$-alkyl-$NR^{12}R^{13}$, $C_0-C_6$-alkyl-$S(=O)_2NR^{12}R^{13}$, $C_0-C_6$-alkyl-$NR^{12}-S(=O)_2R^{13}$, $O-C_1-C_6$-alkyl-$S(=O)_2NR^{12}R^{13}$, $O-C_2-C_6$-alkyl-$NR^{12}-S(=O)_2R^{13}$, $C_0-C_6$-alkyl-$C(=O)-NR^{12}R^{13}$, $C_0-C_6$-alkyl-$NR^{12}C(=O)-R^{13}$, $O-C_1-C_6$-alkyl-$C(=O)-NR^{12}R^{13}$, $O-C_2-C_6$-alkyl-$NR^{12}C(=O)-R^{13}$, $C_0-C_6$-alkyl-$OC(=O)-R^{12}$, $C_0-C_6$-alkyl-$C(=O)-OR^{12}$, $O-C_2-C_6$-alkyl-$OC(=O)-R^{12}$, $O-C_1-C_6$-alkyl-$C(=O)-OR^{12}$, $C_0-C_6$-alkyl-$C(=O)-R^{12}$, $O-C_1-C_6$-alkyl-$C(=O)-R^{12}$, $C_0-C_6$-alkyl-$NR^{12}-C(=O)-OR^{13}$, $C_0-C_6$-alkyl-$O-C(=O)-NR^{12}R^{13}$ or $C_0-C_6$-alkyl-$NR^{12}-C(=O)-NR^{13}R^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent halogen, CN, OH, nitro, an optionally substituted $C_1-C_6$-alkyl, $C_1-C_6$-alkylhalo, $C_2-C_6$-alkynyl, $C_2-C_6$-alkenyl, $O-C_1-C_6$-alkyl, $O-C_1-C_6$-alkylhalo, $O-C_3-C_6$-alkynyl, $O-C_3-C_6$-alkenyl, $O-C_3-C_7$-cycloalkyl, $O-C_1-C_6$-alkyl-heteroaryl, $O-C_1-C_6$-alkylaryl, $C_3-C_7$-cycloalkyl, $C_3-C_7$-cycloalkyl-$C_1-C_6$-alkyl, $O-C_3-C_7$-cycloalkyl-$C_1-C_6$-alkyl, O-heteroaryl, heteroaryl, $C_1-C_6$-alkyl-heteroaryl, aryl, O-aryl;

q is an integer from 1 to 3;

$R^{12}$, $R^{13}$ and $R^{14}$ are each independently selected from the group consisting of hydrogen, an optionally substituted $C_1-C_6$-alkyl, $C_1-C_6$-alkylhalo, $C_2-C_6$-alkynyl, $C_2-C_6$-alkenyl, $C_3-C_7$-cycloalkyl, $C_3-C_7$-cycloalkyl-$C_1-C_6$-alkyl, heteroaryl, $C_1-C_6$-alkyl-heteroaryl, aryl;

Any N may be an N-oxide;

The present invention includes both possible stereoisomers and includes not only racemic compounds but the individual enantiomers as well.

Further preferred compounds of the present invention are compounds of Formula II-C

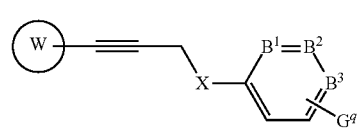

II-C

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

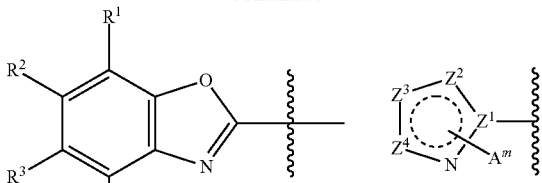

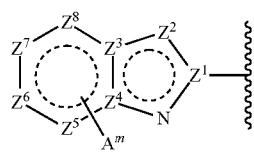

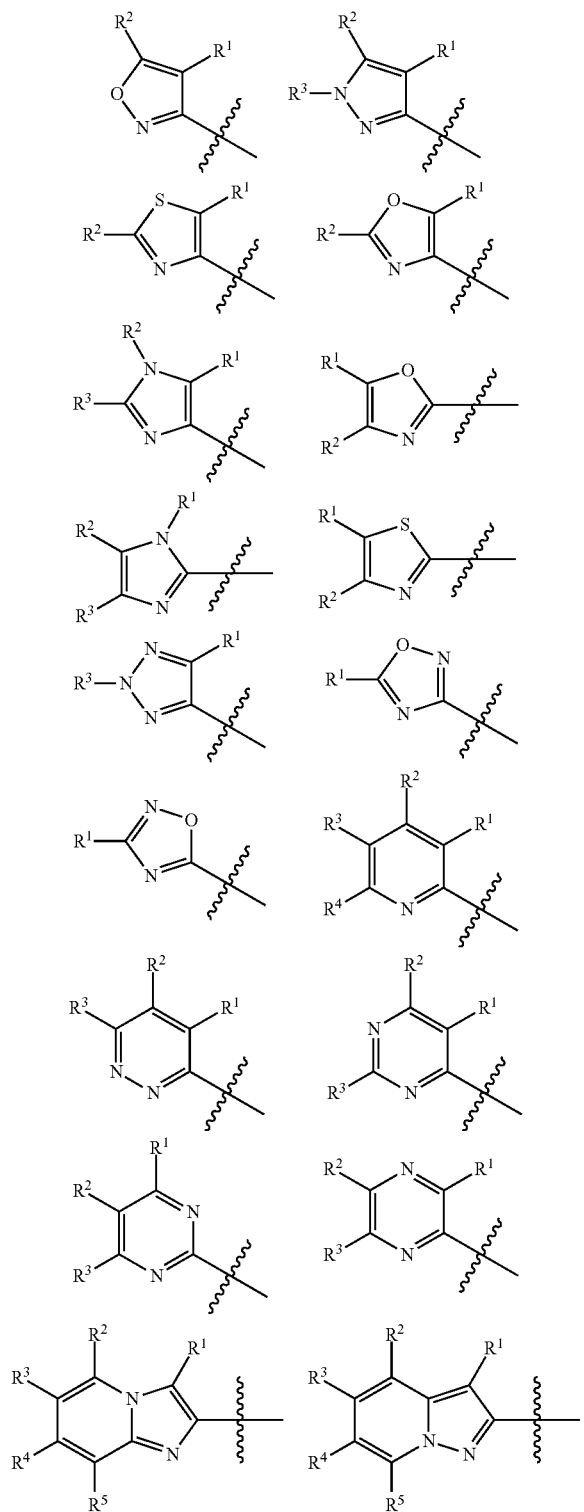

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6$C(=O)—$R^7$, O—$C_1$-$C_6$-alkyl-C(=O)—$NR^6R^7$, O—$C_2$-$C_6$-alkyl-$NR^6$C(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_1$-$C_6$-alkylhalo, $C_2$-$C_6$-alkynyl, $C_2$-$C_6$-alkenyl, O—$C_0$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, $C_0$-$C_6$-alkyl-O, $C_3$-$C_7$-cycloalkyl, $C_3$-$C_7$-cycloalkyl-$C_0$-$C_6$-alkyl, S—$C_0$-$C_6$-alkyl, $C_1$-$C_6$-alkylhalo-O, $C_3$-$C_6$-alkynyl-O, $C_3$-$C_6$-alkenyl-O, $C_0$-$C_6$-alkyl-S, $C_0$-$C_6$-alkyl-S(=O), $C_0$-$C_6$-alkyl-S(=O)$_2$, $C_0$-$C_6$-alkyl-NR$^9$, $C_0$-$C_6$—NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-OC(=O), $C_0$-$C_6$-alkyl-C(=O)—O, $C_0$-$C_6$-alkyl-C(=O), $C_0$-$C_6$-alkyl-NR$^9$—C(=O)—O, $C_0$-$C_6$-alkyl-O—C(=O)—NR$^9$, $C_0$-$C_6$-alkyl-NR$^9$—C(=O)—NR$^{10}$, $C_0$-$C_6$-alkyl-NR$^9$—C(=NR$^{10}$)NR$^{11}$, $C_0$-$C_6$-alkyl-(C=NR$^9$)NR$^{10}$, $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-C(=NOR$^9$) or $C_0$-$C_6$-alkyl-O—N=CR$^9$ substituents;

R$^9$, R$^{10}$ and R$^{11}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl, heterocycle;

B$^1$, B$^2$ and B$^3$ are each independently selected from C or N which may further be substituted by G$^q$ groups;

G$^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{12}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{12}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{12}$, $C_3$-$C_6$-alkynyl-OR$^{12}$, $C_3$-$C_6$-alkenyl-OR$^{12}$, $C_0$-$C_6$-alkyl-S—R$^{12}$, O—$C_2$-$C_6$-alkyl-S—R$^{12}$, $C_0$-$C_6$-alkyl-S(=O)—R$^{12}$, O—$C_2$-$C_6$-alkyl-S(=O)—R$^{12}$, $C_0$-$C_6$-alkyl-S(=O)$_2$—R$^{12}$, O—$C_1$-$C_6$-alkyl-S(=O)$_2$—R$^{12}$, $C_0$-$C_6$-alkyl-NR$^{12}$R$^{13}$, O—$C_2$-$C_6$-alkyl-NR$^{12}$R$^{13}$, $C_0$-$C_6$-alkyl-S(=O)$_2$NR$^{12}$R$^{13}$, $C_0$-$C_6$-alkyl-NR$^{12}$—S(=O)$_2$R$^{13}$, O—$C_1$-$C_6$-alkyl-S(=O)$_2$NR$^{12}$R$^{13}$, O—$C_2$-$C_6$-alkyl-NR$^{12}$—S(=O)$_2$R$^{13}$, $C_0$-$C_6$-alkyl-C(=O)—NR$^{12}$R$^{13}$, $C_0$-$C_6$-alkyl-NR$^{12}$C(=O)—R$^{13}$, O—$C_1$-$C_6$-alkyl-C(=O)—NR$^{12}$R$^{13}$, O—$C_2$-$C_6$-alkyl-NR$^{12}$C(=O)—R$^{13}$, $C_0$-$C_6$-alkyl-OC(=O)—R$^{12}$, $C_0$-$C_6$-alkyl-C(=O)—OR$^{12}$, O—$C_2$-$C_6$-alkyl-OC(=O)—R$^{12}$, O—$C_1$-$C_6$-alkyl-C(=O)—OR$^{12}$, $C_0$-$C_6$-alkyl-C(=O)—R$^{12}$, O—$C_1$-$C_6$-alkyl-C(=O)—R$^{12}$, $C_0$-$C_6$-alkyl-NR$^{12}$—C(=O)—OR$^{13}$, $C_0$-$C_6$-alkyl-O—C(=O)—NR$^{12}$R$^{13}$ or $C_0$-$C_6$-alkyl-NR$^{12}$—C(=O)—NR$^{13}$R$^{14}$ substituents;

wherein optionally two substituents are combined to the intervening atoms to form a bicyclic aryl, cycloalkyl, heterocycloalkyl or heteroaryl ring; wherein each ring is optionally further substituted with 1-5 independent halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

q is an integer from 1 to 5;

R$^{12}$, R$^{13}$ and R$^{14}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

provided that:

when X is independently selected from NR$^{15}$, O, S or an optionally substituted $C_1$-$C_6$-alkyl, G$^q$ and q are as defined above, W is an optionally substituted 2-pyridinyl and R$^{15}$ is independently selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl or aryl, B$_1$, B$_2$ and B$_3$ can not be C;

when X is O, B$^1$, B$^2$ and B$^3$ are each independently selected from C or N, G$^q$ and q are as defined above, W can not be an optionally substituted 3-pyridazinyl or 4-pyrimidinyl;

when X is CH$_2$, B$^1$, B$^2$ and B$^3$ are C and G$^q$ and q are as defined above, W can not be 2-phenyloxazol-4-yl, 4-phenyloxazol-2-yl, 4-(3-(benzyloxy)propyl)-oxazol-2-yl, 4-phenylthiazol-2-yl, 4-methylthiazol-2-yl, benzo[d]oxazol-2-yl or benzo[d]thiazol-2-yl;

when X is O, W is an optionally substituted pyridinyl and G$^q$ and q are as defined above, B$^1$, B$^2$ or B$^3$ can not be N;

when X is CH$_2$CH$_2$, B$^1$, B$^2$ and B$^3$ are C and G$^q$ and q are as defined above, W can not be 4-imidazolyl.

The present invention includes both possible stereoisomers and includes not only racemic compounds but the individual enantiomers as well.

In a more preferred aspect of formula II-C

Wherein

W is a 5-, 6-heterocyclic ring containing a N adjacent to the ethynyl bond, which ring may optionally be fused with a 5- or 6-membered ring containing one or more atoms independently selected from the group consisting of C, N, O and S; provided that W is a heteroaryl selected from the group of formula:

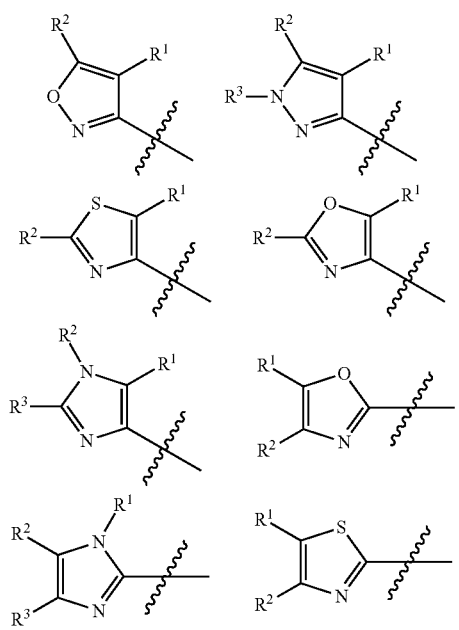

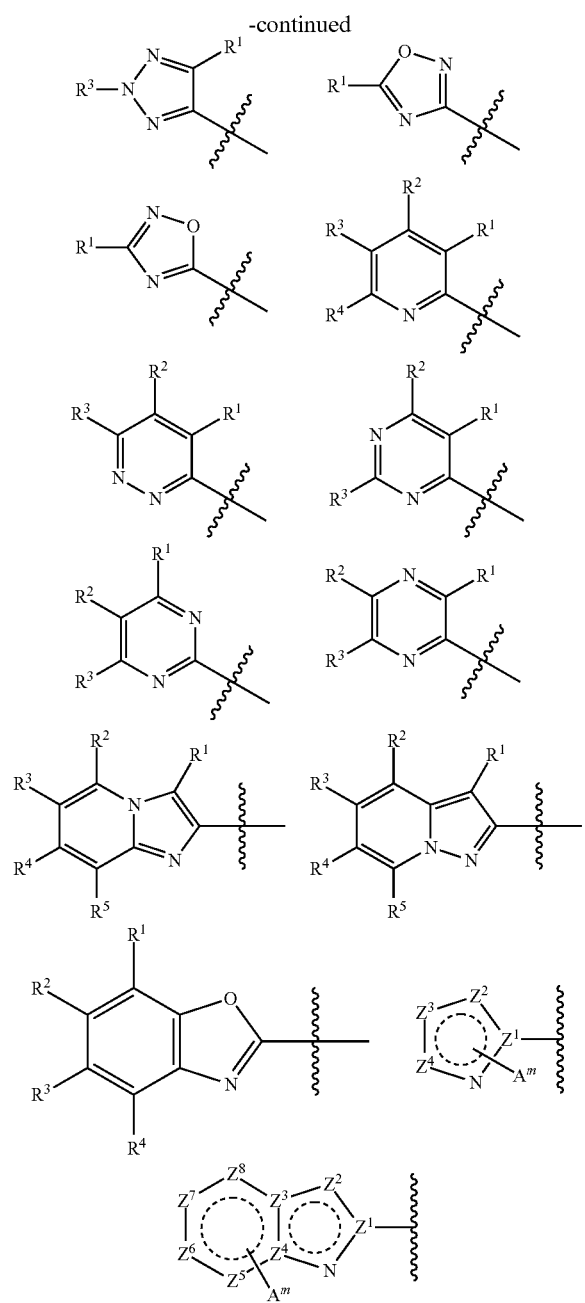

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^6$, $C_3$-$C_6$-alkynyl-OR$^6$, $C_3$-$C_6$-alkenyl-OR$^6$, $C_0$-$C_6$-alkyl-S—R$^6$, O—$C_2$-$C_6$-alkyl-S—R$^6$, $C_0$-$C_6$-alkyl-S(=O)—R$^6$, O—$C_2$-$C_6$-alkyl-S(=O)—R$^6$, $C_0$-$C_6$-alkyl-S(=O)$_2$—R$^6$, O—$C_1$-$C_6$-alkyl-S(=O)$_2$—R$^6$, $C_0$-$C_6$-alkyl-NR$^6$R$^7$, O—$C_2$-$C_6$-alkyl-NR$^6$R$^7$, $C_0$-$C_6$-alkyl-S(=O)$_2$NR$^6$R$^7$, $C_0$-$C_6$-alkyl-NR$^6$—S(=O)$_2$R$^7$, O—$C_1$-$C_6$-alkyl-S(=O)$_2$NR$^6$R$^7$, O—$C_1$-$C_6$-alkyl-NR$^6$—S(=O)$_2$R$^7$, $C_0$-$C_6$-alkyl-C(=O)—NR$^6$R$^7$, $C_0$-$C_6$-alkyl-NR$^6$C(=O)—R$^7$, O—$C_1$-$C_6$-alkyl-C(=O)—NR$^6$R$^7$, O—$C_2$-$C_6$-alkyl-NR$^6$C(=O)—R$^7$, $C_0$-$C_6$-alkyl-OC(=O)—R$^6$, $C_0$-$C_6$-alkyl-C(=O)—OR$^6$, O—$C_2$-$C_6$-alkyl-OC(=O)—R$^6$, O—$C_1$-$C_6$-alkyl-C(=O)—OR$^6$, $C_0$-$C_6$-alkyl-C(=O)—R$^6$, O—$C_1$-$C_6$-alkyl-C(=O)—R$^6$, $C_0$-$C_6$-alkyl-NR$^6$—C(=O)—OR$^7$, $C_0$-$C_6$-alkyl-O—C(=O)—NR$^6$R$^7$ or $C_0$-$C_6$-alkyl-NR$^6$—C(=O)—NR$^7$R$^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_2$-$C_6$-alkynyl, $C_0$-$C_6$-alkyl-NR$^9$S(=O)$_2$, $C_0$-$C_6$-alkyl-S(=O)$_2$NR$^9$, $C_0$-$C_6$-alkyl-C(=O)—NR$^9$, $C_0$-$C_6$-alkyl-NR$^9$C(=O), $C_0$-$C_6$-alkyl-C(=O)—O—$C_0$-$C_6$-alkyl, $C_0$-$C_6$-alkyl-C(=O)—NR$^9$—$C_0$-$C_6$-alkyl, $C_0$-$C_6$-alkyl-OC(=O) or $C_0$-$C_6$-alkyl-C(=O)—O substituents;

$R^9$ is selected from hydrogen, an optionally substituted $C_1$-$C_6$-alkyl, $C_1$-$C_6$-alkylhalo, $C_3$-$C_7$-cyclo alkyl, $C_3$-$C_7$-cycloalkyl-$C_1$-$C_6$-alkyl, heteroaryl, $C_1$-$C_6$-alkyl-heteroaryl, aryl;

$B^1$, $B^2$ and $B^3$ are each independently selected from C or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-OR$^{10}$, O—$C_3$-$C_7$-cycloalkyl, O—$C_1$-$C_6$-alkyl-heteroaryl, O—$C_1$-$C_6$-alkylaryl, $C_0$-$C_6$-alkyl-OR$^{10}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-OR$^{10}$, $C_3$-$C_6$-alkynyl-OR$^{10}$, $C_3$-$C_6$-alkenyl-OR$^{10}$, $C_0$-$C_6$-alkyl-S—R$^{10}$, O—$C_2$-$C_6$-alkyl-S—R$^{10}$, $C_0$-$C_6$-alkyl-S(=O)—R$^{10}$, O—$C_2$-$C_6$-alkyl-S(=O)—R$^{10}$, $C_0$-$C_6$-alkyl-S(=O)$_2$—R$^{10}$, O—$C_1$-$C_6$-alkyl-S(=O)$_2$—R$^{10}$, $C_0$-$C_6$-alkyl-NR$^{10}$R$^{11}$, O—$C_2$-$C_6$-alkyl-NR$^{10}$R$^{11}$, $C_0$-$C_6$-alkyl-S(=O)$_2$NR$^{10}$R$^{11}$, $C_0$-$C_6$-alkyl-NR$^{10}$—S(=O)$_2$R$^{11}$, O—$C_1$-$C_6$-alkyl-S(=O)$_2$NR$^{10}$R$^{11}$, O—$C_2$-$C_6$-alkyl-NR$^{10}$—S(=O)$_2$R$^{11}$, $C_0$-$C_6$-alkyl-C(=O)—NR$^{10}$R$^{11}$, $C_0$-$C_6$-alkyl-NR$^{10}$C(=O)—R$^{11}$, O—$C_1$-$C_6$-alkyl-C(=O)—NR$^{10}$R$^{11}$, O—$C_2$-$C_6$-alkyl-NR$^{10}$C(=O)—R$^{11}$, $C_0$-$C_6$-alkyl-OC(=O)—R$^{10}$, $C_0$-$C_6$-alkyl-C(=O)—$OR^{10}$, O—$C_2$-$C_6$-alkyl-OC(=O)—$R^{10}$, O—$C_1$-$C_6$-alkyl-C(=O)—$OR^{10}$, $C_0$-$C_6$-alkyl-C(=O)—$R^{10}$, O—$C_1$-$C_6$-alkyl-C(=O)—$R^{10}$, $C_0$-$C_6$-alkyl-$NR^{10}$—C(=O)—$OR^{11}$, $C_0$-$C_6$-alkyl-O—C(=O)—$NR^{10}R^{11}$ or $C_0$-$C_6$-alkyl-$NR^{10}$—C(=O)—$NR^{11}R^{12}$ substituents;

q is an integer from 1 to 5;

$R^{10}$, $R^{11}$ and $R^{12}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well.

In a second more preferred aspect of formula II-C

Or a pharmaceutically acceptable salt, hydrate or solvate of such compound

Wherein

W is a 5-, 6-heterocyclic ring containing a N adjacent to the ethynyl bond, which ring may optionally be fused with a 5- or 6-membered ring containing one or more atoms independently selected from a group consisting of C, N, O and S; provided that W can not be a pyridine and W is a heteroaryl selected from the group of formula:

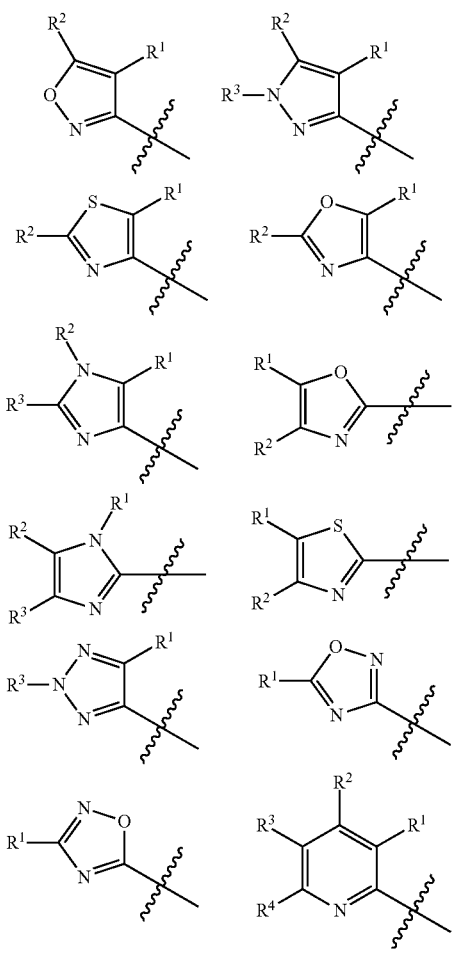

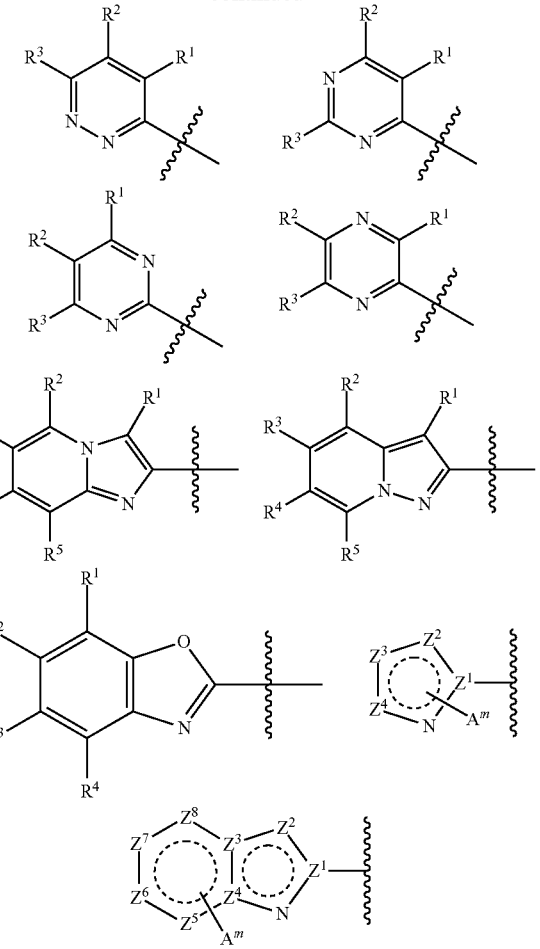

$R^1$, $R^2$, $R^3$, $R^4$, $R^5$ and $A^m$ are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^6$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^6$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^6$, $C_3$-$C_6$-alkynyl-$OR^6$, $C_3$-$C_6$-alkenyl-$OR^6$, $C_0$-$C_6$-alkyl-S—$R^6$, O—$C_2$-$C_6$-alkyl-S—$R^6$, $C_0$-$C_6$-alkyl-S(=O)—$R^6$, O—$C_2$-$C_6$-alkyl-S(=O)—$R^6$, $C_0$-$C_6$-alkyl-S(=O)$_2$—$R^6$, O—$C_1$-$C_6$-alkyl-S(=O)$_2$—$R^6$, $C_0$-$C_6$-alkyl-$NR^6R^7$, O—$C_2$-$C_6$-alkyl-$NR^6R^7$, $C_0$-$C_6$-alkyl-S(=O)$_2NR^6R^7$, $C_0$-$C_6$-alkyl-$NR^6$—S(=O)$_2R^7$, O—$C_1$-$C_6$-alkyl-S(=O)$_2NR^6R^7$, O—$C_1$-$C_6$-alkyl-$NR^6$—S(=O)$_2R^7$, $C_0$-$C_6$-alkyl-C(=O)—$NR^6R^7$, $C_0$-$C_6$-alkyl-$NR^6$C(=O)—$R^7$, O—$C_1$-$C_6$-alkyl-C(=O)—$NR^6R^7$, O—$C_2$-$C_6$-alkyl-$NR^6$C(=O)—$R^7$, $C_0$-$C_6$-alkyl-OC(=O)—$R^6$, $C_0$-$C_6$-alkyl-C(=O)—$OR^6$, O—$C_2$-$C_6$-alkyl-OC(=O)—$R^6$, O—$C_1$-$C_6$-alkyl-C(=O)—$OR^6$, $C_0$-$C_6$-alkyl-C(=O)—$R^6$, O—$C_1$-$C_6$-alkyl-C(=O)—$R^6$, $C_0$-$C_6$-alkyl-$NR^6$—C(=O)—$OR^7$, $C_0$-$C_6$-alkyl-O—C(=O)—$NR^6R^7$ or $C_0$-$C_6$-alkyl-$NR^6$—C(=O)—$NR^7R^8$ substituents;

wherein optionally two substituents are combined to the intervening atoms to form a bicyclic aryl, cycloalkyl, heterocycloalkyl or heteroaryl ring; wherein each ring is optionally further substituted with 1-5 independent hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_3$-$C_7$-cycloalkyl, O—$C_1$-$C_6$-alkyl-heteroaryl, O—$C_1$-$C_6$-alkylaryl, $C_1$-$C_6$-alkylaryl, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl;

$R^6$, $R^7$ and $R^8$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$Z^1$, $Z^2$, $Z^3$, $Z^4$, $Z^5$, $Z^6$, $Z^7$ and $Z^8$ are each independently selected from the group consisting of —C=, —C=C—, —O—, —N=, —N— or —S— which may further be substituted by 1 to 5 $A^m$ groups;

m is an integer from 1 to 5;

X is selected from an optionally substituted $C_1$-$C_6$-alkyl, $C_2$-$C_6$-alkynyl, O—$C_0$-$C_6$-alkyl, $C_0$-$C_6$-alkyl-O, O—$C_3$-$C_6$-alkynyl, S—$C_0$-$C_6$-alkyl, $C_0$-$C_6$-alkyl-S, $C_0$-$C_6$-alkyl-S(=O), $C_0$-$C_6$-alkyl-S(=O)$_2$, S(=O)$_2$—$C_0$-$C_6$-alkyl-, $C_0$-$C_6$-alkyl-$NR^9$, $NR^9$—$C_0$-$C_6$-alkyl, $C_0$-$C_6$—$NR^9$S(=O)$_2$, $C_0$-$C_6$-alkyl-S(=O)$_2NR^9$, $C_0$-$C_6$-alkyl-C(=O)—$NR^9$, $C_0$-$C_6$-alkyl-$NR^9$C(=O), $C_0$-$C_6$-alkyl-C(=O)—O—$C_0$-$C_6$-alkyl, $C_0$-$C_6$-alkyl-C(=O)—$NR^9$—$C_0$-$C_6$-alkyl, C(=O)—$C_0$-$C_6$-alkyl or $C_0$-$C_6$-alkyl-C(=O) substituents;

$R^9$ is selected from hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

$B^1$, $B^2$ and $B^3$ are each independently selected from C or N which may further be substituted by $G^q$ groups;

$G^q$ groups are each independently selected from the group consisting of hydrogen, halogen, CN, OH, nitro, an optionally substituted $C_1$-$C_6$-alkyl, $C_1$-$C_6$-alkylhalo, $C_2$-$C_6$-alkynyl, $C_2$-$C_6$-alkenyl, O—$C_1$-$C_6$-alkyl, O—$C_1$-$C_6$-alkylhalo, O—$C_3$-$C_6$-alkynyl, O—$C_3$-$C_6$-alkenyl, O—$C_2$-$C_6$-alkyl-$OR^{10}$, O—$C_3$-$C_7$-cycloalkyl, O—$C_1$-$C_6$-alkyl-heteroaryl, O—$C_1$-$C_6$-alkylaryl, $C_0$-$C_6$-alkyl-$OR^{10}$, $C_3$-$C_7$-cycloalkyl, $C_3$-$C_7$-cycloalkyl-$C_1$-$C_6$-alkyl, O—$C_3$-$C_7$-cycloalkyl-$C_1$-$C_6$-alkyl, O-heteroaryl, heteroaryl, $C_1$-$C_6$-alkyl-heteroaryl, aryl, O-aryl, $C_1$-$C_6$-alkylaryl, $C_1$-$C_6$-alkylhalo-$OR^{10}$, $C_3$-$C_6$-alkynyl-$OR^{10}$, $C_3$-$C_6$-alkenyl-$OR^{10}$, $C_0$-$C_6$-alkyl-S—$R^{10}$, O—$C_2$-$C_6$-alkyl-S—$R^{10}$, $C_0$-$C_6$-alkyl-S(=O)—$R^{10}$, O—$C_2$-$C_6$-alkyl-S(=O)—$R^{10}$, $C_0$-$C_6$-alkyl-S(=O)$_2$—$R^{10}$, O—$C_1$-$C_6$-alkyl-S(=O)$_2$—$R^{10}$, $C_0$-$C_6$-alkyl-$NR^{10}R^{11}$, O—$C_2$-$C_6$-alkyl-$NR^{10}R^{11}$, $C_0$-$C_6$-alkyl-S(=O)$_2NR^{10}R^{11}$, $C_0$-$C_6$-alkyl-$NR^{10}$—S(=O)$_2R^{11}$, O—$C_1$-$C_6$-alkyl-S(=O)$_2$$NR^{10}R^{11}$, O—$C_2$-$C_6$-alkyl-$NR^{10}$—S(=O)$_2R^{11}$, $C_0$-$C_6$-alkyl-C(=O)—$NR^{10}R^{11}$, $C_0$-$C_6$-alkyl-$NR^{10}$C(=O)—$R^{11}$, O—$C_1$-$C_6$-alkyl-C(=O)—$NR^{10}R^{11}$, O—$C_2$-$C_6$-alkyl-$NR^{10}$C(=O)—$R^{11}$, $C_0$-$C_6$-alkyl-OC(=O)—$R^{10}$, $C_0$-$C_6$-alkyl-C(=O)—$OR^{10}$, O—$C_2$-$C_6$-alkyl-OC(=O)—$R^{10}$, O—$C_1$-$C_6$-alkyl-C(=O)—$OR^{10}$, $C_0$-$C_6$-alkyl-C(=O)—$R^{10}$, O—$C_1$-$C_6$-alkyl-C(=O)—$R^{10}$, $C_0$-$C_6$-alkyl-$N^{10}$—C(=O)—$OR^{11}$, $C_0$-$C_6$-alkyl-O—C(=O)—$NR^{10}R^{11}$ or $C_0$-$C_6$-alkyl-$NR^{10}$—C(=O)—$NR^{11}R^{12}$ substituents;

q is an integer from 1 to 5;

$R^{10}$, $R^{11}$ and $R^{12}$ are each independently selected from the group consisting of hydrogen, an optionally substituted $C_1$-$C_6$-alkyl, $C_1$-$C_6$-alkylhalo, $C_2$-$C_6$-alkynyl, $C_2$-$C_6$-alkenyl, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

Any N may be an N-oxide;

The present invention includes both possible stereoisomers and includes not only racemic compounds but the individual enantiomers as well;

provided that:

when X is O, $B^1$, $B^2$ and $B^3$ are each independently selected from C or N, $G^q$ and q are as defined above, W can not be an optionally substituted 3-pyridazinyl or 4-pyrimidinyl;

when X is $CH_2$, $B^1$, $B^2$ and $B^3$ are C and $G^q$ and q are as defined above, W can not be 2-phenyloxazol-4-yl, 4-phenyloxazol-2-yl, 4-(3-(benzyloxy)propyl)-oxazol-2-yl, 4-phenylthiazol-2-yl, 4-methylthiazol-2-yl, benzo[d]oxazol-2-yl or benzo[d]thiazol-2-yl;

when X is $CH_2CH_2$, $B^1$, $B^2$ and $B^3$ are C and $G^q$ and q are as defined above, W can not be 4-imidazolyl.

In a more preferred aspect of formula II

Or a pharmaceutically acceptable salt, hydrate or solvate of such compound

Wherein

W is a heteroaryl selected from the group of formula:

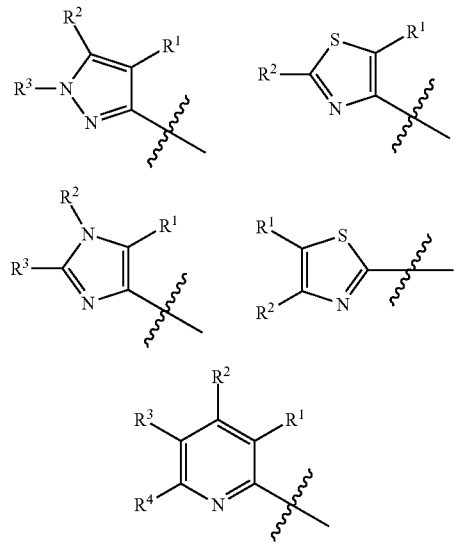

$R^1$, $R^2$, $R^3$ and $R^4$ are each independently selected from the group consisting of hydrogen, halogen, an optionally substituted $C_1$-$C_6$-alkyl, $C_1$-$C_6$-alkylhalo, aryl, $C_0$-$C_6$-alkyl-$OR^5$, $C_0$-$C_6$-alkyl-$NR^5R^6$, $C_0$-$C_6$-alkyl-$NR^5$C(=O)—$R^6$ or $C_0$-$C_6$-alkyl-$NR^5$S(=O)$_2$—$R^6$ substituents;

$R^5$ and $R^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, aryl;

X is selected from an optionally substituted $C_1$-$C_6$-alkyl or $C_1$-$C_6$-alkylhalo;

W' is selected from:

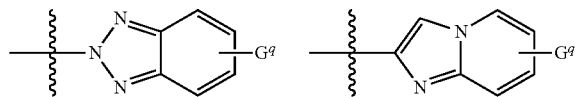

$G^q$ groups are each independently selected from the group consisting of hydrogen, halogen, nitro, an optionally substituted $C_1$-$C_6$-alkyl, $C_1$-$C_6$-alkylhalo, $C_0$-$C_6$-alkyl-$OR^7$, O—$C_0$-$C_6$-alkylaryl, heteroaryl, aryl, $C_0$-$C_6$-alkyl-$NR^7R^8$ or $C_0$-$C_6$-alkyl-$NR^7$—$S(=O)_2R^8$ substituents;

q is an integer from 1 to 5;

$R^7$ and $R^8$ are each independently selected from hydrogen, an optionally substituted $C_1$-$C_6$-alkyl, $C_1$-$C_6$-alkylhalo;

Any N may be an N-oxide;

The present invention includes both possible stereoisomers and includes not only racemic compounds but the individual enantiomers as well.

Specifically preferred compounds are:
2-Methyl-(4-(4-phenyl)but-1-ynyl)thiazole
2-(4-(3-(2-Ethylphenyl)-1,2,4-oxadiazol-5-yl)but-1-ynyl)pyridine
2-(4-(Pyridin-2-yl)but-3-ynyl)isoindoline-1,3-dione
2-(4-(Pyridin-2-yl)but-3-ynyl)phthalazin-1(2H)-one
2-(4-Phenylbut-1-ynyl)quinoline
2-(4-Phenylbut-1-ynyl)pyrimidine
2-(4-Phenylbut-1-ynyl)benzo[d]oxazole
2-(4-(Pyridin-2-yl)but-3-ynyl)benzo[d]oxazole
2-(4-(Pyridin-2-yl)but-3-ynyl)benzo[d]oxazole hydrochloride
2-(4-(3-(4-Fluorophenyl)-1,2,4-oxadiazol-5-yl)but-1-ynyl)pyridine
2-(4-(3-Phenyl)-1,2,4-oxadiazol-5-yl)but-1-ynyl)pyridine
2-Methyl-4-(4-phenylbut-1-ynyl)-1H-imidazole
N-Methyl-N-phenyl-5-(pyridin-2-yl)pent-4-ynamide
N-(4-Fluorophenyl)-N-methyl-5-(pyridin-2-yl)pent-4-ynamide
2-(4-(2-Phenylthiazol-4-yl)but-1-ynyl)pyridine
2-(4-(3-o-Tolyl)-1,2,4-oxadiazol-5-yl)but-1-ynyl)pyridine
2-(4-(3-benzyl-1,2,4-oxadiazol-5-yl)but-1-ynyl)pyridine
2-(4-(3-(2-Fluorobenzyl)-1,2,4-oxadiazol-5-yl)but-1-ynyl)pyridine
2-(4-(3-(2-Methylbenzyl)-1,2,4-oxadiazol-5-yl)but-1-ynyl)pyridine
2-(4-(3-(4-Fluorobenzyl)-1,2,4-oxadiazol-5-yl)but-1-ynyl)pyridine
2-(4-(3-(4-Methoxybenzyl)-1,2,4-oxadiazol-5-yl)but-1-ynyl)pyridine
2-(4-(3-Isopropyl-1,2,4-oxadiazol-5-yl)but-1-ynyl)pyridine
2-(4-(3-Butyl-1,2,4-oxadiazol-5-yl)but-1-ynyl)pyridine
2-(4-(3-(3-Fluorobenzyl)-1,2,4-oxadiazol-5-yl)but-1-ynyl)pyridine
2-(4-(3-(3-Methoxybenzyl)-1,2,4-oxadiazol-5-yl)but-1-ynyl)pyridine
2-(4-(3-(2-Fluorophenyl)-1,2,4-oxadiazol-5-yl)but-1-ynyl)pyridine
2-(4-(3-(3-Fluorophenyl)-1,2,4-oxadiazol-5-yl)but-1-ynyl)pyridine
5-Chloro-(2-(4-pyridin-2-yl)but-3-ynyl)benzo[d]oxazole
5-Methyl-(2-(4-pyridin-2-yl)but-3-ynyl)benzo[d]oxazole
6-Methyl-(2-(4-pyridin-2-yl)but-3-ynyl)benzo[d]oxazole
4-Methyl-(2-(4-pyridin-2-yl)but-3-ynyl)benzo[d]oxazole
2-(4-(2-Methylthiazol-4-yl)but-3-ynyl)benzo[d]oxazole
2-(4-(5-Phenyl-2H-tetrazol-2-yl)but-1-ynyl)pyridine
N-(4-Fluorophenyl)-5-(pyridine-2-yl)pent-4-ynamide
2-(4-(Pyridin-2-yl)but-3-ynyl)benzo[d]thiazole
6-Chloro-(2-(4-pyridin-2-yl)but-3-ynyl)benzo[d]oxazole
5-Fluoro-(2-(4-pyridin-2-yl)but-3-ynyl)benzo[d]oxazole
2-(6-(4-Fluorophenyl)hexa-1,5-diynyl)pyridine
2-(4-(3-(2-Methoxyphenyl)-1,2,4-oxadiazol-5-yl)but-1-ynyl)pyridine
2-(4-(3-(3-Methoxyphenyl)-1,2,4-oxadiazol-5-yl)but-1-ynyl)pyridine
2-(4-(3-(4-Methoxyphenyl)-1,2,4-oxadiazol-5-yl)but-1-ynyl)pyridine
2-(4-(3-m-Tolyl-1,2,4-oxadiazol-5-yl)but-1-ynyl)pyridine
2-(4-(3-p-Tolyl-1,2,4-oxadiazol-5-yl)but-1-ynyl)pyridine
2-(4-(3-(2-Chlorophenyl)-1,2,4-oxadiazol-5-yl)but-1-ynyl)pyridine
2-(4-(3-(3-Chlorophenyl)-1,2,4-oxadiazol-5-yl)but-1-ynyl)pyridine
2-(4-(3-(4-Chlorophenyl)-1,2,4-oxadiazol-5-yl)but-1-ynyl)pyridine
2-(4-(3-(2,6-Dimethylphenyl)-1,2,4-oxadiazol-5-yl)but-1-ynyl)pyridine
2-(4-(3-(2-Trifluoromethyl)phenyl)-1,2,4-oxadiazol-5-yl)but-1-ynyl)pyridine
2-(4-(3-(Naphthalen-1-yl)-1,2,4-oxadiazol-5-yl)but-1-ynyl)pyridine
2-(4-(3-(Naphthalen-2-yl)-1,2,4-oxadiazol-5-yl)but-1-ynyl)pyridine
2-(4-(3-(2,3-dimethylphenyl)-1,2,4-oxadiazol-5-yl)but-1-ynyl)pyridine
2-(4-(3-(2,5-Dichlorophenyl)-1,2,4-oxadiazol-5-yl)but-1-ynyl)pyridine
2-(4-(3-(2,5-dimethylphenyl)-1,2,4-oxadiazol-5-yl)but-1-ynyl)pyridine
2-(4-(3-(2,6-Dichlorophenyl)-1,2,4-oxadiazol-5-yl)but-1-ynyl)pyridine
2-(4-(3-(2,3-dichlorophenyl)-1,2,4-oxadiazol-5-yl)but-1-ynyl)pyridine
2-(4-(3-(2,4-dichlorophenyl)-1,2,4-oxadiazol-5-yl)but-1-ynyl)pyridine
2-(4-(3-(2-chloro-6-methylphenyl)-1,2,4-oxadiazol-5-yl)but-1-ynyl)pyridine
2-(4-(3-(5-Fluoro-2-methylphenyl)-1,2,4-oxadiazol-5-yl)but-1-ynyl)pyridine
2-(4-(3-(5-Chloro-2-methylphenyl)-1,2,4-oxadiazol-5-yl)but-1-ynyl)pyridine
2-(4-(3-(2-(Trifluoromethoxy)phenyl)-1,2,4-oxadiazol-5-yl)but-1-ynyl)pyridine
6-Fluoro-2-(4-(pyridin-2-yl)but-3-ynyl)benzo[d]oxazole
7-Chloro-2-(4-(pyridin-2-yl)but-3-ynyl)benzo[d]oxazole
7-Fluoro-2-(4-(pyridin-2-yl)but-3-ynyl)benzo[d]oxazole
2-(4-(5-Phenyloxazol-2-yl)but-1-ynyl)pyridine
2-(4-(3-(3-Chloro-2-methylphenyl)-1,2,4-oxadiazol-5-yl)but-1-ynyl)pyridine
2-(4-(Pyridin-2-yl)but-3-ynyl)benzo[d]oxazol-4-ol
2-(4-(5-Fluoropyridin-2-yl)but-3-ynyl)benzo[d]oxazole
4-Methoxy-2-(4-(pyridin-2-yl)but-3-ynyl)benzo[d]oxazole
2-(4-(Pyridin-2-yl)but-3-ynyl)oxazolo[5,4-b]pyridine
7-Chloro-5-fluoro-2-(4-(pyridin-2-yl)but-3-ynyl)benzo[d]oxazole
2-(4-(Pyridin-2-yl)but-3-ynyl)oxazolo[4,5-b]pyridine
2-(4-(Pyridin-2-yl)but-3-ynyl)benzo[d]oxazole-5-carbonitrile
7-Chloro-5-fluoro-2-(4-(2-methylthiazol-4-yl)but-3-ynyl)benzo[d]oxazole
7-(Trifluoromethyl)-2-(4-(pyridin-2-yl)but-3-ynyl)benzo[d]oxazole 7-Bromo-5-fluoro-2-(4-(pyridin-2-yl)but-3-ynyl)benzo[d]oxazole
5-Fluoro-7-phenyl-2-(4-(pyridin-2-yl)but-3-ynyl)benzo[d]oxazole
2-(4-(2-Chloropyrimidin-4-yl)but-3-ynyl)benzo[d]oxazole
2-Chloro-4-(4-phenylbut-1-ynyl)pyrimidine
4-Bromo-2-(4-(pyridin-2-yl)but-3-ynyl)benzo[d]oxazole
4-Phenyl-2-(4-(pyridin-2-yl)but-3-ynyl)benzo[d]oxazole
4-Chloro-2-(4-(pyridin-2-yl)but-3-ynyl)benzo[d]oxazole
5,7-Difluoro-2-(4-(pyridin-2-yl)but-3-ynyl)benzo[d]oxazole
4-Fluoro-2-(4-(pyridin-2-yl)but-3-ynyl)benzo[d]oxazole
7-Methyl-2-(4-(pyridin-2-yl)but-3-ynyl)benzo[d]oxazole
2-(4-(Pyridin-2-yl)but-3-ynyl)benzo[d]oxazole-7-carbonitrile
7-Chloro-4-fluoro-2-(4-(pyridin-2-yl)but-3-ynyl)benzo[d]oxazole
7-Methoxy-2-(4-(pyridin-2-yl)but-3-ynyl)benzo[d]oxazole
7-Isopropyl-2-(4-(pyridin-2-yl)but-3-ynyl)benzo[d]oxazole
4,7-Difluoro-2-(4-(pyridin-2-yl)but-3-ynyl)benzo[d]oxazole
7-Fluoro-4-(trifluoromethyl)-2-(4-(pyridin-2-yl)but-3-ynyl)benzo[d]oxazole
2-(4-(Pyrimidin-4-yl)but-3-ynyl)benzo[d]oxazole
N-(3-Chlorophenyl)-N-methyl-5-(pyridin-2-yl)pent-4-ynamide
7-Chloro-4-methyl-2-(4-(pyridin-2-yl)but-3-ynyl)benzo[d]thiazole
4-Fluoro-2-(4-(pyridin-2-yl)but-3-ynyl)benzo[d]thiazole
4,7-Dimethyl-2-(4-(pyridin-2-yl)but-3-ynyl)benzo[d]thiazole
4-Methyl-2-(4-(pyridin-2-yl)but-3-ynyl)benzo[d]thiazole
5-Fluoro-2-(4-(pyridin-2-yl)but-3-ynyl)benzo[d]thiazole
4-Chloro-2-(4-(pyridin-2-yl)but-3-ynyl)benzo[d]thiazole
N-(2-Chlorophenyl)-N-methyl-5-(pyridin-2-yl)pent-4-ynamide
1-Methyl-2-(4-(pyridin-2-yl)but-3-ynyl)-1H-benzo[d]imidazole
2-(4-(Pyridin-2-yl)but-3-ynyl)-2H-indazole
1-(4-(pyridin-2-yl)but-3-ynyl)-1H-indazole
2-(4-(5-Phenyl-1H-pyrazol-1-yl)but-1-ynyl)pyridine
2-(4-(3-Phenylisoxazol-5-yl)but-1-ynyl)pyridine
2-(4-(2-Methylthiazol-4-yl)but-3-ynyl)benzo[d]thiazole
2-(4-(5-Fluoropyridin-2-yl)but-3-ynyl)benzo[d]thiazole
2-(4-(6-Methylpyridin-2-yl)but-3-ynyl)benzo[d]thiazole
2-(4-(6-Chloropyridin-2-yl)but-3-ynyl)benzo[d]thiazole
7-Chloro-4-fluoro-2-(4-(pyridin-2-yl)but-3-ynyl)benzo[d]thiazole
2-(4-(6-Fluoropyridin-2-yl)but-3-ynyl)benzo[d]thiazole
2-(4-(Pyridin-2-yl)but-3-ynyl)quinoline
2-(4-(4-Phenyl-1H-pyrazol-1-yl)but-1-ynyl)pyridine
7-Chloro-2-(4-(pyridin-2-yl)but-3-ynyl)-2H-indazole
2-(6-(Pyridin-2-yl)hex-5-ynyl)-2H-indazole
1-(6-(pyridin-2-yl)hex-5-ynyl)-1H-indazole
2-(4-(6-(Fluoromethyl)pyridin-2-yl)but-3-ynyl)quinoline
2-(4-(6-Methylpyridin-2-yl)but-3-ynyl)quinoline
2-(4-(6-(Fluoromethyl)pyridin-2-yl)but-3-ynyl)quinoxaline
2-(4-(6-(Fluoromethyl)pyridin-2-yl)but-3-ynyl)-2H-indazole
2-(4-(4-(4-Fluorophenyl)-1H-pyrazol-1-yl)but-1-ynyl)pyridine
2-(4-(4-o-Tolyl-1H-pyrazol-1-yl)but-1-ynyl)pyridine
2-(Fluoromethyl)-6-(4-(4-o-tolyl-1H-pyrazol-1-yl)but-1-ynyl)pyridine
2-(Fluoromethyl)-6-(4-(4-(4-fluorophenyl)-1H-pyrazol-1-yl)but-1-ynyl)pyridine
6-Fluoro-2-(4-(6-(fluoromethyl)pyridin-2-yl)but-3-ynyl)quinoxaline
6,7-Difluoro-2-(4-(6-(fluoromethyl)pyridin-2-yl)but-3-ynyl)quinoxaline
4-Fluoro-2-(4-(6-(fluoromethyl)pyridin-2-yl)but-3-ynyl)-2H-indazole
4-Chloro-2-(4-(pyridin-2-yl)but-3-ynyl)-2H-indazole
6-Fluoro-2-(4-(6-(fluoromethyl)pyridin-2-yl)but-3-ynyl)-2H-indazole
4-Chloro-2-(4-(6-(fluoromethyl)pyridin-2-yl)but-3-ynyl)-2H-indazole
7-Fluoro-2-(4-(6-(fluoromethyl)pyridin-2-yl)but-3-ynyl)-2H-indazole
2-(4-(3-Phenyl-1H-pyrazol-1-yl)but-1-ynyl)pyridine
2-(4-(3-(4-Fluorophenyl)isoxazol-5-yl)but-1-ynyl)pyridine
2-(4-(5-(4-Fluorophenyl)-1H-pyrazol-1-yl)but-1-ynyl)pyridine
2-(1-Fluoro-4-(pyridin-2-yl)but-3-ynyl)quinoxaline
2-(4-(3-Methyl-4-phenyl-1H-pyrazol-1-yl)but-1-ynyl)pyridine
2-(4-(5-methyl-4-phenyl-1H-pyrazol-1-yl)but-1-ynyl)pyridine
2-(4-(4-(4-Fluorophenyl)-1H-1,2,3-triazol-1-yl)but-1-ynyl)pyridine
2-(4-(6-(Fluoromethyl)pyridin-2-yl)but-3-ynyl)-3-methylquinoxaline
2-(4-(Pyridin-2-yl)but-3-ynyl)isoquinolin-1(2H)-one
2,6-Dimethoxy-N-methyl-N-(4-(pyridin-2-yl)but-3-ynyl)benzamide
2,6-Difluoro-N-methyl-N-(4-(pyridin-2-yl)but-3-ynyl)benzamide
5-(6-(Fluoromethyl)pyridin-2-yl)-N-(4-fluorophenyl)pent-4-ynamide
2-(4-(Pyridin-2-yl)but-3-ynyl)isoindolin-1-one
N-(2-Fluorophenyl)-5-(pyridin-2-yl)pent-4-ynamide
N-(3-Fluorophenyl)-5-(pyridin-2-yl)pent-4-ynamide
N-(4-Fluoro-2-methyl-phenyl)-5-(pyridin-2-yl)pent-4-ynamide
2,6-Dichloro-N-(4-(6-(fluoromethyl)pyridin-2-yl)but-3-ynyl)benzamide
2-Chloro-N-(4-(6-(fluoromethyl)pyridin-2-yl)but-3-ynyl)benzamide
2-Chloro-N-(4-(6-(fluoromethyl)pyridin-2-yl)but-3-ynyl)benzenesulfonamide
2-Chloro-N-(4-(pyridin-2-yl)but-3-ynyl)benzenesulfonamide
5-(6-(Fluoromethyl)pyridin-2-yl)-N-(4-fluoro-2-methylphenyl)pent-4-ynamide
5-(4-Fluoro-phenyl)-1-(4-pyridin-2-yl-but-3-ynyl)-1H-pyridin-2-one
2-(Fluoromethyl)-6-(4-(4-(4-fluorophenyl)-1H-1,2,3-triazol-1-yl)but-1-ynyl)pyridine
2-(4-(4-(4-Fluorophenyl)-2H-1,2,3-triazol-2-yl)but-1-ynyl)pyridine
2-(Fluoromethyl)-6-(4-(4-(4-fluorophenyl)-2H-1,2,3-triazol-2-yl)but-1-ynyl)pyridine
2-(4-(4-(4-Fluorophenyl)-5-methyl-2H-1,2,3-triazol-2-yl)but-1-ynyl)pyridine
2-(4-(4-(4-Fluorophenyl)-5-methyl-1H-1,2,3-triazol-1-yl)but-1-ynyl)pyridine
2-(4-(4-(2-Chlorophenyl)-2H-1,2,3-triazol-2-yl)but-1-ynyl)pyridine
1-(4-(4-(2-Chlorophenyl)-1H-1,2,3-triazol-1-yl)but-1-ynyl)pyridine
2-(4-(6-(Fluoromethyl)pyridin-2-yl)but-3-ynyl)-1-methyl-1H-benzo[d]imidazole
7-Chloro-2-(4-(6-(fluoromethyl)pyridin-2-yl)but-3-ynyl)-1-methyl-1H-benzo[d]imidazole 7-Chloro-1-methyl-2-(4-(pyridin-2-yl)but-3-ynyl)-1H-benzo[d]imidazole
4,6-Difluoro-2-(4-(6-(fluoromethyl)pyridin-2-yl)but-3-ynyl)-1-methyl-1H-benzo[d]imidazole
1-Isopropyl-2-(4-(pyridin-2-yl)but-3-ynyl)-1H-benzo[d]imidazole
1-Phenethyl-2-(4-(pyridin-2-yl)but-3-ynyl)-1H-benzo[d]imidazole
1-Benzyl-2-(4-(pyridin-2-yl)but-3-ynyl)-1H-benzo[d]imidazole
5-Fluoro-1-methyl-2-(4-(pyridin-2-yl)but-3-ynyl)-1H-benzo[d]imidazole
1-(4-(Pyridin-2-yl)but-3-ynyl)pyridin-2(1H)-one
3-Methoxy-N-methyl-N-(4-(pyridin-2-yl)but-3-ynyl)benzamide
3-Fluoro-N-methyl-N-(4-(pyridin-2-yl)but-3-ynyl)benzamide
N-Methyl-2-phenyl-N-(4-(pyridin-2-yl)but-3-ynyl)acetamide
N-Methyl-N-(4-(pyridin-2-yl)but-3-ynyl)-2-(trifluoromethyl)benzamide
4-Fluoro-N-methyl-N-(4-(pyridin-2-yl)but-3-ynyl)benzamide
2-Chloro-N-methyl-N-(4-(pyridin-2-yl)but-3-ynyl)benzamide
3-Chloro-N-methyl-N-(4-(pyridin-2-yl)but-3-ynyl)benzamide
4-Fluoro-N-methyl-N-(4-(pyridin-2-yl)but-3-ynyl)benzenesulfonamide
2-Chloro-N-methyl-N-(4-(pyridin-2-yl)but-3-ynyl)benzenesulfonamide
2-Chloro-N-(4-(6-(fluoromethyl)pyridin-2-yl)but-3-ynyl)-N-methylbenzamide
2-Chloro-N-(4-(6-(fluoromethyl)pyridin-2-yl)but-3-ynyl)-N-methylbenzene sulfonamide
2,6-Dichloro-N-(4-(6-(fluoromethyl)pyridin-2-yl)but-3-ynyl)-N-methylbenzamide
N-Methyl-N-(4-(pyridin-2-yl)but-3-ynyl)benzamide
N,2-Dimethyl-N-(4-(pyridin-2-yl)but-3-ynyl)benzamide
2-Fluoro-N-methyl-N-(4-(pyridin-2-yl)but-3-ynyl)benzamide
N,4-Dimethyl-N-(4-(pyridin-2-yl)but-3-ynyl)benzamide
N,3-Dimethyl-N-(4-(pyridin-2-yl)but-3-ynyl)benzamide
2-Methoxy-N-methyl-N-(4-(pyridin-2-yl)but-3-ynyl)benzamide
2,3-Difluoro-N-methyl-N-(4-(pyridin-2-yl)but-3-ynyl)benzamide
2,6-Dichloro-N-methyl-N-(4-(pyridin-2-yl)but-3-ynyl)benzamide
N,3,5-Trimethyl-N-(4-(pyridin-2-yl)but-3-ynyl)isoxazole-4-sulfonamide
N-(4-(Pyridin-2-yl)but-3-ynyl)benzo[d]thiazol-2-amine
1-Methyl-3-(5-(pyridin-2-yl)pent-4-ynyl)-1H-benzo[d]imidazol-2(3H)-one
(3-Fluoropyridin-2-yl)but-3-ynyl)benzo[d]oxazole
2-(4-(2-Methyl-1H-imidazol-4-yl)but-3-ynyl)benzo[d]oxazole
2-(4-(1,2-Dimethyl-1H-imidazol-4-yl)but-3-ynyl)benzo[d]oxazole
4-(Pyridin-2-yl)but-3-ynyl 2-chlorobenzoate
4-(Pyridin-2-yl)but-3-ynyl 3-chlorobenzoate
3-Chlorophenyl 5-(pyridin-2-yl)pent-4-ynoate
3-Chlorophenyl 5-(3-fluoropyridin-2-yl)pent-4-ynoate
2-Chlorophenyl 5-(pyridin-2-yl)pent-4-ynoate
2-Chlorophenyl 5-(2-methylthiazol-4-yl)pent-4-ynoate
2-(4-(6-(Fluoromethyl)pyridin-2-yl)but-3-ynyl)benzo[d]thiazole
2-(5-(Pyridin-2-yl)pent-4-ynyl)isoindoline-1,3-dione
2-(6-(Pyridin-2-yl)hex-5-ynyl)phthalazin-1(2H)-one
1-Methyl-3-(5-(pyridin-2-yl)pent-4-ynyl)-1H-benzo[d]imidazol-2(3H)-one
N-(4-Chlorophenyl)-5-(pyridin-2-yl)pent-4-ynamide
N-(3-Chlorophenyl)-5-(pyridin-2-yl)pent-4-ynamide
N-(2,4-Difluorophenyl)-5-(pyridin-2-yl)pent-4-ynamide
2-(4-(Pyridin-2-yl)but-3-ynyl)-imidazo[1,2-a]pyridine
8-Methyl-2-(4-(pyridin-2-yl)but-3-ynyl)-imidazo[1,2-a]pyridine
5-Methyl-2-(4-(pyridin-2-yl)but-3-ynyl)-imidazo[1,2-a]pyridine
5-Phenyl-2-(4-(pyridin-2-yl)but-3-ynyl)-imidazo[1,2-a]pyridine
2-(4-(2-Methylthiazol-4-yl)but-3-ynyl)imidazo[1,2-a]pyridine
6-Fluoro-2-(4-(pyridin-2-yl)but-3-ynyl)-imidazo[1,2-a]pyridine
2-(4-(5-Fluoropyridin-2-yl)but-3-ynyl)-imidazo[1,2-a]pyridine
2-(4-(Pyridin-2-yl)but-3-ynyl)-2H-benzo[d][1,2,3]triazole
1-(4-(pyridin-2-yl)but-3-ynyl)-1H-benzo[d][1,2,3]triazole
2-(4-(Pyridin-2-yl)but-3-ynyl)-2H-benzo[d][1,2,3]triazole hydrochloride
2-(5-(Pyridin-2-yl)pent-4-ynyl)-2H-benzo[d][1,2,3]triazole
1-(5(Pyridin-2-yl)pent-4-ynyl)-1H-benzo[d][1,2,3]triazole
1-(6-(Pyridin-2-yl)hex-5-ynyl)-1H-benzo[d][1,2,3]triazole
2-(6-(pyridin-2-yl)hex-5-ynyl)-2H-benzo[d][1,2,3]triazole
5-Fluoro-2-(4-(pyridin-2-yl)but-3-ynyl)-2H-benzo[d][1,2,3]triazole
2-(4-(6-(Fluoromethyl)pyridin-2-yl)but-3-ynyl)-2H-benzo[d][1,2,3]triazole
2-(4-(6-(Fluoromethyl)pyridin-2-yl)but-3-ynyl)-2H-benzo[d][1,2,3]triazole hydrochloride
4,6-Difluoro-2-(4-(6-(fluoromethyl)pyridin-2-yl)but-3-ynyl)-2H-benzo[d][1,2,3]triazole
4,6-Difluoro-2-(4-(6-(fluoromethyl)pyridin-2-yl)but-3-ynyl)-2H-benzo[d][1,2,3]triazole hydrochloride
4,5-Difluoro-2-(4-(6-(fluoromethyl)pyridin-2-yl)but-3-ynyl)-2H-benzo[d][1,2,3]triazole
4,5-Difluoro-2-(4-(6-(fluoromethyl)pyridin-2-yl)but-3-ynyl)-2H-benzo[d][1,2,3]triazole hydrochloride
2-(4-(6-(Difluoromethyl)pyridin-2-yl)but-3-ynyl)-2H-benzo[d][1,2,3]triazole
4,6-Difluoro-2-(4-(pyridin-2-yl)but-3-ynyl)-2H-benzo[d][1,2,3]triazole
4,5-Difluoro-2-(4-(pyridin-2-yl)but-3-ynyl)-2H-benzo[d][1,2,3]triazole
2-(4-(6-Methylpyridin-2-yl)but-3-ynyl)-2H-benzo[d][1,2,3]triazole
2-(4-(3-Fluoropyridin-2-yl)but-3-ynyl)-2H-benzo[d][1,2,3]triazole
5-Fluoro-2-(4-(6-(fluoromethyl)pyridin-2-yl)but-3-ynyl)-2H-benzo[d][1,2,3]triazole
2-(4-(2-Methylthiazol-4-yl)but-3-ynyl)-2H-benzo[d][1,2,3]triazole
4-Chloro-2-(4-(pyridin-2-yl)but-3-ynyl)-2H-benzo[d][1,2,3]triazole
4-Chloro-2-(4-(6-(fluoromethyl)pyridin-2-yl)but-3-ynyl)-2H-benzo[d][1,2,3]triazole
5,6-Difluoro-2-(4-(pyridin-2-yl)but-3-ynyl)-2H-benzo[d][1,2,3]triazole
5,6-Difluoro-2-(4-(6-(fluoromethyl)pyridin-2-yl)but-3-ynyl)-2H-benzo[d][1,2,3]triazole
4-Chloro-2-(4-(1-methyl-1H-pyrazol-3-yl)but-3-ynyl)-2H-benzo[d][1,2,3]triazole 6-(4-(4,6-Difluoro-2H-benzo[d][1,2,3]triazol-2-yl)but-1-ynyl)pyridin-2-amine
2-(4-(2H-Benzo[d][1,2,3]triazol-2-yl)but-1-ynyl)-6-methylpyridin-3-amine
4-Nitro-2-(4-(pyridin-2-yl)but-3-ynyl)-2H-benzo[d][1,2,3]triazole
2-(4-(6-(Fluoromethyl)pyridin-2-yl)but-3-ynyl)-4-nitro-2H-benzo[d][1,2,3]triazole
2-(4-(Pyridin-2-yl)but-3-ynyl)-2H-benzo[d][1,2,3]triazol-4-amine
4-Methyl-2-(4-(pyridin-2-yl)but-3-ynyl)-2H-benzo[d][1,2,3]triazole
2-(4-(6-(Fluoromethyl)pyridin-2-yl)but-3-ynyl)-4-methyl-2H-benzo[d][1,2,3]triazole
2-(4-(6-(Fluoromethyl)pyridin-2-yl)but-3-ynyl)-5-methyl-2H-benzo[d][1,2,3]triazole
5-Methyl-2-(4-(pyridin-2-yl)but-3-ynyl)-2H-benzo[d][1,2,3]triazole
6-(4-(2H-Benzo[d][1,2,3]triazol-2-yl)but-1-ynyl)-N-methylpyridin-2-amine
N-(6-(4-(2H-Benzo[d][1,2,3]triazol-2-yl)but-1-ynyl)pyridin-2-yl)acetamide
6-(4-(2H-Benzo[d][1,2,3]triazol-2-yl)but-1-ynyl)-N-ethylpyridin-2-amine
N-(6-(4-(2H-Benzo[d][1,2,3]triazol-2-yl)but-1-ynyl)pyridin-2-yl)methylsulfonamide
N-(6-(4-(2H-Benzo[d][1,2,3]triazol-2-yl)but-1-ynyl)pyridin-2-yl)formamide
4-Chloro-2-(4-(1,2-dimethyl-1H-imidazol-4-yl)but-3-ynyl)-2H-benzo[d][1,2,3]triazole
4,5-Dimethyl-2-(4-(pyridin-2-yl)but-3-ynyl)-2H-benzo[d][1,2,3]triazole
2-(4-(6-(Fluoromethyl)pyridin-2-yl)but-3-ynyl)-4,5-dimethyl-2H-benzo[d][1,2,3]triazole
2-(4-(6-Chloropyridin-2-yl)but-3-ynyl)-2H-benzo[d][1,2,3]triazole
2-(4-(6-(1-Fluoroethyl)pyridin-2-yl)but-3-ynyl)-2H-benzo[d][1,2,3]triazole
2-(4-(4,5-Dimethylthiazol-2-yl)but-3-ynyl)-2H-benzo[d][1,2,3]triazole
2-(4-(Pyridin-2-yl)but-3-ynyl)-[1,2,4]triazolo[4,3-a]pyridin-3(2H)-one
2-(4-(6-(Fluoromethyl)pyridin-2-yl)but-3-ynyl)-[1,2,4]triazolo[4,3-a]pyridin-3(2H)-one
2-(4-(4-Methylthiazol-2-yl)but-3-ynyl)-2H-benzo[d][1,2,3]triazole
8-Chloro-2-(4-(6-(fluoromethyl)pyridin-2-yl)but-3-ynyl)-imidazo[1,2-a]pyridine
8-Chloro-2-(4-(pyridin-2-yl)but-3-ynyl)-imidazo[1,2-a]pyridine
6-Fluoro-2-(4-(6-(fluoromethyl)pyridin-2-yl)but-3-ynyl)H-imidazo[1,2-a]pyridine
6-Fluoro-2-(4-(2-(fluoromethyl)thiazol-4-yl)but-3-ynyl)-imidazo[1,2-a]pyridine
8-Bromo-2-(4-(6-(fluoromethyl)pyridin-2-yl)but-3-ynyl)-imidazo[1,2-a]pyridine
8-(Benzyloxy)-2-(4-(6-(fluoromethyl)pyridin-2-yl)but-3-ynyl)-imidazo[1,2-a]pyridine
2-(4-(6-(Fluoromethyl)pyridin-2-yl)but-3-ynyl)-8-phenyl-imidazo[1,2-a]pyridine
6,8-Difluoro-2-(4-(pyridin-2-yl)but-3-ynyl)-imidazo[1,2-a]pyridine
6,8-Difluoro-2-(4-(6-(fluoromethyl)pyridin-2-yl)but-3-ynyl)H-imidazo[1,2-a]pyridine The present invention relates to the pharmaceutically acceptable acid addition salts of compounds of the formula (I) or pharmaceutically acceptable carriers or excipients.

The present invention relates to a method of treating or preventing a condition in a mammal, including a human, the treatment or prevention of which is affected or facilitated by the neuromodulatory effect of mGluR5 antagonists.

The present invention relates to a method useful for treating or preventing peripheral and central nervous system disorders selected from the group consisting of: substance tolerance or dependence, anxiety disorders, depression, mood disorders, psychiatric disease such as psychosis, inflammatory or neuropathic pain, Fragile X syndrome, autism, memory deficits, Alzheimer's disease, Parkinson's disease, migraine, ischemia, drug abuse and addiction.

The present invention relates to pharmaceutical compositions which provide from about 0.01 to 1000 mg of the active ingredient per unit dose. The compositions may be administered by any suitable route. For example orally in the form of capsules, etc. . . . , parenterally in the form of solutions for injection, topically in the form of onguents or lotions, ocularly in the form of eye-drops, rectally in the form of suppositories, intranasally or transcutaneously in the form of delivery system like patches.

The pharmaceutical formulations of the invention may be prepared by conventional methods in the art; the nature of the pharmaceutical composition employed will depend on the desired route of administration. The total daily dose usually ranges from about 0.05-2000 mg.

Methods of Synthesis

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (Green T. W. and Wuts P. G. M. (1991) *Protecting Groups in Organic Synthesis*, John Wiley et Sons). These groups are removed at a convenient stage of the compound synthesis using methods that are readily apparent to those skilled in the art. The selection of process as well as the reaction conditions and order of their execution shall be consistent with the preparation of compounds of formula I.

The compound of formula I may be represented as a mixture of enantiomers, which may be resolved into the individual pure R- or S-enantiomers. If for instance, a particular enantiomer of the compound of formula I is desired, it may be prepared by asymmetric synthesis, or by derivation with a chiral auxiliary, where the resulting diastereomeric mixture is separated and the auxiliary group cleaved to provided the pure desired enantiomers. Alternatively, where the molecule contains a basic functional group such as amino, or an acidic functional group such as carboxyl, this resolution may be conveniently performed by fractional crystallization from various solvents, of the salts of the compounds of formula I with optical active acid or by other methods known in the literature, e.g. chiral column chromatography.

Resolution of the final product, an intermediate or a starting material may be performed by any suitable method known in the art as described by Eliel E. L., Wilen S. H. and Mander L. N. (1984) *Stereochemistry of Organic Compounds*, Wiley-Interscience.

Many of the heterocyclic compounds of formula I can be prepared using synthetic routes well known in the art (Katrizky A. R. and Rees C. W. (1984) *Comprehensive Heterocyclic Chemistry*, Pergamon Press).

The product from the reaction can be isolated and purified employing standard techniques, such as extraction, chromatography, crystallization, distillation, and the like.

The compounds of Formula I may be prepared by general route of synthesis as disclosed in the following methods.

The compounds of formula II-B1 wherein W and $G^1$ are as described above, $B^1$ is N and X is $C_1$-$C_6$ alkyl may be prepared according to the synthetic sequences illustrated in the Schemes 1-3.

Scheme 1

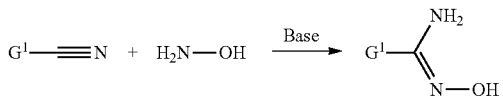

In the turn, an nitrile derivative (for example 4-Fluorobenzonitrile) is reacted with hydroxylamine under neutral or basic conditions such as triethylamine, diisopropyl-ethylamine, sodium carbonate, sodium hydroxyde and the like in a suitable solvent (e.g. methyl alcohol, ethyl alcohol). The reaction typically proceeds by allowing the reaction temperature to heat slowly from ambient temperature to a temperature range of 70° C. up to 80° C. for a time in the range of about 1 hour up to 48 hours inclusive (see for example Lucca, George V. De; Kim, Ui T.; Liang, Jing; Cordova, Beverly; Klabe, Ronald M.; et al; J. Med. Chem.; EN; 41; 13; 1998; 2411-2423, Lila, Christine; Gloanec, Philippe; Cadet, Laurence; Herve, Yolande; Fournier, Jean; et al.; Synth. Commun.; EN; 28; 23; 1998; 4419-4430 and see: Sendzik, Martin; Hui, Hon C.; Tetrahedron Lett.; EN; 44; 2003; 8697-8700 and references therein for reaction under neutral conditions).

Scheme 2

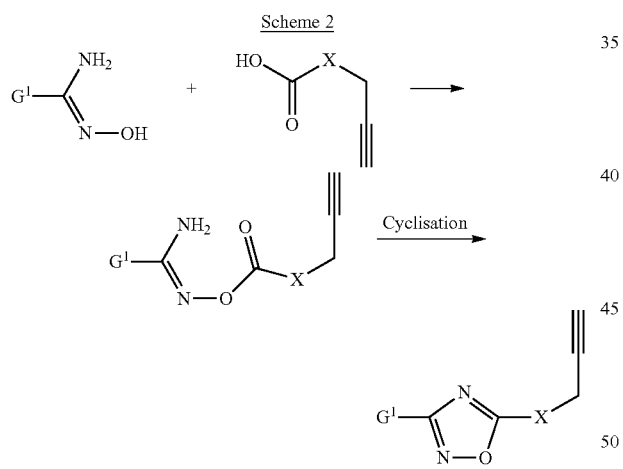

The substituted amidoxime derivative (described in the scheme 1) may be converted to an acyl-amidoxime derivative using the approach outlined in the Scheme 2. The coupling reaction may be promoted by coupling agent known in the art of organic synthesis such as EDCI (1-(3-Dimethylaminopropyl)-3-ethylcarbodiimide), DCC (N,N'-Dicyclohexyl-carbodiimide), in a suitable solvent (e.g. tetrahydrofuran, dichloromethane, N,N-dimethylformamide, dioxane) Typically, a co-catalyst such as DMAP (N,N-dimethylaminopyridine) will also be present in the reaction mixture. The reaction typically proceeds at ambient temperature for a time in the range of about 4 hours up to 12 hours to produce the intermediate acyl-amidoxime. The cyclisation reaction may be effected thermally in a temperature range of about 80° C. up to about 150° C. for a time in the range of about 2 hours up to 12 hours (see for example Suzuki, Takeshi; Iwaoka, Kiyoshi; Imanishi, Naoki; Nagakura, Yukinori; Miyata, Keiji; et al.; Chem. Pharm. Bull; 47; 1; 1999; 120-122). The product from the reaction can be isolated and purified employing standard techniques, such as extraction, chromatography, crystallization, distillation, and the like.

The scheme 3 illustrates the preparation of compounds of formula II-B1 by reacting an alkyne derivative (described in the scheme 2), with a substituted 5-, 6-heterocyclic containing a N adjacent to the leaving group $L_1$ for example 2-iodopyridine. Thus in Scheme 3, $L_1$ includes halides such as Cl, Br, I or trifluoromethanesulfonyl and paratoluenesulfonyl. This general route of synthesis has been described in J. Med. Chem. 2000, 43, 4288-4312.

Scheme 3

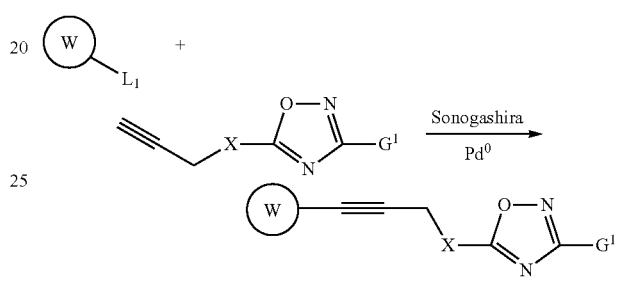

This palladium catalyzed C—C coupling reaction requires a catalyst such as $PdCl_2(PPh_3)_2$, $Pd(PPh_3)_4$, $Pd(OAc)_2$ or Pd on carbon in a suitable solvent like DMF, acetonitrile or benzene. Typically a co-catalyst such as copper(I) iodide and a base (e.g., triethylamine, diisopropylamine, KOAc . . . ) will also be present in the reaction mixture. The coupling reaction typically proceeds by allowing the reaction temperature to warm slowly from about 0° up to ambient temperature, or heated to a temperature anywhere between 30° C. and 150° C. The reaction mixture is then maintained at a suitable temperature for a time in the range of about 1 up to 24 hours, with about 12 hours typically being sufficient. The product from the reaction can be isolated and purified employing standard techniques, such as solvent extraction, chromatography, crystallization, distillation, sublimation, and the like.

In another embodiment of the present invention, compounds of formula II-B1 may be prepared according to the synthetic sequences illustrated in the Schemes 4-5.

Scheme 4

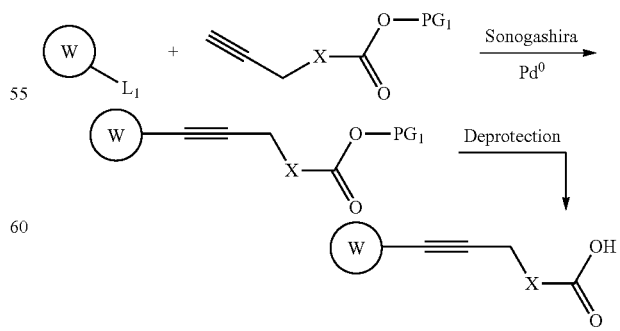

A substituted 5-, 6-heterocyclic containing a N adjacent to the leaving group $L_1$ is reacted with an alkyne derivative, in a manner similar to the procedure presented for Scheme 3. Thus in Scheme 4, $L_1$ includes halides such as Cl, Br, I or trifluoromethanesulfonyl and paratoluenesulfonyl. Protecting groups $PG_1$ are removed using standard methods to produce a carboxylic acid derivative.

Scheme 5

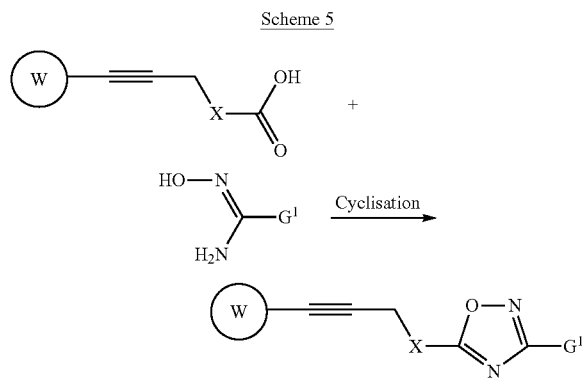

Referring to scheme 5, the di-substituted oxadiazole is prepared as described in scheme 2 from a suitable amidoxime precursor.

The compounds of formula II-C wherein W and $B^1$, $B^2$, $B^3$, and $G^q$ are as described above and X is $CH_2$—$NR^9C(=O)$ may be prepared according to the synthetic sequences illustrates in the Schemes 6-7.

Scheme 6

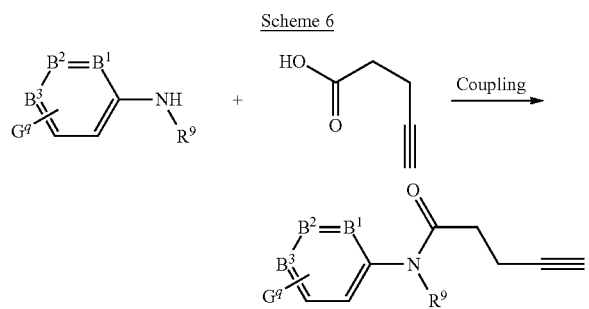

In turn, the pentynoic acid may be converted to amide derivative using the approach outlined in the Scheme 6. The reaction may be promoted by a coupling agent known in the art of organic synthesis such as EDCI (1-(3-Dimethylaminopropyl)-3-ethylcarbodiimide), DCC (N,N'-Dicyclohexylcarbodiimide), in a suitable solvent (e.g. tetrahydrofuran, dichloromethane, N,N-dimethylformamide, dioxane) Typically, a co-catalyst such as HOBT (Hydroxybenzotriazole) will also be present in the reaction mixture. The reaction typically proceeds at ambient temperature for a time in the range of about 4 up to 12 hours. Scheme 7 illustrates the final synthetic step.

Scheme 7

-continued

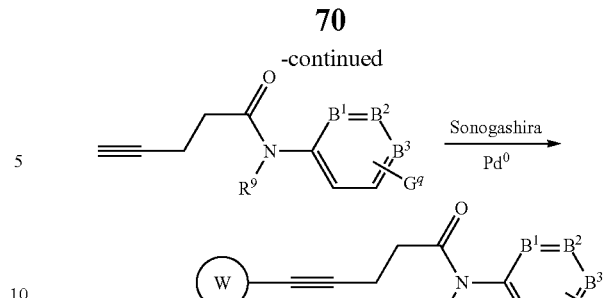

The alkyne product from the reaction in Scheme 7 may be prepared using the approach outlined in Scheme 3.

Thus, in Scheme 7, $L_1$ includes halides such as Cl, Br, I or trifluoromethanesulfonyl and paratoluenesulfonyl.

The compounds of formula II-C wherein W and $B^1$, $B^2$, $B^3$, and $G^q$ are as described above and X is ——≡—— may be prepared according to the synthetic sequences illustrated in the Schemes 8-10.

Scheme 8

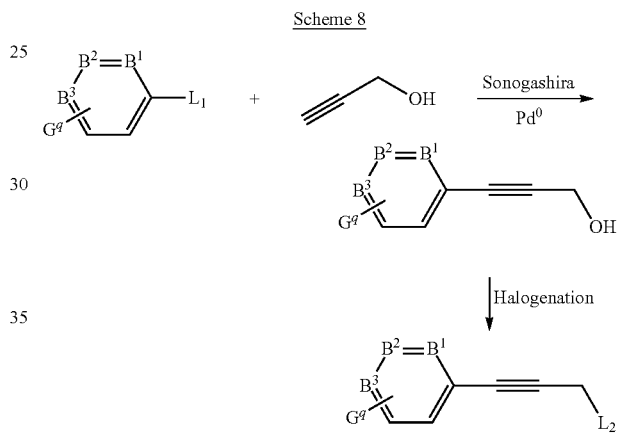

The substituted propargylic alcohol intermediate from the reaction in Scheme 8 may be prepared using the approach outlined in Scheme 3.

The substituted propargylic alcohol derivative may be subsequently converted into the corresponding propargylic halide derivative according to the method illustrated in J. Med. Chem., 2000, 48, 8, 1508-1518. The halogenation reaction may be promoted by a mixture of halogenating reagent (for example carbone tetrabromide, $PPBr_3$, $SOCl_2$, $PCl_5$, $POCl_3$ and the like) in a suitable solvent (e.g. dichloromethane, tetrahydrofuran, diethylether, toluene). If required a co-reagent, such as triphenylphosphine, will also be present in the reaction mixture. The reaction is typically allowed to proceed by maintaining at room temperature for a time in the range of about 2 hours up to 4 hours.

Thus, in Scheme 8, $L_1$ includes halides such as Cl, Br, I or trifluoromethanesulfonyl and paratoluenesulfonyl. And $L_2$ is halides such as Cl, Br, I.

Scheme 9

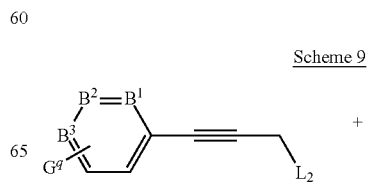

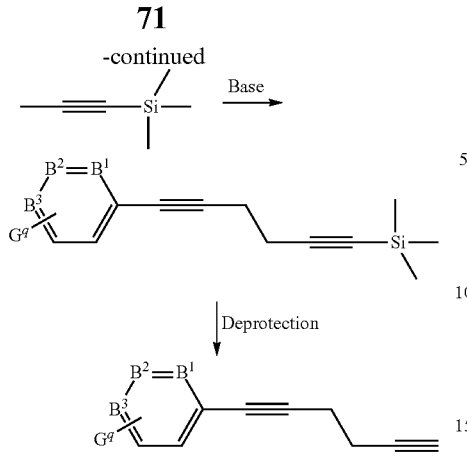

The substituted propargylic halide intermediate from the reaction in Scheme 8 may be transformed into bis-acetylenic derivatives using the approach outlined in Scheme 9.

An appropriate aryl- or heteroaryl-alkyl halide derivative is converted into the corresponding butynyl derivative according to the method illustrated in Tetrahedron, 1999, 55, 49, 13907-13926. The alkylation reaction may be promoted by a mixture of trimethyl(prop-1-ynyl)silane and an organo-lithium reagent such as n-butyllithium, tButyllithium and the like which is capable of undergoing metal exchange reaction in a suitable solvent (e.g. tetrahydrofuran, diethylether), at an appropriate temperature, usually between about −78° C. and 0° C., followed by condensation of aryl- or heteroaryl-alkyl halide derivatives.

Protecting group trimethylsilyl is removed under basic condition such as NaOH, KOH, $K_2CO_3$ or $nBu_4F$ and the like according to standard methods familiar to those skilled in the art (J. Org. Chem., 2003, 68, 4, 1376-1385). The reaction typically proceeds by allowing the reaction temperature to warm slowly from ambient temperature to 65° C. for a time between 1 h and 24 hours in a suitable solvent (e.g. methyl alcohol, ethyl alcohol, tetrahydrofuran, diethylether).

Thus, in Scheme 9, $L_2$ includes halides such as Cl, Br, I or trifluoromethanesulfonyl.

Scheme 10

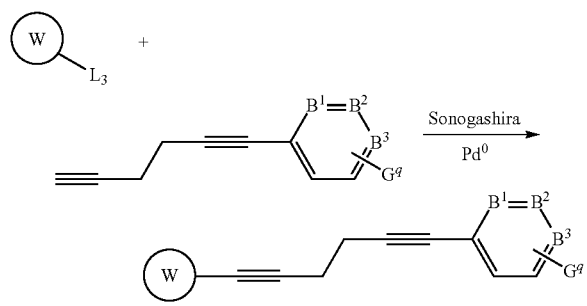

The bis-acetylenic derivative from the reaction in Scheme 9 may be prepared using the approach outlined in Scheme 3.

Thus, in Scheme 10 $L_3$ includes halides such as Cl, Br, I or trifluoromethanesulfonyl and paratoluenesulfonyl.

The compounds of formula II-A2 wherein W, $G^1$, $G^2$, $G^3$, $G^4$ and $G^5$ are as described above, X is $CH_2$ may be prepared according to the synthetic sequences illustrates in the Schemes 11-14

In accordance with the present invention, imidazopyridine derivatives can be prepared by methods known in the art (A. R. Katrizky A. R. and C. W. Rees (1984) Comprehensive Heterocyclic Chemistry, Pergamon Press).

Scheme 11

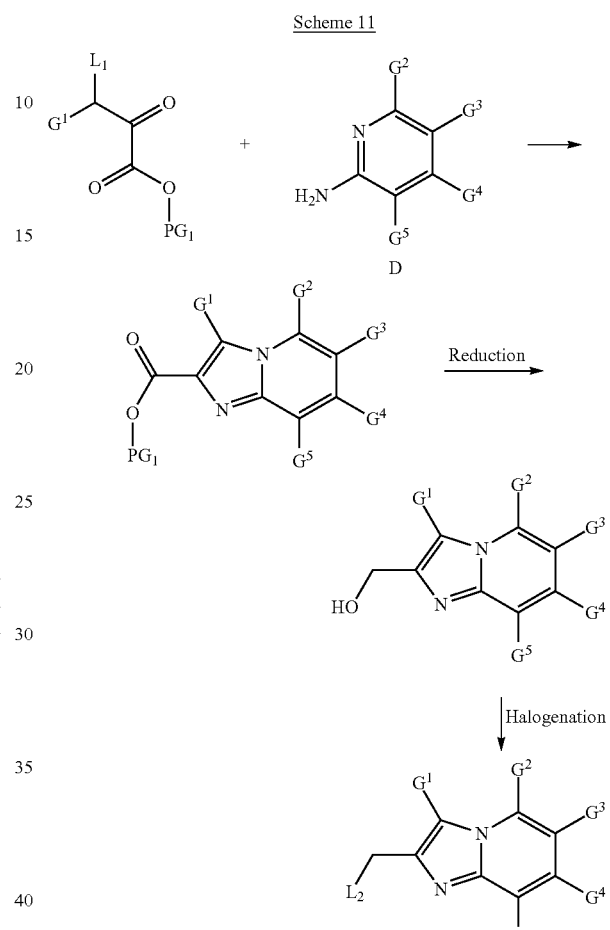

Referring to scheme 11, a substituted aminopyridine derivative D (prepared using synthetic chemistry techniques well known in the art) is reacted with an α-halo-ketoester in a suitable solvent (e.g. EtOH, MeOH, THF, acetone, $CH_3CN$ and the like) at temperature between 50° C. to 90° C. for 5 h to 12 h, to form a substituted imidazopyridine, according to the method illustrated in J. Med. Chem., 1988, 31, 11, 2221-2227.

The resulting imidazopyridine bearing a carboxylic ester group is converted into an alcohol by reacting with a reductive agent such as $LiAlH_4$, $BH_3$ and the like in a suitable solvent (e.g. THF, diethylether) for a period of time sufficient to proceed to completion, typically from about 1 h to 12 h, at ambient temperature being advantageous (see for example J. Heterocycl. Chem., 1988, 25, 129-137).

The heterocyclic alkyl-alcohol derivative may be subsequently converted into the corresponding heterocyclic alkyl-halide derivative according to the method illustrated in J. Med. Chem., 2000, 48, 8, 1508-1518. The halogenation reaction may be promoted by a mixture of halogenating reagent (for example carbone tetrabromide, $PBr_3$, $SOCl_2$, $PCl_5$, $POCl_3$ and the like) in a suitable solvent (e.g. dichloromethane, tetrahydrofuran, diethylether, toluene). If required a co-reagent, such as triphenylphosphine, will also be presented in the reaction mixture. The reaction is typically allowed to proceed by maintaining at room temperature for a time in the range of about 2 hours up to 4 hours.

Thus, in Scheme 11, $L_1$ includes halides such as Cl, Br, I and $PG_1$ includes Methyl, ethyl, isopropyl, tert-Butyl or benzyl and the like.

In another embodiment of the present invention, depicted in Scheme 12, substituted imidazopyridine alkyl-halide derivatives may be prepared from a bis-α-haloketone and a substituted aminopyridine D according to standard methods familiar to those skilled in the art (J. Heterocyclic. Chem., 1988, 25, 129-137).

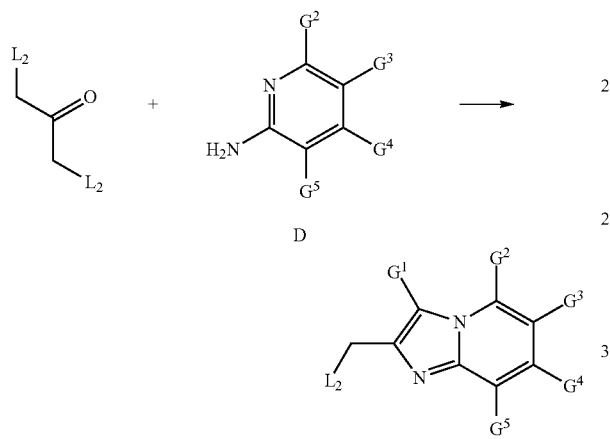

The reaction typically proceeds by allowing the reaction temperature to heat slowly from ambient temperature to 65° C. for a time between 1 h and 12 hours in a suitable solvent (e.g. methyl alcohol, ethyl alcohol, tetrahydrofuran, diethylether, acetone and the like). Thus, in Scheme 12, $L_2$ includes halides such as Cl, Br, I.

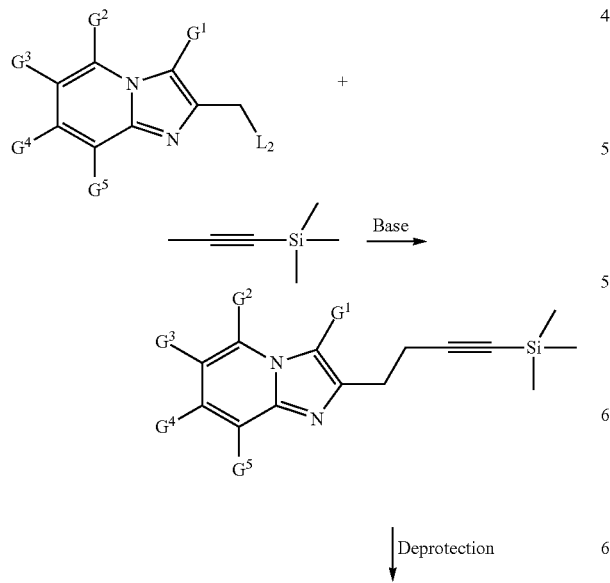

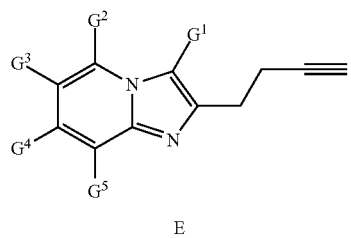

Thus, in the Scheme 13, a substituted imidazopyridine alkyl-halide intermediate may be transformed into a mono substituted acetylenic derivative using the approach outlined in Scheme 9 to produce the compound E.

Thus, in Scheme 13, $L_2$ includes halides such as Cl, Br, I.

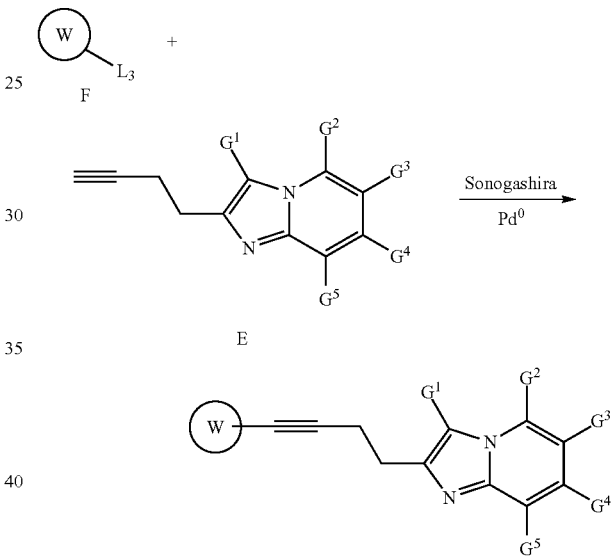

The bis-substituted alkyne product from the reaction in Scheme 14 may be prepared using the approach outlined in Scheme 3.

Thus, in Scheme 14 $L_3$ includes halides such as Cl, Br, I or trifluoromethanesulfonyl and paratoluenesulfonyl.

In accordance with the present invention, imidazopyridine derivatives can be prepared also using the approach outlined in Scheme 15-17

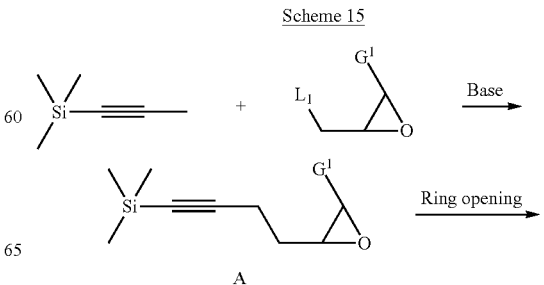

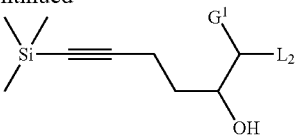

B

↓ Oxydation

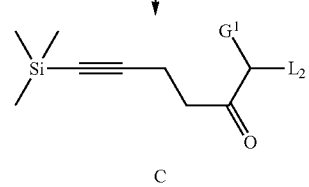

C

Thus, in the Scheme 15, an appropriate epoxyde-alkyl halide derivative (e.g., 2-(chloromethyl)oxirane) is converted into the corresponding butynyl derivative A according to the method illustrated in the Scheme 9. The resulting substituted acethylenic intermediate A may be subsequently converted into the intermediate B according to the method illustrated in S. Hoarau et al., Tetrahedron Asymmetric. 1996, 7, 2585-2593 and in Gene W. Holbert et al., Tetrahedron, 1984, 40, 1141-1144. The ring opening may be promoted by LiBr or KBr and the like in the presence of acetic acid, in a suitable solvent (e.g. mixture tetrahydrofuran and water), at room temperature for a time in a range of about 5 hours up to 12 hours.

In another embodiment of the present invention, depicted in Scheme 15, the intermediate B may be transformed into the corresponding α-halo-ketone C according to the method illustrated in W. Holbert et al., Tetrahedron, 1984, 40, 1141-1144. The oxidation reaction may be promoted by using oxidative agent such as Jone's reagent ($CrO_3/H_2SO_4$), TEMPO, PCC and the like by maintaining at room temperature for a time in the range of about 1 hour up to 2 hours. Thus, in Scheme 15, $L_1$ $L_2$ include halides such as Cl, Br, I.

Scheme 16

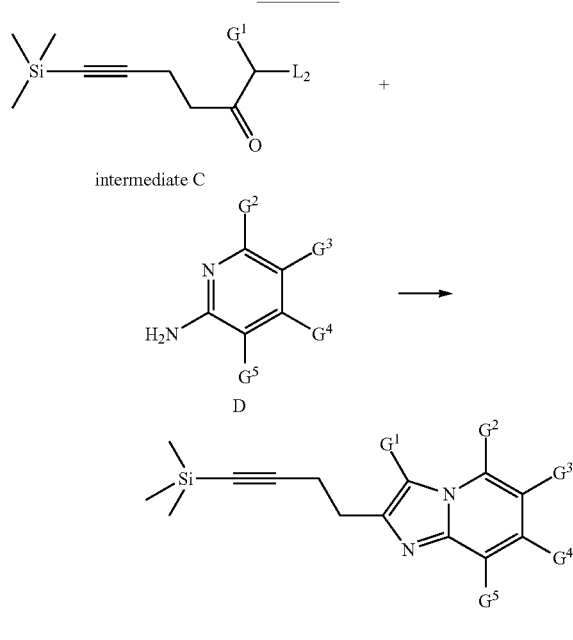

↓ Deprotection

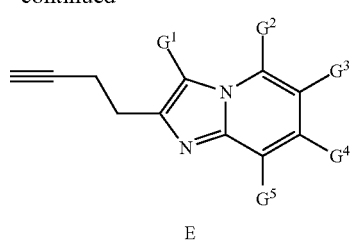

E

Thus, in the Scheme 16, an appropriate α-halo-ketone C is converted into the corresponding imidazopyridine E according to the cyclisation method illustrated in the Scheme 11. Protecting group trimethylsilyl is removed under basic condition such as NaOH, KOH, $K_2CO_3$ or $nBu_4F$ according to the method illustrated in the Scheme 9.

Scheme 17

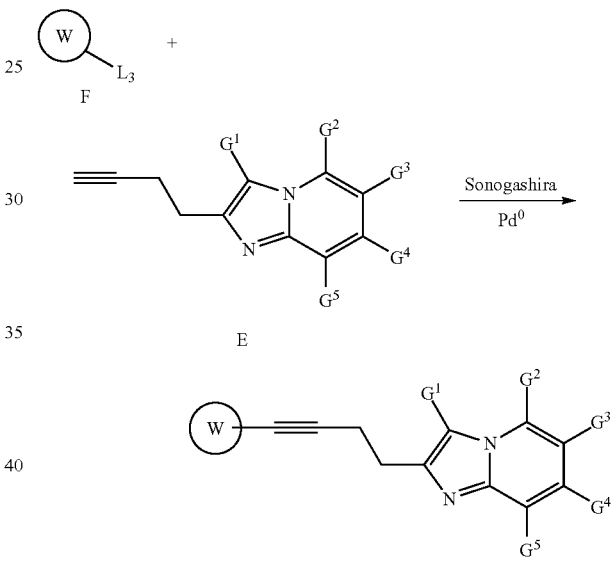

The alkyne products from the reaction in Scheme 17 may be prepared using the approach outlined in Scheme 3.

Thus, in Scheme 17 $L_3$ includes halides such as Cl, Br, I or trifluoromethanesulfonyl and paratoluenesulfonyl.

The compounds of formula II-A1 wherein W, $G^1$, $G^2$, $G^3$, $G^4$ and $G^5$ are as described above, X is $CH_2$, $B^1$, $B^2$ is C and $B^3$ is N which may further be substituted by $G^q$ group, may be prepared according to the synthetic sequences illustrate in the Schemes 18-20.

Scheme 18

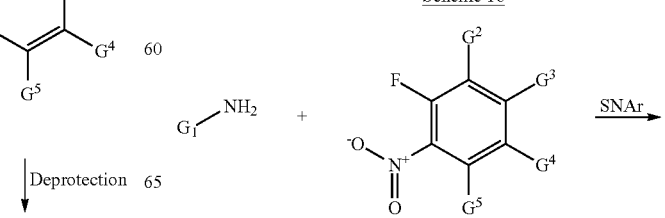

-continued

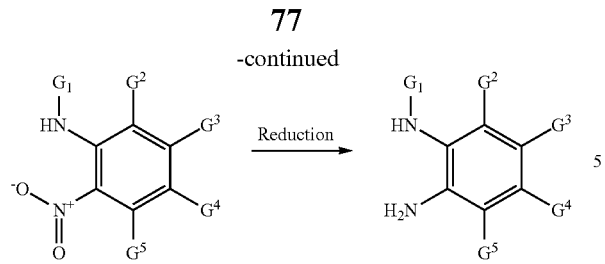

Referring to scheme 18, 1-fluoro-2-nitrobenzene derivative is reacted with a excess of appropriate substituted amine in suitable solvent (e.g. EtOH, MeOH, THF, acetone, CH$_3$CN and the like) at temperature between 50° C. to 90° C. for a time in the range of about 5 h up to 12 h, to form a N-substituted-2-nitrobenzenamine according to the method illustrated in Tetrahedron Letters, 2002, 43, 7303-7306.

The N-substituted-2-nitrobenzenamine may be subsequently converted into the corresponding N-substituted-benzene-1,2-diamine derivative according to the method known in the art. The reduction reaction may be promoted by 10% Pd/C in a presence of hydrogen source (H$_2$, HCOONH$_4$, HCOOH, NaBH$_4$ and the like) or by the presence of metal such as Zinc, Iron and the like in acidic condition (concentrated HCl, H$_2$SO$_4$ or AcOH) in a suitable solvent (e.g. MeOH, AcOH, EtOH). The reaction is typically allowed to proceed by maintaining at room temperature for a time in the range of about 2 hours up to 4 hours.

Scheme 19

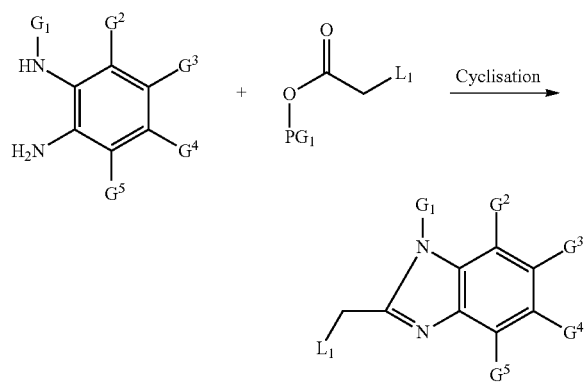

Referring to scheme 19, a N-substituted-benzene-1,2-diamine derivative is reacted with an α-halo-carboxylic ester or an α-halo-carboxylic acid (X is selected from Cl, Br, I, and PG$_1$ includes Methyl, ethyl, isopropyl, tert-Butyl or benzyl and the like) to form an substituted benzimidazole, according to the method illustrated in J. Heterocyclic. Chem., 1983, 20, 1481-1484.

The reaction typically proceeds by allowing the reaction temperature to heat slowly from ambient temperature to 90° C. in acidic condition (aqueous HCl and the like) for a time between 5 h and 12 hours.

Scheme 20

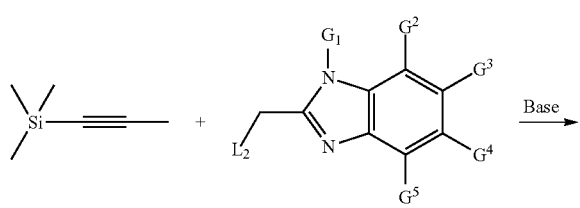

-continued

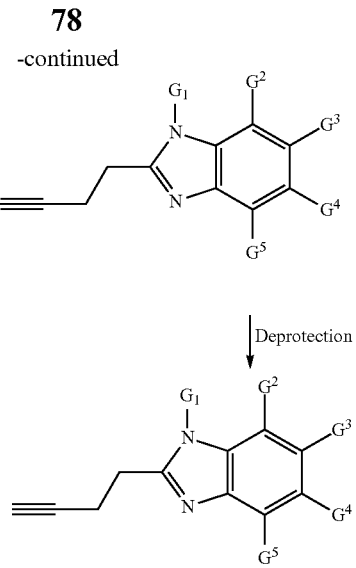

Thus, in the Scheme 20 a substituted imidazopyridine alkyl-halide intermediate may be transformed into a mono substituted acetylenic derivative using the approach outlined in Scheme 9. Thus, in Scheme 20 L$_2$ includes halides such as Cl, Br, I.

The compounds of formula II-B wherein W, Z$^9$, Z$^{10}$, Z$^{11}$, Z$^{12}$ are as described above and X is C$_1$-C$_3$-alkyl may be prepared according to the synthetic sequences illustrate in Scheme 21-23.

Scheme 21

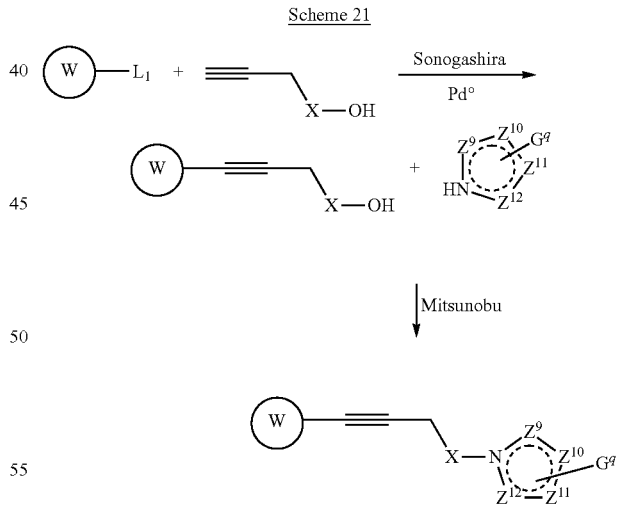

In Scheme 21, a substituted 5-, 6-heterocyclic containing an N adjacent to the leaving group L$_1$ is reacted with acethylenic alcohol under Sonogashira condition as illustrated in Scheme 3 to produce a substituted acetylenic alcohol. The resulting alcohol is reacted with a heterocyclic ring containing an acidic NH, under Mitsunobu conditions according to the method illustrated in M. S. Malamas, J. Sredy, I. Gunawan, B. Mihan, D. R. Sawicki, L. Seestaller, D. Sullivan, B. R. Flam, J. Med. Chem. 2000, 43, 995-1010. The Mitsunobu reaction may be promoted by a reagent such as diethylazodicarboxylate, di-tert-butylazodicarboxylate and the like in the presence of triphenyphosphine, in a suitable solvent (e.g. tetrahydrofuran), at an appropriate temperature. Subsequent deprotection of the trimethylsilyl group according to the method illustrated in Scheme 9 and cross coupling afforded a compound of formula II-B.

Thus, in Scheme 21, $L_1$ may be a good leaving group capable of undergoing a Sonogashira reaction such as Cl, Br, I or trifluoromethanesulfonate and the like.

In another embodiment of the present invention, depicted in Scheme 22, a acetylenic alcohol may be transformed into the corresponding halide derivative, wherein $L_1$ is Cl, Br or I, according to the method illustrated in G. C. Crawley, R. I. Dowell, P. N. Edwards, S. J. Foster, R. M. McMillan, J. Med. Chem. 1992, 35, 2600-2609. The halogenation reaction may be promoted by a mixture of halogenating reagents (for example $Br_2$, carbone tetrabromide, $PBr_3$, $SOCl_2$, $PCl_5$, $POCl_3$ and the like) in a presence of a co-reagent, such as triphenylphosphine, in a suitable solvent (e.g. THF, DCM and the like) and at an appropriate temperature.

Scheme 22

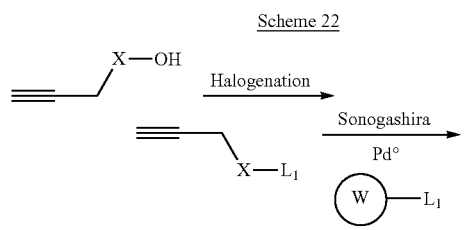

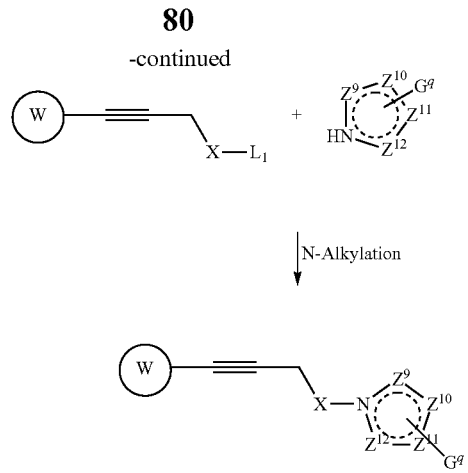

The resulting acetylenic halide may be submitted to substitution as described in Scheme 22 and according to the method illustrated in S. J. Pastine, S. W. Youn, D. Sames, Org. Lett, 2003, 5, 1055-1058. The substitution reaction may be promoted by a nucleophile in the presence of a base such as $K_2CO_3$, $Cs_2CO_3$, NaH and the like in a suitable solvent (e.g. dimethylformamide, acetone, tetrahydrofuran), at an appropriate temperature. The resulting terminal alkyne is coupled to a substituted 5,6-heterocyclic containing nitrogen adjacent to the leaving group $L_1$ by Sonogashira procedure described in Scheme 3.

In another embodiment of the present invention, depicted in Scheme 23, a suitable acetylenic halide bearing an appropriate protecting group (e.g. trimethylsilyl and the like) may be reacted with a substituted 5-, 6-heterocyclic containing an N to produce a N-alkylated heterocyclic derivative as illustrated in Scheme 22. The subsequent deprotection of the $PG_1$ according to methods known in the art, followed by Sonogashira coupling affords the compound of formula II-B.

Scheme 23

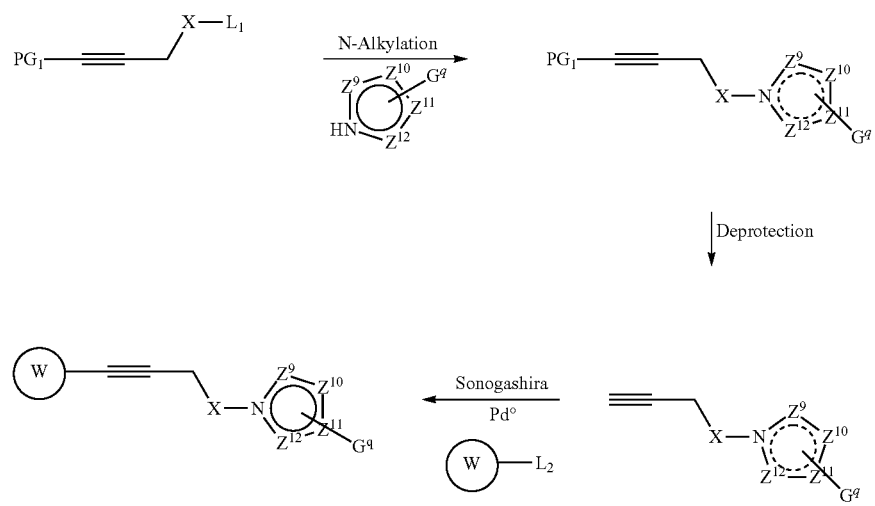

The compounds of formula II-C wherein W, $B^1$, $B^2$, $B^3$ and $G^q$ are as described above and X is $CH_2$—OC(=O) may be prepared according to the synthetic sequences illustrated in Scheme 24.

Scheme 24

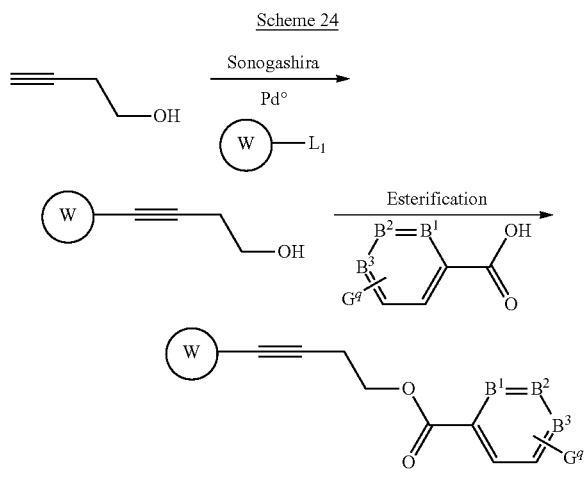

The acetylenic alcohol is reacted with an appropriate substituted 5-, 6-heterocyclic containing an N adjacent to the leaving group $L_1$ under Sonogashira conditions to produce the substituted the heterocyclic acetylenic alcohol.

In turn, the heterocyclic acetylenic alcohol may be converted to an ester derivative using the approach outlined in the Scheme 24. The reaction may be promoted by coupling agents known in the art of organic synthesis such as EDCI (1-(3-Dimethylaminopropyl)-3-ethylcarbodiimide), DCC (N,N'-Dicyclohexyl-carbodiimide), in a suitable solvent (e.g. tetrahydrofuran, dichloromethane, N,N-dimethylformamide, dioxane). Typically, a co-catalyst such as DMAP (N,N-dimethyl-aminopyridine) will also be present in the reaction mixture. The reaction typically proceeds at ambient temperature for a time in the range of about 4 up to 12 hours.

Thus, in Scheme 24, $L_1$ may be a good leaving group capable of undergoing a Sonogashira reaction such as Cl, Br, I or trifluoromethanesulfonate and the like.

In the Scheme 25, a compound of formula II-C wherein W, $B^1$, $B^2$, $B^3$ and $G^q$ are as described above and X is $CH_2$—C(=O)—O may be prepared according to the synthetic sequences illustrated in Scheme 24.

Scheme 25

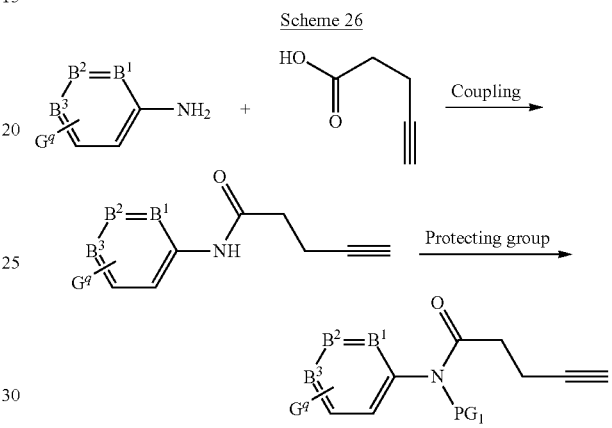

The compounds of formula II-C wherein W and $B^1$, $B^2$, $B^3$, and $G^q$ are as described above and X is $CH_2$—NHC(=O) may be prepared according to the synthetic sequences illustrates in the Schemes 26-27.

Scheme 26

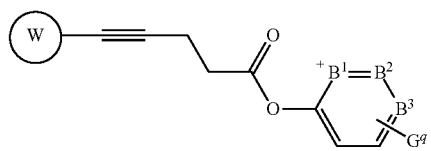

In turn, the pentynoic acid may be converted to amide derivative using the approach outlined in the Scheme 6. The reaction may be promoted by coupling agent known in the art of organic synthesis such as EDCI (1-(3-Dimethylaminopropyl)-3-ethylcarbodiimide), DCC (N,N'-Dicyclohexyl-carbodiimide), in a suitable solvent (e.g. tetrahydrofuran, dichloromethane, N,N-dimethylformamide, dioxane) Typically, a co-catalyst such as HOBT (Hydroxybenzotriazole) will also be present in the reaction mixture. The reaction typically proceeds at ambient temperature for a time in the range of about 4 up to 12 hours.

N-protected derivative of the resulting amide may be prepared according to the method described in J. Med. Chem., 2000, 43, 3718-3735, by using for example $BOC_2O$ in a presence of DMAP in a suitable solvent such as DCM. The reaction typically proceeds at ambient temperature for a time in the range of about 4 up to 12 hours.

Thus, in Scheme 26, $PG_1$ includes carbamates such as EtO—C(=O), MeO—C(=O), Ph-$CH_2$—O—C(=O) or tBuOC(=O) and the like.

Scheme 27

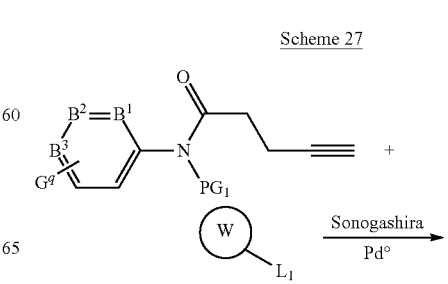

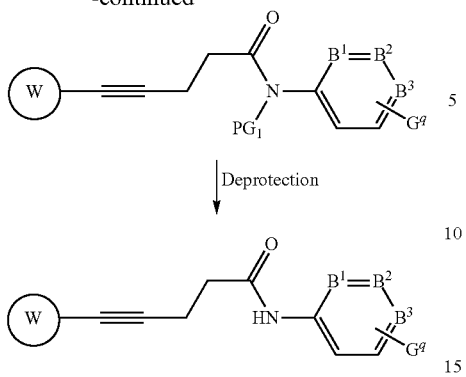

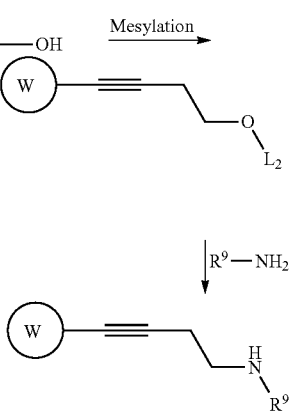

The resulting acetylenic may be submitted to Sonogashira cross coupling as described in Scheme 27 according to the method outlined in the Scheme 3: Removal of the protecting group may be achieved under classical condition well known in the art, either under acidic conditions (HCl, $H_2SO_4$, TFA and the like) or basic condition (NaOH, KOH, $NH_3$ and the like) in a suitable solvent such as THF, DCM or MeOH.

Thus, in Scheme 27, $L_1$ may be a good leaving group capable of undergoing a Sonogashira reaction such as Cl, Br, I or trifluoromethanesulfonate and the like.

The compounds of formula II-C wherein W and $B^1$, $B^2$, $B^3$, and $G^q$ are as described above and X is $CH_2$—$NR^9C(=O)$—$C_1$-$C_6$-alkyl or $CH_2$—$NR^9S(=O)_2$—$C_1$-$C_6$-alkyl may be prepared according to the synthetic sequences illustrated in the Schemes 28-29.

Scheme 28

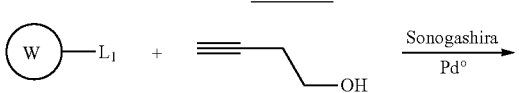

In the Scheme 28, the acetylenic alcohol is reacted with an appropriate substituted 5-, 6-heterocyclic containing an N adjacent to the leaving group $L_1$ to produce a substituted heterocyclic alcohol. The alcohol group is converted to a better leaving group by using an appropriate sulfonyl chloride (e.g. p-toluenesulphonyl chloride or methansulfonyl chloride and the like) in a presence of a base (e.g. $NEt_3$, DIEA) and in a suitable solvent (DCM, THF and the like). The reaction typically proceeds at ambient temperature for a time in the range of about 4 up to 12 hours. The intermediate sulfonate is converted into a N-Alkylated derivative by using an excess of appropriate amine in aqueous solution. The reaction takes place in a range of temperature between 30-50° C. for 3 h according to the method described in the J. Org. Chem.; Gao, Y.; Sharpless, K. B.; 53; 17; 1988; 4081-4084.

Thus, in Scheme 28, $L_1$ may be a good leaving group capable of undergoing a Sonogashira reaction such as Cl, Br, I or trifluoromethanesulfonate and the like, L2 may be a good leaving group capable of undergoing nucleophilic substitution such as trifluoromethanesulfonate, mesylate or p-toluenesulfonate.

Scheme 29

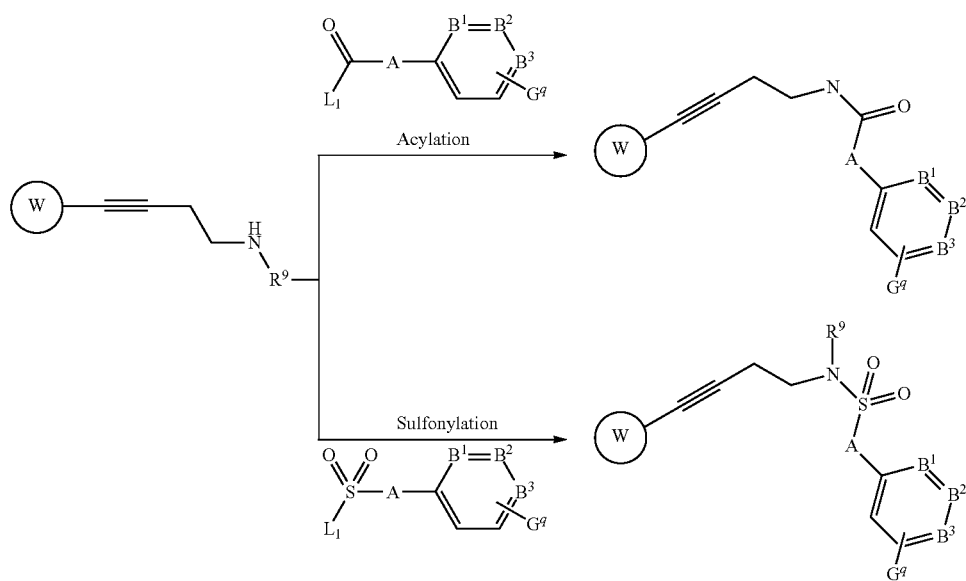

In the Scheme 29, carboxylic acids ($L_1$ is OH) or their more reactive derivatives ($L_1$ may be selected from Cl, Br, and the like) is reacted with an appropriate amine that produce amide according to Scheme 28. The acylation reaction may be promoted by coupling agents known in the art of organic synthesis such as EDCI (1-(3-Dimethylaminopropyl)-3-ethylcarbodiimide), DCC(N,N'-Dicyclohexyl-carbodiimide) or by polymer-supported coupling agents such as polymer-supported carbodiimide (PS-DCC, ex Argonaut Technologies), in the presence of a suitable base such as triethylamine, diisopropyl-ethylamine, in a suitable solvent (e.g. tetrahydrofuran, dichloromethane, N,N-dimethylformamide, dioxane). Typically, a co-catalyst such as HOBT (1-Hydroxy-benzotriazole), HOAT (1-Hydroxy-7-azabenzotriazole) and the like may also be present in the reaction mixture. The reaction typically proceeds at ambient temperature for a time in the range of about 2 hours up to 12 hours.

Similarly, sulfonyl chloride derivatives ($L_1$ is OH) may also reacted with amine derivatives according to the process described in the Scheme 29.

The compounds of formula II-A wherein W, $Z^9$, $Z^{11}$, $Z^{12}$, $Z^{13}$, $Z^{14}$, $Z^{15}$, $Z^{16}$ and $Z^{17}$ are as described above and $Z^{10}$ is N may be prepared according to the synthetic sequences illustrated in Scheme 30.

Scheme 30

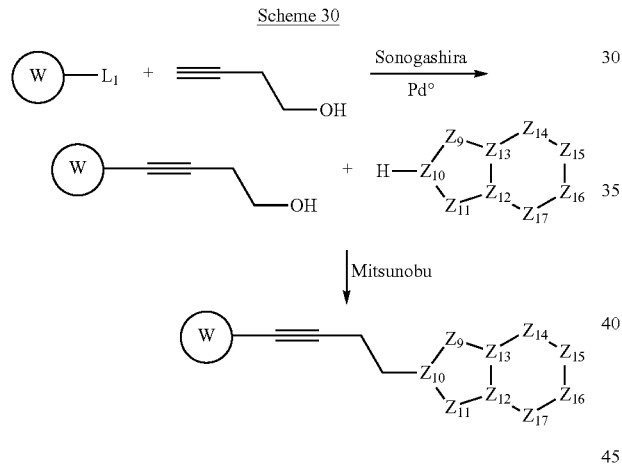

A substituted 5-, 6-heterocyclic containing a N adjacent to the leaving group $L_1$ is reacted with but-3-yn-1-ol in a manner similar to the procedure presented for Scheme 21. Thus, in Scheme 31, $L_1$ may be a good leaving group capable of undergoing a Sonogashira reaction such as Cl, Br, I or trifluoromethanesulfonate and the like. The resulting alcohol may be subsequently converted into a compound of formula II-A according to the method illustrated in M. S. Malamas, J. Sredy, I. Gunawan, B. Mihan, D. R. Sawicki, L. Seestaller, D. Sullivan, B. R. Flam, J. Med. Chem. 2000, 43, 995-1010. The Mitsunobu reaction may be promoted by a reagent such as diethylazodicarboxylate, di-tert-butylazodicarboxylate and the like in the presence of triphenyphosphine, in a suitable solvent (e.g. dichloromethane), at an appropriate temperature.

In another embodiment of the present invention, compounds of formula II-A1 wherein W, $B^1$, $B^2$, $B^3$ and $G^q$ are as described above may be prepared, as depicted in Scheme 31, from the methyl imidate according to the method illustrated in M. M. Ponpipom, R. L. Bugianesi, J. C. Robbins, T. W. Doebber, T. Y. Shen, J. Med. Chem. 1981, 24, 1388-1395. The subsequent cyclization may be promoted under mild conditions and followed by Sonogashira coupling.

Scheme 31

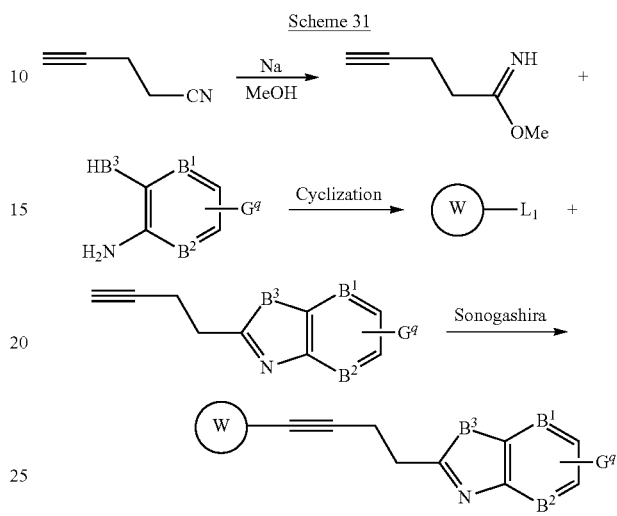

The compounds of formula II-A1 wherein W, $B^1$, $B^2$, $B^3$ and $G^q$ are as described above may be prepared according to the following synthetic sequences describe in Scheme 32.

Scheme 32

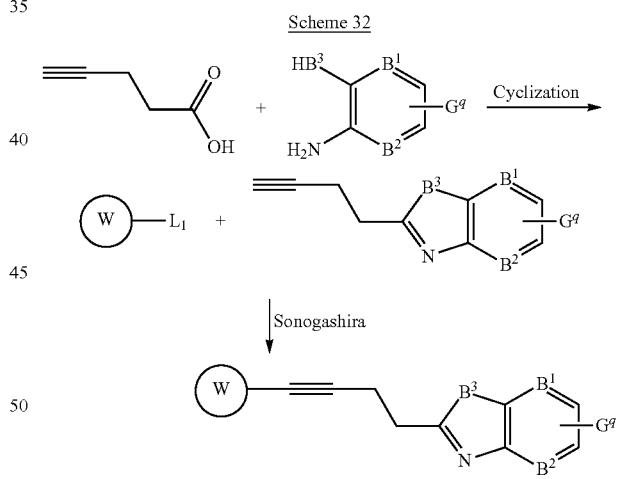

Pentynoic acid is reacted with an aryl- or heteroaryl-amine where $B^3$=O or S, in the presence of a mixture of triphenylphosphine and $CCl_4$, in an appropriate solvent, in the presence o a base, followed by Sonogashira coupling as described in Scheme 3, in order to lead to benzoxazole or benzothiazole compounds.

The compounds of formula II-A1 wherein W, $B^1$, $B^2$, $G^q$ are as described above and $B^3$=C=C or N=C may be prepared according to the following synthetic sequences illustrated in Scheme 33.

Scheme 33

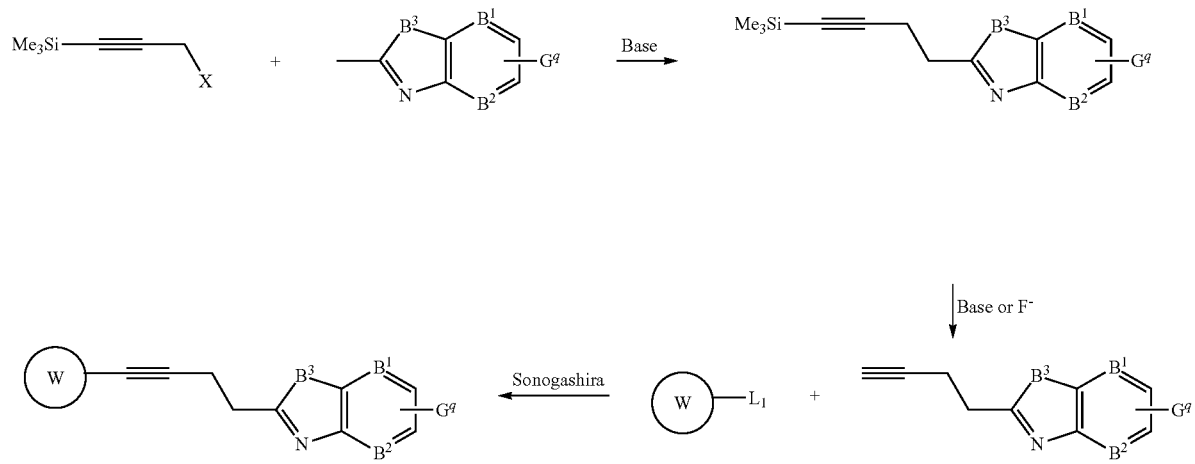

An appropriate 2-methyl-heteroalkyl is coupled to (3-X-prop-1-ynyl)-trimethyl-silane derivative wherein X is a good leaving group such as Cl or Br and the like, in the presence of a strong base such as n-butyllithium, lithium diisopropylamine and the like. Trimethylsilyl group is removed under basic condition (e.g. NaOH, KOH, K$_2$CO$_3$) or in the presence of fluoride ions (N-tetrabutylammonium fluoride and the like). The resulting terminal alkyne is coupled to a substituted 5,6-heterocyclic containing nitrogen adjacent to the leaving group L$_1$ by Sonogashira procedure described in Scheme 3.

The compounds of formula II-A3-a wherein R$^1$, R$^2$, R$^3$, R$^4$ and G$^q$ are as described above and B$^1$=C and X=CH$_2$ may be prepared according to the following synthetic sequences illustrated in Scheme 34.

coupled to a substituted pyridine having a leaving group L$_1$ by Sonogashira procedure described in Scheme 3.

The compounds of formula II-A3-a2 wherein R$^1$, R$^2$, R$^3$, R$^4$ and G$^q$ are as described above may be prepared according to the following synthetic sequences illustrated in Scheme 35.

Scheme 35

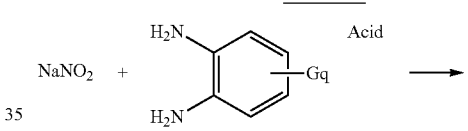

Scheme 34

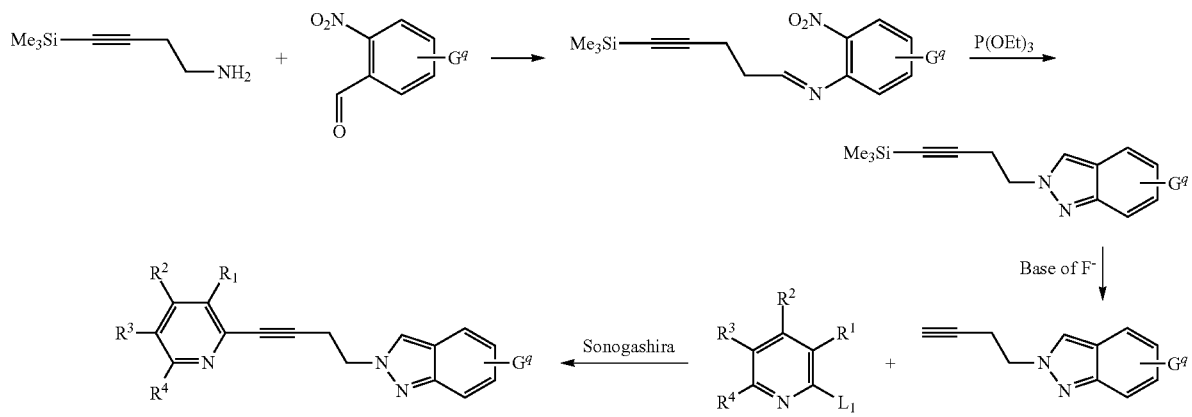

Trimethylsilanyl-but-3-ynylamine is reacted with substituted 1,2-nitrobenzaldehyde in an appropriate solvent such as toluene, ethanol . . . . The resulting imine is reacted in the presence of triethylphosphite at a certain temperature in order to lead to substituted indazoles as in the method illustrated in T. J. Schwan, L. J. Honkomp, C. S. Davis, G. S. Lougheed, J. of Pharm. Sciences 1978, 7, 1022-1024. Trimethylsilyl group is removed under basic condition (e.g. NaOH, KOH, K$_2$CO$_3$) or in the presence of fluoride ions (N-tetrabutylammonium fluoride and the like). The resulting terminal alkyne is -continued

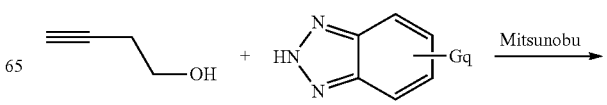

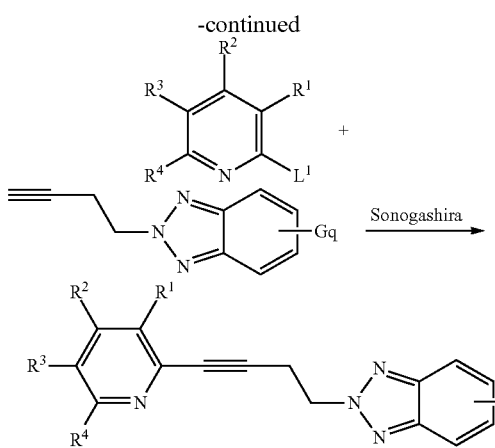

Benzotriazoles are prepared from substituted benzene-1,2-diamine in the presence of sodium nitrite and acetic acid as in the method illustrated in J. A. Montgomery, K. Hewson, J. Med. Chem. 1965, 8, 737-740. Then but-3-yn-1-ol is reacted with benzotriazoles through Mitsunobu reaction which may be promoted by diethylazodicarboxylate, di-tert-butylazodicarboxylate and the like in the presence of triphenyphosphine, in a suitable solvent (e.g. tetrahydrofuran), at an appropriate temperature. The resulting terminal alkyne is coupled to a substituted pyridine via Sonogashira procedure described in Scheme 3.

The compounds of formula II-B1 wherein W and $G^q$ are as described above and $X=CH_2$ and $B^1=C$ may be prepared according to the synthetic sequences illustrated in Scheme 36.

Scheme 36

An acid chloride is reacted with an aminoalcohol under basic conditions such as triethylamine in a suitable solvent (e.g. DCM). The resulting amidoalcohol is oxidized in the presence of PCC followed by cyclization with $POCl_3$ and Sonogashira coupling as described in Scheme 3.

The compounds of formula II-C wherein W, X, $B^1$, $B^2$, $B^3$ and $G^q$ are as described above may be prepared according to the synthetic sequences illustrate in Scheme 37.

Scheme 37

Propargylation may be promoted by an aryl- or heteroarylalkyl halide and propargylmagnesium bromide in the presence of an appropriate solvent (e.g. tetrahydrofuran) at an appropriate temperature, followed by Sonogashira coupling as described in Scheme 3.

Pharmacology

Some of the compounds of Formula I have been tested according to the following methods.

mGluR5 Binding Assay

Activity of compounds of the invention was examined following a radioligand binding technique using whole rat brain and tritiated 2-methyl-6-(phenylethynyl)-pyridine ([$^3$H]-MPEP) as a ligand following similar methods than those described in F. Gasparini et al. Bioorg. Med. Chem. Lett. 2002, 12, 407-409 and in J. F. Anderson et al. J. Pharmacol. Exp. Ther. 2002, 303, 3, 1044-1051.

Membrane Preparation:

Cortices were dissected out from brains of 200-300 g Sprague-Dawley rats (Charles River Laboratories, L'Arbresle, France). Tissues were homogenized in 10 volumes (vol/wt) of ice-cold 50 mM Hepes-NaOH (pH 7.4) using a Polytron disrupter (Kinematica AG, Luzern, Switzerland) and centrifuged for 30 min at 40,000 g. (4° C.). The supernatant was discarded and the pellet washed twice by resuspension in 10 volumes 50 mM HEPES-NaOH. Membranes were then collected by centrifugation and washed before final resuspension in 10 volumes of 20 mM HEPES-NaOH, pH 7.4. Protein concentration was determined by the Bradford method (Bio-Rad protein assay, Reinach, Switzerland) with bovine serum albumin as standard.

[$^3$H]-MPEP Binding Experiments:

Membranes were thawed and resuspended in binding buffer containing 20 mM HEPES-NaOH, 3 mM $MgCl_2$, 3 mM $CaCl_2$, 100 mM NaCl, pH 7.4. Competition studies were carried out by incubating for 1 h at 4° C.: 3 nM [$^3$H]-MPEP (39 Ci/mmol, Tocris, Cookson Ltd, Bristol, U.K.), 50 µg membrane and a concentration range of 0.003 nM-30 µM of compounds, for a total reaction volume of 300 µl. The non-specific binding was defined using 30 µM MPEP. Reaction was terminated by rapid filtration over glass-fiber filter plates (Unifilter 96-well GF/B filter plates, Perkin-Elmer, Schwerzenbach, Switzerland) using 4×400 µl ice cold buffer using cell harvester (Filtermate, Perkin-Elmer, Downers Grove, USA). Radioactivity was determined by liquid scintillation spectrometry using a 96-well plate reader (TopCount, Perkin-Elmer, Downers Grove, USA).

Data Analysis:

The inhibition curves were generated using the Prism GraphPad program (Graph Pad Software Inc, San Diego, USA). $IC_{50}$ determinations were made from data obtained from 8 point-concentration response curves using a non linear regression analysis.

The table below represents the mean of $IC_{50}$ obtained from at least three independent experiments of selected molecules performed in duplicate.

| Example N° | $IC_{50}$ (nM) |
|---|---|
| 1 | <500 |
| 2 | <10 000 |
| 3 | <10 000 |
| 4 | <10 000 |
| 5 | <10 000 |
| 7 | <500 |
| 8 | <50 |
| 9 | <10 000 |
| 10 | <10 000 |
| 12 | <10 000 |
| 13 | <500 |
| 14 | <10 000 |
| 15 | <500 |
| 16 | <10 000 |
| 17 | <10 000 |
| 18 | <10 000 |
| 19 | <10 000 |
| 20 | <10 000 |
| 21 | <10 000 |
| 22 | <10 000 |
| 23 | <10 000 |
| 24 | <10 000 |
| 25 | <500 |
| 26 | <10 000 |
| 28 | <10 000 |
| 29 | <10 000 |
| 30 | <10 000 |
| 31 | <50 |
| 32 | <10 000 |
| 33 | <50 |
| 34 | <1000 |
| 35 | <50 |
| 36 | <10 000 |
| 37 | <10 000 |
| 38 | <10 000 |
| 40 | <10 000 |
| 41 | <10 000 |
| 42 | <10 000 |
| 43 | <10 000 |
| 44 | <10 000 |
| 45 | <10 000 |
| 46 | <10 000 |
| 47 | <10 000 |
| 48 | <500 |
| 49 | <10 000 |
| 50 | <10 000 |
| 51 | <10 000 |
| 52 | <10 000 |
| 53 | <10 000 |
| 54 | <10 000 |
| 55 | <10 000 |
| 56 | <10 000 |
| 57 | <10 000 |
| 58 | <10 000 |
| 59 | <10 000 |
| 60 | <10 000 |
| 61 | <10 000 |
| 62 | <50 |
| 63 | <50 |
| 64 | <50 |
| 65 | <50 |
| 66 | <500 |
| 67 | <10 000 |
| 68 | <10 000 |
| 69 | <50 |
| 70 | <10 000 |
| 71 | <10 000 |
| 72 | <10 000 |
| 73 | <10 000 |
| 74 | <10 000 |
| 75 | <10 000 |
| 76 | <10 000 |
| 77 | <50 |
| 78 | <10 000 |
| 79 | <10 000 |
| 80 | <50 |
| 81 | <50 |
| 82 | <50 |
| 83 | <10 000 |
| 84 | <10 000 |
| 86 | <50 |
| 87 | <10 000 |
| 88 | <50 |
| 89 | <50 |
| 90 | <50 |
| 91 | <50 |
| 92 | <50 |
| 93 | <50 |
| 94 | <50 |
| 95 | <10 000 |
| 96 | <50 |
| 97 | <10 000 |
| 98 | <10 000 |
| 99 | <10 000 |
| 100 | <10 000 |
| 101 | <50 |
| 102 | <10 000 |
| 103 | <50 |
| 104 | <50 |
| 105 | <50 |
| 107 | <500 |
| 108 | <500 |
| 109 | <500 |
| 111 | <10 000 |
| 112 | <50 |
| 113 | <10 000 |
| 114 | <50 |
| 116 | <50 |
| 117 | <10 000 |
| 118 | <500 |
| 120 | <10 000 |
| 121 | <10 000 |
| 122 | <10 000 |
| 123 | <10 000 |
| 124 | <10 000 |
| 125 | <10 000 |
| 126 | <50 |
| 127 | <10 000 |
| 128 | <50 |
| 129 | <50 |
| 130 | <50 |
| 131 | <50 |
| 132 | <50 |
| 133 | <10 000 |
| 134 | <10 000 |
| 135 | <10 000 |
| 136 | <10 000 |
| 137 | <50 |
| 138 | <10 000 |
| 139 | <50 |
| 140 | <10 000 |
| 141 | <50 |
| 142 | <10 000 |
| 143 | <10 000 |
| 144 | <10 000 |
| 145 | <50 |
| 146 | <50 |
| 147 | <50 |

-continued

| Example N° | IC$_{50}$ (nM) |
|---|---|
| 148 | <10 000 |
| 149 | <50 |
| 150 | <50 |
| 151 | <50 |
| 152 | <50 |
| 153 | <10 000 |
| 154 | <10 000 |
| 155 | <50 |
| 156 | <50 |
| 157 | <10 000 |
| 159 | <10 000 |
| 160 | <10 000 |
| 161 | <10 000 |
| 163 | <50 |
| 164 | <50 |
| 165 | <50 |
| 166 | <500 |
| 167 | <500 |
| 168 | <10 000 |
| 169 | <10 000 |
| 170 | <10 000 |
| 171 | <10 000 |
| 172 | <10 000 |
| 174 | <10 000 |
| 175 | <10 000 |
| 176 | <10 000 |
| 177 | <10 000 |
| 178 | <10 000 |
| 179 | <500 |
| 180 | <10 000 |
| 181 | <10 000 |
| 182 | <10 000 |
| 183 | <500 |
| 186 | <10 000 |
| 187 | <10 000 |
| 188 | <10 000 |
| 189 | <10 000 |
| 190 | <500 |
| 191 | <10 000 |
| 192 | <500 |
| 193 | <500 |
| 194 | <10 000 |
| 197 | <10 000 |
| 198 | <10 000 |
| 200 | <10 000 |
| 202 | <10 000 |
| 204 | <10 000 |
| 205 | <10 000 |
| 206 | <10 000 |
| 207 | <10 000 |
| 208 | <500 |
| 209 | <50 |
| 211 | <10 000 |
| 212 | <10 000 |
| 213 | <10 000 |
| 215 | <10 000 |
| 216 | <10 000 |
| 217 | <10 000 |
| 218 | <500 |
| 219 | <10 000 |
| 220 | <10 000 |
| 221 | <10 000 |
| 222 | <10 000 |
| 223 | <500 |
| 224 | <50 |
| 225 | <50 |
| 226 | <10 000 |
| 227 | <10 000 |
| 228 | <50 |
| 230 | <10 000 |
| 231 | <10 000 |
| 232 | <10 000 |
| 233 | <10 000 |
| 234 | <10 000 |
| 235 | <50 |
| 236 | <50 |
| 241 | <50 |
| 242 | <10 000 |
| 243 | <10 000 |
| 244 | <10 000 |
| 245 | <10 000 |
| 246 | <10 000 |
| 247 | <10 000 |
| 249 | <10 000 |
| 255 | <50 |
| 256 | <50 |

The compounds of the present invention present a high affinity for mGluR5 receptor. As allosteric modulators, they are useful for the production of medications, especially for the prevention or treatment of central nervous system disorders as well as other disorders modulated by this receptor.

The compounds of the invention can be administered either alone, or in combination with other pharmaceutical agents effective in the treatment of conditions mentioned above.

Reasonable variations are not to be regarded as a departure from the scope of the invention. It will be obvious that the thus described invention may be varied in many ways by those skilled in the art.

The following non-limiting examples are intending to illustrate the invention. The physical data given for the compounds exemplified is consistent with the assigned structure of those compounds.

Marble Burying Model of Anxiety

Anxiety models in rodents are used as standard tests to demonstrate anxiolytic-like properties of novel compounds. Mice exhibit a tendency to bury harmless novel objects when encountered in a test cage. Marble burying behavior in mice is reduced by compounds which are efficacious anxiolytics in humans. Thus, marble burying in mice has been used as a model for the prediction of anxiolytic-like effects of compounds (Millan, M. J. et al., Neuropharmacology, 42:677-684 (2002)).

Selective negative allosteric modulators (allosteric antagonists) of the metabotropic glutamate receptor subtype 5 (mGluR5) have been shown previously to reduce marble burying in mice (Spooren, W. P. et al., Journal of Pharmacology and Experimental Therapeutics, 295:1267-1275 (2000)). These results demonstrate that the marble burying test is a useful model for demonstrating the anxiolytic potential of compounds which are antagonists of mGluR5. Such compounds may be useful in the treatment of anxiety and related disorders.

Subjects:

The present studies were performed in accordance with the animal care and use policies of Addex Pharmaceuticals and the EEC directives on the protection of animals used for experimental and other scientific purposes (86/609/EEC and subsequent revisions). Male C57BL6/j mice (20-30 g) 7 weeks of age at the time of delivery were group housed in a temperature and humidity controlled facility on a 12 hour light/dark cycle for at least 5 days before use. Mice had access to food and water ad libitum except during marble burying experiments.

Assessment of Marble Burying:

The effect of compounds on marble burying in mice was tested. On the day of the test, animals were marked on their tails and weighed in a separate preparation room 1 hour before drug administration. Test compound or vehicle was administered po 60 minutes prior to the test session. Marble burying was tested in a separate experimental room. For the test, mice were placed individually into clear plastic cages (16×22×14 cm) with 5 cm of sawdust and 10 marbles evenly spaced against the walls of the cage. The mice were left undisturbed in the cages for 30 minutes. After removal of the mice from the test cages, the number of marbles buried was counted. A marble was considered buried if it was ⅔ or more covered.

Compound Administration:

Test compounds were dissolved in a solution of 80% 0.1N hydrochloric acid and 20% Tween 80 and adjusted to pH 6 with 1M NaHCO3. Test compounds were administered by oral gavage (po) in a volume of 10 ml/kg. Compound-vehicle-treated mice received the equivalent volume of vehicle solution po in the absence of added compound.

Statistical Analyses:

Statistical analyses were performed using GraphPad PRISM version 4.01 statistical software (GraphPad, San Diego, Calif., USA). Data were analyzed using one-way analysis of variance (ANOVA) followed by Bonferroni-corrected multiple comparisons, or t tests if only 2 groups were present. The significance level was set at $p<0.05$.

Effect of Compounds on Marble Burying in Mice

The effect of Example 256 on marble burying in mice is shown in FIG. 1. As can be seen in the figure, Example 256 significantly attenuated marble burying in mice (f (3.36)=5.04, n=10/group). Bonferroni-corrected multiple comparisons revealed a statistically significant difference showing that mice treated with 30 mg/kg po of Example 256 buried fewer marbles than vehicle-treated mice (t=3.686, p<0.01). These results demonstrate that Example 256 attenuates marble burying in mice and suggests that compounds of Formula II-A2-a2 may be useful in the treatment of anxiety.

Figure 2:
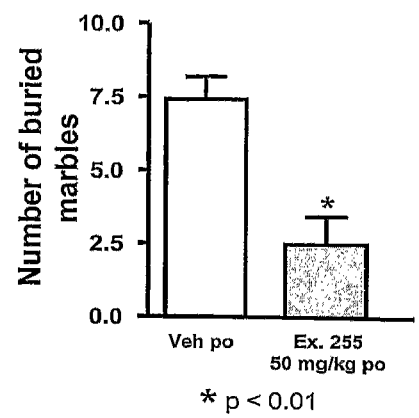
FIG. 2 shows that the representative Example 255 of the invention significantly attenuates marble burying in mice at doses of 50 mg/kg po.

The effect of Example 255 on marble burying in mice is shown in FIG. 2. As can be seen in the figure, mice treated with 50 mg/kg po of Example 255 buried significantly fewer marbles than vehicle-treated mice (t (1, 18)=3.92, n=10/group). These results demonstrate that Example 255 attenuates marble burying in mice and suggests that compounds of the invention may be useful in the treatment of anxiety.

Vogel Conflict Drinking Model of Anxiety in Rats

Anxiety models in rodents are used as standard tests to demonstrate anxiolytic-like properties of novel compounds. The Vogel conflict drinking model involves the conflict between thirst and receiving mild shocks for drinking water (punished drinking). Water-deprived rats are placed in a chamber and are periodically shocked for drinking water. The shocks suppress drinking and anxiolytics reverse this shock-induced suppression of drinking. The Vogel conflict drinking model was first proposed as a screening model for anxiolytics (Vogel, J. R. et al., Psychopharmacologia (Berl.), 21:1-7 (1971)) and is widely accepted as a robust model for testing the anxiolytic-like properties of compounds (Millan, M. J. and Brocco M., European Journal of Pharmacology, 463:67-96 (2003)).

Selective negative allosteric modulators (allosteric antagonists) of the metabotropic glutamate receptor subtype 5 (mGluR5) have been shown to increase punished drinking in rats (Varty, G. B. et al., Psychopharmacology (Berl.) 179: 207-217. (2005)). These results demonstrate that the Vogel conflict drinking test is a useful model for demonstrating the anxiolytic potential of compounds which are antagonists of mGluR5. Such compounds may be useful in the treatment of anxiety and related disorders.

Subjects:

The present studies were performed in accordance with the animal care and use policies of Addex Pharmaceuticals and the EEC directives on the protection of animals used for experimental and other scientific purposes (86/609/EEC and subsequent revisions). Male Sprague-Dawley rats (350 g) 7-9 weeks of age at the time of testing were group housed in a temperature and humidity controlled facility on a 12 hour light/dark cycle for at least 5 days before use. Rats had access to food ad libitum except during Vogel conflict drinking model experiments. Rats had access to water ad libitum until 48 hours prior to the test session.

Assessment of Vogel Conflict Drinking:

The effect of compounds on drinking in the Vogel conflict drinking model in rats was tested. Test chambers are housed in sound-attenuating boxes and each chamber contains a stainless steel drinking spout and a steel grid floor (MedAssociates, Georgia, Vermont, USA). Forty-eight hours prior to the test session, rats were habituated to the test chambers for 10 minutes. Water was removed from the rats immediately after the habituation session. Twenty-four hours before the test session, rats were again placed into the test chambers and allowed to drink for 4 minutes. Rats were then allowed 1 hour of access to water and then water was removed. On the test day, rats were brought to the test room at least 30 minutes before the test session. Rats were placed individually into the test chamber for a 5 minute session. Rats received a shock every $20^{th}$ lick on the drinking spout. The number of punished drinks was counted automatically by the computer interface. The number of punished drinks was compared between treatment groups. An increase in the number of punished drinks in rats treated with a compound is interpreted as an anxiolytic-like effect.

Compound Administration:

Test compounds (Examples 256 and 130) were dissolved either in a solution of 80% 0.1N hydrochloric acid, 20% Tween 80 and adjusted to pH 6 with 1M NaHCO$_3$ (Example 256) or a 7.5% Arabic gum/H$_2$O solution (Example 130). Test compounds were administered by oral gavage (po) in a volume of 3 ml/kg. Compound-vehicle-treated rats received the equivalent volume of vehicle solution po in the absence of added compound.

Statistical Analyses:

Statistical analyses were performed using GraphPad PRISM version 4.01 statistical software (GraphPad, San Diego, Calif., USA). Data were analyzed using one-way analysis of variance (ANOVA) followed by Bonferroni multiple comparisons. The significance level was set at $p<0.05$.

Effect of Compounds on Drinking in the Vogel Conflict Drinking Model in Rats

Figure 3:
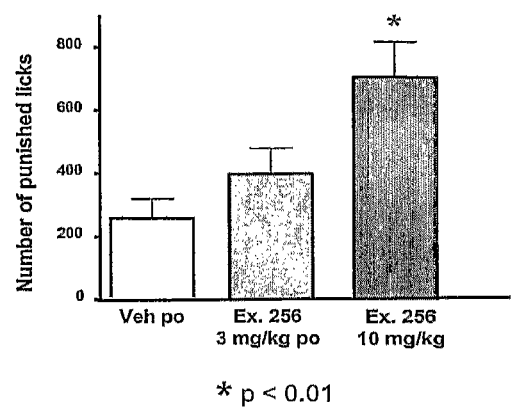
FIG. 3 shows that the representative Example 256 of the invention significantly increases punished drinking in rats at doses of 10 mg/kg po.

The effect of Example 256 on punished drinking in the Vogel conflict drinking test is shown in FIG. 3. As can be seen in the figure, Example 256 significantly increased punished drinking in rats (f (2.26)=6.845, n=9-10/group). Bonferroni-corrected multiple comparisons revealed a statistically significant difference showing that rats treated with 10 mg/kg po of Example 256 accepted significantly more shocks than vehicle-treated rats (t=3.585, p<0.01).

Figure 4:
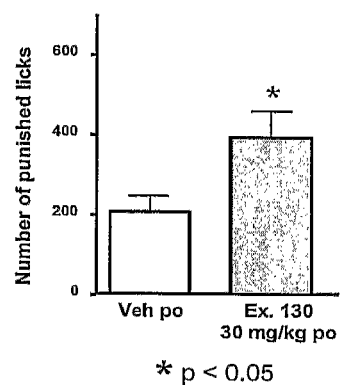
FIG. 4 shows that the representative Example 130 of the invention significantly increases punished drinking in rats at doses of 30 mg/kg po.

Example 130 also induced an anxiolytic effect in the Vogel conflict drinking test (FIG. 4). Specifically, rats that received 30 mg/kg of Example 130 took significantly more punished licks than vehicle injected controls (t(1, 17)=2.593, n=9-10/group). These data indicate that Example 256 and 130 are anxiolytic in the Vogel conflict drinking test.

Summary of Behavioral Results

The results presented above demonstrate that Examples 255, 256, and 130 are effective in specific models of anxiety in rodents. These results suggest that compounds of the invention may be useful in the treatment of anxiety disorders and related disorders and diseases of the central nervous system.

EXAMPLES

Unless otherwise noted, all starting materials were obtained from commercial suppliers and used without further purification.

Specifically, the following abbreviations may be used in the examples and throughout the specification.

| | |
|---|---|
| % (percent) | M (molar) |
| AcOEt (ethyl acetate) | mbar (millibar) |
| (BOC)$_2$O (Di-tert-butyl dicarbonate) | MeOH (methanol) |
| n-BuLi (n-butyllithium) | mg (milligrams) |
| ° C. (Celsius degrees) | MgSO$_4$ (magnesium sulphate) |
| CDCl$_3$ (deuterated chloroform) | MHz (megahertz) |
| CHCl$_3$ (chloroform) | min (minutes) |
| CuI (copper iodide) | µL (microliters) |
| DAST (diethylaminosulfur trifluoride) | mL (milliliters) |
| DCM (dichloromethane) | mmol (millimoles) |
| dec. (decomposition) | Mp (melting point) |
| DIEA (diisopropyl ethyl amine) | N (normal) |
| DMAP (N,N-dimethylaminopyridine) | N$_2$ (nitrogen) |
| DMF (dimethylformamide) | NaCl (Sodium chloride) |
| DMSO (dimethyl sulfoxide) | NaHCO$_3$ (sodium hydrogenocarbonate) |
| EDCI•HCl (1-3(Dimethylaminopropyl)-3-ethylcarbodiimide, hydrochloride) | NaOH (sodium hydroxide) |
| Et$_2$O (diethyl ether) | Na$_2$SO$_4$ (sodium sulphate) |
| g (grams) | NH$_4$Cl (ammonium chloride) |
| h (hour) | NH$_4$OH (ammonium hydroxide) |
| $^1$H (proton) | NMR (Nuclear Magnetic Reasonance) |
| HCl (hydrochloric acid) | PdCl$_2$(PPh$_3$)$_2$ (Bis(triphenylphosphine) palladium (II) dichloride |
| HOBT (1-hydroxybenzotriazole) | Pd(PPh$_3$)$_4$ (tetrakis(triphenylphosphine)palladium(0) |
| HPLC (High Pressure Liquid Chromatography) | P$_2$O$_5$ (phosphorus pentoxide) |
| H$_2$SO$_4$ (Sulfuric acid) | POCl$_3$ (phosphorus oxychloride) |
| Hz (Hertz) | r.t. (room temperature) |
| K$_2$CO$_3$ (potassium carbonate) | THF (tetrahydrofuran) |
| KI (potassium iodide) | TLC (tin chromatography layer) |
| LCMS (Liquid Chromatography Mass Spectrum) | RT (Retention Time) |
| LiAlH$_4$ (lithium aluminium hydride) | |

All references to brine refer to a saturated aqueous solution of NaCl. Unless otherwise indicated, all temperatures are expressed in ° C. (degrees Centigrade). All reactions are conducted not under an inert atmosphere at room temperature unless otherwise noted.

The microwave oven used is an apparatus from Biotage (Optimizer™) equipped with an internal probe that monitors reaction temperature and pressure, and maintains the desired temperature by computer control.

$^1$H NMR spectra were recorded on a Brucker 500 MHz. Chemical shifts are expressed in parts of million (ppm, δ units). Coupling constants are in units of hertz (Hz). Splitting patterns describe apparent multiplicities and are designated as s (singulet), d (doublet), t (triplet), q (quadruplet), quint (quintuplet), m (multiplet).

LCMS were recorded on a Waters Micromass ZQ 2996 system by the following conditions. Column 3.0*50 mm stainless steel packed with 5 µm XTerra RP C-18; flow rate 1 ml/min; mobile phase: A phase=0.1% formic acid in water, B phase=0.07% formic acid in acetonitrile. 0-0.5 min (A: 95%, B: 5%), 0.5-6.0 min (A: 0%, B: 100%), 6.0-6.5 min (A: 95%, B: 5%), 6.5-7 min (A: 95%, B: 5%); UV detection Diode Array: 200-400 nm; Injection volume: 3 µl.

All mass spectra were taken under electrospray ionisation (ESI) methods.

Most of the reaction were monitored by thin-layer chromatography on 0.25 mm Macherey-Nagel silica gel plates (60F-2254), visualized with UV light. Flash column chromatography was performed on silica gel (220-440 mesh, Fluka). Melting point determination was performed on a Buchi B-540 apparatus.

Example 1

2-Methyl-(4-(4-phenyl)but-1-ynyl)thiazole

To a solution of CuI (45 mg, 24 mol) in triethylamine (3 mL) were added 4-bromo-2-methylthiazole (85 mg, 0.48 mmol) and (PPh$_3$)$_2$PdCl$_2$ (17 mg, 24 µmol). The reaction mixture was cooled to 0° C. and 1-(but-3-ynyl)benzene (67 µl, 0.48 mmol) was added. The reaction mixture was allowed to warm to room temperature and then heated under reflux for 3 days. Triethylamine was evaporated, water was added and the aqueous phase was extracted twice with DCM. The organic phase was washed with NH$_4$OH solution, dried over Na$_2$SO$_4$, filtered and concentrated. The crude residue was purified by flash chromatography (cyclohexane/AcOEt 9:1) to yield 25 mg (0.1 mmol, 23%) of 2-methyl-(4-(4-phenyl)but-1-ynyl)thiazole as a yellow oil.

LCMS (RT): 4.87 min; MS (ES+) gave m/z: 229.2.

Example 2

2-(4-(3-(2-Ethylphenyl)-1,2,4-oxadiazol-5-yl)but-1-ynyl)pyridine

2(A) 3-Chloro-N'-hydroxy-2-methylbenzamidine

According to the general protocol for amidoxime synthesis described in Example 15(A), the conversion of 2-ethylbenzonitrile (0.92 g, 7 mmol) afforded 1.12 g of 2-ethyl-N'-hydroxybenzamidine (Yield: 97%) as white powder (M.P.=54-55° C.).

Rf (DCM/MeOH: 97/3): 0.20

LCMS (RT): 0.81 min; MS (ES+) gave m/z: 165.0

2(B) 5-(But-3-ynyl)-3-(2-ethylphenyl)-1,2,4-oxadiazole

According to the general protocol for oxadiazole synthesis described in Example 40(B), the conversion of 3-chloro-N'-hydroxy-2-methylbenzamidine (560 mg, 3.4 mmol) afforded 343 mg of 5-(but-3-ynyl)-3-(2-ethylphenyl)-1,2,4-oxadiazole (Yield: 44%) as yellow oil.

Rf (DCM/MeOH: 99/1): 0.75

LCMS (RT): 4.86 min; MS (ES+) not detected

2(C) 2-(4-(3-(2-Ethylphenyl)-1,2,4-oxadiazol-5-yl)but-1-ynyl)pyridine

According to the general protocol for Sonogashira coupling described in Example 40(C), the conversion of 5-(but-3-ynyl)-3-(2-ethylphenyl)-1,2,4-oxadiazole (342 mg, 1.51 mmol) afforded 213 mg of 2-(4-(3-(2-ethylphenyl)-1,2,4-oxadiazol-5-yl)but-1-ynyl)pyridine (Yield 46%) as yellow oil.

LCMS (RT): 4.71 min; MS (ES+) gave m/z: 304.0
$^1$NMR (CDCl$_3$), δ (ppm): 8.62 (s, H), 7.92 (d, H), 7.63 (t, H), 7.45-7.20 (m, 5H), 3.33 (t, 2H), 3.07 (t, 2H), 3.00 (q, 2H), 1.23 (t, 3H).

Example 3

2-(4-(Pyridin-2-yl)but-3-ynyl)isoindoline-1,3-dione

3(A) 4-(Pyridin-2-yl)but-3-yn-1-ol

The title compound was prepared in accordance with the general method of Example 1, from 2-bromopyridine (10.3 g, 65.1 mmol) and but-3-yn-1-ol (5.08 mL, 67.1 mmol). Reaction time: 14 hours. The crude residue was purified by flash chromatography (DCM/AcOEt 3:7 to 1:9) to yield 6.10 g (41.4 mmol, 64%) of 4-(pyridin-2-yl)but-3-yn-1-ol as a brown oil.

3(B) 2-(4-(Pyridin-2-yl)but-3-ynyl)isoindoline-1,3-dione 4-(Pyridin-2-yl)but-3-yn-1-ol (96 mg, 0.65 mmol), isoindoline-1,3-dione (140 mg, 0.97 mmol) and triphenylphosphine polymer bound 3 mmol/g (340 mg, 1.02 mmol) were dissolved in DCM (2 mL) and cooled to 0° C. Di-tert-butylazodicarboxylate (226 mg, 0.96 mmol) dissolved in DCM (0.5 mL) was added dropwise over 30 min. to the reaction mixture followed by THF (0.5 mL) and the reaction mixture was stirred for 16 h at room temperature. After filtration through celite, the organic phase was washed with a solution of NH$_4$OH, brine, dried over Na$_2$SO$_4$, filtered and concentrated. The crude residue was purified by flash chromatography (cyclohexane/AcOEt 3:7) to yield 130 mg (0.47 mmol, 73%) of 2-(4-(pyridin-2-yl)but-3-ynyl)isoindoline-1,3-dione as an orange solid.

LCMS (RT): 3.08 min; MS (ES+) gave m/z: 277.2.
$^1$H-NMR (CDCl$_3$), δ (ppm): 2.91 (t, J=7.0, 2H), 4.02 (t, J=7.0, 2H), 7.34-7.43 (m, 1H), 7.47-7.55 (m, 1H), 7.73 (dd, J=3.0 and 5.5, 2H), 7.80-7.85 (m, 1H), 7.86 (dd, J=3.0 and 5.5, 2H), 8.56-8.61 (m, 1H).

Example 4

2-(4-(Pyridin-2-yl)but-3-ynyl)phthalazin-1(2H)-one

The title compound was prepared in accordance with the general method of Example 3(B), from 4-(pyridin-2-yl)but-3-yn-1-ol (102 mg, 0.69 mmol, Example 3(A)) and phthalazin-1(2H)-one (152 mg, 1.04 mmol). The crude residue was purified by flash chromatography (DCM/MeOH 99:1 to 97:3) followed by bulb-to-bulb distillation (100° C., 0.1 mbar) to yield 22 mg (79 mmol, 11%) of 2-(4-(pyridin-2-yl)but-3-ynyl)phthalazin-1(2H)-one as a brown solid.

LCMS (RT): 2.70 min; MS (ES+) gave m/z: 276.2.
$^1$H-NMR (CDCl$_3$), δ (ppm): 3.18 (t, J=7.0, 2H), 4.59 (t, J=7.0, 2H), 7.72-7.85 (5H), 8.23 (s, 1H), 8.23-8.28 (m, 1H), 8.43 (d, J=7.5, 1H), 8.72 (d, J=6.0, 1H).

Example 5

2-(4-Phenylbut-1-ynyl)quinoline

The title compound was prepared in accordance with the general method of Example 1, from 2-chloroquinoline (300 mg, 1.83 mmol) and 1-(but-3-ynyl)benzene (200 mg, 1.54 mmol). The crude residue was purified by flash chromatography (cyclohexane/AcOEt 95:5) to yield 148 mg (0.57 mmol, 37%) of 2-(4-phenylbut-1-ynyl)quinoline as an orange oil.

LCMS (RT): 4.51 min; MS (ES+) gave m/z: 258.2.
$^1$H-NMR (CDCl$_3$), δ (ppm): 2.80 (t, J=7.5, 2H), 3.02 (t, J=7.5, 2H), 7.21-7.25 (m, 1H), 7.27-7.35 (4H), 7.43 (d, J=8.5, 1H), 7.52-7.56 (m, 1H), 7.70-7.74 (m, 1H), 7.79 (d, J=8.0, 1H), 8.09-8.20 (2H).

Example 6

2-(4-Phenylbut-1-ynyl)pyrimidine

The title compound was prepared in accordance with the general method of Example 1, from 2-bromopyrimidine (290 mg, 1.82 mmol) and 1-(but-3-ynyl)benzene (200 mg, 1.54 mmol). The crude residue was purified by flash chromatography (cyclohexane/AcOEt 85:15) to yield 275 mg (1.32 mmol, 86%) of 2-(4-phenylbut-1-ynyl)pyrimidine as a yellow oil.

LCMS (RT): 3.51 min; MS (ES+) gave m/z: 209.2.
$^1$H-NMR (CDCl$_3$), δ (ppm): 2.76 (t, J=7.5, 2H), 3.00 (t, J=7.5, 2H), 7.20-7.24 (2H), 7.25-7.28 (2H), 7.29-7.33 (2H), 8.70 (d, J=5.0, 2H).

Example 7

2-(4-Phenylbut-1-ynyl)benzo[d]oxazole

To a solution of CuI (15 mg, 81 mmol) in triethylamine (3 mL) were added 2-chlorobenzo[d]oxazole (250 mg, 1.63 mmol), (PPh$_3$)$_2$PdCl$_2$ (57 mg, 81 µmol), triphenylphosphine polymer bound 3 mmol/g (98 mg, 293 µmol) and a solution of 1-(but-3-ynyl)benzene (250 mg, 1.92 mmol) in DMF (0.5 mL). The reaction mixture was stirred for 25 min. at 120° C. in the microwave cavity. The reaction was quenched as described in Example 1. The crude residue was purified by flash chromatography (cyclohexane/AcOEt 95:5) to yield 163 mg (0.66 mmol, 40%) of 2-(4-phenylbut-1-ynyl)benzo[d]oxazole as an orange oil.

LCMS (RT): 4.84 min; MS (ES+) gave m/z: 248.1.
$^1$H-NMR (CDCl$_3$), δ (ppm): 2.81 (d, J=7.5, 2H), 3.00 (d, J=7.5, 2H), 7.21-7.26 (m, 1H), 7.26-7.29 (2H), 7.31-7.40 (4H), 7.48-7.51 (m, 1H), 7.70-7.72 (m, 1H).

Example 8

2-(4-(Pyridin-2-yl)but-3-ynyl)benzo[d]oxazole Hydrochloride

8(A) 2-(But-3-ynyl)benzo[d]oxazole

A solution of triphenylphosphine (16.0 g, 61.2 mmol) in a mixture of acetonitrile/pyridine 1:1 (30 mL) was added dropwise over 2 hours to a solution of pent-4-ynoic acid (2.00 g, 20.4 mmol), 2-aminophenol (2.31 g, 21.0 mmol), Et$_3$N (8.50 mL, 61.2 mmol) and CCl$_4$ (7.87 mL, 81.6 mmol) in acetonitrile/pyridine 1:1 (20 mL). The reaction mixture was stirred for 2 days at room temperature and the solvent was evaporated. The residue was dissolved in DCM and washed with a saturated solution of NH$_4$OH. The aqueous phase was extracted twice with DCM. The resulting organic phase was dried over MgSO$_4$, filtered and evaporated. The crude residue was purified by flash chromatography (cyclohexane/AcOEt 9:1) to yield 1.37 g (8.03 mmol, 39%) of 2-(but-3-ynyl)benzo[d]oxazole as a red oil.

8(B) 2-(4-(Pyridin-2-yl)but-3-ynyl)benzo[d]oxazole

The title compound was prepared in accordance with the general method of Example 1, from 2-bromopyridine (746 mg, 4.67 mmol) and 2-(but-3-ynyl)benzo[d]oxazole (800 mg, 4.67 mmol). Reaction time: 3 hours. The crude residue was dissolved in DCM, syn-2-pyridinecarboxaldoxime (684 mg, 5.60 mmol) was added and the reaction mixture was stirred overnight. The solvent was evaporated and the resulting crude product was purified by flash chromatography (DCM/MeOH 99:1) to yield 923 mg (3.72 mmol, 79%) of 2-(4-(pyridin-2-yl)but-3-ynyl)benzo[d]oxazole as a yellow solid.

8(C) 2-(4-(Pyridin-2-yl)but-3-ynyl)benzo[d]oxazole Hydrochloride

A solution of HCl in dioxane (4.65 mL, 0.8 M, 3.72 mmol) was added to a solution of 2-(4-(pyridin-2-yl)but-3-ynyl)benzo[d]oxazole (923 mg, 3.72 mmol) in dioxane (50 mL). The resulting suspension was cooled at 0° C. for 1 hour and was filtered. The precipitate was washed twice with dioxane and dried under vacuum to yield 2-(4-(pyridin-2-yl)but-3-ynyl)benzo[d]oxazole hydrochloride (830 mg, 2.91 mmol, 78%) as a white solid (M.P.=143.5-145° C.).

LCMS (RT): 3.29 min; MS (ES+) gave m/z: 249.1.
Rf (DCM/MeOH 98:2)=0.1.
$^1$H-NMR (CDCl$_3$), δ (ppm): 3.25 (t, J=7.4, 2H), 3.43 (t, J=7.4, 2H), 7.32-7.38 (2H), 7.52-7.56 (m, 1H), 7.69-7.73 (m, 1H), 7.74-7.80 (2H), 8.24-8.28 (m, 1H), 8.73 (d, J=6.0, 1H).

Example 9

2-(4-(3-(4-Fluorophenyl)-1,2,4-oxadiazol-5-yl)but-1-ynyl)pyridine

9(A) Ethyl pent-4-ynoate

In analogy to the method as described in Tetrahedron, 2000, 56, 5735-5742, a mixture of the 4-pentynoic acid (10 g, 102 mmol) and H$_2$SO$_4$ 98% (0.338 mL, 6.12 mmol) in ethanol (113 mL) was heated at 50° C. overnight. The reaction mixture was concentrated and the crude product was dissolved in ethyl acetate, washed with NaHCO$_3$ 1M and water. The solvent was removed under reduced pressure to afford 9.04 g of ethyl pent-4-ynoate (Yield: 70%) as a colorless oil.

9(B) Ethyl 5-(pyridin-2-yl)pent-4-ynoate

In a dry reaction tube containing in suspension copper iodide (60 mg, 0.315 mmol) and triethylamine (17.70 mL, 126 mmol), were added 2-iodopyridine (1.29 g, 6.30 mmol) and the Pd(PPh$_3$)$_2$Cl$_2$ (202 mg, 0.315 mmol). A yellow suspension is obtained and after a few minutes of stirring at room temperature, was added ethyl pent-4-ynoate (790 mg, 6.30 mmol) in solution in 2 mL of triethylamine. Immediately the color of the reaction turns to black. The mixture was stirred at room temperature for 30 min and then at 80° C. for 20 h. Triethylamine was concentrated under reduce pressure and the residue was dissolved in DCM. The organic layer was washed with saturated NH$_4$Cl, water and brine. The solvent was removed under reduced pressure and the crude product was purified by flash chromatography system (prepacked silicagel column 25 g, DCM/MeOH: 98/2 as eluent) to afford 1.17 g of ethyl 5-(pyridin-2-yl)pent-4-ynoate (Yield: 78%) as brownish oil.

9(C) 5-(Pyridin-2-yl)pent-4-ynoic Acid

To a aqueous solution of 1M NaOH (9.9 mL) heated at 50° C., was added slowly a solution of ethyl 5-(pyridin-2-yl)pent-4-ynoate (2 g, 9.90 mmol) in 3 mL of ethanol. The reaction mixture was stirred 1 h 30 at 50° C. and cooled to room temperature. An aqueous 1N HCl (9.9 mL, 9.90 mmol) was then added and the solvent was removed under pressure to afford 2.3 g of 5-(pyridin-2-yl)pent-4-ynoic acid (Yield: 99%) as a brown solid which can be used without further purification.

9(D) 2-(4-(3-(4-Fluorophenyl)-1,2,4-oxadiazol-5-yl)but-1-ynyl)pyridine

A mixture of commercially available 4-fluoro-N'-hydroxybenzamidine (220 mg, 1.4 mmol), 5-(pyridin-2-yl)pent-4-ynoic acid (330 mg, 1.4 mmol), HOBT (210 mg, 1.4 mmol) and EDCI.HCl (400 mg, 2.1 mmol) in dioxane (4.5 mL) was stirred at R.T for 7H, The reaction mixture was then heated at 100° C. for 36 h. The solvent was removed under reduced pressure and the residue was dissolved in DCM. The organic layer was washed with water, 1N NaOH and water. The organic layer was dried over Na$_2$SO$_4$, filtered and evaporated. Purification by flash chromatography (prepacked 10 g silicagel column, DCM/MeOH: 99/1 as eluent) to afford 103 mg of 2-(4-(3-(4-fluorophenyl)-1,2,4-oxadiazol-5-yl)but-1-ynyl) pyridine (Yield: 25%) as a yellow oil.

LCMS (RT): 3.99 min; MS (ES+) gave m/z: 294.1
$^1$NMR (CDCl$_3$), δ (ppm): 8.64 (s, H), 8.10 (m, 2H), 7.68 (t, H), 7.41 (d, H), 7.27 (d, H), 7.21-7.14 (m, 2H), 3.32 (t, 2H), 3.07 (t, 2H).

Example 10

2-(4-(3-Phenyl)-1,2,4-oxadiazol-5-yl)but-1-ynyl)pyridine

According to the protocol described in Example 9(D), the conversion of commercially available N'-hydroxybenzamidine (190 mg, 1.4 mmol) afforded 59 mg of 2-(4-(3-phenyl)-1,2,4-oxadiazol-5-yl)but-1-ynyl)pyridine (Yield: 15%) as yellow oil.

LCMS (RT): 3.83 min; MS (ES+) gave m/z: 276.0
$^1$NMR (CDCl$_3$), δ (ppm): 8.64 (s, H), 8.09 (m, H), 7.70 (t, H), 7.54-7.46 (m, 3H), 7.42 (d, H), 7.30-7.25 (m, 2H), 3.33 (t, 2H), 3.09 (t, 2H).

Example 11

2-Methyl-4-(4-phenylbut-1-ynyl)-1H-imidazole

11(A) Ethyl 4-iodo-2-methyl-1H-imidazole-1-carboxylate

In general, modifications were made from the procedure given in J. Org. Chem., 1999, 64, 23, 8608-8615. A solution of commercially available 4-iodo-2-methyl-1H-imidazole (520 mg, 2.5 mmol) in THF (8.3 mL), containing DIEA (1.07 mL, 6.25 mmol) and DMAP (150 mg, 1.30 mmol), was cooled in a ice bath at 0° C. A solution of ethyl chloroformate (678 mg, 6.25 mmol) in THF (2.5 mL) was slowly added over a period of 20 min to the reaction mixture. The reaction mixture was heated at 50° C. for 48 h and the solvent was removed under reduced pressure. The residue was dissolved in DCM and the organic layer was washed with brine, water, dried over MgSO$_4$, filtered and evaporated. Purification by flash chromatography (prepacked 10 g silicagel column, DCM/MeOH: 97/3 as eluent) to afford 660 mg of ethyl 4-iodo-2-methyl-1H-imidazole-1-carboxylate (Yield: 94%) as a colorless oil.

11(B) Ethyl 2-methyl-4-(4-phenylbut-1-ynyl)-1H-imidazole-1-carboxylate

In a dry reaction tube containing in suspension iodide copper (20 mg, 0.1 mmol) and triethylamine (5.81 mL, 41.40 mmol), were added ethyl 4-iodo-2-methyl-1H-imidazole-1-carboxylate (580 mg, 2.07 mmol) and the Pd(PPh$_3$)$_2$Cl$_2$ (66 mg, 0.1 mmol). A yellow suspension is obtained and after a few minutes stirred at room temperature was added the commercially available 4-phenyl-1-butyn (269 mg, 2.07 mmol) in triethylamine (0.5 mL). Immediately the color of the reaction turns to black.

The mixture was stirred at room temperature for 30 min and then at 80° C. for 20 h. Triethylamine was concentrated under reduce pressure and the residue was dissolved in DCM. The organic layer was washed with saturated NH$_4$Cl, water and brine, dried (MgSO$_4$) and concentrated. Purification by flash chromatography (prepacked 25 g silicagel column, DCM/MeOH: 99/1 as eluent) to afford 410 mg of ethyl 2-methyl-4-(4-phenylbut-1-ynyl)-1H-imidazole-1-carboxylate (Yield: 70%) as a brown oil.

Rf (DCM/MeOH: 99/1)=0.3
LCMS (RT): 4.39 min; MS (ES+) gave m/z: 283.1

11(C) 2-Methyl-4-(4-phenylbut-1-ynyl)-1H-imidazole 0.45 mL of NaOH 2.0 N was added dropwise to a solution ethyl 2-methyl-4-(4-phenylbut-1-ynyl)-1H-imidazole-1-carboxylate (250 mg, 0.9 mmol) in ethanol (4.5 mL) and the mixture was heated at 80° C. overnight. Ethanol was concentrated under reduced pressure, To the crude producer was added water and the aqueous layer was extracted with DCM. The recombined organics layers were washed with brine, dried over MgSO$_4$, filtered and concentrated to afford 163 mg of 2-methyl-4-(4-phenylbut-1-ynyl)-1-imidazole (Yield: 86%) as a beige solid (M.P.=124-126° C.).

Rf (DCM/MeOH: 95/5)=0.3
LCMS (RT): 0.64-2.41 min; MS (ES+) gave m/z: 211.2
$^1$NMR (CDCl$_3$), δ (ppm): 7.32-7.19 (m, 6H), 3.80 (s, NH), 2.89 (m, 2H), 2.67 (m 2H), 2.43 (s, 3H).

Example 12

N-Methyl-N-phenyl-5-(pyridin-2-yl)pent-4-ynamide

12(A) N-methyl-N-phenylpent-4-ynamide

To a solution of N-methylbenzenamine (110 mg, 1.02 mmol) in DCM (3 mL) was successively added at R.T. 4-pentynoic acid (100 mg, 1.02 mmol), HOBT (171 mg, 1.12 mmol) and EDCI.HCl (293 mg, 1.53 mmol). The reaction was stirred at R.T. overnight. The reaction was quenched with water. The organic layer was separated and washed with 1M NaHCO$_3$ and water. The solvent was removed under reduced pressure to afford 150 mg N-methyl-N-phenylpent-4-ynamide (Yield: 78%) as an orange oil which can be used without further purification.

LCMS (RT): 3.26 min; MS (ES+) gave m/z: 188.1

12(B) N-Methyl-N-phenyl-5-(pyridin-2-yl)pent-4-ynamide

According to the protocol described in Example 74(E), the conversion of N-methyl-N-phenylpent-4-ynamide (150 mg, 0.80 mmol) afforded 130 mg of N-methyl-N-phenyl-5-(pyridin-2-yl)pent-4-ynamide (Yield: 61%) as orange solid (M.P.=68-71° C.). Purification by flash chromatography (prepacked 25 g silicagel column, DCM/MeOH: 95/5 as eluent)

Rf (DCM/MeOH: 95/5)=0.20
LCMS (RT): 2.89 min; MS (ES+) gave m/z: 265.1
$^1$NMR (CDCl$_3$), δ (ppm): 8.55 (s, H), 7.73 (t, H), 7.48-7.40 (m, 3H), 7.36 (t, H), 7.29 (t, H), 7.25-7.20 (m, 2H), 3.30 (s, 3H), 2.77 (t, 2H), 2.45 (t, 2H).

Example 13

N-(4-Fluorophenyl)-N-methyl-5-(pyridin-2-yl)pent-4-ynamide

13(A) N-(4-fluorophenyl)-N-methylpent-4-ynamide

According to the protocol described in Example 12(A), the conversion of 4-fluoro-N-methylbenzenamine (127 mg, 0.52 mmol) afforded 180 mg of N-(4-fluorophenyl)-N-methylpent-4-ynamide (Yield: 91%) as orange oil.

LCMS (RT): 3.38 min; MS (ES+) gave m/z: 206.1

13(B) N-(4-Fluorophenyl)-N-methyl-5-(pyridin-2-yl)pent-4-ynamide

According to the protocol described in Example 74(E), the conversion of N-(4-fluorophenyl)-N-methylpent-4-ynamide (170 mg, 0.83 mmol) afforded 157 mg of N-(4-fluorophenyl)-N-methyl-5-(pyridin-2-yl)pent-4-ynamide (Yield: 67%) as orange oil. Purification by Flash chromatography (prepacked 25 g silicagel column, DCM/MeOH: 95/5 as eluent)

Rf (DCM/MeOH: 95/5)=0.23
LCMS (RT): 3.06 min; MS (ES+) gave m/z: 283.1
$^1$NMR (CDCl$_3$), δ (ppm): 8.55 (s, H), 7.65 (t, H), 7.47 (d, H), 7.24-7.18 (m, 3H), 7.15-7.08 (m, 2H), 3.26 (s, 3H), 2.75 (t, 2H), 2.41 (t, 2H).

Example 14

2-(4-(2-Phenylthiazol-4-yl)but-1-ynyl)pyridine

14(A) 4-(Bromomethyl)-2-phenylthiazole

Bromine (177 mg, 1.1 mmol) was added directly into a solution of triphenylphosphine (288 mg, 1.1 mmol) in DCM (2 mL) to give a kind of white precipitate. The temperature was cooled to −6° C. A solution of commercially available (2-phenylthiazol-4-yl)methanol (200 mg, 1.04 mmol) in DCM (1 mL) was added dropwise. The resulting mixture was maintained at −6° C. for 15 min and then warmed to room temperature for 1 h. A white precipitate was formed. The solution was filtered and the white precipitate was washed with DCM. The white precipitate was collected and dissolved in NaHCO$_3$ 0.5M After 30 min of stirring, the aqueous layer was extracted with DCM and the organic phase was washed with water, dried over MgSO$_4$, filtered and evaporated to afford 248 mg of 4-(bromomethyl)-2-phenylthiazole (Yield 71%) as a yellow oil.

LCMS (RT): 4.46 min; MS (ES+): no ionisation

14(B) 4-(4-(Trimethylsilyl)but-3-ynyl)-2-phenylthiazole

According to the protocol described in Example 74(C), the conversion of 4-(bromomethyl)-2-phenylthiazole (185 mg, 0.73 mmol) afforded 191 mg of 4-(4-(trimethylsilyl)but-3-ynyl)-2-phenylthiazole (Yield: 92%) as yellow oil.

LCMS (RT): 5.56 min; MS (ES+) gave m/z: 286.1

14(C) 4-(But-3-ynyl)-2-phenylthiazole

According to the protocol described in Example 74(D), the conversion of 4-(4-(trimethylsilyl)but-3-ynyl)-2-phenylthiazole (191 mg, 0.67 mmol) afforded 111 mg of 4-(but-3-ynyl)-2-phenylthiazole (Yield: 77%) as yellow oil.

LCMS (RT): 4.53 min; MS (ES+) gave m/z: 214.1

14(D) 2-(4-(2-Phenylthiazol-4-yl)but-1-ynyl)pyridine

According to the protocol described in Example 74(E), the conversion of 4-(but-3-ynyl)-2-phenylthiazole (111 mg, 0.52 mmol) afforded 88 mg of 2-(4-(2-phenylthiazol-4-yl)but-1-ynyl)pyridine (Yield: 58%) as brown oil. Purification by flash chromatography (prepacked 10 g silicagel column, DCM 100% as eluent).

Rf (Cyclohexane/AcOEt: 60/40)=0.23

LCMS (RT): 4.11 min; MS (ES+) gave m/z: 291.1

$^1$NMR (CDCl$_3$), δ (ppm): 8.61 (s, H), 7.98-7.93 (m, 2H), 7.76 (t, H), 7.48-7.40 (m, 4H), 7.33 (m, H), 7.18 (m, H), 3.20 (t, 2H), 2.98 (t, 2H).

Example 15

2-(4-(3-o-Tolyl)-1,2,4-oxadiazol-5-yl)but-1-ynyl)pyridine

15(A) N'-Hydroxy-2-methylbenzamidine

A mixture of 2-methyl-benzonitrile (0.950 mL, 8 mmol), hydroxylamine 50% in water (1.6 mL, 24 mmol) and EtOH (8 mL) was heated at 70° C. for 48 h. TLC analysis (DCM/MeOH: 97/3 as eluent) indicates the completion of the reaction. The solvent was removed under reduced pressure to afford 1.2 g of N'-hydroxy-2-methylbenzamidine (Yield: 100%) as a white powder (M.P.=147-148.5° C.). which can be used without further purification.

Rf Amidoxime (DCM/MeOH: 97/3 as eluent): 0.2

15(B) 5-(But-3-ynyl)-3-o-tolyl-1,2,4-oxadiazole

In a reactor tube, a mixture of N'-hydroxy-2-methylbenzamidine (555 mg, 3.7 mmol), 4-pentynoic acid (363 mg, 3.7 mmol), HOBT (0.56 g, 3.7 mmol) and EDCI.HCl (1.06 g, 5.55 mmol) in dioxane (7.4 mL) was stirred at R.T for 3 h. After this time the mixture was heated at 80° C. overnight in a reaction block. The mixture was concentrated. The organic layer was washed with water, NaOH 1N and water. The solvent was evaporated in a Genevac for 75 min at 40° C. using the low boiling point program. The crude product was purified by flash chromatography (Prepacked 10 g silicagel column) with DCM as eluent to afford 250 mg of 5-(but-3-ynyl)-3-o-tolyl-1,2,4-oxadiazole (Yield: 32%) as yellow oil.

LCMS (RT): 4.36 min; MS (ES+) gave m/z: 213.1

Rf Oxadiazole (DCM/MeOH: 99/1 as eluent): 0.75

15(C) 2-(4-(3-o-Tolyl)-1,2,4-oxadiazol-5-yl)but-1-ynyl)pyridine

In a dry reaction tube containing in suspension copper iodide (11 mg, 0.06 mmol) and triethylamine (3.3 mL, 24 mmol), were added 2-bromopyridine (115 μL, 1.2 mmol) and the Pd(PPh$_3$)$_2$Cl$_2$ (42 mg, 0.06 mmol) under N$_2$. A yellow suspension is obtained and after 5 min of stirring at room temperature 5-(but-3-ynyl)-3-o-tolyl-1,2,4-oxadiazole (249 mg, 1.2 mmol) in solution in 0.7 mL of triethylamine was added under N$_2$. Immediately the color of the reaction turns to black. The mixture was stirred at room temperature for 30 min and then at 80° C. for 20 h under N$_2$. Triethylamine was concentrated under reduced pressure and the residue was dissolved in DCM. The organic layer was washed with NH$_4$Cl, water, NaCl, dried (MgSO$_4$), and concentrated. The crude product was purified by flash chromatography (Prepacked 10 g silicagel column with DCM/MeOH: 99/1 as eluent) to afford 103 mg of 2-(4-(3-o-tolyl)-1,2,4-oxadiazol-5-yl)but-1-ynyl)pyridine (Yield: 30%) as brown semi-solid.

LCMS (RT): 4.11 min; MS (ES+) gave m/z: 290.1

$^1$H-NMR (CDCl$_3$), δ (ppm): 8.76 (s, H), 8.01 (m, H), 7.81 (m, H), 7.72 (m, H), 7.41-7.31 (m, 4H), 3.37 (m, 2H), 3.04 (m, 2H), 2.63 (s, 3H).

Example 16

2-(4-(3-Benzyl-1,2,4-oxadiazol-5-yl)but-1-ynyl)pyridine

16(A) N'-Hydroxy-2-phenylacetamidine

According to the general protocol for amidoxime synthesis described in Example 15(A), the conversion of 2-phenylacetonitrile (0.93 mL, 8 mmol) afforded 1.2 g of N'-hydroxy-2-phenylacetamidine (Yield: 100%) as beige powder (M.P.=58-60° C.).

16(B) 3-Benzyl-5-(but-3-ynyl)-1,2,4-oxadiazole

According to the general protocol for oxadiazole synthesis described in Example 15(B), the conversion of N'-hydroxy-2-phenylacetamidine (555 mg, 3.7 mmol) afforded 165 mg of 3-benzyl-5-(but-3-ynyl)-1,2,4-oxadiazole (Yield: 21%) as yellow oil.

LCMS (RT): 3.89 min; MS (ES+) gave m/z: 213.1

16(C) 2-(4-(3-Benzyl-1,2,4-oxadiazol-5-yl)but-1-ynyl)pyridine

According to the general protocol for Sonogashira coupling described in Example 15(C), the conversion of 3-benzyl-5-(but-3-ynyl)-1,2,4-oxadiazole (165 mg, 0.8 mmol) afforded 22 mg of 2-(4-(3-benzyl-1,2,4-oxadiazol-5-yl)but-1-ynyl)pyridine (Yield: 10%) as brown oil.

LCMS (RT): 3.61 min; MS (ES+) gave m/z: 290.1

¹H-NMR (CDCl₃), δ (ppm): 8.76 (s, H), 7.72 (t, H), 7.35-7.24 (m, 7H), 4.08 (s, 2H), 3.22 (m, 2H), 2.95 (m, 2H).

Example 17

2-(4-(3-(2-Fluorobenzyl)-1,2,4-oxadiazol-5-yl)but-1-ynyl)pyridine

17(A) (2-(2-Fluorophenyl)-N'-hydroxyacetamidine

According to the general protocol for amidoxime synthesis described in Example 15(A), the conversion of 2-(2-fluorophenyl)acetonitrile (1.03 mL, 8 mmol) afforded 1.33 g of 2-(2-fluorophenyl)-N'-hydroxyacetamidine (Yield: 99%) as white powder (M.P.=85-87° C.).

17(B) 3-(2-Fluorobenzyl)-5-(but-3-ynyl)-1,2,4-oxadiazole

According to the general protocol for oxadiazole synthesis described in Example 15(B), the conversion of 2-(2-fluorophenyl)-N'-hydroxyacetamidine (622 mg, 3.7 mmol) afforded 212 mg of 3-(2-fluorobenzyl)-5-(but-3-ynyl)-1,2,4-oxadiazole (Yield: 25%) as yellow oil.
LCMS (RT): 3.96 min; MS (ES+) gave m/z: 231.1

17(C) 2-(4-(3-(2-Fluorobenzyl)-1,2,4-oxadiazol-5-yl)but-1-ynyl)pyridine

According to the general protocol for Sonogashira coupling described in Example 15(C), the conversion of 3-(2-fluorobenzyl)-5-(but-3-ynyl)-1,2,4-oxadiazole (212 mg, 0.9 mmol) afforded 15 mg of 2-(4-(3-(2-fluorobenzyl)-1,2,4-oxadiazol-5-yl)but-1-ynyl)pyridine (Yield: 5%) as brown oil.
LCMS (RT): 3.63 min; MS (ES+) gave m/z: 308.1
¹H-NMR (CDCl₃), δ (ppm): 8.76 (s, H), 7.85 (s, H), 7.70 (m, H), 7.33-7.22 (m, 3H), 7.12-7.04 (m, 2H), 4.13 (s, 2H), 3.26 (m, 2H), 3.01 (m, 2H).

Example 18

2-(4-(3-(2-Methylbenzyl)-1,2,4-oxadiazol-5-yl)but-1-ynyl)pyridine

18(A) N'-Hydroxy-2-o-tolylacetamidine

According to the general protocol for amidoxime synthesis described in Example 15(A), the conversion of 2-o-tolylacetonitrile (1 mL, 8 mmol) afforded 1.3 g of N'-hydroxy-2-o-tolylacetamidine (Yield: 99%) as white powder (M.P.=116-118° C.).

18(B) 3-(2-Methylbenzyl)-5-(but-3-ynyl)-1,2,4-oxadiazole

According to the general protocol for oxadiazole synthesis described in Example 15(B), the conversion of N'-hydroxy-2-o-tolylacetamidine (607 mg, 3.7 mmol) afforded 126 mg of 3-(2-methylbenzyl)-5-(but-3-ynyl)-1,2,4-oxadiazole (Yield: 15%) as yellow oil.
LCMS (RT): 4.16 min; MS (ES+) gave m/z: 227.1

18(C) 2-(4-(3-(2-Methylbenzyl)-1,2,4-oxadiazol-5-yl)but-1-ynyl)pyridine

According to the general protocol for Sonogashira coupling described in Example 15(C), the conversion of 3-(2-methylbenzyl)-5-(but-3-ynyl)-1,2,4-oxadiazole (126 mg, 0.6 mmol) afforded 68 mg of 2-(4-(3-(2-methylbenzyl)-1,2,4-oxadiazol-5-yl)but-1-ynyl)pyridine (Yield: 37%) as brown oil.
LCMS (RT): 3.84 min; MS (ES+) gave m/z: 304
¹H-NMR (CDCl₃), δ (ppm): 8.57 (d, H), 7.68 (t, H), 7.35 (t, H), 7.30-7.22 (m, 3H), 7.12-7.12 (m, 2H), 4.07 (s, 2H), 3.21 (t, 2H), 2.97 (t, 2H), 2.38 (s, 3H).

Example 19

2-(4-(3-(4-Fluorobenzyl)-1,2,4-oxadiazol-5-yl)but-1-ynyl)pyridine

19(A) 2-(4-Fluorophenyl)-N'-hydroxyacetamidine

According to the general protocol for amidoxime synthesis described in Example 15(A), the conversion of 2-(4-fluorophenyl)acetonitrile (0.97 mL, 8 mmol) afforded 1.34 g of 2-(4-fluorophenyl)-N'-hydroxyacetamidine (Yield: 100%) as white powder (M.P.=104-106° C.).

19(B) 3-(4-Fluorobenzyl)-5-(but-3-ynyl)-1,2,4-oxadiazole

According to the general protocol for oxadiazole synthesis described in Example 15(B), the conversion of 2-(4-fluorophenyl)-N'-hydroxyacetamidine (622 mg, 3.7 mmol) afforded 388 mg of 3-(4-fluorobenzyl)-5-(but-3-ynyl)-1,2,4-oxadiazole (Yield: 46%) as yellow oil.
LCMS (RT): 4.01 min; MS (ES+) gave m/z: 231.1

19(C) 2-(4-(3-(4-Fluorobenzyl)-1,2,4-oxadiazol-5-yl)but-1-ynyl)pyridine

According to the general protocol for Sonogashira coupling described in Example 15(C), the conversion of 3-(4-fluorobenzyl)-5-(but-3-ynyl)-1,2,4-oxadiazole (388 mg, 1.7 mmol) afforded 80 mg of 2-(4-(3-(4-fluorobenzyl)-1,2,4-oxadiazol-5-yl)but-1-ynyl)pyridine (Yield: 15%) as brown oil.
LCMS (RT): 3.71 min; MS (ES+) gave m/z: 308.1
¹H-NMR (CDCl₃), δ (ppm): 8.57 (s, H), 7.80 (s, H), 7.33-7.28 (m, 4H), 7.02-6.96 (m, 2H), 4.05 (s, 2H), 3.26 (m, 2H), 2.96 (m, 2H).

Example 20

2-(4-(3-(4-Methoxybenzyl)-1,2,4-oxadiazol-5-yl)but-1-ynyl)pyridine

20(A) N'-Hydroxy-2-(4-methoxyphenyl)acetamidine

According to the general protocol for amidoxime synthesis described in Example 15(A), the conversion of 2-(4-methoxyphenyl)acetonitrile (1.09 mL, 8 mmol) afforded 1.43 g of N'-hydroxy-2-(4-methoxyphenyl)acetamidine (Yield: 99%) as white powder (M.P.=104-106° C.).

20(B) 3-(4-Methoxybenzyl)-5-(but-3-ynyl)-1,2,4-oxadiazole

According to the general protocol for oxadiazole synthesis described in Example 15(B), the conversion of N'-hydroxy-2-(4-methoxyphenyl)acetamidine (666 mg, 3.7 mmol) afforded 211 mg of 3-(4-methoxybenzyl)-5-(but-3-ynyl)-1,2,4-oxadiazole (Yield: 24%) as yellow oil.
LCMS (RT): 3.89 min; MS (ES+) gave m/z: 243.1

20(C) 2-(4-(3-(4-Methoxybenzyl)-1,2,4-oxadiazol-5-yl)but-1-ynyl)pyridine

According to the general protocol for Sonogashira coupling described in Example 15(C), the conversion of 3-(4-methoxybenzyl)-5-(but-3-ynyl)-1,2,4-oxadiazole (211 mg, 0.9 mmol) afforded 33 mg of 2-(4-(3-(4-Methoxybenzyl)-1,2,4-oxadiazol-5-yl)but-1-ynyl)pyridine (Yield: 11%) as brown oil.

LCMS (RT): 3.56 min; MS (ES+) gave m/z: 320.1
$^1$H-NMR (CDCl$_3$), δ (ppm): 8.57 (s, H), 7.80 (s, H), 7.28-7.26 (m, 4H), 6.87-6.83 (m, 2H), 4.02 (s, 2H), 3.78 (s, 3H), 3.24 (m, 2H), 2.96 (m, 2H).

Example 21

2-(4-(3-Isopropyl-1,2,4-oxadiazol-5-yl)but-1-ynyl)pyridine

21(A) N'-Hydroxy-isobutyramidine

According to the general protocol for amidoxime synthesis described in Example 15(A), the conversion of isobutyronitrile (0.75 mL, 8 mmol) afforded 0.81 g of N'-hydroxy-isobutyramidine (Yield: 99%) as colorless oil.

21(B) 5-(But-3-ynyl)-3-isopropyl-1,2,4-oxadiazole

According to the general protocol for oxadiazole synthesis described in Example 15(B), the conversion of N'-hydroxy-isobutyramidine (378 mg, 3.7 mmol) afforded 151 mg of 5-(but-3-ynyl)-3-isopropyl-1,2,4-oxadiazole (Yield: 25%) as yellow oil.

LCMS (RT): 3.16 min; MS (ES+) gave m/z: 165.1

21(C) 2-(4-(3-Isopropyl-1,2,4-oxadiazol-5-yl)but-1-ynyl)pyridine

According to the general protocol for Sonogashira coupling described in Example 15(C), the conversion of 5-(but-3-ynyl)-3-isopropyl-1,2,4-oxadiazole (151 mg, 0.9 mmol) afforded 62 mg of 2-(4-(3-isopropyl-1,2,4-oxadiazol-5-yl)but-1-ynyl)pyridine (Yield: 29%) as brown oil.

LCMS (RT): 2.93 min; MS (ES+) gave m/z: 242.1
$^1$H-NMR (CDCl$_3$), δ (ppm): 8.57 (s, H), 7.80 (s, H), 7.50-7.30 (m, 2H), 3.27 (m, 2H), 3.12 (m, H), 2.98 (m, 2H), 1.36 (d, 6H).

Example 22

2-(4-(3-Butyl-1,2,4-oxadiazol-5-yl)but-1-ynyl)pyridine

22(A) N'-Hydroxypentanamidine

According to the general protocol for amidoxime synthesis described in Example 15(A), the conversion of pentanenitrile (0.85 mL, 8 mmol) afforded 0.91 g of N'-hydroxypentanamidine (Yield: 98%) as colorless oil.

22(B) 5-(But-3-ynyl)-3-butyl-1,2,4-oxadiazole

According to the general protocol for oxadiazole synthesis described in Example 15(B), the conversion of N'-hydroxypentanamidine (430 mg, 3.7 mmol) afforded 205 mg of 5-(but-3-ynyl)-3-butyl-1,2,4-oxadiazole (Yield: 31%) as yellow oil.

LCMS (RT): 3.75 min; MS (ES+) gave m/z: 179.1

22(C) 2-(4-(3-Butyl-1,2,4-oxadiazol-5-yl)but-1-ynyl)pyridine

According to the general protocol for Sonogashira coupling described in Example 15(C), the conversion of 5-(but-3-ynyl)-3-butyl-1,2,4-oxadiazole (205 mg, 1.2 mmol) afforded 28 mg of 2-(4-(3-butyl-1,2,4-oxadiazol-5-yl)but-1-ynyl)pyridine (Yield: 9%) as brown oil.

LCMS (RT): 3.44 min; MS (ES+) gave m/z: 256.1
$^1$H-NMR (CDCl$_3$), δ (ppm): 8.57 (s, H), 7.65 (t, H), 7.40 (m, H), 7.25 (m, H), 3.23 (t, 2H), 2.98 (t, 2H), 2.74 (t, 2H), 1.74 (m, 2H), 1.40 (m, 2H), 0.94 (t, 3H).

Example 23

2-(4-(3-(3-Fluorobenzyl)-1,2,4-oxadiazol-5-yl)but-1-ynyl)pyridine

23(A) 2-(3-Fluorophenyl)-N'-hydroxyacetamidine

According to the general protocol for amidoxime synthesis described in Example 15(A), the conversion of 2-(3-fluorophenyl)acetonitrile (0.94 mL, 8 mmol) afforded 1.34 g of 2-(3-fluorophenyl)-N'-hydroxyacetamidine (Yield: 99%) as yellow semi-solid.

23(B) 3-(3-Fluorobenzyl)-5-(but-3-ynyl)-1,2,4-oxadiazole

According to the general protocol for oxadiazole synthesis described in Example 15(B), the conversion of 2-(3-fluorophenyl)-N'-hydroxyacetamidine (622 mg, 3.7 mmol) afforded 209 mg of 3-(3-fluorobenzyl)-5-(but-3-ynyl)-1,2,4-oxadiazole (Yield: 25%) as yellow oil.

LCMS (RT): 4.03 min; MS (ES+) gave m/z: 231.1

23(C) 2-(4-(3-(3-Fluorobenzyl)-1,2,4-oxadiazol-5-yl)but-1-ynyl)pyridine

According to the general protocol for Sonogashira coupling described in Example 15(C), the conversion of 3-(3-fluorobenzyl)-5-(but-3-ynyl)-1,2,4-oxadiazole (209 mg, 0.9 mmol) afforded 63 mg of 2-(4-(3-(3-fluorobenzyl)-1,2,4-oxadiazol-5-yl)but-1-ynyl)pyridine (Yield: 23%) as brown oil.

LCMS (RT): 3.69 min; MS (ES+) gave m/z: 308.1
$^1$H-NMR (CDCl$_3$), δ (ppm): 8.57 (s, H), 7.70 (t, H), 7.32-7.24 (m, 3H), 7.12-7.09 (d, H), 7.06-7.02 (s, H), 6.98-6.92 (m, H), 4.07 (s, 2H), 3.21 (t, 2H), 2.96 (t, 2H).

Example 24

2-(4-(3-(3-Methoxybenzyl)-1,2,4-oxadiazol-5-yl)but-1-ynyl)pyridine

24(A) N'-Hydroxy-2-(3-methoxyphenyl)acetamidine

According to the general protocol for amidoxime synthesis described in Example 15(A), the conversion of 2-(3-methoxyphenyl)acetonitrile (1.09 mL, 8 mmol) afforded 1.43 g of N'-hydroxy-2-(3-methoxyphenyl)acetamidine (Yield: 99%) as yellow oil.

24(B) 3-(3-Methoxybenzyl)-5-(but-3-ynyl)-1,2,4-oxadiazole

According to the general protocol for oxadiazole synthesis described in Example 15(B), the conversion of N'-hydroxy-2-(3-methoxyphenyl)acetamidine (667 mg, 3.7 mmol)

afforded 259 mg of 3-(3-methoxybenzyl)-5-(but-3-ynyl)-1,2,4-oxadiazole (Yield: 29%) as yellow oil.

LCMS (RT): 3.91 min; MS (ES+) gave m/z: 243.1

24(C) 2-(4-(3-(3-Methoxybenzyl)-1,2,4-oxadiazol-5-yl)but-1-ynyl)pyridine

According to the general protocol for Sonogashira coupling described in Example 15(C), the conversion of 3-(3-methoxybenzyl)-5-(but-3-ynyl)-1,2,4-oxadiazole (259 mg, 1.1 mmol) afforded 60 mg of 2-(4-(3-(3-methoxybenzyl)-1,2,4-oxadiazol-5-yl)but-1-ynyl)pyridine (Yield: 17%) as brown oil.

LCMS (RT): 3.64 min; MS (ES+) gave m/z: 320.1
$^1$H-NMR (CDCl$_3$), δ (ppm): 8.57 (s, H), 7.70 (t, H), 7.25-7.20 (m, 3H), 6.94-6.86 (m, 2H), 6.80 (m, H), 4.05 (s, 2H), 3.78 (s, 3H), 3.21 (t, 2H), 2.96 (t, 2H).

Example 25

2-(4-(3-(2-Fluorophenyl)-1,2,4-oxadiazol-5-yl)but-1-ynyl)pyridine

25(A) 2-Fluoro-N'-hydroxybenzamidine

According to the general protocol for amidoxime synthesis described in Example 15(A), the conversion of 2-fluorobenzonitrile (0.86 mL, 8 mmol) afforded 1.22 g of 2-fluoro-N'-hydroxybenzamidine (Yield: 99%) as yellow oil.

25(B) 5-(But-3-ynyl)-3-(2-fluorophenyl)-1,2,4-oxadiazole

According to the general protocol for oxadiazole synthesis described in Example 15(B), the conversion of 2-fluoro-N'-hydroxybenzamidine (570 mg, 3.7 mmol) afforded 405 mg of 5-(but-3-ynyl)-3-(2-fluorophenyl)-1,2,4-oxadiazole (Yield: 51%) as yellow oil. LCMS (RT): 3.99 min; MS (ES+) gave m/z: 217.1

25(C) 2-(4-(3-(2-Fluorophenyl)-1,2,4-oxadiazol-5-yl)but-1-ynyl)pyridine

According to the general protocol for Sonogashira coupling described in Example 15(C), the conversion of 5-(but-3-ynyl)-3-(2-fluorophenyl)-1,2,4-oxadiazole (405 mg, 1.9 mmol) afforded 58 mg of 2-(4-(3-(2-fluorophenyl)-1,2,4-oxadiazol-5-yl)but-1-ynyl)pyridine (Yield: 10%) as brown oil.

LCMS (RT): 3.68 min; MS (ES+) gave m/z: 294.1
$^1$H-NMR (CDCl$_3$), δ (ppm): 8.57 (s, H), 8.05 (t, H), 7.70 (m, H), 7.53-7.48 (m, H), 7.32-7.22 (m, 4H), 3.37 (m, 2H), 3.06 (m, 2H).

Example 26

2-(4-(3-(3-Fluorophenyl)-1,2,4-oxadiazol-5-yl)but-1-ynyl)pyridine

26(A) 3-Fluoro-N'-hydroxybenzamidine

According to the general protocol for amidoxime synthesis described in Example 15(A), the conversion of 3-fluorobenzonitrile (0.65 mL, 8 mmol) afforded 0.97 g of 3-fluoro-N'-hydroxybenzamidine (Yield: 99%) as yellow oil.

26(B) 5-(But-3-ynyl)-3-(3-fluorophenyl)-1,2,4-oxadiazole

According to the general protocol for oxadiazole synthesis described in Example 15(B), the conversion of 3-fluoro-N'-hydroxybenzamidine (570 mg, 3.7 mmol) afforded 336 mg of 5-(but-3-ynyl)-3-(3-fluorophenyl)-1,2,4-oxadiazole (Yield: 42%) as yellow oil. LCMS (RT): 4.31 min; MS (ES+) gave m/z: 217.1

26(C) 2-(4-(3-(3-Fluorophenyl)-1,2,4-oxadiazol-5-yl)but-1-ynyl)pyridine

According to the general protocol for Sonogashira coupling described in Example 15(C), the conversion of 5-(but-3-ynyl)-3-(3-fluorophenyl)-1,2,4-oxadiazole (336 mg, 1.6 mmol) afforded 57 mg of 2-(4-(3-(3-fluorophenyl)-1,2,4-oxadiazol-5-yl)but-1-ynyl)pyridine (Yield: 12%) as brown oil.

LCMS (RT): 3.99 min; MS (ES+) gave m/z: 294.1
$^1$H-NMR (CDCl$_3$), δ (ppm): 8.57 (s, H), 7.90 (s, H), 7.80 (d, H), 7.70 (m, H), 7.53-7.48 (m, 2H), 7.32-7.18 (m, 2H), 3.33 (m, 2H), 3.07 (m, 2H).

Example 27

5-Chloro-(2-(4-pyridin-2-yl)but-3-ynyl)benzo[d]oxazole

27(A) Pent-4-ynimidic Acid Methyl Ester

Sodium (291 mg, 12.6 mmol) was dissolved in dry MeOH (40 mL). Pent-4-ynenitrile (2.00 g, 25.3 mmol) was added to the reaction mixture and the solution was stirred for 2 days at room temperature. Acetic acid (746 μL) was added followed by evaporation of the solvent to yield 1.20 g (10.8 mmol, 43%) of pent-4-ynimidic acid methyl ester as a white solid.

27(B) 2-(But-3-ynyl)-5-chlorobenzo[d]oxazole

A mixture of pent-4-ynimidic acid methyl ester (142 mg, 1.28 mmol) and 2-amino-4-chlorophenol (227 mg, 1.53 mmol) in dichloroethane (10 mL) was stirred for 2 days under reflux. The solvent was evaporated, the residue was partly dissolved in MeOH and filtered. The filtrate was concentrated, and the resulting crude residue was purified by flash chromatography (cyclohexane/AcOEt 9:1) to yield 18 mg (87 μmol, 7%) of 2-(but-3-ynyl)-5-chlorobenzo[d]oxazole.

27(C) 5-Chloro-(2-(4-pyridin-2-yl)but-3-ynyl)benzo[d]oxazole

The title compound was prepared in accordance with the general method of Example 1, from 2-bromopyridine (15 mg, 96 mmol) and 2-(but-3-ynyl)-5-chlorobenzo[d]oxazole (18 mg, 87 μmol). Reaction time: 14 hours. The crude residue was purified by flash chromatography (DCM/MeOH 99:1) to yield 6.5 mg (23 mmol, 26%) of 5-chloro-(2-(4-pyridin-2-yl)but-3-ynyl)benzo[d]oxazole as a yellow solid.

LCMS (RT): 3.84 min; MS (ES+) gave m/z: 283.0, 285.0.
$^1$H-NMR (CDCl$_3$), δ (ppm): 3.11 (t, J=7.5, 2H), 3.33 (t, J=7.5, 2H), 7.30 (dd, J=2.5 and 9.0, 1H), 7.33-7.41 (m, 1H), 7.43 (d, J=9.0, 1H), 7.48 (d, J=7.5, 1H), 7.67 (d, J=1.5, 1H), 7.79-7.87 (m, 1H), 8.60 (d, J=5.0, 1H).

Example 28

5-Methyl-(2-(4-pyridin-2-yl)but-3-ynyl)benzo[d]oxazole

28(A) 2-(But-3-ynyl)-5-methylbenzo[d]oxazole

The title compound was prepared in accordance with the general method of Example 27(B) from 2-amino-4-methylphenol (181 mg, 1.43 mmol). The resulting crude residue was purified by flash chromatography (cyclohexane/AcOEt 9:1) to yield 19 mg (0.1 mmol, 7%) of 2-(but-3-ynyl)-5-methylbenzo[d]oxazole.

28(B) 5-Methyl-(2-(4-pyridin-2-yl)but-3-ynyl)benzo[d]oxazole

The title compound was prepared in accordance with the general method of Example 1, from 2-bromopyridine (16 mg, 0.1 mmol) and 2-(but-3-ynyl)-5-methylbenzo[d]oxazole (19 mg, 0.1 mmol). Reaction time: 14 hours. The crude residue was purified by flash chromatography (DCM/MeOH 99:1) and SCX column (DCM/MeOH 95:5, DCM/MeOH/NH$_4$OH 90:10:0.1 to 88:10:2) to yield 2.0 mg (7.6 µmol, 8%) of 5-methyl-(2-(4-pyridin-2-yl)but-3-ynyl)benzo[d]oxazole as a yellow solid.

LCMS (RT): 3.63 min; MS (ES+) gave m/z: 263.1.
Rf (DCM/MeOH 97:3)=0.1.

Example 29

6-Methyl-(2-(4-pyridin-2-yl)but-3-ynyl)benzo[d]oxazole

29(A) 2-(But-3-ynyl)-6-methylbenzo[d]oxazole

The title compound was prepared in accordance with the general method of Example 27(B) from 2-amino-5-methylphenol (192 mg, 1.52 mmol). The crude residue was purified by flash chromatography (cyclohexane/AcOEt 9:1) to yield 14 mg (77 µmol, 6%) of 2-(but-3-ynyl)-6-methylbenzo[d]oxazole.

29(B) 6-Methyl-(2-(4-pyridin-2-yl)but-3-ynyl)benzo[d]oxazole

The title compound was prepared in accordance with the general method of Example 1, from 2-bromopyridine (14 mg, 89 mmol) and 2-(but-3-ynyl)-6-methylbenzo[d]oxazole (15 mg, 81 mmol). Reaction time: 14 hours. The crude residue was purified by flash chromatography (DCM/MeOH 99:1) and SCX column (DCM/MeOH 95:5, DCM/MeOH/NH$_4$OH 90:10:0.1 to 88:10:2) to yield 7.0 mg (27 µmol, 33%) of 6-methyl-(2-(4-pyridin-2-yl)but-3-ynyl)benzo[d]oxazole as a yellow solid.

LCMS (RT): 3.53 min; MS (ES+) gave m/z: 263.1.
$^1$H-NMR (CDCl$_3$), δ (ppm): 2.48 (s, 3H), 3.09 (t, J=7.5, 2H), 3.30 (t, J=7.5, 2H), 7.13 (d, J=8.0, 1H), 7.30 (s, 1H), 7.31-7.37 (m, 1H), 7.46 (d, J=8.0, 1H), 7.55 (d, J=8.0, 1H), 7.75-7.82 (m, 1H), 8.59 (d, J=5.0, 1H).

Example 30

4-Methyl-(2-(4-pyridin-2-yl)but-3-ynyl)benzo[d]oxazole

30(A) 2-(But-3-ynyl)-4-methylbenzo[d]oxazole

The title compound was prepared in accordance with the general method of Example 27(B) from 2-amino-3-methylphenol (183 mg, 1.48 mmol). The crude residue was purified by flash chromatography (cyclohexane/AcOEt 9:1) to yield 12 mg (66 µmol, 5%) of 2-(but-3-ynyl)-4-methylbenzo[d]oxazole.

30(B) 4-Methyl-(2-(4-pyridin-2-yl)but-3-ynyl)benzo[d]oxazole

The title compound was prepared in accordance with the general method of Example 1, from 2-bromopyridine (12 mg, 77 µmol) and 2-(but-3-ynyl)-4-methylbenzo[d]oxazole (13 mg, 70 µmol). Reaction time: 14 hours. The crude residue was purified by flash chromatography (DCM/MeOH 99:1) and SCX column (DCM/MeOH 95:5, DCM/MeOH/NH$_4$OH 90:5:0.1 to 87:10:3) to yield 7.0 mg (27 µmol, 38%) of 4-methyl-(2-(4-pyridin-2-yl)but-3-ynyl)benzo[d]oxazole as an orange solid.

LCMS (RT): 3.61 min; MS (ES+) gave m/z: 263.1.
$^1$H-NMR (CDCl$_3$), δ (ppm): 2.60 (s, 3H), 3.11 (t, J=8.0, 2H), 3.33 (t, J=8.0, 2H), 7.11 (d, J=7.5, 1H), 7.17-7.24 (m, 1H), 7.32 (d, J=7.5, 1H), 7.37-7.45 (m, 1H), 7.50 (d, J=8.0, 1H), 7.81-7.90 (m, 1H), 8.61 (d, J=4.5, 1H).

Example 31

2-(4-(2-Methylthiazol-4-yl)but-3-ynyl)benzo[d]oxazole

The title compound was prepared in accordance with the general method of Example 1, from 4-bromo-2-methylthiazole (47 mg, 2.7 mmol) and 2-(but-3-ynyl)benzo[d]oxazole (454 mg, 2.65 mmol, Example 8(A)). The reaction mixture was stirred for one day under reflux. The crude residue was purified by flash chromatography (cyclohexane/AcOEt 4:1) and trituration with pentane to yield 14 mg (52 µmol, 2%) of 2-(4-(2-methylthiazol-4-yl)but-3-ynyl)benzo[d]oxazole as a beige solid.

Example 32

2-(4-(5-Phenyl-2H-tetrazol-2-yl)but-1-ynyl)pyridine

32(A) 4-(Pyridin-2-yl)but-3-yn-1-ol

In a dry reaction tube containing in suspension iodide copper (38 mg, 0.2 mmol) and triethylamine (11 mL, 80 mmol), were added 2-bromopyridine (632 mg, 4 mmol) and Pd(PPh$_3$)$_2$Cl$_2$ (140 mg, 0.2 mmol). A yellow suspension is obtained and after a few minutes of stirring at room temperature, was added a solution of but-3-yn-1-ol (280 mg, 4 mmol) in triethylamine (2.2 mL). Immediately the color of the reaction turns to black. The mixture was stirred at room temperature for 30 min and then at 80° C. for 20 h. Triethylamine was concentrated under reduced pressure and the residue was dissolved in DCM. The organic layer was washed with saturated NH₄Cl, water and brine, dried (MgSO₄) and concentrated. The product was purified by flash chromatography (prepacked 15 g silicagel column, from DCM 100% to DCM/MeOH: 98/2 as eluent) to afford 440 mg of 4-(pyridin-2-yl)but-3-yn-1-ol (Yield: 74%) as brown oil.

Rf: (DCM/MeOH: 95/5)=0.5
LCMS (RT): 0.60 min; MS (ES+) gave m/z: 148.1

32(B) 2-(4-(5-Phenyl-2H-tetrazol-2-yl)but-1-ynyl)pyridine

A mixture of 5-phenyl-2H-tetrazole (330 mg, 2.2 mmol), 4-(pyridin-2-yl)but-3-yn-1-ol (220 mg, 1.49 mmol) and triphenylphosphine polymer supported (750 mg, 2.2 mmol, loading 3 mmol/g) were dissolved DCM (3 mL) and stirred at 0° C. Diisoprpylazodicarboxylate (452 mg, 2.2 mmol) was added dropwise, at 0° C. over a period of 30 min. The reaction mixture was then warmed to room temperature and stirred over night. The reaction mixture was filtered through celite and the cake was washed with DCM. The combined organic layers were washed with aqueous ammoniac, brine, dried over MgSO₄, filtered and concentrated. The residue was purified by flash chromatography (prepacked 25 g silicagel column, DCM 100% as eluent) to afford 209 mg of 2-(4-(5-phenyl-2H-tetrazol-2-yl)but-1-ynyl)pyridine (Yield: 51%) as a pink powder (M.P.=71-73° C.).

Rf (DCM/MeOH: 97/3)=0.4
LCMS (RT): 3.74 min; MS (ES+) gave m/z: 276.1
¹NMR (CDCl₃), δ (ppm): 8.64 (s, H), 8.17 (m, H), 7.63 (t, H), 7.53-7.46 (m, 2H), 7.36 (d, H), 7.25-7.20 (m, H), 6.36 (m, 2H), 4.93 (t, 2H), 3.25 (t, 2H).

Example 33

2-(4-(Pyridin-2-yl)but-3-ynyl)-imidazo[1,2-a]pyridine

33(A) Ethyl imidazo[1,2-a]pyridine-2-carboxylate

A solution of 2-amino-pyridine (2 g, 21 mmol) and ethyl bromopyruvate (4.14 g, 21 mmol) in ethanol (31 mL) was stirred under reflux for 24 h. The solvent was evaporated, and the residue was dissolved in a minimum volume of water. The solution was neutralized (pH=8) with saturated NaHCO₃. The aqueous layer was extracted with AcOEt and the organic layer was washed with saturated NaCl. The solvent was removed under pressure to afford 2.51 g of ethyl imidazo[1,2-a]pyridine-2-carboxylate (Yield: 62%) as an orange oil which can be used without further purification.

LCMS (RT): 0.72-1.39 min; MS (ES+) gave m/z: 191.1
Rf (DCM/MeOH: 95/5): 0.12

33(B) 2-Hydroxymethyl-imidazo[1,2-a]pyridine

In a dry round flask is added LiAlH₄ (650 mg, 17 mmol) in anhydrous THF (52 mL) under stirring. The solution was cooled to 0° C. A solution of ethyl imidazo[1,2-a]pyridine-2-carboxylate (2.5 g, 13 mmol) in dry THF (3 mL) was added dropwise. The solution became green. The reaction mixture was stirred at 0° C. for 30 min and 2 h at R.T. The reaction mixture was quenched with successively 0.52 mL of water, 0.52 mL of NaOH 1M and 3×0.52 mL of water. The solution is filtered over celite. The organic layer is evaporated to give 2.25 g of an orange liquid. The residue was purified by flash chromatography over silicagel (prepacked 70 g silicagel column, DCM/MeOH: 95/5 as eluent) to afford 1 g of 2-hydroxymethyl-imidazo[1,2-a]pyridine (Yield: 51%) as a brown il.

LCMS (RT): 0.62; MS (ES+) gave m/z: 149.1
Rf (DCM/MeOH: 95/5): 0.13

33(C) 2-(Chloromethyl)-imidazo[1,2-a]pyridine

In a round bottomed flask containing 2-hydroxymethyl-imidazo[1,2-a]pyridine (800 mg, 5.4 mmol) in DCM (8 mL), was added at R.T. thionyl chloride (1.96 mL, 27 mmol). The solution became clear and 10 min later, a precipitated was formed. The reaction mixture was stirred at R.T. for 2 hours and the solvent was removed under reduced pressure to afford 1.10 g of a brownish solid as the chlorhydrate form of 2-(chloromethyl)-imidazo[1,2-a]pyridine (Yield: 100%).

To saturated NaHCO₃ (40 mL) was added the chlorhydrate form of 2-(chloromethyl)-imidazo[1,2-a]pyridine and the aqueous layer was extracted with AcOEt. The organic layers were combined and washed with brine, dried over MgSO₄ and the solvent was removed under reduced pressure to afford 877 mg of 2-(chloromethyl)-imidazo[1,2-a]pyridine (Yield: 80%). as a brownish solid (M.P.: 84-85° C.)

LCMS (RT): 0.64; MS (ES+) gave m/z: 167.1

33(D) 2-(4-(Trimethylsilyl)but-3-ynyl)-imidazo[1,2-a]pyridine

According to the protocol described in Example 38(C), the conversion of 2-(chloromethyl)-imidazo[1,2-a]pyridine (200 mg, 1.2 mmol) afforded 155 mg of 2-(4-(trimethylsilyl)but-3-ynyl)-imidazo[1,2-a]pyridine (Yield: 53%) as yellow oil.

Purification over silicagel chromatography (prepacked 25 g silicagel column, DCM/MeOH from 99/1 to 98/2 as eluent).

LCMS (RT): 0.54-2.71 min; MS (ES+) gave m/z: 243.1
Rf (DCM/MeOH: 95/5): 0.42

33(E) 2-(But-3-ynyl)-imidazo[1,2-a]pyridine

According to the protocol described in Example 38(D), the conversion of 2-(4-(trimethylsilyl)but-3-ynyl)-imidazo[1,2-a]pyridine (140 mg, 0.67 mmol) afforded 70 mg of 2-(but-3-ynyl)-imidazo[1,2-a]pyridine (Yield: 71%) as yellow oil.

Purification over silicagel chromatography (prepacked 25 g silicagel column, DCM/MeOH from 99/1 to 98/2 as eluent).

LCMS (RT): 0.54 min; MS (ES+) gave m/z: 171.1
Rf (DCM/MeOH: 95/5): 0.27

33(F) 2-(4-(Pyridin-2-yl)but-3-ynyl)-imidazo[1,2-a]pyridine

According to the general protocol for Sonogashira coupling described in Example 15(C), the conversion of 2-(but-3-ynyl)-imidazo[1,2-a]pyridine (70 mg, 0.41 mmol) afforded 34 mg of 2-(4-(Pyridin-2-yl)but-3-ynyl)-imidazo[1,2-a]pyridine (Yield: 33%) as yellow oil. Purification over silicagel chromatography (prepacked 10 g silicagel column, DCM/MeOH from 100/0 to 99/1 as eluent).

LCMS (RT): 0.60-1.57 min; MS (ES+) gave m/z: 248.1
Rf (DCM/MeOH: 95/5): 0.32
¹H-NMR (CDCl₃), δ (ppm): 8.54 (d, H), 8.06 (d, H), 7.64-7.57 (m, 2H), 7.50 (s, H), 7.40 (d, H), 7.20-7.12 (m, 2H), 6.75 (t, H), 3.13 (t, 2H), 2.93 (t, 2H).

Example 34

N-(4-Fluorophenyl)-5-(pyridine-2-yl)pent-4-ynamide

34(A) N-(4-Fluorophenyl)pent-4-ynamide

According to the protocol described in Example 12(A), the conversion of N 4-fluorobenzenamine (566 mg, 5.10 mmol) afforded 922 mg of N-(4-fluorophenyl)pent-4-ynamide (Yield: 95%) as brownish solid which can be used without further purification.

LCMS (RT): 0.64 min; MS (ES+) gave m/z: 192.1
Rf (DCM/MeOH: 8/2)=0.2

34(B) tert-Butyl 4-fluorophenylpent-4-ynoylcarbamate

According to the general protocol described in J. Med. Chem., 2000, 43, 20, 3718-3735, to solution of N-(4-fluorophenyl)pent-4-ynamide (200 mg, 1 mmol) in DCM (3 mL) were successively added triethylamine (146 mL, 1.05 mmol), $(BOC)_2O$ (270 mg, 1.3 mmol) and DMAP (13 mg, 0.1 mmol). After stirring for 18 h at room temperature, the solvent was removed under reduced pressure and the crude product was purified by flash chromatography (prepacked 25 g silicagel column, Cyclohexane/AcOEt: 90/10 as eluent) to afford 274 mg of tert-butyl 4-fluorophenylpent-4-ynoylcarbamate (Yield: 90%) as colorless oil.

LCMS (RT): 4.11 min; MS (ES+) gave m/z: 192.1 (MH+-Boc)
Rf (Cyclohexane/AcOEt: 90/10): 0.35

34(C) tert-Butyl 5-(pyridin-2-yl)pent-4-ynoyl-4-fluorophenylcarbamate

According to the protocol described in Example 38(E), the conversion of tert-butyl 4-fluorophenylpent-4-ynoylcarbamate (274 mg, 0.94 mmol) afforded 299 mg of tert-butyl 5-(pyridin-2-yl)pent-4-ynoyl-4-fluorophenylcarbamate (Yield: 86%) as yellow oil. Purification by Flash chromatography (prepacked 25 g silicagel column, DCM/MeOH: 99/1 as eluent)

LCMS (RT): 3.94 min; MS (ES+) gave m/z: 369
Rf (DCM/MeOH: 98/2): 0.19

34(D) N-(4-Fluorophenyl)-5-(pyridine-2-yl)pent-4-ynamide tert-Butyl-5-(pyridin-2-yl)pent-4-ynoyl-4-fluorophenylcarbamate (299 mg, 0.81 mmol) was dissolved in DCM (4 mL) with 0.01% w/w of water. 4 mL of trifluoroacetic acid was added at room temperature to the solution. The resulting mixture was stirred at R.T. for 2 h. The solvent was removed under reduced pressure. The brown oil was dissolved in saturated $NaHCO_3$ until pH=8. The aqueous layer was extracted with ethyl acetate. The combined organic layers were washed with brine, dried over $MgSO_4$ and the solvent was removed under reduced pressure. The brownish solid was triturated in a mixture $Et_2O$/Pentane: 50/50. The solid was collected by filtration and washed with a mixture $Et_2O$/Pentane: 50/50. The solid was dried by lyophilisation to afford 181 mg of N-(4-fluorophenyl)-5-(pyridine-2-yl)pent-4-ynamide (Yield: 83%) as a colorless solid (M.P.=189.9-190.2° C.).

LCMS (RT): 2.83 min; MS (ES+) gave m/z: 269.1
Rf (DCM/MeOH: 95/5): 0.23

$^1$NMR ($CDCl_3$), δ (ppm): 8.56 (s, H), 7.68-7.61 (m, 2H), 7.54-7.49 (m, 2H), 7.38 (d, H), 7.23 (m, H), 7.11 (m, 2H), 2.88 (t, 2H), 2.70 (t, 2H).

Example 35

2-(4-(Pyridin-2-yl)but-3-ynyl)benzo[d]thiazole

35(A) 2-(But-3-ynyl)benzo[d]thiazole

The title compound was prepared in accordance with the general method of Example 8(A), from 2-aminobenzenethiol (387 mg, 3.03 mmol). The crude residue was purified by flash chromatography (cyclohexane/AcOEt 9:1) to yield 453 mg (2.42 mmol, 80%) of 2-(but-3-ynyl)benzo[d]thiazole as an orange oil.

35(B) 2-(4-(Pyridin-2-yl)but-3-ynyl)benzo[d]thiazole

The title compound was prepared in accordance with the general method of Example 1, from 2-bromopyridine (127 mg, 0.80 mmol) and 2-(but-3-ynyl)benzo[d]thiazole (150 mg, 0.80 mmol). Reaction time: 1 day. The crude residue was purified by flash chromatography (DCM/MeOH 99:1) to yield 96 mg (0.36 mmol, 45%) of 2-(4-(pyridin-2-yl)but-3-ynyl)benzo[d]thiazole as an orange solid (M.P.=98.5-99.4° C.).

LCMS (RT): 3.24 min; MS (ES+) gave m/z: 265.0.
Rf (DCM/MeOH 99:1)=0.2.
$^1$H-NMR ($CDCl_3$), δ (ppm): 3.05 (t, J=7.5, 2H), 3.46 (t, J=7.5, 2H), 7.18-7.22 (m, 1H), 7.35-7.39 (2H), 7.45-7.49 (m, 1H), 7.60-7.64 (m, 1H), 7.84-7.87 (m, 1H), 7.99 (d, J=8.0, 1H), 8.54-8.57 (m, 1H).

Example 36

6-Chloro-(2-(4-pyridin-2-yl)but-3-ynyl)benzo[d]oxazole

36(A) 2-(But-3-ynyl)-6-chlorobenzo[d]oxazole

The title compound was prepared in accordance with the general method of Example 8(A), from 2-amino-5-chlorophenol (290 mg, 2.02 mmol). The crude residue was purified by flash chromatography (cyclohexane/AcOEt 9:1) to yield 262 mg (1.28 mmol, 65%) of 2-(but-3-ynyl)-6-chlorobenzo[d]oxazole as an orange solid.

36(B) 6-Chloro-(2-(4-pyridin-2-yl)but-3-ynyl)benzo[d]oxazole

The title compound was prepared in accordance with the general method of Example 1, from 2-bromopyridine (115 mg, 0.73 mmol) and 2-(but-3-ynyl)-6-chlorobenzo[d]oxazole (150 mg, 0.73 mmol). The crude residue was purified by flash chromatography (DCM/MeOH 99:1) to yield 107 mg (0.38 mmol, 52%) of 6-chloro-(2-(4-pyridin-2-yl)but-3-ynyl)benzo[d]oxazole as a yellow solid (M.P.=101.5-102.2° C.).

LCMS (RT): 3.49 min; MS (ES+) gave m/z: 283.0, 285.0.
Rf (DCM/MeOH 99:1)=0.2.
$^1$H-NMR ($CDCl_3$), δ (ppm): 3.05 (t, J=7.5, 2H), 3.28 (t, J=7.5, 2H), 7.18-7.22 (m, 1H), 7.29 (dd, J=2.0 and 8.5, 1H), 7.33-7.36 (m, 1H), 7.51 (d, J=2.0, 1H), 7.59 (d, J=9.0, 1H), 7.59-7.63 (m, 1H), 8.53-8.55 (m, 1H).

Example 37

5-Fluoro-(2-(4-pyridin-2-yl)but-3-ynyl)benzo[d]oxazole

37(A) 2-(But-3-ynyl)-5-fluorobenzo[d]oxazole

The title compound was prepared in accordance with the general method of Example 8(A), from 2-amino-4-fluorophenol (259 mg, 2.04 mmol). The crude residue was purified by flash chromatography (cyclohexane/AcOEt 9:1) to yield 116 mg (0.61 mmol, 30%) of 2-(but-3-ynyl)-5-fluorobenzo[d]oxazole as a yellow solid.

37(B) 5-Fluoro-(2-(4-pyridin-2-yl)but-3-ynyl)benzo[d]oxazole

The title compound was prepared in accordance with the general method of Example 1, from 2-bromopyridine (96.9 mg, 0.61 mmol) and 2-(but-3-ynyl)-5-fluorobenzo[d]oxazole (116 mg, 0.61 mmol). The crude residue was purified by flash chromatography (DCM/MeOH 99:1) to yield 84 mg (0.31 mmol, 51%) of 5-fluoro-(2-(4-pyridin-2-yl)but-3-ynyl)benzo[d]oxazole as a slightly yellow solid (M.P.=100.1-101.0° C.).

LCMS (RT): 3.11 min; MS (ES+) gave m/z: 267.1.
Rf (DCM/MeOH 99:1)=0.2.
$^1$H-NMR (CDCl$_3$), δ (ppm): 3.06 (t, J=6.5, 2H), 3.29 (t, J=6.5, 2H), 7.02-7.07 (m, 1H), 7.18-7.21 (m, 1H), 7.34-7.39 (2H), 7.43 (dd, J=4.5 and 9.0, 1H), 7.59-7.63 (m, 1H), 8.52-8.55 (m, 1H).

Example 38

2-(6-(4-Fluorophenyl)hexa-1,5-diynyl)pyridine

38(A) 3-(4-Fluorophenyl)prop-2-yn-1-ol

In a dry flask containing in suspension copper iodide (84 mg, 0.44 mmol) and triethylamine (24.70 mL), was added Pd(PPh$_3$)$_2$Cl$_2$ (310 mg, 0.44 mmol) under N$_2$. A yellow suspension is obtained. The reaction mixture was cooled to 0° C. in an ice-bath before the addition of 1-fluoro-4-iodobenzene (1.95 g, 8.80 mmol). After five minutes at 0° C., a solution of prop-2-yn-1-ol (493 mg, 8.80 mmol) in triethylamine (4 mL) was slowly added under N$_2$ over a period of 15 min. Immediately the color of the reaction turns to black. The mixture was stirred 0° C. for 30 min and then warmed to room temperature for 20 h under N$_2$. Triethylamine was concentrated under reduce pressure and the residue was dissolved in DCM. The organic layer was washed with saturated NH$_4$Cl, water, brine, dried (MgSO$_4$) and concentrated. The crude product was purified by flash chromatography (prepacked 25 g silicagel column, DCM 100% as eluent) to afford 1.10 g of 3-(4-fluorophenyl)prop-2-yn-1-ol (Yield: 83%) as a yellow oil.

Rf (DCM/MeOH: 95/5)=0.5
LCMS (RT): 2.88 min, MS (ES+): no ionisation

38(B) 1-(3-Bromoprop-1-ynyl)-4-fluorobenzene

A solution of 3-(4-fluorophenyl)prop-2-yn-1-ol (1 g, 6.80 mmol) in DCM (13.6 mL) under N$_2$ was cooled in a ice bath at 0° C. 2.70 g (8.2 mmol, loading 3 mmol/g) of triphenylphosphine polymer supported was then added followed by 2.70 g (8.2 mmol) of carbon tetrabromide. The reaction mixture was stirred 15 min at 0° C. and warmed to room temperature for 90 min. After filtration through celite, the solvent was evaporated under reduce pressure. The crude product was purified by flash chromatography (prepacked 25 g silicagel column, DCM 100% as eluent) to afford 1.44 g of 1-(3-bromoprop-1-ynyl)-4-fluorobenzene as a yellow oil (Yield: 99%).

Rf (DCM/MeOH: 95/5)=0.6
LCMS (RT): 4.14 min, MS (ES+): no ionisation

38(C) (6-(4-Fluorophenyl)hexa-1,5-diynyl)trimethylsilane

To a solution of trimethyl(prop-1-ynyl)silane (2.19 g, 19.50 mmol) in 22 mL of THF at −78° C., was added dropwise n-BuLi 2.5M in hexane (7.8 mL, 20 mmol). After stirring 2 hours at −78° C., 1-(3-bromoprop-1-ynyl)-4-fluorobenzene (1.40 g, 6.5 mmol) in 6 mL of THF was slowly added and the resulting mixture was stirred for 1 h at −78° C. and warmed to room temperature for an additional 1 h. The reaction mixture was quenched with water and extracted with ethyl acetate. The organic layer was dried over MgSO$_4$, filtered and concentrated to afford 1.57 g of (6-(4-fluorophenyl)hexa-1,5-diynyl)trimethylsilane (99%) as a yellow oil.

LCMS (RT): 4.89 min, MS (ES+): no ionisation

38(D) 1-Fluoro-4-(hexa-1,5-diynyl)benzene

To a solution of (6-(4-fluorophenyl)hexa-1,5-diynyl)trimethylsilane (1.90 g, 7.7 mmol) in THF (24 mL) cooled in a ice bath at 0° C., was added dropwise 7.7 mL of tetrabutylammonium fluoride 1M in THF solution (7.70 mmol). The reaction mixture was stirred 15 min at 0° C., and warmed to room temperature for 2 h 30. The reaction was quenched with water and the aqueous layer was extracted with diethyl ether. The organic layer was washed with brine, dried over MgSO$_4$, filtered and concentrated. The product was purified by flash chromatography (prepacked 25 g silicagel column, DCM 100% as eluent) to afford 500 mg of 1-fluoro-4-(hexa-1,5-diynyl)benzene (Yield: 45%) as a yellow oil.

LCMS (RT): 4.11 min, MS (ES+): no ionisation

38(E) 2-(6-(4-Fluorophenyl)hexa-1,5-diynyl)pyridine

In a dry reaction tube containing in suspension copper iodide (11 mg, 0.06 mmol) and triethylamine (3.4 mL), were added 2-iodopyridine (246 mg, 1.2 mmol) and Pd(PPh$_3$)$_2$Cl$_2$ (42 mg, 0.06 mmol) under N$_2$. A yellow suspension was obtained after 5 min of stirring at room temperature. A solution of 1-fluoro-4-(hexa-1,5-diynyl)benzene (210 mg, 1.2 mmol) in triethylamine (0.5 mL) was then added under N$_2$. Immediately the color of the reaction turns to black. The mixture was stirred at room temperature for 48 h. The reaction mixture was concentrated. The crude product was dissolved in DCM and the organic phase was washed with saturated NH$_4$Cl, water and brine. The organic layer was dried over MgSO$_4$, filtered, and concentrated. Purification by Flash chromatography (prepacked 25 g silicagel column, Cyclohexane/ethyl acetate from 90/10 to 80/20 as eluent) to afford 87 mg of 2-(6-(4-fluorophenyl)hexa-1,5-diynyl)pyridine (Yield: 29%) as a brown powder (M.P.=68-69° C.).

Rf (Cyclohexane/AcOEt: 80/20)=0.3
LCMS (RT): 3.91 min; MS (ES+) gave m/z: 250.1
$^1$NMR (CDCl$_3$), δ (ppm): 8.58 (d, H), 7.63 (t, H), 7.42-7.37 (m, 3H), 7.22 (m, H), 7.01-6.95 (m, 2H), 2.76 (m, 4H).

Example 39

2-(4-(Pyridin-2-yl)but-3-ynyl)-[1,2,4]triazolo[4,3-a]pyridin-3(2H)-one

39(A) 2-(But-3-ynyl)-[1,2,4]triazolo[4,3-a]pyridin-3(2H)-one

The title compound was prepared in accordance with the general method of Example 109(D), from [1,2,4]triazolo[4,3-a]pyridin-3(2H)-one (405 mg, 3.00 mmol) and but-3-yn-1-ol (200 mg, 2.85 mmol). The crude residue was purified by flash chromatography (DCM/MeOH 99:1) to yield 140 mg (0.75 mmol, 26%) of 2-(but-3-ynyl)-[1,2,4]triazolo[4,3-a]pyridin-3(2H)-one.

39(B) 2-(4-(Pyridin-2-yl)but-3-ynyl)-[1,2,4]triazolo[4,3-a]pyridin-3(2H)-one The title compound was prepared in accordance with the general method of Example 1, from 2-(but-3-ynyl)-[1,2,4]triazolo[4,3-a]pyridin-3(2H)-one (70 mg, 0.37 mmol) and 2-bromopyridine (65 mg, 0.41 mmol). The crude residue was purified by flash chromatography (DCM/MeOH 98:2) to yield 23 mg (87 mmol, 23%) of 2-(4-(pyridin-2-yl)but-3-ynyl)-[1,2,4]triazolo[4,3-a]pyridin-3(2H)-one as a yellow solid (M.P.=95.5-96° C.).

LCMS (RT): 2.43 min; MS (ES+) gave m/z: 265.0.
Rf (DCM/MeOH 98:2)=0.1.
$^1$H-NMR (CDCl$_3$), δ (ppm): 3.00 (t, J=7.2, 2H), 4.29 (t, J=7.2, 2H), 6.46-6.51 (m, 1H), 7.08-7.11 (2H), 7.19 (ddd, J=1.1, 4.8 and 7.8, 1H), 7.38 (d, J=8.1, 1H), 7.57-7.65 (m, 1H), 7.73-7.78 (m, 1H), 8.50-8.55 (m, 1H).

Example 40

2-(4-(3-(2-Methoxyphenyl)-1,2,4-oxadiazol-5-yl)but-1-ynyl)pyridine

40(A) N'-Hydroxy-2-methoxybenzamidine

According to the general protocol for amidoxime synthesis described in Example 15(A), the conversion of 2-methoxybenzonitrile (0.86 mL, 7 mmol) afforded 1.1 g of N'-hydroxy-2-methoxybenzamidine (Yield: 95%) as white powder (M.P.=66-68° C.).

40(B) 5-(But-3-ynyl)-3-(2-methoxyphenyl)-1,2,4-oxadiazole

In a reactor tube, a mixture of N'-hydroxy-2-methoxybenzamidine (598 mg, 3.6 mmol), 4-pentynoic acid (350 mg, 3.6 mmol), HOBT (0.55 g, 3.6 mmol) and EDCI.HCl (1.03 g, 5.4 mmol) in dioxane (7.4 mL) was stirred at R.T for 3 h. After this time the mixture was heated at 80° C. overnight in a reaction block. The mixture was concentrated and the crude product was purified by flash chromatography (Prepacked column 25 g with DCM as eluent) to afford 299 mg of 5-(but-3-ynyl)-3-(2-methoxyphenyl)-1,2,4-oxadiazole (36%) as yellow oil.

LCMS (RT): 3.39 min; MS (ES+) gave m/z: 229.0
Rf Oxadiazole (DCM/MeOH: 99/1): 0.75.

40(C) 2-(4-(3-(2-Methoxyphenyl)-1,2,4-oxadiazol-5-yl)but-1-ynyl)pyridine

In a dry reaction tube containing in suspension copper iodide (12 mg, 0.07 mmol) and triethylamine (4.1 mL, 29 mmol), were added 2-iodopyridine (139 μL, 1.3 mmol) and Pd(PPh$_3$)$_2$Cl$_2$ (46 mg, 0.07 mmol) under N$_2$. A yellow suspension is obtained and after a few minutes of stirring at room temperature, was added a solution 5-(but-3-ynyl)-3-(2-methoxyphenyl)-1,2,4-oxadiazole (299 mg, 1.3 mmol) in triethylamine (0.7 mL) under N$_2$. Immediately the color of the reaction turns to black. The mixture was stirred at room temperature for 20 h under N$_2$. Triethylamine was removed under reduce pressure and the crude product was purified by flash chromatography (Prepacked column 10 g, cyclohexane/AcOEt: from 60/40 to 50/50 as eluent) to afford 50 mg of 2-(4-(3-(2-methoxyphenyl)-1,2,4-oxadiazol-5-yl)but-1-ynyl)pyridine (13%) as brown oil.

LCMS (RT): 3.04 min; MS (ES+) gave m/z: 306.1
$^1$H-NMR (CDCl$_3$), δ (ppm): 8.56 (d, H), 8.01 (dd, H), 7.62 (t, H), 7.48 (t, H), 7.38 (d, H), 7.23-7.18 (m, H), 7.11-7.04 (m, 2H), 3.98 (s, 3H), 3.32 (t, 2H), 3.06 (t, 2H).

Example 41

2-(4-(3-(3-Methoxyphenyl)-1,2,4-oxadiazol-5-yl)but-1-ynyl)pyridine

41(A) N'-Hydroxy-3-methoxybenzamidine

According to the general protocol for amidoxime synthesis described in Example 15(A), the conversion of 3-methoxybenzonitrile (0.87 mL, 7 mmol) afforded 1.1 g of N'-hydroxy-3-methoxybenzamidine (Yield: 95%) as beige powder (M.P.=59-61° C.).

41(B) 5-(But-3-ynyl)-3-(3-methoxyphenyl)-1,2,4-oxadiazole

According to the general protocol for oxadiazole synthesis described in Example 40(B), the conversion of N'-hydroxy-3-methoxybenzamidine (598 mg, 3.6 mmol) afforded 276 mg of 5-(but-3-ynyl)-3-(3-methoxyphenyl)-1,2,4-oxadiazole (Yield: 34%) as yellow oil. LCMS (RT): 3.79 min; MS (ES+) gave m/z: 229.0

41(C) 2-(4-(3-(3-Methoxyphenyl)-1,2,4-oxadiazol-5-yl)but-1-ynyl)pyridine

According to the general protocol for Sonogashira coupling described in Example 40(C), the conversion of 5-(but-3-ynyl)-3-(3-methoxyphenyl)-1,2,4-oxadiazole (276 mg, 1.2 mmol) afforded 128 mg of 2-(4-(3-(3-methoxyphenyl)-1,2,4-oxadiazol-5-yl)but-1-ynyl)pyridine (Yield: 35%) as brown oil.

LCMS (RT): 3.59 min; MS (ES+) gave m/z: 306.1
$^1$H-NMR (CDCl$_3$), δ (ppm): 8.56 (d, H), 7.68 (d, H), 7.65-7.60 (m, 2H), 7.41-7.36 (m, 2H), 7.22 (m, H), 7.06 (d, H), 3.88 (s, 3H), 3.32 (t, 2H), 3.06 (t, 2H).

Example 42

2-(4-(3-(4-Methoxyphenyl)-1,2,4-oxadiazol-5-yl)but-1-ynyl)pyridine

42(A) N'-Hydroxy-4-methoxybenzamidine

According to the general protocol for amidoxime synthesis described in Example 15(A), the conversion of 4-methoxybenzonitrile (0.93 g, 7 mmol) afforded 1.1 g of N'-hydroxy-4-methoxybenzamidine (Yield: 95%) as beige powder (M.P.=113-115° C.).

42(B) 5-(But-3-ynyl)-3-(4-methoxyphenyl)-1,2,4-oxadiazole

According to the general protocol for oxadiazole synthesis described in Example 40(B), the conversion of N'-hydroxy-4-methoxybenzamidine (598 mg, 3.6 mmol) afforded 343 mg of 5-(but-3-ynyl)-3-(4-methoxyphenyl)-1,2,4-oxadiazole (Yield: 42%) as yellow oil. LCMS (RT): 3.81 min; MS (ES+) gave m/z: 229.0

42(C) 2-(4-(3-(4-Methoxyphenyl)-1,2,4-oxadiazol-5-yl)but-1-ynyl)pyridine

According to the general protocol for Sonogashira coupling described in Example 40(C), the conversion of 5-(but-3-ynyl)-3-(4-methoxyphenyl)-1,2,4-oxadiazole (343 mg, 1.5 mmol) afforded 98 mg of 2-(4-(3-(4-methoxyphenyl)-1,2,4-oxadiazol-5-yl)but-1-ynyl)pyridine (Yield: 21%) as brown oil.

LCMS (RT): 3.51 min; MS (ES+) gave m/z: 306.1
$^1$H-NMR (CDCl$_3$), δ (ppm): 8.56 (d, H), 8.01-8.05 (m, 2H), 7.62 (t, H), 7.38 (d, H), 7.22 (m, H), 7.02-6.97 (m, 2H), 3.88 (s, 3H), 3.28 (t, 2H), 3.04 (t, 2H).

Example 43

2-(4-(3-m-Tolyl-1,2,4-oxadiazol-5-yl)but-1-ynyl)pyridine

43(A) N'-Hydroxy-3-methylbenzamidine

According to the general protocol for amidoxime synthesis described in Example 15(A), the conversion of 3-methylbenzonitrile (0.83 mL, 7 mmol) afforded 1.03 g of N'-hydroxy-3-methylbenzamidine (Yield: 98%) as beige powder (M.P.=86-88° C.).

43(B) 5-(But-3-ynyl)-3-m-tolyl-1,2,4-oxadiazole

According to the general protocol for oxadiazole synthesis described in Example 40(B), the conversion of N'-hydroxy-3-methylbenzamidine (541 mg, 3.6 mmol) afforded 226 mg of 5-(but-3-ynyl)-3-m-tolyl-1,2,4-oxadiazole (Yield: 30%) as yellow oil.

LCMS (RT): 3.98 min; MS (ES+) gave m/z: 213.1

43(C) 2-(4-(3-m-Tolyl-1,2,4-oxadiazol-5-yl)but-1-ynyl)pyridine

According to the general protocol for Sonogashira coupling described in Example 40(C), the conversion of 5-(but-3-ynyl)-3-m-tolyl-1,2,4-oxadiazole (226 mg, 1.1 mmol) afforded 144 mg of 2-(4-(3-m-tolyl-1,2,4-oxadiazol-5-yl)but-1-ynyl)pyridine (Yield: 45%) as brown oil.

LCMS (RT): 3.76 min; MS (ES+) gave m/z: 290.1
$^1$NMR (CDCl$_3$), δ (ppm): 8.56 (d, H), 7.93-7.87 (m, 2H), 7.62 (t, H), 7.41-7.36 (m, 2H), 7.32 (m, H), 7.22 (m, H), 3.31 (t, 2H), 3.06 (t, 2H), 2.43 (s, 3H).

Example 44

2-(4-(3-p-Tolyl-1,2,4-oxadiazol-5-yl)but-1-ynyl)pyridine

44(A) N'-Hydroxy-4-methylbenzamidine

According to the general protocol for amidoxime synthesis described in Example 15(A), the conversion of 4-methylbenzonitrile (0.82 g, 7 mmol) afforded 1.03 g of N'-hydroxy-4-methylbenzamidine (Yield: 98%) as white powder (M.P.=143-144° C.).

44(B) 5-(But-3-ynyl)-3-p-tolyl-1,2,4-oxadiazole

According to the general protocol for oxadiazole synthesis described in Example 40(B), the conversion of N'-hydroxy-4-methylbenzamidine (541 mg, 3.6 mmol) afforded 482 mg of 5-(but-3-ynyl)-3-p-tolyl-1,2,4-oxadiazole (Yield: 63%) as yellow oil.

LCMS (RT): 3.99 min; MS (ES+) gave m/z: 213.1

44(C) 2-(4-(3-p-Tolyl-1,2,4-oxadiazol-5-yl)but-1-ynyl)pyridine

According to the general protocol for Sonogashira coupling described in Example 40(C), the conversion of 5-(but-3-ynyl)-3-p-tolyl-1,2,4-oxadiazole (482 mg, 2.3 mmol) afforded 175 mg of 2-(4-(3-p-tolyl-1,2,4-oxadiazol-5-yl)but-1-ynyl)pyridine (Yield: 26%) as brown oil.

LCMS (RT): 3.76 min; MS (ES+) gave m/z: 290.1
$^1$NMR (CDCl$_3$), δ (ppm): 8.56 (d, H), 7.93-7.87 (m, 2H), 7.62 (t, H), 7.38 (d, H), 7.32-7.28 (m, 2H), 7.22 (m, H), 3.31 (t, 2H), 3.06 (t, 2H), 2.42 (s, 3H).

Example 45

2-(4-(3-(2-Chlorophenyl)-1,2,4-oxadiazol-5-yl)but-1-ynyl)pyridine

45(A) 2-Chloro-N'-hydroxybenzamidine

According to the general protocol for amidoxime synthesis described in Example 15(A), the conversion of 2-chlorobenzonitrile (0.96 g, 7 mmol) afforded 1.01 g of 2-chloro-N'-hydroxybenzamidine (Yield: 85%) as beige powder (M.P.=79-81° C.).

45(B) 5-(But-3-ynyl)-3-(2-chlorophenyl)-1,2,4-oxadiazole

According to the general protocol for oxadiazole synthesis described in Example 40(B), the conversion of 2-chloro-N'-hydroxybenzamidine (614 mg, 3.6 mmol) afforded 210 mg of 5-(but-3-ynyl)-3-(2-chlorophenyl)-1,2,4-oxadiazole (Yield: 25%) as yellow oil.

LCMS (RT): 3.83 min; MS (ES+) gave m/z: 233.0

45(C) 2-(4-(3-(2-Chlorophenyl)-1,2,4-oxadiazol-5-yl)but-1-ynyl)pyridine

According to the general protocol for Sonogashira coupling described in Example 40(C), the conversion of 5-(but-3-ynyl)-3-(2-chlorophenyl)-1,2,4-oxadiazole (210 mg, 0.9 mmol) afforded 124 mg of 2-(4-(3-(2-chlorophenyl)-1,2,4-oxadiazol-5-yl)but-1-ynyl)pyridine (Yield: 45%) as brown oil.

LCMS (RT): 3.59 min; MS (ES+) gave m/z: 310.1
$^1$NMR (CDCl$_3$), δ (ppm): 8.56 (d, H), 7.93 (d, H), 7.62 (t, H), 7.48-7.37 (m, 3H), 7.22 (m, H), 7.22 (m, H), 3.35 (t, 2H), 3.08 (t, 2H).

Example 46

2-(4-(3-(3-Chlorophenyl)-1,2,4-oxadiazol-5-yl)but-1-ynyl)pyridine

46(A) 3-Chloro-N'-hydroxybenzamidine

According to the general protocol for amidoxime synthesis described in Example 15(A), the conversion of 3-chlorobenzonitrile (0.96 g, 7 mmol) afforded 1.18 g of 3-chloro-N'-hydroxybenzamidine (Yield: 99%) as beige powder (M.P.=103-105° C.).

46(B) 5-(But-3-ynyl)-3-(3-chlorophenyl)-1,2,4-oxadiazole

According to the general protocol for oxadiazole synthesis described in Example 40(B), the conversion of 3-chloro-N'-hydroxybenzamidine (614 mg, 3.6 mmol) afforded 344 mg of 5-(but-3-ynyl)-3-(3-chlorophenyl)-1,2,4-oxadiazole (Yield: 41%) as yellow oil.
LCMS (RT): 4.14 min; MS (ES+) gave m/z: 233.0

46(C) 2-(4-(3-(3-Chlorophenyl)-1,2,4-oxadiazol-5-yl)but-1-ynyl)pyridine

According to the general protocol for Sonogashira coupling described in Example 40(C), the conversion of 5-(but-3-ynyl)-3-(3-chlorophenyl)-1,2,4-oxadiazole (344 mg, 1.5 mmol) afforded 281 mg of 2-(4-(3-(3-chlorophenyl)-1,2,4-oxadiazol-5-yl)but-1-ynyl)pyridine (Yield: 61%) as brown oil.
LCMS (RT): 3.94 min; MS (ES+) gave m/z: 310.1
$^1$NMR (CDCl$_3$), δ (ppm): 8.56 (d, H), 8.10 (t, H), 7.98 (d, H), 7.63 (t, H), 7.48 (d, H), 7.44-7.36 (m, 2H), 7.22 (m, H), 3.32 (t, 2H), 3.06 (t, 2H).

Example 47

2-(4-(3-(4-Chlorophenyl)-1,2,4-oxadiazol-5-yl)but-1-ynyl)pyridine

47(A) 4-Chloro-N'-hydroxybenzamidine

According to the general protocol for amidoxime synthesis described in Example 15(A), the conversion of 4-chlorobenzonitrile (0.96 g, 7 mmol) afforded 1.17 g of 4-chloro-N'-hydroxybenzamidine (Yield: 98%) as beige powder (M.P.=133-134° C.).

47(B) 5-(But-3-ynyl)-3-(4-chlorophenyl)-1,2,4-oxadiazole

According to the general protocol for oxadiazole synthesis described in Example 40(B), the conversion of 4-chloro-N'-hydroxybenzamidine (614 mg, 3.6 mmol) afforded 329 mg of 5-(but-3-ynyl)-3-(4-chlorophenyl)-1,2,4-oxadiazole (Yield: 39%) as yellow oil.
LCMS (RT): 4.13 min; MS (ES+) gave m/z: 233.0

47(C) 2-(4-(3-(4-Chlorophenyl)-1,2,4-oxadiazol-5-yl)but-1-ynyl)pyridine

According to the general protocol for Sonogashira coupling described in Example 40(C), the conversion of 5-(but-3-ynyl)-3-(4-chlorophenyl)-1,2,4-oxadiazole (329 mg, 1.4 mmol) afforded 227 mg of 2-(4-(3-(4-chlorophenyl)-1,2,4-oxadiazol-5-yl)but-1-ynyl)pyridine (Yield: 52%) as white solid (M.P.=75-77° C.).
LCMS (RT): 3.93 min; MS (ES+) gave m/z: 310
$^1$NMR (CDCl$_3$), δ (ppm): 8.56 (d, H), 8.06-8.02 (m, 2H), 7.63 (t, H), 7.49-7.45 (m, 2H), 7.38 (d, H), 7.22 (m, H), 3.31 (t, 2H), 3.06 (t, 2H).

Example 48

2-(4-(3-(2,6-Dimethylphenyl)-1,2,4-oxadiazol-5-yl)but-1-ynyl)pyridine

48(A) N'-Hydroxy-2,6-dimethylbenzamidine

According to the general protocol for amidoxime synthesis described in Example 15(A), the conversion of 2,6-dimethylbenzonitrile (0.92 g, 7 mmol) afforded 0.95 g of N'-hydroxy-2,6-dimethylbenzamidine (Yield: 83%) as beige powder (M.P.=77-79° C.).

48(B) 5-(But-3-ynyl)-3-(2,6-dimethylphenyl)-1,2,4-oxadiazole

According to the general protocol for oxadiazole synthesis described in Example 40(B), the conversion of N'-hydroxy-2,6-dimethylbenzamidine (591 mg, 3.6 mmol) afforded 485 mg of 5-(but-3-ynyl)-3-(2,6-dimethylphenyl)-1,2,4-oxadiazole (Yield: 60%) as yellow oil.
LCMS (RT): 3.88 min; MS (ES+) gave m/z: 227.1

48(C) 2-(4-(3-(2,6-Dimethylphenyl)-1,2,4-oxadiazol-5-yl)but-1-ynyl)pyridine According to the general protocol for Sonogashira coupling described in Example 40(C), the conversion of 5-(but-3-ynyl)-3-(2,6-dimethylphenyl)-1,2,4-oxadiazole (485 mg, 2.1 mmol) afforded 71 mg of 2-(4-(3-(2,6-dimethylphenyl)-1,2,4-oxadiazol-5-yl)but-1-ynyl)pyridine (Yield: 11%) as a brown oil.
LCMS (RT): 3.61 min; MS (ES+) gave m/z: 304.1
$^1$NMR (CDCl$_3$), δ (ppm): 8.56 (d, H), 7.63 (t, H), 7.48 (d, H), 7.29-7.22 (m, 2H), 7.12-7.08 (d, 2H), 3.35 (t, 2H), 3.07 (t, 2H).

Example 49

2-(4-(3-(2-Trifluoromethyl)phenyl)-1,2,4-oxadiazol-5-yl)but-1-ynyl)pyridine

49(A) 2-(Trifluoromethyl)-N'-hydroxybenzamidine

According to the general protocol for amidoxime synthesis described in Example 15(A), the conversion of 2-(trifluoromethyl)benzonitrile (1.2 g, 7 mmol) afforded 1.4 g of 2-(trifluoromethyl)-N'-hydroxybenzamidine (Yield: 99%) as white powder (M.P.=74-76° C.).

49(B) 5-(But-3-ynyl)-3-(2-(trifluoromethyl)phenyl)-1,2,4-oxadiazole

According to the general protocol for oxadiazole synthesis described in Example 40(B), the conversion of 2-(trifluoromethyl)-N'-hydroxybenzamidine (735 mg, 3.6 mmol) afforded 126 mg of 5-(but-3-ynyl)-3-(2-(trifluoromethyl)phenyl)-1,2,4-oxadiazole (Yield: 13%) as yellow oil.
LCMS (RT): 3.89 min; MS (ES+) gave m/z: 267.0

49(C) 2-(4-(3-(2-Trifluoromethyl)phenyl)-1,2,4-oxadiazol-5-yl)but-1-ynyl)pyridine According to the general protocol for Sonogashira coupling described in Example 40(C), the conversion of 5-(but-3-ynyl)-3-(2-(trifluoromethyl)phenyl)-1,2,4-oxadiazole (126 mg, 0.5 mmol) afforded 66 mg of 2-(4-(3-(2-trifluoromethyl)phenyl)-1,2,4-oxadiazol-5-yl)but-1-ynyl)pyridine (Yield: 39%) as a brown oil.

LCMS (RT): 3.61 min; MS (ES+) gave m/z: 344.1
$^1$NMR (CDCl$_3$), δ (ppm): 8.56 (d, H), 7.87-7.78 (m, 2H), 7.68-7.62 (m, 3H), 7.38 (d, H), 7.22 (m, H), 3.35 (t, 2H), 3.07 (t, 2H).

Example 50

2-(4-(3-(Naphthalen-1-yl)-1,2,4-oxadiazol-5-yl)but-1-ynyl)pyridine

50(A) N'-Hydroxy-1-naphthamidine

According to the general protocol for amidoxime synthesis described in Example 15(A), the conversion of 1-naphthonitrile (1.07 g, 7 mmol) afforded 1.28 g of N'-hydroxy-1-naphthamidine (Yield: 98%) as white powder (M.P.=128-130° C.).

50(B) 5-(But-3-ynyl)-3-(naphthalen-1-yl)-1,2,4-oxadiazole

According to the general protocol for oxadiazole synthesis described in Example 40(B), the conversion of N'-hydroxy-1-naphthamidine (670 mg, 3.6 mmol) afforded 264 mg of 5-(but-3-ynyl)-3-(naphthalen-1-yl)-1,2,4-oxadiazole (Yield: 30%) as yellow oil.

LCMS (RT): 4.24 min; MS (ES+) gave m/z: 249.1

50(C) 2-(4-(3-(Naphthalen-1-yl)-1,2,4-oxadiazol-5-yl)but-1-ynyl)pyridine

According to the general protocol for Sonogashira coupling described in Example 40(C), the conversion of 5-(but-3-ynyl)-3-(naphthalen-1-yl)-1,2,4-oxadiazole (264 mg, 1.1 mmol) afforded 105 mg of 2-(4-(3-(naphthalen-1-yl)-1,2,4-oxadiazol-5-yl)but-1-ynyl)pyridine (Yield: 29%) as a brown oil.

LCMS (RT): 4.03 min; MS (ES+) gave m/z: 326.1
$^1$NMR (CDCl$_3$), δ (ppm): 8.91 (d, H), 8.56 (d, H), 8.26 (d, H), 8.02 (d, H), 7.93 (d, H), 7.66-7.56 (m, 4H), 7.40 (d, H), 7.22 (m, H), 3.39 (t, 2H), 3.13 (t, 2H).

Example 51

2-(4-(3-(Naphthalen-2-yl)-1,2,4-oxadiazol-5-yl)but-1-ynyl)pyridine

51(A) N'-Hydroxy-2-naphthamidine

According to the general protocol for amidoxime synthesis described in Example 15(A), the conversion of 2-naphthonitrile (1.07 g, 7 mmol) afforded 1.27 g of N'-hydroxy-2-naphthamidine (Yield: 98%) as white powder (M.P.=147-149° C.).

51(B) 5-(But-3-ynyl)-3-(naphthalen-2-yl)-1,2,4-oxadiazole

According to the general protocol for oxadiazole synthesis described in Example 40(B), the conversion of N'-hydroxy-2-naphthamidine (670 mg, 3.6 mmol) afforded 436 mg of 5-(but-3-ynyl)-3-(naphthalen-2-yl)-1,2,4-oxadiazole (Yield: 49%) as yellow oil.

LCMS (RT): 4.29 min; MS (ES+) gave m/z: 249.0

51(C) 2-(4-(3-(Naphthalen-2-yl)-1,2,4-oxadiazol-5-yl)but-1-ynyl)pyridine

According to the general protocol for Sonogashira coupling described in Example 40(C), the conversion of 5-(but-3-ynyl)-3-(naphthalen-2-yl)-1,2,4-oxadiazole (436 mg, 1.8 mmol) afforded 152 mg of 2-(4-(3-(naphthalen-2-yl)-1,2,4-oxadiazol-5-yl)but-1-ynyl)pyridine (Yield: 26%) as white solid (M.P.=76-78° C.).

LCMS (RT): 4.11 min; MS (ES+) gave m/z: 326.1
$^1$NMR (CDCl$_3$), δ (ppm): 8.64 (s, H), 8.54 (d, H), 8.15 (d, H), 7.99-7.93 (m, 2H), 7.90 (d, H), 7.65-7.60 (m, H), 7.58-7.53 (m, 2H), 7.40 (d, H), 7.22 (m, H), 3.36 (t, 2H), 3.11 (t, 2H).

Example 52

2-(4-(3-(2,3-Dimethylphenyl)-1,2,4-oxadiazol-5-yl)but-1-ynyl)pyridine

52(A) N'-Hydroxy-2,3-dimethylbenzamidine

According to the general protocol for amidoxime synthesis described in Example 15(A), the conversion of (2,3-dimethylbenzonitrile (0.92 g, 7 mmol) afforded 1.12 g of N'-hydroxy-2,3-dimethylbenzamidine (Yield: 97%) as white powder (M.P.=110-111° C.).

52(B) 5-(But-3-ynyl)-3-(2,3-dimethylphenyl)-1,2,4-oxadiazole

According to the general protocol for oxadiazole synthesis described in Example 40(B), the conversion of N'-hydroxy-2,3-dimethylbenzamidine (558 mg, 3.4 mmol) afforded 345 mg of 5-(but-3-ynyl)-3-(2,3-dimethylphenyl)-1,2,4-oxadiazole (Yield: 45%) as yellow oil.

LCMS (RT): 4.01 min; MS (ES+) gave m/z: 227.1

52(C) 2-(4-(3-(2,3-Dimethylphenyl)-1,2,4-oxadiazol-5-yl)but-1-ynyl)pyridine According to the general protocol for Sonogashira coupling described in Example 40(C), the conversion of 5-(but-3-ynyl)-3-(2,3-dimethylphenyl)-1,2,4-oxadiazole (345 mg, 1.5 mmol) afforded 175 mg of 2-(4-(3-(2,3-dimethylphenyl)-1,2,4-oxadiazol-5-yl)but-1-ynyl)pyridine (Yield: 38%) as brown oil.

LCMS (RT): 3.81 min; MS (ES+) gave m/z: 304.1
$^1$NMR (CDCl$_3$), δ (ppm): 8.64 (s, H), 7.70-7.61 (m, 2H), 7.40 (d, H), 7.32-7.18 (m, 3H), 3.33 (t, 2H), 3.07 (t, 2H), 2.47 (s, 3H), 2.37 (s, 3H).

Example 53

2-(4-(3-(2,5-Dichlorophenyl)-1,2,4-oxadiazol-5-yl)but-1-ynyl)pyridine

53(A) 2,5-Dichloro-N'-hydroxybenzamidine

According to the general protocol for amidoxime synthesis described in Example 15(A), the conversion of 2,5-dichlorobenzonitrile (1.21 mmol) afforded 1.35 g of 2,5-dichloro-N'-hydroxybenzamidine (Yield: 94%) as yellow oil.

53(B) 5-(But-3-ynyl)-3-(2,5-dichlorophenyl)-1,2,4-oxadiazole

According to the general protocol for oxadiazole synthesis described in Example 40(B), the conversion of 2,5-dichloro-N'-hydroxybenzamidine (697 mg, 3.4 mmol) afforded 425 mg of 5-(but-3-ynyl)-3-(2,5-dichlorophenyl)-1,2,4-oxadiazole (Yield: 47%) as yellow oil.
LCMS (RT): 4.21 min; MS (ES+) gave m/z: 267.0

53(C) 2-(4-(3-(2,5-Dichlorophenyl)-1,2,4-oxadiazol-5-yl)but-1-ynyl)pyridine

According to the general protocol for Sonogashira coupling described in Example 40(C), the conversion of 5-(but-3-ynyl)-3-(2,5-dichlorophenyl)-1,2,4-oxadiazole (425 mg, 1.6 mmol) afforded 342 mg of 2-(4-(3-(2,5-dichlorophenyl)-1,2,4-oxadiazol-5-yl)but-1-ynyl)pyridine (Yield: 65%) as brown semi-solid.
LCMS (RT): 4.06 min; MS (ES+) gave m/z: 346.1
$^1$NMR (CDCl$_3$), δ (ppm): 8.64 (s, H), 7.97 (d, H), 7.63 (t, H), 7.48 (d, H), 7.43-7.37 (m, 2H), 7.22 (t, H), 3.35 (t, 2H), 3.07 (t, 2H).

Example 54

2-(4-(3-(2,5-Dimethylphenyl)-1,2,4-oxadiazol-5-yl)but-1-ynyl)pyridine

54(A) N'-Hydroxy-2,5-dimethylbenzamidine

According to the general protocol for amidoxime synthesis described in Example 15(A), the conversion of 2,5-dimethylbenzonitrile (0.92 g, 7 mmol) afforded 1.14 g of N'-hydroxy-2,5-dimethylbenzamidine (Yield: 99%) as yellow oil.

54(B) 5-(But-3-ynyl)-3-(2,5-dimethylphenyl)-1,2,4-oxadiazole

According to the general protocol for oxadiazole synthesis described in Example 40(B), the conversion of N'-hydroxy-2,5-dimethylbenzamidine (558 mg, 3.4 mmol) afforded 329 mg of 5-(but-3-ynyl)-3-(2,5-dimethylphenyl)-1,2,4-oxadiazole (Yield: 43%) as yellow oil.
LCMS (RT): 4.18 min; MS (ES+) gave m/z: 227.1

54(C) 2-(4-(3-(2,5-Dimethylphenyl)-1,2,4-oxadiazol-5-yl)but-1-ynyl)pyridine According to the general protocol for Sonogashira coupling described in Example 40(C), the conversion of (329 mg, 1.5 mmol) of 5-(but-3-ynyl)-3-(2,5-dimethylphenyl)-1,2,4-oxadiazole afforded 58 mg of 2-(4-(3-(2,5-dimethylphenyl)-1,2,4-oxadiazol-5-yl)but-1-ynyl)pyridine (Yield: 13%) as brown oil.
LCMS (RT): 3.98 min; MS (ES+) gave m/z: 304.1
$^1$NMR (CDCl$_3$), δ (ppm): 8.64 (s, H), 7.80 (s, H), 7.65 (t, H), 7.40 (d, H), 7.25-7.18 (m, 3H), 3.32 (t, 2H), 3.08 (t, 2H), 2.58 (s, 3H), 2.38 (s, 3H).

Example 55

2-(4-(3-(2,6-Dichlorophenyl)-1,2,4-oxadiazol-5-yl)but-1-ynyl)pyridine

55(A) 2,6-Dichloro-N'-hydroxybenzamidine

According to the general protocol for amidoxime synthesis described in Example 15(A), the conversion of 2,6-dichlorobenzonitrile (1.20 g, 7 mmol) afforded 1.09 g of 2,6-dichloro-N'-hydroxybenzamidine (Yield: 76%) as beige powder (M.P.=163-164° C.).

55(B) 5-(But-3-ynyl)-3-(2,6-dichlorophenyl)-1,2,4-oxadiazole

According to the general protocol for oxadiazole synthesis described in Example 40(B), the conversion of 2,6-dichloro-N'-hydroxybenzamidine (697 mg, 3.4 mmol) afforded 480 mg of 5-(but-3-ynyl)-3-(2,6-dichlorophenyl)-1,2,4-oxadiazole (Yield: 53%) as yellow oil.
LCMS (RT): 3.89 min; MS (ES+) gave m/z: 267.0

55(C) 2-(4-(3-(2,6-Dichlorophenyl)-1,2,4-oxadiazol-5-yl)but-1-ynyl)pyridine According to the general protocol for Sonogashira coupling described in Example 40(C), the conversion of 5-(but-3-ynyl)-3-(2,6-dichlorophenyl)-1,2,4-oxadiazole (480 mg, 1.8 mmol) afforded 365 mg of 2-(4-(3-(2,6-dichlorophenyl)-1,2,4-oxadiazol-5-yl)but-1-ynyl)pyridine (Yield: 59%) as brown oil.
LCMS (RT): 3.73 min; MS (ES+) gave m/z: 344.1
$^1$NMR (CDCl$_3$), δ (ppm): 8.64 (s, H), 7.63 (t, H), 7.45-7.36 (m, 4H), 7.22 (t, H), 3.38 (t, 2H), 3.08 (t, 2H).

Example 56

2-(4-(3-(2,3-Dichlorophenyl)-1,2,4-oxadiazol-5-yl)but-1-ynyl)pyridine

56(A) 2,3-Dichloro-N'-hydroxybenzamidine

According to the general protocol for amidoxime synthesis described in Example 15(A), the conversion of 2,3-dichlorobenzonitrile (1.20 g, 7 mmol) afforded 1.36 g of 2,3-dichloro-N'-hydroxybenzamidine (Yield: 95%) as beige powder (M.P.=115-117° C.).

56(B) 5-(But-3-ynyl)-3-(2,3-dichlorophenyl)-1,2,4-oxadiazole

According to the general protocol for oxadiazole synthesis described in Example 40(B), the conversion of 2,3-dichloro-N'-hydroxybenzamidine (697 mg, 3.4 mmol) afforded 374 mg of 5-(but-3-ynyl)-3-(2,3-dichlorophenyl)-1,2,4-oxadiazole (Yield: 41%) as yellow oil.
LCMS (RT): 4.09 min; MS (ES+) gave m/z: 267.0

56(C) 2-(4-(3-(2,3-Dichlorophenyl)-1,2,4-oxadiazol-5-yl)but-1-ynyl)pyridine According to the general protocol for Sonogashira coupling described in Example 40(C), the conversion of 5-(but-3-ynyl)-3-(2,3-dichlorophenyl)-1,2,4-oxadiazole (374 mg, 1.4 mmol) afforded 193 mg of 2-(4-(3-(2,3-dichlorophenyl)-1,2,4-oxadiazol-5-yl)but-1-ynyl)pyridine (Yield: 40%) as brown oil.

LCMS (RT): 3.91 min; MS (ES+) gave m/z: 346.1
$^1$NMR (CDCl$_3$), δ (ppm): 8.64 (s, H), 7.81 (d, H), 7.66-7.61 (m, 2H), 7.38 (d, H), 7.34 (t, H), 7.22 (t, H), 3.35 (t, 2H), 3.07 (t, 2H).

Example 57

2-(4-(3-(2,4-Dichlorophenyl)-1,2,4-oxadiazol-5-yl)but-1-ynyl)pyridine

57(A) 2,4-Dichloro-N'-hydroxybenzamidine

According to the general protocol for amidoxime synthesis described in Example 15(A), the conversion of 2,4-dichlorobenzonitrile (1.20 g, 7 mmol) afforded 1.40 g of 2,4-dichloro-N'-hydroxybenzamidine (Yield: 98%) as beige powder (M.P.=149-151° C.).

57(B) 5-(But-3-ynyl)-3-(2,4-dichlorophenyl)-1,2,4-oxadiazole

According to the general protocol for oxadiazole synthesis described in Example 40(B), the conversion of 2,4-dichloro-N'-hydroxybenzamidine (697 mg, 3.4 mmol) afforded 553 mg of 5-(but-3-ynyl)-3-(2,4-dichlorophenyl)-1,2,4-oxadiazole (Yield: 61%) as yellow oil.

LCMS (RT): 4.21 min; MS (ES+) gave m/z: 267.0

57(C) 2-(4-(3-(2,4-Dichlorophenyl)-1,2,4-oxadiazol-5-yl)but-1-ynyl)pyridine

According to the general protocol for Sonogashira coupling described in Example 40(C), the conversion of 5-(but-3-ynyl)-3-(2,4-dichlorophenyl)-1,2,4-oxadiazole (553 mg, 2.1 mmol) afforded 430 mg of 2-(4-(3-(2,4-dichlorophenyl)-1,2,4-oxadiazol-5-yl)but-1-ynyl)pyridine (Yield: 59%) as beige powder (M.P.=77-78° C.).

LCMS (RT): 4.04 min; MS (ES+) gave m/z: 344.0
$^1$NMR (CDCl$_3$), δ (ppm): 8.64 (s, H), 7.92 (d, H), 7.65 (t, H), 7.57 (d, H), 7.41-7.37 (m, 2H), 7.23 (t, H), 3.34 (t, 2H), 3.06 (t, 2H).

Example 58

2-(4-(3-(2-Chloro-6-methylphenyl)-1,2,4-oxadiazol-5-yl)but-1-ynyl)pyridine

58(A) 2-Chloro-N'-hydroxy-6-methylbenzamidine

According to the general protocol for amidoxime synthesis described in Example 15(A), the conversion of 2-chloro-6-methylbenzonitrile (1.06 g, 7 mmol) afforded 1.28 g of 2-chloro-N'-hydroxy-6-methylbenzamidine (Yield: 99%) as beige powder (M.P.=136-137° C.).

58(B) 5-(But-3-ynyl)-3-(2-chloro-6-methylphenyl)-1,2,4-oxadiazole

According to the general protocol for oxadiazole synthesis described in Example 40(B), the conversion of 2-chloro-N'-hydroxy-6-methylbenzamidine (628 mg, 3.4 mmol) afforded 458 mg of 5-(but-3-ynyl)-3-(2-chloro-6-methylphenyl)-1,2,4-oxadiazole (Yield: 55%) as yellow oil.

LCMS (RT): 3.84 min; MS (ES+) gave m/z: no ionisation

58(C) 2-(4-(3-(2-Chloro-6-methylphenyl)-1,2,4-oxadiazol-5-yl)but-1-ynyl)pyridine According to the general protocol for Sonogashira coupling described in Example 40(C), the conversion of 5-(but-3-ynyl)-3-(2-chloro-6-methylphenyl)-1,2,4-oxadiazole (458 mg, 1.9 mmol) afforded 420 mg of 2-(4-(3-(2-chloro-6-methylphenyl)-1,2,4-oxadiazol-5-yl)but-1-ynyl)pyridine (Yield: 68%) as brown oil.

LCMS (RT): 3.66 min; MS (ES+) gave m/z: 324.1
$^1$NMR (CDCl$_3$), δ (ppm): 8.64 (s, H), 7.63 (t, H), 7.37 (d, H), 7.35-7.30 (m, 2H), 7.24-7.18 (m, 2H), 3.36 (t, 2H), 3.08 (t, 2H), 2.22 (s, 3H).

Example 59

2-(4-(3-(5-Fluoro-2-methylphenyl)-1,2,4-oxadiazol-5-yl)but-1-ynyl)pyridine

59(A) 5-Fluoro-N'-hydroxy-2-methylbenzamidine

According to the general protocol for amidoxime synthesis described in Example 15(A), the conversion of 5-fluoro-2-methylbenzonitrile (0.95 g, 7 mmol) afforded 1.27 g of 5-fluoro-N'-hydroxy-2-methylbenzamidine (Yield: 98%) as yellow oil.

59(B) 5-(But-3-ynyl)-3-(5-fluoro-2-methylphenyl)-1,2,4-oxadiazole

According to the general protocol for oxadiazole synthesis described in Example 40(B), the conversion of 5-fluoro-N'-hydroxy-2-methylbenzamidine (572 mg, 3.4 mmol) afforded 325 mg of 5-(but-3-ynyl)-3-(5-fluoro-2-methylphenyl)-1,2,4-oxadiazole (Yield: 42%) as yellow oil.

LCMS (RT): 4.06 min; MS (ES+) gave m/z: 231.1

59(C) 2-(4-(3-(5-Fluoro-2-methylphenyl)-1,2,4-oxadiazol-5-yl)but-1-ynyl)pyridine According to the general protocol for Sonogashira coupling described in Example 40(C), the conversion of 5-(but-3-ynyl)-3-(5-fluoro-2-methylphenyl)-1,2,4-oxadiazole (325 mg, 1.4 mmol) afforded 190 mg of 2-(4-(3-(5-fluoro-2-methylphenyl)-1,2,4-oxadiazol-5-yl)but-1-ynyl)pyridine (Yield: 44%) as beige powder (M.P.=90-91° C.).

LCMS (RT): 3.91 min; MS (ES+) gave m/z: 308.0
$^1$NMR (CDCl$_3$), δ (ppm): 8.64 (s, H), 7.63 (t, H), 7.37 (d, H), 7.34-7.29 (m, 2H), 7.24-7.18 (m, 2H), 3.36 (t, 2H), 3.08 (t, 2H), 2.22 (s, 3H).

Example 60

2-(4-(3-(5-Chloro-2-methylphenyl)-1,2,4-oxadiazol-5-yl)but-1-ynyl)pyridine

60(A) 5-Chloro-N'-hydroxy-2-methylbenzamidine

According to the general protocol for amidoxime synthesis described in Example 15(A), the conversion of 5-chloro-2-methylbenzonitrile (1.06 g, 7 mmol) afforded 1.27 g of 5-chloro-N'-hydroxy-2-methylbenzamidine (Yield: 98%) as beige powder (M.P.=111-113° C.).

60(B) 5-(But-3-ynyl)-3-(5-chloro-2-methylphenyl)-1,2,4-oxadiazole

According to the general protocol for oxadiazole synthesis described in Example 40(B), the conversion of 5-chloro-N'-hydroxy-2-methylbenzamidine (628 mg, 3.4 mmol) afforded 376 mg of 5-(but-3-ynyl)-3-(5-chloro-2-methylphenyl)-1,2,4-oxadiazole (Yield: 45%) as yellow oil.
LCMS (RT): 4.34 min; MS (ES+) gave m/z: 247.1

60(C) 2-(4-(3-(5-Chloro-2-methylphenyl)-1,2,4-oxadiazol-5-yl)but-1-ynyl)pyridine According to the general protocol for Sonogashira coupling described in Example 40(C), the conversion of 5-(but-3-ynyl)-3-(5-chloro-2-methylphenyl)-1,2,4-oxadiazole (376 mg, 1.5 mmol) afforded 310 mg of 2-(4-(3-(5-chloro-2-methylphenyl)-1,2,4-oxadiazol-5-yl)but-1-ynyl)pyridine (Yield: 64%) as beige powder (M.P.=66-68° C.).
LCMS (RT): 4.16 min; MS (ES+) gave m/z: 324.1
$^1$NMR (CDCl$_3$), δ (ppm): 8.64 (s, H), 8.02 (d, H), 7.63 (t, H), 7.40 (d, H), 7.35 (d, H), 7.28-7.21 (m, 2H), 3.33 (t, 2H), 3.07 (t, 2H), 2.60 (s, 3H).

Example 61

2-(4-(3-(2-(Trifluoromethoxy)phenyl)-1,2,4-oxadiazol-5-yl)but-1-ynyl)pyridine

61(A) N'-Hydroxy-2-(trifluoromethoxy)benzamidine

According to the general protocol for amidoxime synthesis described in Example 15(A), the conversion of 2-(trifluoromethoxy)benzonitrile (1.31 g, 7 mmol) afforded 1.55 g of N'-hydroxy-2-(trifluoromethoxy)benzamidine (Yield: 96%) as beige powder (M.P.=95-97° C.).

61(B) 5-(But-3-ynyl)-3-(2-(trifluoromethoxy)phenyl)-1,2,4-oxadiazole

According to the general protocol for oxadiazole synthesis described in Example 40(B), the conversion of N'-hydroxy-2-(trifluoromethoxy)benzamidine (749 mg, 3.4 mmol) afforded 303 mg of 5-(but-3-ynyl)-3-(2-(trifluoromethoxy)phenyl)-1,2,4-oxadiazole (Yield: 32%) as yellow oil.
LCMS (RT): 4.03 min; MS (ES+) gave m/z: 263.1

61(C) 2-(4-(3-(2-(Trifluoromethoxy)phenyl)-1,2,4-oxadiazol-5-yl)but-1-ynyl)pyridine According to the general protocol for Sonogashira coupling described in Example 40(C), the conversion of 5-(but-3-ynyl)-3-(2-(trifluoromethoxy)phenyl)-1,2,4-oxadiazole (303 mg, 1.1 mmol) afforded 213 mg of 2-(4-(3-(2-(trifluoromethoxy)phenyl)-1,2,4-oxadiazol-5-yl)but-1-ynyl)pyridine (Yield: 54%) as brown oil.
LCMS (RT): 3.84 min; MS (ES+) gave m/z: 360.1
$^1$NMR (CDCl$_3$), δ (ppm): 8.64 (s, H), 8.11 (d, H), 7.63 (t, H), 7.56 (t, H), 7.48-7.42 (m, 2H), 7.37 (d, H), 7.23 (t, H), 3.33 (t, 2H), 3.07 (t, 2H).

Example 62

6-Fluoro-2-(4-(pyridin-2-yl)but-3-ynyl)benzo[d]oxazole

62(A) 2-Amino-5-fluorophenol

A suspension of 3-fluoro-6-nitrophenol (500 mg, 3.18 mmol) and zinc (2.10 g, 31.8 mmol) in acetic acid (7.3 mL) was stirred overnight at room temperature. The reaction mixture was filtered through celite and washed with DCM. After evaporation and distillation under vacuum (2.10$^{-2}$ mbar) of the solvents, the residue was dissolved in DCM. The organic phase was washed with a saturated solution of NaHCO$_3$ and brine, dried over MgSO$_4$, filtered and evaporated. The crude residue was purified by flash chromatography (DCM/MeOH 99.5:0.5) to yield 177 mg (1.39 mmol, 44%) of 2-amino-5-fluorophenol as an orange solid.

62(B) 2-(But-3-ynyl)-6-fluorobenzo[d]oxazole

The title compound was prepared in accordance with the general method of Example 8(A), from 2-amino-5-fluorophenol (177 mg, 1.39 mmol). Reaction time: 3 days. The crude residue was purified by flash chromatography (cyclohexane/AcOEt 4:1) to yield 47 mg (0.25 mmol, 18%) of 2-(but-3-ynyl)-6-fluorobenzo[d]oxazole.

62(C) 6-Fluoro-(2-(4-pyridin-2-yl)but-3-ynyl)benzo[d]oxazole

The title compound was prepared in accordance with the general method of Example 1, from 2-bromopyridine (39 mg, 0.25 mmol) and 2-(but-3-ynyl)-6-fluorobenzo[d]oxazole (47 mg, 0.25 mmol). The crude residue was purified by flash chromatography (DCM/MeOH 99:1) to yield 21 mg (78 mmol, 31%) of 6-fluoro-(2-(4-pyridin-2-yl)but-3-ynyl)benzo[d]oxazole as a brown solid.
LCMS (RT): 3.04 min; MS (ES+) gave m/z: 267.0.
$^1$H-NMR (CDCl$_3$), δ (ppm): 3.05 (t, J=7.5, 2H), 3.28 (t, J=7.5, 2H), 7.04-7.09 (m, 1H), 7.18-7.22 (m, 1H), 7.23 (dd, J=2.5 and 8.0, 1H), 7.35 (d, J=2.5, 1H), 7.59-7.63 (2H), 8.53-8.56 (m, 1H).

Example 63

7-Chloro-2-(4-(pyridin-2-yl)but-3-ynyl)benzo[d]oxazole

63(A) 2-Amino-6-chlorophenol

The title compound was prepared in accordance with the general method of Example 62(A), from 6-chloro-2-nitrophenol (500 mg, 2.88 mmol). The crude residue was purified by flash chromatography (DCM/MeOH 99.5:0.5) to yield 73 mg (0.51 mmol, 18%) of 2-amino-6-chlorophenol.

63(B) 2-(But-3-ynyl)-7-chlorobenzo[d]oxazole

The title compound was prepared in accordance with the general method of Example 8(A), from 2-amino-6-chlorophenol (73 mg, 0.51 mmol). The crude residue was purified by flash chromatography (cyclohexane/AcOEt 9:1) to yield 42 mg (0.20 mmol, 40%) of 2-(but-3-ynyl)-7-chlorobenzo[d]oxazole.

63(C) 7-Chloro-2-(4-(pyridin-2-yl)but-3-ynyl)benzo[d]oxazole

The title compound was prepared in accordance with the general method of Example 1, from 2-bromopyridine (32 mg, 0.20 mmol) and 2-(but-3-ynyl)-7-chlorobenzo[d]oxazole (42 mg, 0.20 mmol). The crude residue was purified by flash chromatography (DCM/MeOH 99:1) to yield 25 mg (90 mmol, 44%) of 7-chloro-2-(4-(pyridin-2-yl)but-3-ynyl)benzo[d]oxazole as a brown oil.
LCMS (RT): 3.44 min; MS (ES+) gave m/z: 283.0, 285.0.

$^1$H-NMR (CDCl$_3$), δ (ppm): 3.08 (t, J=8.0, 2H), 3.33 (t, J=8.0, 2H), 7.18-7.21 (m, 1H), 7.24-7.28 (m, 1H), 7.32 (dd, J=1.0 and 8.0, 1H), 7.36-7.39 (m, 1H), 7.57-7.63 (2H), 8.53-8.55 (m, 1H).

Example 64

7-Fluoro-2-(4-(pyridin-2-yl)but-3-ynyl)benzo[d]oxazole

64(A) 2-Amino-6-fluorophenol

The title compound was prepared in accordance with the general method of Example 62(A), from 6-fluoro-2-nitrophenol (500 mg, 3.18 mmol). The crude residue was purified by flash chromatography (AcOEt/cyclohexane 7:3) to yield 213 mg (1.68 mmol, 54%) of 2-amino-6-fluorophenol as a brown solid.

64(B) 2-(But-3-ynyl)-7-fluorobenzo[d]oxazole

The title compound was prepared in accordance with the general method of Example 8(A), from 2-amino-6-fluorophenol (213 mg, 1.68 mmol). The crude residue was purified by flash chromatography (cyclohexane/AcOEt 9:1) to yield 128 mg (0.68 mmol, 40%) of 2-(but-3-ynyl)-7-fluorobenzo[d]oxazole.

64(C) 7-Fluoro-2-(4-(pyridin-2-yl)but-3-ynyl)benzo[d]oxazole

The title compound was prepared in accordance with the general method of Example 1, from 2-bromopyridine (107 mg, 0.68 mol) and 2-(but-3-ynyl)-7-fluorobenzo[d]oxazole (128 mg, 0.68 mmol). The crude residue was purified by flash chromatography (DCM/MeOH 99:1) to yield 94 mg (0.35 mmol, 52%) of 7-fluoro-2-(4-(pyridin-2-yl)but-3-ynyl)benzo[d]oxazole as a brown oil.
LCMS (RT): 3.13 min; MS (ES+) gave m/z: 267.1.
$^1$H-NMR (CDCl$_3$), δ (ppm): 3.08 (t, J=7.0, 2H), 3.32 (t, J=7.0, 2H), 7.05-7.10 (m, 1H), 7.18-7.21 (m, 1H), 7.23-7.28 (m, 1H), 7.36-7.38 (m, 1H), 7.48 (dd, J=1.0 and 8.0, 1H), 7.59-7.63 (m, 1H), 8.53-8.55 (m, 1H).

Example 65

2-(4-(5-Phenyloxazol-2-yl)but-1-ynyl)pyridine

65(A) N-(2-Hydroxy-2-phenylethyl)pent-4-ynamide

To a solution of pent-4-ynoic acid (1.00 g, 10.2 mmol) in dry DCM (10 mL) was added at room temperature oxalyl chloride (1.75 mL, 20.0 mmol) and some drops of DMF. The reaction mixture was stirred for 2 hours and was concentrated to dryness to yield pent-4-ynoyl chloride which was used without further purification. A solution of 390 mg (3.35 mmol) of pent-4-ynoyl chloride in dry DCM (5 mL) was added slowly to a solution of 2-amino-1-phenylethanol (480 mg, 3.30 mmol) and triethylamine (0.93 mL, 6.69 mmol) in dry DCM (10 mL). The reaction mixture was stirred for 20 min. at room temperature. After evaporation of the solvent, the crude product was dissolved in DCM. The organic phase was washed with a saturated solution of NaHCO$_3$, brine, dried over MgSO$_4$, filtered and concentrated to lead in a quantitative yield to 727 mg (3.35 mmol) of N-(2-hydroxy-2-phenylethyl)pent-4-ynamide.

65(B) Pent-4-ynoic Acid (2-oxo-2-phenyl-ethyl)-amide 169 mg (0.78 mmol) of N-(2-hydroxy-2-phenylethyl)pent-4-ynamide in DCM (1 mL) were added to a solution of PCC (326 mg, 1.48 mmol) in DCM (4 mL). The reaction mixture was stirred for 4 hours at room temperature, dissolved in DCM and then quenched with NaOH 1N. The organic phase was washed with brine, dried over MgSO$_4$, filtered and concentrated to yield 160 mg (0.74 mmol, 95%) of pent-4-ynoic acid (2-oxo-2-phenyl-ethyl)-amide as a yellow solid.

65(C) 2-(But-3-ynyl)-5-phenyloxazole 907 mg (6.39 mmol) of P$_2$O$_5$ were added to a solution of pent-4-ynoic acid (2-oxo-2-phenyl-ethyl)-amide (160 mg, 0.74 mmol) in POCl$_3$ (10.4 mL). The reaction mixture was stirred for 2 hours at 105° C. and then poured carefully onto ice. The solution was basified with NaOH 1N followed by NaOH pellets till pH=8. The aqueous phase was extracted thrice with DCM. The organic phase was washed with brine, dried over MgSO$_4$, filtered and evaporated. The crude residue was purified by flash chromatography (DCM/MeOH 99:1) to yield 31 mg (0.16 mmol, 21%) of 2-(but-3-ynyl)-5-phenyloxazole as an orange oil.

65(D) 2-(4-(5-Phenyloxazol-2-yl)but-1-ynyl)pyridine

The title compound was prepared in accordance with the general method of Example 1, from 2-bromopyridine (25 mg, 0.16 mmol) and 2-(but-3-ynyl)-5-phenyloxazole (31 mg, 0.16 mmol). The crude residue was purified by flash chromatography (DCM/MeOH 99:1) and SCX column (DCM/MeOH 95:5, DCM/MeOH/NH$_4$OH 90:5:0.1 to 90:9:1) to yield 4.0 mg (15 μmol, 9%) of 2-(4-(5-phenyloxazol-2-yl)but-1-ynyl)pyridine as a yellow oil.
LCMS (RT): 3.33 min; MS (ES+) gave m/z: 275.1.

Example 66

2-(4-(3-(3-Chloro-2-methylphenyl)-1,2,4-oxadiazol-5-yl)but-1-ynyl)pyridine

66(A) 3-Chloro-N'-hydroxy-2-methylbenzamidine

According to the general protocol for amidoxime synthesis described in Example 15(A), the conversion of 3-chloro-2-methylbenzonitrile (1.06 g, 7 mmol) afforded 1.28 g of 3-chloro-N'-hydroxy-2-methylbenzamidine (Yield: 99%) as beige powder (M.P.=119-121° C.).

66(B) 5-(But-3-ynyl)-3-(3-chloro-2-methylphenyl)-1,2,4-oxadiazole

According to the general protocol for oxadiazole synthesis described in Example 40(B), the conversion of 3-chloro-N'-hydroxy-2-methylbenzamidine (628 mg, 3.4 mmol) afforded 387 mg of 5-(but-3-ynyl)-3-(3-chloro-2-methylphenyl)-1,2,4-oxadiazole (Yield: 46%) as yellow oil.
LCMS (RT): 4.26 min; MS (ES+) gave m/z: 247.1

66(C) 2-(4-(3-(3-Chloro-2-methylphenyl)-1,2,4-oxadiazol-5-yl)but-1-ynyl)pyridine According to the general protocol for Sonogashira coupling described in Example 40(C), the conversion of 5-(but- 3-ynyl)-3-(3-chloro-2-methylphenyl)-1,2,4-oxadiazole (628 mg, 3.4 mmol) afforded 387 mg of 2-(4-(3-(3-chloro-2-methylphenyl)-1,2,4-oxadiazol-5-yl)but-1-ynyl)pyridine (Yield 46%) as brown oil.

LCMS (RT): 4.08 min; MS (ES+) gave m/z: 324.1

$^1$NMR (CDCl$_3$), δ (ppm): 8.64 (s, H), 7.79 (d, H), 7.64 (t, H), 7.52 (d, H), 7.38 (d, H), 7.28-7.20 (m, 2H), 3.34 (t, 2H), 3.07 (t, 2H), 2.64 (s, 3H).

Example 67

8-Methyl-2-(4-(pyridin-2-yl)but-3-ynyl)-imidazo[1,2-a]pyridine

67(A) Ethyl 8-methyl-imidazo[1,2-a]pyridine-2-carboxylate

According to the general protocol as described in Example 33(A), the conversion of 3-methylpyridin-2-amine (2.3 g, 21 mmol) afforded 2.97 g of ethyl 8-methyl-imidazo[1,2-a]pyridine-2-carboxylate (Yield: 69%) as a red solid. Purification over silicagel chromatography (DCM/MeOH from 100/0 to 97/3 as eluent).

LCMS (RT): 0.72-1.77 min; MS (ES+) gave m/z: 205.1
Rf (DCM/MeOH: 98/2): 0.22
djg15@cam.ac.uk 67(B) (8-Methyl-imidazo[1,2-a]pyridin-2-yl)methanol According to the general protocol as described in Example 33(B), the conversion of ethyl 8-methyl-imidazo[1,2-a]pyridine-2-carboxylate (2.97 g, 14.5 mmol) afforded 1.17 g of (8-methyl-imidazo[1,2-a]pyridin-2-yl)methanol (Yield: 50%) as a orange oil. Purification over silicagel chromatography (prepacked 70 g silicagel column, DCM/MeOH from 100/0 to 95/5 as eluent).

LCMS (RT): 0.67 min; MS (ES+) gave m/z: 163.1
Rf (DCM/MeOH: 95/5): 0.10

67(C) 2-(Chloromethyl)-8-methyl-imidazo[1,2-a]pyridine

According to the general protocol as described in Example 33(C), the conversion of (8-methyl-imidazo[1,2-a]pyridin-2-yl)methanol (1.17 g, 7.21 mmol) afforded 1.23 g of 2-(chloromethyl)-8-methyl-imidazo[1,2-a]pyridine (Yield: 94%) as a brownish solid (M.P.: 115.4-116.8° C.).

LCMS (RT): 0.64-1.05 min; MS (ES+) gave m/z: 181.1
Rf (DCM/MeOH: 95/5): 0.27

67(D) 8-Methyl-2-(4-(trimethylsilyl)but-3-ynyl)-imidazo[1,2-a]pyridine

To a solution of trimethyl(prop-1-ynyl)silane (259 mg, 2.31 mmol) in THF (7.5 mL) at −78° C. was added n-BuLi 2.5M in hexane (1.1 mL, 2.8 mmol). After 90 min at −78° C. 2-(chloromethyl)-8-methyl-imidazo[1,2-a]pyridine (500 mg, 2.8 mmol) in THF (5 mL) was added dropwise. The solution became blue-green at −78° C. The solution was stirred at −78° C. for an additional 1 h. The reaction was quenched with water and the solvent was removed under reduced pressure. The crude product was purified over silicagel chromatography (prepacked 25 g silicagel column, DCM/MeOH from 100/0 to 99/1 as eluent) to afford 590 mg of 8-methyl-2-(4-(trimethylsilyl)but-3-ynyl)-imidazo[1,2-a]pyridine (Yield: 100%) as an yellow oil.

LCMS (RT): 0.59-2.61 min; MS (ES+) gave m/z: 257.1
Rf (DCM/MeOH: 95/5): 0.22

67(E) 2-(But-3-ynyl)-8-methyl-imidazo[1,2-a]pyridine

According to the protocol described in Example 38(D), the conversion of 8-methyl-2-(4-(trimethylsilyl)but-3-ynyl)-imidazo[1,2-a]pyridine (590 mg, 2.30 mmol) afforded 424 mg of 2-(but-3-ynyl)-8-methyl-imidazo[1,2-a]pyridine (Yield: 100%) as yellow oil. Purification over silicagel chromatography (prepacked 25 g silicagel column, DCM/MeOH: 95/5 as eluent).

LCMS (RT): 2.89 min; MS (ES+) gave m/z: 265.1

67(F) 8-Methyl-2-(4-(pyridin-2-yl)but-3-ynyl)-imidazo[1,2-a]pyridine

According to the general protocol for Sonogashira coupling described in Example 15(C), the conversion of 2-(but-3-ynyl)-8-methyl-imidazo[1,2-a]pyridine (100 mg, 0.54 mmol) afforded 114 mg of 8-methyl-2-(4-(pyridin-2-yl)but-3-ynyl)-imidazo[1,2-a]pyridine (Yield: 80%) as yellow oil. Purification over silicagel chromatography (prepacked 10 g silicagel column, DCM/MeOH: 97/3 as eluent).

LCMS (RT): 2.16 min; MS (ES+) gave m/z: 262.1
Rf (DCM/MeOH: 95/5): 0.33

$^1$H-NMR (CDCl$_3$), δ (ppm): 8.54 (d, H), 7.98 (d, H), 7.62 (t, H), 7.55 (s, H), 7.36 (d, H), 7.18 (m, H), 7.00 (d, H), 6.72 (t, H), 3.20 (t, 2H), 2.94 (t, 2H), 2.64 (s, 3H).

Example 68

5-Methyl-2-(4-(pyridin-2-yl)but-3-ynyl)-imidazo[1,2-a]pyridine

68(A) Ethyl 5-methyl-imidazo[1,2-a]pyridine-2-carboxylate

According to the general protocol as described in Example 33(A), the conversion of 6-methylpyridin-2-amine (2.3 g, 21 mmol) afforded 2.59 g of ethyl 5-methyl-imidazo[1,2-a]pyridine-2-carboxylate (Yield: 60%) as a brownish solid. Purification over silicagel chromatography (DCM/MeOH from 100/0 to 97/3 as eluent).

LCMS (RT): 0.72-1.49 min; MS (ES+) gave m/z: 205.1
Rf (DCM/MeOH: 98/2): 0.22

68(B) (5-Methyl-imidazo[1,2-a]pyridin-2-yl)methanol

According to the general protocol as described in Example 33(B), the conversion of ethyl 5-methyl-imidazo[1,2-a]pyridine-2-carboxylate (2.59 g, 12.7 mmol) afforded 1.58 g of (5-methyl-imidazo[1,2-a]pyridin-2-yl)methanol (Yield: 77%) as a yellowish solid. Purification over silicagel chromatography (prepacked 70 g silicagel column, DCM/MeOH from 100/0 to 95/5 as eluent).

LCMS (RT): 0.67 min; MS (ES+) gave m/z: 163.1
Rf (DCM/MeOH: 95/5): 0.32

68(C) 2-(Chloromethyl)-5-methyl-imidazo[1,2-a]pyridine

According to the general protocol as described in Example 33(C), the conversion of (5-methyl-imidazo[1,2-a]pyridin-2-yl)methanol (1.58 g, 9.74 mmol) afforded 1.67 g of 2-(chloromethyl)-5-methyl-imidazo[1,2-a]pyridine (Yield: 95%) as a beige solid (M.P.: 120-120.6° C.).
LCMS (RT): 0.64-1.05 min; MS (ES+) gave m/z: 181.1
Rf (DCM/MeOH: 95/5): 0.27

68(D) 5-Methyl-2-(4-(trimethylsilyl)but-3-ynyl)-imidazo[1,2-a]pyridine

According to the general protocol as described in Example 67(D), the conversion of 2-(chloromethyl)-5-methyl-imidazo[1,2-a]pyridine (500 mg, 2.80 mmol) afforded 525 mg of 5-methyl-2-(4-(trimethylsilyl)but-3-ynyl)-imidazo[1,2-a]pyridine (Yield: 89%) as an yellow oil. Purification over silicagel chromatography (prepacked 25 g silicagel column, DCM/MeOH from 100/0 to 99/1 as eluent).
LCMS (RT): 0.59-2.59 min; MS (ES+) gave m/z: 257.1
Rf (DCM/MeOH: 95/5): 0.19

68(E) 2-(But-3-ynyl)-5-methyl-imidazo[1,2-a]pyridine

According to the protocol described in Example 38(D), the conversion of 5-methyl-2-(4-(trimethylsilyl)but-3-ynyl)-imidazo[1,2-a]pyridine (525 mg, 2.04 mmol) afforded 352 mg of 2-(but-3-ynyl)-5-methyl-imidazo[1,2-a]pyridine (Yield: 93%) as yellow oil. Purification over silicagel chromatography (prepacked 25 g silicagel column, DCM/MeOH: 95/5 as eluent).
LCMS (RT): 2.89 min; MS (ES+) gave m/z: 265.1

68(F) 5-Methyl-2-(4-(pyridin-2-yl)but-3-ynyl)-imidazo[1,2-a]pyridine

According to the general protocol for Sonogashira coupling described in Example 15(C), the conversion of 2-(but-3-ynyl)-5-methyl-imidazo[1,2-a]pyridine (100 mg, 0.54 mmol) afforded 78 mg of 5-methyl-2-(4-(pyridin-2-yl)but-3-ynyl)-imidazo[1,2-a]pyridine (Yield: 55%) as yellow oil. Purification over silicagel chromatography (prepacked 10 g silicagel column, DCM/MeOH: 97/3 as eluent).
LCMS (RT): 2.19 min; MS (ES+) gave m/z: 262.1
Rf (DCM/MeOH: 95/5): 0.30
$^1$H-NMR (CDCl$_3$), δ (ppm): 8.54 (d, H), 7.61 (t, H), 7.53 (d, H), 7.44 (s, H), 7.37 (d, H), 7.22-7.15 (m, 2H), 6.65 (d, H), 3.20 (t, 2H), 2.95 (t, 2H), 2.59 (s, 3H).

Example 69

5-Phenyl-2-(4-(pyridin-2-yl)but-3-ynyl)-imidazo[1,2-a]pyridine

69(A) Ethyl 5-bromo-imidazo[1,2-a]pyridine-2-carboxylate

According to the general protocol as described in Example 33(A), the conversion of 6-bromopyridin-2-amine (3.6 g, 21 mmol) afforded 4.70 g of ethyl 5-bromo-imidazo[1,2-a]pyridine-2-carboxylate (Yield: 83%) as a yellow solid. Purification over silicagel chromatography (DCM/MeOH from 100/0 to 97/3 as eluent).
LCMS (RT): 2.87 min; MS (ES+) gave m/z: 270.1
Rf (DCM/MeOH: 98/2): 0.22

69(B) Ethyl 5-phenyl-imidazo[1,2-a]pyridine-2-carboxylate

To a suspension of ethyl 5-bromo-imidazo[1,2-a]pyridine-2-carboxylate (1.50 g, 5.6 mmol), Pd(PPh$_3$)$_4$ (322 mg, 0.279 mmol) in a mixture of toluene (17 mL), NaHCO$_3$ 1M (6 mL) and MeOH (4 mL) was added phenylboronic acid at room temperature. The resulting reaction mixture was heated at 80° C. for 12 h, cooled, and diluted with water (50 mL). The insoluble matter was filtered off, and the phases were separated. The aqueous phase was extracted with ethyl acetate, the combined organic layers were washed with water and the solvent was removed under reduced pressure. The crude product was purified by chromatography (prepacked 25 g silicagel column, DCM/MeOH from 100/0 to 99/1 as eluent) to afford 1.41 g of ethyl 5-phenyl-imidazo[1,2-a]pyridine-2-carboxylate (Yield: 95%) as a yellowish solid (M.P.: 123-123.8° C.)
LCMS (RT): 3.06 min; MS (ES+) gave m/z: 266.1
Rf (DCM/MeOH: 98/2): 0.18

69(C) (5-Phenyl-imidazo[1,2-a]pyridin-2-yl)methanol

According to the general protocol as described in Example 33(B), the conversion of ethyl 5-phenyl-imidazo[1,2-a]pyridine-2-carboxylate (1.40 g, 5.26 mmol) afforded 538 mg of (5-phenyl-imidazo[1,2-a]pyridin-2-yl)methanol (Yield: 45%) as an orange oil. Purification over silicagel chromatography (prepacked 25 g silicagel column, DCM/MeOH from 100/0 to 98/2 as eluent).
LCMS (RT): 0.65-1.77 min; MS (ES+) gave m/z: 225.1
Rf (DCM/MeOH: 90/10): 0.28

69(D) 2-(Chloromethyl)-5-phenyl-imidazo[1,2-a]pyridine

According to the general protocol as described in Example 33(C), the conversion of (5-phenyl-imidazo[1,2-a]pyridin-2-yl)methanol (538 mg, 2.40 mmol) afforded 555 mg of 2-(chloromethyl)-5-phenyl-imidazo[1,2-a]pyridine (Yield: 95%) as a beige solid (M.P.: 125.8-126.6° C.).
LCMS (RT): 0.65-2.31 min; MS (ES+) gave m/z: 243.1
Rf (DCM/MeOH: 90/10): 0.31

69(E) 2-(4-(Trimethylsilyl)but-3-ynyl)-5-phenyl-imidazo[1,2-a]pyridine

According to the general protocol as described in Example 67(D), the conversion of 2-(chloromethyl)-5-phenyl-imidazo[1,2-a]pyridine (500 mg, 2.10 mmol) afforded 543 mg of 2-(4-(trimethylsilyl)but-3-ynyl)-5-phenyl-imidazo[1,2-a]pyridine (Yield: 99%) as an yellow oil Purification over silicagel chromatography (prepacked 25 g silicagel column, DCM/MeOH from 100/0 to 99/1 as eluent).
LCMS (RT): 3.08 min; MS (ES+) gave m/z: 319.1
Rf (DCM/MeOH: 95/5): 0.31

69(F) 2-(But-3-ynyl)-5-phenyl-imidazo[1,2-a]pyridine

According to the protocol described in Example 38(D), the conversion of 2-(4-(trimethylsilyl)but-3-ynyl)-5-phenyl-imidazo[1,2-a]pyridine (500 mg, 1.90 mmol) afforded 350 mg of 2-(but-3-ynyl)-5-phenyl-imidazo[1,2-a]pyridine (Yield: 97%) as yellow oil. Purification over silicagel chromatography (prepacked 25 g silicagel column, DCM/MeOH: 95/5 as eluent).
LCMS (RT): 2.89 min; MS (ES+) gave m/z: 265.1

69(G) 5-Phenyl-2-(4-(pyridin-2-yl)but-3-ynyl)-imidazo[1,2-a]pyridine

According to the general protocol for Sonogashira coupling described in Example 15(C), the conversion of 2-(but- 3-ynyl)-5-phenyl-imidazo[1,2-a]pyridine (100 mg, 0.40 mmol) afforded 100 mg of 5-phenyl-2-(4-(pyridin-2-yl)but-3-ynyl)-imidazo[1,2-a]pyridine (Yield: 76%) as yellow oil. Purification over silicagel chromatography (prepacked 10 g silicagel column, DCM/MeOH: 97/3 as eluent).

LCMS (RT): 2.84 min; MS (ES+) gave m/z: 324.1
Rf (DCM/MeOH: 95/5): 0.30
$^1$H-NMR (CDCl$_3$), δ (ppm): 8.54 (d, H), 7.61-7.65 (m, 2H), 7.61-7.57 (m, 3H), 7.52-7.48 (m, 3H), 7.32-7.24 (m, 2H), 7.18 (m, H), 6.74 (d, H), 3.12 (t, 2H), 2.90 (t, 2H).

Example 70

2-(4-(Pyridin-2-yl)but-3-ynyl)benzo[d]oxazol-4-ol

70(A) 2-Aminobenzene-1,3-diol

The title compound was prepared in accordance with the general method of Example 62(A), from 2-nitrobenzene-1,3-diol (1.37 g, 8.81 mmol). 1.10 g (8.81 mmol, 100%) of 2-aminobenzene-1,3-diol were obtained as an orange solid and used without purification.

70(B) 2-(But-3-ynyl)benzo[d]oxazol-4-ol

The title compound was prepared in accordance with the general method of Example 8(A), from 2-aminobenzene-1,3-diol (272 mg, 2.17 mmol). The crude residue was purified by flash chromatography (cyclohexane/AcOEt 9:1) to yield 241 mg (1.29 mmol, 60%) of 2-(but-3-ynyl)benzo[d]oxazol-4-ol as an orange solid.

70(C) 2-(4-(Pyridin-2-yl)but-3-ynyl)benzo[d]oxazol-4-ol

The title compound was prepared in accordance with the general method of Example 1, from 2-bromopyridine (203 mg, 1.29 mol) and 2-(but-3-ynyl)benzo[d]oxazol-4-ol (241 mg, 1.29 mmol). The crude residue was purified by flash chromatography (DCM/MeOH 99:1 to 98:2) and SCX column (DCM/MeOH 100:0 to 94:6, DCM/MeOH/NH$_4$OH 94:5:1 to 90:8:2) to yield 25 mg (95 mmol, 7%) of 2-(4-(pyridin-2-yl)but-3-ynyl)benzo[d]oxazol-4-ol as an orange solid.

LCMS (RT): 3.26 min; MS (ES+) gave m/z: 265.0.
Rf (DCM/MeOH 98:2)=0.04.

Example 71

2-(4-(5-Fluoropyridin-2-yl)but-3-ynyl)benzo[d]oxazole

The title compound was prepared in accordance with the general method of Example 1, from 2-bromo-5-fluoropyridine (200 mg, 1.14 mol) and 2-(but-3-ynyl)benzo[d]oxazole (195 mg, 1.14 mmol, Example 8(A)). The crude residue was purified by flash chromatography (DCM/MeOH 99:1) and SCX column (DCM/MeOH 100:0 to 94:6, DCM/MeOH/NH$_4$OH 94:5:1 to 90:8:2) to yield 15 mg (56 μmol, 5%) of 2-(4-(5-fluoropyridin-2-yl)but-3-ynyl)benzo[d]oxazole as a white solid.

LCMS (RT): 4.19 min; MS (ES+) gave m/z: 267.0.

Example 72

4-Methoxy-2-(4-(pyridin-2-yl)but-3-ynyl)benzo[d]oxazole

A mixture of 2-(4-(pyridin-2-yl)but-3-ynyl)benzo[d]oxazol-4-ol (20 mg, 76 mmol, Example 70), methyl iodide (57 μL, 114 μmol) and K$_2$CO$_3$ (18 mg, 130 μmol) in DMF (2 mL) was stirred under reflux for 3 h. The reaction mixture was then allowed to cool to room temperature and was dissolved in DCM. The organic phase was washed with water, HCl 1N, saturated solution of NaHCO$_3$, brine, dried over MgSO$_4$, filtered and evaporated. The crude residue was purified by flash chromatography (DCM/MeOH 99:1) to yield 10 mg (36 μmol, 47%) of 4-methoxy-2-(4-(pyridin-2-yl)but-3-ynyl) benzo[d]oxazole as a brown solid.

LCMS (RT): 3.69 min; MS (ES+) gave m/z: 279.1.

Example 73

2-(4-(2-Methylthiazol-4-yl)but-3-ynyl)imidazo[1,2-a]pyridine

73(A) 4-Bromo-2-methylthiazole

To a solution of 2,4-Dibromothiazole (5.00 g, 20.6 mmol) in anhydrous Diethyl ether (70 mL) was added dropwise at −78° C., 11 mL of BuLi 2.5M in hexane. The mixture was stirred for 2 h at −78° C. A solution of methyl trifluoromethanesulfonate (3.38 g, 20.6 mmol) in 10 mL of Diethyl ether was added dropwise at −78° C. to the resulting mixture. After 30 min of stirring at −78° C., the reaction mixture was slowly warmed to room temperature for 2 h. The reaction was cooled with a ice bath at −10° C. and quenched with water. The layers were separated; the aqueous layer was extracted with Diethyl ether. The combined organic layers were dried over Na$_2$SO$_4$, filtered and concentrated under medium pressure 700 mbar, bath 35° C., because the bromothiazole is very volatile. The crude product was purified by flash chromatography (Prepacked 70 g silicagel column with Pentane/Diethyl ether: 95/5 as eluent) to afford 2 g of 4-bromo-2-methylthiazole (Yield: 54%) as a yellow oil.

Rf (Pentane/Diethyl ether 95/5): 0.30
LCMS (RT): 3.33 min; MS (ES+) gave m/z: 179.0

73(B) 4-Iodo-2-methylthiazole

To a solution of 4-bromo-2-methylthiazole (2.0 g, 11 mmol) in anhydrous Diethyl ether (44 mL) was added dropwise at −78° C., 5.30 mL of BuLi 2.5M in hexane. The mixture was stirred for 1 h at −78° C. A solution of diiodoethane (6.20 g, 22 mmol) in 27 mL of Diethyl ether was added dropwise at −78° C. to the reaction mixture. The resulting solution was stirred 30 min at −78° C. and slowly warmed to room temperature over a period of 2 h. The reaction cooled with a ice bath at −10° C. and quenched with water. The two layers were separated; the aqueous layer was extracted with Diethyl ether. The combined organic layers were dried over Na$_2$SO$_4$, filtered and concentrated under medium pressure. The crude product was purified by flash chromatography (Prepacked 10 g silicagel column with Pentane/Diethyl ether: 95/5 as eluent) to afford 1.17 g of 4-iodo-2-methylthiazole (Yield: 47%) as a colorless oil.

LCMS (RT): 3.49 min; MS (ES+) gave m/z: 225.0

73(C) 2-(4-(2-Methylthiazol-4-yl)but-3-ynyl)-imidazo[1,2-a]pyridine

In a dry reaction tube containing in suspension copper iodide (6.5 mg, 0.03 mmol) and triethylamine (2.33 mL, 13.60 mmol), were added 4-iodo-2-methylthiazole (150 mg, 0.68 mmol) and Pd(PPh$_3$)$_2$Cl$_2$ (39 mg, 0.03 mmol) under N$_2$. A yellow suspension is obtained and after a few minutes of stirring at room temperature, was added a solution 2-(but-3- ynyl)-imidazo[1,2-a]pyridine (115 mg, 0.68 mmol) in triethylamine (0.5 mL) under N$_2$. Immediately the color of the reaction turns to black. The mixture was stirred at room temperature for 4 h and 50° C. overnight under N$_2$. Triethylamine was removed under reduce pressure. The crude product was purified by flash chromatography (Prepacked 25 g silicagel column from DCM/MeOH: 100/0 to 97/3 as eluent) to afford 25 mg of 2-(4-(2-methylthiazol-4-yl)but-3-ynyl)-imidazo[1,2-a]pyridine (Yield: 14%) as a yellow oil.

Rf (DCM/MeOH: 95/5): 0.50

LCMS (RT): 0.79-2.38 min; MS (ES+) gave m/z: 268.0

$^1$H-NMR (CDCl$_3$), δ (ppm): 8.09 (d, H), 7.66 (d, H), 7.52 (s, H), 7.23-7.18 (m, 2H), 6.81 (t, H), 3.14 (t, 2H), 2.92 (t, 2H), 2.70 (s, 3H).

Example 74

6-Fluoro-2-(4-(pyridin-2-yl)but-3-ynyl)-imidazo[1,2-a]pyridine

74(A)
2-(Chloromethyl)-6-fluoro-imidazo[1,2-a]pyridine

According to the general protocol described in J. Heterocyclic. Chem., 1988, 25, 129-137, to solution of 5-fluoropyridin-2-amine (1.80 g, 16 mmol) in EtOH (24 mL) was added 1,3-dichloropropan-2-one (2.03 g, 16 mmol) and the resulting mixture was stirred overnight at 80° C. The solvent was evaporated, and the residue was dissolved in a minimum volume of water. The solution was neutralized (pH=8) with saturated NaHCO$_3$. The aqueous layer was extracted with AcOEt and the organic layer was washed with saturated NaCl. The solvent was evaporated and the crude product was purified by chromatography (prepacked 25 g silicagel column, DCM as eluent) to afford 1.7 g of 2-(chloromethyl)-6-fluoro-imidazo[1,2-a]pyridine (Yield: 57%) as a beige solid.

LCMS (RT): 0.88-1.68 min; MS (ES+) gave m/z: 185.0

Rf (DCM/MeOH: 98/2): 0.50

74(B) 6-Fluoro-2-(4-(trimethylsilyl)but-3-ynyl)-imidazo[1,2-a]pyridine

According to the general protocol as described in Example 38(C), the conversion of 2-(chloromethyl)-6-fluoro-imidazo[1,2-a]pyridine (1.70 g, 9.1 mmol) afforded 496 mg of 6-fluoro-2-(4-(trimethylsilyl)but-3-ynyl)-imidazo[1,2-a]pyridine (Yield: 25%) as white powder. Purification over silicagel chromatography (prepacked 25 g silicagel column, Cyclohexane/AcOEt from 70/30 to 60/40 as eluent).

LCMS (RT): 3.01 min; MS (ES+) gave m/z: 261.0

Rf (Cyclohexane/AcOEt: 50/50): 0.50

74(C) 2-(But-3-ynyl)-6-fluoro-imidazo[1,2-a]pyridine

According to the protocol described in Example 38(D), the conversion of 6-fluoro-2-(4-(trimethylsilyl)but-3-ynyl)-imidazo[1,2-a]pyridine (490 mg, 1.90 mmol) afforded 333 mg of 2-(but-3-ynyl)-6-fluoro-imidazo[1,2-a]pyridine (Yield: 93%) as yellow oil.

Purification over silicagel chromatography (prepacked 25 g silicagel column, DCM/MeOH: 98/2 as eluent).

LCMS (RT): 0.79 min; MS (ES+) gave m/z: 189.0

Rf (DCM/MeOH: 98/2): 0.30

74(D) 6-Fluoro-2-(4-(pyridin-2-yl)but-3-ynyl)-imidazo[1,2-a]pyridine

According to the general protocol for Sonogashira coupling described in Example 40(C), the conversion of 2-(but-3-ynyl)-6-fluoro-imidazo[1,2-a]pyridine (331 mg, 1.76 mmol) afforded 230 mg of 6-fluoro-2-(4-(pyridin-2-yl)but-3-ynyl)-imidazo[1,2-a]pyridine (Yield 49%) as yellow oil. Purification over silicagel chromatography (prepacked 25 g silicagel column, DCM/MeOH: from 100/0 to 97/3 as eluent).

LCMS (RT): 0.79-2.06 min; MS (ES+) gave m/z: 266.0

Rf (DCM/MeOH: 95/5): 0.50

$^1$H-NMR (CDCl$_3$), δ (ppm): 8.54 (d, H), 8.01 (m, H), 7.62 (m, H), 7.56-7.51 (m, 2H), 7.37 (d, H), 7.22-7.18 (m, H), 7.07 (m, H), 3.14 (t, 2H), 2.92 (t, 2H).

Example 75

2-(4-(5-Fluoropyridin-2-yl)but-3-ynyl)-imidazo[1,2-a]pyridine

75(A) 2-(Chloromethyl)-imidazo[1,2-a]pyridine

According to the general described in Example 74(A), the conversion of 2-aminopyridine (4.90 g, 52 mmol) afforded 2.66 g of 2-(chloromethyl)-imidazo[1,2-a]pyridine (Yield 40%) as yellow semi-solid. Purification over silicagel chromatography (prepacked 70 g silicagel column, DCM as eluent).

LCMS (RT): 0.81 min; MS (ES+) gave m/z: 167.0

Rf (DCM/MeOH: 98/2): 0.50

75(B) 2-(4-(Trimethylsilyl)but-3-ynyl)-imidazo[1,2-a]pyridine

According to the protocol described in Example 38(C), the conversion of 2-(chloromethyl)-imidazo[1,2-a]pyridine (2.50 g, 15 mmol) afforded 555 mg of 2-(4-(trimethylsilyl)but-3-ynyl)-imidazo[1,2-a]pyridine (Yield: 15%) as yellow oil. Purification over silicagel chromatography (prepacked 70 g silicagel column, Cyclohexane/AcOEt from 60/40 to 50/50 as eluent).

LCMS (RT): 3.00 min; MS (ES+) gave m/z: 243.0

Rf (Cyclohexane/AcOEt: 50/50): 0.30

75(C) 2-(But-3-ynyl)-imidazo[1,2-a]pyridine

According to the protocol described in Example 38(D), the conversion of 2-(4-(trimethylsilyl)but-3-ynyl)-imidazo[1,2-a]pyridine (555 mg, 2.29 mmol) afforded 352 mg of 2-(but-3-ynyl)-imidazo[1,2-a]pyridine (Yield: 90%) as yellow oil. Purification over silicagel chromatography (prepacked 25 g silicagel column, DCM/MeOH from 98/2 as eluent).

LCMS (RT): 2.84 min; MS (ES+) gave m/z: 171.0

Rf (DCM/MeOH: 98/2): 0.30

75(D) 2-(4-(5-Fluoropyridin-2-yl)but-3-ynyl)-imidazo[1,2-a]pyridine

In a dry reaction tube containing in suspension copper iodide (6.5 mg, 0.03 mmol) and triethylamine (2.3 mL), were added 2-bromo-5-fluoropyridine (120 mg, 0.68 mmol) and Pd(PPh$_3$)$_2$Cl$_2$ (39 mg, 0.03 mmol) under N$_2$. A yellow suspension was obtained after 5 min of stirring at room temperature. A solution of 2-(but-3-ynyl)-imidazo[1,2-a]pyridine (120 mg, 0.68 mmol) in triethylamine (0.5 mL) was then added under N$_2$. Immediately the color of the reaction turns to black. The mixture was stirred at room temperature for 30 min and heated at 80° C. overnight. The reaction mixture was concentrated and the crude product was purified by Flash chromatography (prepacked 25 g silicagel column, DCM/

MeOH from 100/0 to 97/3 as eluent) to afford 15 mg of 2-(4-(5-fluoropyridin-2-yl)but-3-ynyl)-imidazo[1,2-a]pyridine (Yield: 8%) as a brown semi-solid.

Rf (DCM/MeOH: 95/5)=0.5.

LCMS (RT): 0.79-2.38 min; MS (ES+) gave m/z: 266.0

$^1$H-NMR (CDCl$_3$), δ (ppm): 8.40 (d, H), 8.08 (d, H), 7.63-7.58 (m, H), 7.42-7.38 (m, 2H), 7.36-7.31 (m, H), 7.17 (t, H), 6.77 (m, H), 3.14 (t, 2H), 2.92 (t, 2H).

Example 76

2-(4-(Pyridin-2-yl)but-3-ynyl)oxazolo[5,4-b]pyridine

76(A) 2-(But-3-ynyl)oxazolo[5,4-b]pyridine

The title compound was prepared in accordance with the general method of Example 8(A), from 3-aminopyridin-2-ol (449 mg, 4.08 mmol). The crude residue was purified by flash chromatography (cyclohexane/AcOEt 7:3) to yield 500 mg (2.90 mmol, 71%) of 2-(but-3-ynyl)oxazolo[5,4-b]pyridine.

LCMS (RT): 3.16 min; MS (ES+) gave m/z: 173.0.

76(B) 2-(4-(Pyridin-2-yl)but-3-ynyl)oxazolo[5,4-b]pyridine

The title compound was prepared in accordance with the general method of Example 1, from 2-bromopyridine (92 mg, 0.58 mmol) and 2-(but-3-ynyl)oxazolo[5,4-b]pyridine (100 mg, 0.58 mmol). The crude residue was purified by flash chromatography (DCM/MeOH 98.5:1.5 to 98:2) to yield 56 mg (0.22 mmol, 39%) of 2-(4-(pyridin-2-yl)but-3-ynyl)oxazolo[5,4-b]pyridine as a colorless oil.

LCMS (RT): 2.91 min; MS (ES+) gave m/z: 250.1.

Rf (DCM/MeOH 98:2)=0.2.

$^1$H-NMR (CDCl$_3$), δ (ppm): 3.08 (t, J=7.5, 2H), 3.33 (t, J=7.5, 2H), 7.17-7.21 (m, 1H), 7.31 (dd, J=5.0 and 8.0, 1H), 7.34-7.38 (m, 1H), 7.58-7.62 (m, 1H), 8.00 (dd, J=1.5 and 8.0, 1H), 8.32 (dd, J=1.5 and 4.5, 1H), 8.53-8.54 (d, J=4.5, 1H).

Example 77

7-Chloro-5-fluoro-2-(4-(pyridin-2-yl)but-3-ynyl)benzo[d]oxazole

77(A) 2-Chloro-4-fluoro-6-nitrophenol

2-Chloro-4-fluorophenol (5.64 g, 38.5 mmol) was added to a solution of acetic acid (16.5 mL), nitric acid (8.66 mL) and water (7.5 mL) at 0° C. The reaction mixture was stirred vigorously for 5 hours at 0° C. The resulting precipitate was filtered, washed with water and dried under vacuum to yield 2-chloro-4-fluoro-6-nitrophenol (6.12 g, 32.0 mmol, 83%) as a yellow powder.

77(B) 2-Amino-6-chloro-4-fluorophenol

The title compound was prepared in accordance with the general method of Example 62(A), from 2-chloro-4-fluoro-6-nitrophenol (6.12 g, 32.0 mmol). The crude residue was purified by flash chromatography (cyclohexane/AcOEt 4:1) to yield 1.66 g (10.3 mmol, 29%) of 2-amino-6-chloro-4-fluorophenol.

77(C) 2-(But-3-ynyl)-7-chloro-5-fluorobenzo[d]oxazole

The title compound was prepared in accordance with the general method of Example 8(A), from 2-amino-6-chloro-4-fluorophenol (1.66 g, 10.3 mmol). The crude residue was purified by flash chromatography (cyclohexane/AcOEt 4:1) to yield 690 mg (3.08 mmol, 30%) of 2-(but-3-ynyl)-7-chloro-5-fluorobenzo[d]oxazole.

77(D) 7-Chloro-5-fluoro-2-(4-(pyridin-2-yl)but-3-ynyl)benzo[d]oxazole

The title compound was prepared in accordance with the general method of Example 1, from 2-bromopyridine (141 mg, 0.89 mmol) and 2-(but-3-ynyl)-7-chloro-5-fluorobenzo[d]oxazole (200 mg, 0.89 mmol). The crude residue was purified by flash chromatography (DCM/MeOH 99:1) to yield 160 mg (0.53 mmol, 59%) of 7-chloro-5-fluoro-2-(4-(pyridin-2-yl)but-3-ynyl)benzo[d]oxazole as an orange solid.

LCMS (RT): 4.38 min; MS (ES+) gave m/z: 301.1, 303.0.

$^1$H-NMR (CDCl$_3$), δ (ppm): 3.07 (t, J=7.5, 2H), 3.32 (t, J=7.5, 2H), 7.11 (dd, J=2.4 and 9.3, 1H), 7.17-7.24 (m, 1H), 7.30 (dd, J=2.4 and 8.1, 1H), 7.37 (d, J=8.1, 1H), 7.58-7.66 (m, 1H), 8.54 (d, J=4.8, 1H).

Example 78

2-(4-(Pyridin-2-yl)but-3-ynyl)oxazolo[4,5-b]pyridine

78(A) 2-(But-3-ynyl)oxazolo[4,5-b]pyridine

The title compound was prepared in accordance with the general method of Example 8(A), from 2-aminopyridin-3-ol (449 mg, 4.08 mmol). The crude residue was purified by flash chromatography (cyclohexane/AcOEt 7:3 to 3:2) to yield 180 mg (1.04 mmol, 26%) of 2-(but-3-ynyl)oxazolo[4,5-b]pyridine as a yellow solid.

LCMS (RT): 3.03 min; MS (ES+) gave m/z: 173.0.

78(B) 2-(4-(Pyridin-2-yl)but-3-ynyl)oxazolo[4,5-b]pyridine

The title compound was prepared in accordance with the general method of Example 1, from 2-iodopyridine (100 mg, 0.49 mmol) and 2-(but-3-ynyl)oxazolo[4,5-b]pyridine (100 mg, 0.58 mmol) at room temperature. The crude residue was purified by flash chromatography (DCM/MeOH 99:1 to 98:2) to yield 35 mg (0.14 mmol, 29%) of 2-(4-(pyridin-2-yl)but-3-ynyl)oxazolo[4,5-b]pyridine as a brown semi-solid with a purity of 86%.

LCMS (RT): 2.78 min; MS (ES+) gave m/z: 250.1.

Rf (DCM/MeOH 98:2)=0.2.

$^1$H-NMR (CDCl$_3$), δ (ppm): 3.10 (t, J=7.5, 2H), 3.35 (t, J=7.5, 2H), 7.18-7.21 (m, 1H), 7.26-7.29 (m, 1H), 7.34-7.38 (m, 1H), 7.58-7.63 (m, 1H), 7.79 (dd, J=1.5 and 8.0, 1H), 8.52-8.56 (m, 1H), 8.54 (dd, J=1.5 and 5.0, 1H).

Example 79

2-(4-(Pyridin-2-yl)but-3-ynyl)benzo[d]oxazole-5-carbonitrile

79(A) 3-Amino-4-hydroxybenzonitrile

The title compound was prepared in accordance with the general method of Example 62(A), from 4-hydroxy-3-nitrobenzonitrile (1.00 g, 6.09 mmol). 817 mg (6.09 mmol, 100%) of 3-amino-4-hydroxybenzonitrile as an orange solid were obtained and used without purification.

79(B) 2-(But-3-ynyl)benzo[d]oxazole-5-carbonitrile

The title compound was prepared in accordance with the general method of Example 8(A), from 3-amino-4-hydroxybenzonitrile (547 mg, 4.08 mmol). The crude residue was purified by flash chromatography (cyclohexane/AcOEt 85:15) to yield 212 mg (1.08 mmol, 26%) of 2-(but-3-ynyl)benzo[d]oxazole-5-carbonitrile.
LCMS (RT): 3.79 min; MS (ES+) gave m/z: 197.0.

79(C) 2-(4-(Pyridin-2-yl)but-3-ynyl)benzo[d]oxazole-5-carbonitrile

The title compound was prepared in accordance with the general method of Example 1, from 2-iodopyridine (89 mg, 0.43 mmol) and 2-(but-3-ynyl)benzo[d]oxazole-5-carbonitrile (100 mg, 0.51 mmol) at room temperature. The crude residue was purified by flash chromatography (DCM/MeOH 99:1) to yield 45 mg (0.16 mmol, 37%) of 2-(4-(pyridin-2-yl)but-3-ynyl)benzo[d]oxazole-5-carbonitrile as a brown solid.
LCMS (RT): 3.53 min; MS (ES+) gave m/z: 274.0.
Rf (DCM/MeOH 98:2)=0.2.
$^1$H-NMR (DMSO[D]$_6$), δ (ppm): 3.05 (t, J=7.5, 2H), 3.34 (t, J=7.5, 2H), 7.30-7.35 (m, 1H), 7.37-7.41 (m, 1H), 7.72-7.77 (m, 1H), 7.86 (dd, J=1.5 and 8.5, 1H), 7.95 (dd, J=0.5 and 8.5, 1H), 8.34 (d, J=1.5, 1H), 8.49 (d, J=4.5, 1H).

Example 80

7-Chloro-5-fluoro-2-(4-(2-methylthiazol-4-yl)but-3-ynyl)benzo[d]oxazole

The title compound was prepared in accordance with the general method of Example 1, from 4-iodo-2-methylthiazole (200 mg, 0.89 mmol) and 2-(but-3-ynyl)-7-chloro-5-fluorobenzo[d]oxazole (199 mg, 0.89 mmol). The crude residue was purified by flash chromatography (cyclohexane/AcOEt 85:15) to yield 157 mg (0.49 mmol, 55%) of 7-chloro-5-fluoro-2-(4-(2-methylthiazol-4-yl)but-3-ynyl)benzo[d]oxazole as a yellow solid.
LCMS (RT): 4.78 min; MS (ES+) gave m/z: 321.0, 323.0.
Rf (cyclohexane/AcOEt 4:1)=0.2.
$^1$H-NMR (DMSO[D]$_6$), δ (ppm): 2.60 (s, 3H), 3.00 (t, J=7.5, 2H), 3.30 (t, J=7.5, 2H), 7.55 (dd, J=2.5 and 8.5, 1H), 7.63 (s, 1H), 7.67 (dd, J=2.5 and 8.5, 1H).

Example 81

7-(Trifluoromethyl)-2-(4-(pyridin-2-yl)but-3-ynyl)benzo[d]oxazole

81(A) 2-Nitro-6-(trifluoromethyl)phenol

The title compound was prepared in accordance with the general method of Example 77(A) from 2-(trifluoromethyl)phenol (1.98 g, 12.2 mmol). Reaction time: 5 hours. The resulting precipitate was filtered, washed with water and dried under vacuum to yield 2-nitro-6-(trifluoromethyl)phenol (1.10 g, 5.31 mmol, 43%) as a yellow powder.

81(B) 2-Amino-6-(trifluoromethyl)phenol

The title compound was prepared in accordance with the general method of Example 62(A), from 2-nitro-6-(trifluoromethyl)phenol (1.10 g, 5.31 mmol). Reaction time: 2 days. The crude residue was purified by flash chromatography (DCM/MeOH 99:1) to yield 510 mg (2.88 mmol, 54%) of 2-amino-6-(trifluoromethyl)phenol.
Rf (DCM/MeOH 99:1)=0.35.

81(C) 2-(But-3-ynyl)-7-(trifluoromethyl)benzo[d]oxazole

The title compound was prepared in accordance with the general method of Example 8(A), from 2-amino-6-(trifluoromethyl)phenol (510 mg, 2.88 mmol). Reaction time: 3 days. The crude residue was purified by flash chromatography (cyclohexane/AcOEt 9:1) to yield 90 mg (0.38 mmol, 13%) of 2-(but-3-ynyl)-7-(trifluoromethyl)benzo[d]oxazole as a red oil.

81(D) 7-(Trifluoromethyl)-2-(4-(pyridin-2-yl)but-3-ynyl)benzo[d]oxazole

The title compound was prepared in accordance with the general method of Example 1, from 2-iodopyridine (77 mg, 0.38 mmol) and 2-(but-3-ynyl)-7-(trifluoromethyl)benzo[d]oxazole (90 mg, 0.38 mmol). The crude residue was purified by flash chromatography (cyclohexane/AcOEt 9:1 to DCM/MeOH 99:1) to yield 63 mg (0.20 mmol, 53%) of 7-(trifluoromethyl)-2-(4-(pyridin-2-yl)but-3-ynyl)benzo[d]oxazole as a brown solid.
LCMS (RT): 4.33 min; MS (ES+) gave m/z: 317.0.
Rf (DCM/MeOH 98:2)=0.2.
$^1$H-NMR (CDCl$_3$), δ (ppm): 3.09 (t, J=8.0, 2H), 3.35 (t, J=8.0, 2H), 7.17-7.22 (m, 1H), 7.37 (d, J=7.5, 1H), 7.39-7.43 (m, 1H), 7.56 (d, J=8.0, 1H), 7.59-7.63 (m, 1H), 7.88 (d, J=8.0, 1H), 8.50-8.60 (m, 1H).

Example 82

7-Bromo-5-fluoro-2-(4-(pyridin-2-yl)but-3-ynyl)benzo[d]oxazole

82(A) 2-Bromo-4-fluoro-6-nitrophenol

The title compound was prepared in accordance with the general method of Example 77(A) from 2-bromo-4-fluorophenol (1.00 g, 5.24 mmol). Reaction time: 2 hours. The resulting precipitate was filtered, washed with water and dried under vacuum to yield 2-bromo-4-fluoro-6-nitrophenol (1.20 g, 5.08 mmol, 97%) as a yellow powder.

82(B) 2-Amino-6-bromo-4-fluorophenol

The title compound was prepared in accordance with the general method of Example 62(A), from 2-bromo-4-fluoro-6-nitrophenol (1.20 g, 5.08 mmol). Reaction time: 2 days. The crude residue was purified by flash chromatography (DCM/MeOH 99.5:0.5 to 98:2) to yield 510 mg (2.48 mmol, 49%) of 2-amino-6-bromo-4-fluorophenol.

82(C) 7-Bromo-2-(but-3-ynyl)-5-fluorobenzo[d]oxazole

The title compound was prepared in accordance with the general method of Example 8(A), from 2-amino-6-bromo-4-fluorophenol (510 mg, 2.48 mmol). Reaction time: 5 days. The crude residue was purified by flash chromatography (cyclohexane/AcOEt 9:1) to yield 223 mg (0.83 mmol, 67%) of 7-bromo-2-(but-3-ynyl)-5-fluorobenzo[d]oxazole.

82(D) 7-Bromo-5-fluoro-2-(4-(pyridin-2-yl)but-3-ynyl)benzo[d]oxazole

The title compound was prepared in accordance with the general method of Example 1, from 2-bromopyridine (131 mg, 0.83 mmol) and 7-bromo-2-(but-3-ynyl)-5-fluoro-benzo[d]oxazole (223 mg, 0.83 mmol). The crude residue was purified by flash chromatography (DCM/MeOH 99:1) to yield 130 mg (0.38 mmol, 45%) of 7-bromo-5-fluoro-2-(4-(pyridin-2-yl)but-3-ynyl)benzo[d]oxazole as a brown solid.

LCMS (RT): 4.44 min; MS (ES+) gave m/z: 345.0, 346.9.
Rf (DCM/MeOH 99:1)=0.1.
$^1$H-NMR (CDCl$_3$), δ (ppm): 3.08 (t, J=7.9, 2H), 3.33 (t, J=7.9, 2H), 7.19-7.23 (m, 1H), 7.24-7.28 (m, 1H), 7.34 (dd, J=2.3 and 8.0, 1H), 7.36-7.40 (m, 1H), 7.61-7.65 (m, 1H), 8.54-8.57 (m, 1H).

Example 83

5-Fluoro-7-phenyl-2-(4-(pyridin-2-yl)but-3-ynyl)benzo[d]oxazole

To a solution of 7-bromo-5-fluoro-2-(4-(pyridin-2-yl)but-3-ynyl)benzo[d]oxazole (100 mg, 0.29 mmol, Example 82) in dioxane/aqueous saturated solution of NaHCO$_3$ (1:1, 8 mL) were added Pd(PPh$_3$)$_4$ (33 mg, 29 µmol) and phenylboronic acid (53.0 mg, 0.43 mmol). The reaction mixture was stirred at 60° C. for 7 hours, then AcOEt and brine were added and the organic phase was discarded. The aqueous phase was extracted thrice with AcOEt. The combined organic phases were washed with brine, dried over MgSO$_4$, filtered and concentrated. The crude residue was purified by flash chromatography (DCM/MeOH 99:1) to yield 86 mg (0.25 mmol, 87%) of 5-fluoro-7-phenyl-2-(4-(pyridin-2-yl)but-3-ynyl)benzo[d]oxazole as an orange oil.

LCMS (RT): 4.83 min; MS (ES+) gave m/z: 343.1.
Rf (DCM/MeOH 98:2)=0.2.
$^1$H-NMR (CDCl$_3$), δ (ppm): 3.08 (t, J=7.7, 2H), 3.33 (t, J=7.7, 2H), 7.19-7.22 (m, 1H), 7.25-7.29 (m, 1H), 7.32-7.34 (m, 1H), 7.36 (dd, J=2.5 and 8.0, 1H), 7.41-7.46 (2H), 7.47-7.52 (2H), 7.58-7.62 (m, 1H), 7.81-7.84 (m, 1H), 8.54-8.56 (m, 1H).

Example 84

2-(4-(2-Chloropyrimidin-4-yl)but-3-ynyl)benzo[d]oxazole

The title compound was prepared in accordance with the general method of Example 1, from 2,4-dichloropyrimidine (200 mg, 1.34 mmol) and 2-(but-3-ynyl)benzo[d]oxazole (230 mg, 1.34 mmol, Example 8(A)) at room temperature. The crude residue was purified by flash chromatography (cyclohexane/AcOEt 9:1) to yield 35 mg (0.12 mmol, 9%) of 2-(4-(2-chloropyrimidin-4-yl)but-3-ynyl)benzo[d]oxazole as a yellow solid.

LCMS (RT): 4.11 min; MS (ES+) gave m/z: 284.0.

Example 85

2-Chloro-4-(4-phenylbut-1-ynyl)pyrimidine

The title compound was prepared in accordance with the general method of Example 1, from 2,4-dichloropyrimidine (250 mg, 1.68 mmol) and 1-(but-3-ynyl)benzene (218 mg, 1.68 mmol). The crude residue was purified by flash chromatography (cyclohexane/AcOEt 9:1) to yield 280 mg (1.15 mmol, 69%) of 2-chloro-4-(4-phenylbut-1-ynyl)pyrimidine as a brown oil.

LCMS (RT): 4.74 min; MS (ES+) gave m/z: 243.1.
Rf (cyclohexane/AcOEt 9:1)=0.3.

Example 86

4-Bromo-2-(4-(pyridin-2-yl)but-3-ynyl)benzo[d]oxazole

86(A) 3-Methoxy-2-nitrophenylamine

Triethylamine (6.29 mL) and diphenyl azidophosphate (6.66 mL, 30.1 mmol) were added to a suspension of 3-methoxy-2-nitrobenzoic acid (3.00 g, 15.2 mmol) in toluene (50 mL). The reaction mixture was stirred under reflux for 2 hours, water (10 mL) was added and it was stirred overnight under reflux. After evaporation of the solvent, the residue was dissolved in AcOEt and the resulting solution was filtered through celite. The organic phase was washed with saturated solution of NaHCO$_3$, brine, dried over MgSO$_4$, filtered and evaporated. The crude residue was purified by flash chromatography (cyclohexane/AcOEt 4:1) to yield 900 mg (5.35 mmol, 35%) of 3-methoxy-2-nitrophenylamine as a yellow solid.

Rf (DCM/MeOH 4:1)=0.1.

86(B) 1-Bromo-3-methoxy-2-nitrobenzene

3-Methoxy-2-nitro-phenylamine (360 mg, 2.14 mmol) was dissolved in HBr (48%, 4.8 mL) at 0° C. A solution of sodium nitrite (0.16 g, 2.40 mmol) in water (360 µL) was added dropwise to the stirred solution over one hour period while the temperature was maintained at 0° C. Then a cold (0° C.) freshly prepared solution of CuBr$_2$ (from CuSO$_4$.5H$_2$O (1.0 g) and HBr (48%, 1.0 mL) mixed 30 min. at room temperature to give a dark purple solution) was added at 0° C. to the reaction mixture. The resulting solution was stirred at 0° C. for 3 hours and at room temperature for 2 days. The reaction mixture was poured onto ice and neutralized carefully with a saturated solution of NaHCO$_3$. The aqueous phase was extracted with AcOEt. The resulting organic phase was washed with brine, dried over MgSO$_4$, filtered and evaporated to yield 482 mg (2.08 mmol, 97%) of 1-bromo-3-methoxy-2-nitrobenzene as an orange solid.

86(C) 2-Bromo-6-methoxyphenylamine

The title compound was prepared in accordance with the general method of Example 62(A), from 1-bromo-3-methoxy-2-nitrobenzene (482 mg, 2.08 mmol) to yield 375 mg (1.86 mmol, 89%) of 2-bromo-6-methoxyphenylamine.

86(D) 2-Amino-3-bromophenol

BBr$_3$ (3.71 mL, 3.71 mmol, 1 M in DCM) was added at 0° C. to a solution of 2-bromo-6-methoxyphenylamine (375 mg, 1.86 mmol) in DCM (10 mL). The reaction mixture was stirred under reflux for 2 hours and was quenched by the addition of MeOH followed by a saturated solution of NaHCO$_3$. The aqueous phase was extracted with AcOEt. The resulting organic layer was washed with brine dried over MgSO$_4$, filtered and evaporated. The crude residue was purified by flash chromatography (cyclohexane/AcOEt 7:3 to DCM) to yield 204 mg (1.08 mmol, 58%) of 2-amino-3-bromophenol as a solid.

86(E) 4-Bromo-2-(but-3-ynyl)benzo[d]oxazole

The title compound was prepared in accordance with the general method of Example 8(A), from 2-amino-3-bromophenol (200 mg, 1.06 mmol). Reaction time: 4 days. The crude residue was purified by flash chromatography (cyclohexane/AcOEt 4:1) to yield 100 mg (0.40 mmol, 38%) of 4-bromo-2-(but-3-ynyl)benzo[d]oxazole.

86(F) 4-Bromo-2-(4-(pyridin-2-yl)but-3-ynyl)benzo[d]oxazole

The title compound was prepared in accordance with the general method of Example 1, from 2-bromopyridine (63 mg, 0.40 mmol) and 4-bromo-2-(but-3-ynyl)-benzo[d]oxazole (100 mg, 0.40 mmol). The crude residue was purified by flash chromatography (DCM/MeOH 99:1) to yield 60 mg (0.18 mmol, 46%) of 4-bromo-2-(4-(pyridin-2-yl)but-3-ynyl)benzo[d]oxazole as a brown solid with a purity of 85%.

LCMS (RT): 4.09 min; MS (ES+) gave m/z: 327.0, 329.0.
Rf (DCM/MeOH 99:1)=0.1.

Example 87

4-Phenyl-2-(4-(pyridin-2-yl)but-3-ynyl)benzo[d]oxazole

The title compound was prepared in accordance with the general method of Example 83, from 4-bromo-2-(4-(pyridin-2-yl)but-3-ynyl)benzo[d]oxazole (60 mg, 0.18 mmol, Example 86). The crude residue was purified by flash chromatography (DCM/MeOH 99:1) to yield 8 mg (25 mmol, 10%) of 4-phenyl-2-(4-(pyridin-2-yl)but-3-ynyl)benzo[d]oxazole as a brown oil with a purity of 80%.

LCMS (RT): 4.89 min; MS (ES+) gave m/z: 325.2.
Rf (DCM/MeOH 99:1)=0.1.
$^1$H-NMR (CDCl$_3$), δ (ppm): 3.08 (t, J=7.3, 2H), 3.34 (t, J=7.3, 2H), 7.19-7.23 (m, 1H), 7.35-7.42 (3H), 7.47-7.53 (4H), 7.58-7.63 (m, 1H), 7.93-7.98 (2H), 8.53-8.57 (m, 1H).

Example 88

4-Chloro-2-(4-(pyridin-2-yl)but-3-ynyl)benzo[d]oxazole

88(A) 1-Chloro-3-methoxy-2-nitrobenzene

A solution of sodium nitrite (180 mg, 2.60 mmol) in water (0.5 mL) was added dropwise to a solution of 3-methoxy-2-nitro-phenylamine (400 mg, 2.38 mmol, Example 86(A)) in HCl (37%, 3.9 mL) at 0° C. over one hour period. Then the reaction mixture was added to a cold (0° C.) solution of CuCl$_2$ (640 mg, 4.76 mmol) in HCl (6 N, 3.5 mL). The resulting green solution was stirred at room temperature for 2 days. Then, the reaction mixture was poured onto ice and neutralized carefully with a saturated solution of NaHCO$_3$. The aqueous phase was extracted with AcOEt. The resulting organic phase was washed with brine, dried over MgSO$_4$, filtered and evaporated to yield 293 mg (1.56 mmol, 66%) of 1-chloro-3-methoxy-2-nitrobenzene as a brown oil.

88(B) 2-Chloro-6-methoxyphenylamine

The title compound was prepared in accordance with the general method of Example 62(A), from 1-chloro-3-methoxy-2-nitrobenzene (293 mg, 1.56 mmol) to yield 214 mg (1.36 mmol, 87%) of 2-chloro-6-methoxyphenylamine.
Rf (DCM/MeOH 99:1)=0.3.

88(C) 2-Amino-3-chlorophenol

The title compound was prepared in accordance with the general method of Example 86(D), from 2-chloro-6-methoxyphenylamine (397 mg, 2.52 mmol). The crude residue was purified by flash chromatography (cyclohexane/AcOEt 4:1 to DCM) to yield 45 mg (0.31 mmol, 12%) of 2-amino-3-chlorophenol as a red oil.

88(D) 2-(But-3-ynyl)-4-chlorobenzo[d]oxazole

The title compound was prepared in accordance with the general method of Example 8(A), from 2-amino-3-chlorophenol (50.0 mg, 0.35 mmol). Reaction time: 4 days. The crude residue was purified by flash chromatography (cyclohexane/AcOEt 4:1) to yield 20 mg (97 mmol, 28%) of 2-(but-3-ynyl)-4-chlorobenzo[d]oxazole.

88(E) 4-Chloro-2-(4-(pyridin-2-yl)but-3-ynyl)benzo[d]oxazole

The title compound was prepared in accordance with the general method of Example 1, from 2-bromopyridine (15 mg, 97 μmol) and 2-(but-3-ynyl)-4-chlorobenzo[d]oxazole (20 mg, 97 μmol). The crude residue was purified by flash chromatography (cyclohexane/AcOEt 4:1) to yield 3 mg (11 μmol, 11%) of 4-chloro-2-(4-(pyridin-2-yl)but-3-ynyl)benzo[d]oxazole as a brown solid.

LCMS (RT): 3.99 min; MS (ES+) gave m/z: 283.0, 285.0.
Rf (cyclohexane/AcOEt 4:1)=0.05.

Example 89

5,7-Difluoro-2-(4-(pyridin-2-yl)but-3-ynyl)benzo[d]oxazole

89(A) 2-(But-3-ynyl)-5,7-difluorobenzo[d]oxazole

The title compound was prepared in accordance with the general method of Example 8(A), from 2-amino-4,6-difluorophenol (500 mg, 3.45 mmol). Reaction time: 3 days. The crude residue was purified by flash chromatography (cyclohexane/AcOEt 9:1) to yield 309 mg (1.49 mmol, 43%) of 2-(but-3-ynyl)-5,7-difluorobenzo[d]oxazole.

89(B) 5,7-Difluoro-2-(4-(pyridin-2-yl)but-3-ynyl)benzo[d]oxazole

The title compound was prepared in accordance with the general method of Example 1, from 2-bromopyridine (236 mg, 1.49 mmol) and 2-(but-3-ynyl)-5,7-difluoro benzo[d]oxazole (309 mg, 1.49 mmol). The crude residue was purified by flash chromatography (DCM/MeOH 99:1) to yield 86 mg (0.3 mmol, 20%) of 5,7-difluoro-2-(4-(pyridin-2-yl)but-3-ynyl)benzo[d]oxazole as a brown solid (M.P.: 93.5-94° C.).

LCMS (RT): 4.09 min; MS (ES+) gave m/z: 285.1.
Rf (DCM/MeOH 99:1)=0.05.
$^1$H-NMR (CDCl$_3$), δ (ppm): 3.07 (t, J=8.0, 2H), 3.31 (t, J=8.0, 2H), 6.85-6.90 (m, 1H), 7.18-7.22 (2H), 7.35-7.38 (m, 1H), 7.59-7.64 (m, 1H), 8.53-8.56 (m, 1H).

Example 90

4-Fluoro-2-(4-(pyridin-2-yl)but-3-ynyl)benzo[d]oxazole

90(A) 6-Bromo-3-fluoro-2-nitrophenol

The title compound was prepared in accordance with the general method of Example 77(A) from 2-bromo-5-fluorophenol (1.16 mL, 10.5 mmol). Reaction time: 6 hours. As there was no precipitate, the reaction mixture was poured onto ice, neutralized with NaOH and extracted with DCM. The organic phase was washed with brine, dried over MgSO$_4$, filtered and evaporated to yield 6-bromo-3-fluoro-2-nitrophenol (2.30 g, 9.75 mmol, 93%) mixed with 2-bromo-5-fluoro-4-nitrophenol.

90(B) 2-Amino-3-fluorophenol

The title compound was prepared in accordance with the general method of Example 62(A), from crude 6-bromo-3-fluoro-2-nitrophenol (2.30 g, 9.75 mmol). Reaction time: 2 days. The crude residue was purified by flash chromatography (DCM/MeOH 99.5:0.5) to yield 56.0 mg (0.44 mmol, 5%) of 2-amino-3-fluorophenol.

90(C) 2-(But-3-ynyl)-4-fluorobenzo[d]oxazole

The title compound was prepared in accordance with the general method of Example 8(A), from 2-amino-3-fluorophenol (56 mg, 0.44 mmol). Reaction time: 2 days. The crude residue was purified by flash chromatography (cyclohexane/AcOEt 9:1) to yield 35 mg (0.18 mmol, 42%) of 2-(but-3-ynyl)-4-fluorobenzo[d]oxazole.

90(D) 4-Fluoro-2-(4-(pyridin-2-yl)but-3-ynyl)benzo[d]oxazole

The title compound was prepared in accordance with the general method of Example 1, from 2-bromopyridine (29.2 mg, 0.18 mmol) and 2-(but-3-ynyl)-4-fluorobenzo[d]oxazole (35 mg, 0.18 mmol). The crude residue was purified by flash chromatography (DCM/MeOH 99:1 to 98:2) to yield 24 mg (90 mmol, 49%) of 4-fluoro-2-(4-(pyridin-2-yl)but-3-ynyl) benzo[d]oxazole as an orange solid (M.P.=89-89.5° C.).
LCMS (RT): 3.81 min; MS (ES+) gave m/z: 267.0.
Rf (DCM/MeOH 98:2)=0.1.
$^1$H-NMR (CDCl$_3$), δ (ppm): 3.06 (t, J=8.0, 2H), 3.29 (t, J=8.0, 2H), 7.04-7.09 (m, 1H), 7.18-7.21 (m, 1H), 7.23 (dd, J=2.5 and 8.0, 1H), 7.36 (d, J=8.0, 1H), 7.59-7.63 (2H), 8.52-8.56 (m, 1H).

Example 91

7-Methyl-2-(4-(pyridin-2-yl)but-3-ynyl)benzo[d]oxazole

91(A) 2-Amino-6-methylphenol

The title compound was prepared in accordance with the general method of Example 62(A), from 2-methyl-6-nitrophenol (170 mg, 1.11 mmol). Reaction time: 1 day. The crude residue was purified by flash chromatography (DCM/MeOH 99:1) to yield 41 mg (0.33 mmol, 30%) of 2-amino-6-methylphenol.
Rf (DCM/MeOH 99:1)=0.1.

91(B) 2-(But-3-ynyl)-7-methylbenzo[d]oxazole

The title compound was prepared in accordance with the general method of Example 8(A), from 2-amino-6-methylphenol (41 mg, 0.33 mmol). Reaction time: 2 days. The crude residue was purified by flash chromatography (cyclohexane/AcOEt 9:1) to yield 30 mg (0.16 mmol, 49%) of 2-(but-3-ynyl)-7-methylbenzo[d]oxazole.

91(C) 7-Methyl-2-(4-(pyridin-2-yl)but-3-ynyl)benzo[d]oxazole

The title compound was prepared in accordance with the general method of Example 1, from 2-bromopyridine (26 mg, 0.16 mmol) and 2-(but-3-ynyl)-7-methyl benzo[d]oxazole (30 mg, 0.16 mmol). The crude residue was purified by flash chromatography (DCM/MeOH 98.5:1.5) to yield 23 mg (87 µmol, 54%) of 7-methyl-2-(4-(pyridin-2-yl)but-3-ynyl) benzo[d]oxazole as a brown oil.
LCMS (RT): 3.99 min; MS (ES+) gave m/z: 263.1.
Rf (DCM/MeOH 99:1)=0.1.
$^1$H-NMR (CDCl$_3$), δ (ppm): 2.51 (s, 3H), 3.07 (t, J=8.0, 2H), 3.30 (t, J=8.0, 2H), 7.11 (d, J=7.5, 1H), 7.17-7.24 (2H), 7.36 (d, J=7.5, 1H), 7.51 (d, J=8.0, 1H), 7.59-7.63 (m, 1H), 8.54 (d, J=4.0, 1H).

Example 92

2-(4-(Pyridin-2-yl)but-3-ynyl)benzo[d]oxazole-7-carbonitrile

92(A) 2-(But-3-ynyl)benzo[d]oxazole-7-carbonitrile

The title compound was prepared in accordance with the general method of Example 8(A), from 3-amino-2-hydroxybenzonitrile (500 mg, 3.73 mmol). Reaction time: 3 days. The crude residue was purified by flash chromatography (cyclohexane/AcOEt 9:1) to yield 535 mg (2.73 mmol, 73%) of 2-(but-3-ynyl)benzo[d]oxazole-7-carbonitrile.

92(B) 2-(4-(Pyridin-2-yl)but-3-ynyl)benzo[d]oxazole-7-carbonitrile

The title compound was prepared in accordance with the general method of Example 1, from 2-bromopyridine (161 mg, 1.02 mmol) and 2-(but-3-ynyl)benzo[d]oxazole-7-carbonitrile (200 mg, 1.02 mmol). The crude residue was purified by flash chromatography (DCM/MeOH 99:1) to yield 48 mg (0.18 mmol, 17%) of 2-(4-(pyridin-2-yl)but-3-ynyl) benzo[d]oxazole-7-carbonitrile as a yellow solid (M.P.=126-126.5° C.).
LCMS (RT): 3.61 min; MS (ES+) gave m/z: 274.1.
$^1$H-NMR (CDCl$_3$), δ (ppm): 3.10 (t, J=7.5, 2H), 3.36 (t, J=7.5, 2H), 7.18-7.22 (m, 1H), 7.39 (d, J=7.5, 1H), 7.39-7.44 (m, 1H), 7.59-7.64 (2H), 7.93 (dd, J=1.0 and 8.0, 1H), 8.54 (d, J=4.5, 1H).

Example 93

7-Chloro-4-fluoro-2-(4-(pyridin-2-yl)but-3-ynyl)benzo[d]oxazole

93(A) 6-Chloro-3-fluoro-2-nitrophenol

The title compound was prepared in accordance with the general method of Example 77(A) from 2-chloro-5-fluorophenol (2.00 g, 13.6 mmol). Reaction time: 5 hours. The reaction mixture was poured onto ice and extracted with AcOEt. The organic phase was washed with saturated solution of NaHCO$_3$, water, dried over MgSO$_4$, filtered and evaporated to yield 6-chloro-3-fluoro-2-nitrophenol (2.56 g, 13.4 mmol).

93(B) 2-Amino-6-chloro-3-fluorophenol

The title compound was prepared in accordance with the general method of Example 62(A), from 6-chloro-3-fluoro- 2-nitrophenol (2.56 g, 13.4 mmol). Reaction time: 1 day. The crude residue was purified by flash chromatography (DCM/MeOH 99:1) to yield 1.01 g (6.26 mmol, 47%) of 2-amino-6-chloro-3-fluorophenol.

93(C) 2-(But-3-ynyl)-7-chloro-4-fluoro-benzo[d]oxazole

The title compound was prepared in accordance with the general method of Example 8(A), from 2-amino-6-chloro-3-fluorophenol (1.01 g, 6.26 mmol). Reaction time: 3 days. The crude residue was purified by flash chromatography (cyclohexane/AcOEt 9:1) to yield 176 mg (0.79 mmol, 13%) of 2-(but-3-ynyl)-7-chloro-4-fluoro-benzo[d]oxazole.

93(D) 7-Chloro-4-fluoro-2-(4-(pyridin-2-yl)but-3-ynyl)benzo[d]oxazole

The title compound was prepared in accordance with the general method of Example 1, from 2-bromopyridine (124 mg, 0.79 mmol) and 2-(but-3-ynyl)-7-chloro-4-fluoro-benzo[d]oxazole (176 mg, 0.79 mmol). The crude residue was purified by flash chromatography (DCM/MeOH 99:1) to yield 30 mg (99 mmol, 13%) of 7-chloro-4-fluoro-2-(4-(pyridin-2-yl)but-3-ynyl)benzo[d]oxazole as a brown solid (M.P.=102-103° C.).

LCMS (RT): 4.31 min; MS (ES+) gave m/z: 301.0, 303.0.
$^1$H-NMR (CDCl$_3$), δ (ppm): 3.09 (t, J=8.0, 2H), 3.34 (t, J=8.0, 2H), 6.99-7.04 (m, 1H), 7.18-7.22 (m, 1H), 7.24-7.29 (m, 1H), 7.36-7.40 (m, 1H), 7.60-7.64 (m, 1H), 8.53-8.55 (m, 1H).

Example 94

7-Methoxy-2-(4-(pyridin-2-yl)but-3-ynyl)benzo[d]oxazole

94(A) 3-Aminobenzene-1,2-diol

The title compound was prepared in accordance with the general method of Example 62(A), from 3-nitrobenzene-1,2-diol (1.00 g, 6.45 mmol). 392 mg (3.13 mmol, 49%) of 3-aminobenzene-1,2-diol as a brown solid were obtained and used without purification.

94(B) 2-(But-3-ynyl)benzo[d]oxazol-7-ol

The title compound was prepared in accordance with the general method of Example 8(A), from 3-aminobenzene-1,2-diol (392 mg, 3.13 mmol). The crude residue was purified by flash chromatography (cyclohexane/AcOEt 9:1 to 7:3) to yield 130 mg (0.69 mmol, 22%) of 2-(but-3-ynyl)benzo[d]oxazol-7-ol.

94(C) 2-(4-(Pyridin-2-yl)but-3-ynyl)benzo[d]oxazol-7-ol

The title compound was prepared in accordance with the general method of Example 1, from 2-bromopyridine (110 mg, 0.69 mol) and 2-(but-3-ynyl)benzo[d]oxazol-7-ol (130 mg, 0.69 mmol). The crude residue was purified by flash chromatography (DCM/MeOH 98:2) to yield 10 mg (38 μmol, 5%) of 2-(4-(pyridin-2-yl)but-3-ynyl)benzo[d]oxazol-7-ol.

Rf (DCM/MeOH 98:2)=0.1.

94(D) 7-Methoxy-2-(4-(pyridin-2-yl)but-3-ynyl)benzo[d]oxazole

The title compound was prepared in accordance with the general method of Example 72, from 2-(4-pyridin-2-yl-but-3-ynyl)-benzo[d]oxazol-7-ol (10 mg, 38 μmol). The crude residue was purified by flash chromatography (DCM/MeOH 99:1) to yield 3.7 mg (13 μmol, 35%) of 7-methoxy-2-(4-(pyridin-2-yl)but-3-ynyl)benzo[d]oxazole as a brown oil with a purity of 82%.

LCMS (RT): 3.56 min; MS (ES+) gave m/z: 279.2.
Rf (DCM/MeOH 99:1)=0.1.
$^1$H-NMR (CDCl$_3$), δ (ppm): 3.08 (t, J=8.1, 2H), 3.31 (t, J=8.1, 2H), 4.03 (s, 3H), 6.86 (d, J=8.1, 1H), 7.18-7.22 (m, 1H), 7.22-7.26 (m, 1H), 7.32 (dd, J=0.8 and 8.0, 1H), 7.39 (d, J=8.0, 1H), 7.59-7.64 (m, 1H), 8.53-8.57 (m, 1H).

Example 95

7-Isopropyl-2-(4-(pyridin-2-yl)but-3-ynyl)benzo[d]oxazole

95(A) 2-Isopropyl-6-nitrophenol

The title compound was prepared in accordance with the general method of Example 77(A) from 2-isopropylphenol (2.00 g, 14.7 mmol). Reaction time: 6 hours. The reaction mixture was poured onto ice and extracted with AcOEt. The organic phase was washed with brine, dried over MgSO$_4$, filtered and evaporated to yield 2-isopropyl-6-nitrophenol (2.50 g, 13.8 mmol, 94%).

95(B) 2-Amino-6-isopropylphenol

The title compound was prepared in accordance with the general method of Example 62(A), from 2-isopropyl-6-nitrophenol (2.50 g, 13.8 mmol). The crude residue was purified by flash chromatography (DCM/MeOH 99:1) to yield 974 mg (6.44 mmol, 47%) of 2-amino-6-isopropylphenol.

95(C) 2-But-3-ynyl-7-isopropyl-benzo[d]oxazole

The title compound was prepared in accordance with the general method of Example 8(A), from 2-amino-6-isopropylphenol (974 mg, 6.44 mmol). Reaction time: 2 days. The crude residue was purified by flash chromatography (cyclohexane/AcOEt 9:1) to yield 55 mg (0.26 mmol, 4%) of 2-(but-3-ynyl)-7-isopropyl-benzo[d]oxazole.

95(D) 7-Isopropyl-2-(4-(pyridin-2-yl)but-3-ynyl)benzo[d]oxazole

The title compound was prepared in accordance with the general method of Example 1, from 2-bromopyridine (41 mg, 0.26 mmol) and 2-(but-3-ynyl)-7-isopropyl-benzo[d]oxazole (55 mg, 0.26 mmol). The crude residue was purified by flash chromatography (DCM/MeOH 99:1) to yield 4.2 mg (14 μmol, 6%) of 7-isopropyl-2-(4-(pyridin-2-yl)but-3-ynyl)benzo[d]oxazole as a red oil.

LCMS (RT): 4.56 min; MS (ES+) gave m/z: 291.2.
Rf (DCM/MeOH 97.5:2.5)=0.3.
$^1$H-NMR (CDCl$_3$), δ (ppm): 1.37 (d, J=7.0, 6H), 3.07 (t, J=8.0, 2H), 3.31 (t, J=8.0, 2H), 3.31-3.37 (m, 1H), 7.15 (dd, J=1.0 and 7.5, 1H), 7.17-7.21 (m, 1H), 7.22-7.26 (m, 1H), 7.34-7.37 (m, 1H), 7.52 (dd, J=1.0 and 8.0, 1H), 7.58-7.62 (m, 1H), 8.53-8.56 (m, 1H).

Example 96

4,7-Difluoro-2-(4-(pyridin-2-yl)but-3-ynyl)benzo[d]oxazole

96(A) 3,6-Difluoro-2-nitrophenol

The title compound was prepared in accordance with the general method of Example 77(A) from 2,5-difluorophenol (1.00 g, 7.69 mmol). Reaction time: 6 hours. The reaction mixture was poured onto ice and extracted with AcOEt. The organic phase was washed with brine, dried over $MgSO_4$, filtered and evaporated to yield 3,6-difluoro-2-nitrophenol (1.28 g, 7.30 mmol).

96(B) 2-Amino-3,6-difluorophenol

The title compound was prepared in accordance with the general method of Example 62(A), from 3,6-difluoro-2-nitrophenol (1.28 g, 7.30 mmol). Reaction time: 4 days. The crude residue was purified by flash chromatography (DCM/MeOH 99:1) to yield 836 mg (5.76 mmol, 79%) of 2-amino-3,6-difluorophenol.

96(C) 2-(But-3-ynyl)-4,7-difluoro-benzo[d]oxazole

The title compound was prepared in accordance with the general method of Example 8(A), from 2-amino-3,6-difluorophenol (836 mg, 5.76 mmol). The crude residue was purified by flash chromatography (cyclohexane/AcOEt 4:1) to yield 90 mg (0.43 mmol, 7%) of 2-(but-3-ynyl)-4,7-difluoro-benzo[d]oxazole.

96(D) 4,7-Difluoro-2-(4-(pyridin-2-yl)but-3-ynyl)benzo[d]oxazole

The title compound was prepared in accordance with the general method of Example 1, from 2-bromopyridine (69 mg, 0.43 mmol) and 2-(but-3-ynyl)-4,7-difluoro-benzo[d]oxazole (90 mg, 0.43 mmol). The crude residue was purified by flash chromatography (DCM/MeOH 98.5:1.5) to yield 17 mg (61 µmol, 14%) of 4,7-difluoro-2-(4-(pyridin-2-yl)but-3-ynyl)benzo[d]oxazole as an orange solid.

LCMS (RT): 3.99 min; MS (ES+) gave m/z: 285.1.
Rf (DCM/MeOH 98.5:1.5)=0.1.
$^1$H-NMR ($CDCl_3$), δ (ppm): 3.09 (t, J=7.5, 2H), 3.33 (t, J=7.5, 2H), 6.94-7.05 (2H), 7.18-7.22 (m, 1H), 7.36-7.39 (m, 1H), 7.59-7.64 (m, 1H), 8.53-8.56 (m, 1H).

Example 97

7-Fluoro-4-(trifluoromethyl)-2-(4-(pyridin-2-yl)but-3-ynyl)benzo[d]oxazole

97(A) 6-Fluoro-2-nitro-3-(trifluoromethyl)phenol

The title compound was prepared in accordance with the general method of Example 77(A) from 2-fluoro-5-(trifluoromethyl)phenol (1.00 g, 5.55 mmol). Reaction time: 6 hours. The reaction mixture was poured onto ice and extracted with AcOEt. The organic phase was washed with brine, dried over $MgSO_4$, filtered and evaporated to yield 6-fluoro-2-nitro-3-(trifluoromethyl)phenol (1.21 g, 5.39 mmol).

97(B) 2-Amino-6-fluoro-3-(trifluoromethyl)phenol

The title compound was prepared in accordance with the general method of Example 62(A), from 6-fluoro-2-nitro-3-(trifluoromethyl)phenol (1.21 g, 5.38 mmol). Reaction time: 1 day. The crude residue was purified by flash chromatography (DCM/MeOH 99:1) to yield 320 mg (1.64 mmol, 30%) of 2-amino-6-fluoro-3-(trifluoromethyl)phenol.

97(C) 2-(But-3-ynyl)-7-fluoro-4-(trifluoromethyl)-benzo[d]oxazole

The title compound was prepared in accordance with the general method of Example 8(A), from 2-amino-6-fluoro-3-(trifluoromethyl)phenol (320 mg, 1.64 mmol). Reaction time: 2 days. The crude residue was purified by flash chromatography (cyclohexane/AcOEt 4:1) to yield 80 mg (0.31 mmol, 19%) of 2-(but-3-ynyl)-7-fluoro-4-(trifluoromethyl)-benzo[d]oxazole.

97(D) 7-Fluoro-4-(trifluoromethyl)-2-(4-(pyridin-2-yl)but-3-ynyl)benzo[d]oxazole The title compound was prepared in accordance with the general method of Example 1, from 2-bromopyridine (49 mg, 0.31 mmol) and 2-(but-3-ynyl)-7-fluoro-4-(trifluoromethyl)-benzo[d]oxazole (80 mg, 0.31 mmol). The crude residue was purified by flash chromatography (DCM/MeOH 98.5:1.5) to yield 15 mg (44 µmol, 14%) of 7-fluoro-4-(trifluoromethyl)-2-(4-(pyridin-2-yl)but-3-ynyl)benzo[d]oxazole as an orange solid.

LCMS (RT): 4.44 min; MS (ES+) gave m/z: 335.1.
Rf (DCM/MeOH 98.5:1.5)=0.2.
$^1$H-NMR ($CDCl_3$), δ (ppm): 3.09 (t, J=8.0, 2H), 3.39 (t, J=8.0, 2H), 7.13-7.18 (m, 1H), 7.19-7.22 (m, 1H), 7.35-7.38 (m, 1H), 7.55-7.59 (m, 1H), 7.60-7.64 (m, 1H), 8.52-8.56 (m, 1H).

Example 98

2-(4-(Pyrimidin-4-yl)but-3-ynyl)benzo[d]oxazole

98(A) 4-Chloropyrimidine

Pyrimidin-4-ol (200 mg, 2.08 mmol) was dissolved in phosphorous chloride (2 mL), the reaction mixture was stirred for 1 hour at 100° C. and poured onto ice. The aqueous phase was neutralized with NaOH and extracted with AcOEt. The organic phase was washed with brine, dried over $MgSO_4$, filtered and evaporated to yield 4-chloropyrimidine (85 mg, 0.74 mmol, 36%) as an orange oil.

98(B) 2-(4-(Pyrimidin-4-yl)but-3-ynyl)benzo[d]oxazole

The title compound was prepared in accordance with the general method of Example 1, from 4-chloropyrimidine (85 mg, 0.74 mmol) and 2-(but-3-ynyl)benzo[d]oxazole (127 mg, 0.74 mmol). The crude residue was purified by flash chromatography (cyclohexane/AcOEt 3:2) to yield 32 mg (128 µmol, 17%) of 2-(4-(pyrimidin-4-yl)but-3-ynyl)benzo[d]oxazole as a white solid.

Rf (cyclohexane/AcOEt 1:1)=0.2.
$^1$H-NMR ($CDCl_3$), δ (ppm): 3.12 (t, J=7.9, 2H), 3.32 (t, J=7.9, 2H), 7.31 (dd, J=1.1 and 5.1, 1H), 7.33-7.36 (2H), 7.50-7.54 (m, 1H), 7.69-7.72 (m, 1H), 8.67 (d, J=5.1 1H), 9.15 (d, J=1.1, 1H).

Example 99

N-(3-Chlorophenyl)-N-methyl-5-(pyridin-2-yl)pent-4-ynamide

99(A) Pent-4-ynoic acid (3-chloro-phenyl)-methyl-amide

Oxayl chloride (89 µL, 1.02 mmol) was added to a solution of pent-4-ynoic acid (50 mg, 0.51 mmol) in DCM (3 mL). The reaction mixture was stirred at 50° C. for 1 hour, was cooled to 0° C. and was added dropwise to a solution of (3-chlorophenyl)-methyl-amine (62 µL, 0.51 mmol). The reaction mixture was stirred for 2 hours at room temperature. After evaporation of the solvent, the crude residue was purified by flash chromatography (DCM/MeOH 99:1) to yield 100 mg (0.45 mmol, 88%) of pent-4-ynoic acid (3-chloro-phenyl)-methyl-amide.

LCMS (RT): 3.94 min; MS (ES+) gave m/z: 222.0.

99(B) N-(3-Chlorophenyl)-N-methyl-5-(pyridin-2-yl)pent-4-ynamide

The title compound was prepared in accordance with the general method of Example 1, from 2-bromopyridine (80 mg, 0.51 mmol) and pent-4-ynoic acid (3-chloro-phenyl)-methyl-amide (113 mg, 0.51 mmol). The crude residue was purified by $C_{18}$ flash chromatography to yield 51 mg (0.17 mmol, 33%) of N-(3-chlorophenyl)-N-methyl-5-(pyridin-2-yl)pent-4-ynamide as a brown liquid.

LCMS (RT): 3.73 min; MS (ES+) gave m/z: 299.1, 301.1.
$^1$H-NMR (CDCl$_3$), δ (ppm): 2.39-2.50 (m, 2H), 2.76 (t, J=7.5, 2H), 3.28 (s, 3H), 7.11-7.15 (m, 1H), 7.16-7.20 (m, 1H), 7.24-7.27 (m, 1H), 7.32-7.39 (m, 1H), 7.45-7.50 (m, 1H), 7.58-7.63 (m, 1H), 7.65-7.71 (m, 1H), 8.52 (d, J=4.8, 1H).

Example 100

7-Chloro-4-methyl-2-(4-(pyridin-2-yl)but-3-ynyl)benzo[d]thiazole

100(A) 2-Amino-6-chloro-3-methyl-benzenethiol

To a solution of NaOH (10N, 8.0 mL) was added 7-chloro-4-methyl-benzothiazol-2-ylamine (530 mg, 2.67 mmol) and ethylene glycol (10 mL) then the reaction mixture was stirred at 150° C. for 1 day. After being cooled down, the reaction mixture was filtered. The filtrate was extracted with DCM. The aqueous phase was acidified with HCl 1N and extracted with DCM. Then, the combined organic phases were washed with brine, dried over MgSO$_4$, filtered and evaporated to yield 2-amino-6-chloro-3-methyl-benzenethiol (252 mg, 1.45 mmol, 54%) as a yellow oil.

100(B) 2-But-3-ynyl-7-chloro-4-methyl-benzo[d]thiazole

The title compound was prepared in accordance with the general method of Example 8(A), from 2-amino-6-chloro-3-methyl-benzenethiol (252 mg, 1.45 mmol). Reaction time: 2 days. The crude residue was purified by flash chromatography (cyclohexane/AcOEt 9:1) to yield 30 mg (0.13 mmol, 9%) of 2-but-3-ynyl-7-chloro-4-methyl-benzo[d]thiazole as an orange oil.

100(C) 7-Chloro-4-methyl-2-(4-(pyridin-2-yl)but-3-ynyl)benzo[d]thiazole

The title compound was prepared in accordance with the general method of Example 1, from 2-bromopyridine (20 mg, 0.13 mmol) and 2-but-3-ynyl-7-chloro-4-methyl-benzo[d]thiazole (30 mg, 0.13 mmol). The crude residue was purified by flash chromatography (DCM/MeOH 99:1 to 98:2) to yield 2.9 mg (9.3 µmol, 7%) of 7-chloro-4-methyl-2-(4-(pyridin-2-yl)but-3-ynyl)benzo[d]thiazole as a brown oil.

LCMS (RT): 5.04 min; MS (ES+) gave m/z: 313.1, 315.0.
Rf (DCM/MeOH 97:3)=0.3.
$^1$H-NMR (CDCl$_3$), δ (ppm): 2.70 (s, 3H), 3.05 (t, J=7.5, 2H), 3.46 (t, J=7.5, 2H), 7.18-7.22 (2H), 7.24-7.27 (m, 1H), 7.37-7.40 (m, 1H), 7.60-7.64 (m, 1H), 8.54-8.57 (m, 1H).

Example 101

4-Fluoro-2-(4-(pyridin-2-yl)but-3-ynyl)benzo[d]thiazole

101(A) 2-Amino-3-fluoro-benzenethiol

The title compound was prepared in accordance with the general method of Example 100(A), from 4-fluoro-benzothiazol-2-ylamine (603 mg, 3.58 mmol) to yield 2-amino-3-fluoro-benzenethiol (513 mg, 3.58 mmol) as a yellow solid.

101(B) 2-But-3-ynyl-4-fluoro-benzo[d]thiazole

The title compound was prepared in accordance with the general method of Example 8(A), from 2-amino-3-fluoro-benzenethiol (513 mg, 3.58 mmol). Reaction time: 2 days. The crude residue was purified by flash chromatography (cyclohexane/AcOEt 9:1) to yield 378 mg (1.84 mmol, 51%) of 2-but-3-ynyl-4-fluoro-benzo[d]thiazole as an orange oil.

101(C) 4-Fluoro-2-(4-(pyridin-2-yl)but-3-ynyl)benzo[d]thiazole

The title compound was prepared in accordance with the general method of Example 1, from 2-bromopyridine (291 mg, 1.84 mmol) and 2-but-3-ynyl-4-fluoro-benzo[d]thiazole (378 mg, 1.84 mmol). The crude residue was purified by flash chromatography (DCM/MeOH 99:1) to yield 10 mg (37 µmol, 2%) of 4-fluoro-2-(4-(pyridin-2-yl)but-3-ynyl)benzo[d]thiazole as a yellow solid.

LCMS (RT): 3.89 min; MS (ES+) gave m/z: 283.0.
Rf (DCM/MeOH 98:2)=0.1.
$^1$H-NMR (CDCl$_3$), δ (ppm): 3.05 (t, J=7.5, 2H), 3.48 (t, J=7.5, 2H), 7.15-7.22 (2H), 7.30-7.35 (m, 1H), 7.38 (d, J=8.0, 1H), 7.60-7.65 (2H), 8.55 (d, J=5.0, 1H).

Example 102

4,7-Dimethyl-2-(4-(pyridin-2-yl)but-3-ynyl)benzo[d]thiazole

102(A) 2-Amino-3,6-dimethyl-benzenethiol

The title compound was prepared in accordance with the general method of Example 100(A), from 4,7-dimethyl-benzothiazol-2-ylamine (580 mg, 3.25 mmol) to yield 2-amino-3,6-dimethyl-benzenethiol (200 mg, 1.30 mmol, 40%) as a yellow oil.

102(B) 2-But-3-ynyl-4,7-dimethyl-benzo[d]thiazole

The title compound was prepared in accordance with the general method of Example 8(A), from 2-amino-3,6-dimethyl-benzenethiol (200 mg, 1.30 mmol). Reaction time: 2 days. The crude residue was purified by flash chromatography (cyclohexane/AcOEt 9:1) to yield 63 mg (0.29 mmol, 22%) of 2-but-3-ynyl-4,7-dimethyl-benzo[d]thiazole.

102(C) 4,7-Dimethyl-2-(4-(pyridin-2-yl)but-3-ynyl)benzo[d]thiazole

The title compound was prepared in accordance with the general method of Example 1, from 2-bromopyridine (46 mg, 0.29 mmol) and 2-but-3-ynyl-4,7-dimethyl-benzo[d]thiazole (63 mg, 0.29 mmol). The crude residue was purified by flash chromatography (DCM/MeOH 99:1 to 98:2) to yield 15 mg (52 µmol, 18%) of 4,7-dimethyl-2-(4-(pyridin-2-yl)but-3-ynyl)benzo[d]thiazole as a yellow solid.

LCMS (RT): 4.73 min; MS (ES+) gave m/z: 293.1.
Rf (DCM/MeOH 98:2)=0.1.
$^1$H-NMR (CDCl$_3$), δ (ppm): 2.50 (s, 3H), 2.70 (s, 3H), 3.04 (t, J=7.5, 2H), 3.47 (t, J=7.5, 2H), 7.06 (d, J=7.5, 1H), 7.18 (d, J=7.5, 1H), 7.19-7.21 (m, 1H), 7.36-7.39 (m, 1H), 7.60-7.64 (m, 1H), 8.54-8.57 (m, 1H).

Example 103

4-Methyl-2-(4-(pyridin-2-yl)but-3-ynyl)benzo[d]thiazole

103(A) 2-Amino-3-methyl-benzenethiol

The title compound was prepared in accordance with the general method of Example 100(A), from 4-methyl-benzothiazol-2-ylamine (1.00 g, 6.09 mmol) to yield 2-amino-3-methyl-benzenethiol (463 mg, 3.33 mmol, 55%).

103(B) 2-But-3-ynyl-4-methyl-benzo[d]thiazole

The title compound was prepared in accordance with the general method of Example 8(A), from 2-amino-3-methyl-benzenethiol (463 mg, 3.33 mmol). Reaction time: 2 days. The crude residue was purified by flash chromatography (cyclohexane/AcOEt 9:1) to yield 246 mg (1.22 mmol, 37%) of 2-but-3-ynyl-4-methyl-benzo[d]thiazole.

103(C) 4-Methyl-2-(4-(pyridin-2-yl)but-3-ynyl)benzo[d]thiazole

The title compound was prepared in accordance with the general method of Example 1, from 2-bromopyridine (193 mg, 1.22 mmol) and 2-but-3-ynyl-4-methyl-benzo[d]thiazole (246 mg, 1.22 mmol). The crude residue was purified by flash chromatography (DCM/MeOH 99:1 to 98:2) to yield 86 mg (0.31 mmol, 25%) of 4-methyl-2-(4-(pyridin-2-yl)but-3-ynyl)benzo[d]thiazole as a brown oil.

LCMS (RT): 4.33 min; MS (ES+) gave m/z: 279.1.
Rf (DCM/MeOH 98:2)=0.2.
$^1$H-NMR (CDCl$_3$), δ (ppm): 2.74 (s, 3H), 3.04 (t, J=7.5, 2H), 3.46 (t, J=7.5, 2H), 7.18-7.22 (m, 1H), 7.24-7.26 (2H), 7.36-7.39 (m, 1H), 7.59-7.64 (m, 1H), 7.65-7.70 (m, 1H), 8.54-8.57 (m, 1H).

Example 104

5-Fluoro-2-(4-(pyridin-2-yl)but-3-ynyl)benzo[d]thiazole

104(A) 2-Amino-4-fluoro-benzenethiol

The title compound was prepared in accordance with the general method of Example 100(A), from 5-fluoro-benzothiazol-2-ylamine (520 mg, 3.09 mmol) to yield 2-amino-4-fluoro-benzenethiol (443 mg, 3.09 mmol) as a yellow solid.

104(B) 2-But-3-ynyl-5-fluoro-benzo[d]thiazole

The title compound was prepared in accordance with the general method of Example 8(A), from 2-amino-4-fluoro-benzenethiol (443 mg, 3.09 mmol). Reaction time: 2 days. The crude residue was purified by flash chromatography (cyclohexane/AcOEt 9:1) to yield 286 mg (1.39 mmol, 45%) of 2-but-3-ynyl-5-fluoro-benzo[d]thiazole.

104(C) 5-Fluoro-2-(4-(pyridin-2-yl)but-3-ynyl)benzo[d]thiazole

The title compound was prepared in accordance with the general method of Example 1, from 2-bromopyridine (220 mg, 1.39 mmol) and 2-but-3-ynyl-5-fluoro-benzo[d]thiazole (286 mg, 1.39 mmol). The crude residue was purified by flash chromatography (DCM/MeOH 99:1 to 98:2) to yield 38 mg (0.13 mmol, 10%) of 5-fluoro-2-(4-(pyridin-2-yl)but-3-ynyl)benzo[d]thiazole as an orange solid.

LCMS (RT): 3.98 min; MS (ES+) gave m/z: 283.1.
Rf (DCM/MeOH 98:2)=0.2.
$^1$H-NMR (CDCl$_3$), δ (ppm): 3.03 (t, J=7.5, 2H), 3.43 (t, J=7.5, 2H), 7.17-7.22 (2H), 7.36-7.38 (m, 1H), 7.53 (dd, J=2.5 and 8.5, 1H), 7.59-7.64 (m, 1H), 7.92 (dd, J=4.5 and 8.5, 1H), 8.54-8.56 (m, 1H).

Example 105

4-Chloro-2-(4-(pyridin-2-yl)but-3-ynyl)benzo[d]thiazole

105(A) 2-Amino-3-chloro-benzenethiol

The title compound was prepared in accordance with the general method of Example 100(A), from 4-chloro-benzothiazol-2-ylamine (584 mg, 3.16 mmol) to yield 2-amino-3-chloro-benzenethiol (364 mg, 2.28 mmol, 74%) as a yellow solid.

105(B) 2-But-3-ynyl-4-chloro-benzo[d]thiazole

The title compound was prepared in accordance with the general method of Example 8(A), from 2-amino-3-chloro-benzenethiol (364 mg, 2.28 mmol). Reaction time: 2 days. The crude residue was purified by flash chromatography (cyclohexane/AcOEt 9:1) to yield 233 mg (1.05 mmol, 46%) of 2-but-3-ynyl-4-chloro-benzo[d]thiazole.

105(C) 4-Chloro-2-(4-(pyridin-2-yl)but-3-ynyl)benzo[d]thiazole

The title compound was prepared in accordance with the general method of Example 1, from 2-bromopyridine (166 mg, 1.05 mmol) and 2-but-3-ynyl-4-chloro-benzo[d]thiazole (233 mg, 1.05 mmol). The crude residue was purified by flash chromatography (DCM/MeOH 99:1 to 98:2) to yield 46 mg (0.15 mmol, 14%) of 4-chloro-2-(4-(pyridin-2-yl)but-3-ynyl)benzo[d]thiazole as a brown oil.

LCMS (RT): 4.18 min; MS (ES+) gave m/z: 299.1, 301.1.
Rf (DCM/MeOH 98:2)=0.1.
$^1$H-NMR (CDCl$_3$), δ (ppm): 3.04 (t, J=7.5, 2H), 3.50 (t, J=7.5, 2H), 7.18-7.22 (m, 1H), 7.27-7.32 (m, 1H), 7.39 (d, J=7.5, 1H), 7.49 (dd, J=1.0 and 8.0, 1H), 7.60-7.65 (m, 1H), 7.75 (dd, J=1.0 and 8.0, 1H), 8.53-8.59 (m, 1H).

Example 106

N-(2-Chlorophenyl)-N-methyl-5-(pyridin-2-yl)pent-4-ynamide

106(A) Pent-4-ynoic Acid (2-chloro-phenyl)-methyl-amide

The title compound was prepared in accordance with the general method of Example 99(A), from (2-chloro-phenyl)-methyl-amine (0.19 mL, 1.53 mmol). The crude residue was purified by flash chromatography (DCM/MeOH 99:1) to yield 220 mg (1.00 mmol, 65%) of pent-4-ynoic acid (2-chloro-phenyl)-methyl-amide.
LCMS (RT): 3.91 min; MS (ES+) gave m/z: 222.0.

106(B) N-(2-Chlorophenyl)-N-methyl-5-(pyridin-2-yl)pent-4-ynamide

The title compound was prepared in accordance with the general method of Example 1, from 2-bromopyridine (157 mg, 1.00 mmol) and pent-4-ynoic acid (2-chloro-phenyl)-methyl-amide (220 mg, 1.00 mmol). The crude residue was purified by flash chromatography (DCM/MeOH 98:2) to yield 20 mg (66 mmol, 7%) of N-(2-chlorophenyl)-N-methyl-5-(pyridin-2-yl)pent-4-ynamide as a brown liquid.
LCMS (RT): 3.61 min; MS (ES+) gave m/z: 299.1.
$^1$H-NMR (CDCl$_3$), δ (ppm): 2.26-2.40 (m, 2H), 2.68-2.81 (m, 2H), 3.22 (s, 3H), 7.14-7.19 (m, 1H), 7.28-7.40 (4H), 7.49-7.53 (m, 1H), 7.55-7.61 (m, 1H), 8.49 (d, J=6.0, 1H).

Example 107

1-Methyl-2-(4-(pyridin-2-yl)but-3-ynyl)-1H-benzo[d]imidazole

107(A) 2-Chloromethyl-1-methyl-1H-benzoimidazole

A solution of (1-methyl-1H-benzoimidazol-2-yl)-methanol (500 mg, 3.08 mmol) and SOCl$_2$ (1.1 mL) in DCM (2 mL) was stirred at room temperature for 3 hours. After evaporation of the solvents, 2-chloromethyl-1-methyl-1H-benzoimidazole (556 mg, 3.08 mmol) was obtained and was used without any purification.

107(B) 1-Methyl-2-(4-trimethylsilanyl-but-3-ynyl)-1H-benzoimidazole n-BuLi (1.35 mL, 3.39 mmol, 2.5 M) was added to a solution of trimethyl-prop-1-ynyl-silane (0.55 mL, 3.69 mmol) in THF (1 mL) at −78° C. After 2 hours, a solution of 2-chloromethyl-1-methyl-1H-benzoimidazole (556 mg, 3.08 mmol) in THF (8 mL) was added to the reaction mixture at −78° C. then the reaction mixture was stirred for 30 min. at −78° C. and 1 hour at room temperature and was quenched with water. The aqueous phase was extracted with DCM. The organic phase was washed with water, dried over MgSO$_4$, filtered and evaporated to yield 1-methyl-2-(4-trimethylsilanyl-but-3-ynyl)-1H-benzoimidazole (178 mg, 0.69 mmol, 23%).
LCMS (RT): 3.13 min; MS (ES+) gave m/z: 257.2.

107(C) 2-But-3-ynyl-1-methyl-1H-benzoimidazole

TBAF (0.24 mL, 0.83 mmol) was added to a solution of 1-methyl-2-(4-trimethylsilanyl-but-3-ynyl)-1H-benzoimidazole (178 mg, 0.69 mmol) in THF (2.5 mL) and the reaction mixture was stirred for 2 hours at room temperature. After the addition of water, the solvent was evaporated and the aqueous phase was extracted with DCM. The organic phase was washed with brine, dried over MgSO$_4$, filtered and evaporated. The crude residue was purified by flash chromatography (cyclohexane/AcOEt 4:1) to yield 90 mg (0.49 mmol, 70%) of 2-but-3-ynyl-1-methyl-1H-benzoimidazole as a brown solid.
LCMS (RT): 1.99 min; MS (ES+) gave m/z: 185.2.

107(D) 1-Methyl-2-(4-(pyridin-2-yl)but-3-ynyl)-1H-benzo[d]imidazole

The title compound was prepared in accordance with the general method of Example 1, from 2-iodo-pyridine (100 mg, 0.49 mmol) and 2-but-3-ynyl-1-methyl-1H-benzoimidazole (90 mg, 0.49 mmol). Reaction time: 18 hours. The crude residue was purified by flash chromatography (DCM/MeOH 98:2) to yield 39 mg (0.15 mmol, 31%) of 1-methyl-2-(4-(pyridin-2-yl)but-3-ynyl)-1H-benzo[d]imidazole as a brown solid.
LCMS (RT): 2.33 min; MS (ES+) gave m/z: 262.1.
$^1$H-NMR (CDCl$_3$), δ (ppm): 3.10 (t, J=7.2, 2H), 3.27 (t, J=7.2, 2H), 3.81 (s, 3H), 7.19-7.23 (m, 1H), 7.24-7.30 (2H), 7.31-7.34 (m, 1H), 7.36 (d, J=7.8, 1H), 7.59-7.65 (m, 1H), 7.72-7.76 (m, 1H), 8.56 (d, J=4.3, 1H).

Example 108

2-(4-(Pyridin-2-yl)but-3-ynyl)-2H-indazole

108(A) 2-(4-Trimethylsilanyl-but-3-ynyl)-2H-indazole and 1-(4-trimethylsilanyl-but-3-ynyl)-1H-indazole A suspension of (4-bromo-but-1-ynyl)-trimethyl-silane (374 mg, 1.83 mmol), indazole (200 mg, 1.69 mmol) and K$_2$CO$_3$ (459 mg, 3.32 mmol) in acetone (2 mL) was heated at 150° C. for 900 s in a microwave. After the addition of water, acetone was evaporated. The aqueous phase was extracted with DCM. The organic phase was washed with brine, dried over MgSO$_4$, filtered and evaporated to yield 250 mg (1.03 mmol, 62%) of 2-(4-trimethylsilanyl-but-3-ynyl)-2H-indazole and 1-(4-trimethylsilanyl-but-3-ynyl)-1H-indazole.

108(B) 2-(But-3-ynyl)-2H-indazole and 1-(but-3-ynyl)-1H-indazole

TBAF (1.24 mL, 1.24 mmol) was added to a solution of 2-(4-trimethylsilanyl-but-3-ynyl)-2H-indazole and 1-(4-trimethylsilanyl-but-3-ynyl)-1H-indazole (250 mg, 1.03 mmol) in THF (5 mL) and the reaction mixture was stirred for 2 hours at room temperature. After the addition of water, the solvent was evaporated and the aqueous phase was extracted with DCM. The organic phase was washed with brine, dried over MgSO$_4$, filtered and evaporated. The crude residue was purified by bulb-to-bulb distillation (0.2 mbar, 100-120° C.) to yield 160 mg (0.94 mmol, 91%) of 2-(but-3-ynyl)-2H-indazole and 1-(but-3-ynyl)-1H-indazole.

108(C) 2-(4-(Pyridin-2-yl)but-3-ynyl)-2H-indazole and 1-(4-(pyridin-2-yl)but-3-ynyl)-1H-indazole A solution of 2-(but-3-ynyl)-2H-indazole and 1-(but-3-ynyl)-1H-indazole (160 mg, 0.94 mmol) in DMF (0.5 mL) was added to a suspension of CuI (8.9 mg, 47 µmol), Et$_3$N (2.5 mL), Pd(PPh$_3$)$_2$Cl$_2$ (33 mg, 47 µmol), PPh$_3$ (6.2 mg, 23 µmol) and 2-bromopyridine (149 mg, 0.94 mmol). The reaction mixture was heated at 120° C. for 900 s in a microwave. The reaction mixture was quenched with water, Et$_3$N was evaporated and the aqueous phase was extracted with DCM. The organic phase was washed with a saturated solution of NH$_4$OH, brine, dried over MgSO$_4$, filtered and evaporated. The crude residue was purified by flash chromatography (DCM/MeOH 99:1) and SCX column (DCM, DCM/MeOH 98:2, DCM/MeOH/NH$_4$OH 95:4:1 to 94:4:2) to yield 6.8 mg (27 µmol, 3%) of 2-(4-(pyridin-2-yl)but-3-ynyl)-2H-indazole as a yellow solid and 4.6 mg (19 µmol, 2%) of 1-(4-(pyridin-2-yl)but-3-ynyl)-1H-indazole as an orange oil.

2-(4-(Pyridin-2-yl)but-3-ynyl)-2H-indazole

LCMS (RT): 3.53 min; MS (ES+) gave m/z: 248.2.
Rf (DCM/MeOH 98:2)=0.1.
$^1$H-NMR (CDCl$_3$), δ (ppm): 3.18 (t, J=6.9, 2H), 4.69 (t, J=6.9, 2H), 7.06-7.11 (m, 1H), 7.20-7.25 (m, 1H), 7.28-7.33 (2H), 7.59-7.64 (m, 1H), 7.65-7.68 (m, 1H), 7.72 (dd, J=0.9 and 8.8, 1H), 8.08 (d, J=0.9, 1H), 8.57 (d, J=4.3, 1H).

1-(4-(Pyridin-2-yl)but-3-ynyl)-1H-indazole

LCMS (RT): 3.24 min; MS (ES+) gave m/z: 248.2.
Rf (DCM/MeOH 98:2)=0.03.
$^1$H-NMR (CDCl$_3$), δ (ppm): 3.07 (t, J=7.3, 2H), 4.68 (t, J=7.3, 2H), 7.14-7.23 (3H), 7.36-7.42 (m, 1H), 7.51-7.55 (m, 1H), 7.57-7.62 (m, 1H), 7.75 (d, J=8.1, 1H), 8.04 (s, 1H), 8.52-8.57 (m, 1H).

Example 109

2-(4-(Pyridin-2-yl)but-3-ynyl)-2H-benzo[d][1,2,3]triazole

Method A

109(A) 2-(4-Trimethylsilanyl-but-3-ynyl)-2H-benzo[d][1,2,3]triazole and 1-(4-trimethylsilanyl-but-3-ynyl)-1H-benzo[d][1,2,3]triazole The title compounds were prepared in accordance with the general method of Example 108(A), from benzotriazole (116 mg, 0.97 mmol) to yield 157 mg (0.64 mmol, 67%) of 2-(4-trimethylsilanyl-but-3-ynyl)-2H-benzo[d][1,2,3]triazole and 1-(4-trimethylsilanyl-but-3-ynyl)-1H-benzo[d][1,2,3]triazole.

109(B) 2-(But-3-ynyl)-2H-benzo[d][1,2,3]triazole and 1-(but-3-ynyl)-1H-benzo[d][1,2,3]triazole The title compounds were prepared in accordance with the general method of Example 108(B), from 2-(4-trimethylsilanyl-but-3-ynyl)-2H-benzo[d][1,2,3]triazole and 1-(4-trimethylsilanyl-but-3-ynyl)-1H-benzo[d][1,2,3]triazole (157 mg, 0.64 mmol) to yield after bulb-to-bulb distillation (0.2 mbar, 80-100° C.), 90 mg (0.53 mmol, 83%) of 2-(but-3-ynyl)-2H-benzo[d][1,2,3]triazole and 1-(but-3-ynyl)-1H-benzo[d][1,2,3]triazole.

109(C) 2-(4-(Pyridin-2-yl)but-3-ynyl)-2H-benzo[d][1,2,3]triazole and 1-(4-(pyridin-2-yl)but-3-ynyl)-1H-benzo[d][1,2,3]triazole The title compounds were prepared in accordance with the general method of Example 108(C), from 90 mg (0.53 mmol) of 2-(but-3-ynyl)-2H-benzo[d][1,2,3]triazole and 1-(but-3-ynyl)-1H-benzo[d][1,2,3]triazole. The crude residue was purified by flash chromatography (DCM/MeOH 99:1 to 98:2) to yield 10 mg (42 µmol, 8%) of 2-(4-(pyridin-2-yl)but-3-ynyl)-2H-benzo[d][1,2,3]triazole as an orange oil with a purity of 82%. Another fraction yielded after SCX column (DCM, DCM/MeOH 98:2, DCM/MeOH/NH$_4$OH 95:4:1 to 94:4:2) 19 mg (76 µmol, 14%) of 1-(4-(pyridin-2-yl)but-3-ynyl)-1H-benzo[d][1,2,3]triazole as an orange oil.

2-(4-(Pyridin-2-yl)but-3-ynyl)-2H-benzo[d][1,2,3]triazole

LCMS (RT): 3.49 min; MS (ES+) gave m/z: 249.1.
Rf (DCM/MeOH 98:2)=0.2.
$^1$H-NMR (CDCl$_3$), δ (ppm): 3.31 (t, J=7.6, 2H), 5.01 (t, J=7.6, 2H), 7.19-7.24 (m, 1H), 7.35 (d, J=7.8, 1H), 7.41 (dd, J=3.1 and 6.6, 2H), 7.60-7.65 (m, 1H), 7.89 (dd, J=3.1 and 6.6, 2H), 8.56 (d, J=4.1, 1H).

1-(4-(Pyridin-2-yl)but-3-ynyl)-1H-benzo[d][1,2,3]triazole

LCMS (RT): 3.06 min; MS (ES+) gave m/z: 249.1.
Rf (DCM/MeOH 98:2)=0.1.
$^1$H-NMR (CDCl$_3$), δ (ppm): 3.17 (t, J=7.1, 2H), 4.93 (t, J=7.1, 2H), 7.17-7.23 (2H), 7.35-7.40 (m, 1H), 7.46-7.51 (m, 1H), 7.57-7.62 (m, 1H), 7.65 (d, J=8.3, 1H), 8.08 (d, J=8.4, 1H), 8.54 (d, J=4.6, 1H).

Method B 2-(4-(Pyridin-2-yl)but-3-ynyl)-2H-benzo[d][1,2,3]triazole hydrochloride 109(D) 2-(But-3-ynyl)-2H-benzo[d][1,2,3]triazole A solution of di-tert-butylazodicarboxylate (3.15 g, 13.4 mmol) in DCM (3 mL) was added dropwise over 30 min. at 0° C. to a suspension of benzotriazole (2.40 g, 1.50 mmol), but-3-yn-1-ol (940 mg, 13.4 mmol) and polymer bounded triphenylphosphine (4.40 g, 16.8 mmol, 3 mmol/g) in DCM (3 mL). The reaction mixture was stirred at room temperature with a polymix agitation for 2 days and filtered through celite. The organic phase was washed with NH$_4$OH, brine, dried over MgSO$_4$, filtered and evaporated. The crude residue was purified by flash chromatography (cyclohexane/AcOEt 9:1) to yield 571 mg (3.33 mmol, 25%) of 2-(but-3-ynyl)-2H-benzo[d][1,2,3]triazole as a yellow solid.
LCMS (RT): 3.73 min; MS (ES+) gave m/z: 172.0.
Rf (cyclohexane/AcOEt 9:1)=0.3.

109(E) 2-(4-(Pyridin-2-yl)but-3-ynyl)-2H-benzo[d][1,2,3]triazole

The title compound was prepared in accordance with the general method of Example 1, from 2-bromopyridine (92 mg, 0.58 mmol) and 2-(but-3-ynyl)-2H-benzo[d][1,2,3]triazole (100 mg, 0.58 mmol). Reaction time: 3 hours. The crude residue was purified by flash chromatography (DCM/MeOH 99:1) to yield 90 mg of 2-(4-(pyridin-2-yl)but-3-ynyl)-2H-benzo[d][1,2,3]triazole.
Rf (DCM/MeOH 99:1)=0.1.

109(F) 2-(4-(Pyridin-2-yl)but-3-ynyl)-2H-benzo[d][1,2,3]triazole hydrochloride

A solution of HCl (0.8 N, 906 µl) was added to a solution of 2-(4-(pyridin-2-yl)but-3-ynyl)-2H-benzo[d][1,2,3]triazole (90 mg) in dioxane (5 mL). The reaction mixture was cooled in the fridge for 1 hour. The resulting precipitate was filtered, washed with cold dioxane and diethyl ether and dried to yield 2-(4-(pyridin-2-yl)but-3-ynyl)-2H-benzo[d][1,2,3]triazole hydrochloride (99 mg, 0.35 mmol, 60%) as a white solid.

LCMS (RT): 3.51 min; MS (ES+) gave m/z: 249.2.

$^1$H-NMR (CDCl$_3$), δ (ppm): 3.46 (t, J=7.0, 2H), 5.09 (t, J=7.0, 2H), 7.42 (dd, J=3.1 and 6.6, 2H), 7.66 (d, J=8.0, 1H), 7.72-7.78 (m, 1H), 7.89 (dd, J=3.1 and 6.6, 2H), 8.20-8.26 (m, 1H), 8.72 (d, J=4.6, 1H).

Example 110

2-(4-(5-Phenyl-1H-pyrazol-1-yl)but-1-ynyl)pyridine

110(A) 5-Phenyl-1-(4-trimethylsilanyl-but-3-ynyl)-1H-pyrazole and 5-phenyl-2-(4-trimethylsilanyl-but-3-ynyl)-2H-pyrazole The title compounds were prepared in accordance with the general method of Example 108(A), from 3-phenyl-1H-pyrazole (200 mg, 1.39 mmol) to yield 300 mg (1.12 mmol, 81%) of 5-phenyl-1-(4-trimethylsilanyl-but-3-ynyl)-1H-pyrazole and 5-phenyl-2-(4-trimethylsilanyl-but-3-ynyl)-2H-pyrazole.

110(B) 1-But-3-ynyl-5-phenyl-1H-pyrazole and 2-but-3-ynyl-5-phenyl-2H-pyrazole

The title compounds were prepared in accordance with the general method of Example 108(B), from 5-phenyl-1-(4-trimethylsilanyl-but-3-ynyl)-1H-pyrazole and 5-phenyl-2-(4-trimethylsilanyl-but-3-ynyl)-2H-pyrazole (300 mg, 1.12 mmol). The crude residue was purified by flash chromatography (cyclohexane/AcOEt 9:1) to yield 29 mg (0.15 mmol, 13%) of 2-but-3-ynyl-5-phenyl-2H-pyrazole and 13 mg (66 μmol, 6%) of 1-but-3-ynyl-5-phenyl-1H-pyrazole.

110(C) 2-(4-(5-Phenyl-1H-pyrazol-1-yl)but-1-ynyl)pyridine

The title compound was prepared in accordance with the general method of Example 108(C), from 30 mg (0.15 mmol) of 2-but-3-ynyl-5-phenyl-2H-pyrazole. The crude residue was purified by flash chromatography (DCM/MeOH 99:1) and SCX column (DCM, DCM/MeOH 95:5, DCM/MeOH/NH$_4$OH 94:5:1 to 94:4:2) to yield 5 mg (18 μmol, 10%) of 2-(4-(5-phenyl-1H-pyrazol-1-yl)but-1-ynyl)pyridine as a yellow solid.

LCMS (RT): 3.86 min; MS (ES+) gave m/z: 274.1.

Rf (DCM/MeOH 98:2)=0.2.

$^1$H-NMR (DMSO[D]$_6$), δ (ppm): 3.01 (t, J=6.7, 2H), 4.39 (t, J=6.7, 2H), 6.70 (d, J=2.3, 1H), 7.25-7.29 (m, 1H), 7.30-7.35 (m, 1H), 7.36-7.41 (3H), 7.72-7.77 (m, 1H), 7.78-7.80 (2H), 7.87 (d, J=2.3, 1H), 8.48-8.51 (m, 1H).

Example 111

2-(4-(3-Phenylisoxazol-5-yl)but-1-ynyl)pyridine

111(A) 3-Phenyl-5-(4-trimethylsilanyl-but-3-ynyl)-isoxazole

The title compound was prepared in accordance with the general method of Example 107(B), from 5-chloromethyl-3-phenyl-isoxazole (200 mg, 1.03 mmol, reaction time: 1 day), to yield 3-phenyl-5-(4-trimethylsilanyl-but-3-ynyl)-isoxazole (127 mg, 0.47 mmol, 45%) as a white solid.

LCMS (RT): 5.59 min; MS (ES+) gave m/z: 270.1.

111(B) 5-But-3-ynyl-3-phenyl-isoxazole

The title compound was prepared in accordance with the general method of Example 108(B), from 3-phenyl-5-(4-trimethylsilanyl-but-3-ynyl)-isoxazole (127 mg, 0.47 mmol). The crude residue was purified by flash chromatography (cyclohexane/AcOEt 9:1) to yield 67 mg (0.34 mmol, 72%) of 5-but-3-ynyl-3-phenyl-isoxazole as a brown solid.

111(C) 2-(4-(3-Phenylisoxazol-5-yl)but-1-ynyl)pyridine

The title compound was prepared in accordance with the general method of Example 1, from 2-iodo-pyridine (70 mg, 0.34 mmol) and 5-but-3-ynyl-3-phenyl-isoxazole (67 mg, 0.34 mmol). Reaction time: 24 hours. The crude residue was purified by flash chromatography (DCM/MeOH 98:2) to yield 70 mg (0.26 mmol, 75%) of 2-(4-(3-phenylisoxazol-5-yl)but-1-ynyl)pyridine as a brown solid.

LCMS (RT): 4.18 min; MS (ES+) gave m/z: 275.1.

$^1$H-NMR (CDCl$_3$), δ (ppm): 2.91 (t, J=7.4, 2H), 3.17 (t, J=7.4, 2H), 6.49 (s, 1H), 7.19-7.23 (m, 1H), 7.35-7.39 (m, 1H), 7.41-7.48 (3H), 7.60-7.65 (m, 1H), 7.77-7.83 (2H), 8.54-8.58 (m, 1H).

Example 112

2-(4-(2-Methylthiazol-4-yl)but-3-ynyl)benzo[d]thiazole

The title compound was prepared in accordance with the general method of Example 1, from 4-iodo-2-methyl-thiazole (120 mg, 0.53 mmol) and 2-but-3-ynyl-benzo[d]thiazole (100 mg, 0.53 mmol, Example 35(A)). The crude residue was purified by flash chromatography (cyclohexane/AcOEt 4:1) to yield 152 mg (0.28 mmol, 53%) of 2-(4-(2-methylthiazol-4-yl)but-3-ynyl)benzo[d]thiazole as a yellow solid.

LCMS (RT): 4.33 min; MS (ES+) gave m/z: 285.1.

Rf (cyclohexane/AcOEt 4:1)=0.2.

$^1$H-NMR (CDCl$_3$), δ (ppm): 2.70 (s, 3H), 3.02 (t, J=7.5, 2H), 3.44 (t, J=7.5, 2H), 7.22 (s, 1H), 7.35-7.40 (m, 1H), 7.45-7.50 (m, 1H), 7.86 (dd, J=0.5 and 8.0, 1H), 8.09 (d, J=8.0, 1H).

Example 113

2-(4-(5-Fluoropyridin-2-yl)but-3-ynyl)benzo[d]thiazole

The title compound was prepared in accordance with the general method of Example 1, from 2-bromo-5-fluoro-pyridine (103 mg, 0.59 mmol) and 2-but-3-ynyl-benzo[d]thiazole (110 mg, 0.59 mmol, Example 35(A)). The crude residue was purified by flash chromatography (cyclohexane/AcOEt 4:1) to yield 78 mg (0.28 mmol, 47%) of 2-(4-(5-fluoropyridin-2-yl)but-3-ynyl)benzo[d]thiazole as a white solid.

LCMS (RT): 4.36 min; MS (ES+) gave m/z: 283.1.

Rf (cyclohexane/AcOEt 4:1)=0.2.

$^1$H-NMR (CDCl$_3$), δ (ppm): 3.05 (t, J=7.4, 2H), 3.46 (t, J=7.4, 2H), 7.32-7.41 (3H), 7.45-7.50 (m, 1H), 7.87 (dd, J=0.5 and 8.1, 1H), 8.00 (d, J=8.1, 1H), 8.41 (d, J=2.8, 1H).

Example 114

2-(4-(6-Methylpyridin-2-yl)but-3-ynyl)benzo[d]thiazole

The title compound was prepared in accordance with the general method of Example 1, from 2-bromo-6-methyl-pyridine (110 mg, 0.64 mmol) and 2-but-3-ynyl-benzo[d]thiazole (120 mg, 0.64 mmol, Example 35(A)). The crude residue was purified by flash chromatography (cyclohexane/AcOEt 7:3) to yield 122 mg (0.44 mmol, 68%) of 2-(4-(6-methylpyridin-2-yl)but-3-ynyl)benzo[d]thiazole as a beige solid.

LCMS (RT): 3.53 min; MS (ES+) gave m/z: 279.1.
Rf (cyclohexane/AcOEt 7:3)=0.2.
$^1$H-NMR (CDCl$_3$), δ (ppm): 2.55 (s, 3H), 3.04 (t, J=7.4, 2H), 3.46 (t, J=7.4, 2H), 7.08 (d, J=7.8, 1H), 7.21 (d, J=7.7, 1H), 7.35-7.40 (m, 1H), 7.45-7.49 (m, 1H), 7.50-7.53 (m, 1H), 7.86 (d, J=8.0, 1H), 8.00 (d, J=8.0, 1H).

Example 115

2-(4-(6-Chloropyridin-2-yl)but-3-ynyl)benzo[d]thiazole

The title compound was prepared in accordance with the general method of Example 108(C), from 2,6-dichloro-pyridine (395 mg, 2.67 mmol) and 2-but-3-ynyl-benzo[d]thiazole (100 mg, 0.53 mmol, Example 35(A)). The crude residue was purified by flash chromatography (cyclohexane/AcOEt 4:1) to yield 31 mg (0.10 mmol, 19%) of 2-(4-(6-chloropyridin-2-yl)but-3-ynyl)benzo[d]thiazole as a white solid.

LCMS (RT): 4.73 min; MS (ES+) gave m/z: 299.1, 301.0.
Rf (cyclohexane/AcOEt 4:1)=0.2.
$^1$H-NMR (CDCl$_3$), δ (ppm): 3.05 (t, J=7.5, 2H), 3.45 (t, J=7.5, 2H), 7.25 (dd, J=0.7 and 8.0, 1H), 7.30 (dd, J=0.7 and 7.6, 1H), 7.36-7.41 (m, 1H), 7.46-7.50 (m, 1H), 7.56-7.61 (m, 1H), 7.85-7.89 (m, 1H), 8.00 (d, J=8.1, 1H).

Example 116

7-Chloro-4-fluoro-2-(4-(pyridin-2-yl)but-3-ynyl)benzo[d]thiazole

116(A) 2-Amino-6-chloro-3-fluoro-benzenethiol

The title compound was prepared in accordance with the general method of Example 100(A), from 7-chloro-4-fluoro-benzothiazol-2-ylamine (1.1 g, 5.4 mmol) to yield 2-amino-6-chloro-3-fluoro-benzenethiol (350 mg, 1.97 mmol, 36%) as an orange oil.

116(B) 2-But-3-ynyl-7-chloro-4-fluoro-benzo[d]thiazole

The title compound was prepared in accordance with the general method of Example 8(A), from 2-amino-6-chloro-3-fluoro-benzenethiol (350 mg, 1.97 mmol). Reaction time: 2 days. The crude residue was purified by flash chromatography (cyclohexane/AcOEt 95:5) to yield 100 mg (0.42 mmol, 21%) of 2-but-3-ynyl-7-chloro-4-fluoro-benzo[d]thiazole as an orange oil.

LCMS (RT): 4.88 min; MS (ES+) gave m/z: 240.1.

116(C) 7-Chloro-4-fluoro-2-(4-(pyridin-2-yl)but-3-ynyl)benzo[d]thiazole

The title compound was prepared in accordance with the general method of Example 1, from 2-bromopyridine (66 mg, 0.42 mmol) and 2-but-3-ynyl-7-chloro-4-fluoro-benzo[d]thiazole (100 mg, 0.42 mmol). The crude residue was purified by flash chromatography (cyclohexane/AcOEt 7:3) to yield 15 mg (47 mmol, 11%) of 7-chloro-4-fluoro-2-(4-(pyridin-2-yl)but-3-ynyl)benzo[d]thiazole as a brown oil.

LCMS (RT): 4.59 min; MS (ES+) gave m/z: 317.1, 319.1.
Rf (cyclohexane/AcOEt 7:3)=0.2.
$^1$H-NMR (CDCl$_3$), δ (ppm): 3.07 (t, J=7.3, 2H), 3.49 (t, J=7.3, 2H), 7.16 (dd, J=8.6 and 9.8, 1H), 7.20-7.25 (m, 1H), 7.32 (dd, J=3.8 and 8.6, 1H), 7.38-7.42 (m, 1H), 7.61-7.68 (m, 1H), 8.57 (s, 1H).

Example 117

2-(4-(6-Fluoropyridin-2-yl)but-3-ynyl)benzo[d]thiazole

The title compound was prepared in accordance with the general method of Example 1, from 2-bromo-6-fluoro-pyridine (66 mg, 0.37 mmol) and 2-but-3-ynyl-benzo[d]thiazole (70 mg, 0.37 mmol, Example 35(A)). The crude residue was purified by flash chromatography (cyclohexane/AcOEt 7:3) to yield 31 mg (0.11 mmol, 29%) of 2-(4-(6-fluoropyridin-2-yl)but-3-ynyl)benzo[d]thiazole as a white solid.

LCMS (RT): 4.51 min; MS (ES+) gave m/z: 283.1.
Rf (cyclohexane/AcOEt 7:3)=0.2.
$^1$H-NMR (CDCl$_3$), δ (ppm): 3.05 (t, J=7.5, 2H), 3.46 (t, J=7.5, 2H), 6.87 (dd, J=2.4 and 8.2, 1H), 7.26 (d, J=1.6, 1H), 7.36-7.41 (m, 1H), 7.46-7.50 (m, 1H), 7.68-7.75 (m, 1H), 7.85-7.88 (m, 1H), 8.00 (d, J=8.1, 1H).

Example 118

2-(4-(Pyridin-2-yl)but-3-ynyl)quinoline

118(A) 2-(4-Trimethylsilanyl-but-3-ynyl)-quinoline

2-Methyl-quinoline (0.28 mL, 2.09 mmol) was added dropwise to a solution of LDA (3.0 mL, 0.8 M in THF) in THF (3 mL) at −78° C. and the reaction mixture was stirred for 1 hour at −78° C. Then (3-bromo-prop-1-ynyl)-trimethyl-silane (0.39 mL, 2.51 mmol) was added to the reaction mixture, the solution was stirred for 18 hours at room temperature and was quenched with water. The aqueous phase was extracted with DCM. The organic phase was washed with water, dried over MgSO$_4$, filtered and evaporated. The crude residue was purified by flash chromatography (cyclohexane/AcOEt 9:1) to yield 338 mg (1.33 mmol, 64%) of 2-(4-trimethylsilanyl-but-3-ynyl)-quinoline as a yellow solid.

LCMS (RT): 3.93 min; MS (ES+) gave m/z: 254.2.

118(B) 2-But-3-ynyl-quinoline

The title compound was prepared in accordance with the general method of Example 108(B), from 2-(4-trimethylsilanyl-but-3-ynyl)-quinoline (803 mg, 3.17 mmol). The crude residue was purified by flash chromatography (cyclohexane/AcOEt 94:6 to 90:10) to yield 419 mg (2.31 mmol, 73%) of 2-but-3-ynyl-quinoline as a yellow liquid.

LCMS (RT): 2.29 min; MS (ES+) gave m/z: 182.1.

118(C) 2-(4-(Pyridin-2-yl)but-3-ynyl)quinoline

The title compound was prepared in accordance with the general method of Example 1, from 2-bromo-pyridine (87 mg, 0.55 mmol) and 2-but-3-ynyl-quinoline (100 mg, 0.55 mmol). Reaction time: 120° C. for 15 minutes. The crude residue was purified by flash chromatography (cyclohexane/AcOEt 1:1) to yield 74 mg (0.29 mmol, 52%) of 2-(4-(pyridin-2-yl)but-3-ynyl)quinoline as a yellow oil.

LCMS (RT): 2.56 min; MS (ES+) gave m/z: 259.2.

$^1$H-NMR (CDCl$_3$), δ (ppm): 3.02 (t, J=7.5, 2H), 3.34 (t, J=7.5, 2H), 7.17-7.21 (m, 1H), 7.33 (d, J=7.8, 1H), 7.43 (d, J=8.4, 1H), 7.49-7.54 (m, 1H), 7.58-7.63 (m, 1H), 7.69-7.74 (m, 1H), 7.81 (d, J=8.1, 1H), 8.08 (d, J=8.4, 1H), 8.12 (d, J=8.4, 1H), 8.55 (d, J=4.7, 1H).

Example 119

2-(5-(Pyridin-2-yl)pent-4-ynyl)-2H-benzo[d][1,2,3]triazole

119(A) 5-Pyridin-2-yl-pent-4-yn-1-ol

The title compound was prepared in accordance with the general method of Example 1, from 2-bromopyridine (4.46 g, 28.2 mmol) and pent-4-yn-1-ol (2.50 g, 29.7 mmol). Reaction time: 14 hours. The crude residue was purified by flash chromatography (DCM/MeOH 97:3) to yield 4.00 g (24.8 mmol, 88%) of 5-pyridin-2-yl-pent-4-yn-1-ol as a brown oil.

119(B) 2-(5-Bromo-pent-1-ynyl)-pyridine

Br$_2$ (1.11 mL, 21.4 mmol) was added to a solution of triphenylphosphine (8.30 g, 30.7 mmol) in DCM (40 mL) at −5° C. A solution of 5-pyridin-2-yl-pent-4-yn-1-ol (3.00, 18.6 mmol) in DCM (10 mL) was added dropwise to the reaction mixture in order to maintain a temperature lower than 5° C. The reaction mixture was stirred for 5 hours at −10° C. and was quenched with a saturated solution of NaHCO$_3$. The aqueous phase was extracted with DCM. The resulting organic phase was washed with brine, dried over MgSO$_4$, filtered and evaporated. The crude residue was purified by flash chromatography (DCM/MeOH 99.5:0.5) to yield 2-(5-bromo-pent-1-ynyl)-pyridine (1.20 g, 5.35 mmol, 29%) with a purity of 50%.

119(C) 2-(5-(Pyridin-2-yl)pent-4-ynyl)-2H-benzo[d][1,2,3]triazole and 1-(5-(pyridin-2-yl)pent-4-ynyl)-1H-benzo[d][1,2,3]triazole The title compounds were prepared in accordance with the general method of Example 108(A), from 2-(5-bromo-pent-1-ynyl)-pyridine (298 mg, 0.66 mmol) and benzotriazole (72 mg, 0.60 mmol). The crude product was purified by flash chromatography (DCM/MeOH 99:1 to 98:2) to yield 2-(5-(pyridin-2-yl)pent-4-ynyl)-2H-benzo[d][1,2,3]triazole (27 mg, 0.1 mmol) as an orange oil and 1-(5-(pyridin-2-yl)pent-4-ynyl)-1H-benzo[d][1,2,3]triazole (27 mg, 0.1 mmol) as an orange solid.

2-(5-(pyridin-2-yl)pent-4-ynyl)-2H-benzo[d][1,2,3]triazole

LCMS (RT): 3.46 min; MS (ES+) gave m/z: 263.2.
Rf (DCM/MeOH 98:2)=0.2.
$^1$H-NMR (CDCl$_3$), δ (ppm): 2.43-2.50 (2H), 2.58 (t, J=6.8, 2H), 4.93 (t, J=6.8, 2H), 7.18-7.22 (m, 1H), 7.33-7.36 (m, 1H), 7.39 (dd, J=3.1 and 6.6, 2H), 7.59-7.64 (m, 1H), 7.87 (dd, J=3.1 and 6.6, 2H), 8.53-8.56 (m, 1H).

1-(5-(pyridin-2-yl)pent-4-ynyl)-1H-benzo[d][1,2,3]triazole

LCMS (RT): 3.14 min; MS (ES+) gave m/z: 263.2.
Rf (DCM/MeOH 98:2)=0.1.

$^1$H-NMR (CDCl$_3$), δ (ppm): 2.37-2.41 (2H), 2.52 (t, J=6.7, 2H), 4.85 (t, J=6.7, 2H), 7.21-7.25 (m, 1H), 7.35-7.40 (2H), 7.46-7.51 (m, 1H), 7.62-7.66 (2H), 8.04-8.08 (m, 1H), 8.58 (d, J=4.4, 1H).

Example 120

2-(4-(6-(Fluoromethyl)pyridin-2-yl)but-3-ynyl)-[1,2,4]triazolo[4,3-a]pyridin-3(2H)-one The title compound was prepared in accordance with the general method of Example 1, from 2-(but-3-ynyl)-[1,2,4]triazolo[4,3-a]pyridin-3(2H)-one (70 mg, 0.37 mmol, Example 39(A)) and 2-bromo-6-(fluoromethyl)pyridine (78 mg, 0.41 mmol, Example 190(E)). The crude residue was purified by flash chromatography (DCM/MeOH 98:2) to yield 20 mg (67 µmol, 18%) of 2-(4-(6-(fluoromethyl)pyridin-2-yl)but-3-ynyl)-[1,2,4]triazolo[4,3-a]pyridin-3(2H)-one as an orange solid (M.P.=106-107° C.).

LCMS (RT): 3.08 min; MS (ES+) gave m/z: 297.0.
Rf (DCM/MeOH 98:2)=0.05.
$^1$H-NMR (CDCl$_3$), δ (ppm): 3.00 (t, J=7.2, 2H), 4.29 (t, J=7.2, 2H), 5.36-5.54 (m, 2H), 6.46-6.52 (m, 1H), 7.09 (dd, J=1.2 and 3.6, 2H), 7.33 (d, J=7.8, 1H), 7.38 (d, J=7.8, 1H), 7.66-7.72 (m, 1H), 7.73-7.78 (m, 1H).

Example 121

2-(4-(1-Methyl-1H-pyrazol-3-yl)but-3-ynyl)benzo[d]thiazole

The title compound was prepared in accordance with the general method of Example 108(C), from 3-bromo-1-methyl-1H-pyrazole (100 mg, 0.62 mmol) and 2-but-3-ynyl-benzo[d]thiazole (233 mg, 1.24 mmol, Example 35(A)). The crude residue was purified by flash chromatography (cyclohexane/AcOEt 7:3) to yield 35 mg (0.13 mmol, 21%) of 2-(4-(1-methyl-1H-pyrazol-3-yl)but-3-ynyl)benzo[d]thiazole as a brown semi-solid.

LCMS (RT): 3.96 min; MS (ES+) gave m/z: 268.1.
Rf (cyclohexane/AcOEt 7:3)=0.2.

Example 122

2-(4-(4-Phenyl-1H-pyrazol-1-yl)but-1-ynyl)pyridine

122(A) 4-Phenyl-1-(4-trimethylsilanyl-but-3-ynyl)-1H-pyrazole

The title compound was prepared in accordance with the general method of Example 108(A), from 4-phenyl-1H-pyrazole (250 mg, 1.73 mmol) to yield 380 mg (1.42 mmol, 82%) of 4-phenyl-1-(4-trimethylsilanyl-but-3-ynyl)-1H-pyrazole.

122(B) 1-But-3-ynyl-4-phenyl-1H-pyrazole

The title compound was prepared in accordance with the general method of Example 108(B), from 4-phenyl-1-(4-trimethylsilanyl-but-3-ynyl)-1H-pyrazole (380 mg, 1.42 mmol). The crude residue was purified by flash chromatography (cyclohexane/AcOEt 9:1) to yield 80 mg (0.41 mmol, 29%) of 1-but-3-ynyl-4-phenyl-1H-pyrazole.

122(C) 2-(4-(4-Phenyl-1H-pyrazol-1-yl)but-1-ynyl)pyridine

The title compound was prepared in accordance with the general method of Example 1, from 80 mg (0.41 mmol) of 1-but-3-ynyl-4-phenyl-1H-pyrazole. The crude residue was purified by flash chromatography (DCM/MeOH 99:1 to 98:2) and SCX column (DCM, DCM/MeOH 97:3, DCM/MeOH/NH₄OH 94:5:1) to yield 2 mg (7 μmol, 2%) of 2-(4-(4-phenyl-1H-pyrazol-1-yl)but-1-ynyl)pyridine.

LCMS (RT): 3.76 min; MS (ES+) gave m/z: 274.1.
Rf (DCM/MeOH 98:2)=0.3.

Example 123

7-Chloro-2-(4-(pyridin-2-yl)but-3-ynyl)-2H-indazole

123(A) 7-Chloro-1H-indazole

A solution of 2-chloro-6-methyl-phenylamine (500 mg, 3.53 mmol) in H₂SO₄ (1.37 mL) was diluted by adding over 15 min. 2 mL of water in order to maintain a temperature below 90° C. Then the reaction mixture was cooled to 5-10° C. and a solution of sodium nitrite (246 mg, 3.57 mmol) in water (1 mL) was added over 2 hours. The resulting diazonium solution was then added to a solution of sodium acetate (5.21 g, 63.6 mmol) in water (20 mL) at a temperature maintained between 65 to 75° C. The resulting precipitate was filtered and treated with a solution of NaOH (6.00 g) in water (100 mL) at 95-100° C. The aqueous phase was separated while hot from the small amount of black tarry by-products, cooled to 50-60° C. and acidified with HCl (37%, 12.5 mL). The reaction mixture was cooled down to room temperature, the resulting precipitate was filtered, was washed thrice with cold water and was dried under vacuum to yield 7-chloro-1H-indazole (220 mg, 1.44 mmol, 41%) as a white solid.

123(B) 7-Chloro-2-(4-trimethylsilanyl-but-3-ynyl)-2H-indazole and 7-chloro-1-(4-trimethylsilanyl-but-3-ynyl)-1H-indazole The title compounds were prepared in accordance with the general method of Example 108(A), from 7-chloro-1H-indazole (220 mg, 1.44 mmol) to yield 250 mg (0.90 mmol, 63%) of 7-chloro-2-(4-trimethylsilanyl-but-3-ynyl)-2H-indazole and 7-chloro-1-(4-trimethylsilanyl-but-3-ynyl)-1H-indazole.

123(C) 2-But-3-ynyl-7-chloro-2H-indazole

The title compound was prepared in accordance with the general method of Example 108(B), from 7-chloro-2-(4-trimethylsilanyl-but-3-ynyl)-2H-indazole and 7-chloro-1-(4-trimethylsilanyl-but-3-ynyl)-1H-indazole (250 mg, 0.90 mmol). The crude residue was purified by flash chromatography (cyclohexane/AcOEt 9:1) to yield 44 mg (0.21 mmol, 23%) of 2-(but-3-ynyl)-7-chloro-2H-indazole as an orange oil.

123(D) 7-Chloro-2-(4-(pyridin-2-yl)but-3-ynyl)-2H-indazole

The title compound was prepared in accordance with the general method of Example 1, from 2-bromopyridine (36 mg, 0.23 mmol) and 2-but-3-ynyl-7-chloro-2H-indazole (44 mg, 0.21 mmol). Reaction time: 1 day. The crude residue was purified by flash chromatography (DCM/MeOH 98:2) to yield 11 mg (41 μmol, 19%) of 7-chloro-2-(4-(pyridin-2-yl)but-3-ynyl)-2H-indazole as a brown oil.

Rf (DCM/MeOH 98:2)=0.05.
LCMS (RT): 4.13 min; MS (ES+) gave m/z: 282.1.
¹H-NMR (CDCl₃), δ (ppm): 3.06 (t, J=7.5, 2H), 5.07 (t, J=7.5, 2H), 7.05-7.10 (m, 1H), 7.18-7.22 (m, 1H), 7.27-7.30 (m, 1H), 7.37 (dd, J=0.9 and 7.5, 1H), 7.58-7.63 (m, 1H), 7.64 (dd, J=0.9 and 8.0, 1H), 8.04 (s, 1H), 8.52-8.56 (m, 1H).

Example 124

2-(6-(Pyridin-2-yl)hex-5-ynyl)-2H-benzo[d][1,2,3]triazole

124(A) 6-Pyridin-2-yl-hex-5-yn-1-ol

The title compound was prepared in accordance with the general method of Example 1, from 2-bromopyridine (6.44 g, 40.8 mmol) and hex-5-yn-1-ol (4.00 g, 40.8 mmol). The crude residue was purified by flash chromatography (DCM/MeOH 1:1) to yield 5.56 g (31.7 mmol, 78%) of 6-pyridin-2-yl-hex-5-yn-1-ol as an orange oil.

124(B) 2-(6-Bromo-hex-1-ynyl)-pyridine

The title compound was prepared in accordance with the general method of Example 119(B), from 6-pyridin-2-yl-hex-5-yn-1-ol (1.00 g, 5.77 mmol). The crude residue was purified by flash chromatography (cyclohexane/AcOEt 1:1) to yield 2-(6-bromo-hex-1-ynyl)-pyridine (0.74 g, 3.10 mmol, 54%) as an orange oil.

LCMS (RT): 3.94 min; MS (ES+) gave m/z: 240.2.

124(C) 1-(6-(Pyridin-2-yl)hex-5-ynyl)-1H-benzo[d][1,2,3]triazole and 2-(6-(pyridin-2-yl)hex-5-ynyl)-2H-benzo[d][1,2,3]triazole The title compounds were prepared in accordance with the general method of Example 109(D), from 2-(6-bromo-hex-1-ynyl)-pyridine (250 mg, 1.05 mmol) and benzotriazole (125 mg, 1.05 mmol). The crude product was purified by flash chromatography (cyclohexane/AcOEt 3:2) to yield 2-(6-(pyridin-2-yl)hex-5-ynyl)-2H-benzo[d][1,2,3]triazole (38 mg, 0.14 mmol, 13%) as a brown oil and (cyclohexane/AcOEt 1:1) to yield 1-(6-(pyridin-2-yl)hex-5-ynyl)-1H-benzo[d][1,2,3]triazole (48 mg, 0.17 mmol, 16%) as a brown oil.

2-(6-(Pyridin-2-yl)hex-5-ynyl)-2H-benzo[d][1,2,3]triazole

LCMS (RT): 3.93 min; MS (ES+) gave m/z: 277.2.
Rf (DCM/MeOH 98:2)=0.2.
¹H-NMR (CDCl₃), δ (ppm): 1.68-1.73 (2H), 2.30-2.36 (2H), 2.53 (t, J=7.0, 2H), 4.81 (t, J=7.0, 2H), 7.19 (ddd, J=1.1, 4.9 and 7.6, 1H), 7.34-7.41 (3H), 7.59-7.64 (m, 1H), 7.84-7.89 (2H), 8.55 (d, J=4.3, 1H).

1-(6-(Pyridin-2-yl)hex-5-ynyl)-1H-benzo[d][1,2,3]triazole

LCMS (RT): 3.43 min; MS (ES+) gave m/z: 277.2.
Rf (cyclohexane/AcOEt 1:1)=0.2.
¹H-NMR (CDCl₃), δ (ppm): 1.65-1.73 (2H), 2.21-2.28 (2H), 2.53 (t, J=7.0, 2H), 4.72 (t, J=7.0, 2H), 7.20 (ddd, J=1.1, 4.9 and 7.6, 1H), 7.34 (d, J=7.8, 1H), 7.35-7.40 (m, 1H), 7.45-7.50 (m, 1H), 7.54-7.68 (m, 1H), 7.59-7.64 (m, 1H), 8.05-8.09 (m, 1H), 8.55 (d, J=4.4, 1H).

Example 125

2-(6-(Pyridin-2-yl)hex-5-ynyl)-2H-indazole

The title compounds were prepared in accordance with the general method of Example 109(D), from 2-(6-bromo-hex- 1-ynyl)-pyridine (250 mg, 1.05 mmol, Example 124(B)) and indazole (124 mg, 1.05 mmol). The crude product was purified by flash chromatography (cyclohexane/AcOEt 75:25) to yield 2-(6-(pyridin-2-yl)hex-5-ynyl)-2H-indazole (26 mg, 94 μmol, 9%) as a brown oil and (cyclohexane/AcOEt 1:1) to yield 1-(6-(pyridin-2-yl)hex-5-ynyl)-1H-indazole (15 mg, 54 μmol, 5%) as a brown oil.

2-(6-(Pyridin-2-yl)hex-5-ynyl)-2H-indazole

LCMS (RT): 3.93 min; MS (ES+) gave m/z: 276.2.
Rf (cyclohexane/AcOEt 1:1)=0.3.
$^1$H-NMR (CDCl$_3$), δ (ppm): 1.62-1.69 (2H), 2.11-2.18 (2H), 2.49 (t, J=7.0, 2H), 4.46 (t, J=7.0, 2H), 7.12-7.17 (m, 1H), 7.19 (ddd, J=1.1, 4.9 and 7.6, 1H), 7.32-7.35 (m, 1H), 7.35-7.39 (m, 1H), 7.44 (dd, J=0.9 and 8.5, 1H), 7.58-7.63 (m, 1H), 7.72-7.76 (m, 1H), 8.00 (d, J=0.9, 1H), 8.52-8.56 (m, 1H).

1-(6-(Pyridin-2-yl)hex-5-ynyl)-1H-indazole

LCMS (RT): 3.54 min; MS (ES+) gave m/z: 276.2.
Rf (cyclohexane/AcOEt 1:1)=0.2.
$^1$H-NMR (CDCl$_3$), δ (ppm): 1.64-1.71 (2H), 2.20-2.27 (2H), 2.51 (t, J=7.0, 2H), 4.50 (t, J=7.0, 2H), 7.09 (ddd, J=0.8, 6.6 and 8.4, 1H), 7.20 (ddd, J=1.1, 4.9 and 7.6, 1H), 7.28-7.31 (m, 1H), 7.36 (d, J=7.6, 1H), 7.59-7.64 (m, 1H), 7.64-7.67 (m, 1H), 7.70-7.73 (m, 1H), 7.95 (d, J=0.8, 1H), 8.55 (d, J=4.3, 1H).

Example 126

2-(4-(6-(Fluoromethyl)pyridin-2-yl)but-3-ynyl)quinoline

The title compound was prepared in accordance with the general method of Example 108(C), from 2-bromo-6-(fluoromethyl)-pyridine (157 mg, 0.83 mmol) and 2-but-3-ynyl-quinoline (150 mg, 0.83 mmol, Example 118(B)). Microwave conditions: 120° C. for 15 minutes. The crude residue was purified by flash chromatography (cyclohexane/AcOEt 4:1) to yield 127 mg (0.44 mmol, 53%) of 2-(4-(6-(fluoromethyl)pyridin-2-yl)but-3-ynyl)quinoline as an orange solid (M.P.=70.2-74.3° C.).

LCMS (RT): 2.98 min; MS (ES+) gave m/z: 291.2.
$^1$H-NMR (CDCl$_3$), δ (ppm): 3.03 (t, J=7.5, 2H), 3.33 (t, J=7.5, 2H), 5.40-5.53 (m, 2H), 7.29 (d, J=7.8, 1H), 7.38 (d, J=7.8, 1H), 7.40 (d, J=8.4, 1H), 7.49-7.54 (m, 1H), 7.65-7.70 (m, 1H), 7.70-7.74 (m, 1H), 7.81 (d, J=8.1, 1H), 8.07 (d, J=8.4, 1H), 8.11 (d, J=8.4, 1H).

Example 127

5-Fluoro-2-(4-(pyridin-2-yl)but-3-ynyl)-2H-benzo[d][1,2,3]triazole

127(A) 5-Fluoro-1H-benzo[d][1,2,3]triazole

A solution of sodium nitrite (284 mg, 4.12 mmol) in water (1 mL) was added to a solution of 4-fluoro-benzene-1,2-diamine (520 mg, 4.12 mmol) in acetic acid (0.50 mL) and water (2.50 mL) at 0° C. The reaction mixture was stirred for few minutes at 50° C. and 1 hour at 0° C. The precipitate was filtered, washed with cold water and dried to yield 5-fluoro-1H-benzo[d][1,2,3]triazole (565 mg, 3.50 mmol, 85%).

127(B) 5-Fluoro-2-(4-trimethylsilanyl-but-3-ynyl)-2H-benzo[d][1,2,3]triazole (4-Bromo-but-1-ynyl)-trimethyl-silane (294 mg, 1.43 mmol) was added to a solution of 5-fluoro-1H-benzo[d][1,2,3]triazole (187 mg, 1.36 mmol) in a solution of NaOH (2N, 955 μL). The reaction mixture was heated at 100° C. for 14 hours, then it was cooled down and was extracted with DCM. The organic phase was washed with water, brine, dried over MgSO$_4$, filtered and evaporated to yield 355 mg (1.36 mmol) 5-fluoro-2-(4-trimethylsilanyl-but-3-ynyl)-2H-benzo[d][1,2,3]triazole including the two others isomers.

127(C)
2-But-3-ynyl-5-fluoro-2H-benzo[d][1,2,3]triazole

The title compound was prepared in accordance with the general method of Example 108(B), from 5-fluoro-2-(4-trimethylsilanyl-but-3-ynyl)-2H-benzo[d][1,2,3]triazole (355 mg, 1.36 mmol). The crude residue was purified by flash chromatography (cyclohexane/AcOEt 9:1) to yield 27 mg (0.14 mmol, 10%) of 2-(but-3-ynyl)-5-fluoro-2H-benzo[d][1,2,3]triazole.

Rf (cyclohexane/AcOEt 9:1)=0.3.

127(D) 5-Fluoro-2-(4-(pyridin-2-yl)but-3-ynyl)-2H-benzo[d][1,2,3]triazole

The title compound was prepared in accordance with the general method of Example 1, from 2-bromopyridine (20 mg, 0.13 mmol) and 2-(but-3-ynyl)-5-fluoro-2H-benzo[d][1,2,3]triazole (24 mg, 0.13 mmol). Reaction time: 1 day. The crude residue was purified by flash chromatography (DCM/MeOH 99:1) and SCX column (DCM, DCM/MeOH 98:2 to DCM/MeOH/NH$_4$OH 95:4:1) to yield 7.6 mg (26 mmol, 21%) of 5-fluoro-2-(4-(pyridin-2-yl)but-3-ynyl)-2H-benzo[d][1,2,3]triazole as a yellow solid.

Rf (DCM/MeOH 97:3)=0.2.
LCMS (RT): 3.71 min; MS (ES+) gave m/z: 267.2.
$^1$H-NMR (CDCl$_3$), δ (ppm): 3.29 (t, J=7.5, 2H), 4.97 (t, J=7.5, 2H), 7.18-7.24 (2H), 7.32-7.36 (m, 1H), 7.47 (ddd, J=0.6, 2.4 and 8.7, 1H), 7.59-7.65 (m, 1H), 7.86 (ddd, J=0.6, 4.8 and 9.3, 1H), 8.53-8.57 (m, 1H).

Example 128

2-(4-(6-Methylpyridin-2-yl)but-3-ynyl)quinoline

The title compound was prepared in accordance with the general method of Example 108(C), from 2-bromo-6-methyl-pyridine (209 mg, 1.21 mmol) and 2-but-3-ynyl-quinoline (220 mg, 1.21 mmol Example 118(B)). Microwave conditions: 120° C. for 15 minutes. The crude residue was purified by flash chromatography (cyclohexane/AcOEt 1:1) to yield 98 mg (0.36 mmol, 30%) of 2-(4-(6-methylpyridin-2-yl)but-3-ynyl)quinoline as a yellow oil.

LCMS (RT): 2.44 min; MS (ES+) gave m/z: 273.2.
$^1$H-NMR (CDCl$_3$), δ (ppm): 2.54 (s, 3H), 3.01 (t, J=7.5, 2H), 3.32 (t, J=7.5, 2H), 7.05 (d, J=7.7, 1H), 7.15 (d, J=7.7, 1H), 7.41 (d, J=8.4, 1H), 7.46-7.50 (m, 1H), 7.49-7.54 (m, 1H), 7.68-7.73 (m, 1H), 7.78-7.82 (m, 1H), 8.07 (d, J=8.4, 1H), 8.11 (d, J=8.4, 1H).

Example 129

2-(4-(6-(Fluoromethyl)pyridin-2-yl)but-3-ynyl)quinoxaline

129(A) 2-(4-Trimethylsilanyl-but-3-ynyl)-quinoxaline

The title compound was prepared in accordance with the general method of Example 118(A), from 2-methyl-quinoxaline (0.47 mL, 3.47 mmol). The crude residue was purified by flash chromatography (cyclohexane/AcOEt 85:15) to yield 291 mg (1.11 mmol, 32%) of 2-(4-trimethylsilanyl-but-3-ynyl)-quinoxaline as an orange oil.

LCMS (RT): 5.16 min; MS (ES+) gave m/z: 255.1.

129(B) 2-But-3-ynyl-quinoxaline

The title compound was prepared in accordance with the general method of Example 108(B), from 2-(4-trimethylsilanyl-but-3-ynyl)-quinoxaline (291 mg, 1.11 mmol). The crude residue was purified by flash chromatography (cyclohexane/AcOEt 94:6 to 90:10) to yield 120 mg (0.66 mmol, 71%) of 2-but-3-ynyl-quinoxaline as a yellow liquid.

LCMS (RT): 3.59 min; MS (ES+) gave m/z: 183.1.

129(C) 2-(4-(6-(Fluoromethyl)pyridin-2-yl)but-3-ynyl)quinoxaline

The title compound was prepared in accordance with the general method of Example 108(C), from 2-bromo-6-(fluoromethyl)-pyridine (104 mg, 0.55 mmol) and 2-but-3-ynyl-quinoxaline (100 mg, 0.55 mmol). Microwave conditions: 120° C. for 15 minutes. The crude residue was purified by flash chromatography (cyclohexane/AcOEt 3:2) to yield 116 mg (0.40 mmol, 72%) of 2-(4-(6-(fluoromethyl)pyridin-2-yl)but-3-ynyl)quinoxaline as an orange solid (M.P.: 136° C. dec.).

LCMS (RT): 3.96 min; MS (ES+) gave m/z: 292.1.
$^1$H-NMR (CDCl$_3$), δ (ppm): 3.06 (t, J=7.4, 2H), 3.37 (t, J=7.4, 2H), 5.40-5.53 (m, 2H), 7.26-7.30 (m, 1H), 7.39 (d, J=7.8, 1H), 7.66-7.71 (m, 1H), 7.72-7.81 (2H), 8.06-8.12 (2H), 8.86 (s, 1H).

Example 130

2-(4-(6-(Fluoromethyl)pyridin-2-yl)but-3-ynyl)-2H-benzo[d][1,2,3]triazole hydrochloride

130(A) 2-(4-(6-(Fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (111 mg, 0.58 mmol, Example 190(E)) and 2-(but-3-ynyl)-2H-benzo[d][1,2,3]triazole (100 mg, 0.58 mmol, Example 109(D)). Reaction time: 3 hours. The crude residue was purified by flash chromatography (DCM/MeOH 99:1) to yield 61 mg (0.22 mmol, 37%) of 2-(4-(6-(fluoromethyl)pyridin-2-yl)but-3-ynyl)-2H-benzo[d][1,2,3]triazole as a grey solid.

Rf (DCM/MeOH 98:2)=0.2.
LCMS (RT): 4.06 min; MS (ES+) gave m/z: 281.1.
$^1$H-NMR, CDCl$_3$, δ (ppm): 3.31 (t, J=7.5, 2H), 5.00 (t, J=7.5, 2H), 5.40-5.53 (m, 2H), 7.29 (d, J=7.8, 1H), 7.39-7.43 (3H), 7.68-7.72 (m, 1H), 7.88 (dd, J=3.0 and 6.6, 2H).

130(B) 2-(4-(6-(Fluoromethyl)pyridin-2-yl)but-3-ynyl)-2H-benzo[d][1,2,3]triazole hydrochloride The title compound was prepared in accordance with the general method of Example 109(F), from 2-(4-(6-(fluoromethyl)pyridin-2-yl)but-3-ynyl)-2H-benzo[d][1,2,3]triazole (60 mg, 0.21 mmol) to yield 2-(4-(6-(fluoromethyl)pyridin-2-yl)but-3-ynyl)-2H-benzo[d][1,2,3]triazole hydrochloride (33 mg, 0.11 mmol, 48%) as a white solid (M.P.: 172.5-173.5° C.).

LCMS (RT): 4.08 min; MS (ES+) gave m/z: 281.2.
$^1$H-NMR CDCl$_3$, δ (ppm): 1.72-2.80 (br. s, 1H), 3.36 (t, J=7.0, 2H), 5.03 (t, J=7.0, 2H), 5.64-5.78 (m, 2H), 7.38-7.42 (3H), 7.58 (d, J=8.0, 1H), 7.87 (dd, J=3.0 and 6.5, 2H), 7.89-7.94 (m, 1H).

Example 131

4,6-Difluoro-2-(4-(6-(fluoromethyl)pyridin-2-yl)but-3-ynyl)-2H-benzo[d][1,2,3]triazole hydrochloride

131(A) 5,7-Difluoro-1H-benzo[d][1,2,3]triazole

The title compound was prepared in accordance with the general method of Example 127(A), from 3,5-difluorobenzene-1,2-diamine (520 mg, 3.61 mmol) to yield 5,7-difluoro-1H-benzo[d][1,2,3]triazole (492 mg, 3.17 mmol, 88%) as a dark solid.

131(B) 2-(But-3-ynyl)-4,6-difluoro-2H-benzo[d][1,2,3]triazole

The title compound was prepared in accordance with the general method of Example 109(D), from 5,7-difluoro-1H-benzo[d][1,2,3]triazole (271 mg, 1.75 mmol). The crude residue was purified by flash chromatography (cyclohexane/AcOEt 9:1) to yield 100 mg (0.48 mmol, 33%) of 2-(but-3-ynyl)-4,6-difluoro-2H-benzo[d][1,2,3]triazole.

Rf (DCM/MeOH 9:1)=0.3.

131(C) 4,6-Difluoro-2-(4-(6-(fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (50 mg, 0.27 mmol) and 2-(but-3-ynyl)-4,6-difluoro-2H-benzo[d][1,2,3]triazole (50 mg, 0.24 mmol). Reaction time: 3 hours. The crude residue was purified by flash chromatography (DCM/MeOH 99:1) to yield 45 mg (0.14 mol, 53%) of 4,6-difluoro-2-(4-(6-(fluoromethyl)pyridin-2-yl)but-3-ynyl)-2H-benzo[d][1,2,3]triazole as a brown oil.

Rf (DCM/MeOH 98:2)=0.2.
LCMS (RT): 4.44 min; MS (ES+) gave m/z: 317.1.
$^1$H-NMR, δ (ppm): 3.31 (t, J=7.3, 2H), 4.99 (t, J=7.3, 2H), 5.42 (s, 1H), 5.51 (s, 1H), 6.89-6.95 (m, 1H), 7.28-7.33 (2H), 7.41 (d, J=7.8, 1H), 7.68-7.73 (m, 1H).

131(D) 4,6-Difluoro-2-(4-(6-(fluoromethyl)pyridin-2-yl)but-3-ynyl)-2H-benzo[d][1,2,3]triazole hydrochloride The title compound was prepared in accordance with the general method of Example 109(F), from 4,6-difluoro-2-(4-(6-(fluoromethyl)pyridin-2-yl)but-3-ynyl)-2H-benzo[d][1,2,3]triazole (45 mg) to yield the corresponding hydrochloride (50 mg, 0.14 mmol) as a white solid (M.P.: 128-130° C.).

LCMS (RT): 4.46 min; MS (ES+) gave m/z: 317.1.
$^1$H-NMR, δ (ppm): 3.40 (t, J=7.1, 2H), 5.07 (t, J=7.1, 2H), 5.40-5.53 (m, 2H), 6.89-6.95 (m, 1H), 7.31 (dd, J=2.0 and 8.2, 1H), 7.54 (d, J=7.9, 1H), 7.74 (d, J=7.9, 1H), 8.08-8.13 (m, 1H).

Example 132

4,5-Difluoro-2-(4-(6-(fluoromethyl)pyridin-2-yl)but-3-ynyl)-2H-benzo[d][1,2,3]triazole hydrochloride

132(A) 4,5-Difluoro-1H-benzo[d][1,2,3]triazole

The title compound was prepared in accordance with the general method of Example 127(A), from 3,4-difluorobenzene-1,2-diamine (490 mg, 3.40 mmol) to yield 4,5-difluoro-1H-benzo[d][1,2,3]triazole (485 mg, 3.13 mmol, 92%).

132(B) 2-(But-3-ynyl)-4,5-difluoro-2H-benzo[d][1,2,3]triazole

The title compound was prepared in accordance with the general method of Example 109(D), from 4,5-difluoro-1H-benzo[d][1,2,3]triazole (266 mg, 1.71 mmol). The crude residue was purified by flash chromatography (cyclohexane/AcOEt 9:1) to yield 100 mg (0.48 mmol, 34%) of 2-(but-3-ynyl)-4,5-difluoro-2H-benzo[d][1,2,3]triazole.

Rf (DCM/MeOH 9:1)=0.2.

132(C) 4,5-Difluoro-2-(4-(6-(fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (50 mg, 0.27 mmol) and 2-(but-3-ynyl)-4,5-difluoro-2H-benzo[d][1,2,3]triazole (50 mg, 0.24 mmol). Reaction time: 13 hours. The crude residue was purified by flash chromatography (DCM/MeOH 99:1) to yield 45 mg (0.14 mmol, 59%) of 4,5-difluoro-2-(4-(6-(fluoromethyl)pyridin-2-yl)but-3-ynyl)-2H-benzo[d][1,2,3]triazole.

Rf (DCM/MeOH 98:2)=0.2.

LCMS (RT): 4.43 min; MS (ES+) gave m/z: 317.1.

$^1$H-NMR, δ (ppm): 3.31 (t, J=7.3, 2H), 5.00 (t, J=7.3, 2H), 5.40-5.53 (m, 2H), 7.26-7.32 (2H), 7.41 (d, J=7.8, 1H), 7.64 (dd, J=1.3, 3.7 and 9.2, 1H), 7.68-7.73 (m, 1H).

132(D) 4,5-Difluoro-2-(4-(6-(fluoromethyl)pyridin-2-yl)but-3-ynyl)-2H-benzo[d][1,2,3]triazole hydrochloride The title compound was prepared in accordance with the general method of Example 109(F), from 4,5-difluoro-2-(4-(6-(fluoromethyl)pyridin-2-yl)but-3-ynyl)-2H-benzo[d][1,2,3]triazole (45 mg, 0.14 mmol) to yield the corresponding hydrochloride (50 mg, 0.14 mmol) as a white solid (M.P.: 157-159° C.).

LCMS (RT): 4.41 min; MS (ES+) gave m/z: 317.1.

$^1$H-NMR (DMSO[D]$_6$), δ (ppm): 3.32 (t, J=6.7, 2H), 5.04 (t, J=6.7, 2H), 5.32-5.45 (m, 2H), 5.40-5.70 (br. s, 1H), 7.31 (d, J=7.8, 1H), 7.42 (d, J=7.8, 1H), 7.55-7.61 (m, 1H), 7.80-7.85 (m, 1H), 7.89 (ddd, J=0.9, 3.8 and 9.3, 1H).

Example 133

2-(4-(6-(Fluoromethyl)pyridin-2-yl)but-3-ynyl)-2H-indazole

The title compound was prepared in accordance with the general method of Example 108(C), from 2-bromo-6-(fluoromethyl)-pyridine (204 mg, 1.07 mmol) and 2-but-3-ynyl-2H-indazole (183 mg, 1.07 mmol). The crude residue was purified by flash chromatography (cyclohexane/AcOEt 3:2) to yield 50 mg (0.18 mmol, 17%) of 2-(4-(6-(fluoromethyl)pyridin-2-yl)but-3-ynyl)-2H-indazole as a colorless oil.

$^1$H-NMR (CDCl$_3$), δ (ppm): 3.07 (t, J=7.3, 2H), 4.68 (t, J=7.3, 2H), 5.40-5.53 (m, 2H), 7.12 (d, J=7.7, 1H), 7.14-7.19 (m, 1H), 7.37-7.41 (2H), 7.52 (d, J=8.5, 1H), 7.64-7.69 (m, 1H), 7.75 (d, J=8.1, 1H), 8.04 (s, 1H).

Example 134

2-(4-(6-(Difluoromethyl)pyridin-2-yl)but-3-ynyl)-2H-benzo[d][1,2,3]triazole

134(A) 2-Bromo-6-difluoromethyl-pyridine

DAST (0.99 mL, 8.06 mmol) was added dropwise to a solution of 6-bromo-pyridine-2-carbaldehyde (1.00 g, 5.38 mmol) in DCM (28 mL) at 0° C. The reaction mixture was stirred for 24 hours at room temperature, quenched by the addition of saturated aqueous solution of NaHCO$_3$ and extracted twice with DCM. The organic phase was washed with water, dried over MgSO$_4$, filtered and evaporated. The crude residue was purified by flash chromatography (cyclohexane/AcOEt 9:1) to yield 0.74 g (3.56 mmol, 66%) of 2-bromo-6-difluoromethyl-pyridine as a yellow oil.

134(B) 2-(4-(6-(Difluoromethyl)pyridin-2-yl)but-3-ynyl)-2H-benzo[d][1,2,3]triazole The title compound was prepared in accordance with the general method of Example 1, from 2-bromo-6-(difluoromethyl)-pyridine (121 mg, 0.58 mmol) and 2-(but-3-ynyl)-2H-benzo[d][1,2,3]triazole (100 mg, 0.58 mmol, Example 109 (D)). Reaction time: 2 hours. The crude residue was purified by preparative chromatography plate (DCM/MeOH 99:1) to yield 15 mg (49 µmol, 8%) of 2-(4-(6-(difluoromethyl)pyridin-2-yl)but-3-ynyl)-2H-benzo[d][1,2,3]triazole as a white solid (M.P.: 101.8-102.9° C.).

LCMS (RT): 4.31 min; MS (ES+) gave m/z: 299.1.

$^1$H-NMR CDCl$_3$, δ (ppm): 3.32 (t, J=7.4, 2H), 5.01 (t, J=7.4, 2H), 6.49-6.71 (m, 1H), 7.38-7.45 (3H), 7.58 (d, J=7.7, 1H), 7.76-7.81 (m, 1H), 7.89 (dd, J=3.1 and 6.6, 2H).

Example 135

4,6-Difluoro-2-(4-(pyridin-2-yl)but-3-ynyl)-2H-benzo[d][1,2,3]triazole

135(A) 5,7-Difluoro-1H-benzo[d][1,2,3]triazole

The title compound was prepared in accordance with the general method of Example 127(A), from 3,5-difluorobenzene-1,2-diamine (520 mg, 3.61 mmol) to yield 5,7-difluoro-1H-benzo[d][1,2,3]triazole (492 mg, 3.17 mmol, 88%).

135(B) 2-(But-3-ynyl)-4,6-difluoro-2H-benzo[d][1,2,3]triazole

The title compound was prepared in accordance with the general method of Example 109(D), from 5,7-difluoro-1H-benzo[d][1,2,3]triazole (271 mg, 1.75 mmol). The crude residue was purified by flash chromatography (cyclohexane/AcOEt 9:1) to yield 100 mg (0.48 mmol, 33%) of 2-(but-3-ynyl)-4,6-difluoro-2H-benzo[d][1,2,3]triazole.

Rf (cyclohexane/AcOEt 9:1)=0.3.

135(C) 4,6-Difluoro-2-(4-(pyridin-2-yl)but-3-ynyl)-2H-benzo[d][1,2,3]triazole The title compound was prepared in accordance with the general method of Example 1, from 2-bromopyridine (42 mg, 0.26 mmol) and 2-(but-3-ynyl)-4,6-difluoro-2H-benzo[d][1,2,3]triazole (50 mg, 0.24 mmol). Reaction time: 3 hours. The crude residue was purified by flash chromatography (DCM/MeOH 99:1) to yield 31 mg (0.11 mmol, 46%) of 4,6-difluoro-2-(4-(pyridin-2-yl)but-3-ynyl)-2H-benzo[d][1,2,3]triazole as a yellow solid.

Rf (DCM/MeOH 99:1)=0.1.
LCMS (RT): 4.03 min; MS (ES+) gave m/z: 285.1.
$^1$H-NMR (CDCl$_3$), δ (ppm): 3.30 (t, J=7.4, 2H), 4.99 (t, J=7.4, 2H), 6.88-6.94 (m, 1H), 7.18-7.24 (m, 1H), 7.32 (dd, J=2.0 and 8.3, 1H), 7.35 (d, J=7.8, 1H), 7.60-7.65 (m, 1H), 8.55 (d, J=4.8, 1H).

Example 136

4,5-Difluoro-2-(4-(pyridin-2-yl)but-3-ynyl)-2H-benzo[d][1,2,3]triazole

136(A) 4,5-Difluoro-1H-benzo[d][1,2,3]triazole

The title compound was prepared in accordance with the general method of Example 127(A), from 3,4-difluorobenzene-1,2-diamine (490 mg, 3.40 mmol) to yield 4,5-difluoro-1H-benzo[d][1,2,3]triazole (485 mg, 3.13 mmol, 92%).

136(B) 2-(But-3-ynyl)-4,5-difluoro-2H-benzo[d][1,2,3]triazole

The title compound was prepared in accordance with the general method of Example 109(D) from 4,5-difluoro-1H-benzo[d][1,2,3]triazole (266 mg, 1.71 mmol). The crude residue was purified by flash chromatography (cyclohexane/AcOEt 9:1) to yield 100 mg (0.48 mmol, 33%) of 2-(but-3-ynyl)-4,5-difluoro-2H-benzo[d][1,2,3]triazole.

Rf (DCM/MeOH 9:1)=0.2.

136(C) 4,5-Difluoro-2-(4-(pyridin-2-yl)but-3-ynyl)-2H-benzo[d][1,2,3]triazole

The title compound was prepared in accordance with the general method of Example 1, from 2-bromopyridine (42 mg, 0.26 mmol) and 2-(but-3-ynyl)-4,5-difluoro-2H-benzo[d][1,2,3]triazole (50 mg, 0.24 mmol). Reaction time: 13 hours. The crude residue was purified by flash chromatography (DCM/MeOH 99:1) to yield 41 mg (0.14 mmol, 60%) of 4,5-difluoro-2-(4-(pyridin-2-yl)but-3-ynyl)-2H-benzo[d][1,2,3]triazole as a yellow solid.

Rf (DCM/MeOH 99:1)=0.1.
LCMS (RT): 4.01 min; MS (ES+) gave m/z: 285.2.
$^1$H-NMR (CDCl$_3$), δ (ppm): 3.31 (t, J=7.4, 2H), 5.00 (t, J=7.4, 2H), 7.20-7.24 (m, 1H), 7.26-7.32 (m, 1H), 7.35 (d, J=7.8, 1H), 7.60-7.66 (2H), 8.55 (d, J=4.8, 1H).

Example 137

2-(4-(6-Methylpyridin-2-yl)but-3-ynyl)-2H-benzo[d][1,2,3]triazole

The title compound was prepared in accordance with the general method of Example 1, from 2-bromo-6-methylpyridine (55 mg, 0.32 mmol) and 2-(but-3-ynyl)-2H-benzo[d][1,2,3]triazole (50 mg, 0.29 mmol, Example 109(D)). Reaction time: 13 hours. The crude residue was purified by flash chromatography (DCM/MeOH 99:1) to yield 40 mg (0.15 mmol, 53%) of 2-(4-(6-methylpyridin-2-yl)but-3-ynyl)-2H-benzo[d][1,2,3]triazole as a yellow solid.

Rf (DCM/MeOH 98:2)=0.2.
LCMS (RT): 3.23 min; MS (ES+) gave m/z: 263.2.
$^1$H-NMR (CDCl$_3$), δ (ppm): 2.54 (s, 3H), 3.30 (t, J=7.6, 2H), 5.00 (t, J=7.6, 2H), 7.08 (d, J=7.7, 1H), 7.17 (d, J=7.7, 1H), 7.40 (dd, J=3.1 and 6.6, 2H), 7.48-7.53 (m, 1H), 7.88 (dd, J=3.1 and 6.6, 2H).

Example 138

2-(4-(3-Fluoropyridin-2-yl)but-3-ynyl)-2H-benzo[d][1,2,3]triazole

The title compound was prepared in accordance with the general method of Example 1, from 2-chloro-3-fluoropyridine (42 mg, 0.32 mmol) and 2-(but-3-ynyl)-2H-benzo[d][1,2,3]triazole (50 mg, 0.29 mmol, Example 109(D)). Reaction time: 13 hours. The crude residue was purified by flash chromatography (DCM/MeOH 99:1) to yield 21 mg (80 μmol, 27%) of 2-(4-(3-fluoropyridin-2-yl)but-3-ynyl)-2H-benzo[d][1,2,3]triazole as a yellow solid.

Rf (DCM/MeOH 98:2)=0.1.
LCMS (RT): 3.91 min; MS (ES+) gave m/z: 267.2.
$^1$H-NMR (CDCl$_3$), δ (ppm): 3.37 (t, J=7.6, 2H), 5.03 (t, J=7.6, 2H), 7.23-7.29 (2H), 7.38-7.43 (2H), 7.89 (dd, J=3.0 and 6.6, 2H), 8.35-8.40 (m, 1H).

Example 139

5-Fluoro-2-(4-(6-(fluoromethyl)pyridin-2-yl)but-3-ynyl)-2H-benzo[d][1,2,3]triazole 139(A) 5-Fluoro-1H-benzo[d][1,2,3]triazole The title compound was prepared in accordance with the general method of Example 127(A), from 4-fluorobenzene-1,2-diamine (500 mg, 3.96 mmol) to yield 5-fluoro-1H-benzo[d][1,2,3]triazole (376 mg, 2.74 mmol, 69%) as a dark solid.

139(B) 2-(But-3-ynyl)-5-fluoro-2H-benzo[d][1,2,3]triazole

The title compound was prepared in accordance with the general method of Example 109(D), from 5-fluoro-1H-benzo[d][1,2,3]triazole (360 mg, 2.63 mmol). The crude residue was purified by flash chromatography (cyclohexane/AcOEt 9:1) to yield 137 mg (0.72 mmol, 32%) of 2-(but-3-ynyl)-5-fluoro-2H-benzo[d][1,2,3]triazole.

Rf (cyclohexane/AcOEt 9:1)=0.3.

139(C) 5-Fluoro-2-(4-(6-(fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (55 mg, 0.29 mmol) and 2-(but-3-ynyl)-5-fluoro-2H-benzo[d][1,2,3]triazole (50 mg, 0.26 mmol). Reaction time: 13 hours. The crude residue was purified by flash chromatography (DCM/MeOH 99:1) to yield 50 mg (0.17 mmol, 64%) of 5-fluoro-2-(4-(6-fluoromethyl)pyridin-2-yl)but-3-ynyl)-2H-benzo[d][1,2,3]triazole as a yellow solid.

Rf (DCM/MeOH 99:1)=0.1.
LCMS (RT): 4.26 min; MS (ES+) gave m/z: 299.2.
$^1$H-NMR (CDCl$_3$), δ (ppm): 3.29 (t, J=7.4, 2H), 4.97 (t, J=7.4, 2H), 5.40-5.53 (m, 2H), 7.18-7.24 (m, 1H), 7.28 (d, J=7.8, 1H), 7.41 (d, J=7.8, 1H), 7.47 (ddd, J=0.5, 2.3 and 8.7, 1H), 7.68-7.72 (m, 1H), 7.86 (ddd, J=0.5, 4.8 and 9.2, 1H).

Example 140

2-(4-(4-(4-Fluorophenyl)-1H-pyrazol-1-yl)but-1-ynyl)pyridine

140(A) 1-But-3-ynyl-4-(4-fluoro-phenyl)-1H-pyrazole

The title compound was prepared in accordance with the general method of Example 109(D), from 4-(4-fluoro-phenyl)-1H-pyrazole (255 mg, 1.57 mmol). The crude residue was purified by flash chromatography (cyclohexane/AcOEt 9:1) to yield 223 mg (1.04 mmol, 73%) of 1-but-3-ynyl-4-(4-fluoro-phenyl)-1H-pyrazole.

140(B) 2-(4-(4-(4-Fluorophenyl)-1H-pyrazol-1-yl)but-1-ynyl)pyridine

The title compound was prepared in accordance with the general method of Example 1, from 50 mg (0.23 mmol) of 1-but-3-ynyl-4-(4-fluoro-phenyl)-1H-pyrazole. Reaction time: 13 hours. The crude residue was purified by flash chromatography (DCM/MeOH 98:2) and SCX column (DCM, DCM/MeOH 95:5, DCM/MeOH/NH$_4$OH 94:5:1) to yield 2 mg (7 µmol, 3%) of 2-(4-(4-(4-fluorophenyl)-1H-pyrazol-1-yl)but-1-ynyl)pyridine as a yellow solid.

LCMS (RT): 3.88 min; MS (ES+) gave m/z: 292.2.
Rf (DCM/MeOH 98:2)=0.3.
$^1$H-NMR (CDCl$_3$), δ (ppm): 3.05 (t, J=6.9, 2H), 4.42 (t, J=6.9, 2H), 7.03-7.27 (2H), 7.19-7.24 (m, 1H), 7.34 (d, J=7.8, 1H), 7.41-7.45 (2H), 7.58-7.64 (m, 1H), 7.76 (d, J=8.3, 2H), 8.55-8.59 (m, 1H).

Example 141

2-(4-(2-Methylthiazol-4-yl)but-3-ynyl)-2H-benzo[d][1,2,3]triazole

The title compound was prepared in accordance with the general method of Example 1, from 4-bromo-2-methylthiazole (30 mg, 0.13 mmol) and 2-(but-3-ynyl)-2H-benzo[d][1,2,3]triazole (30 mg, 0.17 mmol, Example 109(D)). Reaction time: 13 hours. The crude residue was purified by flash chromatography (DCM/MeOH 98:2) to yield 18 mg (66 µmol, 50%) of 2-(4-(2-methylthiazol-4-yl)but-3-ynyl)-2H-benzo[d][1,2,3]triazole as a yellow solid.

Rf (DCM/MeOH 98:2)=0.2.
LCMS (RT): 4.01 min; MS (ES+) gave m/z: 269.1.
$^1$H-NMR (CDCl$_3$), δ (ppm): 2.69 (s, 3H), 3.27 (t, J=7.6, 2H), 4.97 (t, J=7.6, 2H), 7.20 (s, 1H), 7.40 (dd, J=3.1 and 6.6, 2H), 7.88 (dd, J=3.1 and 6.6, 2H).

Example 142

2-(4-(4-o-Tolyl-1H-pyrazol-1-yl)but-1-ynyl)pyridine

142(A) 1-But-3-ynyl-4-o-tolyl-1H-pyrazole

The title compound was prepared in accordance with the general method of Example 109(D), from 4-o-tolyl-1H-pyrazole (325 mg, 2.05 mmol). The crude residue was purified by flash chromatography (cyclohexane/AcOEt 9:1) to yield 318 mg (1.51 mmol, 88%) of 1-but-3-ynyl-4-o-tolyl-1H-pyrazole.

142(B) 2-(4-(4-o-Tolyl-1H-pyrazol-1-yl)but-1-ynyl)pyridine

The title compound was prepared in accordance with the general method of Example 1, from 50 mg (0.24 mmol) of 1-but-3-ynyl-4-o-tolyl-1H-pyrazole. Reaction time: 13 hours. The crude residue was purified by flash chromatography (DCM/MeOH 98:2) and SCX column (DCM, DCM/MeOH 95:5, DCM/MeOH/NH$_4$OH 94:5:1) to yield 2 mg (9 µmol, 4%) of 2-(4-(4-o-tolyl-1H-pyrazol-1-yl)but-1-ynyl)pyridine as an orange oil.

LCMS (RT): 4.03 min; MS (ES+) gave m/z: 288.2.
Rf (DCM/MeOH 98:2)=0.2.
$^1$H-NMR (CDCl$_3$), δ (ppm): 2.37 (s, 3H), 3.07 (t, J=6.9, 2H), 4.45 (t, J=6.9, 2H), 7.17-7.25 (4H), 7.32-7.36 (2H), 7.59-7.64 (m, 1H), 7.65 (s, 1H), 7.68 (s, 1H), 8.54-8.58 (m, 1H).

Example 143

2-(Fluoromethyl)-6-(4-(4-o-tolyl-1H-pyrazol-1-yl)but-1-ynyl)pyridine

The title compound was prepared in accordance with the general method of Example 1, from 2-bromo-6-(fluoromethyl)-pyridine (50 mg, 0.26 mmol) and 1-but-3-ynyl-4-o-tolyl-1H-pyrazole (50 mg, 0.24 mmol, Example 142(A)). Reaction time: 3 hours. The crude residue was purified by flash chromatography (DCM/MeOH 98:2) to yield 23 mg (72 µmol, 30%) of 2-(fluoromethyl)-6-(4-(4-o-tolyl-1H-pyrazol-1-yl)but-1-ynyl)pyridine as a yellow solid with a purity of 81%.

Rf (DCM/MeOH 98:2)=0.2.
LCMS (RT): 4.43 min; MS (ES+) gave m/z: 320.2.
$^1$H-NMR (CDCl$_3$), δ (ppm): 2.37 (s, 3H), 3.07 (t, J=6.9, 2H), 4.44 (t, J=6.9, 2H), 5.40-5.53 (m, 2H), 7.17-7.25 (3H), 7.27-7.32 (m, 1H), 7.32-7.43 (2H), 7.65 (s, 1H), 7.68 (s, 1H), 7.68-7.72 (m, 1H).

Example 144

2-(Fluoromethyl)-6-(4-(4-(4-fluorophenyl)-1H-pyrazol-1-yl)but-1-ynyl)pyridine The title compound was prepared in accordance with the general method of Example 1, from 2-bromo-6-(fluoromethyl)-pyridine (49 mg, 0.26 mmol) and 1-but-3-ynyl-4-(4-fluoro-phenyl)-1H-pyrazole (50 mg, 0.23 mmol, Example 140(A)). Reaction time: 13 hours. The crude residue was purified by flash chromatography (DCM/MeOH 98:2) to yield 29 mg (88 µmol, 38%) of 2-(fluoromethyl)-6-(4-(4-(4-fluorophenyl)-1H-pyrazol-1-yl)but-1-ynyl)pyridine as a yellow solid.

Rf (DCM/MeOH 98:2)=0.2.
LCMS (RT): 4.29 min; MS (ES+) gave m/z: 324.2.
$^1$H-NMR (CDCl$_3$), δ (ppm): 3.05 (t, J=6.9, 2H), 4.42 (t, J=6.9, 2H), 5.40-5.53 (m, 2H), 7.03-7.18 (2H), 7.27-7.32 (m, 1H), 7.38-7.45 (3H), 7.66-7.71 (m, 1H), 7.73 (s, 1H), 7.77 (s, 1H).

Example 145

6-Fluoro-2-(4-(6-(fluoromethyl)pyridin-2-yl)but-3-ynyl)quinoxaline

145(A) 6-Fluoro-2-methyl-quinoxaline

A solution of 2-oxo-propionaldehyde (0.19 mL, 1.20 mmol) and 4-fluoro-benzene-1,2-diamine (150 mg, 1.19 mmol) in water (1.3 mL) was placed in a microwave tube and heated for 1 min. at 150 W. Then the reaction mixture was diluted with water and extracted twice with AcOEt. The organic phase was washed with water, brine, dried over MgSO$_4$, filtered and evaporated. The crude residue was purified by flash chromatography (cyclohexane/AcOEt 4:1) to yield 154 mg (0.95 mmol, 80%) of 6-fluoro-2-methyl-quinoxaline.

LCMS (RT): 3.24 min; MS (ES+) gave m/z: 163.2.

145(B) 6-Fluoro-2-(4-trimethylsilanyl-but-3-ynyl)-quinoxaline

The title compound was prepared in accordance with the general method of Example 118(A), from 6-fluoro-2-methyl-quinoxaline (100 mg, 0.62 mmol). The crude residue was purified by flash chromatography (cyclohexane/AcOEt 4:1) to yield 66 mg (0.24 mmol, 39%) of 6-fluoro-2-(4-trimethylsilanyl-but-3-ynyl)-quinoxaline as an orange oil.

LCMS (RT): 5.34 min; MS (ES+) gave m/z: 273.3.

145(C) 2-But-3-ynyl-6-fluoro-quinoxaline

The title compound was prepared in accordance with the general method of Example 108(B), from 6-fluoro-2-(4-trimethylsilanyl-but-3-ynyl)-quinoxaline (298 mg, 1.09 mmol). The crude residue was purified by flash chromatography (cyclohexane/AcOEt 94:6 to 90:10) to yield 90 mg (0.45 mmol, 41%) of 2-but-3-ynyl-6-fluoro-quinoxaline as a yellow liquid.

LCMS (RT): 3.89 min; MS (ES+) gave m/z: 201.2.

145(D) 6-Fluoro-2-(4-(6-(fluoromethyl)pyridin-2-yl)but-3-ynyl)quinoxaline

The title compound was prepared in accordance with the general method of Example 108(C), from 2-bromo-6-(fluoromethyl)-pyridine (43 mg, 0.22 mmol) and 2-but-3-ynyl-6-fluoro-quinoxaline (45 mg, 0.22 mmol). Microwave conditions: 120° C. for 15 minutes. The crude residue was purified by flash chromatography (cyclohexane/AcOEt 3:2) to yield 45 mg (0.15 mmol, 65%) of 6-fluoro-2-(4-(6-(fluoromethyl)pyridin-2-yl)but-3-ynyl)quinoxaline as an orange solid with a purity of 85%.

LCMS (RT): 4.21 min; MS (ES+) gave m/z: 310.3.
$^1$H-NMR (CDCl$_3$), δ (ppm): 3.05 (t, J=7.3, 2H), 3.36 (t, J=7.3, 2H), 5.40-5.53 (m, 2H), 7.26-7.30 (m, 1H), 7.39 (d, J=7.8, 1H), 7.49-7.55 (m, 1H), 7.65-7.71 (2H), 8.10 (dd, J=5.8 and 9.2, 1H), 8.82 (s, 1H).

Example 146

4-Chloro-2-(4-(pyridin-2-yl)but-3-ynyl)-2H-benzo[d][1,2,3]triazole

146(A) 4-Chloro-1H-benzo[d][1,2,3]triazole

The title compound was prepared in accordance with the general method of Example 127(A), from 3-chlorobenzene-1,2-diamine (1.00 g, 7.01 mmol) to yield 4-chloro-1H-benzo[d][1,2,3]triazole (975 mg, 6.35 mmol, 91%) as a dark solid.

146(B) 2-(But-3-ynyl)-4-chloro-2H-benzo[d][1,2,3]triazole

The title compound was prepared in accordance with the general method of Example 109(D), from 4-chloro-1H-benzo[d][1,2,3]triazole (504 mg, 3.28 mmol). The crude residue was purified by flash chromatography (cyclohexane/AcOEt 93:7) to yield 60 mg (0.29 mmol, 10%) of 2-(but-3-ynyl)-4-chloro-2H-benzo[d][1,2,3]triazole as a yellow solid.

Rf (DCM/MeOH 97:3)=0.3.

146(C) 4-Chloro-2-(4-(pyridin-2-yl)but-3-ynyl)-2H-benzo[d][1,2,3]triazole

The title compound was prepared in accordance with the general method of Example 1, from 2-bromo-pyridine (25 mg, 0.16 mmol) and 2-(but-3-ynyl)-4-chloro-2H-benzo[d][1,2,3]triazole (30 mg, 0.15 mmol). Reaction time: 3 hours. The crude residue was purified by flash chromatography (DCM/MeOH 99:1) to yield 12 mg (42 µmol, 29%) of 4-chloro-2-(4-(pyridin-2-yl)but-3-ynyl)-2H-benzo[d][1,2,3]triazole as an orange solid.

Rf (DCM/MeOH 99:1)=0.05.
LCMS (RT): 3.96 min; MS (ES+) gave m/z: 283.1.
$^1$H-NMR (CDCl$_3$), δ (ppm): 3.32 (t, J=7.5, 2H), 5.03 (t, J=7.5, 2H), 7.21 (ddd, J=1.1, 4.9 and 7.6, 1H), 7.31-7.38 (2H), 7.41 (d, J=7.3, 1H), 7.59-7.65 (m, 1H), 7.80 (dd, J=0.5 and 8.5, 1H), 8.55 (dd, J=0.5 and 4.9, 1H).

Example 147

4-Chloro-2-(4-(6-(fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (30 mg, 0.16 mmol) and 2-(but-3-ynyl)-4-chloro-2H-benzo[d][1,2,3]triazole (30 mg, 0.15 mmol, Example 146(B)). Reaction time: 3 hours. The crude residue was purified by flash chromatography (DCM/MeOH 99:1) to yield 16 mg (51 µmol, 35%) of 4-chloro-2-(4-(6-(fluoromethyl)pyridin-2-yl)but-3-ynyl)-2H-benzo[d][1,2,3]triazole as a brown oil.

Rf (DCM/MeOH 99:1)=0.1.
LCMS (RT): 4.44 min; MS (ES+) gave m/z: 315.1, 317.2.
$^1$H-NMR (CDCl$_3$), δ (ppm): 3.32 (t, J=7.4, 2H), 5.03 (t, J=7.4, 2H), 5.40-5.53 (m, 2H), 7.27-7.35 (2H), 7.40-7.43 (2H), 7.69-7.72 (m, 1H), 7.80 (d, J=8.5, 1H).

Example 148

6,7-Difluoro-2-(4-(6-(fluoromethyl)pyridin-2-yl)but-3-ynyl)quinoxaline

148(A) 6,7-Difluoro-2-methyl-quinoxaline

The title compound was prepared in accordance with the general method of Example 145(A), from 4,5-difluoro-benzene-1,2-diamine (400 mg, 2.77 mmol). The crude residue was purified by flash chromatography (cyclohexane/AcOEt 7:3) to yield 333 mg (1.85 mmol, 67%) of 6,7-difluoro-2-methyl-quinoxaline.

LCMS (RT): 3.56 min; MS (ES+) gave m/z: 181.1.

148(B) 6,7-Difluoro-2-(4-trimethylsilanyl-but-3-ynyl)-quinoxaline

The title compound was prepared in accordance with the general method of Example 118(A), from 6,7-difluoro-2-methyl-quinoxaline (333 mg, 1.85 mmol). The crude residue was purified by flash chromatography (cyclohexane/AcOEt 9:1) to yield 233 mg (0.85 mmol, 46%) of 6,7-difluoro-2-(4-trimethylsilanyl-but-3-ynyl)-quinoxaline as an orange oil.

LCMS (RT): 5.59 min; MS (ES+) gave m/z: 291.3.

148(C) 2-But-3-ynyl-6,7-difluoro-quinoxaline

The title compound was prepared in accordance with the general method of Example 108(B), from 6,7-difluoro-2-(4-trimethylsilanyl-but-3-ynyl)-quinoxaline (233 mg, 0.85 mmol). The crude residue was purified by flash chromatography (cyclohexane/AcOEt 9:1) to yield 80 mg (0.37 mmol, 52%) of 2-but-3-ynyl-6,7-difluoro-quinoxaline as an orange solid.

LCMS (RT): 4.19 min; MS (ES+) gave m/z: 219.1.

148(D) 6,7-Difluoro-2-(4-(6-(fluoromethyl)pyridin-2-yl)but-3-ynyl)quinoxaline The title compound was prepared in accordance with the general method of Example 108(C), from 2-bromo-6-(fluoromethyl)-pyridine (70 mg, 0.37 mmol) and 2-but-3-ynyl-6,7-difluoro-quinoxaline (80 mg, 0.37 mmol). Microwave conditions: 120° C. for 15 minutes. The crude residue was purified by flash chromatography (cyclohexane/AcOEt 3:2) to yield 16 mg (50 μmol, 14%) of 6,7-difluoro-2-(4-(6-(fluoromethyl)pyridin-2-yl)but-3-ynyl)quinoxaline as a yellow solid (M.P.: 134.9-138.5° C.).

LCMS (RT): 4.44 min; MS (ES+) gave m/z: 328.1.
$^1$H-NMR (CDCl$_3$), δ (ppm): 3.04 (t, J=7.3 2H), 3.35 (t, J=7.3, 2H), 5.40-5.53 (m, 2H), 7.25-7.29 (m, 1H), 7.39 (d, J=7.8, 1H), 7.67-7.72 (m, 1H), 7.78-7.88 (2H), 8.82 (s, 1H).

Example 149

4-Fluoro-2-(4-(6-(fluoromethyl)pyridin-2-yl)but-3-ynyl)-2H-indazole

149(A) 4-Fluoro-2-(4-trimethylsilanyl-but-3-ynyl)-2H-indazole

2-Fluoro-6-nitro-benzaldehyde (180 mg, 1.06 mmol) was added to a solution of 4-trimethylsilanyl-but-3-ynylamine (200 mg, 1.40 mmol) in toluene (2 mL) and the reaction mixture was stirred under reflux for 30 min in a Dean-Stark. After evaporation of the solvent, the crude product was dissolved in triethylphosphite (1 mL) and the reaction mixture was stirred at 80° C. for 4 hours. After evaporation, the crude product was purified by flash chromatography (cyclohexane/AcOEt 92.5:7.5) to yield 4-fluoro-2-(4-trimethylsilanyl-but-3-ynyl)-2H-indazole (142 mg, 0.59 mmol, 52%) as a yellow oil.

Rf (cyclohexane/AcOEt 4:1)=0.3.
LCMS (RT): 5.01 min; MS (ES+) gave m/z: 261.1.

149(B) 2-But-3-ynyl-4-fluoro-2H-indazole

The title compound was prepared in accordance with the general method of Example 108(B), from 4-fluoro-2-(4-trimethylsilanyl-but-3-ynyl)-2H-indazole (142 mg, 0.59 mmol) to yield 104 mg (0.55 mmol) of 2-but-3-ynyl-4-fluoro-2H-indazole.

149(C) 4-Fluoro-2-(4-(6-(fluoromethyl)pyridin-2-yl)but-3-ynyl)-2H-indazole

The title compound was prepared in accordance with the general method of Example 1, from 2-bromo-6-(fluoromethyl)-pyridine (0.12 g, 0.61 mmol) and 2-but-3-ynyl-4-fluoro-2H-indazole (104 mg, 0.55 mmol). Reaction time: 3 hours. The crude residue was purified by flash chromatography (cyclohexane/AcOEt 3:2) to yield 60 mg (0.20 mmol, 36%) of 4-fluoro-2-(4-(6-(fluoromethyl)pyridin-2-yl)but-3-ynyl)-2H-indazole as a brown solid.

Rf (cyclohexane/AcOEt 1:1)=0.2.
LCMS (RT): 4.04 min; MS (ES+) gave m/z: 298.1.
$^1$H-NMR (CDCl$_3$), δ (ppm): 3.18 (t, J=6.9, 2H), 4.68 (t, J=6.9, 2H), 5.41-5.54 (m, 2H), 6.71 (dd, J=7.5 and 10.4, 1H), 7.19-7.25 (m, 1H), 7.26-7.29 (m, 1H), 7.42 (d, J=7.9, 1H), 7.50 (d, J=8.7, 1H), 7.68-7.73 (m, 1H), 8.14 (s, 1H).

Example 150

4-Chloro-2-(4-(pyridin-2-yl)but-3-ynyl)-2H-indazole

150(A) 4-Chloro-2-(4-trimethylsilanyl-but-3-ynyl)-2H-indazole

The title compound was prepared in accordance with the general method of Example 149(A), from 2-chloro-6-nitro-benzaldehyde (210 mg, 1.13 mmol) and 4-trimethylsilanyl-but-3-ynylamine (210 mg, 1.50 mmol). The crude product was purified by flash chromatography (cyclohexane/AcOEt 92.5:7.5) to yield 4-chloro-2-(4-trimethylsilanyl-but-3-ynyl)-2H-indazole (134 mg, 0.48 mmol, 43%) as a yellow oil.

Rf (cyclohexane/AcOEt 4:1)=0.3.
LCMS (RT): 5.21 min; MS (ES+) gave m/z: 277.1.

150(B) 2-But-3-ynyl-4-chloro-2H-indazole

The title compound was prepared in accordance with the general method of Example 108(B), from 4-chloro-2-(4-trimethylsilanyl-but-3-ynyl)-2H-indazole (134 mg, 0.48 mmol) to yield 99 mg (0.48 mmol) of 2-but-3-ynyl-4-chloro-2H-indazole.

150(C) 4-Chloro-2-(4-(pyridin-2-yl)but-3-ynyl)-2H-indazole

The title compound was prepared in accordance with the general method of Example 1, from 2-bromopyridine (42 mg, 0.27 mmol) and 2-but-3-ynyl-4-chloro-2H-indazole (50 mg, 0.24 mmol). Reaction time: 8 hours. The crude residue was purified by flash chromatography (cyclohexane/AcOEt 1:1) to yield 12 mg (43 μmol, 17%) of 4-chloro-2-(4-(pyridin-2-yl)but-3-ynyl)-2H-indazole as a brown solid.

Rf (cyclohexane/AcOEt 1:1)=0.1.
LCMS (RT): 3.91 min; MS (ES+) gave m/z: 282.1.
$^1$H-NMR (CDCl$_3$), δ (ppm): 3.18 (t, J=6.9, 2H), 4.69 (t, J=6.9, 2H), 7.08 (d, J=7.1, 1H), 7.20-7.25 (2H), 7.33 (d, J=7.8, 1H), 7.60-7.65 (2H), 8.16 (s, 1H), 8.57 (d, J=4.3, 1H).

Example 151

6-Fluoro-2-(4-(6-(fluoromethyl)pyridin-2-yl)but-3-ynyl)-2H-indazole

151(A) 6-Fluoro-2-(4-trimethylsilanyl-but-3-ynyl)-2H-indazole

The title compound was prepared in accordance with the general method of Example 149(A), from 4-fluoro-2-nitro-benzaldehyde (180 mg, 1.06 mmol) and 4-trimethylsilanyl-but-3-ynylamine (200 mg, 1.40 mmol). The crude product was purified by flash chromatography (cyclohexane/AcOEt 4:1) to yield 6-fluoro-2-(4-trimethylsilanyl-but-3-ynyl)-2H-indazole (310 mg, 1.06 mmol).

151(B) 2-But-3-ynyl-6-fluoro-2H-indazole

The title compound was prepared in accordance with the general method of Example 108(B), from 6-fluoro-2-(4-trimethylsilanyl-but-3-ynyl)-2H-indazole (310 mg, 1.13 mmol) to yield 93 mg (0.49 mmol, 43%) of 2-but-3-ynyl-6-fluoro-2H-indazole as an orange oil.

151(C) 6-Fluoro-2-(4-(6-(fluoromethyl)pyridin-2-yl)but-3-ynyl)-2H-indazole

The title compound was prepared in accordance with the general method of Example 1, from 2-bromo-6-(fluoromethyl)pyridine (100 mg, 0.54 mmol) and 2-but-3-ynyl-6-fluoro-2H-indazole (93 mg, 0.49 mmol). Reaction time: 3 hours. The crude residue was purified by flash chromatography (cyclohexane/AcOEt 3:2) to yield 40 mg (0.13 mmol, 27%) of 6-fluoro-2-(4-(6-(fluoromethyl)pyridin-2-yl)but-3-ynyl)-2H-indazole as a brown solid.

Rf (cyclohexane/AcOEt 1:1)=0.2.
LCMS (RT): 3.93 min; MS (ES+) gave m/z: 298.1.
$^1$H-NMR (CDCl$_3$), δ (ppm): 3.17 (t, J=6.9, 2H), 4.65 (t, J=6.9, 2H), 5.40-5.53 (m, 2H), 6.88-6.93 (m, 1H), 7.26 (d, J=7.8, 1H), 7.28-7.32 (m, 1H), 7.41 (d, J=7.8, 1H), 7.60-7.65 (m, 1H), 7.67-7.72 (m, 1H), 8.05 (s, 1H).

Example 152

4-Chloro-2-(4-(6-(fluoromethyl)pyridin-2-yl)but-3-ynyl)-2H-indazole

The title compound was prepared in accordance with the general method of Example 1, from 2-bromo-6-(fluoromethyl)-pyridine (51 mg, 0.27 mmol) and 2-but-3-ynyl-4-chloro-2H-indazole (50 mg, 0.24 mmol, Example 150(B)). Reaction time: 3 hours. The crude residue was purified by flash chromatography (cyclohexane/AcOEt 3:2) to yield 54 mg (0.17 mmol, 70%) of 4-chloro-2-(4-(6-(fluoromethyl)pyridin-2-yl)but-3-ynyl)-2H-indazole as a brown solid.

Rf (cyclohexane/AcOEt 1:1)=0.2.
LCMS (RT): 4.29 min; MS (ES+) gave m/z: 314.1.
$^1$H-NMR (CDCl$_3$), δ (ppm): 3.18 (t, J=6.9, 2H), 4.69 (t, J=6.9, 2H), 5.41-5.54 (m, 2H), 7.08 (d, J=7.2, 1H), 7.20-7.24 (m, 1H), 7.26-7.30 (m, 1H), 7.42 (d, J=7.8, 1H), 7.62 (d, J=8.7, 1H), 7.68-7.72 (m, 1H), 8.15 (s, 1H).

Example 153

5,6-Difluoro-2-(4-(pyridin-2-yl)but-3-ynyl)-2H-benzo[d][1,2,3]triazole

153(A) 5,6-Difluoro-1H-benzo[d][1,2,3]triazole

The title compound was prepared in accordance with the general method of Example 127(A), from 4,5-difluorobenzene-1,2-diamine (420 mg, 2.91 mmol) to yield 5,6-difluoro-1H-benzo[d][1,2,3]triazole (361 mg, 2.33 mmol, 80%) as a dark solid.

153(B) 2-(But-3-ynyl)-5,6-difluoro-2H-benzo[d][1,2,3]triazole

The title compound was prepared in accordance with the general method of Example 109(D), from 5,6-difluoro-1H-benzo[d][1,2,3]triazole (389 mg, 2.51 mmol). The crude residue was purified by flash chromatography (cyclohexane/AcOEt 9:1) to yield 244 mg (1.18 mmol, 52%) of 2-(but-3-ynyl)-5,6-difluoro-2H-benzo[d][1,2,3]triazole as a white solid.

Rf (cyclohexane/AcOEt 4:1)=0.4.

153(C) 5,6-Difluoro-2-(4-(pyridin-2-yl)but-3-ynyl)-2H-benzo[d][1,2,3]triazole The title compound was prepared in accordance with the general method of Example 1, from 2-bromo-pyridine (50 mg, 0.32 mmol) and 2-(but-3-ynyl)-5,6-difluoro-2H-benzo[d][1,2,3]triazole (60 mg, 0.29 mmol). Reaction time: 3 hours. The crude residue was purified by flash chromatography (DCM/MeOH 99:1) to yield 54 mg (0.19 mol, 66%) of 5,6-difluoro-2-(4-(pyridin-2-yl)but-3-ynyl)-2H-benzo[d][1,2,3]triazole as a yellow solid (M.P.=131-132° C.).

Rf (DCM/MeOH 99:1)=0.1.
LCMS (RT): 3.85 min; MS (ES+) gave m/z: 285.1.
$^1$H-NMR (CDCl$_3$), δ (ppm): 3.28 (t, J=7.4, 2H), 4.95 (t, J=7.4, 2H), 7.20-7.23 (m, 1H), 7.33 (d, J=7.8, 1H), 7.58-7.64 (3H), 8.55 (d, J=4.3, 1H).

Example 154

5,6-Difluoro-2-(4-(6-(fluoromethyl)pyridin-2-yl)but-3-ynyl)-2H-benzo[d][1,2,3]triazole The title compound was prepared in accordance with the general method of Example 1, from 2-bromo-6-(fluoromethyl)-pyridine (50 mg, 0.32 mmol) and 2-(but-3-ynyl)-5,6-difluoro-2H-benzo[d][1,2,3]triazole (60 mg, 0.29 mmol, Example 153(B)). Reaction time: 3 hours. The crude residue was purified by flash chromatography (DCM/MeOH 99:1) to yield 29 mg (92 µmol, 32%) of 5,6-difluoro-2-(4-(6-(fluoromethyl)pyridin-2-yl)but-3-ynyl)-2H-benzo[d][1,2,3]triazole as a grey solid (M.P.=104-105° C.).

Rf (DCM/MeOH 99:1)=0.1.
LCMS (RT): 4.28 min; MS (ES+) gave m/z: 317.1.
$^1$H-NMR (CDCl$_3$), δ (ppm): 3.28 (t, J=7.4, 2H), 4.95 (t, J=7.4, 2H), 5.40-5.53 (m, 2H), 7.29 (d, J=7.8, 1H), 7.41 (d, J=7.8, 1H), 7.57-7.63 (2H), 7.68-7.73 (m, 1H).

Example 155

7-Fluoro-2-(4-(6-(fluoromethyl)pyridin-2-yl)but-3-ynyl)-2H-indazole

155(A) 7-Fluoro-2-(4-trimethylsilanyl-but-3-ynyl)-2H-indazole

The title compound was prepared in accordance with the general method of Example 149(A), from 3-fluoro-2-nitrobenzaldehyde (0.2 g, 1.2 mmol) and 4-trimethylsilanyl-but-3-ynylamine (0.22 g, 1.5 mmol). The crude product was purified by flash chromatography (cyclohexane/AcOEt 92.5:7.5) to yield 7-fluoro-2-(4-trimethylsilanyl-but-3-ynyl)-2H-indazole (117 mg, 0.45 mmol) as a yellow oil.

Rf (cyclohexane/AcOEt 4:1)=0.1.
LCMS (RT): 4.83 min; MS (ES+) gave m/z: 261.1.

155(B) 2-But-3-ynyl-7-fluoro-2H-indazole

The title compound was prepared in accordance with the general method of Example 108(B), from 7-fluoro-2-(4-trimethylsilanyl-but-3-ynyl)-2H-indazole (134 mg, 0.48 mmol) to yield 99 mg (0.48 mmol) of 2-but-3-ynyl-7-fluoro-2H-indazole.

155(C) 7-Fluoro-2-(4-(6-(fluoromethyl)pyridin-2-yl)but-3-ynyl)-2H-indazole

The title compound was prepared in accordance with the general method of Example 1, from 2-bromo-6-fluoromethylpyridine (93 mg, 0.49 mmol) and 2-but-3-ynyl-7-fluoro-2H-indazole (84 mg, 0.45 mmol). Reaction time: 6 hours. The crude residue was purified by flash chromatography (cyclohexane/AcOEt 3:2) to yield 17 mg (57 µmol, 13%) of 7-fluoro-2-(4-(6-(fluoromethyl)pyridin-2-yl)but-3-ynyl)-2H-indazole as a brown solid.

Rf (cyclohexane/AcOEt 1:1)=0.2.
LCMS (RT): 3.83 min; MS (ES+) gave m/z: 298.1.
$^1$H-NMR (CDCl$_3$), δ (ppm): 3.17 (t, J=6.9, 2H), 4.66 (t, J=6.9, 2H), 5.40-5.54 (m, 2H), 7.07-7.13 (m, 1H), 7.23 (dd, J=1.9 and 9.1, 1H), 7.26 (d, J=7.8, 1H), 7.41 (d, J=7.8, 1H), 7.67-7.71 (2H), 8.01 (s, 1H).

Example 156

4-Chloro-2-(4-(1-methyl-1H-pyrazol-3-yl)but-3-ynyl)-2H-benzo[d][1,2,3]triazole

The title compound was prepared in accordance with the general method of Example 108(C), from 3-bromo-1-methyl-1H-pyrazole (70 mg, 0.43 mmol) and 2-but-3-ynyl-4-chloro-2H-benzo[d][1,2,3]triazole (89 mg, 0.43 mmol, Example 146 (B)). Microwave conditions: The crude residue was purified by flash chromatography (cyclohexane/AcOEt 7:3) to yield 12 mg (42 µmol, 10%) of 4-chloro-2-(4-(1-methyl-1H-pyrazol-3-yl)but-3-ynyl)-2H-benzo[d][1,2,3]triazole as a brown semi-solid.

Rf (cyclohexane/AcOEt 7:3)=0.2.
LCMS (RT): 3.93 min; MS (ES+) gave m/z: 286.1, 288.1.
$^1$H-NMR (CDCl$_3$), δ (ppm): 3.27 (t, J=7.6, 2H), 3.88 (s, 3H), 5.00 (t, J=7.6, 2H), 6.31 (d, J=2.2, 1H), 7.28 (d, J=2.2, 1H), 7.32 (dd, J=7.4 and 8.5, 1H), 7.41 (dd, J=0.7 and 7.4, 1H), 7.79 (dd, J=0.7 and 8.5, 1H).

Example 157

6-(4-(4,6-Difluoro-2H-benzo[d][1,2,3]triazol-2-yl)but-1-ynyl)pyridin-2-amine

The title compound was prepared in accordance with the general method of Example 1, from 6-bromo-pyridin-2-ylamine (60 mg, 0.35 mmol) and 2-but-3-ynyl-4,6-difluoro-2H-benzo[d][1,2,3]triazole (72 mg, 0.35 mmol, Example 135 (B)). Reaction time: 3 hours. The crude residue was purified by flash chromatography (DCM/AcOEt 1:1) to yield 65 mg (0.22 mmol, 63%) of 6-(4-(4,6-difluoro-2H-benzo[d][1,2,3]triazol-2-yl)but-1-ynyl)pyridin-2-amine as a brown solid.

Rf (DCM/AcOEt 1:1)=0.2.
LCMS (RT): 2.63 min; MS (ES+) gave m/z: 300.1.
$^1$H-NMR (CDCl$_3$), δ (ppm): 3.27 (t, J=7.5, 2H), 4.45-4.53 (br. s, 2H), 4.97 (t, J=7.5, 2H), 6.45 (d, J=8.3, 1H), 6.75 (d, J=7.3, 1H), 6.88-6.95 (m, 1H), 7.31 (dd, J=2.0 and 8.3, 1H), 7.37 (dd, J=7.3 and 8.3, 1H).

Example 158

2-(4-(2H-Benzo[d][1,2,3]triazol-2-yl)but-1-ynyl)-6-methylpyridin-3-amine

The title compound was prepared in accordance with the general method of Example 1, from 2-bromo-6-methyl-pyridin-3-ylamine (80 mg, 0.43 mmol) and 2-but-3-ynyl-2H-benzo[d][1,2,3]triazole (73 mg, 0.43 mmol, Example 109 (D)). Reaction time: 3 hours. The crude residue was purified by flash chromatography (DCM/AcOEt 1:1) to yield 53 mg (0.19 mmol, 45%) of 2-(4-(2H-benzo[d][1,2,3]triazol-2-yl)but-1-ynyl)-6-methylpyridin-3-amine as a brown solid.

Rf (DCM/AcOEt 1:1)=0.2.
LCMS (RT): 2.33 min; MS (ES+) gave m/z: 278.1.
$^1$H-NMR (CDCl$_3$), δ (ppm): 2.40 (s, 3H), 3.31 (t, J=6.7, 2H), 4.10-4.18 (br. s, 2H), 5.02 (t, J=6.7, 2H), 6.87-6.91 (2H), 7.41 (dd, J=3.1 and 6.6, 2H), 7.87 (dd, J=3.1 and 6.6, 2H).

Example 159

2-(4-(3-Phenyl-1H-pyrazol-1-yl)but-1-ynyl)pyridine

159(A) 1-But-3-ynyl-3-phenyl-1H-pyrazole

The title compound was prepared in accordance with the general method of Example 109(D), from 3-phenyl-1H-pyrazole (617 mg, 4.28 mmol). The crude residue was purified by flash chromatography (cyclohexane/AcOEt 9:1) to yield 140 mg (0.71 mmol, 25%) of 1-but-3-ynyl-3-phenyl-1H-pyrazole.

159(B) 2-(4-(3-Phenyl-1H-pyrazol-1-yl)but-1-ynyl)pyridine

The title compound was prepared in accordance with the general method of Example 1, from 140 mg (0.71 mmol) of 1-but-3-ynyl-3-phenyl-1H-pyrazole. The crude residue was purified by flash chromatography (DCM/MeOH 99:1) to yield 44 mg (0.16 mmol, 22%) of 2-(4-(3-phenyl-1H-pyrazol-1-yl)but-1-ynyl)pyridine as a yellow solid.

LCMS (RT): 3.84 min; MS (ES+) gave m/z: 274.1.
Rf (DCM/MeOH 97:3)=0.2.

Example 160

4-Nitro-2-(4-(pyridin-2-yl)but-3-ynyl)-2H-benzo[d][1,2,3]triazole

160(A) 4-Nitro-1H-benzo[d][1,2,3]triazole

The title compound was prepared in accordance with the general method of Example 127(A), from 3-nitro-benzene-1,2-diamine (2.50 g, 16.3 mmol) to yield 4-nitro-1H-benzo[d][1,2,3]triazole (2.65 g, 16.1 mmol) as a dark solid.

160(B) 2-But-3-ynyl-4-nitro-2H-benzo[d][1,2,3]triazole

The title compound was prepared in accordance with the general method of Example 109(D), from 4-nitro-1H-benzo[d][1,2,3]triazole (1.35 g, 8.20 mmol). The crude residue was purified by flash chromatography (cyclohexane/AcOEt 95:5 to 90:10) to yield 191 mg (0.88 mmol, 12%) of 2-but-3-ynyl-4-nitro-2H-benzo[d][1,2,3]triazole.

Rf (cyclohexane/AcOEt 9:1)=0.1.

160(C) 4-Nitro-2-(4-(pyridin-2-yl)but-3-ynyl)-2H-benzo[d][1,2,3]triazole

The title compound was prepared in accordance with the general method of Example 1, from 2-bromo-pyridine (76 mg, 0.48 mmol) and 2-but-3-ynyl-4-nitro-2H-benzo[d][1,2,3]triazole (95 mg, 0.44 mmol). Reaction time: 3 hours. The crude residue was purified by flash chromatography (DCM/MeOH 99:1) to yield 40 mg (0.14 mmol, 31%) of 4-nitro-2-(4-(pyridin-2-yl)but-3-ynyl)-2H-benzo[d][1,2,3]triazole as an orange oil.

Rf (DCM/MeOH 99:1)=0.1.
LCMS (RT): 3.47 min; MS (ES+) gave m/z: 294.1.

$^1$H-NMR (CDCl$_3$), δ (ppm): 3.12 (t, J=6.9, 2H), 5.37 (t, J=6.9, 2H), 7.18-7.22 (m, 1H), 7.26-7.30 (m, 1H), 7.50-7.54 (m, 1H), 7.59-7.64 (m, 1H), 8.38 (dd, J=0.9 and 7.8, 1H), 8.45 (dd, J=0.9 and 8.2, 1H), 8.49-8.53 (m, 1H).

Example 161

2-(4-(6-(Fluoromethyl)pyridin-2-yl)but-3-ynyl)-4-nitro-2H-benzo[d][1,2,3]triazole The title compound was prepared in accordance with the general method of Example 1, from 2-bromo-6-(fluoromethyl)-pyridine (92 mg, 0.48 mmol) and 2-but-3-ynyl-4-nitro-2H-benzo[d][1,2,3]triazole (95 mg, 0.44 mmol, Example, 160(B)). Reaction time: 3 hours. The crude residue was purified by flash chromatography (DCM/MeOH 99:1) to yield 59 mg (0.18 mol, 42%) of 2-(4-(6-(fluoromethyl)pyridin-2-yl)but-3-ynyl)-4-nitro-2H-benzo[d][1,2,3]triazole as an orange oil.
Rf (DCM/MeOH 99:1)=0.1.
LCMS (RT): 3.97 min; MS (ES+) gave m/z: 326.1.
$^1$H-NMR (CDCl$_3$), δ (ppm): 3.12 (t, J=6.8, 2H), 5.37 (t, J=6.8, 2H), 5.36 (m, 2H), 7.24 (d, J=7.7, 1H), 7.39 (d, J=7.7, 1H), 7.50-7.56 (m, 1H), 7.67-7.72 (m, 1H), 8.38 (dd, J=0.9 and 7.8, 1H), 8.46 (dd, J=0.9 and 8.2, 1H).

Example 162

2-(4-(Pyridin-2-yl)but-3-ynyl)-2H-benzo[d][1,2,3]triazol-4-amine

The title compound was prepared in accordance with the general method of Example 62(A), from 4-nitro-2-(4-(pyridin-2-yl)but-3-ynyl)-2H-benzo[d][1,2,3]triazole (40 mg, 0.14 mmol, Example 160(C)). The crude residue was purified by flash chromatography (DCM/MeOH 98:2) to yield 7 mg (27 mmol, 19%) of 2-(4-(pyridin-2-yl)but-3-ynyl)-2H-benzo[d][1,2,3]triazol-4-amine as an orange solid.
Rf (DCM/MeOH 98:2)=0.03.
LCMS (RT): 2.62 min; MS (ES+) gave m/z: 264.1.
$^1$H-NMR (CDCl$_3$), δ (ppm): 3.22 (t, J=6.7, 2H), 4.00-4.30 (br. s, 2H), 5.12 (t, J=6.7, 2H), 6.72 (dd, J=0.5 and 7.3, 1H), 7.12-7.18 (2H), 7.20-7.24 (m, 1H), 7.56 (d, J=8.4, 1H), 7.57-7.62 (m, 1H), 8.55 (d, J=4.3, 1H).

Example 163

4-Methyl-2-(4-(pyridin-2-yl)but-3-ynyl)-2H-benzo[d][1,2,3]triazole

163(A) 4-Methyl-1H-benzo[d][1,2,3]triazole

The title compound was prepared in accordance with the general method of Example 127(A), from 3-methyl-benzene-1,2-diamine (1.95 g, 16.0 mmol) to yield 4-methyl-1H-benzo[d][1,2,3]triazole (1.76 g, 13.2 mmol, 83%) as a dark solid.

163(B)
2-But-3-ynyl-4-methyl-2H-benzo[d][1,2,3]triazole

The title compound was prepared in accordance with the general method of Example 109(D), from 4-methyl-1H-benzo[d][1,2,3]triazole (418 mg, 3.14 mmol). The crude residue was purified by flash chromatography (cyclohexane/AcOEt 9:1) to yield 255 mg (1.38 mmol, 48%) of 2-but-3-ynyl-4-methyl-2H-benzo[d][1,2,3]triazole.
Rf (cyclohexane/AcOEt 9:1)=0.2.

163(C) 4-Methyl-2-(4-(pyridin-2-yl)but-3-ynyl)-2H-benzo[d][1,2,3]triazole

The title compound was prepared in accordance with the general method of Example 1, from 2-bromo-pyridine (66 mg, 0.42 mmol) and 2-but-3-ynyl-4-methyl-2H-benzo[d][1,2,3]triazole (70 mg, 0.38 mmol). Reaction time: 3 hours. The crude residue was purified by flash chromatography (DCM/MeOH 99:1) to yield 50 mg (0.19 mmol, 50%) of 4-methyl-2-(4-(pyridin-2-yl)but-3-ynyl)-2H-benzo[d][1,2,3]triazole as a yellow semi-solid.
Rf (DCM/MeOH 98:2)=0.1.
LCMS (RT): 3.73 min; MS (ES+) gave m/z: 263.1.
$^1$H-NMR (CDCl$_3$), δ (ppm): 2.67 (s, 3H), 3.30 (t, J=7.5, 2H), 5.00 (t, J=7.5, 2H), 7.12-7.16 (m, 1H), 7.21 (ddd, J=1.1, 4.9 and 7.6, 1H), 7.27-7.31 (m, 1H), 7.33-7.36 (m, 1H), 7.59-7.64 (m, 1H), 7.69 (d, J=8.6, 1H), 8.55 (d, J=4.3, 1H).

Example 164

2-(4-(6-(Fluoromethyl)pyridin-2-yl)but-3-ynyl)-4-methyl-2H-benzo[d][1,2,3]triazole The title compound was prepared in accordance with the general method of Example 1, from 2-bromo-6-(fluoromethyl)-pyridine (73 mg, 0.39 mmol) and 2-but-3-ynyl-4-methyl-2H-benzo[d][1,2,3]triazole (65 mg, 0.35 mmol, 163(B)). Reaction time: 3 hours. The crude residue was purified by flash chromatography (DCM/MeOH 99:1) to yield 65 mg (0.22 mmol, 63%) of 2-(4-(6-(fluoromethyl)pyridin-2-yl)but-3-ynyl)-4-methyl-2H-benzo[d][1,2,3]triazole as a yellow semi-solid.
Rf (DCM/MeOH 98:2)=0.7.
LCMS (RT): 4.22 min; MS (ES+) gave m/z: 295.1.
$^1$H-NMR (CDCl$_3$), δ (ppm): 2.67 (s, 3H), 3.30 (t, J=7.5, 2H), 5.00 (t, J=7.5, 2H), 5.40-5.53 (m, 2H), 7.12-7.16 (m, 1H), 7.27-7.31 (2H), 7.41 (d, J=7.8, 1H), 7.67-7.72 (2H).

Example 165

2-(4-(6-(Fluoromethyl)pyridin-2-yl)but-3-ynyl)-5-methyl-2H-benzo[d][1,2,3]triazole 165(A) 5-Methyl-1H-benzo[d][1,2,3]triazole The title compound was prepared in accordance with the general method of Example 127(A), from 4-methyl-benzene-1,2-diamine (2.02 g, 16.5 mmol) to yield 5-methyl-1H-benzo[d][1,2,3]triazole (2.05 g, 15.4 mmol, 93%).

165(B)
2-But-3-ynyl-5-methyl-2H-benzo[d][1,2,3]triazole

The title compound was prepared in accordance with the general method of Example 109(D), from 5-methyl-1H-benzo[d][1,2,3]triazole (418 mg, 3.14 mmol). The crude residue was purified by flash chromatography (cyclohexane/AcOEt 9:1) to yield 135 mg (0.73 mmol, 26%) of 2-but-3-ynyl-5-methyl-2H-benzo[d][1,2,3]triazole.
Rf (cyclohexane/AcOEt 9:1)=0.3.

165(C) 2-(4-(6-(Fluoromethyl)pyridin-2-yl)but-3-ynyl)-5-methyl-2H-benzo[d][1,2,3]triazole The title compound was prepared in accordance with the general method of Example 1, from 2-bromo-6-(fluoromethyl)-pyridine (73 mg, 0.39 mmol) and 2-but-3-ynyl-5-methyl-2H-benzo[d][1,2,3]triazole (65 mg, 0.35 mmol). Reaction time: 3 hours. The crude residue was purified by flash chromatography (DCM/MeOH 99:1) to yield 40 mg (0.14 mmol, 39%) of 2-(4-(6-(fluoromethyl)pyridin-2-yl)but-3-ynyl)-5-methyl-2H-benzo[d][1,2,3]triazole as a yellow solid.

Rf (DCM/MeOH 99:1)=0.1.

LCMS (RT): 4.20 min; MS (ES+) gave m/z: 295.1.

$^1$H-NMR (CDCl$_3$), δ (ppm): 2.50 (s, 3H), 3.28 (t, J=7.5, 2H), 4.96 (t, J=7.5, 2H), 5.40-5.53 (m, 2H), 7.23 (dd, J=1.4 and 8.8, 1H), 7.29 (d, J=7.7, 1H), 7.40 (d, J=7.8, 1H), 7.60-7.62 (m, 1H), 7.67-7.72 (m, 1H), 7.76 (d, J=8.8, 1H).

Example 166

5-Methyl-2-(4-(pyridin-2-yl)but-3-ynyl)-2H-benzo [d][1,2,3]triazole

The title compound was prepared in accordance with the general method of Example 1, from 2-bromo-pyridine (66 mg, 0.42 mmol) and 2-but-3-ynyl-5-methyl-2H-benzo[d][1,2,3]triazole (70 mg, 0.38 mmol, Example 165(B)). Reaction time: 3 hours. The crude residue was purified by flash chromatography (DCM/MeOH 99:1) to yield 36 mg (0.14 mmol, 37%) of 5-methyl-2-(4-(pyridin-2-yl)but-3-ynyl)-2H-benzo [d][1,2,3]triazole as an orange solid.

Rf (DCM/MeOH 99:1)=0.05.

LCMS (RT): 3.72 min; MS (ES+) gave m/z: 263.1.

$^1$H-NMR (CDCl$_3$), δ (ppm): 2.50 (s, 3H), 3.28 (t, J=7.5, 2H), 4.96 (t, J=7.5, 2H), 7.19-7.25 (2H), 7.34 (d, J=7.8, 1H), 7.59-7.64 (2H), 7.76 (d, J=8.8, 1H), 8.55 (d, J=4.5, 1H).

Example 167

6-(4-(2H-Benzo[d][1,2,3]triazol-2-yl)but-1-ynyl)-N-methylpyridin-2-amine

167(A) (6-Bromo-pyridin-2-yl)-methyl-amine

NaH (150 mg, 3.80 mmol, 60%) was added to a solution of 6-bromo-pyridin-2-ylamine (300 mg, 1.73 mmol) in DMF at 0° C. followed by iodomethane (3.47 mL, 6.94 mmol). The reaction mixture was stirred for 1 hour at room temperature and was quenched with water. The aqueous phase was extracted with Et$_2$O. The organic phase was washed with water, brine, dried over MgSO$_4$, filtered and evaporated. The crude residue was purified by flash chromatography (cyclohexane/AcOEt 95:5) to yield 90 mg (0.48 mmol, 28%) of (6-bromo-pyridin-2-yl)-methyl-amine.

LCMS (RT): 3.45 min; MS (ES+) gave m/z: 189.1.

167(B) 6-(4-(2H-Benzo[d][1,2,3]triazol-2-yl)but-1-ynyl)-N-methylpyridin-2-amine

The title compound was prepared in accordance with the general method of Example 1, from (6-bromo-pyridin-2-yl)-methyl-amine (105 mg, 0.56 mmol) and 2-but-3-ynyl-2H-benzo[d][1,2,3]triazole (96 mg, 0.56 mmol, Example 109 (D)). Reaction time: 3 hours. The crude residue was purified by C$_{18}$ flash chromatography (water to water/acetonitrile 3:2) to yield 22 mg (80 µmol, 14%) of 6-(4-(2H-benzo[d][1,2,3] triazol-2-yl)but-1-ynyl)-N-methylpyridin-2-amine as a white solid (M.P.=150-154° C.).

Rf (cyclohexane/AcOEt 7:3)=0.2.

LCMS (RT): 2.47 min; MS (ES+) gave m/z: 278.2.

$^1$H-NMR (CDCl$_3$), δ (ppm): 2.89 (d, J=5.4, 3H), 3.26 (t, J=7.5, 2H), 4.56-4.67 (br. s, 1H), 4.97 (t, J=7.5, 2H), 6.32 (d, J=8.4, 1H), 6.67 (d, J=7.2, 1H), 7.32-7.41 (3H), 7.86 (dd, J=3.0 and 6.6, 2H).

Example 168

2-(4-(3-(4-Fluorophenyl)isoxazol-5-yl)but-1-ynyl) pyridine

168(A)
5-Bromomethyl-3-(4-fluoro-phenyl)-isoxazole

The title compound was prepared in accordance with the general method of Example 119(B), from [3-(4-fluoro-phenyl)-isoxazol-5-yl]-methanol (200 mg, 1.03 mmol). The crude residue was purified by flash chromatography (cyclohexane/AcOEt 9:1) to yield 250 mg (0.98 mmol, 94%) of 5-bromomethyl-3-(4-fluoro-phenyl)-isoxazole.

168(B) 3-(4-Fluoro-phenyl)-5-(4-trimethylsilanyl-but-3-ynyl)-isoxazole

The title compound was prepared in accordance with the general method of Example 107(B), from 5-bromomethyl-3-(4-fluoro-phenyl)-isoxazole (100 mg, 0.39 mmol) to yield 3-(4-fluoro-phenyl)-5-(4-trimethylsilanyl-but-3-ynyl)-isoxazole (110 mg, 0.38 mmol, 98%) as a brown oil.

168(C) 5-But-3-ynyl-3-(4-fluoro-phenyl)-isoxazole

The title compound was prepared in accordance with the general method of Example 108(B), from 3-(4-fluoro-phenyl)-5-(4-trimethylsilanyl-but-3-ynyl)-isoxazole (110 mg, 0.38 mmol). The crude residue was purified by flash chromatography (cyclohexane/AcOEt 9:1) to yield 55 mg (0.25 mmol, 67%) of 5-but-3-ynyl-3-(4-fluoro-phenyl)-isoxazole as a white solid.

168(D) 2-(4-(3-(4-Fluorophenyl)isoxazol-5-yl)but-1-ynyl)pyridine

The title compound was prepared in accordance with the general method of Example 1, from 2-bromo-pyridine (40 mg, 0.26 mmol) and 5-but-3-ynyl-3-(4-fluoro-phenyl)-isoxazole (55 mg, 0.26 mmol). Reaction time: 2 hours. The crude residue was purified by flash chromatography (cyclohexane/AcOEt 9:1 to 7:3) to yield 19 mg (65 µmol, 25%) of 2-(4-(3-(4-fluorophenyl)isoxazol-5-yl)but-1-ynyl)pyridine as a white solid (M.P.=83-84° C.).

Rf (cyclohexane/AcOEt 7:3)=0.2.

LCMS (RT): 4.15 min; MS (ES+) gave m/z: 293.2.

$^1$H-NMR (CDCl$_3$), δ (ppm): 2.90 (t, J=7.2, 2H), 3.15 (t, J=7.2, 2H), 6.45 (s, 1H), 7.09-7.17 (2H), 7.21 (ddd, J=1.2, 5.1 and 7.5, 1H), 7.36 (d, J=8.1, 1H), 7.58-7.65 (m, 1H), 7.74-7.82 (2H), 8.55 (d, J=4.8, 1H).

Example 169

N-(6-(4-(2H-Benzo[d][1,2,3]triazol-2-yl)but-1-ynyl) pyridin-2-yl)acetamide

169(A) 6-(4-Benzotriazol-2-yl-but-1-ynyl)-pyridin-2-ylamine

The title compound was prepared in accordance with the general method of Example 1, from 6-bromo-pyridin-2- ylamine (960 mg, 5.55 mmol) and 2-but-3-ynyl-2H-benzo[d][1,2,3]triazole (950 mg, 5.55 mmol, Example 109(D)). Reaction time: 3 hours. The crude residue was purified by flash chromatography (DCM/AcOEt 1:1) to yield 0.45 g (1.71 mmol, 31%) of 6-(4-benzotriazol-2-yl-but-1-ynyl)-pyridin-2-ylamine as a brown solid Rf (cyclohexane/AcOEt 7:3)=0.2.

LCMS (RT): 2.47 min; MS (ES+) gave m/z: 264.2.

169(B) N-(6-(4-(2H-Benzo[d][1,2,3]triazol-2-yl)but-1-ynyl)pyridin-2-yl)acetamide A solution of anhydride acetic (34.9 mg, 0.34 mmol) in DCM was added to a solution of 6-(4-benzotriazol-2-yl-but-1-ynyl)-pyridin-2-ylamine (90 mg, 0.34 mmol) and $Et_3N$ (52 µl, 0.38 mmol) in DCM (2 mL). The reaction mixture was stirred at room temperature for 2 hours and then the solvent was evaporated. The crude residue was purified by flash chromatography (cyclohexane/AcOEt 3:2) to yield 68 mg (0.22 mmol, 65%) of N-(6-(4-(2H-benzo[d][1,2,3]triazol-2-yl)but-1-ynyl)pyridin-2-yl)acetamide as a white solid (M.P.=93-94° C.).

Rf (cyclohexane/AcOEt 3:2)=0.2.

LCMS (RT): 3.62 min; MS (ES+) gave m/z: 306.1.

$^1$H-NMR (CDCl$_3$), δ (ppm): 2.15 (s, 3H), 3.27 (t, J=7.5, 2H), 4.97 (t, J=7.5, 2H), 7.06 (dd, J=0.6 and 7.5, 1H), 7.38 (dd, J=3.3 and 6.6, 2H), 7.57-7.64 (m, 1H), 7.86 (dd, J=3.0 and 6.6, 2H), 8.13 (d, J=8.4, 1H), 8.15-8.20 (br. s, 1H).

Example 170

6-(4-(2H-Benzo[d][1,2,3]triazol-2-yl)but-1-ynyl)-N-ethylpyridin-2-amine

170(A) (6-Bromo-pyridin-2-yl)-ethyl-amine

The title compound was prepared in accordance with the general method of Example 167(A), from 6-bromo-pyridin-2-ylamine (500 mg, 2.89 mmol). The crude residue was purified by flash chromatography (cyclohexane/AcOEt 95:5) to yield 280 mg (1.39 mmol, 48%) of (6-bromo-pyridin-2-yl)-ethyl-amine as a colorless liquid.

LCMS (RT): 3.97 min; MS (ES+) gave m/z: 202.1.

170(B) 6-(4-(2H-Benzo[d][1,2,3]triazol-2-yl)but-1-ynyl)-N-ethylpyridin-2-amine The title compound was prepared in accordance with the general method of Example 1, from (6-bromo-pyridin-2-yl)-ethyl-amine (100 mg, 0.50 mmol) and 2-but-3-ynyl-2H-benzo[d][1,2,3]triazole (0.13 g, 0.75 mmol, Example 109 (D)). Reaction time: 3 hours. The crude residue was purified by flash chromatography (cyclohexane/AcOEt 7:3) to yield 35 mg (0.12 mmol, 24%) of 6-(4-(2H-benzo[d][1,2,3]triazol-2-yl)but-1-ynyl)-N-ethylpyridin-2-amine as a brown solid (M.P.=73-78° C.).

Rf (cyclohexane/AcOEt 7:3)=0.2.

LCMS (RT): 2.77 min; MS (ES+) gave m/z: 292.2.

$^1$H-NMR (CDCl$_3$), δ (ppm): 1.23 (t, J=7.2, 3H), 2.88 (s, 1H), 2.95 (s, 1H), 3.26 (t, J=7.5, 2H), 4.97 (t, J=7.5, 2H), 6.31 (dd, J=0.6 and 8.4, 1H), 6.66 (dd, J=0.6 and 7.5, 1H), 7.33 (d, J=7.5, 1H), 7.38 (dd, J=0.6 and 6.6, 2H), 7.87 (dd, J=3.0 and 6.6, 2H).

Example 171

2-(4-(5-(4-Fluorophenyl)-1H-pyrazol-1-yl)but-1-ynyl)pyridine

171(A) 1-But-3-ynyl-5-(4-fluoro-phenyl)-1H-pyrazole

The title compound was prepared in accordance with the general method of Example 109(D), from 5-(4-fluoro-phenyl)-1H-pyrazole (694 mg, 4.28 mmol). The crude residue was purified by flash chromatography (cyclohexane/AcOEt 9:1) to yield 126 mg (0.59 mmol, 21%) of 1-but-3-ynyl-5-(4-fluoro-phenyl)-1H-pyrazole.

171(B) 2-(4-(5-(4-Fluorophenyl)-1H-pyrazol-1-yl)but-1-ynyl)pyridine

The title compound was prepared in accordance with the general method of Example 1, from 360 mg (1.68 mmol) of 1-but-3-ynyl-5-(4-fluoro-phenyl)-1H-pyrazole. The crude residue was purified by flash chromatography (DCM/MeOH 99:1) to yield 51 mg (0.17 mmol, 10%) of 2-(4-(5-(4-fluorophenyl)-1H-pyrazol-1-yl)but-1-ynyl)pyridine as a yellow solid.

LCMS (RT): 3.85 min; MS (ES+) gave m/z: 292.0.

Rf (DCM/MeOH 97:3)=0.1.

Example 172

2-(1-Fluoro-4-(pyridin-2-yl)but-3-ynyl)quinoxaline

172(A) 1-Quinoxalin-2-yl-but-3-yn-1-ol

To a mixture of magnesium (229 mg, 9.41 mmol), mercuric chloride (13 mg, 47 µmol) and few crystals of iodine in $Et_2O$ (1.5 mL), a solution of propargyl bromide (0.53 mL, 5.88 mmol) in $Et_2O$ (4.5 mL) was added slowly in order to maintain a reflux. The reaction mixture was stirred 1 hour and added to a solution of quinoxaline-2-carbaldehyde (500 mg, 3.16 mmol) in THF (2 mL). The resulting reaction mixture was stirred at 0° C. for 30 min., at room temperature for 30 min. and was poured onto saturated $NH_4Cl$ solution. The aqueous phase was extracted with $Et_2O$. The aqueous phase was washed with water, brine, dried over $MgSO_4$, filtered and evaporated. The crude residue was purified by $C_{18}$ flash chromatography ($H_2O$/acetonitrile 100:0 to 80:20) to yield 90 mg (0.45 mmol, 14%) of 1-quinoxalin-2-yl-but-3-yn-1-ol as a yellow oil.

LCMS (RT): 2.41 min; MS (ES+) gave m/z: 199.1.

172(B) 4-Pyridin-2-yl-1-quinoxalin-2-yl-but-3-yn-1-ol

The title compound was prepared in accordance with the general method of Example 1, from 2-iodo-pyridine (72 mg, 0.35 mmol) and 1-quinoxalin-2-yl-but-3-yn-1-ol (70 mg, 0.35 mmol). Reaction time: 14 hours. The crude residue was purified by flash chromatography (cyclohexane/AcOEt 3:2 to DCM/MeOH 9:1) to yield 60 mg (0.22 mmol, 62%) of 4-pyridin-2-yl-1-quinoxalin-2-yl-but-3-yn-1-ol.

LCMS (RT): 2.47 min; MS (ES+) gave m/z: 276.1.

172(C) 2-(1-Fluoro-4-(pyridin-2-yl)but-3-ynyl)quinoxaline

DAST (19 µL, 0.15 mmol) was added dropwise to a solution of 4-pyridin-2-yl-1-quinoxalin-2-yl-but-3-yn-1-ol (30 mg, 0.11 mmol) in DCM (1.5 mL) at −78° C. The reaction mixture was stirred for 15 min. at −78° C., quenched by the addition of water at 0° C. and extracted twice with DCM. The organic phase was washed with water, dried over Na$_2$SO$_4$, filtered and evaporated. The crude residue was purified by flash chromatography (cyclohexane/AcOEt 1:1) to yield 10 mg (36 μmol, 33%) of 2-(1-fluoro-4-(pyridin-2-yl)but-3-ynyl)quinoxaline as an orange semi-solid with a purity of 70%.

LCMS (RT): 3.55 min; MS (ES+) gave m/z: 278.0.
$^1$H-NMR (CDCl$_3$), δ (ppm): 3.20-3.56 (2H), 5.90-6.11 (m, 1H), 7.17-7.22 (m, 1H), 7.31-7.35 (m, 1H), 7.56-7.63 (m, 1H), 7.77-7.83 (2H), 8.07-8.18 (2H), 8.50-8.55 (m, 1H), 9.15 (s, 1H).

Example 173

N-(6-(4-(2H-Benzo[d][1,2,3]triazol-2-yl)but-1-ynyl)pyridin-2-yl)methylsulfonamide

173(A) N-Methylsulfonyl-N-[6-(4-benzo[d][1,2,3]triazol-2-yl-but-1-ynyl)-pyridin-2-yl]-methylsulfonamide A solution of methanesulfonyl chloride (98 mg, 0.85 mmol) in DCM was added to a solution of 6-(4-benzotriazol-2-yl-but-1-ynyl)-pyridin-2-ylamine (100 mg, 0.38 mmol, Example 169(A)) and Et$_3$N (0.12 mL, 0.85 mmol) in DCM (2 mL). The reaction mixture was stirred at room temperature for 2 hours and then the solvent was evaporated. The crude residue was purified by flash chromatography (cyclohexane/AcOEt 3:2) to yield 140 mg (0.33 mmol, 88%) of N-methylsulfonyl-N-[6-(4-benzo[d][1,2,3]triazol-2-yl-but-1-ynyl)-pyridin-2-yl]-methylsulfonamide as a white solid.

LCMS (RT): 4.00 min; MS (ES+) gave m/z: 420.1.

173(B) N-(6-(4-(2H-Benzo[d][1,2,3]triazol-2-yl)but-1-ynyl)pyridin-2-yl)methylsulfonamide A solution of NaOH (130 mg, 3.30 mmol) in water (3M) was added to a solution of N-methylsulfonyl-N-[6-(4-benzo[d][1,2,3]triazol-2-yl-but-1-ynyl)-pyridin-2-yl]-methylsulfonamide (140 mg, 0.33 mmol) in THF (3 mL). The reaction mixture was stirred 4 hours at room temperature. The aqueous phase was extracted with DCM. The organic phase was washed with water, dried over Na$_2$SO$_4$, filtered and evaporated. Diisopropyl ether was added and the crude product was triturated, filtered and dried to yield 70 mg (0.20 mmol, 62%) of N-(6-(4-(2H-benzo[d][1,2,3]triazol-2-yl)but-1-ynyl)pyridin-2-yl)methylsulfonamide as a white powder (M.P.=65-68° C.).

LCMS (RT): 3.75 min; MS (ES+) gave m/z: 342.1.

Example 174

2-(4-(3-Methyl-4-phenyl-1H-pyrazol-1-yl)but-1-ynyl)pyridine and 2-(4-(5-methyl-4-phenyl-1H-pyrazol-1-yl)but-1-ynyl)pyridine

174(A) 1-But-3-ynyl-5-methyl-4-phenyl-1H-pyrazole and 1-but-3-ynyl-3-methyl-4-phenyl-1H-pyrazole The title compounds were prepared in accordance with the general method of Example 109(D), from 5-methyl-4-phenyl-1H-pyrazole (515 mg, 3.25 mmol). The crude residue was purified by flash chromatography (cyclohexane/AcOEt 4:1) to yield 255 mg (1.21 mmol, 42%) of 1-but-3-ynyl-5-methyl-4-phenyl-1H-pyrazole and 1-but-3-ynyl-3-methyl-4-phenyl-1H-pyrazole.

174(B) 2-(4-(3-Methyl-4-phenyl-1H-pyrazol-1-yl)but-1-ynyl)pyridine and 2-(4-(5-methyl-4-phenyl-1H-pyrazol-1-yl)but-1-ynyl)pyridine The title compounds were prepared in accordance with the general method of Example 1, from 255 mg (1.21 mmol) of 1-but-3-ynyl-5-methyl-4-phenyl-1H-pyrazole and 1-but-3-ynyl-3-methyl-4-phenyl-1H-pyrazole. The crude residue was purified by flash chromatography (DCM/MeOH 99:1 to 98:2) to yield 33 mg (0.11 mol, 10%) of 2-(4-(3-methyl-4-phenyl-1H-pyrazol-1-yl)but-1-ynyl)pyridine and 2-(4-(5-methyl-4-phenyl-1H-pyrazol-1-yl)but-1-ynyl)pyridine as a orange oil.

LCMS (RT): 3.80 min; MS (ES+) gave m/z: 288.0.
Rf (DCM/MeOH 98:2)=0.2.
$^1$H-NMR (CDCl$_3$), δ (ppm): 2.41 (s, 3H), 2.46 (s, 3H), 3.01 (t, J=6.9, 2H), 3.02 (t, J=6.9, 2H), 4.34 (t, J=6.9, 2H), 4.38 (t, 6.9, 2H), 7.20-7.25 (2H), 7.28-7.40 (12H), 7.57-7.63 (4H), 8.55-8.57 (2H).

Example 175

N-(6-(4-(2H-Benzo[d][1,2,3]triazol-2-yl)but-1-ynyl)pyridin-2-yl)formamide

A solution of anhydride acetic (0.75 mL) and formic acid (0.32 mL) was heated at 60° C. for 3 hours. The reaction mixture was cooled to room temperature, 6-(4-benzotriazol-2-yl-but-1-ynyl)-pyridin-2-ylamine (70 mg, 0.27 mmol, 169 (A)) was added over 15 min. and the reaction mixture was stirred at room temperature for 1 day. After evaporation of the solvent, the crude residue was triturated with diisopropyl ether, filtered and dried to yield 25 mg (86 μmol, 32%) of N-(6-(4-(2H-benzo[d][1,2,3]triazol-2-yl)but-1-ynyl)pyridin-2-yl)formamide as a brown solid.

LCMS (RT): 3.38 min; MS (ES+) gave m/z: 292.1.
$^1$H-NMR (CDCl$_3$), δ (ppm): 3.31 (t, J=7.2, 2H), 5.00 (t, J=7.2, 2H), 7.31-7.44 (3H), 7.49 (dd, J=0.6 and 8.1, 1H), 7.72-7.79 (m, 1H), 7.84-7.91 (2H), 9.34 (s, 1H).

Example 176

4-Chloro-2-(4-(1,2-dimethyl-1H-imidazol-4-yl)but-3-ynyl)-2H-benzo[d][1,2,3]triazole The title compound was prepared in accordance with the general method of Example 108(C), from 4-bromo-1,2-dimethyl-1H-imidazole (85 mg, 0.49 mmol) and 2-but-3-ynyl-4-chloro-2H-benzo[d][1,2,3]triazole (100 mg, 0.49 mmol, Example 146(B)). Microwave conditions: 100° C. for 15 min. The crude residue was purified by C$_{18}$ flash chromatography to yield 8.0 mg (27 mmol, 5%) of 4-chloro-2-(4-(1,2-dimethyl-1H-imidazol-4-yl)but-3-ynyl)-2H-benzo[d][1,2,3]triazole as a brown semi-solid.

Rf (cyclohexane/AcOEt 7:3)=0.2.
LCMS (RT): 2.55 min; MS (ES+) gave m/z: 300.2, 302.1.
$^1$H-NMR (CDCl$_3$), δ (ppm): 2.33 (s, 3H), 3.24 (t, J=7.5, 2H), 3.52 (s, 3H), 4.96 (t, J=7.5, 2H), 6.90 (s, 1H), 7.27-7.34 (m, 1H), 7.39 (dd, J=0.9 and 7.2, 1H), 7.77 (dd, J=0.9 and 8.4, 1H).

Example 177

4,5-Dimethyl-2-(4-(pyridin-2-yl)but-3-ynyl)-2H-benzo[d][1,2,3]triazole

177(A) 4,5-Dimethyl-1H-benzo[d][1,2,3]triazole

The title compound was prepared in accordance with the general method of Example 127(A), from 3,4-dimethyl-benzene-1,2-diamine (500 mg, 3.67 mmol) to yield 4,5-dimethyl-1H-benzo[d][1,2,3]triazole (520 mg, 3.53 mmol, 95%) as a brown solid.

177(B) 2-But-3-ynyl-4,5-dimethyl-2H-benzo[d][1,2,3]triazole

The title compound was prepared in accordance with the general method of Example 109(D), from 4,5-dimethyl-1H-benzo[d][1,2,3]triazole (520 mg, 3.53 mmol). The crude residue was purified by flash chromatography (cyclohexane/AcOEt 9:1) to yield 131 mg (0.66 mmol, 20%) of 2-but-3-ynyl-4,5-dimethyl-2H-benzo[d][1,2,3]triazole.

Rf (cyclohexane/AcOEt 4:1)=0.5.

177(C) 4,5-Dimethyl-2-(4-(pyridin-2-yl)but-3-ynyl)-2H-benzo[d][1,2,3]triazole The title compound was prepared in accordance with the general method of Example 1, from 2-bromo-pyridine (65 mg, 0.41 mmol) and 2-but-3-ynyl-4,5-dimethyl-2H-benzo[d][1,2,3]triazole (75 mg, 0.38 mmol). Reaction time: 3 hours. The crude residue was purified by flash chromatography (DCM/MeOH 98:2) to yield 65 mg (0.23 mmol, 63%) of 4,5-dimethyl-2-(4-(pyridin-2-yl)but-3-ynyl)-2H-benzo[d][1,2,3]triazole as an orange oil.

Rf (DCM/MeOH 98:2)=0.1.

LCMS (RT): 4.05 min; MS (ES+) gave m/z: 277.1.

$^1$H-NMR (CDCl$_3$), δ (ppm): 2.39 (s, 3H), 2.57 (s, 3H), 3.27 (t, J=7.5, 2H), 4.96 (t, J=7.5, 2H), 7.19-7.25 (2H), 7.34 (d, J=8.1, 1H), 7.58 (d, J=8.7, 1H), 7.58-7.63 (m, 1H), 8.55 (d, J=5.1, 1H).

Example 178

2-(4-(6-(Fluoromethyl)pyridin-2-yl)but-3-ynyl)-4,5-dimethyl-2H-benzo[d][1,2,3]triazole

The title compound was prepared in accordance with the general method of Example 1, from 2-bromo-6-(fluoromethyl)-pyridine (79 mg, 0.41 mmol) and 2-but-3-ynyl-4,5-dimethyl-2H-benzo[d][1,2,3]triazole (75 mg, 0.38 mmol, 177(B)). Reaction time: 3 hours. The crude residue was purified by flash chromatography (DCM/MeOH 98:2) to yield 46 mg (0.15 mmol, 40%) of 2-(4-(6-(fluoromethyl)pyridin-2-yl)but-3-ynyl)-4,5-dimethyl-2H-benzo[d][1,2,3]triazole as an orange oil.

Rf (DCM/MeOH 98:2)=0.1.

LCMS (RT): 4.48 min; MS (ES+) gave m/z: 309.1.

$^1$H-NMR (CDCl$_3$), δ (ppm): 2.40 (s, 3H), 2.58 (s, 3H), 3.27 (t, J=7.5, 2H), 4.95 (t, J=7.5, 2H), 5.40-5.55 (m, 2H), 7.20 (d, J=8.7, 1H), 7.29 (d, J=7.8, 1H), 7.40 (d, J=8.0, 1H), 7.58 (d, J=8.7, 1H), 7.66-7.72 (m, 1H).

Example 179

2-(4-(4-(4-Fluorophenyl)-1H-1,2,3-triazol-1-yl)but-1-ynyl)pyridine

179(A) 4-(4-Fluoro-phenyl)-1H-[1,2,3]triazole

Sodium azide (4.28 g, 65.8 mmol) was added to a solution (E)-1-fluoro-4-(2-nitro-vinyl)-benzene (1.00 g, 5.98 mmol) in DMSO (50 mL), the solution was stirred at room temperature for 14 hours and the reaction mixture was poured onto water. The aqueous phase was extracted with AcOEt. The organic phase was washed with saturated solution of NaHCO$_3$, brine, dried over MgSO$_4$, filtered and evaporated to yield 300 mg (1.84 mmol, 31%) of 4-(4-fluoro-phenyl)-1H-[1,2,3]triazole.

179(B) 1-But-3-ynyl-4-(4-fluoro-phenyl)-1H-[1,2,3]triazole

The title compound was prepared in accordance with the general method of Example 109(D), from 4-(4-fluoro-phenyl)-1H-[1,2,3]triazole (306 mg, 1.87 mmol). The crude residue was purified by flash chromatography (cyclohexane/AcOEt 95:5 to 90:10) to yield 80 mg (0.37 mmol, 21%) of 1-but-3-ynyl-4-(4-fluoro-phenyl)-1H-[1,2,3]triazole.

Rf (cyclohexane/AcOEt 4:1)=0.1.

179(C) 2-(4-(4-(4-Fluorophenyl)-1H-1,2,3-triazol-1-yl)but-1-ynyl)pyridine

The title compound was prepared in accordance with the general method of Example 1, from 2-bromo-pyridine (65 mg, 0.41 mmol) and 1-but-3-ynyl-4-(4-fluoro-phenyl)-1H-[1,2,3]triazole (80 mg, 0.37 mmol). Reaction time: 13 hours. The crude residue was purified by flash chromatography (DCM/MeOH 98.5:1.5) to yield 28 mg (96 μmol, 26%) of 2-(4-(4-(4-fluorophenyl)-1H-1,2,3-triazol-1-yl)but-1-ynyl)pyridine as a brown solid (M.P.=120-122° C.).

Rf (DCM/MeOH 98.5:1.5)=0.1.

LCMS (RT): 3.45 min; MS (ES+) gave m/z: 293.1.

$^1$H-NMR (CDCl$_3$), δ (ppm): 3.10 (t, J=6.7, 2H), 4.68 (t, J=6.7, 2H), 7.07-7.14 (m, 2H), 7.22-7.26 (m, 1H), 7.34 (d, J=7.8, 1H), 7.61-7.65 (m, 1H), 7.81 (dd, J=5.1 and 8.7, 2H), 7.97 (s, 1H), 8.58 (d, J=4.5, 1H).

Example 180

2-(4-(6-Chloropyridin-2-yl)but-3-ynyl)-2H-benzo[d][1,2,3]triazole

The title compound was prepared in accordance with the general method of Example 108(C), from 2,6-dichloropyridine (150 mg, 1.01 mmol) and 2-but-3-ynyl-2H-benzo[d][1,2,3]triazole (0.17 g, 1.00 mmol, Example 109(D)). Microwave conditions: 120° C. for 15 min. The crude residue was purified by flash chromatography (cyclohexane/AcOEt 4:1) to yield 15 mg (53 mmol, 5%) of 2-(4-(6-chloropyridin-2-yl)but-3-ynyl)-2H-benzo[d][1,2,3]triazole as a yellow solid.

Rf (cyclohexane/AcOEt 4:1)=0.2.

LCMS (RT): 4.32 min; MS (ES+) gave m/z: 283.1, 285.1.

Example 181

2-(4-(6-(Fluoromethyl)pyridin-2-yl)but-3-ynyl)-3-methylquinoxaline

181(A) 2-Methyl-3-(4-trimethylsilanyl-but-3-ynyl)-quinoxaline

The title compound was prepared in accordance with the general method of Example 118(A), from 2,3-dimethyl-quinoxaline (300 mg, 1.90 mmol). The crude residue was purified by flash chromatography (cyclohexane/AcOEt 9:1) to yield 200 mg (0.74 mmol, 39%) of 2-methyl-3-(4-trimethylsilanyl-but-3-ynyl)-quinoxaline as an orange oil.
LCMS (RT): 5.12 min; MS (ES+) gave m/z: 269.1.

181(B) 2-But-3-ynyl-3-methyl-quinoxaline

The title compound was prepared in accordance with the general method of Example 108(B), from 2-methyl-3-(4-trimethylsilanyl-but-3-ynyl)-quinoxaline (143 mg, 0.53 mmol). The crude residue was purified by flash chromatography (cyclohexane/AcOEt 94:6 to 90:10) to yield 20 mg (0.10 mmol, 19%) of 2-but-3-ynyl-3-methyl-quinoxaline as an orange liquid.
LCMS (RT): 3.59 min; MS (ES+) gave m/z: 197.1.

181(C) 2-(4-(6-(Fluoromethyl)pyridin-2-yl)but-3-ynyl)-3-methylquinoxaline

The title compound was prepared in accordance with the general method of Example 1, from 2-bromo-6-(fluoromethyl)-pyridine (24 mg, 0.13 mmol) and 2-but-3-ynyl-3-methyl-quinoxaline (25 mg, 0.13 mmol). Reaction time: 14 hours. The crude residue was purified by preparative chromatography plate (Et$_2$O/pentane 7:3) to yield 6.4 mg (21 mmol, 13%) of 2-(4-(6-(fluoromethyl)pyridin-2-yl)but-3-ynyl)-3-methylquinoxaline as a yellow solid.
$^1$H-NMR (CDCl$_3$), δ (ppm): 2.73 (s, 3H), 3.04 (t, J=7.1, 2H), 3.29 (t, J=7.1, 2H), 5.30-5.49 (m, 2H), 7.23 (d, J=7.7, 1H), 7.31 (d, J=7.8, 1H), 7.59-7.65 (3H), 7.91-7.98 (2H).

Example 182

2-(4-(6-(1-Fluoroethyl)pyridin-2-yl)but-3-ynyl)-2H-benzo[d][1,2,3]triazole

182(A) 1-[6-(4-Benzotriazol-2-yl-but-1-ynyl)-pyridin-2-yl]-ethanone

The title compound was prepared in accordance with the general method of Example 1, from 1-(6-bromo-pyridin-2-yl)-ethanone (500 mg, 2.66 mmol) and 2-but-3-ynyl-2H-benzo[d][1,2,3]triazole (455 mg, 2.66 mmol, Example 109 (D)). Reaction time: 3 hours. The crude residue was purified by flash chromatography (cyclohexane/AcOEt 4:1) to yield 380 mg (1.36 mmol, 51%) of 1-[6-(4-benzotriazol-2-yl-but-1-ynyl)-pyridin-2-yl]-ethanone as a white solid.
Rf (cyclohexane/AcOEt 7:3)=0.3.
LCMS (RT): 4.14 min; MS (ES+) gave m/z: 279.0.

182(B) 1-[6-(4-Benzotriazol-2-yl-but-1-ynyl)-pyridin-2-yl]-ethanol

NaBH$_4$ (99 mg, 1.6 mmol) was added to a solution of 1-[6-(4-benzotriazol-2-yl-but-1-ynyl)-pyridin-2-yl-]-ethanone (380 mg, 1.31 mmol) in MeOH (5 mL) at 0° C. The reaction mixture was stirred at room temperature for 30 min., quenched by the addition of water at 0° C. and extracted twice with DCM. The organic phase was washed with water, dried over Na$_2$SO$_4$, filtered and evaporated. The crude residue was purified by flash chromatography (cyclohexane/AcOEt 3:2) to yield 202 mg (0.69 mmol, 53%) of 1-[6-(4-benzotriazol-2-yl-but-1-ynyl)-pyridin-2-yl]-ethanol as a colorless oil.

182(C) 2-(4-(6-(1-Fluoroethyl)pyridin-2-yl)but-3-ynyl)-2H-benzo[d][1,2,3]triazole The title compound was prepared in accordance with the general method of Example 172(C) from 1-[6-(4-benzotriazol-2-yl-but-1-ynyl)-pyridin-2-yl]-ethanol (100 mg, 0.34 mmol). The crude residue was purified by flash chromatography (cyclohexane/AcOEt 4:1) to yield 50 mg (0.17 mmol, 50%) of 2-(4-(6-(1-fluoroethyl)pyridin-2-yl)but-3-ynyl)-2H-benzo[d][1,2,3]triazole as a colorless oil.
Rf (cyclohexane/AcOEt 4:1)=0.2.
LCMS (RT): 4.28 min; MS (ES+) gave m/z: 295.2.
$^1$H-NMR (CDCl$_3$), δ (ppm): 1.65 (dd, J=6.3 and 24.6, 3H), 3.30 (t, J=7.5, 2H), 4.99 (t, J=7.5, 2H), 5.53-5.76 (m, 1H), 7.24-7.28 (m, 1H), 7.36-7.43 (3H), 7.63-7.70 (m, 1H), 7.84-7.91 (2H).

Example 183

2-(4-(Pyridin-2-yl)but-3-ynyl)isoquinolin-1(2H)-one

183(A) 2-But-3-ynyl-2H-isoquinolin-1-one

The title compound was prepared in accordance with the general method of Example 109(D), from 2H-isoquinolin-1-one (200 mg, 1.38 mmol). The crude residue was purified by flash chromatography (DCM/MeOH 99:1) to yield 125 mg (0.63 mmol, 46%) of 2-but-3-ynyl-2H-isoquinolin-1-one.
Rf (DCM/MeOH 99:1)=0.2.
LCMS (RT): 3.47 min; MS (ES+) gave m/z: 198.1.

183(B) 2-(4-(Pyridin-2-yl)but-3-ynyl)isoquinolin-1(2H)-one

The title compound was prepared in accordance with the general method of Example 1, from 2-bromopyridine (100 mg, 0.63 mmol) and 2-but-3-ynyl-2H-isoquinolin-1-one (120 mg, 0.63 mmol). Reaction time: 3 hours. The crude residue was purified by flash chromatography (cyclohexane/AcOEt 4:1) to yield 17 mg (62 mmol, 10%) of 2-(4-(pyridin-2-yl)but-3-ynyl)isoquinolin-1(2H)-one as a white solid (M.P.=85-90° C.).
LCMS (RT): 3.25 min; MS (ES+) gave m/z: 275.2.
$^1$H-NMR (CDCl$_3$), δ (ppm): 2.98 (t, J=6.6, 2H), 4.25 (t, J=6.6, 2H), 6.50 (d, J=7.5, 1H), 7.17-7.23 (m, 1H), 7.32 (d, J=7.8, 1H), 7.42-7.55 (3H), 7.57-7.71 (2H), 8.44 (d, J=8.1, 1H), 8.55 (d, J=4.8, 1H).

Example 184

2,6-Dimethoxy-N-methyl-N-(4-(pyridin-2-yl)but-3-ynyl)benzamide 2,6-Dimethoxy-benzoyl chloride (81 mg, 0.41 mmol) was added to a solution of methyl-(4-pyridin-2-yl-but-3-ynyl)-amine (50 mg, 0.31 mmol) and DIEA (69 μL, 0.41 mmol) in chloroform (2 mL) at 0° C. The reaction mixture was stirred at 0° C. for 10 min., at room temperature for 14 hours, quenched by the addition of water and extracted twice with chloroform. The organic phase was washed with saturated solution of NaHCO$_3$, brine, dried over MgSO$_4$, filtered and evaporated. The crude residue was purified by flash chromatography (DCM/MeOH 95:5) to yield 2,6-dimethoxy-N-methyl-N-(4-(pyridin-2-yl)but-3-ynyl)benzamide (12 mg, 37 µmol, 12%).

LCMS (RT): 3.00 min; MS (ES+) gave m/z: 325.1.
$^1$H-NMR (CDCl$_3$), δ (ppm): 3.02 (t, J=7.5, 2H), 3.34 (t, J=7.5, 2H), 7.17-7.21 (m, 1H), 7.33 (d, J=7.8, 1H), 7.43 (d, J=8.4, 1H), 7.49-7.54 (m, 1H), 7.58-7.63 (m, 1H), 7.69-7.74 (m, 1H), 7.81 (d, J=8.1, 1H), 8.08 (d, J=8.4, 1H), 8.12 (d, J=8.4, 1H), 8.55

Example 185

2,6-Difluoro-N-methyl-N-(4-(pyridin-2-yl)but-3-ynyl)benzamide

The title compound was prepared in accordance with the general method of Example 186, from 2,6-difluoro-benzoyl chloride (51 µL, 0.41 mmol). The crude residue was purified by flash chromatography (DCM/MeOH 95:5) to yield 38 mg (13 µmol, 40%) of 2,6-difluoro-N-methyl-N-(4-(pyridin-2-yl)but-3-ynyl)benzamide.

LCMS (RT): 3.22 min; MS (ES+) gave m/z: 301.1.

Example 186

N-(2-Fluorophenyl)-5-(pyridin-2-yl)pent-4-ynamide

186(A) N-(2-Fluorophenyl)pent-4-ynamide

The title compound was prepared in accordance with the general method of Example 34(A), from 2-fluoro-aniline (566 mg, 5.10 mmol). The crude residue was purified by flash chromatography (DCM) to yield 710 mg (3.71 mmol, 73%) of N-(2-fluorophenyl)pent-4-ynamide as a white solid.

LCMS (RT): 3.33 min; MS (ES+) gave m/z: 192.1.
Rf (DCM)=0.2.

186(B) (2-Fluoro-phenyl)-pent-4-ynoyl-carbamic acid tert-butyl ester

The title compound was prepared in accordance with the general method of Example 34(B), from N-(2-fluorophenyl)pent-4-ynamide (700 mg, 3.66 mmol). The crude residue was purified by flash chromatography (cyclohexane/AcOEt 9:1) to yield 1.08 g (3.71 mmol, 100%) of (2-fluoro-phenyl)-pent-4-ynoyl-carbamic acid tert-butyl ester as a colourless oil.

LCMS (RT): 4.75 min; MS (ES+) gave m/z: 192.1.
Rf (cyclohexane/AcOEt 9:1)=0.3.

186(C) (2-Fluoro-phenyl)-(5-pyridin-2-yl-pent-4-ynoyl)-carbamic acid tert-butyl Ester The title compound was prepared in accordance with the general method of Example 1, from 2-bromo-pyridine (136 mg, 0.86 mmol) and (2-fluoro-phenyl)-pent-4-ynoyl-carbamic acid tert-butyl ester (250 mg, 0.86 mmol). The crude residue was purified by flash chromatography (cyclohexane/AcOEt 4:1) to yield 240 mg (0.65 mmol, 76%) of (2-fluoro-phenyl)-(5-pyridin-2-yl-pent-4-ynoyl)-carbamic acid-tert-butyl ester as a white solid.

LCMS (RT): 4.60 min; MS (ES+) gave m/z: 369.1.
Rf (cyclohexane/AcOEt 4:1)=0.2.

186(D) N-(2-Fluorophenyl)-5-(pyridin-2-yl)pent-4-ynamide

The title compound was prepared in accordance with the general method of Example 34(D), from (2-fluoro-phenyl)-(5-pyridin-2-yl-pent-4-ynoyl)-carbamic acid-tert-butyl ester (240 mg, 0.65 mmol). After the work-up, the crude residue was washed with diisopropyl ether/pentane 1:1 to yield 120 mg (0.45 mmol, 69%) of N-(2-fluorophenyl)-5-(pyridin-2-yl)pent-4-ynamide as a beige powder (M.P.=82-84° C.).

LCMS (RT): 3.10 min; MS (ES+) gave m/z: 269.1.
$^1$H-NMR (CDCl$_3$), δ (ppm): 2.75 (t, J=6.9, 2H), 2.87 (t, J=6.9, 2H), 7.00-7.16 (3H), 7.20 (ddd, J=1.2, 5.1 and 7.8, 1H), 7.37 (d, J=7.8, 1H), 7.57-7.66 (m, 1H), 7.67-7.77 (m, 1H), 8.24-8.35 (m, 1H), 8.53 (d, J=4.8, 1H).

Example 187

N-(3-Fluorophenyl)-5-(pyridin-2-yl)pent-4-ynamide

187(A) N-(3-Fluorophenyl)pent-4-ynamide

The title compound was prepared in accordance with the general method of Example 34(A), from 3-fluoro-aniline (566 mg, 5.10 mmol). The crude residue was purified by flash chromatography (DCM) to yield 660 mg (3.45 mmol, 68%) of N-(3-fluorophenyl)pent-4-ynamide as a white solid.

LCMS (RT): 3.53 min; MS (ES+) gave m/z: 192.1.
Rf (DCM)=0.2.

187(B) (3-Fluoro-phenyl)-pent-4-ynoyl-carbamic Acid tert-butyl Ester

The title compound was prepared in accordance with the general method of Example 34(B), from N-(3-fluorophenyl)pent-4-ynamide (660 mg, 3.45 mmol). The crude residue was purified by flash chromatography (cyclohexane/AcOEt 9:1) to yield 1.00 g (3.43 mmol) of (3-fluoro-phenyl)-pent-4-ynoyl-carbamic acid tert-butyl ester as a colourless oil.

LCMS (RT): 4.68 min; MS (ES+) gave m/z: 191.1.
Rf (Cyclohexane/AcOEt 9:1)=0.3.

187(C) (3-Fluoro-phenyl)-(5-pyridin-2-yl-pent-4-ynoyl)-carbamic Acid tert-butyl Ester The title compound was prepared in accordance with the general method of Example 1, from 2-bromo-pyridine (137 mg, 0.86 mmol) and (3-fluoro-phenyl)-pent-4-ynoyl-carbamic acid tert-butyl ester (250 mg, 0.86 mmol). Reaction time: 3 hours. The crude residue was purified by flash chromatography (cyclohexane/AcOEt 4:1) to yield 190 mg (0.52 mmol, 60%) of (3-fluoro-phenyl)-(5-pyridin-2-yl-pent-4-ynoyl)-carbamic acid tert-butyl ester as a white solid.

LCMS (RT): 4.48 min; MS (ES+) gave m/z: 369.1.
Rf (cyclohexane/AcOEt 4:1)=0.2.

187(D) N-(3-Fluorophenyl)-5-(pyridin-2-yl)pent-4-ynamide

The title compound was prepared in accordance with the general method of Example 34(D), from (3-fluoro-phenyl)-(5-pyridin-2-yl-pent-4-ynoyl)-carbamic acid tert-butyl ester (190 mg, 0.52 mmol). After the work-up, the crude residue was washed with pentane to yield 125 mg (0.47 mmol, 90%) of N-(3-fluorophenyl)-5-(pyridin-2-yl)pent-4-ynamide as a beige powder (M.P.=110-114° C.).

LCMS (RT): 3.40 min; MS (ES+) gave m/z: 269.1.

Example 188

N-(4-Fluoro-2-methyl-phenyl)-5-(pyridin-2-yl)pent-4-ynamide

188(A) N-(4-Fluoro-2-methyl-phenyl)pent-4-ynamide

The title compound was prepared in accordance with the general method of Example 34(A), from 4-fluoro-2-methyl-phenylamine (638 mg, 5.10 mmol). The crude residue was purified by flash chromatography (DCM) to yield 510 mg (2.49 mmol, 49%) of N-(4-fluoro-2-methyl-phenyl)pent-4-ynamide as a white solid.

Rf (DCM)=0.2.

188(B) (4-Fluoro-2-methyl-phenyl)-pent-4-ynoyl-carbamic Acid tert-butyl Ester The title compound was prepared in accordance with the general method of Example 34(B), from N-(4-fluoro-2-methyl-phenyl)pent-4-ynamide (500 mg, 2.63 mmol). The crude residue was purified by flash chromatography (cyclohexane/AcOEt 9:1) to yield 790 mg (2.59 mmol) of (4-fluoro-2-methyl-phenyl)-pent-4-ynoyl-carbamic acid tert-butyl ester as a colourless oil.

Rf (Cyclohexane/AcOEt 9:1)=0.3.

188(C) (4-Fluoro-2-methyl-phenyl)-(5-pyridin-2-yl-pent-4-ynoyl)-carbamic Acid tert-butyl Ester The title compound was prepared in accordance with the general method of Example 1, from 2-bromo-pyridine (129 mg, 0.82 mmol) and (4-fluoro-2-methyl-phenyl)-pent-4-ynoyl-carbamic acid tert-butyl ester (250 mg, 0.82 mmol). Reaction time: 3 hours. The crude residue was purified by flash chromatography (cyclohexane/AcOEt 4:1) to yield 190 mg (0.50 mmol, 61%) of (4-fluoro-2-methyl-phenyl)-(5-pyridin-2-yl-pent-4-ynoyl)-carbamic acid tert-butyl ester as a white solid.

LCMS (RT): 4.78 min; MS (ES+) gave m/z: 382.4.

188(D) N-(4-Fluoro-2-methyl-phenyl)-5-(pyridin-2-yl)pent-4-ynamide

The title compound was prepared in accordance with the general method of Example 34(D), from (4-fluoro-2-methyl-phenyl)-(5-pyridin-2-yl-pent-4-ynoyl)-carbamic acid tert-butyl ester (220 mg, 0.58 mmol). After the work-up, the crude residue was washed with pentane to yield 85 mg (0.30 mmol, 52%) of N-(4-fluoro-2-methyl-phenyl)-5-(pyridin-2-yl)pent-4-ynamide as a beige powder (M.P.=110-114° C.).

LCMS (RT): 3.13 min; MS (ES+) gave m/z: 283.1.

Example 189

2,6-Dichloro-N-(4-(6-(fluoromethyl)pyridin-2-yl)but-3-ynyl)benzamide

189(A) 2-(4-(Trimethylsilyl)but-3-ynyl)isoindoline-1,3-dione

The title compound was prepared in accordance with the general method of Example 109(D), from 4-(trimethylsilyl)but-3-yn-1-ol (3.20 g, 22.5 mmol) and phthalimide (3.50 g, 23.8 mmol).

The crude residue was purified by flash chromatography (cyclohexane/AcOEt 9:1) to yield 3.1 g (11 mmol, 51%) of 2-(4-(trimethylsilyl)but-3-ynyl)isoindoline-1,3-dione as a white solid.

189(B) 2-(But-3-ynyl)isoindoline-1,3-dione

The title compound was prepared in accordance with the general method of Example 108(B), from 2-(4-(trimethylsilyl)but-3-ynyl)isoindoline-1,3-dione (3.10 g, 11.4 mmol). The crude residue was purified by flash chromatography (cyclohexane/AcOEt 9:1) to yield 985 mg (4.94 mmol, 43%) of 2-(but-3-ynyl)isoindoline-1,3-dione as a white solid.

189(C) 2-(4-(6-(Fluoromethyl)pyridin-2-yl)but-3-ynyl)isoindoline-1,3-dione

The title compound was prepared in accordance with the general method of Example 1, from 2-bromo-6-(fluoromethyl)pyridine (336 mg, 1.77 mmol, Example 190(E)) and 2-(but-3-ynyl)isoindoline-1,3-dione (320 mg, 1.61 mmol). The crude residue was purified by flash chromatography (cyclohexane/AcOEt 75:25) to yield 320 mg (1.04 mmol, 65%) of 2-(4-(6-(fluoromethyl)pyridin-2-yl)but-3-ynyl)isoindoline-1,3-dione as a white solid.

LCMS (RT): 3.97 min; MS (ES+) gave m/z: 309.1.

189(D) 4-(6-(Fluoromethyl)pyridin-2-yl)but-3-yn-1-amine

Hydrazine hydrate (1.0 mL, 5.2 mmol) was added to a solution of 2-(4-(6-(fluoromethyl)pyridin-2-yl)but-3-ynyl)isoindoline-1,3-dione (320 mg, 1.04 mmol) in EtOH (3 mL) and the reaction mixture was stirred for 4 hours at 50° C. The mixture was cooled down, DCM was added and the aqueous phase was extracted. The organic phase was washed with saturated solution of NaHCO$_3$, dried over Na$_2$SO$_4$, filtered and concentrated to yield 117 mg (0.66 mmol, 63%) of 4-(6-(fluoromethyl)pyridin-2-yl)but-3-yn-1-amine as a white solid.

189(E) 2,6-Dichloro-N-(4-(6-(fluoromethyl)pyridin-2-yl)but-3-ynyl)benzamide The title compound was prepared in accordance with the general method of Example 184, from 4-(6-(fluoromethyl)pyridin-2-yl)but-3-yn-1-amine (39 mg, 0.22 mmol) and 2,6-dichlorobenzoyl chloride (60 mg, 0.28 mmol). The crude residue was purified by flash chromatography (cyclohexane/AcOEt 7:3) to yield 21 mg (0.06 mmol, 27%) of 2,6-dichloro-N-(4-(6-(fluoromethyl)pyridin-2-yl)but-3-ynyl)benzamide as a yellow oil.

LCMS (RT): 3.72 min; MS (ES+) gave m/z: 351.0, 3.53.0.

Example 190

2-(4-(6-(Fluoromethyl)pyridin-2-yl)but-3-ynyl)-1-methyl-1H-benzo[d]imidazole

190(A) (1-Methyl-1H-benzo[d]imidazol-2-yl)methanol

A solution of 1-methyl-1H-benzo[d]imidazole-2-carbaldehyde (473 mg, 2.95 mmol) in MeOH (0.3 M, 10 mL) was cooled at 0° C. before the addition in small portions of NaBH$_4$ (559 mg, 14.80 mmol). After 90 min at 0° C., the reaction mixture was quenched with saturated NaHCO$_3$, extracted twice with Et$_2$O. The combined organic layers were washed with saturated brine and dried over MgSO$_4$. The solvent was removed under reduced pressure to afford 418 mg of 1-methyl-1H-benzo[d]imidazol-2-yl)methanol (Yield: 87%) as a white solid. The crude product was used in the next step without any further purification.

Rf (DCM/MeOH: 95/5)=0.19

190(B) 2-(Chloromethyl)-1-methyl-1H-benzo[d]imidazole

1-Methyl-1H-benzo[d]imidazol-2-yl)methanol (418 mg, 2.58 mmol) was partially dissolved in DCM (2 mL). At room temperature thionyl chloride (12.90 mmol, 0.935 mL) was added in one portion to the resulting suspension. The reaction mixture was stirred at room temperature for 90 min. The solvent was removed under reduced pressure to give a yellow solid. The solid was poured into saturated NaHCO$_3$ and extracted twice with Et$_2$O. The combined organic layers were washed with saturated brine and dried over MgSO$_4$. The solvent was removed under reduced pressure and the crude product was purified by Flash chromatography (prepacked 25 g silicagel column, DCM/MeOH from 100/0 to 97/3 as eluent) to afford 380 mg of 2-(chloromethyl)-1-methyl-1H-benzo[d]imidazole (Yield: 81%) as a white-pink solid.

Rf (DCM/MeOH: 95/5)=0.50

190(C) 1-Methyl-2-(4-(trimethylsilyl)but-3-ynyl)-1H-benzo[d]imidazole

The title compound was prepared in accordance with the general method of Example 67(D), from trimethyl(prop-1-ynyl)silane (283 mg, 2.52 mmol) and 2-(chloromethyl)-1-methyl-1H-benzo[d]imidazole (380 mg, 2.10 mmol). The crude product was purified over prepacked 25 g silicagel column (DCM/MeOH from 100/0 to 98/2 as eluent) to afford 317 mg of 1-methyl-2-(4-(trimethylsilyl)but-3-ynyl)-1H-benzo[d]imidazole (Yield: 59%) as red solid.

Rf (DCM/MeOH: 98/2)=0.37
LCMS (RT): 3.25 min; MS (ES+) gave m/z: 257.2

190(D) 2-(But-3-ynyl)-1-methyl-1H-benzo[d]imidazole

According to the protocol described in Example 38(D), the conversion of 1-methyl-2-(4-(trimethylsilyl)but-3-ynyl)-1H-benzo[d]imidazole (317 mg, 1.23 mmol) afforded 146 mg of 2-(but-3-ynyl)-1-methyl-1H-benzo[d]imidazole (Yield: 64%) as yellow-orange solid. Purification over silicagel chromatography (prepacked 25 g silicagel column, DCM/MeOH: 99/1 as eluent).

LCMS (RT): 0.65-1.93 min; MS (ES+) gave m/z: 185
Rf (DCM/MeOH: 95/5)=0.29

190(E) 2-Bromo-6-(fluoromethyl)pyridine

A solution of (6-bromopyridin-2-yl)methanol (5 g, 27 mmol) in dry DCM (60 mL) was added dropwise at −78° C. to a cooled solution of DAST (13 g, 80 mmol) in dry DCM (50 mL). The reaction mixture was stirred 1 h at −78° C. then 1 h at room temperature. To complete the reaction, an additional 5 mL of DAST were slowly added at −60° C. and the reaction mixture was kept overnight at room temperature. The reaction was quenched with water and the organic layer extracted with DCM, dried over MgSO$_4$ and evaporated. Purification over silicagel chromatography (prepacked 85 g silicagel column, Cyclohexane/AcOEt: 90/10 as eluent) to afford 4.50 g of 2-bromo-6-(fluoromethyl)pyridine (Yield: 89%) as pale yellow oil which crystallized at 0° C.
LCMS (RT): 3.42 min; MS (ES+) gave m/z: 191, 192
Rf (Cyclohexane/AcOEt: 90/10)=0.4
$^1$NMR (CDCl$_3$), δ (ppm): 7.60-7.50 (m, 1H), 7.40-7.30 (m, 2H), 5.55-5.25 (d, 2H)

190(F) 2-(4-(6-(Fluoromethyl)pyridin-2-yl)but-3-ynyl)-1-methyl-1H-benzo[d]imidazole In a dry microwave tube were placed in suspension CuI (7.55 mg, 0.039 mmol) and triethylamine (1.45 mL, 10.30 mmol). Then under nitrogen atmosphere, were added the 2-bromo-6-(fluoromethyl)pyridine (151 mg, 0.79 mmol), PdCl$_2$(PPh$_3$)$_2$ (27.80 mg, 0.039 mmol) and triphenyl phosphine polymerbound (41.6 mg, 0.158 mmol). The suspension was stirred at room temperature for few minutes, finally the 2-(but-3-ynyl)-1-methyl-1H-benzo[d]imidazole (146 mg, 0.792 mmol) in 1.1 mL of DMF was added, and the reaction mixture was stirred at room temperature for 30 min.

The reaction mixture was stirred and heated under micro wave irradiation for 15 min at 120° C. After filtering to remove triphenyl phosphine polymerbound, the triethylamine was concentrated under reduce pressure and the residue was dissolved in DCM. The organic layer was washed with saturated NaHCO$_3$, H$_2$O and saturated brine. The organic layer was dried over Na$_2$SO$_4$, filtered and concentrated.

Purification over silicagel chromatography (prepacked 25 g silicagel column, DCM/MeOH: from 100/0 to 98.5/1.5 as eluent) to afford 127 mg of 2-(4-(6-(fluoromethyl)pyridin-2-yl)but-3-ynyl)-1-methyl-1H-benzo[d]imidazole as a yellow solid (Mp=95.3-96.3° C.).

Rf (DCM/MeOH: 95/5)=0.13
LCMS (RT): 2.41 min; MS (ES+) gave m/z: 294
$^1$H-NMR (CDCl$_3$), δ (ppm): 7.80-7.65 (m, 2H), 7.45-7.20 (m, 5H), 5.60-5.38 (d, 2H), 3.80 (s, 3H), 3.30-3.20 (m, 2H), 3.15-3.05 (m, 2H).

Example 191

7-Chloro-2-(4-(6-(fluoromethyl)pyridin-2-yl)but-3-ynyl)-1-methyl-1H-benzo[d]imidazole

191(A) 2-Chloro-N-methyl-6-nitrobenzenamine

2-Fluoro-3-chloronitrobenzene (3.0 g, 17 mmol) was dissolved in EtOH (6 mL) and Methylamine 40% in Water (6 mL) was added dropwise at 0° C. and mixture was warmed up to RT overnight. Mixture went to a dark orange precipitate within 10 min. The solid was isolated by filtration, rinsed with water (2*10 mL) and dried in a desiccators under vacuum to afford 3 g of 2-chloro-N-methyl-6-nitrobenzenamine (Yield: 90%) as an orange crystalline solid.

Rf (Cyclohexane/EtOAc: 80/20)=0.52
LCMS (RT): 4.29 min

191(B) 6-Chloro-N$^1$-methylbenzene-1,2-diamine

2-Chloro-N-methyl-6-nitrobenzenamine (1.5 g, 8.0 mmol) was dissolved in a mixture of EtOH (15 mL) and H$_2$O (15 ml). Iron powder (2.2 g, 40 mmol) was added followed by Acetic acid (0.55 mL, 9.6 mmol). The reaction was monitored by TLC, after 30 min, the reaction was completed. The reaction mixture was filtered over celite pad and the filtrate was neutralized by saturated NaHCO$_3$ (10 mL). The product was extracted by EtOAc (2*10 mL), the organic layer was washed with brine (10 mL), dried over MgSO$_4$ and concentrated to dryness to afford 920 mg of 6-chloro-N$^1$-methylbenzene-1,2-diamine (Yield: 73%) as dark brown oil.

Rf (Cyclohexane/EtOAc: 70/30)=0.51
LCMS (RT): 2.18 min

191(C) 7-Chloro-2-(chloromethyl)-1-methyl-1H-benzo[d]imidazole

6-Chloro-N$^1$-methylbenzene-1,2-diamine (800 mg, 5 mmol) and 2-chloroacetic acid (700 mg, 8 mmol) were dissolved in HCl 2N (5.7 mL). The resulting solution was heated at 90° C. for 18 h. The aqueous layer was neutralized by 3N NaOH. After extraction with EtOAc (3*10 mL), the organic layer was washed with water (10 mL), brine (10 mL) and dried over Na$_2$SO$_4$. The solvent was removed under reduced pressure and the resulting crude product was purified over silicagel chromatography (prepacked 25 g silicagel column, Cyclohexane/AcOEt: 70/30 as eluent) to afford 478 mg of 7-chloro-2-(chloromethyl)-1-methyl-1H-benzo[d]imidazole (Yield: 40%) as a pink solid Rf (DCM/MeOH: 95/5)=0.35
LCMS (RT): 3.70 min; MS (ES+) gave m/z: 217

191(D) 7-Chloro-1-methyl-2-(4-(trimethylsilyl)but-3-ynyl)-1H-benzo[d]imidazole To a solution of the trimethyl(prop-1-ynyl)silane (0.21 mL, 1.4 mmol) in THF (4 mL), was added at −78° C. nBuLi 2.5M in hexane (0.56 mL, 1.3 mmol). After 90 min at −78° C., a solution of 7-chloro-2-(chloromethyl)-1-methyl-1H-benzo[d]imidazole (250 mg, 1.2 mmol) in THF (2 mL) was added. Mixture went from purple to orange and then dark brown. The reaction was quenched after 1 h at −78° C. with water and the solvent was evaporated to dryness to afford 338 mg of 7-chloro-1-methyl-2-(4-(trimethylsilyl)but-3-ynyl)-1H-benzo[d]imidazole (Yield: 100%) as a brown oily solid. It was carried through to the next step without purification.

LCMS (RT): 4.43 min; MS (ES+) gave m/z: 291

191(E) 2-(But-3-ynyl)-7-chloro-1-methyl-1H-benzo[d]imidazole

According to the protocol described in Example 38(D), the conversion of 7-chloro-1-methyl-2-(4-(trimethylsilyl)but-3-ynyl)-1H-benzo[d]imidazole (338 mg, 1.16 mmol) afforded 116 mg of 2-(but-3-ynyl)-7-chloro-1-methyl-1H-benzo[d]imidazole (Yield: 45%) as orange-brown oily solid.

Purification over silicagel chromatography (prepacked 25 g silicagel column, Cyclohexane/AcOEt: from 80/20 to 70/30 as eluent).

LCMS (RT): 2.68 min; MS (ES+) gave m/z: 219
Rf (Cyclohexane/AcOEt: 70/30)=0.17

191(F) 7-Chloro-2-(4-(6-(fluoromethyl)pyridin-2-yl)but-3-ynyl)-1-methyl-1H-benzo[d]imidazole The title compound was prepared in accordance with the general method of Example 190(F), from 2-bromo-6-(fluoromethyl)pyridine (30 mg, 0.16 mmol) and 2-(but-3-ynyl)-7-chloro-1-methyl-1H-benzo[d]imidazole (35 mg, 0.16 mmol). The crude residue was purified over silicagel chromatography (prepacked 10 g silicagel column, DCM/MeOH: from 100/0 to 99/1 as eluent) to afford 43 mg of a light brown solid. The resulting solid was triturated into isopropyl ether to give 6 mg of 7-chloro-2-(4-(6-(fluoromethyl)pyridin-2-yl)but-3-ynyl)-1-methyl-1H-benzo[d]imidazole (Yield: 10%) as white solid.

LCMS (RT): 3.25 min; MS (ES+) gave m/z: 328
Rf (DCM/MeOH: 95/5)=0.30

Example 192

7-Chloro-1-methyl-2-(4-(pyridin-2-yl)but-3-ynyl)-1H-benzo[d]imidazole

In a dry reaction tube containing copper iodide (1 mg, 0.0055 mmol) and triethylamine (0.50 mL, 0.1 mmol), were added 2-iodopyridine (22 mg, 0.11 mmol) and Pd(PPh$_3$)$_2$Cl$_2$ (2.4 mg, 0.0055 mmol). A yellow suspension was obtained and after a few minutes of stirring at room temperature, 2-(but-3-ynyl)-7-chloro-1-methyl-1H-benzo[d]imidazole (compound 191(E), 24 mg, 0.11 mmol) in triethylamine (0.2 mL) was added. Immediately the color of the reaction turns to black. The mixture was stirred at room temperature for 30 min and then at 50° C. for 3 h. Triethylamine was concentrated under reduce pressure and the residue was dissolved in DCM. The organic layer was washed with saturated NH$_4$Cl, water and brine. The solvent was removed under reduced pressure and the crude product was purified by flash chromatography system (prepacked silicagel column 2 g, DCM/MeOH: 98/2 as eluent) to afford 2 mg g of 7-chloro-1-methyl-2-(4-(pyridin-2-yl)but-3-ynyl)-1H-benzo[d]imidazole (Yield: 6%) as brown solid.

LCMS (RT): 2.84 min; MS (ES+) gave m/z: 296
Rf (DCM/MeOH: 95/5)=0.30

Example 193

4,6-Difluoro-2-(4-(6-(fluoromethyl)pyridin-2-yl)but-3-ynyl)-1-methyl-1H-benzo[d]imidazole

193(A) 3,5-Difluoro-N-methyl-2-nitrobenzenamine 1,3,5-Trifluoro-2-nitrobenzene (3.0 g, 16.90 mmol) was dissolved in EtOH (29.7 mL) and Methylamine 40% in Water (1.44 mL, 17.80 mmol) was added dropwise at 0° C. The color went from bright yellow to an orange precipitate within 20 min. After 4 h at RT. 0.66 mL of Methylamine was added (9 mmol). To complete the reaction, an additional 0.26 ml (3.6 mmol) of Methylamine was added after 2 h at RT. The completion was achieved within 20 min. Water (75 mL) was added to the reaction mixture and the solid was isolated by filtration, washed with water (2*10 mL) and dried over high vacuum to afford 2.64 g of 3,5-difluoro-N-methyl-2-nitrobenzenamine (Yield: 83%) as an orange solid.

Rf (Cyclohexane/EtOAc: 70/30)=0.57
LCMS (RT): 4.13 min

193(B) 3,5-Difluoro-N$^1$-methylbenzene-1,2-diamine

The title compound was prepared in accordance with the general method of Example 191(B), from 3,5-difluoro-N-methyl-2-nitrobenzenamine (1.5 g, 8 mmol) to afford 933 mg of 3,5-difluoro-M-methylbenzene-1,2-diamine (Yield: 74%) as a deep purple oily liquid.

Rf (DCM/MeOH: 95/5)=0.66

193(C) 2-(Chloromethyl)-4,6-difluoro-1-methyl-1H-benzo[d]imidazole

The title compound was prepared in accordance with the general method of Example 191(C), from 3,5-difluoro-N$^1$- methylbenzene-1,2-diamine (1.50 g, 9.50 mmol) and 2-chloroacetic acid (1.3 g, 14 mmol). The crude residue was purified over silicagel chromatography (prepacked 25 g silicagel column, Cyclohexane/AcOEt: 70/30 as eluent) to afford 443 mg of 2-(chloromethyl)-4,6-difluoro-1-methyl-1H-benzo[d]imidazole (Yield: 22%) as a purple solid.
LCMS (RT): 3.46 min; MS (ES+) gave m/z: 217
Rf (DCM/MeOH: 95/5)=0.43

193(D) 4,6-Difluoro-1-methyl-2-(4-(trimethylsilyl)but-3-ynyl)-1H-benzo[d]imidazole The title compound was prepared in accordance with the general method of Example 191(D), from 2-(chloromethyl)-4,6-difluoro-1-methyl-1H-benzo[d]imidazole (440 mg, 2.03 mmol) and trimethyl(prop-1-ynyl)silane (274 mg, 2.44 mmol). 4,6-difluoro-1-methyl-2-(4-(trimethylsilyl)but-3-ynyl)-1H-benzo[d]imidazole (539 mg, Yield: 91%) was obtained as a brown oil which can be used in the next step without any purification.
LCMS (RT): 4.67 min; MS (ES+) gave m/z: 293

193(E) 2-(But-3-ynyl)-4,6-difluoro-1-methyl-1H-benzo[d]imidazole

According to the protocol described in Example 38(D), the conversion of 4,6-difluoro-1-methyl-2-(4-(trimethylsilyl)but-3-ynyl)-1H-benzo[d]imidazole (539 mg, 1.84 mmol) afforded 126 mg of 2-(but-3-ynyl)-4,6-difluoro-1-methyl-1H-benzo[d]imidazole (Yield: 31%) as an orange solid.
Purification over silicagel chromatography (prepacked 25 g silicagel column, Cyclohexane/AcOEt: from 80/20 to 70/30).
LCMS (RT): 3.22 min; MS (ES+) gave m/z: 221

193(F) 4,6-Difluoro-2-(4-(6-(fluoromethyl)pyridin-2-yl)but-3-ynyl)-1-methyl-1H-benzo[d]imidazole The title compound was prepared in accordance with the general method of Example 190(F), from 2-bromo-6-(fluoromethyl)pyridine (109 mg, 0.57 mol) and 2-(but-3-ynyl)-4,6-difluoro-1-methyl-1H-benzo[d]imidazole (126 mg, 0.57 mmol). The crude residue was purified over silicagel chromatography (prepacked 25 g silicagel column, DCM/MeOH: from 100/0 to 99/1 as eluent) to afford 43 mg of a light brown solid. The resulting solid was dissolved in Dioxane and 0.5N HCl in dioxan was added (0.14 mL, 0.07 mmol). A green solid was formed and it was collected by filtration and washed with AcOEt. The chlorhydrate salt was dissolved in MeOH, neutralized by saturated NaHCO$_3$. The aqueous layer was extracted twice with AcOEt. The organic layer was dried over MgSO$_4$ and the solvent removed under reduced pressure to afford 9 mg of 4,6-difluoro-2-(4-(6-(fluoromethyl)pyridin-2-yl)but-3-ynyl)-1-methyl-1H-benzo[d]imidazole (Yield: 5%) as purple oily solid (Mp=103° C.-104° C.).
LCMS (RT): 3.68 min; MS (ES+) gave m/z: 330
Rf (DCM/MeOH: 95/5)=0.36
$^1$H-NMR (CDCl$_3$), δ (ppm): 7.70-7.60 (t, 1H), 7.40-7.30 (d, 1H), 7.30-7.20 (d, 1H), 6.80-6.60 (m, 2H), 5.46-5.31 (d, 2H), 3.68 (s, 3H), 3.18-3.12 (m, 2H), 3.02-2.95 (m, 2H)

Example 194

1-Isopropyl-2-(4-(pyridin-2-yl)but-3-ynyl)-1H-benzo[d]imidazole

194(A) N-Isopropyl-2-nitrobenzenamine

To a solution of 1-fluoro-2-nitrobenzene (4.406 g, 31.22 mmol) in EtOH (32 mL) was added at 0° C. isopropyl amine (2.97 mL, 32.80 mmol). The mixture turned from light yellow to bright orange instantly. It was stirred overnight at RT. Another 1 eq of isopropyl amine (2.97 mL, 32.80 mmol) was added and after 3 h of stirring 2 eq of isopropyl amine were added (6 mL, 64 mmol) and the resulting solution was kept at room temperature overnight. The reaction mixture was concentrated and another equivalent of isopropyl amine was added (2.97 mL) following by EtOH (2 mL). For completion, the reaction was heated at 50° C. for 2 h. Mixture was evaporated to dryness and dissolved in EtOAc (25 mL) and the organic phase was washed with water (3*10 mL). Aqueous phase was re-extracted with EtOAc (10 mL) and the combined organics were washed with brine and dried over Na$_2$SO$_4$. The solvent was evaporated under reduced pressure to afford 5.24 g of N-isopropyl-2-nitrobenzenamine (Yield: 93%) as an orange liquid
Rf (Cyclohexane/AcOEt: 70/30)=0.67
LCMS (RT): 4.58 min

194(B) M-Isopropylbenzene-1,2-diamine

The title compound was prepared in accordance with the general method of Example 191(B), from N-isopropyl-2-nitrobenzenamine (5.24 g, 29.1 mmol) to afford 3.88 g of M-isopropylbenzene-1,2-diamine (Yield: 89%) as a dark brown liquid.
Rf (Cyclohexane/AcOEt: 70/30)=0.36
LCMS (RT): 1.68 min; MS (ES+) gave m/z: 151

194(C) 2-(Chloromethyl)-1-isopropyl-1H-benzo[d]imidazole

The title compound was prepared in accordance with the general method of Example 191(C), from N$^1$-isopropylbenzene-1,2-diamine (3.88 g, 25.82 mmol) and 2-chloroacetic acid (3.70 g, 39 mmol). The crude residue was purified over silicagel chromatography (prepacked 85 g silicagel column, Cyclohexane/AcOEt: 70/30 as eluent) to afford 2.05 g of 2-(chloromethyl)-1-isopropyl-1H-benzo[d]imidazole (Yield: 38%) as a light brown oil.
LCMS (RT): 2.88 min; MS (ES+) gave m/z: 209
Rf (Cyclohexane/AcOEt: 70/30)=0.27
$^1$H-NMR (CDCl$_3$), δ (ppm): 7.74-7.64 (m, 1H), 7.55-7.45 (m, 1H), 7.25-7.16 (m, 2H), 4.80-4.70 (m, 3H), 1.64-1.55 (d, 6H).

194(D) 1-Isopropyl-2-(4-(trimethylsilyl)but-3-ynyl)-1H-benzo[d]imidazole

The title compound was prepared in accordance with the general method of Example 191(D), from of 2-(chloromethyl)-1-isopropyl-1H-benzo[d]imidazole (500 mg, 2.4 mmol) and trimethyl(prop-1-ynyl)silane (323 mg, 2.88 mmol). 1-isopropyl-2-(4-(trimethylsilyl)but-3-ynyl)-1H-benzo[d]imidazole (680 mg, Yield: 100%) was obtained as a brown oil which was used in the next step without any purification.
LCMS (RT): 3.27 min; MS (ES+) gave m/z: 285

194(E) 2-(But-3-ynyl)-1-isopropyl-1H-benzo[d]imidazole

According to the protocol described in Example 38(D), the conversion of 1-isopropyl-2-(4-(trimethylsilyl)but-3-ynyl)-1H-benzo[d]imidazole (680 mg, 2.39 mmol) afforded 84 mg of 2-(but-3-ynyl)-1-isopropyl-1H-benzo[d]imidazole (Yield: 17%) as an orange solid.

Purification over silicagel chromatography (prepacked 25 g silicagel column, Cyclohexane/AcOEt: from 80/20 to 70/30).

LCMS (RT): 2.32 min; MS (ES+) gave m/z: 213

$^1$H-NMR (CDCl$_3$), δ (ppm): 7.75-7.63 (m, 1H), 7.54-7.43 (m, 1H), 7.27-7.15 (m, 2H), 4.70-4.63 (m, 1H), 3.14-3.00 (m, 2H), 2.81-2.74 (m, 2H), 1.92 (s, 1H), 1.66-1.55 (d, 6H).

194(F) 1-Isopropyl-2-(4-(pyridin-2-yl)but-3-ynyl)-1H-benzo[d]imidazole

The title compound was prepared in accordance with the general method of Example 192(A), from 2-iodopyridine (81 mg, 0.39 mmol) and 2-(but-3-ynyl)-1-isopropyl-1H-benzo[d]imidazole (84 mg, 0.39 mmol). The crude residue was purified over silicagel chromatography (prepacked 5 g silicagel column, DCM/MeOH: from 100/0 to 96/4 as eluent) to afford 47 mg of 1-isopropyl-2-(4-(pyridin-2-yl)but-3-ynyl)-1H-benzo[d]imidazole as a light brown oil (Yield: 41%).

LCMS (RT): 2.42 min; MS (ES+) gave m/z: 290

$^1$H-NMR (CDCl$_3$), δ (ppm): 8.55-8.45 (d, 1H), 7.80-7.05 (m, 7H), 4.80-4.57- (m, 1H), 3.30-2.92 (m, 4H), 1.69-1.50 (d, 6H).

Example 195

1-Phenethyl-2-(4-(pyridin-2-yl)but-3-ynyl)-1H-benzo[d]imidazole

195(A) 2-Nitro-N-phenethylbenzenamine

To a solution of 1-fluoro-2-nitrobenzene (4.4 g, 31.2 mmol) in EtOH (32 mL) was added at 0° C., 2-phenylethanamine (4.11 mL, 32.8 mmol). Mixture went from light yellow to bright orange instantly and it was stirring overnight at RT. Another equivalent of 2-phenylethanamine was added (4.11 mL, 32.8 mmol) and the mixture was heated to 50° C. overnight. Water was added (20 ml) and the resulting orange solid was isolated by filtration to afford 6.99 g of 2-nitro-N-phenethylbenzenamine (Yield: 92%) as an orange crystalline solid.

LCMS (RT): 4.95 min; MS (ES+) gave m/z: 243

195(B) N$^1$-Phenethylbenzene-1,2-diamine

The title compound was prepared in accordance with the general method of Example 191(B), from 2-nitro-N-phenethylbenzenamine (6.99 g, 28.9 mmol) to afford 5.66 g of M-phenethylbenzene-1,2-diamine (Yield: 92%) as a brown oily solid.

Rf (Cyclohexane/AcOEt: 70/30)=0.41

LCMS (RT): 3.03 min; MS (ES+) gave m/z: 213

195(C) 2-(Chloromethyl)-1-phenethyl-1H-benzo[d]imidazole

The title compound was prepared in accordance with the general method of Example 191(C), from N$^1$-phenethylbenzene-1,2-diamine (2.57 g, 12.11 mmol) and 2-chloroacetic acid (1.70 g, 18 mmol). The crude residue was purified over silicagel chromatography (prepacked 70 g silicagel column, Cyclohexane/AcOEt: from 80/20 to 70/30 as eluent) to afford 2.02 g of 2-(chloromethyl)-1-phenethyl-1H-benzo[d]imidazole (Yield: 61%) as a white crystalline solid.

LCMS (RT): 3.88 min; MS (ES+) gave m/z: 271

Rf (Cyclohexane/AcOEt: 70/30)=0.18

195(D) 1-Phenethyl-2-(4-(trimethylsilyl)but-3-ynyl)-1H-benzo[d]imidazole

The title compound was prepared in accordance with the general method of Example 191(D), from of 2-(chloromethyl)-1-phenethyl-1H-benzo[d]imidazole (500 mg, 1.8 mmol) and trimethyl(prop-1-ynyl)silane (249 mg, 2.22 mmol). 1-phenethyl-2-(4-(trimethylsilyl)but-3-ynyl)-1H-benzo[d]imidazole (639 mg, Yield: 100%) was obtained as a brown oil which was used in the next step without purification.

LCMS (RT): 3.90 min; MS (ES+) gave m/z: 347

195(E) 2-(But-3-ynyl)-1-phenethyl-1H-benzo[d]imidazole

According to the protocol described in Example 38(D), the conversion of 1-phenethyl-2-(4-(trimethylsilyl)but-3-ynyl)-1H-benzo[d]imidazole (639 mg, 1.84 mmol) afforded 62 mg of 2-(but-3-ynyl)-1-phenethyl-1H-benzo[d]imidazole (Yield: 12%) as an orange oily solid. Purification over silicagel chromatography (prepacked 25 g silicagel column, Cyclohexane/AcOEt: 70/30).

LCMS (RT): 3.07 min; MS (ES+) gave m/z: 275

$^1$H-NMR (CDCl$_3$), δ (ppm): 7.70-7.63 (m, 1H), 7.28.7.12 (m, 6H), 7.27-7.15 (m, 2H), 4.35-4.25 (t, 2H), 3.08-2.95 (t, 2H), 2.65-2.55 (m, 4H), 1.90 (s, 1H).

195(F) 1-Phenethyl-2-(4-(pyridin-2-yl)but-3-ynyl)-1H-benzo[d]imidazole

The title compound was prepared in accordance with the general method of Example 192(A), from 2-iodopyridine (46 mg, 0.22 mmol) and 2-(but-3-ynyl)-1-phenethyl-1H-benzo[d]imidazole (62 mg, 0.22 mmol). The crude residue was purified over silicagel chromatography (prepacked 5 g silicagel column, DCM/MeOH: from 100/0 to 96/4 as eluent) to afford 20 mg of 1-phenethyl-2-(4-(pyridin-2-yl)but-3-ynyl)-1H-benzo[d]imidazole as a light brown oil (Yield: 25%).

LCMS (RT): 3.00 min; MS (ES+) gave m/z: 352

$^1$H-NMR (CDCl$_3$), δ (ppm): 8.50-8.45 (d, 1H), 7.72-7.65 (m, 1H), 7.58-7.48 (t, 1H), 7.31-7.10 (m, 8H), 6.93-6.86 (m, 2H), 4.37-4.25 (t, 2H), 3.08-2.95 (t, 2H), 2.86-2.68 (m, 4H).

Example 196

1-Benzyl-2-(4-(pyridin-2-yl)but-3-ynyl)-1H-benzo[d]imidazole

196(A) N-Benzyl-2-nitrobenzenamine

The title compound was prepared in accordance with the general method of Example 195(A), from phenylmethanamine (3.51 g, 32.78 mmol) and 1-fluoro-2-nitrobenzene (4.40 g, 31.22 mmol). 6.65 g of N-benzyl-2-nitrobenzenamine (Yield: 93%) was obtained as an orange crystalline solid which was used without further purification.

LCMS (RT): 3.70 min; MS (ES+) gave m/z: 229

196(B) N$^1$-Benzylbenzene-1,2-diamine

The title compound was prepared in accordance with the general method of Example 191(B), from N-benzyl-2-nitrobenzenamine (6.65 g, 29.1 mol) to afford 4.66 g of N$^1$-benzylbenzene-1,2-diamine (Yield: 80%) as a brown oil which was used in the next step without further purification.

Rf (Cyclohexane/AcOEt: 70/30)=0.45

LCMS (RT): 2.83 min; MS (ES+) gave m/z: 199

196(C)
1-Benzyl-2-(chloromethyl)-1H-benzo[d]imidazole

The title compound was prepared in accordance with the general method of Example 191(C), from N$^1$-benzylbenzene-1,2-diamine (2.93 g, 14.78 mmol) and 2-chloroacetic acid (2.10 g, 22 mmol). The crude residue was purified over silicagel chromatography (prepacked 70 g silicagel column, Cyclohexane/AcOEt: from 80/20 to 70/30 as eluent) to afford 2.34 g of 1-benzyl-2-(chloromethyl)-1H-benzo[d]imidazole (Yield: 61%) as a yellow oil.
LCMS (RT): 3.87 min; MS (ES+) gave m/z: 257
Rf (Cyclohexane/AcOEt: 70/30)=0.28

196(D) 1-Benzyl-2-(4-(trimethylsilyl)but-3-ynyl)-1H-benzo[d]imidazole

The title compound was prepared in accordance with the general method of Example 191(D), from of 1-benzyl-2-(chloromethyl)-1H-benzo[d]imidazole (500 mg, 1.9 mmol) and trimethyl(prop-1-ynyl)silane (262 mg, 2.34 mmol). 1-benzyl-2-(4-(trimethylsilyl)but-3-ynyl)-1H-benzo[d]imidazole (647 mg, Yield: 100%) was obtained as a brown oil which was used in the next step without purification.
LCMS (RT): 3.83 min; MS (ES+) gave m/z: 333

196(E) 1-Benzyl-2-(but-3-ynyl)-1H-benzo[d]imidazole

According to the protocol described in Example 38(D), the conversion of 1-benzyl-2-(4-(trimethylsilyl)but-3-ynyl)-1H-benzo[d]imidazole (647 mg, 1.94 mmol) afforded 41 mg of 1-benzyl-2-(but-3-ynyl)-1H-benzo[d]imidazole (Yield: 8%) as orange oily solid.
Purification over silicagel chromatography (prepacked 25 g silicagel column, Cyclohexane/AcOEt: from 80/20 to 70/30).
LCMS (RT): 2.80 min; MS (ES+) gave m/z: 261
$^1$H-NMR (CDCl$_3$), δ (ppm): 7.75-7.63 (m, 1H), 7.30.7.10 (m, 7H), 7.00-6.95 (m, 1H), 5.30 (s, 2H), 3.05-2.95 (t, 2H), 2.70-2.80 (t, 2H), 1.92 (s, 1H)

196(F) 1-Benzyl-2-(4-(pyridin-2-yl)but-3-ynyl)-1H-benzo[d]imidazole

The title compound was prepared in accordance with the general method of Example 192(A), from 2-iodopyridine (38 mg, 0.18 mmol) and 1-benzyl-2-(but-3-ynyl)-1H-benzo[d]imidazole (49 mg, 0.18 mmol). The crude residue was purified over silicagel chromatography (prepacked 2 g silicagel column, DCM/MeOH: from 100/0 to 98/2 as eluent) to afford 15 mg of 1-benzyl-2-(4-(pyridin-2-yl)but-3-ynyl)-1H-benzo[d]imidazole as a yellow oily solid (Yield: 23%).
LCMS (RT): 2.90 min; MS (ES+) gave m/z: 338
$^1$H-NMR (CDCl$_3$), δ (ppm): 8.50 (d, 1H), 7.70-7.65 (d, 1H), 7.55-7.44 (t, 1H), 7.25-7.05 (m, 8H), 7.00-6.88 (m, 2H), 5.30 (s, 2H), 3.14-3.07 (m, 2H), 3.05-2.92 (m, 2H)

Example 197

5-Fluoro-1-methyl-2-(4-(pyridin-2-yl)but-3-ynyl)-1H-benzo[d]imidazole

197(A) 4-Fluoro-N-methyl-2-nitrobenzenamine 1,4-Difluoro-2-nitrobenzene (2.63 g, 16.53 mmol) was dissolved in EtOH (9 mL) and Methylamine 40% in Water (9 mL) was added dropwise at 0° C. and the mixture was warming up to RT overnight. 75 mL of water was added to the reaction mixture and the orange solid was filtered and washed with water (2*10 ml) to afford 2.78 g of 4-fluoro-N-methyl-2-nitrobenzenamine (Yield: 99%) as an orange crystalline solid.
Rf (Cyclohexane/AcOEt: 80/20)=0.34
LCMS (RT): 4.03 min; MS (ES+) gave m/z: 171

197(B) 4-Fluoro-N$^1$-methylbenzene-1,2-diamine

The title compound was prepared in accordance with the general method of Example 191(B), from 4-fluoro-N-methyl-2-nitrobenzenamine (1.5 g, 8.8 mmol) to afford 1.08 g of 4-fluoro-N$^1$-methylbenzene-1,2-diamine (Yield: 88%) as a brown oil which was used in the next step without purification.
Rf (DCM/MeOH: 95/5)=0.61
LCMS (RT): 0.84 min; MS (ES+) gave m/z: 141

197(C) 2-(Chloromethyl)-5-fluoro-1-methyl-1H-benzo[d]imidazole

The title compound was prepared in accordance with the general method of Example 191(C), from 4-fluoro-N$^1$-methylbenzene-1,2-diamine (2.5 g, 17.84 mmol) and 2-chloroacetic acid (2.50 g, 27 mmol). The crude residue was purified over silicagel chromatography (prepacked 70 g silicagel column, Cyclohexane/AcOEt: 60/40 as eluent) to afford 277 mg of 2-(chloromethyl)-5-fluoro-1-methyl-1H-benzo[d]imidazole (Yield: 8%) as a semi-solid.
LCMS (RT): 2.88 min; MS (ES+) gave m/z: 199
Rf (DCM/MeOH: 95/5)=0.29

197(D) 5-Fluoro-1-methyl-2-(4-(trimethylsilyl)but-3-ynyl)-1H-benzo[d]imidazole The title compound was prepared in accordance with the general method of Example 191(D), from of 2-(chloromethyl)-5-fluoro-1-methyl-1H-benzo[d]imidazole (270 mg, 1.36 mmol) and trimethyl(prop-1-ynyl)silane (183 mg, 1.63 mmol). The crude residue was used in the next step without any purification. 5-fluoro-1-methyl-2-(4-(trimethylsilyl)but-3-ynyl)-1H-benzo[d]imidazole (373 mg, Yield: 100%) as a brown oil.
LCMS (RT): 3.37 min; MS (ES+) gave m/z: 275
Rf (DCM/MeOH: 95/5)=0.36

197(E) 2-(But-3-ynyl)-5-fluoro-1-methyl-1H-benzo[d]imidazole

According to the protocol described in Example 38(D), the conversion of 5-fluoro-1-methyl-2-(4-(trimethylsilyl)but-3-ynyl)-1H-benzo[d]imidazole (373 mg, 1.35 mmol) afforded 73 mg of 2-(but-3-ynyl)-5-fluoro-1-methyl-1H-benzo[d]imidazole (Yield: 26%) as an orange solid.
Purification over silicagel chromatography (prepacked 25 g silicagel column, Cyclohexane/AcOEt: from 80/20 to 70/30).
LCMS (RT): 1.85 min; MS (ES+) gave m/z: 203
$^1$H-NMR (CDCl$_3$), δ (ppm): 7.40-6.95 (m, 3H), 3.70 (s, 3H), 3.10-3.00 (m, 2H), 2.80-2.70 (m, 2H), 1.95 (m, 1H)

197 (F) 5-Fluoro-1-methyl-2-(4-(pyridin-2-yl)but-3-ynyl)-1H-benzo[d]imidazole The title compound was prepared in accordance with the general method of Example 192(A), from 2-iodopyridine (74 mg, 0.36 mmol) and 2-(but-3-ynyl)-5-fluoro-1-methyl-1H-benzo[d]imidazole (73 mg, 0.36 mmol). The crude residue was purified over silicagel chromatography (prepacked 2 g silicagel column, DCM/MeOH: from 100/0 to 98/2 as eluent) to afford 28 mg of 5-fluoro-1-methyl-2-(4-(pyridin-2-yl)but-3-ynyl)-1H-benzo[d]imidazole as a orange oily solid (Yield: 27%).

LCMS (RT): 2.35 min; MS (ES+) gave m/z: 280
Rf (DCM/MeOH: 95/5)=0.37
$^1$H-NMR (CDCl$_3$), δ (ppm): 8.50 (d, 1H), 7.62-7.50 (t, 1H), 7.33-7.25 (m, 2H), 7.18-7.05 (m, 2H), 7.00-6.90 (t, 1H), 3.70 (s, 3H), 3.22-3.11 (m, 2H), 3.02-2.95 (m, 2H)

Example 198

1-(4-(Pyridin-2-yl)but-3-ynyl)pyridin-2(1H)-one

198(A) 4-Bromobut-1-ynyl)trimethylsilane

To a solution of 3-butyn-1-ol (4 g, 57 mmol) in THF (0.7M, 80 mL)) at −78° C. was added 2.1N n-BuLi in hexane (52 mL, 110 mmol). After 1 h at −78° C., the reaction mixture was treated with chlorotrimethylsilane (13 g, 120 mmol) and the resulting mixture was warmed to room temperature over 2 h. The reaction mixture was quenched with water, extracted with Et$_2$O, and concentrated. The concentrate was treated with HCl 3N, extracted with Et$_2$O (3×), washed with saturated aqueous NaHCO$_3$ (3×) and NaCl (1×), dried (MgSO$_4$), and concentrated. The crude product was diluted in THF (50 mL), the solution was cooled to −78° C. before the addition of 26 mL of n-BuLi 2.1N in hexane (52 mmol.). After 1 h at −78° C. p-toluenesulfonyl chloride (12 g, 63 mmol.) in THF solution (35 mL) was added. The reaction mixture was stirred over night at room temperature. The reaction mixture was treated with water, followed by extraction with ether, washing with saturated aqueous NaHCO$_3$, with NaCl, dried (MgSO$_4$) and concentrated The crude product was dissolved in acetone (100 mL) containing LiBr (5 g, 57 mmol.) and the reaction mixture was stirred at room temperature for 5 h. The reaction mixture was poured into water. Extraction with pentane (4×), washing with saturated aqueous NaHCO$_3$ and NaCl, drying (MgSO$_4$), concentration to give 7.50 g of 4-bromobut-1-ynyl) trimethylsilane (Yield: 64%) as a brown oil which was used in the next step without further purification.

198(B) 1-(But-3-ynyl)pyridin-2(1H)-one 4-bromobut-1-ynyl)trimethylsilane (700 mg, 3 mmol), pyridin-2-ol (300 mg, 3 mmol) and K$_2$CO$_3$ (900 mg, 6 mmol) were poured into acetone (4.2 ml) and the resulting mixture was heated in the microwave at 150° C. for 7 min. The solvent was evaporated and the crude product was dissolved DCM and the organic layer was washed with water. The crude residue was purified over silicagel chromatography (prepacked 5 g silicagel column, DCM/MeOH: 99/1 as eluent) to afford 33 mg of 1-(but-3-ynyl)pyridin-2(1H)-one as a brown oil (Yield: 5%).

LCMS (RT): 2.20 min; MS (ES+) gave m/z: 148
Rf (DCM/MeOH: 95/5)=0.19
$^1$H-NMR (CDCl$_3$), δ (ppm): 7.35-7.25 (m, 2H), 6.55-6.45 (d, 1H), 6.15-6.05 (t, 1H), 4.00-3.93 (t, 2H), 2.58-2.64 (m, 2H), 1.95-1.90 (t, 1H)

198(C) 1-(4-(Pyridin-2-yl)but-3-ynyl)pyridin-2(1H)-one

The title compound was prepared in accordance with the general method of Example 192(A), from 2-iodopyridine (50 mg, 0.2 mmol) and 1-(but-3-ynyl)pyridin-2(1H)-one (33 mg, 0.2 mmol). The crude residue was purified over silicagel chromatography (prepacked 10 g silicagel column, DCM/MeOH: from 100/0 to 97/3 as eluent) to afford 10 mg of 1-(4-(pyridin-2-yl)but-3-ynyl)pyridin-2(1H)-one as a yellow oil (Yield: 20%).

LCMS (RT): 2.22 min; MS (ES+) gave m/z: 225
$^1$H-NMR (CDCl$_3$), δ (ppm): 8.55-8.45 (m, 1H), 7.62-7.50 (t, 1H), 7.41-7.12 (m, 4H), 6.55-6.45 (m, 1H), 6.10-6.05 (t, 1H), 4.10-4.05 (t, 2H), 2.90-2.80 (t, 2H)

Example 199

3-Methoxy-N-methyl-N-(4-(pyridin-2-yl)but-3-ynyl) benzamide

199(A) 4-(Pyridin-2-yl)but-3-yn-1-ol

To a suspension of CuI (301 mg, 1.58 mmol) in TEA (40 mL) were added 2-bromopyridine (5 g, 31.6 mmol), followed by Pd$_2$Cl$_2$(PPh$_3$)$_2$ (1.11 g, 1.58 mmol) to give a yellow orange suspension. After cooling down to 0° C. under N$_2$, 3-butyn-1-ol (2.28 g, 31.6 mmol) was added. The resulting reaction mixture turned black and it was stirred overnight at 70° C. The reaction mixture was quenched at 0° C. with water, TEA was removed under low pressure, and the organic layer was extracted 3× using DCM, washed with Ammonia, water, brine, dried over MgSO$_4$, filtered and concentrated. The crude residue was purified over silicagel chromatography (prepacked 250 g silicagel column, DCM/MeOH: from 99/1 to 95/5 as eluent) to afford 3.60 g of 4-(pyridin-2-yl)but-3-yn-1-ol as a brown oil (Yield: 77%).

LCMS (RT): 1.58 min; MS (ES+) gave m/z: 148
Rf (DCM/MeOH: 95/5)=0.23

199(B) 4-(Pyridin-2-yl)but-3-ynyl Methanesulfonate

To a stirred solution of 4-(pyridin-2-yl)but-3-yn-1-ol (3.60 g, 24 mmol) in dry methylene chloride (30 mL) was added triethylamine (4.40 mL, 32 mmol). The mixture was cooled at 4° C. and methanesulfonyl chloride (2.50 mL, 32 mmol) was added and the reaction was stirred at room temperature overnight. The reaction mixture was then poured over ice/water (100 mL) and stirred for 5 min. To this mixture was added saturated aqueous sodium bicarbonate solution (50 mL) chilled to 4° C., and the mixture was stirred for 30 min, then extracted with DCM. The combined organic fractions were dried over MgSO$_4$, filtered and concentrated under pressure to afford 4.60 g of 4-(pyridin-2-yl)but-3-ynyl methanesulfonate (Yield: 83%) as a brown oil which can be used in the next step without further purification.

LCMS (RT): 2.43 min; MS (ES+) gave m/z: 226
Rf (DCM/MeOH: 95/5)=0.6

199(C) N-Methyl-4-(pyridin-2-yl)but-3-yn-1-amine 4-(Pyridin-2-yl)but-3-ynyl methanesulfonate (2.90 g, 12.87 mmol) was dissolved in methylamine 40% in aqueous solution (20 mL) and stirred for 3 hours under nitrogen at 45° C. The reaction mixture was cooled with ice, quenched with water and extracted with DCM. The organic phases were washed with brine, dried over MgSO$_4$ and concentrated. The crude residue was purified over silicagel chromatography (prepacked 70 g silicagel column, DCM/MeOH: from 90/10 to 90/10 with 1% of TEA as eluent) to afford 817 mg N-methyl-4-(pyridin-2-yl)but-3-yn-1-amine (Yield: 39%) as a brown oil LCMS (RT): 0.65 min; MS (ES+) gave m/z: 161
¹H-NMR (CDCl₃), δ (ppm): 8.55-8.52 (m, 1H), 7.58-7.68 (t, 1H), 7.43-7.38 (d, 1H), 7.23-7.18 (d, 1H), 2.90-2.82 (t, 2H), 2.70-2.63 (t, 2H), 2.48 (s 3H)

199(D) 3-Methoxy-N-methyl-N-(4-(pyridin-2-yl) but-3-ynyl)benzamide

N-Methyl-4-(pyridin-2-yl)but-3-yn-1-amine (50 mg, 0.31 mmol) was dissolved in DCM (2 mL) and DIEA (67 µl, 0.41 mmol) was added at room temperature. The resulting mixture was cooled to 0° C. before the addition of 3-methoxybenzoyl chloride (69 mg, 0.41 mmol). After stirring overnight at room temperature, the mixture was quenched with water and extracted with DCM. DCM fractions were washed with water (10 mL), NaHCO₃ sat (2*10 mL), water (10 mL), brine (10 mL). The solvent was removed and the crude residue was purified over silicagel chromatography (prepacked 10 g silicagel column, DCM/MeOH: from 100/0 to 95/5 as eluent) to afford 58 mg of 3-methoxy-N-methyl-N-(4-(pyridin-2-yl) but-3-ynyl)benzamide (Yield: 63%) as a brown oil.

LCMS (RT): 3.17 min; MS (ES+) gave m/z: 295
¹H-NMR (CDCl₃), δ (ppm) 2 conformers A/B=57/43 ratio: 8.56-8.44 (m, 1H), 7.64-7.52 (m, 2H), 7.36-7.08 (m, 2H), 6.96-6.80 (m, 3H), 3.80-3.65 (s, 3H and m, 2H, conformer A), 3.75-3.40 (t, 2H, conformers B), 3.10-2.98 (2 s, 3H, conformer A and B), 2.85-2.70 (t, 2H, conformer A), 2.65-2.50 (t, 2H, conformer B)

Example 200

3-Fluoro-N-methyl-N-(4-(pyridin-2-yl)but-3-ynyl) benzamide

The title compound was prepared in accordance with the general method of Example 199(D), from N-methyl-4-(pyridin-2-yl)but-3-yn-1-amine (50 mg, 0.31 mmol) and 3-fluorobenzoyl chloride (64 mg, 0.41 mmol). The crude residue was purified over silicagel chromatography (prepacked 10 g silicagel column, DCM/MeOH: from 100/0 to 97/3 as eluent) to afford 34 mg of 3-fluoro-N-methyl-N-(4-(pyridin-2-yl) but-3-ynyl)benzamide as a brown oil (Yield: 39%).

LCMS (RT): 3.21 min; MS (ES+) gave m/z: 283
Rf (DCM/MeOH: 95/5)=0.22
¹H-NMR (CDCl₃), δ (ppm) 2 conformers A/B=60/40 ratio: 8.55-8.45 (d, 1H), 7.62-7.50 (t, 1H), 7.35-7.22 (m, 2H), 7.18-6.95 (m, 4H), 3.78-3.63 (s, 2H, conformer A), 3.60-3.50 (s, 2H, conformer B), 3.10-2.95 (2 s, 3H conformers A+B), 2.85-2.70 (s, 2H, conformer A), 2.68-2.50 (s, 2H, conformer B)

Example 201

N-Methyl-2-phenyl-N-(4-(pyridin-2-yl)but-3-ynyl) acetamide

The title compound was prepared in accordance with the general method of Example 199(D), from N-methyl-4-(pyridin-2-yl)but-3-yn-1-amine (50 mg, 0.31 mmol) and 2-phenylacetyl chloride (60 mg, 0.41 mmol). The crude residue was purified over silicagel chromatography (prepacked 10 g silicagel column, DCM/MeOH: from 100/0 to 97/3 as eluent) to afford 64 mg of N-methyl-2-phenyl-N-(4-(pyridin-2-yl)but-3-ynyl)acetamide as a brown oil (Yield: 74%).

LCMS (RT): 3.15 min; MS (ES+) gave m/z: 279
¹H-NMR (CDCl₃), δ (ppm) 2 conformers A/B=63/37 ratio: 8.55-8.45 (m, 1H), 7.62-7.52 (t, 1H), 7.38-7.12 (m, 7H), 3.80 (s, 2H, conformer B), 3.70 (s, 2H, conformer A), 3.65-3.55 (m, 2H), 3.10 (s, 3H, conformer A), 2.95 (s, 3H, conformer B), 2.70 (t, 2H, conformer A), −2.53 (t, 2H, conformer B)

Example 202

N-Methyl-N-(4-(pyridin-2-yl)but-3-ynyl)-2-(trifluoromethyl)benzamide

The title compound was prepared in accordance with the general method of Example 199(D), from N-methyl-4-(pyridin-2-yl)but-3-yn-1-amine (50 mg, 0.31 mmol) and 2-(trifluoromethyl)benzoyl chloride (80 mg, 0.41 mmol). The crude residue was purified over silicagel chromatography (prepacked 10 g silicagel column, DCM/MeOH: from 100/0 to 97/3 as eluent) to afford 63 mg of N-methyl-N-(4-(pyridin-2-yl)but-3-ynyl)-2-(trifluoromethyl)benzamide as a brown oil (Yield: 61%).

LCMS (RT): 3.57 min; MS (ES+) gave m/z: 333
¹H-NMR (CDCl₃), δ (ppm) 2 conformers A/B=65/35 ratio: 8.55-8.45 (d, 1H), 7.65-7.10 (m, 7H), 3.90-3.60 (m, 2H, conformer A), 3.45-3.20 (m, 2H, conformer B), 3.10 (s, 3H, conformer B), 2.85 (s, 3H, conformer A), 2.80-2.70 (m, 2H, conformer A), 2.60-2.50 (m, 2H, conformer B).

Example 203

4-Fluoro-N-methyl-N-(4-(pyridin-2-yl)but-3-ynyl) benzamide

The title compound was prepared in accordance with the general method of Example 199(D), from N-methyl-4-(pyridin-2-yl)but-3-yn-1-amine (100 mg, 0.62 mmol) and 4-fluorobenzoyl chloride (99 mg, 0.62 mmol). The crude residue was purified over silicagel chromatography (prepacked 10 g silicagel column, DCM/MeOH: 98/2 as eluent) to afford 103 mg of 4-fluoro-N-methyl-N-(4-(pyridin-2-yl)but-3-ynyl) benzamide as a brown oil (Yield: 58%).

LCMS (RT): 3.03 min; MS (ES+) gave m/z: 283
Rf (DCM/MeOH: 95/5)=0.41
¹H-NMR (CDCl₃), δ (ppm): 8.55-8.45 (m, 1H), 7.65-7.58 (m, 1H), 7.48-7.32 (m, 3H), 7.23-7.18 (m, 1H), 7.10-7.02 (m, 2H), 3.85-3.50 (m, 2H), 3.10 (s, 3H), 2.90-2.60 (m, 2H).

Example 204

2-Chloro-N-methyl-N-(4-(pyridin-2-yl)but-3-ynyl) benzamide

The title compound was prepared in accordance with the general method of Example 199(D), from N-methyl-4-(pyridin-2-yl)but-3-yn-1-amine (100 mg, 0.62 mmol) and 2-chlorobenzoyl chloride (109 mg, 0.62 mmol). The crude residue was purified over silicagel chromatography (prepacked 10 g silicagel column, DCM/MeOH: 98/2 as eluent) to afford 118 mg of 2-chloro-N-methyl-N-(4-(pyridin-2-yl)but-3-ynyl) benzamide as a brown oil (Yield: 63%).

LCMS (RT): 3.20 min; MS (ES+) gave m/z: 299
Rf (DCM/MeOH: 95/5)=0.42
¹H-NMR (CDCl₃), δ (ppm) 2 conformers A/B=59/41 ratio: 8.55-8.45 (m, 1H), 7.65-7.58 (t, 1H), 7.43-7.15 (m, 6H), 3.95-3.40 (m, 2H), 3.20 (s, 3H, conformer B), 2.95 (s, 3H, conformer A), 2.90-2.83 (m, 2H, conformer A), 2.68-2.60 (m, 2H, conformer B).

Example 205

3-Chloro-N-methyl-N-(4-(pyridin-2-yl)but-3-ynyl) benzamide

The title compound was prepared in accordance with the general method of Example 199(D), from N-methyl-4-(pyridin-2-yl)but-3-yn-1-amine (100 mg, 0.62 mmol) and 3-chlorobenzoyl chloride (109 mg, 0.62 mmol). The crude residue was purified over silicagel chromatography (prepacked 10 g silicagel column, DCM/MeOH: 98/2 as eluent) to afford 112 mg of 3-chloro-N-methyl-N-(4-(pyridin-2-yl)but-3-ynyl) benzamide as a brown oil (Yield: 60%).

LCMS (RT): 3.35 min; MS (ES+) gave m/z: 299
Rf (DCM/MeOH: 95/5)=0.42
$^1$H-NMR (CDCl$_3$), δ (ppm) 2 conformers A/B=63/37 ratio: 8.55-8.45 (m, 1H), 7.60-7.50 (t, 1H), 7.40-7.10 (m, 6H), 3.90-3.70 (m, 2H, conformer A), 3.60-3.50 (m, 2H, conformer B), 3.05 (s, 3H), 2.90-2.80 (m, 2H, conformer A), 2.75-2.60 (m, 2H, conformer B).

Example 206

4-Fluoro-N-methyl-N-(4-(pyridin-2-yl)but-3-ynyl) benzenesulfonamide

The title compound was prepared in accordance with the general method of Example 199(D), from N-methyl-4-(pyridin-2-yl)but-3-yn-1-amine (100 mg, 0.62 mmol) and 4-fluorobenzene-1-sulfonyl chloride (121 mg, 0.62 mmol). The crude residue was purified over silicagel chromatography (prepacked 10 g silicagel column, DCM/MeOH: 98/2 as eluent) to afford 32 mg of 4-fluoro-N-methyl-N-(4-(pyridin-2-yl)but-3-ynyl)benzenesulfonamide as a yellow oil (Yield: 16%).

LCMS (RT): 3.70 min; MS (ES+) gave m/z: 319
$^1$H-NMR (CDCl$_3$), δ (ppm): 8.55-8.45 (m, 1H), 7.85-7.75 (t, 2H), 7.60-7.50 (t, 1H), 7.30 (d, 1H), 7.20-7.00 (m, 3H), 3.30-3.20 (t, 2H), 2.80 (s, 3H), 2.70-2.60 (m, 2H).

Example 207

2-Chloro-N-methyl-N-(4-(pyridin-2-yl)but-3-ynyl) benzenesulfonamide

The title compound was prepared in accordance with the general method of Example 199(D), from N-methyl-4-(pyridin-2-yl)but-3-yn-1-amine (50 mg, 0.31 mmol) and 2-chlorobenzene-1-sulfonyl chloride (79 mg, 0.37 mmol). The crude residue was purified over silicagel chromatography (prepacked 10 g silicagel column, DCM/MeOH: from 100/0 to 98/2 as eluent) to afford 37 mg of 2-chloro-N-methyl-N-(4-(pyridin-2-yl)but-3-ynyl)benzenesulfonamide as a brown oil (Yield: 35%).

Rf (DCM/MeOH: 95/5)=0.51
LCMS (RT): 3.78 min; MS (ES+) gave m/z: 335
$^1$H-NMR (CDCl$_3$), δ (ppm): 8.55-8.45 (m, 1H), 8.15-8.05 (d, 1H), 7.68-7.60 (t, 1H), 7.55-7.35 (m, 4H), 7.23-7.15 (m, 1H), 3.60-3.50 (t, 2H), 3.00 (s, 3H), 2.80-2.70 (t, 2H).

Example 208

2-Chloro-N-(4-(6-(fluoromethyl)pyridin-2-yl)but-3-ynyl)-N-methylbenzamide

208(A) 4-(6-(Fluoromethyl)pyridin-2-yl)but-3-yn-1-ol

The title compound was prepared in accordance with the general method of Example 199(A), from 2-bromo-6-(fluoromethyl)pyridine (compound 190(E), 3.50 g, 18 mmol) and 3-butyn-1-ol (1.3 g, 18 mmol). The crude residue was purified over silicagel chromatography (prepacked 85 g silicagel column, DCM/MeOH: from 100/0 to 97/3 as eluent) to afford 2.60 g of 4-(6-(fluoromethyl)pyridin-2-yl)but-3-yn-1-ol as an orange solid (Yield: 79%).

Rf (DCM/MeOH: 95/5)=0.31
LCMS (RT): 2.52 min; MS (ES+) gave m/z: 180

208(B) 4-(6-(Fluoromethyl)pyridin-2-yl)but-3-ynyl Methanesulfonate

The title compound was prepared in accordance with the general method of Example 199(B), from 4-(6-(fluoromethyl)pyridin-2-yl)but-3-yn-1-ol (2.60 g, 15 mmol) and methanesulfonyl chloride (1.50 mL, 19 mmol) to afford 2.90 g of 4-(6-(fluoromethyl)pyridin-2-yl)but-3-ynyl methanesulfonate (Yield: 78%) as a pale yellow oil which was used in the next step without further purification.

Rf (DCM/MeOH: 95/5)=0.60
LCMS (RT): 3.28 min; MS (ES+) gave m/z: 258

208C) 4-(6-(Fluoromethyl)pyridin-2-yl)-N-methyl-but-3-yn-1-amine

The title compound was prepared in accordance with the general method of Example 199(C), from 4-(6-(fluoromethyl)pyridin-2-yl)but-3-ynyl methanesulfonate (2.90 g, 11 mmol) and N-methylamine 40% in aqueous solution (20 mL). The crude residue was purified over silicagel chromatography (prepacked 70 g silicagel column, DCM/MeOH: from 90/10 to 90/10 with 1% TEA as eluent) to afford 324 mg of 4-(6-(fluoromethyl)pyridin-2-yl)-N-methylbut-3-yn-1-amine as a pale oil (Yield: 15%).

LCMS (RT): 0.65-71.83 min; MS (ES+) gave m/z: 193

208(D) 2-Chloro-N-(4-(6-(fluoromethyl)pyridin-2-yl)but-3-ynyl)-N-methylbenzamide The title compound was prepared in accordance with the general method of Example 199(D), from 4-(6-(fluoromethyl)pyridin-2-yl)-N-methylbut-3-yn-1-amine (70 mg, 0.36 mmol) and 2-chlorobenzoyl chloride (76 mg, 0.44 mmol). The crude residue was purified over silicagel chromatography (prepacked 10 g silicagel column, DCM/MeOH: from 100/0 to 98/2 as eluent) to afford 37 mg of 2-chloro-N-(4-(6-(fluoromethyl)pyridin-2-yl)but-3-ynyl)-N-methylbenzamide as a brown oil (Yield: 31%).

LCMS (RT): 3.82 min; MS (ES+) gave m/z: 331
Rf (DCM/MeOH: 95/5)=0.25
$^1$H-NMR (CDCl$_3$), δ (ppm) 2 conformers A/B=61/39 ratio: 7.75-7.65 (t, 1H), 7.45-7.23 (m, 6H), 5.60-5.35 (2d, 2H, conformer A+B), 3.95-3.70 (m, 2H, conformer A), 3.50-3.40 (m, 2H, conformer B), 3.20 (s, 3H, conformer B), 2.95 (s, 3H, conformer A), 2.90-2.82 (t, 2H, conformer A), 2.70-2.60 (t, 2H, conformer B)

Example 209

2-Chloro-N-(4-(6-(fluoromethyl)pyridin-2-yl)but-3-ynyl)-N-methylbenzene sulfonamide The title compound was prepared in accordance with the general method of Example 199(D), from 4-(6-(fluoromethyl)pyridin-2-yl)-N-methylbut-3-yn-1-amine (70 mg, 0.36 mmol) and 2-chlorobenzene-1-sulfonyl chloride (92 mg, 0.44 mmol). The crude residue was purified over silicagel chromatography (prepacked 10 g silicagel column, Cyclohexane/AcOEt: 70/30 as eluent) to afford 41 mg of 2-chloro-N-(4-(6-(fluoromethyl)pyridin-2-yl)but-3-ynyl)-N-methylbenzenesulfonamide as a yellow oil (Yield: 31%).

Rf (Cyclohexane/AcOEt: 70/30)=0.26
LCMS (RT): 4.30 min; MS (ES+) gave m/z: 367
$^1$H-NMR (CDCl$_3$), δ (ppm): 8.10 (d, 1H), 7.75-7.65 (t, 1H), 7.52-7.30 (m, 5H), 5.53-5.38 (d, 2H), 3.60-3.50 (t, 2H), 3.00 (s, 3H), 2.80-2.70 (t, 2H)

Example 210

2,6-Dichloro-N-(4-(6-(fluoromethyl)pyridin-2-yl)but-3-ynyl)-N-methylbenzamide

The title compound was prepared in accordance with the general method of Example 199(D), from 4-(6-(fluoromethyl)pyridin-2-yl)-N-methylbut-3-yn-1-amine (180 mg, 0.93 mmol) and 2,6-dichlorobenzoyl chloride (255 mg, 1.22 mmol). The crude residue was purified over silicagel chromatography (prepacked 10 g silicagel column, DCM/MeOH: from 100/0 to 98/2 as eluent) to afford 18.5 mg of 2,6-dichloro-N-(4-(6-(fluoromethyl)pyridin-2-yl)but-3-ynyl)-N-methylbenzamide as a yellow oil (Yield: 5%).

Rf (Cyclohexane/AcOEt: 70/30)=0.26
LCMS (RT): 3.93 and 4.04 min; MS (ES+) gave m/z: 365
$^1$H-NMR (CDCl$_3$), δ (ppm) 2 conformers A/B=90/10 ratio: 7.75-7.65 (t, 1H), 7.48-7.20 (m, 5H), 5.60-5.35 (2d, 2H, conformers A+B), 3.80-3.70 (t, 2H, conformer A), 3.50-3.40 (t, 2H, conformer B), 3.22 (s, 3H, conformer B), 2.98 (s, 3H, conformer A), 2.95-2.85 (t, 2H, conformer A), 2.75-2.65 (t, 2H, conformer B)

Example 211

N-Methyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and benzoyl chloride (53 mg, 0.37 mmol). The crude residue was purified over silicagel chromatography (prepacked 10 g silicagel column, DCM/MeOH: from 100/0 to 98/2 as eluent) to afford 30 mg of N-methyl-N-(4-(pyridin-2-yl)but-3-ynyl)benzamide as a brown oil (Yield: 36%).

Rf (DCM/MeOH: 95/5)=0.31
LCMS (RT): 2.92 min; MS (ES+) gave m/z: 265
$^1$H-NMR (CDCl$_3$), δ (ppm) 2 conformers A/B=59/41 ratio: 8.55-8.45 (m, 1H), 7.60-7.50 (t, 1H), 7.40-7.10 (m, 7H), 3.80-3.60 (m, 2H, conformer A), 3.55-3.40 (m, 2H, conformer B), 3.15-3.10 (2 s, 3H), 2.85-2.70 (m, 2H, conformer A), 2.65-2.50 (m, 2, conformer B).

Example 212

N,2-Dimethyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 2-methylbenzoyl chloride (58 mg, 0.37 mmol). The crude residue was purified over silicagel chromatography (prepacked 10 g silicagel column, DCM/MeOH: from 100/0 to 98/2 as eluent) to afford 32.5 mg of N,2-dimethyl-N-(4-(pyridin-2-yl)but-3-ynyl)benzamide as a brown oil (Yield: 37%).

LCMS (RT): 3.15 min; MS (ES+) gave m/z: 279
Rf (DCM/MeOH: 95/5)=0.33
$^1$H-NMR (CDCl$_3$), δ (ppm) 2 conformers A/B=59/41 ratio: 8.55-8.45 (m, 1H), 7.60-7.50 (t, 1H), 7.30-7.10 (m, 6H), 3.90-3.70 (m, 2H, conformer A), 3.40-3.30 (t, 2H, conformer B), 3.15 (s, 3H, conformer B), 2.90 (s, 3H, conformer A), 2.85-2.75 (t, 2H, conformer A), 2.60-2.50 (t, 2H, conformer B), 2.25-2.15 (2 s, 3H, conformer A+B)

Example 213

2-Fluoro-N-methyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 2-fluorobenzoyl chloride (59 mg, 0.37 mmol). The crude residue was purified over silicagel chromatography (prepacked 10 g silicagel column, DCM/MeOH: from 100/0 to 98/2 as eluent) to afford 28 mg of 2-fluoro-N-methyl-N-(4-(pyridin-2-yl)but-3-ynyl)benzamide as a brown oil (Yield: 32%).

LCMS (RT): 3.00 min; MS (ES+) gave m/z: 283
Rf (DCM/MeOH: 95/5)=0.33
$^1$H-NMR (CDCl$_3$), δ (ppm) 2 conformers A/B=57/43 ratio: 8.55-8.45 (m, 1H), 7.70-7.60 (t, 1H), 7.45-7.30 (m, 3H), 7.25-7.05 (m, 3H), 3.88-3.75 (t, 2H, conformer A), 3.55-3.45 (t, 2H, conformer B), 3.20 (s, 3H, conformer B)-3.00 (s, 3H, conformer A), 2.90-2.80 (t, 2H, conformer A), 2.70-2.60 (t, 2H, conformer B).

Example 214

N,4-Dimethyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 4-methylbenzoyl chloride (58 mg, 0.37 mmol). The crude residue was purified over silicagel chromatography (prepacked 10 g silicagel column, DCM/MeOH: from 100/0 to 98/2 as eluent) to afford 31 mg of N,4-dimethyl-N-(4-(pyridin-2-yl)but-3-ynyl)benzamide as a brown oil (Yield: 36%).

Rf (DCM/MeOH: 95/5)=0.35
LCMS (RT): 3.28 min; MS (ES+) gave m/z: 279
$^1$H-NMR (CDCl$_3$), δ (ppm) 2 conformers A/B=58/42 ratio: 8.55-8.45 (m, 1H), 7.70-7.60 (t, 1H), 7.40-7.15 (m, 6H), 3.85-3.70 (m, 2H, conformer A), 3.65-3.50 (m, 2H, conformer B), 3.10 (s, 3H), 2.92-2.80 (m, 2H, conformer A), 2.78-2.60 (m, 2H, conformer B), 2.35 (s, 3H)

Example 215

N,3-Dimethyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 3-methylbenzoyl chloride (58 mg, 0.37 mmol). The crude residue was purified over silicagel chromatography (prepacked 10 g silicagel column, DCM/MeOH: from 100/0 to 98/2 as eluent) to afford 25 mg of N,3-dimethyl-N-(4-(pyridin-2-yl)but-3-ynyl)benzamide as a yellow pale oil (Yield: 29%).

LCMS (RT): 3.37 min; MS (ES+) gave m/z: 279
Rf (DCM/MeOH: 95/5)=0.36
$^1$H-NMR (CDCl$_3$), δ (ppm) 2 conformers A/B=55/45 ratio: 8.55-8.45 (m, 1H), 7.60-7.50 (t, 1H), 7.35-7.10 (m, 6H), 3.80-3.70 (m, 2H, conformer A), 3.55-3.40 (m, 2H, conformer B), 3.10-3.00 (s, 3H, conformer A+B), 2.80-2.70 (m, 2H, conformer A), 2.65-2.50 (m, 2H, conformer B), 2.25 (s, 3H)

Example 216

2-Methoxy-N-methyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 2-methoxybenzoyl chloride (69 mg, 0.41 mmol). The crude residue was purified over silicagel chromatography (prepacked 10 g silicagel column, DCM/MeOH: from 100/0 to 98/2 as eluent) to afford 71 mg of 2-methoxy-N-methyl-N-(4-(pyridin-2-yl)but-3-ynyl)benzamide as a green-brown oil (Yield: 77%).

LCMS (RT): 3.08 min; MS (ES+) gave m/z: 295
Rf (DCM/MeOH: 95/5)=0.39
$^1$H-NMR (CDCl$_3$), δ (ppm) 2 conformers A/B=50/50 ratio: 8.55-8.45 (m, 1H), 7.68-7.58 (t, 1H), 7.42-7.18 (m, 4H), 7.00-6.88 (m, 2H), 3.90-3.80 (m, 4H), 3.50-3.40 (m, 1H), 3.20 (s, 3H, conformer A), 2.95 (s, 3H, conformer B), 2.90-2.80 (t, 2H, conformer A), 2.70-2.60 (t, 2H, conformer B).

Example 217

2,3-Difluoro-N-methyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 2,3-difluorobenzoyl chloride (72 mg, 0.41 mmol). The crude residue was purified over silicagel chromatography (prepacked 10 g silicagel column, DCM/MeOH: from 100/0 to 98/2 as eluent) to afford 67 mg of 2,3-difluoro-N-methyl-N-(4-(pyridin-2-yl)but-3-ynyl)benzamide as a brown oil (Yield: 71%).

LCMS (RT): 3.32 min; MS (ES+) gave m/z: 301
Rf (DCM/MeOH: 95/5)=0.28
$^1$H-NMR (CDCl$_3$), δ (ppm) 2 conformers A/B=60/40 ratio: 8.55-8.45 (m, 1H), 7.60-7.50 (t, 1H), 7.35-7.20 (m, 1H), 7.20-7.00 (m, 4H), 3.80-3.70 (t, 2H, conformer A), 3.50-3.40 (t, 2H, conformer B), 3.15 (s, 3H, conformer B), 2.95 (s, 3H, conformer A), 2.80-2.70 (t, 2H, conformer A), 2.65-2.50 (t, 2H, conformer B).

Example 218

2,6-Dichloro-N-methyl-N-(4-(pyridin-2-yl)but-3-ynyl)benzamide

The title compound was prepared in accordance with the general method of Example 199(D), from N-methyl-4-(pyridin-2-yl)but-3-yn-1-amine (50 mg, 0.31 mmol) and 2,6-dichlorobenzoyl chloride (85 mg, 0.41 mmol). The crude residue was purified over silicagel chromatography (prepacked 10 g silicagel column, DCM/MeOH: from 100/0 to 98/2 as eluent) to afford 47 mg of 2,6-dichloro-N-methyl-N-(4-(pyridin-2-yl)but-3-ynyl)benzamide as a brown oil (Yield: 45%).

Rf (DCM/MeOH: 95/5)=0.38
LCMS (RT): 3.53 min; MS (ES+) gave m/z: 333
$^1$H-NMR (CDCl$_3$), δ (ppm) 2 conformers A/B=71/29 ratio: 8.55-8.45 (m, 1H), 7.60-7.50 (t, 1H), 7.30-7.10 (m, 5H), 3.80-3.70 (t, 2H, conformer A), 3.40-3.30 (t, 2H, conformer B), 3.15 (s, 3H, conformer B), 2.90 (s, 3H, conformer A), 2.85-2.75 (t, 2H, conformer A), 2.70-2.60 (t, 2H, conformer B).

Example 219

N,3,5-Trimethyl-N-(4-(pyridin-2-yl)but-3-ynyl)isoxazole-4-sulfonamide

The title compound was prepared in accordance with the general method of Example 199(D), from N-methyl-4-(pyridin-2-yl)but-3-yn-1-amine (50 mg, 0.31 mmol) and 3,5-dimethylisoxazole-4-sulfonyl chloride (79 mg, 0.41 mmol). The crude residue was purified over silicagel chromatography (prepacked 10 g silicagel column, DCM/MeOH: from 100/0 to 98/2 as eluent) to afford 17 mg of N,3,5-trimethyl-N-(4-(pyridin-2-yl)but-3-ynyl)isoxazole-4-sulfonamide as a brown oil (Yield: 17%).

Rf (DCM/MeOH: 95/5)=0.42
LCMS (RT): 3.47 min; MS (ES+) gave m/z: 320
$^1$H-NMR (CDCl$_3$), δ (ppm): 8.60-8.50 (d, 1H), 7.70-7.60 (t, 1H), 7.40-7.30 (d, 1H), 7.30-7.15 (m, 1H), 3.50-3.40 (t, 2H), 2.93 (s, 3H), 2.80-2.70 (t, 2H), 2.65 (s, 3H), 2.40 (s, 3H)

Example 220

N-(4-(Pyridin-2-yl)but-3-ynyl)benzo[d]thiazol-2-amine

220(A) 4-(Pyridin-2-yl)but-3-yn-1-amine

To a solution of 2-(4-(Pyridin-2-yl)but-3-ynyl)isoindoline-1,3-dione (compound 3(B), 6.81 g, 34 mmol) in ethanol (20 mL, 0.3M) was added 6.6 mL of hydrazine hydrate 25%. The reaction mixture was heated 4 hours at 50° C. The awaited product was formed and the starting material was completely consumed. The reaction mixture was washed twice with NaHCO$_3$ saturated, and the organic layer was dried, filtrated and concentrated.

Purification by flash chromatography reverse phase (C18 column, pack 35 g, with H$_2$O/Acetonitrile: 95/5 as eluent), to afford 814 mg of 4-(pyridin-2-yl)but-3-yn-1-amine (Yield: 82%) as yellow solid.

220(B) N-(4-(Pyridin-2-yl)but-3-ynyl)benzo[d]thiazol-2-amine 4-(pyridin-2-yl)but-3-yn-1-amine (640 mg, 4.40 mmol), 2-chlorobenzo[d]thiazole (373 mg, 2.2 mmol) and DIEA (452 µL, 2.64 mmol) were poured into DMF (2.2 mL) and the resulting solution was heated two days at 120° C. The solvent was removed under reduce pressure and the crude product was purified over silicagel chromatography (prepacked 25 g silicagel column, Cyclohexane/AcOEt: 70/30 as eluent) to afford 582 mg of N-(4-(pyridin-2-yl)but-3-ynyl)benzo[d]thiazol-2-amine (Yield: 95%) as a brownish oil.

LCMS (RT): 3.09 min; MS (ES+) gave m/z: 280
Rf (Cyclohexane/AcOEt: 70/30)=0.30

Example 221

1-Methyl-3-(5-(pyridin-2-yl)pent-4-ynyl)-1H-benzo[d]imidazol-2(3H)-one

221(A) 2-(5-Chloropent-1-ynyl)pyridine

The title compound was prepared in accordance with the general method of Example 190(F), from 2-bromopyridine (948 mg, 6.0 mmol) and 5-chloropent-1-yne (620 mg, 6.0 mmol). The crude residue was purified over silicagel chromatography (prepacked 25 g silicagel column, Cyclohexane/AcOEt: from 100/0 to 80/20 as eluent) to afford 655 mg of 2-(5-chloropent-1-ynyl)pyridine as a yellow oil (Yield: 61%).

LCMS (RT): 3.56 min; MS (ES+) gave m/z: 180
Rf (Cyclohexane/AcOEt: 80/20)=0.30

221(B) 1-Methyl-3-(5-(pyridin-2-yl)pent-4-ynyl)-1H-benzo[d]imidazol-2(3H)-one 2-(5-chloropent-1-ynyl)pyridine (59 mg, 0.33 mmol), 1-methyl-1H-benzo[d]imidazol-2(3H)-one (44 mg, 0.3 mmol) and $K_2CO_3$ (70 mg, 0.51 mmol) were poured into DMF (0.45 mL) and the resulting mixture was heated at 50° C. overnight. The mixture was purified over silicagel chromatography (prepacked 25 g silicagel column, DCM 100% as eluent) to afford 40 mg of 1-methyl-3-(5-(pyridin-2-yl)pent-4-ynyl)-1H-benzo[d]imidazol-2(3H)-one as a yellow oil (Yield: 43%).

LCMS (RT): 3.29 min; MS (ES+) gave m/z: 292
$^1$H-NMR (CDCl$_3$), δ (ppm): 8.55-8.54 (d, 1H), 7.63-7.60 (m, 1H), 7.37-7.35 (d, 1H), 7.21-7.18 (m, 1H), 7.12-7.07 (m, 3H), 6.97-6.95 (m, 1H), 4.07-4.04 (t, 2H), 3.41 (s, 3H), 2.54-2.51 (t, 2H), 2.13-2.07 (m, 2H).

Example 222

2-(4-(4,5-Dimethylthiazol-2-yl)but-3-ynyl)-2H-benzo[d][1,2,3]triazole

222(A) 2-Bromo-4,5-dimethylthiazole

Bromine (272 μL, 5.30 mmol) was added dropwise to a solution of 4,5-dimethylthiazole (200 mg, 1.77 mmol) in chloroform (5 mL) at 0° C. and the reaction mixture was stirred for 5 hours at room temperature. Sodium thiosulfate solution was added to the reaction mixture and the aqueous phase was extracted with DCM. The organic phase was washed with water, brine, dried over Na$_2$SO$_4$, filtered and concentrated. The crude residue was purified by flash chromatography (pentane/Et$_2$O 95:5) to yield 250 mg (1.30 mmol, 74%) of 2-bromo-4,5-dimethylthiazole.

222(B) 2-(4-(4,5-Dimethylthiazol-2-yl)but-3-ynyl)-2H-benzo[d][1,2,3]triazole The title compound was prepared in accordance with the general method of Example 1, from 2-bromo-4,5-dimethylthiazole (100 mg, 0.52 mmol) and 2-(but-3-ynyl)-2H-benzo[d][1,2,3]triazole (89 mg, 0.52 mmol, Example 109 (D)). The crude residue was purified by flash chromatography (cyclohexane/AcOEt 4:1) to yield 25 mg (89 mmol, 17%) of 2-(4-(4,5-dimethylthiazol-2-yl)but-3-ynyl)-2H-benzo[d][1,2,3]triazole as a yellow solid (M.P.=96-98° C.).

LCMS (RT): 4.50 min; MS (ES+) gave m/z: 283.1
Rf (cyclohexane/AcOEt 7:3)=0.3.

$^1$H-NMR (CDCl$_3$), δ (ppm): 2.31 (s, 3H), 2.34 (s, 3H), 3.29 (t, J=7.5, 2H), 4.96 (t, J=7.5, 2H), 7.39 (dd, J=3.0 and 6.3, 2H), 7.86 (dd, J=3.0 and 6.3, 2H).

Example 223

6-Fluoro-2-(4-(6-(fluoromethyl)pyridin-2-yl)but-3-ynyl)H-imidazo[1,2-a]pyridine

223(A) Trimethyl(4-(oxiran-2-yl)but-1-ynyl)silane

To a stirred solution of trimethyl(prop-1-ynyl)silane (3 g, 26.7 mmol) in dry THF (100 mL) cooled at −72° C., was added drop by drop 2.5 N nBuLi in hexane solution (10.5 mL, 26.2 mmol). The resulting mixture was stirred at −75° C. for 1 h 30. Then 2-(chloromethyl)oxirane (2.42 g, 26.2 mmol) in dry THF (2 mL) was slowly added. The resulting mixture was stirred at −72° C. for 1 h 30, then warmed up to room temperature for an additional 1 h. The reaction mixture was quenched with water and extracted with diethyl ether. The organic phase was dried over MgSO$_4$, filtered and concentrated under reduced pressure to afford 4.50 g trimethyl(4-(oxiran-2-yl)but-1-ynyl)silane (Yield: 100%) as a yellow oil which was used in the next step without further purification.

Rf (Cyclohexane/AcOEt: 70/30)=0.61

223 (B) 1-Bromo-6-(trimethylsilyl)hex-5-yn-2-ol

To a stirred solution of trimethyl(4-(oxiran-2-yl)but-1-ynyl)silane (4.5 g, 27 mmol) in THF (90 mL) containing acetic acid (4.81 g, 80.21 mmol), was added at 0° C. anhydrous LiBr (3.71 g, 42.78 mmol). The reaction mixture was left stirring overnight at room temperature. The reaction was quenched with saturated NaCl and extracted with Et$_2$O. The organic phase was washed once with a solution of 1M K$_2$CO$_3$ saturated with NaCl, brine, dried over MgSO$_4$, filtered and concentrated. The crude residue was purified over silicagel chromatography (prepacked 70 g silicagel column, from Cyclohexane 100% to DCM 100% as eluent) to afford 2.5 g of 1-bromo-6-(trimethylsilyl)hex-5-yn-2-ol (Yield: 38%) as a yellow oil.

$^1$H-NMR (CDCl$_3$), δ (ppm): 3.95-3.80 (m, 1H), 3.65-3.30 (m, 2H), 2.38-2.20 (m, 3H), 1.75-1.65 (m, 2H), 0.05 (s, 9H)

223(C) 1-Bromo-6-(trimethylsilyl)hex-5-yn-2-one 1-bromo-6-(trimethylsilyl)hex-5-yn-2-ol (2.85 g, 10 mmol) were dissolved in acetone (13 mL).
Preparation of Jone's Reagent:

1.2 gr of CrO$_3$ are dissolved in conc. H$_2$SO$_4$ (1.2 mL). 5 mL of H$_2$O were added. The resulting mixture was stirred 10 min until CrO$_3$ was completely dissolved to give a red orange solution.

The Jone's reagent was slowly added to the solution of 1-bromo-6-(trimethylsilyl)hex-5-yn-2-ol in acetone; the color gets green, green-brown then dark brown. Jone's reagent was added until the dark brown color remains. The reaction was monitored by TLC (DCM 100%), Rf=0.75

Isopropanol was added to quench the excess of Jone's reagent, and the product was extracted with DCM. The organic phases were washed twice with water, dried over MgSO$_4$, filtered and concentrated under reduced pressure to afford 1.85 g which was a mixture of 1-chloro-6-(trimethylsilyl)hex-5-yn-2-one and 1-bromo-6-(trimethylsilyl)hex-5-yn-2-one (in 1/1 ratio) as a yellow oil (Yield: 75%). The product was immediately used in next step without further purification.

Rf (DCM: 100%)=0.75

$^1$H-NMR (CDCl$_3$), δ (ppm) mixture of α-chloroketone/α-bromoketone 1/1 ratio: 4.04 (s, 2H, α-chloroketone), 3.84 (s, 2H, α-bromoketone), 2.90-2.70 (m, 2H, α-chloroketone+α-bromoketone), 2.50-2.40 (t, α-chloroketone+α-bromoketone), 0.03 (s, 9H, α-chloroketone+α-bromoketone).

223(D) 6-Fluoro-2-(4-(trimethylsilyl)but-3-ynyl)-imidazo[1,2-a]pyridine

To a stirred solution of 1-bromo-6-(trimethylsilyl)hex-5-yn-2-one (2.50 g, 10.11 mmol) in EtOH (8 mL) was added potassium carbonate (350 mg, 2.53 mmol) and 5-fluoropyridin-2-amine (567 mg, 5.06 mmol). The mixture was heated at 80° C. overnight. The mixture was concentrated, the residue was dissolved in EtOAc, and the organic layer was washed with brine, dried over MgSO$_4$, filtered and concentrated under reduced pressure. The crude residue was purified over silicagel chromatography (prepacked 70 g silicagel column, from DCM/MeOH: 100/0 to 96/4 as eluent) to afford 400 mg of 6-fluoro-2-(4-(trimethylsilyl)but-3-ynyl)-imidazo[1,2-a]pyridine (Yield: 30%) as an orange-brown solid.

Rf (DCM/MeOH: 95/5)=0.38
LCMS (RT): 3.05 min; MS (ES+) gave m/z: 261

223(E) 2-(But-3-ynyl)-6-fluoro-imidazo[1,2-a]pyridine

According to the protocol described in Example 38(D), the conversion of 6-fluoro-2-(4-(trimethylsilyl)but-3-ynyl)-imidazo[1,2-a]pyridine (400 mg, 1.53 mmol) afforded 220 mg of 2-(but-3-ynyl)-6-fluoro-imidazo[1,2-a]pyridine (Yield: 76%) as yellow-oil.

Purification over silicagel chromatography (prepacked 25 g silicagel column, DCM/MeOH: 98/2 as eluent).

LCMS (RT): 0.63-1.61 min; MS (ES+) gave m/z: 189
Rf (DCM/MeOH: 95/5)=0.37

223(F) 6-Fluoro-2-(4-(6-(fluoromethyl)pyridin-2-yl)but-3-ynyl)-imidazo[1,2-a]pyridine The title compound was prepared in accordance with the general method of Example 190(F), from 2-bromo-6-(fluoromethyl)pyridine (220 mg, 1.10 mol) and 2-(but-3-ynyl)-6-fluoro-imidazo[1,2-a]pyridine (220 mg, 1.14 mmol). The crude residue was purified over C18 chromatography (prepacked 35 g silicagel column, H$_2$O/CH$_3$CN: from 95/5 to 55/45 as eluent) to afford 155 mg of 6-fluoro-2-(4-(6-(fluoromethyl)pyridin-2-yl)but-3-ynyl)H-imidazo[1,2-a]pyridine (Yield: 46%) as a white powder (Mp=140-141.8° C.).

LCMS (RT): 2.49 min; MS (ES+) gave m/z: 298
Rf (DCM/MeOH: 95/5)=0.32
$^1$H-NMR (CDCl$_3$), δ (ppm): 8.65-8.60 (m, 1H), 7.80-7.70 (m, 2H), 7.50-7.40 (m, 1H, 7.38-7.30 (m, 1H), 7.25-7.10 (m, 1H), 5.41-2.25 (d, 2H), 2.93-2.88 (m, 2H), 2.80-2.75 (m, 2H).

Example 224

6-Fluoro-2-(4-(2-(fluoromethyl)thiazol-4-yl)but-3-ynyl)-imidazo[1,2-a]pyridine

224(A) 4-Bromothiazole-2-carbaldehyde

To a solution of 2,4-dibromothiazole (730 mg, 3.0 mmol) in anhydrous Et$_2$O (15 mL) was added at −78° C., nBuLi 2.5M in hexane (1.4 mL, 3.6 mmol), and the resulting solution was stirred at the same temperature for 30 min. DMF (0.46 mL, 6 mmol) was added at −78° C. and, after being stirred at −78° C. for 30 min, the reaction mixture was slowly warmed up to room temperature over a period of 2 h. Cyclohexane was added and the resulting mixture was passed through a short silica gel cake eluting with Cyclohexane/AcOEt 70/30 to give the 462 mg of 4-bromothiazole-2-carbaldehyde (Yield: 80%) which was used directly in the next step.

224(B) (4-Bromothiazol-2-yl)methanol

To a solution of 4-bromothiazole-2-carbaldehyde (462 mg, 2.40 mmol) in methanol (24 mL) was added at room temperature sodium borohydride (140 mg, 3.60 mmol), and the resulting mixture was stirred 1 h at the same temperature. EtOAc (3 mL) and cyclohexane (6 mL) were added, and the mixture was passed through a short silica gel cake and eluting with EtOAc 100% to give 390 mg of (4-bromothiazol-2-yl)methanol (Yield: 83%) as a beige oil which slowly crystallize.

LCMS (RT): 2.43 min; MS (ES+) gave m/z: 194

224(C) 4-Bromo-2-(fluoromethyl)thiazole

A solution of (4-bromothiazol-2-yl)methanol (390 mg, 2.0 mmol) in 7 mL of dry DCM, was added dropwise −78° C. to a solution at of DAST (0.738 mL, 6.0 mmol) in dry DCM (5.5 mL). The reaction mixture was stirred 1 h at −78° C. then 1 h at room temperature. The reaction was quenched with water, and the organic layer extracted with DCM, dried over MgSO$_4$, filtrated and evaporated.

The crude residue was purified over silicagel chromatography (prepacked 25 g silicagel column, Cyclohexane/AcOEt: 95/5 as eluent) to afford 84 mg of 4-bromo-2-(fluoromethyl)thiazole as a yellow oil (Yield: 21%).

LCMS (RT): 3.38 min; MS (ES+) gave m/z: 197

224(D) 6-Fluoro-2-(4-(2-(fluoromethyl)thiazol-4-yl)but-3-ynyl)-imidazo[1,2-a]pyridine The title compound was prepared in accordance with the general method of Example 190(F), from 4-bromo-2-(fluoromethyl)thiazole (84 mg, 0.43 mmol) and 2-(but-3-ynyl)-6-fluoro-imidazo[1,2-a]pyridine (compound 223(E), 80 mg, 0.43 mmol). The crude residue was purified over C18 chromatography (prepacked 35 g silicagel column, H$_2$O/CH$_3$CN: from 100/0 to 80/20 as eluent) to afford 65 mg of 6-fluoro-2-(4-(2-(fluoromethyl)thiazol-4-yl)but-3-ynyl)-imidazo[1,2-a]pyridine (Yield: 47%) as a beige powder (Mp=82-84° C.).

LCMS (RT): 2.54 min; MS (ES+) gave m/z: 304
Rf (DCM/MeOH: 95/5)=0.32
$^1$H-NMR (CDCl$_3$), δ (ppm): 8.06-8.01 (t, 1H), 7.72-7.65 (m, 1H), 7.62-7.44 (m, 2H), 7.16-7.10 (t, 1H), 5.64-5.54 (d, 2H), 3.15-3.12 (t, 2H), 2.92-2.89 (t, 2H)

Example 225

8-Bromo-2-(4-(6-(fluoromethyl)pyridin-2-yl)but-3-ynyl)-imidazo[1,2-a]pyridine

225(A) 8-Bromo-2-(4-(trimethylsilyl)but-3-ynyl)-imidazo[1,2-a]pyridine

The title compound was prepared in accordance with the general method of Example 223(D), from 3-bromopyridin-2-amine (280 mg, 1.60 mmol) and 1-bromo-6-(trimethylsilyl)hex-5-yn-2-one (compound 223(C), 870 mg, 3.5 mmol). The crude residue was purified over silicagel chromatography (prepacked 25 g silicagel column, DCM/MeOH: from 100/0 to 98/2 as eluent) to afford 315 mg of 8-bromo-2-(4-(trimethylsilyl)but-3-ynyl)-imidazo[1,2-a]pyridine (Yield: 61%) as a yellow oil.

225(B) 8-Bromo-2-(but-3-ynyl)-imidazo[1,2-a]pyridine

According to the protocol described in Example 38(D), the conversion of 8-bromo-2-(4-(trimethylsilyl)but-3-ynyl)-imidazo[1,2-a]pyridine (315 mg, 0.98 mmol) afforded 241 mg of 8-bromo-2-(but-3-ynyl)-imidazo[1,2-a]pyridine (Yield: 98%) as yellow-oil.

LCMS (RT): 0.76 min; MS (ES+) gave m/z: 250

225(C) 8-Bromo-2-(4-(6-(fluoromethyl)pyridin-2-yl)but-3-ynyl)H-imidazo[1,2-a]pyridine The title compound was prepared in accordance with the general method of Example 190(F), from 2-bromo-6-(fluoromethyl)pyridine (180 mg, 0.97 mmol) and 8-bromo-2-(but-3-ynyl)-imidazo[1,2-a]pyridine (242 mg, 0.97 mmol). The crude residue was purified over silicagel chromatography (prepacked 25 g silicagel column, Cyclohexane/AcOEt: from 100/0 to 60/40 as eluent) to afford 36 mg of 8-bromo-2-(4-(6-(fluoromethyl)pyridin-2-yl)but-3-ynyl)-imidazo[1,2-a]pyridine (Yield: 10%) as a yellow oil.

LCMS (RT): 2.58 min; MS (ES+) gave m/z: 358
$^1$H-NMR (CDCl$_3$), δ (ppm): 8.08-8.04 (d, 1H), 7.73-7.67 (t, 1H), 7.62 (s, 1H), 7.45-7.41 (d, 1H), 7.41-7.37 (d, 1H), 7.34-7.31 (d, 1H), 6.67-6.62 (t, 1H), 3.15-3.25 (t, 2H), 3.00-2.90 (t, 2H)

Example 226

8-(Benzyloxy)-2-(4-(6-(fluoromethyl)pyridin-2-yl)but-3-ynyl)-imidazo[1,2-a]pyridine

226(A) 8-(Benzyloxy)-2-(4-(trimethylsilyl)but-3-ynyl)-imidazo[1,2-a]pyridine The title compound was prepared in accordance with the general method of Example 223(D), from 3-(benzyloxy)pyridin-2-amine (274 mg, 1.37 mmol) and 1-bromo-6-(trimethylsilyl)hex-5-yn-2-one (compound 223(C), 750 mg, 3.0 mmol). The crude residue was purified over silicagel chromatography (prepacked 25 g silicagel column, DCM/MeOH: from 98/2 to 95/5 as eluent) to afford 331 mg of 8-(benzyloxy)-2-(4-(trimethylsilyl)but-3-ynyl)H-imidazo[1,2-a]pyridine (Yield: 69%) as a yellow oil.

LCMS (RT): 3.68 min; MS (ES+) gave m/z: 349

226(B) 8-(Benzyloxy)-2-(but-3-ynyl)-imidazo[1,2-a]pyridine

According to the protocol described in Example 38(D), the conversion of 8-bromo-2-(4-(trimethylsilyl)but-3-ynyl)-imidazo[1,2-a]pyridine (331 mg, 0.95 mmol) afforded 183 mg of 8-(benzyloxy)-2-(but-3-ynyl)-imidazo[1,2-a]pyridine (Yield: 70%) as yellow-oil.

LCMS (RT): 2.58 min; MS (ES+) gave m/z: 277

226(C) 8-(Benzyloxy)-2-(4-(6-(fluoromethyl)pyridin-2-yl)but-3-ynyl)H-imidazo[1,2-a]pyridine The title compound was prepared in accordance with the general method of Example 190(F), from 2-bromo-6-(fluoromethyl)pyridine (82 mg, 0.43 mmol) and 8-(benzyloxy)-2-(but-3-ynyl)-imidazo[1,2-a]pyridine (119 mg, 0.43 mmol). The crude residue was purified over silicagel chromatography (prepacked 25 g silicagel column, Cyclohexane/AcOEt: from 100/0 to 60/40 as eluent) to afford 10 mg of 8-(benzyloxy)-2-(4-(6-(fluoromethyl)pyridin-2-yl)but-3-ynyl)-imidazo[1,2-a]pyridine (Yield: 6%) beige solid (Mp=92-94° C.)

LCMS (RT): 3.01 min; MS (ES+) gave m/z: 386
$^1$H-NMR (CDCl$_3$), δ (ppm): 7.75-7.65 (m, 2H), 7.55-7.30 (m, 8H), 6.60-6.50 (t, 1H), 6.45-6.35 (d, 1H), 5.55-5.40 (d, 2H), 5.35 (s, 2H), 3.19-3.14 (t, 2H), 2.96-2.91 (t, 2H)

Example 227

2-(4-(6-(Fluoromethyl)pyridin-2-yl)but-3-ynyl)-8-phenyl-imidazo[1,2-a]pyridine To a solution of 8-bromo-2-(4-(6-(fluoromethyl)pyridin-2-yl)but-3-ynyl)-imidazo[1,2-a]pyridine (compound 171(C), 301 mg, 0.84 mmol) and phenylboronic acid (50 mg, 1.3 mmol) in degazed DME (4.2 mL) was added 1.32 mL of a solution of K$_3$PO$_4$ 2M (degazed before use). After stirring at room temperature for 5 min under N$_2$, Pd(PPh$_3$)$_4$ (190 mg, 0.17 mmol) was added in one portion. The resulting mixture was heated at 80° C. for 4 h. The Mixture was cooled down to room temperature and diluted in AcOEt. The organic layer was washed twice with saturated NaCl, dried over magnesium sulfate, filtered and concentrated. The crude product was purified over silicagel chromatography (prepacked 25 g silicagel column, Cyclohexane/AcOEt: 60/40 as eluent) to afford 137 mg of 2-(4-(6-(fluoromethyl)pyridin-2-yl)but-3-ynyl)-8-phenyl-imidazo[1,2-a]pyridine (Yield: 46%) as a yellow oil.

LCMS (RT): 3.19 min; MS (ES+) gave m/z: 356
$^1$H-NMR (CDCl$_3$), δ (ppm): 8.80-8.40 (d, 1H), 8.40-8.00 (m, 2H), 7.72-7.66 (t, 1H), 7.57 (s, 1H), 7.51-7.23 (m, 6H), 6.87-6.81 (t, 1H), 5.52-5.41 (d, 2H), 3.19-3.16 (t, 2H), 2.96-2.93 (t, 2H)

Example 228

6,8-Difluoro-2-(4-(pyridin-2-yl)but-3-ynyl)-imidazo[1,2-a]pyridine

228(A) 6,8-Difluoro-2-(4-(trimethylsilyl)but-3-ynyl)-imidazo[1,2-a]pyridine The title compound was prepared in accordance with the general method of Example 223(D), from 3,5-difluoropyridin-2-amine (492 mg, 3.78 mmol) and 1-bromo-6-(trimethylsilyl)hex-5-yn-2-one (compound 223(C), 1.87 mg, 7.56 mmol). The crude residue was purified over silicagel chromatography (prepacked 25 g silicagel column, from DCM/Cyclohexane: 70/30 to DCM/MeOH: 95/5 as eluent) to afford 517 mg of 6,8-difluoro-2-(4-(trimethylsilyl)but-3-ynyl)-imidazo[1,2-a]pyridine (Yield: 49%) as a brown oil.

LCMS (RT): 4.43 min; MS (ES+) gave m/z: 279
$^1$H-NMR (CDCl$_3$), δ (ppm): 7.80 (s, 1H), 7.45 (d, 1H), 7.81-7.72 (t, 1H), 3.00-2.90 (t, 2H), 2.65-2.50 (t, 2H), 0.05 (s, 9H)

228(B) 2-(But-3-ynyl)-6,8-difluoro-imidazo[1,2-a]pyridine

According to the protocol described in Example 38(D), the conversion of 6,8-difluoro-2-(4-(trimethylsilyl)but-3-ynyl)- imidazo[1,2-a]pyridine (517 mg, 1.86 mmol) afforded 363 mg of 2-(but-3-ynyl)-6,8-difluoro-imidazo[1,2-a]pyridine (Yield: 95%) as yellow-oil.

LCMS (RT): 2.55 min; MS (ES+) gave m/z: 207

$^1$H-NMR (CDCl$_3$), δ (ppm): 7.80 (s, 1H), 7.50 (s, 1H), 6.84-6.70 (t, 1H), 3.00-2.90 (t, 2H), 2.65-2.50 (t, 2H), 1.90 (s, 1H)

228(C) 6,8-Difluoro-2-(4-(pyridin-2-yl)but-3-ynyl)-imidazo[1,2-a]pyridine

In a dry flask were added CuI (16.9 mg, 0.08 mmol) and TEA (5 mL) followed by 2-iodopyridine (363 mg, 1.77 mmol) and Pd(PPh$_3$)$_2$Cl$_2$ (82 mg, 0.088 mmol). A yellow suspension was obtained after 5 min of stirring. To this suspension was added 2-(but-3-ynyl)-6,8-difluoro-imidazo[1,2-a]pyridine (365 mg, 1.77 mmol) and the reaction mixture turns to black. After 4 h at room temperature, the TEA was evaporated; the crude product was dissolved in DCM and filtered over celite. The organic layer was washed with aqueous 2N ammonia, brine, dried over MgSO$_4$, and the solvent was evaporated to give a brown solid (588 mg). The crude product was purified over silicagel chromatography (pre-packed 25 g silicagel column, DCM/AcOEt: form 100/0 to 95/5 as eluent) to afford 293 mg of 6,8-difluoro-2-(4-(pyridin-2-yl)but-3-ynyl)-imidazo[1,2-a]pyridine. A second purification over C18 was performed using H$_2$O/CH$_3$CN: from 80/20 to 70/30 as eluent) to afford 146 mg of the title compound as a brownish powder contaminated by PPh$_3$O. The solid was dissolved in aqueous 0.1N HCl (20 mL) 1 and the aqueous phase was washed twice with DCM (3*10 mL). The aqueous layer was neutralised with sat NaHCO$_3$ and extracted in ether (3*10 mL). The organic layer was washed with water (10 mL), brine (10 mL), and dried over MgSO$_4$. Evaporation of the solvent afford 124 mg of 6,8-difluoro-2-(4-(pyridin-2-yl)but-3-ynyl)-imidazo[1,2-a]pyridine (Yield: 25%) as a white solid (Mp=130-131° C.).

LCMS (RT): 2.67 min; MS (ES+) gave m/z: 284

Rf (DCM/MeOH: 96/4)=0.23

$^1$H-NMR (CDCl$_3$), δ (ppm): 8.50-8.40 (d, 1H), 7.90-7.80 (m, 1H), 7.60-7.50 (m, 2H), 7.35-7.25 (d, 1H), 7.18-7.08 (m, 1H), 6.86-6.72 (t, 1H), 3.15-3.00 (t, 2H), 2.90-2.80 (t, 2H)

Example 229

2-(4-(4-Methylthiazol-2-yl)but-3-ynyl)-2H-benzo[d][1,2,3]triazole

229(A) 2-Bromo-4-methylthiazole

A solution of sodium nitrite (378 mg, 5.47 mmol) in water (2.25 mL) was added to a mixture of 4-methyl-thiazol-2-ylamine (500 mg, 4.38 mmol), phosphoric acid (4.50 mL) and nitric acid (2.25 mL) at –10° C. After stirring the reaction mixture for 45 min. at –10° C., it was poured onto a solution of CuSO$_4$ (1.37 g, 5.47 mmol) and sodium bromide (1.13 g, 10.9 mmol). Then the solution was stirred for 30 min. at room temperature, for 3 hours at 50° C. and was neutralized with a solution of NaOH (2M). The aqueous phase was extracted with DCM. The organic phase was washed with water, brine, dried over Na$_2$SO$_4$, filtered and concentrated. The crude residue was purified by flash chromatography (pentane/ether 95:5) to yield 250 mg (1.40 mmol, 32%) of 2-bromo-4-methylthiazole as an orange oil.

LCMS (RT): 3.62 min; MS (ES+) gave m/z: 179.1.

229(B) 2-(4-(4-Methylthiazol-2-yl)but-3-ynyl)-2H-benzo[d][1,2,3]triazole

The title compound was prepared in accordance with the general method of Example 1, from 2-bromo-4-methylthiazole (100 mg, 0.56 mmol) and 2-(but-3-ynyl)-2H-benzo[d][1,2,3]triazole (96 mg, 0.56 mmol, Example 109(D)). The crude residue was purified by flash chromatography (cyclohexane/AcOEt 4:1) to yield 40 mg (0.15 mmol, 27%) of 2-(4-(4-methylthiazol-2-yl)but-3-ynyl)-2H-benzo[d][1,2,3]triazole as a white solid (M.P.=78-80° C.).

LCMS (RT): 4.05 min; MS (ES+) gave m/z: 269.1

Rf (cyclohexane/AcOEt 7:3)=0.3.

$^1$H-NMR (CDCl$_3$), δ (ppm): 2.44 (s, 3H), 3.31 (t, J=7.5, 2H), 4.98 (t, J=7.5, 2H), 6.85 (s, 1H), 7.39 (dd, J=3.3 and 6.3, 2H), 7.87 (dd, J=3.3 and 6.3, 2H).

Example 230

(3-Fluoropyridin-2-yl)but-3-ynyl)benzo[d]oxazole

230(A) 3-Fluoro-2-iodopyridine

To a solution of 2-chloro-3-fluoropyridine (400 mg, 3 mmol) in dioxane (6 mL, 0.5M) was added in one portion chlorotrimethylsilane (652 mg, 6 mmol) and sodium iodide (2.20 g, 15 mmol). The resulting mixture was stirred at 80° C. overnight. The reaction mixture was concentrated to afford 660 mg of 3-fluoro-2-iodopyridine (Yield: 98%) as a yellow oil which was used in the next step without further purification.

230(B) (3-Fluoropyridin-2-yl)but-3-ynyl)benzo[d]oxazole

In a dry reaction tube containing in suspension copper iodide (28 mg, 0.148 mol) and triethylamine (8.30 mL, 59.20 mmol), were added 3-fluoro-2-iodopyridine (660 mg, 2.96 mmol) and Pd(PPh$_3$)$_2$Cl$_2$ (104 mg, 0.148 mmol) under N$_2$. A yellow suspension was obtained. After a 5 minutes of stirring at room temperature, was added a solution 2-(But-3-ynyl) benzo[d]oxazole (compound 8(A), 510 mg, 3 mmol) in triethylamine (0.2 mL) under N$_2$. Immediately the color of the reaction turns to black. The mixture was stirred at room temperature for 30 min and heated at 50° C. overnight under N$_2$. Triethylamine was removed under reduce pressure and the crude product was purified by flash chromatography (Pre-packed column 50 g, Cyclohexane/AcOEt: 60/40 as eluent) following by C18 chromatography (Prepacked column 15 g, H$_2$O/CH$_3$CN: from 80/20 to 40/600 as eluent) to afford 120 mg of 2-(4-(3-fluoropyridin-2-yl)but-3-ynyl)benzo[d]oxazole (Yield: 15%) as white powder (Mp=86-88° C.).

LCMS (RT): 4.06 min; MS (ES+) gave m/z: 267

$^1$H-NMR (CDCl$_3$), δ (ppm): 8.39-8.36 (m, 1H), 7.73-7.68 (m, 1H), 7.53-7.49 (m, 1H), 7.42-7.38 (m, 1H), 7.35-7.30 (m, 2H), 7.27-7.22 (m, 1H), 3.35-3.32 (t, 2H), 3.15-3.12 (t, 2H)

Example 231

2-(4-(2-Methyl-1H-imidazol-4-yl)but-3-ynyl)benzo[d]oxazole

231(A) Ethyl 4-iodo-2-methyl-1H-imidazole-1-carboxylate

To a solution of 4-iodo-2-methyl-1H-imidazole (162 mg, 0.78 mmol) in THF (2.6 mL, 0.3M) containing DIEA (0.33 mL, 1.95 mmol) and DMAP (47 mg, 0.039 mmol), cooled in a ice bath at 0° C., was added a solution of Ethyl chloroformate (211 mg, 1.95 mmol) in THF (2 mL, 1M). The reaction mixture was heated at 50° C. for 48 h and then concentrated. The residue was dissolved in DCM and the organic layer was washed with saturated NaCl, dried over magnesium sulfate, filtered and evaporated. The crude product was purified by flash chromatography (Prepacked column 10 g, DCM/MeOH: 97/3 as eluent) to afford 208 mg of ethyl 4-iodo-2-methyl-1H-imidazole-1-carboxylate (95%) as colorless oil.

LCMS (RT): 3.69 min; MS (ES+) gave m/z: 281

231(B) Ethyl 4-(4-(benzo kg oxazol-2-yl)but-1-ynyl)-2-methyl-1H-imidazole-1-carboxylate According to the general protocol for Sonogashira coupling described in Example 38(E), the conversion of ethyl 4-iodo-2-methyl-1H-imidazole-1-carboxylate (686 mg, 2.45 mmol) afforded 369 mg of ethyl 4-(4-(benzo[d]oxazol-2-yl)but-1-ynyl)-2-methyl-1H-imidazole-1-carboxylate (Yield: 46%) as a beige powder.

The crude residue was purified over silicagel chromatography (prepacked 25 g silicagel column, Cyclohexane/AcOEt: 50/50 as eluent)

LCMS (RT): 4.18 min; MS (ES+) gave m/z: 324
Rf (Cyclohexane/AcOEt: 50/50)=0.35

231(C) 2-(4(2-Methyl-1H-imidazol-4-yl)but-3-ynyl)benzo[d]oxazole

A solution 2.0 N of NaOH was added dropwise to a solution of ethyl 4-(4-(benzo[d]oxazol-2-yl)but-1-ynyl)-2-methyl-1H-imidazole-1-carboxylate (369 mg, 1.14 mmol) in EtOH (5.7 mL) and the mixture was heated at 80° C. overnight. Ethanol was concentrated under reduce pressure, then water was added and the aqueous layer was extracted with DCM. The recombined organics layers were washed once with saturated NaCl, dried over $MgSO_4$, filtered and concentrated.

The crude residue was purified over silicagel chromatography (prepacked 25 g silicagel column, DCM/MeOH: 97/3 as eluent) to afford 102 mg of 2-(4-(2-methyl-1H-imidazol-4-yl)but-3-ynyl)benzo[d]oxazole (Yield: 35%) as a beige powder (Mp=152-154° C.).

LCMS (RT): 2.46 min; MS (ES+) gave m/z: 252
Rf (DCM/MeOH: 95/5)=0.4
$^1$H-NMR (CDCl$_3$), δ (ppm): 7.70-7.67 (m, 1H), 7.52-7.48 (m, 1H), 7.34-7.27 (m, 2H), 7.03 (s, 1H), 3.25-3.22 (t, 2H), 3.03-3.00 (t, 2H), 2.38 (s, 3H)

Example 232

5-(6-(Fluoromethyl)pyridin-2-yl)-N-(4-fluorophenyl)pent-4-ynamide

232(A) (4-Fluoro-phenyl)-pent-4-ynoyl-carbamic acid tert-butyl ester

The title compound was prepared in accordance with the general method of Example 34(B), from N-(4-fluorophenyl)pent-4-ynamide (400 mg, 2.09 mmol, 34(A)). The crude residue was purified by flash chromatography (cyclohexane/AcOEt 9:1) to yield 505 mg (1.73 mmol, 83%) of (4-fluorophenyl)-pent-4-ynoyl-carbamic acid tert-butyl ester as a colourless oil.

LCMS (RT): 4.72 min; MS (ES+) gave m/z: 192.1.

232(B)[5-(6-Fluoromethyl-pyridin-2-yl)-pent-4-ynoyl]-(4-fluoro-phenyl)-carbamic Acid tert-butyl Ester The title compound was prepared in accordance with the general method of Example 1, from 2-bromo-6-(fluoromethyl)pyridine (180 mg, 0.95 mmol, Example 190(E)) and (4-fluoro-phenyl)-pent-4-ynoyl-carbamic acid tert-butyl ester (276 mg, 0.95 mmol). Reaction time: 3 hours. The crude residue was purified by flash chromatography (cyclohexane/AcOEt 4:1) to yield 300 mg (0.75 mmol, 79%) of [5-(6-fluoromethyl-pyridin-2-yl)-pent-4-ynoyl]-(4-fluoro-phenyl)-carbamic acid tert-butyl ester as a white solid.

LCMS (RT): 4.90 min; MS (ES+) gave m/z: 301.1.
Rf (cyclohexane/AcOEt 4:1)=0.2.

232(C) 5-(6-(Fluoromethyl)pyridin-2-yl)-N-(4-fluorophenyl)pent-4-ynamide

The title compound was prepared in accordance with the general method of Example 34(D), from [5-(6-fluoromethyl-pyridin-2-yl)-pent-4-ynoyl]-(4-fluoro-phenyl)-carbamic acid tert-butyl ester (300 mg, 0.75 mmol). After the work-up, the crude residue was washed with diisopropyl ether to yield 120 mg (0.40 mmol, 53%) of 5-(6-(fluoromethyl)pyridin-2-yl)-N-(4-fluorophenyl)pent-4-ynamide as a beige powder (M.P.=110° C.).

LCMS (RT): 3.77 min; MS (ES+) gave m/z: 301.1.
$^1$H-NMR (CDCl$_3$), δ (ppm): 2.68 (t, J=6.9, 2H), 2.88 (t, J=6.9, 2H), 5.46 (d, J=46.8, 2H), 6.95-7.04 (2H), 7.32 (d, J=8.1, 1H), 7.40 (d, J=7.5, 1H), 7.43-7.52 (3H), 7.67-7.74 (m, 1H).

Example 233

2-(4-(1,2-Dimethyl-1H-imidazol-4-yl)but-3-ynyl)benzo[d]oxazole

In a dry microwave tube were placed in suspension CuI (19 mg, 0.1 mmol) and triethylamine (3.79 mL, 27 mmol). Then under nitrogen atmosphere, were added the 4-bromo-1,2-dimethyl-1H-imidazole (350 mg, 2.0 mmol), PdCl$_2$(PPh$_3$)$_2$ (70 mg, 0.1 mmol), and triphenyl phosphine polymerbound (130 mg, 0.4 mmol). The suspension was stirred at room temperature for few minutes, finally the 2-(But-3-ynyl)benzo[d]oxazole (compound 43(A), 340 mg, 2.0 mmol) in 0.4 mL of DMF was added, and the reaction mixture is stirred at room temperature for 30 min. The reaction mixture was stirred and heated under micro wave irradiation for 25 min at 120° C. After filtering to remove triphenyl phosphine polymerbound, the triethylamine was concentrated under reduce pressure and the residue was dissolved in DCM. The organic layer was washed with saturated NaHCO$_3$, H$_2$O and brine. The organic layer was dried over Na$_2$SO$_4$, filtered and concentrated.

Purification over C18 chromatography (prepacked 35 g C18 column, H$_2$O/CH$_3$CN: from 100/0 to 60/40 as eluent) to afford 28 mg of 2-(4-(1,2-dimethyl-1H-imidazol-4-yl)but-3-ynyl)benzo[d]oxazole (Yield: 5%) as a beige powder (Mp=117-119° C.).

LCMS (RT): 2.53 min; MS (ES+) gave m/z: 266
$^1$H-NMR (CDCl$_3$), δ (ppm): 7.69-7.67 (m, 1H), 7.50-7.48 (m, 1H), 7.32-7.27 (m, 2H), 6.89 (s, 1H), 3.54 (s, 3H), 3.28-3.22 (t, 2H), 3.04-2.98 (t, 2H), 2.36 (s, 3H)

Example 234

2-(4-(Pyridin-2-yl)but-3-ynyl)isoindolin-1-one

234(A) Methyl-2-(bromomethyl)benzoate

A solution of methyl-2-methylbenzoate (250 mg, 1.66 mmol), NBS (296 mg, 1.66 mmol) and dibenzoylperoxide (403 mg, 1.66 mmol) was stirred under reflux for one day. After purification by flash chromatography, 350 mg (1.53 mmol, 92%) of methyl-2-(bromomethyl)benzoate were obtained as a colorless oil.

234(B) 2-(4-(Trimethylsilyl)but-3-ynyl)isoindolin-1-one

4-Trimethylsilyl)but-3-yn-1-amine (215 mg, 1.52 mmol), methyl-2-(bromomethyl)benzoate (349 mg, 1.52 mmol) and $Et_3N$ (0.42 mL, 3.04 mmol) were placed in a microwave tube and heated for 10 min. at 100° C. The solvent was evaporated and the crude residue was dissolved in DCM. The organic phase was washed with water, brine, dried over $Na_2SO_4$, filtered and concentrated to yield 250 mg (0.97 mmol, 64%) of 2-(4-(trimethylsilyl)but-3-ynyl)isoindolin-1-one as a colourless oil.

234(C) 2-(But-3-ynyl)isoindolin-1-one

The title compound was prepared in accordance with the general method of Example 108(B), from 2-(4-(trimethylsilyl)but-3-ynyl)isoindolin-1-one (250 mg, 0.97 mmol). The crude residue was purified by flash chromatography (cyclohexane/AcOEt 3:2) to yield 85 mg (0.46 mmol, 47%) of 2-(but-3-ynyl)isoindolin-1-one as a colourless oil.

LCMS (RT): 3.03 min; MS (ES+) gave m/z: 186.1.

234(D) 2-(4-(Pyridin-2-yl)but-3-ynyl)isoindolin-1-one

The title compound was prepared in accordance with the general method of Example 1, from 2-iodopyridine (94 mg, 0.46 mmol) and 2-(but-3-ynyl)isoindolin-1-one (85 mg, 0.46 mmol). Reaction conditions: 14 hours at room temperature. The crude residue was purified by flash chromatography (cyclohexane/AcOEt 1:1 to 0:1) to yield 45 mg (0.17 mmol, 37%) of 2-(4-(pyridin-2-yl)but-3-ynyl)isoindolin-1-one as a white solid (M.P.=94-98° C.).

LCMS (RT): 2.90 min; MS (ES+) gave m/z: 263.2.
Rf (AcOEt)=0.3.
$^1$H-NMR (CDCl$_3$), δ (ppm): 2.83 (t, J=6.6, 2H), 3.89 (t, J=6.6, 2H), 4.60 (d, J=6.6, 2H), 7.14-7.24 (m, 1H), 7.33 (d, J=7.8, 1H), 7.40-7.55 (3H), 7.56-7.67 (m, 1H), 7.84 (d, J=6.9, 1H), 8.48-8.60 (m, 1H).

Example 235

4-(Pyridin-2-yl)but-3-ynyl 2-chlorobenzoate

235(A) 4-(Pyridin-2-yl)but-3-yn-1-ol

In a dry microwave tube were placed in suspension CuI (49.5 mg, 0.26 mmol) and triethylamine (9.85 mL, 70.20 mmol). Then under nitrogen atmosphere, were added the 2-bromopyridine (822 mg, 5.2 mmol), PdCl$_2$(PPh$_3$)$_2$ (182 mg, 0.26 mmol), and triphenyl phosphine polymerbound (350 mg, 1.0 mmol). The suspension was stirred at room temperature for few minutes, finally the but-3-yn-1-ol (364 mg, 5.20 mmol) in 0.5 mL of DMF was added, and the reaction mixture is stirred at room temperature for 30 min.

The reaction mixture was stirred and heated under micro wave irradiation for 10 min at 120° C. After filtering to remove triphenyl phosphine polymerbound, the triethylamine was concentrated under reduce pressure and the residue was dissolved in DCM. The organic layer was washed with saturated NaHCO$_3$, H$_2$O and brine. The organic layer was dried over Na$_2$SO$_4$, filtered and concentrated.

Purification over silicagel chromatography (prepacked 50 g silicagel column, DCM/MeOH: 98/2 as eluent) to afford 620 mg of 4-(pyridin-2-yl)but-3-yn-1-ol (Yield: 81%) as a yellow oil.

LCMS (RT): 1.76 min; MS (ES+) gave m/z: 148

235(B) 4-(Pyridin-2-yl)but-3-ynyl 2-chlorobenzoate

To solution of 2-chlorobenzoic acid (330 mg, 2.10 mmol), 4-(pyridin-2-yl)but-3-yn-1-ol (310 mg, 2.1 mmol), in DCM (7 mL), was successively added EDCI.HCl (600 mg, 3.2 mmol) and DMAP (13 mg, 0.105 mmol). The resulting mixture was then stirred overnight at ambient temperature. The reaction mixture was concentrated.

Purification over silicagel chromatography (prepacked 25 g silicagel column, Cyclohexane/AcOEt: 80/20 as eluent) to afford 260 mg of 4-(pyridin-2-yl)but-3-ynyl 2-chlorobenzoate (Yield: 43%) as a yellow oil.

Rf (Cyclohexane/AcOEt: 80/20)=0.30
LCMS (RT): 4.19 min; MS (ES+) gave m/z: 286
$^1$H-NMR (CDCl$_3$), δ (ppm): 8.55 (s, 1H), 8.06 (s, 1H), 7.98-7.95 (d, 1H), 7.67-7.61 (t, 1H), 7.56-7.52 (d, 1H), 7.42-7.37 (m, 2H), 7.24-7.18 (m, 1H), 4.55-4.52 (t, 2H), 2.95-2.93 (t, 2H)

Example 236

4-(Pyridin-2-yl)but-3-ynyl 3-chlorobenzoate

According to the protocol described in Example 235(B), the conversion of 3-chlorobenzoic acid (330 mg, 2.10 mmol) afforded 350 mg of 4-(pyridin-2-yl)but-3-ynyl 3-chlorobenzoate (Yield: 58%) as yellow-oil.

Purification over silicagel chromatography (prepacked 25 g silicagel column, Cyclohexane/AcOEt: 80/20 as eluent)
Rf (Cyclohexane/AcOEt: 80/20)=0.30
LCMS (RT): 4.53 min; MS (ES+) gave m/z: 286
$^1$H-NMR (CDCl$_3$), δ (ppm): 8.58-8.55 (d, 1H), 7.91-7.87 (d, 1H), 7.66-7.60 (t, 1H), 7.48-7.38 (m, 3H), 7.35-7.30 (t, 1H), 7.24-7.19 (m, 1H), 4.57-4.54 (t, 2H), 2.96-2.93 (t, 2H).

Example 237

3-Chlorophenyl 5-(pyridin-2-yl)pent-4-ynoate

237(A) 3-Chlorophenyl pent-4-ynoate

According to the protocol described in Example 235(B), the reaction between pent-4-ynoic acid (590 mg, 6.0 mmol) and 3-chlorophenol (771 mg, 6.0 mmol) afforded 1.19 g of 3-chlorophenyl pent-4-ynoate (Yield: 95%) as colorless-oil.

Purification over silicagel chromatography (prepacked 25 g silicagel column, Cyclohexane/AcOEt: 90/10 as eluent)
Rf (Cyclohexane/AcOEt: 90/10)=0.30
LCMS (RT): 4.68 min; MS (ES+) no MH+ detected

237(B) 3-Chlorophenyl 5-(pyridin-2-yl)pent-4-ynoate

In a dry microwave tube were placed in suspension CuI (26.7 mg, 0.14 mmol) and triethylamine (5.30 mL, 37.80 mmol). Then under nitrogen atmosphere, were added the 2-iodopyridine (574 mg, 2.80 mmol), PdCl$_2$(PPh$_3$)$_2$ (98 mg, 0.14 mmol), and triphenyl phosphine polymerbound (190 mg, 0.56 mmol). The suspension was stirred at room temperature for few minutes, finally the 3-chlorophenyl pent-4-ynoate (580 mg, 2.80 mmol) in 0.2 mL of DMF was added, and the reaction mixture is stirred at room temperature for 30 min. The reaction mixture was stirred and heated under micro wave irradiation for 8 min at 120° C. After filtering to remove triphenyl phosphine polymerbound, the triethylamine was concentrated under reduce pressure, the residue was dissolved in DCM. The organic layer was washed with saturated NaHCO$_3$, H$_2$O and brine. The organic layer was dried over Na$_2$SO$_4$, filtered and concentrated.

Purification over silicagel chromatography (prepacked 25 g silicagel column, Cyclohexane/AcOEt: 80/20 as eluent) to afford 210 mg of 3-chlorophenyl 5-(pyridin-2-yl)pent-4-ynoate (Yield: 26%) as a yellow oil.

Rf (Cyclohexane/AcOEt: 80/20)=0.30
LCMS (RT): 4.33 min; MS (ES+) gave m/z: 286
$^1$H-NMR (CDCl$_3$), δ (ppm): 8.59-8.56 (d, 1H), 7.66-7.61 (t, 1H), 7.42-7.38 (d, 1H), 7.34-7.17 (m, 4H), 7.06-7.02 (d, 1H), 2.95-2.86 (m, 4H)

Example 238

3-Chlorophenyl
5-(3-fluoropyridin-2-yl)pent-4-ynoate

According to the protocol described in Example 237(B), the reaction between 3-chlorophenyl pent-4-ynoate (580 mg, 2.80 mmol) and 2-chloro-3-fluoropyridine (370 mg, 2.80 mmol) afforded 111 mg of 3-chlorophenyl 5-(3-fluoropyridin-2-yl)pent-4-ynoate (Yield: 13%) as yellow-oil.

Purification over silicagel chromatography (prepacked 25 g silicagel column, Cyclohexane/AcOEt: 80/20 as eluent)
Rf (Cyclohexane/AcOEt: 80/20)=0.32
LCMS (RT): 4.61 min; MS (ES+) gave m/z: 304
$^1$H-NMR (CDCl$_3$), δ (ppm): 8.42-8.38 (m, 1H), 7.45-7.40 (t, 1H), 7.34-7.17 (m, 4H), 7.07-7.03 (m, 1H), 2.95 (s, 4H)

Example 239

2-Chlorophenyl 5-(pyridin-2-yl)pent-4-ynoate

239(A) 2-Chlorophenyl pent-4-ynoate

According to the protocol described in Example 235(B), the reaction between pent-4-ynoic acid (590 mg, 6.0 mmol) and 2-chlorophenol (771 mg, 6.0 mmol) afforded 1.09 g of 2-chlorophenyl pent-4-ynoate (Yield: 87%) as colorless-oil.

Purification over silicagel chromatography (prepacked 25 g silicagel column, Cyclohexane/AcOEt: 90/10 as eluent)
Rf (Cyclohexane/AcOEt: 90/10)=0.30
LCMS (RT): 4.41 min; MS (ES+) no MH+ detected 239(B) 2-Chlorophenyl
5-(pyridin-2-yl)pent-4-ynoate According to the protocol described in Example 237(B), the reaction between 2-chlorophenyl pent-4-ynoate (420 mg, 2.00 mmol) and 2-iodopyridine (410 mg, 2.00 mmol) afforded 208 mg of 2-chlorophenyl 5-(3-fluoropyridin-2-yl) pent-4-ynoate (Yield: 36%) as yellow-oil.

Purification over silicagel chromatography (prepacked 25 g silicagel column, Cyclohexane/AcOEt: form 90/10 to 80/20 as eluent) Rf (Cyclohexane/AcOEt: 80/20)=0.32

LCMS (RT): 4.21 min; MS (ES+) gave m/z: 286
$^1$H-NMR (CDCl$_3$), δ (ppm): 8.59-8.55 (d, 1H), 7.66-7.61 (t, 1H), 7.47-7.43 (d, 1H), 7.42-7.38 (d, 1H), 7.32-7.26 (m, 1H), 7.24-7.16 (m, 3H), 3.03-2.98 (m, 2H), 2.96-2.90 (m, 2H)

Example 240

2-Chlorophenyl
5-(2-methylthiazol-4-yl)pent-4-ynoate

240(A) 4-Bromo-2-methylthiazole

To a solution of 2,4-Dibromothiazole (1.00 g, 4.10 mmol) in anhydrous Et$_2$O (14 mL) was added dropwise at −78° C., 2.1 mL of nBuLi 2.5M in hexane (5.30 mmol). The mixture was stirred for 2 h at −78° C. Then a solution of methyl trifluoromethanesulfonate (673 mg, 4.10 mmol) in THF (2 mL) was added dropwise at −78° C., the resulting mixture was stirred 30 min at −78° C. The reaction mixture was warmed slowly to room temperature. The reaction was cooled with an ice bath at −10° C. and quenched with water. The two layers were separated; the aqueous layer was extracted with Ethylic ether. The combined organic layers were dried over Na$_2$SO$_4$, filtered and concentrated under medium pressure 700 mbar, bath 35° C., because the bromothiazole is very volatile. The product was purified by flash chromatography silice 40-60, pack 70 g, Pentane/Et$_2$O: 95/5 as eluent to afford 420 mg of 4-bromo-2-methylthiazole
(Yield: 57%) as a colorless oil.
Rf (Pentane/Et$_2$O: 95/5)=0.32
LCMS (RT): 3.29 min; MS (ES+) gave m/z: 179

240(B) 4-Iodo-2-methylthiazole

To a solution of 4-bromo-2-methylthiazole (418 mg, 2.35 mmol) in anhydrous Et$_2$O (3 mL) was added dropwise at −78° C., 0.14 mL of nBuLi 2.5M in hexane (2.80 mmol). The mixture was stirred for 1 h at −78° C. Then a solution of diiodoethane (1.30 g, 4.70 mmol) in 0.4 mL of Et$_2$O was added dropwise at −78° C., and the resulting mixture was stirred 30 min at −78° C. The reaction was then warmed slowly to room temperature over a period of 2 h. The reaction was cooled with a ice bath at −10° C. was quenched with water. The two layers were separated and the aqueous layer was extracted with Et$_2$O. The combined organic layers were dried over Na$_2$SO$_4$, filtered and concentrated under medium pressure.

Purification over silicagel chromatography (prepacked 10 g silicagel column, Pentane/Et$_2$O: 95/5 as eluent) to afford 240 mg of 4-iodo-2-methylthiazole (Yield: 45%) as a colorless oil.
LCMS (RT): 3.49 min; MS (ES+) gave m/z: 225

240(C) 2-Chlorophenyl 5-(2-methylthiazol-4-yl)
pent-4-ynoate

According to the protocol described in Example 237(B), the reaction between 2-chlorophenyl pent-4-ynoate (compound 160(A), 290 mg, 1.40 mmol) and 4-iodo-2-methylthiazole (315 mg, 1.40 mmol) afforded 145 mg of 2-chlorophenyl 5-(2-methylthiazol-4-yl)pent-4-ynoate (Yield: 34%) as yellow-oil.

Purification over silicagel chromatography (prepacked 25 g silicagel column, Cyclohexane/AcOEt: form 90/10 to 80/20 as eluent)
Rf (Cyclohexane/AcOEt: 80/20)=0.32
LCMS (RT): 4.61 min; MS (ES+) gave m/z: 306

¹H-NMR (CDCl₃), δ (ppm): 7.47-7.43 (m, 1H), 7.32-7.26 (m, 1H), 7.23-7.15 (m, 3H), 3.00-2.95 (m, 2H), 2.92-2.87 (m, 2H)

Example 241

2-(4-(6-(Fluoromethyl)pyridin-2-yl)but-3-ynyl)benzo[d]thiazole

The title compound was prepared in accordance with the general method of Example 190(F), from 2-bromo-6-(fluoromethyl)pyridine (266 mg, 1.40 mmol) and 2-(but-3-ynyl)benzo[d]thiazole (compound 35(A), 260 mg, 1.40 mmol). The crude residue was purified over silicagel chromatography (prepacked 25 g silicagel column, Cyclohexane/AcOEt: from 100/0 to 80/20 as eluent) to afford 160 mg of 2-(4-(6-(fluoromethyl)pyridin-2-yl)but-3-ynyl)benzo[d]thiazole (Yield: 38%) as a beige powder (Mp=74-76° C.).

LCMS (RT): 4.38 min; MS (ES+) gave m/z: 297
Rf (Cyclohexane/AcOEt: 80/20)=0.30
¹H-NMR (CDCl₃), δ (ppm): 8.03-7.99 (d, 1H), 7.89-7.85 (d, 1H), 7.73-7.67 (t, 1H), 7.51-7.45 (t, 1H), 7.42-7.32 (m, 3H), 5.52-5.43 (d, 2H), 3.49-3.44 (t, 2H), 3.09-3.04 (t, 2H)

Example 242

2-(5-(Pyridin-2-yl)pent-4-ynyl)isoindoline-1,3-dione

242(A) 5-(Pyridin-2-yl)pent-4-yn-1-ol

In a dry microwave tube were placed in suspension, CuI (57 mg, 0.30 mmol) and triethylamine (10.10 ml, 72 mmol). Then under nitrogen, were added the 2-bromopyridine (948 mg, 6.0 mmol), PdCl₂(PPh₃)₂ (211 mg, 0.30 mmol) and triphenyl phosphine polymerbound (310 mg, 1.20 mmol). The suspension was stirred at room temperature for 5 minutes, finally pent-4-yn-1-ol (500 mg, 6.0 mmol) in DMF (8.60 mL) was added, and the reaction mixture was stirred at room temperature for 30 min.

The reaction mixture was stirred and heated with micro wave for 20 min at 120° C.

Triethylamine was concentrated under reduce pressure; the residue was dissolved in DCM. The organic layer was washed with NaHCO₃, H₂O and saturated brine. The organic layer was dried over Na₂SO₄, filtered and concentrated.

Purification by flash chromatography pack 50 g, silice 40-60, DCM/AcOEt: from 100/0 to 50/50 as eluent to afford 702 mg of 5-(pyridin-2-yl)pent-4-yn-1-ol (Yield: 72%) as a colorless oil.

LCMS (RT): 1.94 min; MS (ES+) gave m/z: 162
Rf (DCM/AcOEt: 50/50)=0.30

242(B) 2-(5-Bromopent-1-ynyl)pyridine

Bromine (3.45 g, 21.4 mmol) was added to a solution of triphenylphosphine (8.30 g, 30.7 mmol) in DCM (40 mL) cooled to −5° C. The flask was protected from the light and a white precipitate was formed after 5 min. A solution of the 5-(pyridin-2-yl)pent-4-yn-1-ol (3 g, 18.6 mmol) in DCM (10 mL) was added at a rate to raise the reaction temperature to 5° C. at the end of the addition. The reaction solution was cooled to −10° C. and stirred for 5 h. The colour turned dark green. LCMS shown that the reaction was not completed. As no precipitate appeared, ¾ of the solvent were removed under low pressure and the mixture cooled down to −10° C., as no precipitate appeared the mixture was concentrated to remove ¾ of the solvent and then cooled down overnight in the fridge. No precipitate appeared; the reaction was then taken in saturated NaHCO₃ and extracted with DCM. The organic layer was washed with brine, dried over MgSO₄, filtrated and concentrated.

The crude was purified by flash pack chromatography in DCM/MeOH 99.5:0.5 to afford 1.20 g of 2-(5-bromopent-1-ynyl)pyridine contaminated with triphenylphosphine. The compound was used in the next step with no further purification.

242(C) 2-(5-(Pyridin-2-yl)pent-4-ynyl)isoindoline-1,3-dione 2-(5-bromopent-1-ynyl)pyridine (118 mg, 0.525 mmol), isoindoline-1,3-dione (74 mg, 0.5 mmol) and potassium carbonate (140 mg, 1 mmol) were dissolved in acetone (1 mL). The resulting mixture was heated with microwave at 150° C. for 15 min. The reaction was quenched with water, then acetone was evaporated under reduced pressure. The aqueous layer was extracted with DCM, and the organic layer was washed one time with saturated brine, dried over MgSO₄, filtrated and concentrated.

Purification by flash chromatography pack 15 g silice 40-60, Cyclohexane/AcOEt: 50/50 to afford 30 mg of 2-(5-(pyridin-2-yl)pent-4-ynyl)isoindoline-1,3-dione (Yield: 20%) as a beige powder (Mp=127-129° C.).

LCMS (RT): 3.46 min; MS (ES+) gave m/z: 291
Rf (Cyclohexane/AcOEt: 50/50)=0.35
¹H-NMR (CDCl₃), δ (ppm): 8.54-8.49 (d, 1H), 7.86-7.83 (m, 2H), 7.72-7.67 (m, 2H), 7.62-7.56 (t, 1H), 7.33-7.29 (d, 1H), 7.19-7.14 (m, 1H), 3.90-3.84 (t, 2H), 2.57-2.52 (t, 2H), 2.10-2.02 (m, 2H)

Example 243

2-(6-(Pyridin-2-yl)hex-5-ynyl)phthalazin-1(2H)-one

243(A) 6-(Pyridin-2-yl)hex-5-yn-1-ol

In a dry microwave tube were placed in suspension CuI (76 mg, 0.4 mmol) and triethylamine (14.60 mL, 104 mmol). Then under nitrogen atmosphere, were added the 2-bromopyridine (1.26 g, 8.00 mmol), PdCl₂(PPh₃)₂ (281 mg, 0.40 mmol) and triphenyl phosphine polymerbound (530 mg, 1.60 mmol). The suspension was stirred at room temperature for 5 minutes, finally the hex-5-yn-1-ol (790 mg, 8.0 mmol) in 11.5 mL of DMF was added, and the reaction mixture is stirred at room temperature for 30 min.

The reaction mixture was stirred and heated under micro wave irradiation for 20 min at 120° C. After filtering to remove triphenyl phosphine polymerbound, the triethylamine was concentrated under reduced pressure and the residue was dissolved in DCM. The organic layer was washed with saturated NaHCO₃, H₂O and saturated brine. The organic layer was dried over Na₂SO₄, filtered and concentrated.

Purification over silicagel chromatography (prepacked 50 g silicagel column, DCM/AcOEt: from 100/0 to 50/50 as eluent) to afford 1.32 g of 6-(pyridin-2-yl)hex-5-yn-1-ol (Yield: 94%) as a colorless oil.

Rf (DCM/AcOEt: 50/50)=0.30
LCMS (RT): 2.09 min; MS (ES+) gave m/z: 176

243(B) 2-(6-Bromohex-1-ynyl)pyridine

The title compound was prepared in accordance with the general method of Example 242(A), from 6-(pyridin-2-yl)

hex-5-yn-1-ol (1.30 g, 7.50 mmol) to afford 138 mg of 2-(6-bromohex-1-ynyl)pyridine (Yield: 8%) as a colorless oil.

The crude residue was purified over silicagel chromatography (prepacked 70 g silicagel column, Cyclohexane/AcOEt: 50/50 as eluent).

LCMS (RT): 3.94 min; MS (ES+) gave m/z: 239
Rf (Cyclohexane/AcOEt: 50/50)=0.40

243(C) 2-(6-(Pyridin-2-yl)hex-5-ynyl)phthalazin-1(2H)-one

The title compound was prepared in accordance with the general method of Example 242(B), from 2-(6-bromohex-1-ynyl)pyridine (138 mg, 0.578 mmol) and phthalazin-1(2H)-one (80 mg, 0.55 mmol).

The crude residue was purified over silicagel chromatography (prepacked 25 g silicagel column, DCM/MeOH: 98/2 as eluent) to afford 35 mg of 2-(6-(pyridin-2-yl)hex-5-ynyl)phthalazin-1(2H)-one (Yield: 21%) as a yellow oil.

LCMS (RT): 3.48 min; MS (ES+) gave m/z: 304
Rf (DCM/MeOH: 98/2)=0.30
$^1$H-NMR (CDCl$_3$), δ (ppm): 8.55-8.52 (d, 1H), 8.47-8.42 (d, 1H), 8.18 (s, 1H), 7.84-7.75 (m, 2H), 7.72-7.68 (d, 1H), 7.63-7.58 (t, 1H), 7.39-7.35 (d, 1H), 7.20-7.15 (m, 1H), 4.32-4.29 (t, 2H), 2.54-2.51 (t, 2H), 2.07-2.04 (m, 2H), 1.75-1.72 (m, 2H)

Example 244

N-(4-Chlorophenyl)-5-(pyridin-2-yl)pent-4-ynamide

244(A) N-(4-Chlorophenyl)pent-4-ynamide

According to the protocol described in Example 12(A), the conversion of 4-chlorobenzenamine (650 mg, 5.10 mmol) afforded 820 mg of N-(4-chlorophenyl)pent-4-ynamide (Yield: 77%) as brownish solid.

Purification over silicagel chromatography (prepacked 25 g silicagel column, DCM 100% as eluent)
Rf (100% DCM)=0.35
$^1$NMR (CDCl$_3$), δ (ppm): 7.60 (s, 1H), 7.40-6.90 (m, 4H), 2.60-2.40 (m, 4H), 1.95 (s, 1H)

244(B) tert-Butyl 4-chlorophenyl(pent-4-ynoyl)carbamate

The title compound was prepared in accordance with the general method of Example 34(B), from N-(4-chlorophenyl)pent-4-ynamide (820 mg, 3.95 mmol) and (BOC)$_2$O (1.03 g, 4.74 mmol). The crude residue was purified over silicagel chromatography (prepacked 25 g silicagel column, DCM 100% as eluent) to afford 1.13 g of tert-butyl 4-chlorophenyl(pent-4-ynoyl)carbamate as a colorless oil (Yield: 94%).

Rf (100% DCM)=0.63
LCMS (RT): 4.90 min; MS (ES+) gave m/z: MH+-Boc: 208

244(C) tert-Butyl 4-chlorophenyl(5-(pyridin-2-yl)pent-4-ynoyl)carbamate

To a solution of CuI (7.7 mg, 0.041 mmol) in triethylamine (2.28 mL) were added 2-bromopyridine (129 mg, 0.82 mmol) and (PPh$_3$)$_2$PdCl$_2$ (28.7 mg, 0.041 mmol). The reaction mixture was cooled to 0° C. and tert-butyl 4-chlorophenyl(pent-4-ynoyl)carbamate (250 mg, 0.82 mmol) was added. The reaction mixture was allowed to warm to room temperature and then heated under reflux for 3 h. at 70° C. Triethylamine was evaporated, water was added and the aqueous phase was extracted twice with DCM. The organic phase was dried over Na$_2$SO$_4$, filtered and concentrated. The crude residue was purified by flash chromatography (prepacked 25 g silicagel column, Cyclohexane/AcOEt: 70/30 as eluent) to afford 172 mg (Yield: 55%) of tert-butyl 4-chlorophenyl(5-(pyridin-2-yl)pent-4-ynoyl)carbamate as a yellow oil.

Rf (Cyclohexane/AcOEt: 70/30)=0.18
LCMS (RT): 4.83 min; MS (ES+) gave m/z: 385

244(D) N-(4-Chlorophenyl)-5-(pyridin-2-yl)pent-4-ynamide

According to the protocol described in Example 34(D), the conversion of tert-butyl 4-chlorophenyl(5-(pyridin-2-yl)pent-4-ynoyl)carbamate (172 mg, 0.45 mmol) afford 67 mg of N-(4-chlorophenyl)-5-(pyridin-2-yl)pent-4-ynamide (Yield: 53%) as white powder (Mp=110-111° C.).

The crude product was triturated twice with a mixture containing pentane/isopropyl ether 50/50, to obtain the desired compound as a white powder.

LCMS (RT): 3.63 min; MS (ES+) gave m/z: 285
$^1$NMR (CDCl$_3$), δ (ppm): 8.55 (s, 1H), 7.70-7.50 (m, 3H), 7.40-7.20 (t, 2H), 7.18-7.05 (m, 2H), 7.00-6.90 (m, 1H), 2.85-2.75 (t, 2H), 2.68-2.58 (t, 2H)

Example 245

N-(3-Chlorophenyl)-5-(pyridin-2-yl)pent-4-ynamide

245(A) N-(3-Chlorophenyl)pent-4-ynamide

According to the protocol described in Example 12(A), the conversion of 3-chlorobenzenamine (650 mg, 5.10 mmol) afforded 630 mg of N-(3-chlorophenyl)pent-4-ynamide (Yield: 59%) as brownish solid.

Purification over silicagel chromatography (prepacked 25 g silicagel column, DCM 100% as eluent)
Rf (100% DCM)=0.26

245(B) tert-Butyl 3-chlorophenyl(pent-4-ynoyl)carbamate

The title compound was prepared in accordance with the general method of Example 34(B), from N-(3-chlorophenyl)pent-4-ynamide (630 mg, 3.03 mmol) and (BOC)$_2$O (795 mg, 3.64 mmol). The crude residue was purified over silicagel chromatography (prepacked 25 g silicagel column 100% DCM as eluent) to afford 824 mg of tert-butyl 3-chlorophenyl(pent-4-ynoyl)carbamate as a colorless oil (Yield: 88%).

LCMS (RT): 4.93 min; MS (ES+) gave m/z: MH+-Boc: 208
Rf (100% DCM)=0.57

245(C) tert-Butyl 3-chlorophenyl(5-(pyridin-2-yl)pent-4-ynoyl)carbamate

The title compound was prepared in accordance with the general method of Example 244(C), from tert-butyl 3-chlorophenyl(pent-4-ynoyl)carbamate (250 mg, 0.82 mmol) and 2-bromopyridine (129 mg, 0.82 mmol). The crude residue was purified over silicagel chromatography (prepacked 25 g silicagel column cyclohexane/AcOEt: 70/30 as eluent) to afford 226 mg of tert-butyl 3-chlorophenyl(pent-4-ynoyl)carbamate as a brown oil (Yield: 72%).

LCMS (RT): 4.87 min; MS (ES+) gave m/z: 385
Rf (Cyclohexane/AcOet: 70/30)=0.18

245(D) N-(3-Chlorophenyl)-5-(pyridin-2-yl)pent-4-ynamide

According to the protocol described in Example 34(D), the conversion of tert-butyl 3-chlorophenyl(5-(pyridin-2-yl)pent-4-ynoyl)carbamate (226 mg, 0.58 mmol) afford 140 mg of N-(3-chlorophenyl)-5-(pyridin-2-yl)pent-4-ynamide (Yield: 84%) as beige powder (Mp=167.8-168.8° C.).

The crude product was triturated twice with a mixture containing pentane/isopropyl ether 50/50, to obtain the desired compound as a beige powder.

LCMS (RT): 3.58 min; MS (ES+) gave m/z: 285
$^1$NMR (CDCl$_3$), δ (ppm): 8.50 (d, 1H), 7.70-7.10 (m, 8H), 2.85-2.72 (t, 2H), 2.65-2.55 (t, 2H)

Example 246

N-(2,4-Difluorophenyl)-5-(pyridin-2-yl)pent-4-ynamide

246(A) N-(2,4-Difluorophenyl)pent-4-ynamide

According to the protocol described in Example 12(A), the conversion of 2,4-difluorobenzenamine (658 mg, 5.10 mmol) afforded 630 mg of N-(2,4-difluorophenyl)pent-4-ynamide (Yield: 59%) as brownish solid.

Purification over silicagel chromatography (prepacked 25 g silicagel column, DCM 100% as eluent)
Rf (100% DCM)=0.35
$^1$NMR (CDCl$_3$), δ (ppm): 8.30-8.10 (m, 1H), 7.40 (s, 1H), 6.90-6.70 (m, 2H), 2.50 (s, 4H), 1.98 (s, 1H).

246(B) tert-Butyl 2,4-difluorophenyl(pent-4-ynoyl)carbamate

The title compound was prepared in accordance with the general method of Example 34(B), from N-(2,4-difluorophenyl)pent-4-ynamide (630 mg, 3.01 mmol) and (BOC)$_2$O (789 mg, 3.61 mmol). The crude residue was purified over silicagel chromatography (prepacked 25 g silicagel column, 100% DCM as eluent) to afford 924 mg of tert-butyl 2,4-difluorophenyl(pent-4-ynoyl)carbamate as a colorless oil (Yield: 99%).

LCMS (RT): 4.82 min; MS (ES+) gave m/z: MH+-Boc: 210)
Rf (100% DCM)=0.63

246(C) tert-Butyl 2,4-difluorophenyl(5-(pyridin-2-yl)pent-4-ynoyl)carbamate The title compound was prepared in accordance with the general method of Example 244(C), from tert-butyl 2,4-difluorophenyl(pent-4-ynoyl)carbamate (250 mg, 0.82 mmol) and 2-bromopyridine (129 mg, 0.82 mmol). The crude residue was purified over silicagel chromatography (prepacked 25 g silicagel column cyclohexane/AcOEt: 70/30 as eluent) to afford 193 mg of tert-butyl 2,4-difluorophenyl(5-(pyridin-2-yl)pent-4-ynoyl)carbamate as a brown oil (Yield: 61%).

LCMS (RT): 4.72 min; MS (ES+) gave m/z: 387
Rf (Cyclohexane/AcOet: 70/30)=0.18

246(D) N-(2,4-Difluorophenyl)-5-(pyridin-2-yl)pent-4-ynamide

According to the protocol described in Example 34(D), the conversion of tert-butyl 2,4-difluorophenyl(5-(pyridin-2-yl)pent-4-ynoyl)carbamate (193 mg, 0.50 mmol) afford 123 mg of N-(2,4-difluorophenyl)-5-(pyridin-2-yl)pent-4-ynamide (yield: 86%) a beige powder (Mp=132-133.2° C.).

The crude product was triturated twice with a mixture containing pentane/isopropyl ether 50/50, to obtain the desired compound as a beige powder.

LCMS (RT): 3.20 min; MS (ES+) gave m/z: 287.
$^1$NMR (CDCl$_3$), δ (ppm): 8.50 (d, 1H), 8.30-8.10 (m. 1H), 7.70-7.10 (m, 4H), 6.90-6.70 (m, 2H), 2.90-2.80 (t, 2H), 2.70-2.60 (t, 2H).

Example 247

2-Chloro-N-(4-(6-(fluoromethyl)pyridin-2-yl)but-3-ynyl)benzamide

The title compound was prepared in accordance with the general method of Example 184, from 4-(6-(fluoromethyl)pyridin-2-yl)but-3-yn-1-amine (39 mg, 0.22 mmol, Example 189(D)) and 2-chlorobenzoyl chloride (50 mg, 0.28 mmol). The crude residue was purified by flash chromatography (cyclohexane/AcOEt 7:3) to yield 13.5 mg (43 μmol, 19%) of 2-chloro-N-(4-(6-(fluoromethyl)pyridin-2-yl)but-3-ynyl)benzamide as a colorless oil.

LCMS (RT): 3.52 min; MS (ES+) gave m/z: 317.1, 319.1.

Example 248

2-Chloro-N-(4-(6-(fluoromethyl)pyridin-2-yl)but-3-ynyl)benzenesulfonamide

The title compound was prepared in accordance with the general method of Example 184, from 4-(6-(fluoromethyl)pyridin-2-yl)but-3-yn-1-amine (39 mg, 0.22 mmol, Example 189(D)) and 2-chlorobenzenesulfonyl chloride (60 mg, 0.28 mmol). The crude residue was purified by flash chromatography (cyclohexane/AcOEt 7:3) to yield 14.4 mg (41 μmol, 19%) of 2-chloro-N-(4-(6-(fluoromethyl)pyridin-2-yl)but-3-ynyl)benzenesulfonamide as an orange oil.

LCMS (RT): 3.92 min; MS (ES+) gave m/z: 353.1, 355.1.

Example 249

2-(4-(4-(4-Fluorophenyl)-2H-1,2,3-triazol-2-yl)but-1-ynyl)pyridine

The title compound was prepared in accordance with the general method of Example 1, from 2-(but-3-ynyl)-4-(4-fluorophenyl)-2H-1,2,3-triazole (150 mg, 0.70 mmol, Example 254(B)) and 2-bromopyridine (122 mg, 0.77 mmol). The crude residue was purified by flash chromatography (DCM/MeOH 99:1) to yield 84 mg (0.29 mmol, 41%) of 2-(4-(4-(4-fluorophenyl)-2H-1,2,3-triazol-2-yl)but-1-ynyl)pyridine as a yellow solid (M.P.=83.5-84.5° C.).

LCMS (RT): 4.07 min; MS (ES+) gave m/z: 293.1.
Rf (DCM/MeOH 98:2)=0.2.
$^1$H-NMR (CDCl$_3$), δ (ppm): 3.16 (t, J=7.2, 2H), 4.71 (t, J=7.2, 2H), 7.08-7.16 (2H), 7.21 (ddd, J=1.2, 4.8 and 7.8, 1H), 7.35 (d, J=7.8, 1H), 7.58-7.65 (m, 1H), 7.73-7.78 (2H), 7.81 (s, 1H), 8.55 (d, J=4.5, 1H).

Example 250

2-(Fluoromethyl)-6-(4-(4-(4-fluorophenyl)-2H-1,2,3-triazol-2-yl)but-1-ynyl)pyridine The title compound was prepared in accordance with the general method of Example 1, from 2-(but-3-ynyl)-4-(4-fluorophenyl)-2H-1,2,3-triazole (150 mg, 0.70 mmol, Example 254(B)) and 2-bromo-6-(fluoromethyl)pyridine (146 mg, 0.77 mmol, Example 190(E)). The crude residue was purified by flash chromatography (DCM/MeOH 99.5:0.5 to 99:1) to yield 101 mg (0.31 mmol, 45%) of 2-(fluoromethyl)-6-(4-(4-(4-fluorophenyl)-2H-1,2,3-triazol-2-yl)but-1-ynyl)pyridine as a yellow solid (M.P.=84-86° C.).

LCMS (RT): 4.44 min; MS (ES+) gave m/z: 325.2.
Rf (DCM/MeOH 98:2)=0.3.
$^1$H-NMR (CDCl$_3$), δ (ppm): 3.16 (t, J=7.5, 2H), 4.71 (t, J=7.5, 2H), 5.36-5.54 (m, 2H), 7.08-7.16 (2H), 7.31 (d, J=7.8, 1H), 7.40 (d, J=7.8, 1H), 7.66-7.72 (m, 1H), 7.73-7.79 (2H), 7.81 (s, 1H).

Example 251

2-Chloro-N-(4-(pyridin-2-yl)but-3-ynyl)benzene-sulfonamide

251(A) 2-(4-(Pyridin-2-yl)but-3-ynyl)isoindoline-1,3-dione

The title compound was prepared in accordance with the general method of Example 1, from 2-iodopyridine (453 mg, 2.21 mmol) and 2-(but-3-ynyl)isoindoline-1,3-dione (400 mg, 2.01 mmol, Example 189(B)). The crude residue was purified by flash chromatography (cyclohexane/AcOEt 70:30) to yield 250 mg (0.90 mmol, 45%) of 2-(4-(pyridin-2-yl)but-3-ynyl)isoindoline-1,3-dione as.

LCMS (RT): 3.43 min; MS (ES+) gave m/z: 277.1.

251(B) 4-(Pyridin-2-yl)but-3-yn-1-amine

The title compound was prepared in accordance with the general method of Example 189(D), from 2-(4-(pyridin-2-yl)but-3-ynyl)isoindoline-1,3-dione (250 mg, 0.90 mmol) to yield 32 mg (0.22 mmol, 24%) of 4-(pyridin-2-yl)but-3-yn-1-amine as a white solid.

251(C) 2-Chloro-N-(4-(pyridin-2-yl)but-3-ynyl)benzenesulfonamide

The title compound was prepared in accordance with the general method of Example 184, from 4-(pyridin-2-yl)but-3-yn-1-amine (16 mg, 0.11 mmol) and 2-chlorobenzene-1-sulfonyl chloride (30 mg, 0.14 mmol). The crude residue was purified by flash chromatography (cyclohexane/AcOEt 7:3) to yield 11.2 mg (35 mmol, 32%) of 2-chloro-N-(4-(pyridin-2-yl)but-3-ynyl)benzenesulfonamide as a brown oil.

LCMS (RT): 3.48 min; MS (ES+) gave m/z: 321.1, 323.1.

Example 252

5-(6-(Fluoromethyl)pyridin-2-yl)-N-(4-fluoro-2-methyl-phenyl)pent-4-ynamide

252(A) [5-(6-Fluoromethyl-pyridin-2-yl)-pent-4-ynoyl]-(4-fluoro-2-methyl-phenyl)-carbamic Acid tert-butyl Ester The title compound was prepared in accordance with the general method of Example 1, from 2-bromo-6-(fluoromethyl)pyridine (150 mg, 0.79 mmol, Example 190(E)) and (4-fluoro-2-methyl-phenyl)-pent-4-ynoyl-carbamic acid tert-butyl ester (241 mg, 0.79 mmol, 188(B)). Reaction time: 3 hours. The crude residue was purified by flash chromatography (cyclohexane/AcOEt 4:1) to yield 260 mg (0.63 mmol, 79%) of [5-(6-fluoromethyl-pyridin-2-yl)-pent-4-ynoyl]-(4-fluoro-2-methyl-phenyl)-carbamic acid tert-butyl ester as a white solid.

Rf (cyclohexane/AcOEt 4:1)=0.2.

252(B) 5-(6-(Fluoromethyl)pyridin-2-yl)-N-(4-fluoro-2-methyl-phenyl)pent-4-ynamide The title compound was prepared in accordance with the general method of Example 34(D), from [5-(6-fluoromethyl-pyridin-2-yl)-pent-4-ynoyl]-(4-fluoro-2-methyl-phenyl)-carbamic acid tert-butyl ester (260 mg, 0.63 mmol). After the work-up, the crude residue was washed with diisopropyl ether to yield 190 mg (0.60 mmol, 97%) of 5-(6-(fluoromethyl)pyridin-2-yl)-N-(4-fluoro-2-methyl-phenyl)pent-4-ynamide as a white powder (M.P.=122-125° C.).

LCMS (RT): 3.08 min; MS (ES+) gave m/z: 315.1.
$^1$NMR (CDCl$_3$), δ (ppm): 2.23 (s, 3H), 2.72 (t, J=7.5, 2H), 2.90 (t, J=7.5, 2H), 5.36-5.54 (m, 2H), 6.84-6.94 (2H), 7.32 (d, J=7.5, 1H), 7.40 (d, J=7.5, 1H), 7.60-7.79 (2H).

Example 253

5-(4-Fluoro-phenyl)-1-(4-pyridin-2-yl-but-3-ynyl)-1H-pyridin-2-one

253(A) 5-Bromo-1-(4-pyridin-2-yl-but-3-ynyl)-1H-pyridin-2-one

The title compound was prepared in accordance with the general method of Example 109(D), from 4-(pyridin-2-yl)but-3-yn-1-ol (700 mg, 4.76 mmol, Example 3(A)) and 5-bromo-1H-pyridin-2-one (870 mg, 5.00 mmol). The crude residue was purified by flash chromatography (cyclohexane/AcOEt 9:1) to yield 334 mg (1.10 mmol, 23%) of 5-bromo-1-(4-pyridin-2-yl-but-3-ynyl)-1H-pyridin-2-one.

253(B) 5-(4-Fluoro-phenyl)-1-(4-pyridin-2-yl-but-3-ynyl)-1H-pyridin-2-one

The title compound was prepared in accordance with the general method of Example 83, from 5-bromo-1-(4-pyridin-2-yl-but-3-ynyl)-1H-pyridin-2-one (50 mg, 0.16 mmol) and 4-fluorophenylboronic acid (35 mg, 0.25 mmol). The crude residue was purified by flash chromatography (cyclohexane/AcOEt 9:1) to yield 18 mg (57 µmol, 34%) of 5-(4-fluoro-phenyl)-1-(4-pyridin-2-yl-but-3-ynyl)-1H-pyridin-2-one.

LCMS (RT): 4.66 min; MS (ES+) gave m/z: 319.2.

Example 254

2-(Fluoromethyl)-6-(4-(4-(4-fluorophenyl)-1H-1,2,3-triazol-1-yl)but-1-ynyl)pyridine 254(A) 4-(4-Fluorophenyl)-2H-1,2,3-triazole The title compound was prepared in accordance with the general method of Example 179(A), from (E)-1-fluoro-4-(2-nitrovinyl)benzene (2.00 g, 12.0 mmol). The crude residue was purified by flash chromatography (cyclohexane/AcOEt 4:1) to yield 1.08 g (6.62 mmol, 55%) of 4-(4-fluorophenyl)-2H-1,2,3-triazole as an orange solid.

Rf (cyclohexane/AcOEt 4:1)=0.1.

254(B) 1-(But-3-ynyl)-4-(4-fluorophenyl)-1H-1,2,3-triazole and 2-(but-3-ynyl)-4-(4-fluorophenyl)-2H-1,2,3-triazole The title compounds were prepared in accordance with the general method of Example 109(D), from 4-(4-fluorophenyl)-2H-1,2,3-triazole (1.08 g, 6.62 mmol). The crude residue was purified by flash chromatography (cyclohexane/AcOEt 95:5 to 80:20) to yield 200 mg (0.92 mmol, 14%) of 1-(but-3-ynyl)-4-(4-fluorophenyl)-1H-1,2,3-triazole as a yellow solid and 300 mg (1.40 mmol, 21%) of 2-(but-3-ynyl)-4-(4-fluorophenyl)-2H-,2,3-triazole as a orange solid.

1-(But-3-ynyl)-4-(4-fluorophenyl)-1H-1,2,3-triazole

LCMS (RT): 3.57 min; MS (ES+) gave m/z: 216.1.
Rf (cyclohexane/AcOEt 4:1)=0.1.

2-(But-3-ynyl)-4-(4-fluorophenyl)-2H-,2,3-triazole

LCMS (RT): 4.20 min; MS (ES+) gave m/z: 216.1.
Rf (cyclohexane/AcOEt 4:1)=0.5.

254(C) 2-(Fluoromethyl)-6-(4-(4-(4-fluorophenyl)-1H-1,2,3-triazol-1-yl)but-1-ynyl)pyridine The title compound was prepared in accordance with the general method of Example 1, from 1-(but-3-ynyl)-4-(4-fluorophenyl)-1H-1,2,3-triazole (100 mg, 0.47 mmol) and 2-bromo-6-(fluoromethyl)pyridine (97 mg, 0.51 mmol, Example 190(E)). Reaction time: 2 hours. The crude residue was purified by flash chromatography (DCM/MeOH 98.5:1.5) to yield 32 mg (0.10 mmol, 21%) of 2-(fluoromethyl)-6-(4-(4-(4-fluorophenyl)-1H-1,2,3-triazol-1-yl)but-1-ynyl)pyridine as a yellow solid (M.P.=100-103° C.).
LCMS (RT): 3.90 min; MS (ES+) gave m/z: 325.1.
Rf (DCM/MeOH 98:2)=0.2.
$^1$H-NMR (CDCl$_3$), δ (ppm): 3.10 (t, J=6.6, 2H), 4.67 (t, J=6.6, 2H), 5.37-5.55 (m, 2H), 7.08-7.15 (2H), 7.30 (d, J=8.1, 1H), 7.42 (d, J=8.1, 1H), 7.67-7.74 (m, 1H), 7.77-7.83 (2H), 7.93 (s, 1H).

Example 255

8-Chloro-2-(4-(pyridin-2-yl)but-3-ynyl)-imidazo[1,2-a]pyridine

255(A) 8-Chloro-2-(4-(trimethylsilyl)but-3-ynyl)-imidazo[1,2-a]pyridine

The title compound was prepared in accordance with the general method of Example 223(D), from 1-bromo-6-(trimethylsilyl)hex-5-yn-2-one (4.96 g, 20.1 mmol, Example 223 (C)) and 3-chloropyridin-2-amine (1.29 g, 10.0 mmol). The crude residue was purified by flash chromatography (cyclohexane/AcOEt 4:1) to yield 2.00 g (7.22 mmol, 72%) of 8-chloro-2-(4-(trimethylsilyl)but-3-ynyl)-imidazo[1,2-a]pyridine as a brown solid.
$^1$H-NMR (CDCl$_3$), δ (ppm): 0.14 (s, 12H), 2.66 (t, J=6.9, 2H), 3.06 (t, J=7.2, 2H), 6.69 (t, J=7.2, 1H), 7.21 (d, J=7.5, 1H), 7.53 (s, 1H), 7.99 (d, J=6.6, 1H).

255(B) 2-(But-3-ynyl)-8-chloro-imidazo[1,2-a]pyridine

The title compound was prepared in accordance with the general method of Example 108(B), from 8-chloro-2-(4-(trimethylsilyl)but-3-ynyl)-imidazo[1,2-a]pyridine (2.00 g, 7.22 mmol). The crude residue was taken in Et$_2$O, filtered and concentrated to yield 1.09 mg (5.31 mmol, 74%) of 2-(but-3-ynyl)-8-chloro-imidazo[1,2-a]pyridine as a yellow solid.

$^1$H-NMR (CDCl$_3$), δ (ppm): 1.97 (t, J=2.7, 1H), 2.66 (t, J=7.2, 2H), 3.07 (t, J=6.9, 2H), 6.69 (t, J=6.9, 1H), 7.21 (d, J=7.2, 1H), 7.54 (s, 1H), 8.0 (d, J=6.9, 1H).

255(C) 8-Chloro-2-(4-(pyridin-2-yl)but-3-ynyl)-imidazo[1,2-a]pyridine

The title compound was prepared in accordance with the general method of Example 1, from 2-(but-3-ynyl)-8-chloro-imidazo[1,2-a]pyridine (500 mg, 2.44 mmol) and 2-bromopyridine (405 mg, 2.57 mmol). The crude residue was purified by flash chromatography (DCM/MeOH 99:1 to 98:2) to yield 293 mg (1.04 mmol, 43%) of 8-chloro-2-(4-(pyridin-2-yl)but-3-ynyl)H-imidazo[1,2-a]pyridine as a white solid (M.P.=106-107° C.).
LCMS (RT): 2.22 min; MS (ES+) gave m/z: 282.1, 284.0.
Rf (DCM/MeOH 98:2)=0.1.
$^1$H-NMR (CDCl$_3$), δ (ppm): 2.92 (t, J=7.2, 2H), 3.18 (t, J=7.2, 2H), 6.65-6.71 (m, 1H), 7.15-7.24 (2H), 7.35 (d, J=7.8, 1H), 7.57-7.63 (2H), 8.01 (d, J=7.2, 1H), 8.52-8.56 (m, 1H).

Example 256

8-Chloro-2-(4-(6-(fluoromethyl)pyridin-2-yl)but-3-ynyl)-imidazo[1,2-a]pyridine

The title compound was prepared in accordance with the general method of Example 1, from 2-(but-3-ynyl)-8-chloro-imidazo[1,2-a]pyridine (500 mg, 2.44 mmol, Example 255 (B)) and 2-bromo-6-(fluoromethyl)pyridine (487 mg, 2.57 mmol, Example 190(E)). The crude residue was purified by flash chromatography (DCM/MeOH 99:1) to yield 420 mg (1.34 mmol, 55%) of 8-chloro-2-(4-(6-(fluoromethyl)pyridin-2-yl)but-3-ynyl)-imidazo[1,2-a]pyridine as a slightly yellow solid (M.P.=73-74.5° C.).
LCMS (RT): 2.57 min; MS (ES+) gave m/z: 314.1, 316.1.
Rf (DCM/MeOH 98:2)=0.2.
$^1$H-NMR (CDCl$_3$), δ (ppm): 2.92 (t, J=7.2, 2H), 3.18 (t, J=7.2, 2H), 5.36-5.55 (m, 2H), 6.66-6.73 (m, 1H), 7.22 (dd, J=0.9 and 7.8, 1H), 7.32 (d, J=8.1, 1H), 7.37 (d, J=7.8, 1H), 7.57 (s, 1H), 7.65-7.72 (m, 1H), 8.00 (dd, J=0.9 and 6.6, 1H).

Example 257

2-(4-(4-(4-Fluorophenyl)-5-methyl-2H-1,2,3-triazol-2-yl)but-1-ynyl)pyridine

257(A) 4-(4-Fluorophenyl)-5-methyl-2H-1,2,3-triazole

The title compound was prepared in accordance with the general method of Example 179(A), from (E)-1-fluoro-4-(2-nitroprop-1-enyl)benzene (1.01 g, 5.60 mmol). The crude residue was purified by flash chromatography (cyclohexane/AcOEt 4:1) to yield 407 mg (2.30 mmol, 41%) of 4-(4-fluorophenyl)-5-methyl-2H-1,2,3-triazole as a slightly yellow solid.
Rf (cyclohexane/AcOEt 4:1)=0.05.

257(B) 2-(But-3-ynyl)-4-(4-fluorophenyl)-5-methyl-2H-1,2,3-triazole and 1-(but-3-ynyl)-4-(4-fluorophenyl)-5-methyl12H-1,2,3-triazole The title compounds were prepared in accordance with the general method of Example 109(D), from 4-(4-fluorophenyl)-5-methyl-2H-1,2,3-triazole (407 mg, 2.30 mmol). The crude residue was purified by flash chromatography (cyclohexane/AcOEt 95:5 to 80:20) to yield 265 mg (1.16 mmol, 51%) of 2-(but-3-ynyl)-4-(4-fluorophenyl)-5-methyl-2H-1,2,3-triazole as a colorless oil and 87 mg (0.38 mmol, 17%) of 1-(but-3-ynyl)-4-(4-fluorophenyl)-5-methyl-1H-1,2,3-triazole as a white solid.

2-(But-3-ynyl)-4-(4-fluorophenyl)-5-methyl-2H-1,2,3-triazole

LCMS (RT): 4.32 min; MS (ES+) gave m/z: 230.1.
Rf (cyclohexane/AcOEt 4:1)=0.4.

1-(But-3-ynyl)-4-(4-fluorophenyl)-5-methyl-1H-1,2,3-triazole

LCMS (RT): 3.63 min; MS (ES+) gave m/z: 230.1.
Rf (cyclohexane/AcOEt 4:1)=0.1.

257(C) 2-(4-(4-(4-Fluorophenyl)-5-methyl-2H-1,2,3-triazol-2-yl)but-1-ynyl)pyridine The title compound was prepared in accordance with the general method of Example 1, from 2-(but-3-ynyl)-4-(4-fluorophenyl)-5-methyl-2H-1,2,3-triazole (265 mg, 1.16 mmol) and 2-bromopyridine (201 mg, 1.27 mmol). Reaction time: 2 hours. The crude residue was purified by flash chromatography (DCM/MeOH 99:1) to yield 306 mg (1.00 mmol, 86%) of 2-(4-(4-(4-fluorophenyl)-5-methyl-2H-1,2,3-triazol-2-yl)but-1-ynyl)pyridine as a brown oil.
LCMS (RT): 4.19 min; MS (ES+) gave m/z: 307.1.
Rf (DCM/MeOH 98:2)=0.2.
$^1$H-NMR (CDCl$_3$), δ (ppm): 2.46 (s, 3H), 3.12 (t, J=7.2, 2H), 4.63 (t, J=7.2, 2H), 7.08-7.16 (2H), 7.18-7.23 (m, 1H), 7.36 (dd, J=0.9 and 7.5, 1H), 7.58-7.67 (3H), 8.52-8.56 (m, 1H).

Example 258

2-(4-(4-(4-Fluorophenyl)-5-methyl-1H-1,2,3-triazol-1-yl)but-1-ynyl)pyridine

The title compound was prepared in accordance with the general method of Example 1, from 1-(but-3-ynyl)-4-(4-fluorophenyl)-5-methyl-1H-1,2,3-triazole (87 mg, 0.38 mmol, Example 257(B)) and 2-bromopyridine (66 mg, 0.42 mmol). Reaction time: 2 hours. The crude residue was purified by flash chromatography (DCM/MeOH 99:1) to yield 68 mg (0.22 mmol, 58%) of 2-(4-(4-(4-fluorophenyl)-5-methyl-1H-1,2,3-triazol-1-yl)but-1-ynyl)pyridine as a white powder (M.P.=130-131° C.).
LCMS (RT): 3.56 min; MS (ES+) gave m/z: 307.
Rf (DCM/MeOH 98:2)=0.2.
$^1$H-NMR (CDCl$_3$), δ (ppm): 2.53 (s, 3H), 3.11 (t, J=7.2, 2H), 4.57 (t, J=7.2, 2H), 7.09-7.17 (2H), 7.20-7.25 (m, 1H), 7.34 (d, J=7.8, 1H), 7.59-7.70 (3H), 8.55 (d, J=4.5, 1H).

Example 259

2-(4-(4-(2-Chlorophenyl)-2H-1,2,3-triazol-2-yl)but-1-ynyl)pyridine

259(A) 4-(2-Chlorophenyl)-2H-1,2,3-triazole

The title compound was prepared in accordance with the general method of Example 179(A), from (E)-1-chloro-2-(2-nitrovinyl)benzene (2.06 g, 11.2 mmol). The crude residue was purified by flash chromatography (cyclohexane/AcOEt 4:1) to yield 1.05 g (5.85 mmol, 52%) of 4-(2-chlorophenyl)-2H-1,2,3-triazole as an orange solid.
Rf (cyclohexane/AcOEt 4:1)=0.1.

259(B) 2-(But-3-ynyl)-4-(2-chlorophenyl)-2H-1,2,3-triazole and 1-(but-3-ynyl)-4-(2-chlorophenyl)-1H-1,2,3-triazole The title compounds were prepared in accordance with the general method of Example 109(D), from 4-(2-chlorophenyl)-2H-1,2,3-triazole (1.05 g, 5.85 mmol). The crude residue was purified by flash chromatography (cyclohexane/AcOEt 95:5 to 80:20) to yield 660 mg (2.85 mmol, 50%) of 2-(but-3-ynyl)-4-(2-chlorophenyl)-2H-1,2,3-triazole as a yellow oil and 400 mg (1.73 mmol, 30%) of 1-(but-3-ynyl)-4-(2-chlorophenyl)-1H-1,2,3-triazole as a yellow oil.

2-(But-3-ynyl)-4-(2-chlorophenyl)-2H-1,2,3-triazole

LCMS (RT): 4.47 min; MS (ES+) gave m/z: 232.1.
Rf (cyclohexane/AcOEt 4:1)=0.4.

1-(But-3-ynyl)-4-(2-chlorophenyl)-1H-1,2,3-triazole

LCMS (RT): 3.86 min; MS (ES+) gave m/z: 232.1.
Rf (cyclohexane/AcOEt 4:1)=0.2.

259(C) 2-(4-(4-(2-Chlorophenyl)-2H-1,2,3-triazol-2-yl)but-1-ynyl)pyridine

The title compound was prepared in accordance with the general method of Example 1, from 2-(but-3-ynyl)-4-(2-chlorophenyl)-2H-1,2,3-triazole (200 mg, 0.86 mmol) and 2-bromopyridine (150 mg, 0.95 mmol). The crude residue was purified by flash chromatography (DCM/MeOH 98.5:1.5) to yield 120 mg (0.39 mmol, 45%) of 2-(4-(4-(2-chlorophenyl)-2H-1,2,3-triazol-2-yl)but-1-ynyl)pyridine as a brown oil.
LCMS (RT): 4.34 min; MS (ES+) gave m/z: 309.1, 311.1.
Rf (DCM/MeOH 98:2)=0.3.
$^1$H-NMR (CDCl$_3$), δ (ppm): 3.18 (t, J=7.5, 2H), 4.75 (t, J=7.5, 2H), 7.21 (ddd, J=1.2, 4.8 and 7.5, 1H), 7.28-7.39 (3H), 7.45-7.48 (m, 1H), 7.58-7.65 (m, 1H), 7.85-7.88 (m, 1H), 8.14 (s, 1H), 8.55 (d, J=4.8, 1H).

Example 260

2-(4-(4-(2-Chlorophenyl)-1H-1,2,3-triazol-1-yl)but-1-ynyl)pyridine

The title compound was prepared in accordance with the general method of Example 1, from 1-(but-3-ynyl)-4-(2-chlorophenyl)-1H-1,2,3-triazole (200 mg, 0.86 mmol, Example 259(B)) and 2-bromopyridine (150 mg, 0.95 mmol). The crude residue was purified by flash chromatography (DCM/MeOH 99:1) to yield 93.4 mg (0.30 mmol, 35%) of 2-(4-(4-(2-chlorophenyl)-1H-1,2,3-triazol-1-yl)but-1-ynyl)pyridine as a yellow oil.
LCMS (RT): 3.74 min; MS (ES+) gave m/z: 309.1, 311.1.
Rf (DCM/MeOH 98:2)=0.2.
$^1$H-NMR (CDCl$_3$), δ (ppm): 3.12 (t, J=6.6, 2H), 4.70 (t, J=6.6, 2H), 7.20-7.25 (m, 1H), 7.26-7.29 (m, 1H), 7.34-7.44 (3H), 7.59-7.66 (m, 1H), 8.24 (dd, J=1.8 and 7.5, 1H), 8.40 (s, 1H), 8.56 (d, J=4.8, 1H).

Example 261

6,8-Difluoro-2-(4-(6-(fluoromethyl)pyridin-2-yl)but-3-ynyl)H-imidazo[1,2-a]pyridine

261(A) 6,8-Difluoro-2-(4-(trimethylsilyl)but-3-ynyl)H-imidazo[1,2-a]pyridine The title compound was prepared in accordance with the general method of Example 223(D), from 1-bromo-6-(trimethylsilyl)hex-5-yn-2-one (2.0 g, 8.1 mmol, Example 223 (C)) and 3,5-difluoropyridin-2-amine (0.56 g, 4.30 mmol). The crude residue was purified by flash chromatography (DCM 100% to DCM/MeOH 99:1) to yield 200 mg (2.02 mmol, 18%) of 6,8-difluoro-2-(4-(trimethylsilyl)but-3-ynyl) H-imidazo[1,2-a]pyridine as a brown solid.

261(B) 2-(But-3-ynyl)-6,8-difluoroH-imidazo[1,2-a]pyridine

The title compound was prepared in accordance with the general method of Example 108(B), from 6,8-difluoro-2-(4-(trimethylsilyl)but-3-ynyl)H-imidazo[1,2-a]pyridine (200 mg, 2.02 mmol). The crude residue was taken in ether, filtered and concentrated to yield 150 mg (0.73 mmol, 100%) of 2-(but-3-ynyl)-6,8-difluoroH-imidazo[1,2-a]pyridine as a brown solid.

261(C) 6,8-Difluoro-2-(4-(6-(fluoromethyl)pyridin-2-yl)but-3-ynyl)H-imidazo[1,2-a]pyridine The title compound was prepared in accordance with the general method of Example 1, from 2-(but-3-ynyl)-6,8-difluoroH-imidazo[1,2-a]pyridine (150 mg, 0.73 mmol) and 2-bromo-6-(fluoromethyl)pyridine (200 mg, 1.05 mmol, Example 190(E)). The crude residue was purified by flash chromatography (DCM/MeOH 99:1 to 98:2) to yield 110 mg (0.35 mmol, 48%) of 6,8-difluoro-2-(4-(6-(fluoromethyl)pyridin-2-yl)but-3-ynyl)H-imidazo[1,2-a]pyridine as a yellow solid (M.P.=113-114° C.).

LCMS (Tr): 3.28 min; MS (ES+) gave m/z: 316.2.
Rf (DCM/MeOH 98:2)=0.1.
$^1$H-NMR (CDCl$_3$), δ (ppm): 2.92 (t, J=7.2, 2H), 3.14 (t, J=7.8, 2H), 5.46 (d, J=46.8, 2H), 6.83-6.89 (m, 1H), 7.31 (d, J=7.8, 1H), 7.38 (d, J=7.5, 1H), 7.58 (d, J=3.0, 1H), 7.70 (t, J=7.5, 1H), 7.89 (m, 1H).

Formulation Examples

Typical examples of recipes for the formulation of the invention are as follows:
1) Tablets

| | |
|---|---|
| Compound of the example 256 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this example, the compound of the example 256 can be replaced by the same amount of any of the described examples 1 to 261.

2) Suspension

An aqueous suspension is prepared for oral administration so that each 1 milliliter contains 1 to 5 mg of one of the described example, 50 mg of sodium carboxymethyl cellulose, 1 mg of sodium benzoate, 500 mg of sorbitol and water ad 1 ml.

3) Injectable

A parenteral composition is prepared by stirring 1.5% by weight of active ingredient of the invention in 10% by volume propylene glycol and water.

4) Ointment

| | |
|---|---|
| Compound of the example 256 | 5 to 1000 mg |
| Stearyl alcohol | 3 g |
| Lanoline | 5 g |
| White petroleum | 15 g |
| Water | ad 100 g |

In this example, the compound 256 can be replaced by the same amount of any of the described examples 1 to 261.

Reasonable variations are not to be regarded as a departure from the scope of the invention. It will be obvious that the thus described invention may be varied in many ways by those skilled in the art.

The invention claimed is:
1. A method for treating a disorder selected from the group consisting of alcohol, nicotine, cocaine, amphetamine, benzodiazepine, analgesics, opiate or other substance dependence, and obsessive compulsive disorders, the method comprising administering to a mammalian patient in need of such treatment, an effective amount of a compound represented by the formula II-A2-a2:

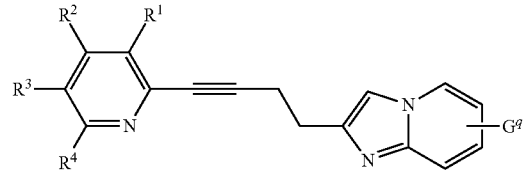

II-A2-a2 or a pharmaceutically acceptable salt or hydrate thereof;
wherein
R$^1$, R$^2$, R$^3$ and R$^4$ are each independently selected from the group consisting of hydrogen, halogen, optionally substituted C$_1$-C$_6$-alkyl, C$_1$-C$_6$-alkylhalo and C$_0$-C$_6$-alkyl-NR$^5$R$^6$;
R$^5$ and R$^6$ are each independently selected from the group consisting of hydrogen, optionally substituted C$_1$-C$_6$-alkyl, C$_1$-C$_6$-alkylhalo C$_3$-C$_7$-cycloalkyl, C$_3$-C$_7$-cycloalkyl-C$_1$-C$_6$-alkyl, heteroaryl, C$_1$-C$_6$-alkyl-heteroaryl, and aryl;
G$^q$ groups are each independently selected from the group consisting of hydrogen, halogen, CN, an optionally substituted C$_1$-C$_6$-alkyl, C$_1$-C$_6$-alkylhalo, O—C$_0$-C$_6$-alkyl, O—C$_0$-C$_6$-alkylaryl, heteroaryl and aryl;
q is an integer from 1 to 5; and
any N may be an N-oxide.

2. A method useful for treating anxiety, posttraumatic stress disorder, generalized anxiety disorder, or acute stress disorder, the method comprising administering to a mammalian patient in need of such treatment, an effective amount of a compound represented by the formula II-A2-a2:

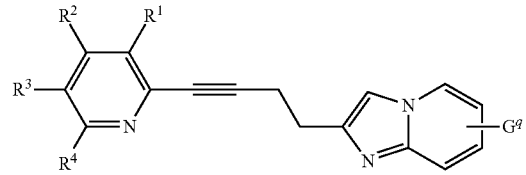

II-A2-a2 or a pharmaceutically acceptable salt or hydrate thereof;

$R^1$, $R^2$, $R^3$ and $R^4$ are each independently selected from the group consisting of hydrogen, halogen, optionally substituted $C_1$-$C_6$-alkyl, $C_1$-$C_6$-alkylhalo and $C_0$-$C_6$-alkyl-$NR^5R^6$;

$R^5$ and $R^6$ are each independently selected from the group consisting of hydrogen, optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

$G^q$ groups are each independently selected from the group consisting of hydrogen, halogen, CN, an optionally substituted $C_1$-$C_6$-alkyl, $C_1$-$C_6$-alkylhalo O—$C_0$-$C_6$-alkyl, O—$C_0$-$C_6$-alkylaryl, heteroaryl, and aryl;

q is an integer from 1 to 5; and any N may be an N-oxide.

3. A method useful for treating migraine, the method comprising administering to a mammalian patient in need of such treatment, an effective amount of a compound represented by the formula II-A2-a2:

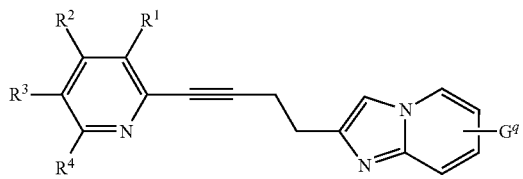

II-A2-a2 or a pharmaceutically acceptable salt or hydrate thereof;

wherein $R^1$, $R^2$, $R^3$ and $R^4$ are each independently selected from the group consisting of hydrogen, halogen, optionally substituted $C_1$-$C_6$-alkyl, $C_1$-$C_6$-alkylhalo, and $C_0$-$C_6$-alkyl-$NR^5R^6$;

$R^5$ and $R^6$ are each independently selected from the group consisting of hydrogen, optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

$G^q$ groups are each independently selected from the group consisting of hydrogen, halogen, CN, an optionally substituted $C_1$-$C_6$-alkyl, $C_1$-$C_6$-alkylhalo, O—$C_0$-$C_6$-alkyl, O—$C_0$-$C_6$-alkylaryl, heteroaryl and aryl;

q is an integer from 1 to 5; and any N may be an N-oxide.

4. A method for treating schizophrenia or depression, the method comprising administering to a mammalian patient in need of such treatment, an effective amount of a compound represented by the formula II-A2-a2:

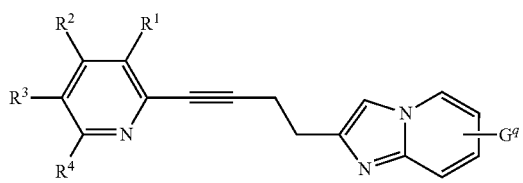

II-A2-a2 or a pharmaceutically acceptable salt or hydrate thereof;

wherein $R^1$, $R^2$, $R^3$ and $R^4$ are each independently selected from the group consisting of hydrogen, halogen, optionally substituted $C_1$-$C_6$-alkyl, $C_1$-$C_6$-alkylhalo, and $C_0$-$C_6$-alkyl-$NR^5R^6$;

$R^5$ and $R^6$ are each independently selected from the group consisting of hydrogen, optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

$G^q$ groups are each independently selected from the group consisting of hydrogen, halogen, CN, an optionally substituted $C_1$-$C_6$-alkyl, $C_1$-$C_6$-alkylhalo, O—$C_0$-$C_6$-alkyl, O—$C_0$-$C_6$-alkylaryl, heteroaryl, and aryl;

q is an integer from 1 to 5; and any N may be an N-oxide.

5. A method for treating disorder selected from the group consisting of alcohol, nicotine, cocaine, amphetamine, benzodiazepine, analgesics, opiate or other substance dependence, and obsessive compulsive disorders, the method comprising administering to a mammalian patient in need of such treatment, an effective amount of a compound represented by the formula II

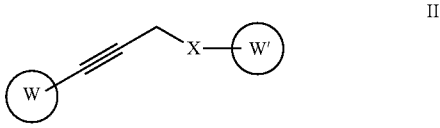

II or a pharmaceutically acceptable salt or hydrate thereof; wherein

W is a heteroaryl selected from:

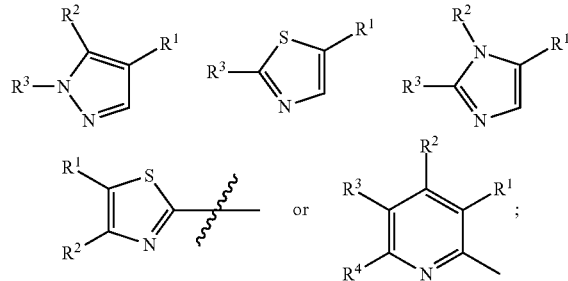

$R^1$, $R^2$, $R^3$ and $R^4$ are each independently selected from the group consisting of hydrogen, halogen, an optionally substituted $C_1$-$C_6$-alkyl, $C_1$-$C_6$-alkylhalo, aryl, $C_0$-$C_6$-alkyl-$OR^5$, $C_0$-$C_6$-alkyl-$NR^5R^6$, $C_0$-$C_6$-alkyl-$NR^5C(=O)$—$R^6$ and $C_0$-$C_6$-alkyl-$NR^5S(=O)_2$—$R^6$;

$R^5$ and $R^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

X is an optionally substituted $C_1$-alkyl;

W' is

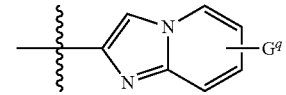

G<sup>q</sup> groups are each independently selected from the group consisting of hydrogen, halogen, nitro, optionally substituted $C_1$-$C_6$-alkyl, $C_1$-$C_6$-alkylhalo, $C_0$-$C_6$-alkyl-OR$^7$, O—$C_0$-$C_6$-alkylaryl, heteroaryl, aryl, $C_0$-$C_6$-alkyl-NR$^7$R$^8$ and $C_0$-$C_6$-alkyl-NR$^7$—S(=O)$_2$R$^8$ substituents;

q is an integer from 1 to 5;

R$^7$ and R$^8$ are each independently selected from hydrogen, an optionally substituted $C_1$-$C_6$-alkyl, or $C_1$-$C_6$-alkylhalo; and any N may be an N-oxide.

6. A method for treating anxiety, posttraumatic stress disorder, generalized anxiety disorder, or acute stress disorder, the method comprising administering to a mammalian patient in need of such treatment, an effective amount of a compound represented by the formula II

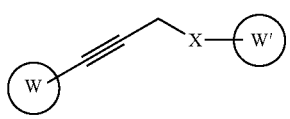
II or a pharmaceutically acceptable salt or hydrate thereof; wherein W is a heteroaryl selected from:

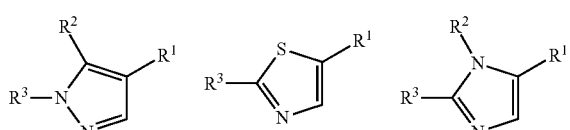

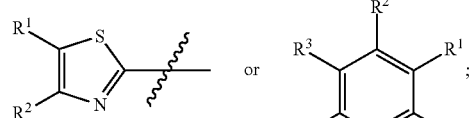

R$^1$, R$^2$, R$^3$ and R$^4$ are each independently selected from the group consisting of hydrogen, halogen, an optionally substituted $C_1$-$C_6$-alkyl, $C_1$-$C_6$-alkylhalo, aryl, $C_0$-$C_6$-alkyl-OR$^5$, $C_0$-$C_6$-alkyl-NR$^5$R$^6$, $C_0$-$C_6$-alkyl-NR$^5$C(=O)—R$^6$ and CoC$_6$-alkyl-NR$^5$S(=O)$_2$—R$^6$ substituents;

R$^5$ and R$^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

X is an optionally substituted CI-alkyl

W' is

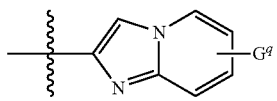

G$^q$ groups are each independently selected from the group consisting of hydrogen, halogen, nitro, optionally substituted $C_1$-$C_6$-alkyl, $C_1$-$C_6$-alkylhalo, $C_0$-$C_6$-alkyl-OR$^7$, O—$C_0$-$C_6$-alkylaryl, heteroaryl, aryl, $C_0$-$C_6$-alkyl-NR$^7$R$^8$ and $C_0$-$C_6$-alkyl-NR$^7$—S(O)$_2$R$^8$ substituents;

q is an integer from 1 to 5;

R$^7$ and R$^8$ are each independently selected from hydrogen, an optionally substituted $C_1$-$C_6$-alkyl, or $C_1$-$C_6$-alkylhalo; and any N may be an N-oxide.

7. A method for treating migraine, the method comprising administering to a mammalian patient in need of such treatment, an effective amount of a compound represented by the formula II

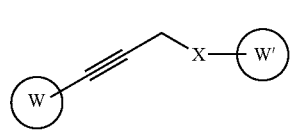
II or a pharmaceutically acceptable salt or hydrate thereof; wherein W is a heteroaryl selected from:

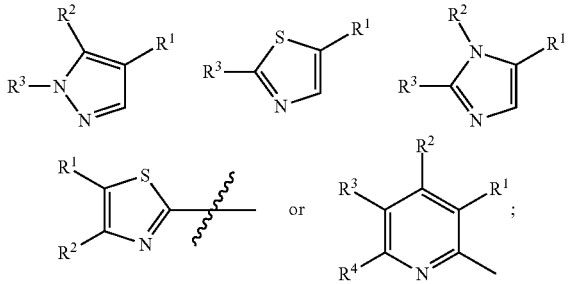

R$^1$, R$^2$, R$^3$ and R$^4$ are each independently selected from the group consisting of hydrogen, halogen, an optionally substituted $C_1$-$C_6$-alkyl, $C_1$-$C_6$-alkylhalo, aryl, $C_0$-$C_6$-alkyl-OR$^5$, $C_0$-$C_6$-alkyl-NR$^5$R$^6$, $C_0$-$C_6$-alkyl-NR$^5$C(O)—R$^6$ and CoC$_6$-alkyl-NR$^5$S(=O)$_2$—R$^6$ substituents;

R$^5$ and R$^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, Ci-C$_6$-alkyl-heteroaryl, and aryl;

X is an optionally substituted $C_1$-alkyl

W' is

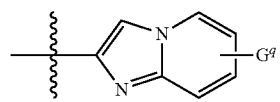

G$^q$ groups are each independently selected from the group consisting of hydrogen, halogen, nitro, optionally substituted $C_1$-$C_6$-alkyl, $C_1$-$C_6$-alkylhalo, $C_0$-$C_6$-alkyl-OR$^7$, O—$C_0$-$C_6$-alkylaryl, heteroaryl, aryl, $C_0$-$C_6$-alkyl-NR$^7$R$^8$ and $C_0$-$C_6$-alkyl-NR$^7$—S(=O)$_2$R$^8$ substituents;

q is an integer from 1 to 5;

R$^7$ and R$^8$ are each independently selected from hydrogen, an optionally substituted $C_1$-$C_6$-alkyl, or $C_1$-$C_6$-alkylhalo; and any N may be an N-oxide.

8. A method for treating schizophrenia or depression, the method comprising administering to a mammalian patient in need of such treatment, an effective amount of a compound represented by the formula II

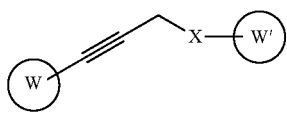

or a pharmaceutically acceptable salt or hydrate thereof; wherein
W is a heteroaryl selected from:

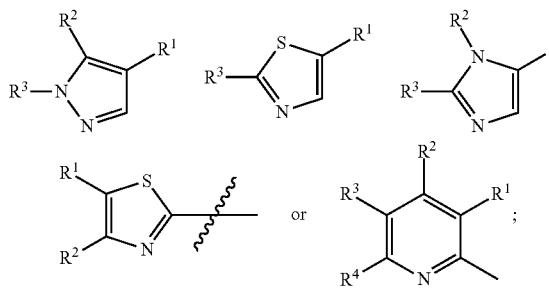

$R^1$, $R^2$, $R^3$ and $R^4$ are each independently selected from the group consisting of hydrogen, halogen, an optionally substituted $C_1$-$C_6$-alkyl, $C_1$-$C_6$-alkylhalo, aryl, $C_0$-$C_6$-alkyl-$OR^5$, $C_0$-$C_6$-alkyl-$NR^5R^6$, $C_0$-$C_6$-alkyl-$NR^5C(O)$—$R^6$ and $CoC_6$-alkyl-$NR^5S(=O)_2$—$R^6$ substituents;

$R^5$ and $R^6$ are each independently selected from the group consisting of hydrogen, an optionally substituted $C_1$-$C_6$-alkyl, $C_1$-$C_6$-alkylhalo, $C_3$-$C_7$-cycloalkyl, $C_3$-$C_7$-cycloalkyl-$C_1$-$C_6$-alkyl, heteroaryl, $C_1$-$C_6$-alkyl-heteroaryl, and aryl;

X is an optionally substituted $C_1$-alkyl
W' is

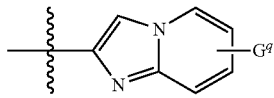

$G^q$ groups are each independently selected from the group consisting of hydrogen, halogen, nitro, optionally substituted $C_1$-$C_6$-alkyl, $C_1$-$C_6$-alkylhalo, $C_0$-$C_6$-alkyl-$OR^7$, O—$C_0$-$C_6$-alkylaryl, heteroaryl, aryl, $C_0$-$C_6$-alkyl-$NR^7R^8$ and $C_0$-$C_6$-alkyl-$NR^7$—$S(O)_2R^8$ substituents;

q is an integer from 1 to 5;
$R^7$ and $R^8$ are each independently selected from hydrogen, an optionally substituted $C_1$-$C_6$-alkyl, or $C_1$-$C_6$-alkylhalo; and
any N may be an N-oxide.

9. The method of claim 1, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethyl)thiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

10. The method of claim 2, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine; 8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethyl)thiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine;
and 6,8-Difluoro-2-(4-(6-(fluoromethyl)pyridin-2-yl)but-3-ynyl)H-imidazo[1,2-a]pyridine;
or a pharmaceutically acceptable salt thereof.

11. The method of claim 3, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;

5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethypthiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

12. The method of claim 4, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethyl)thiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

13. The method of claim 5, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethyl)thiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

14. The method of claim 6, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethyl)thiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

15. The method of claim 7, wherein the compound is selected from the group consisting of:

2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyl)imidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethypthiazol-4-yl)but-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

16. The method of claim 8, wherein the compound is selected from the group consisting of:
2-(4-(Pyridin-2-yl)but-3-ynyl)-imidazo[1,2-a]pyridine;
8-Methyl-2-(4-(pyridin-2-yl)but-3-ynyl)-imidazo[1,2-a]pyridine;
5-Methyl-2-(4-(pyridin-2-yl)but-3-ynyl)-imidazo[1,2-a]pyridine;
5-Phenyl-2-(4-(pyridin-2-yl)but-3-ynyl)-imidazo[1,2-a]pyridine;
2-(4-(2-Methylthiazol-4-yl)but-3-ynyhimidazo[1,2-a]pyridine;
6-Fluoro-2-(4-(pyridin-2-yl)but-3-ynyl)-imidazo[1,2-a]pyridine;
2-(4-(5-Fluoropyridin-2-yl)but-3-ynyl)-imidazo[1,2-a]pyridine;
8-Chloro-2-(4-(6-(fluoromethyl)pyridin-2-yl)but-3-ynyl)-imidazo[1,2-a]pyridine;
8-Chloro-2-(4-(pyridin-2-yl)but-3-ynyl)-imidazo[1,2-a]pyridine;
6-fluoro-2-(4-(6-(fluoromethyl)pyridin-2-yl)but-3-ynyl)H-imidazo[1,2-a]pyridine;
6-fluoro-2-(4-(2-(fluoromethypthiazol-4-Abut-3-ynyl)-imidazo[1,2-a]pyridine;
8-bromo-2-(4-(6-(fluoromethyl)pyridin-2-yl)but-3-ynyl)-imidazo[1,2-a]pyridine;
8-(benzyloxy)-2-(4-(6-(fluoromethyl)pyridin-2-yl)but-3-ynyl)-imidazo[1,2-a]pyridine;
2-(4-(6-(fluoromethyl)pyridin-2-yl)but-3-ynyl)-8-phenyl-imidazo[1,2-a]pyridine;
6,8-difluoro-2-(4-(pyridin-2-yl)but-3-ynyl)-imidazo[1,2-a]pyridine; and
6,8-Difluoro-2-(4-(6-(fluoromethyl)pyridin-2-yl)but-3-ynyl)H-imidazo[1,2-a]pyridine;
or a pharmaceutically acceptable salt thereof.

17. The method of claim 1, wherein the disorder is alcohol or nicotine dependence or obsessive compulsive disorders.

18. The method of claim 2, wherein the disorder is anxiety.

19. The method of claim 4, wherein the disorder is depression.

* * * * *